United States Patent
Holland et al.

(10) Patent No.: US 10,130,623 B2
(45) Date of Patent: Nov. 20, 2018

(54) TYROSINE KINASE INHIBITORS

(71) Applicant: Rigel Pharmaceuticals, Inc., South San Francisco, CA (US)

(72) Inventors: Sacha Holland, San Francisco, CA (US); Rajinder Singh, Belmont, CA (US); Somasekhar Bhamidipati, Foster City, CA (US); Pingyu Ding, Foster City, CA (US); Rao Kolluri, Foster City, CA (US); Ihab Darwish, San Carlos, CA (US); Esteban Masuda, Menlo Park, CA (US); Jiaxin Yu, San Carlos, CA (US)

(73) Assignee: RIGEL PHARMACEUTICALS, INC., South San Francisco, CA (US)

( * ) Notice: Subject to any disclaimer, the term of this patent is extended or adjusted under 35 U.S.C. 154(b) by 0 days.

(21) Appl. No.: 15/645,775

(22) Filed: Jul. 10, 2017

(65) Prior Publication Data

US 2018/0008589 A1 Jan. 11, 2018

Related U.S. Application Data

(60) Provisional application No. 62/360,297, filed on Jul. 8, 2016.

(51) Int. Cl.
| | | |
|---|---|---|
| A61K 31/506 | (2006.01) | |
| A61K 31/4545 | (2006.01) | |
| A61K 31/519 | (2006.01) | |

(52) U.S. Cl.
CPC ........ *A61K 31/4545* (2013.01); *A61K 31/519* (2013.01)

(58) Field of Classification Search
CPC .................................................. C07D 471/05
See application file for complete search history.

(56) References Cited

U.S. PATENT DOCUMENTS

2016/0333008 A1* 11/2016 Sun .................... C07D 471/04

FOREIGN PATENT DOCUMENTS

| | | |
|---|---|---|
| WO | WO 2012/135800 | 10/2012 |
| WO | WO 2014/164729 | 10/2014 |
| WO | WO 2016/183071 | 11/2016 |

OTHER PUBLICATIONS

Z. Wang et al., 19 Drug Discovery Today, 145-150 (2014).*
U.K. Marelli et al., 3 Frontiers in Oncology, 1-12 (2013).*
R. Linger et al., Advances in Cancer Research, 35-83 (2008).*
C.V. Rothin et al., 22 Current Opinion in Immunology, 740-746 (2010).*
A. Zagórska et al. 15, Nature Immunology, 920-928 (2014).*
C.V. Rothin et al., 33 Annual Reviews of Immunology, 355-391 (2015).*
L. Di. et al., Drug-Like Properties (Second Edition), 2016, pp. 471-485.*
International Search Report and Written Opinion dated Oct. 10, 2017 for International Application No. PCT/US2017/041396 filed Jul. 10, 2017, 12 pages.

* cited by examiner

*Primary Examiner* — Alexander R Pagano
(74) *Attorney, Agent, or Firm* — McDonnell Boehnen Hulbert & Berghoff LLP

(57) ABSTRACT

Disclosed are imidazole compounds, as well as pharmaceutical compositions and methods of use thereof. One embodiment is a compound having the structure

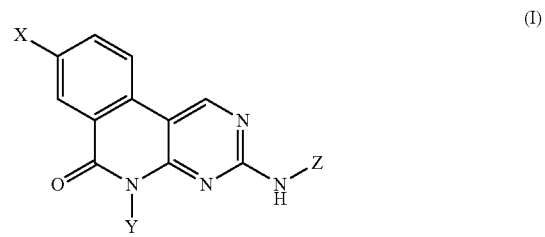

and pharmaceutically acceptable salts, prodrugs and N-oxides thereof (and solvates and hydrates thereof), wherein X, Y and Z are as described herein. In certain embodiments, a compound disclosed herein inhibits a cellular TAM receptor, and can be used to treat disease mediated by or involving the TAM receptor family.

39 Claims, No Drawings

TYROSINE KINASE INHIBITORS

BACKGROUND

Field of Invention

This invention relates to the field of compounds, pharmaceutical compositions, and methods of using the compounds and compositions containing them. This invention relates more particularly to the field of pyrimidoisoquinolone compounds and pharmaceutical compositions thereof, methods of inhibiting one or more kinases, such as one or more of the TAM (Tyro 3, Axl and Mer) receptor family with the compounds, and methods of treating and/or preventing disease with the compounds.

Technical Background

In recent years, inhibition of specific cancer-associated tyrosine kinases has emerged as an important approach for cancer therapy. Tyrosine kinases as mediators of cell signaling, play a role in many diverse physiological pathways including cell growth and differentiation. Deregulation of tyrosine kinases activity can result in cellular transformation leading to the development of cancer.

Tyro 3 has been implicated in several malignant diseases, and its expression is upregulated in AML, CML, multiple myeloma, endometrial cancer and melanoma. Tyro 3 has also been shown to have transforming abilities, and may function as a prosurvival factor in tumorigenesis. In melanoma cells, Tyro 3 knockdown inhibits proliferation and leads to increased sensitivity to chemotherapeutic agents in vitro.

The Axl receptor tyrosine kinase (Axl) is overexpressed in a number of different tumor cell types. Axl signaling has been shown to favor tumor growth through activation of proliferative and anti-apoptotic signaling pathways, as well as through promotion of angiogenesis and tumor invasiveness. Axl is associated with the development and maintenance of various cancers including lung cancer, myeloid leukemia, uterine cancer, ovarian cancer, gliomas, melanoma, prostate cancer, breast cancer, gastric cancer, osteosarcoma, renal cell carcinoma, and thyroid cancer. In some type of cancers, particularly non-small cell lung cancer (NSCLC), myeloid leukemia, and gastric cancers, the overexpression of this cell signaling molecule indicates a poor prognosis for the patient.

Mer is a transmembrane receptor tyrosine kinase composed of two immunoglobulin domains and two fibronectin III domains in the extracellular portion, and a tyrosine kinase domain in the intracellular portion. Mer overexpression has been linked to a number of different cancers including subsets of B and T cell leukemia, lymphoma, pituitary adenoma, gastric cancer, and rhabdomyosarcoma.

SUMMARY

In view of the foregoing, we recognized that new therapeutic agents that inhibit one or more kinases, in particular tyrosine receptor kinases of the TAM (Tyro 3, Axl and Mer) receptor family may be useful and therefore desirable for the treatment of proliferative disorders, in particular hematological neoplasms, such as acute myeloid leukemia (AML).

Accordingly, the present invention comprises compounds, pharmaceutical compositions, and methods of using them to treat and/or prevent disease by inhibiting one or more of the TAM (Tyro 3, Axl and Mer) receptor family.

Disclosed herein are compounds having structural formula (I)

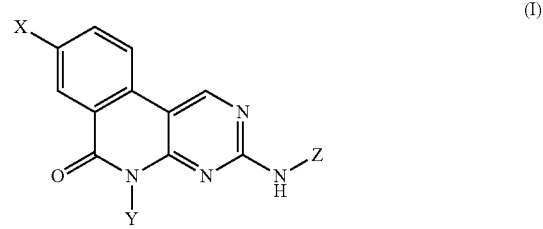

and pharmaceutically acceptable salts, prodrugs, and N-oxides thereof (and solvates and hydrates thereof), wherein X, Y, and Z are as described herein.

Also disclosed herein are pharmaceutical compositions. Examples of such compositions include those having at least one pharmaceutically acceptable carrier, diluent, or excipient; and a compound, pharmaceutically acceptable salt, prodrug, or N-oxide (or solvate or hydrate) as described herein.

Another aspect of the present invention comprises methods for treating and/or preventing disease by inhibiting a cellular TAM receptor. Accordingly, the invention also comprises methods for treating disease using the presently disclosed compounds and pharmaceutical compositions.

All publications referenced herein are incorporated by reference in their entirety to the extent they are not inconsistent with the teachings presented herein.

DETAILED DESCRIPTION

In one aspect, the invention comprises compounds that inhibit one or more of the TAM (Tyro 3, Axl and Mer) receptor family.

In embodiment $I_0$ of this first aspect, the compounds have structural formula (I):

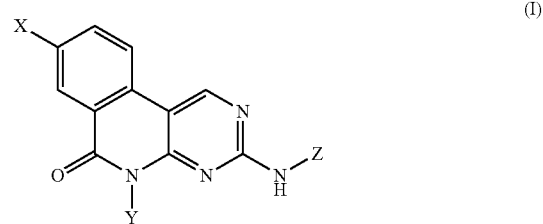

or a pharmaceutically acceptable salt, prodrug, or N-oxide thereof, or a solvate or hydrate thereof,
wherein
X is hydrogen, Cak($C_0$-$C_6$alkyl), Hca($C_0$-$C_6$alkyl), Ar($C_0$-$C_6$alkyl), Het($C_0$-$C_6$alkyl), halogen or Hca($C_1$-$C_6$alkyl)-O—, wherein Ar, Het, Cak, Hca and the alkyl group is optionally substituted by one to four —$R^{X1}$ groups, wherein
  each —$R^{X1}$ is independently halogen, cyano, $C_1$-$C_6$alkyl, $C_1$-$C_6$haloalkyl, —$C_1$-$C_6$alkoxy, oxo, —OR, —SR, —$NR_2$, —C(O)R, —C(O)OR, —C(O)$NR_2$, —S(O)$_2$$NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)

(OR)$_2$, —CH$_2$—OP(O)(OR), Ar(C$_0$-C$_6$alkyl), Het(C$_0$-C$_6$alkyl), Cak(C$_0$-C$_6$alkyl) or Hca(C$_0$-C$_6$alkyl), or two —R$^{X1}$ groups taken together, when attached to adjacent atoms, form a Cak, Hca or Het, wherein the Cak, Hca and the Het comprise a 3-8 membered ring optionally substituted with one or two —R$^{X2}$ groups, or two —R$^{X1}$ groups taken together, when attached to the same carbon atom, form a Hca, wherein the Hca comprises a 3-8 membered ring optionally substituted with one or two —R$^{X2}$ groups, or two —R$^{X1}$ groups taken together, when attached to non-adjacent atoms, and combined with X, form a bridged Hca optionally substituted with one or two —R$^{X2}$ groups, wherein each —R$^{X2}$ is independently halogen, cyano, nitro, oxo, —OR, —SR, —NR$_2$, —C(O)OR, —C(O)NR$_2$, —C(O)R, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, —N(R)S(O)$_2$R, C$_1$-C$_6$alkyl, or C$_1$-C$_6$haloalkyl;

Y is Cak(C$_0$-C$_8$alkyl) or Hca(C$_0$-C$_6$alkyl), each optionally substituted by one or two —R$^{Y1}$ groups;

wherein each —R$^{Y1}$ is independently halogen, cyano, C$_1$-C$_6$alkyl, C$_1$-C$_6$haloalkyl, —C$_1$-C$_6$alkoxy, oxo, —OR, —SR, —NR$_2$, N(R)C(NR$_2$)NR$_2$, —C(O)R, —C(O)OR, C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR), or two —R$^{Y1}$ groups taken together, when attached to the same carbon atom, form a Cak, wherein the Cak comprises a 3-8 membered ring optionally substituted with —OR;

Z is C$_1$-C$_6$alkyl or Cak(C$_0$-C$_6$alkyl), each optionally substituted by one to three —R$^{Z1}$ groups;

wherein each —R$^{Z1}$ is independently halogen, cyano, C$_1$-C$_6$alkyl, C$_1$-C$_6$haloalkyl, —C$_1$-C$_6$alkoxy, oxo, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR); and each R is independently hydrogen, C$_1$-C$_6$alkyl, C$_1$-C$_6$haloalkyl, Hca(C$_0$-C$_6$alkyl), Cak(C$_0$-C$_8$alkyl), C$_1$-C$_6$alkyl-CN, —CH$_2$C(O)NH$_2$, C$_1$-C$_6$alkyl-OH, wherein Hca is a 3-15 membered ring or ring system comprising at least one ring, 1-4 O, S, or N atoms, provided no O or S is adjacent to another O or S;

Het is a 5-15 membered aromatic ring or ring system comprising at least one ring and 1-4 O, S, or N atoms, provided no O or S is adjacent to another O or S;

Cak is a 3-8 membered non-aromatic carbocyclic ring or ring system, which may be saturated or partially unsaturated; and Ar is a 6-16 membered aromatic ring or ring system having at least one carbocyclic aromatic ring optionally fused one or more aromatic or non-aromatic rings.

provided that the compound is not
3-(butylamino)-8-chloro-5-(4-hydroxycyclohexyl)pyrimido[4,5-c]isoquinolin-6(5H)-one;
3-(butylamino)-5-(4-hydroxycyclohexyl)-8-(morpholinomethyl)pyrimido[4,5-c]isoquinolin-6(5H)-one;
3-(butylamino)-8-(2,6-difluorophenyl)-5-(4-hydroxycyclohexyl)pyrimido[4,5-c]isoquinolin-6(5H)-one; or
3-(butylamino)-5-(4-hydroxycyclohexyl)-8-(1-methyl-1H-pyrazol-4-yl)pyrimido[4,5-c]isoquinolin-6(5H)-one.

In some embodiments, the invention comprises compounds of embodiment I$_0$ wherein X is hydrogen, Cak(C$_0$-C$_6$alkyl), Hca(C$_0$-C$_6$alkyl) or Het(C$_0$-C$_6$alkyl, wherein Ar, Het, Cak, Hca and the alkyl group is optionally substituted by one to four —R$^{X1}$ groups.

In some embodiments, the invention comprises compounds of embodiment I$_0$ wherein X is hydrogen, Cak(C$_0$-C$_6$alkyl), Hca(C$_0$-C$_6$alkyl) or Het(C$_0$-C$_6$alkyl, wherein Ar, Het, Cak, Hca and the alkyl group is optionally substituted by one to four —R$^{X1}$ groups, provided that when X is morpholinyl(C$_1$alkyl), Z is C$_1$-C$_6$alkyl substituted by one to three —R$^{Z1}$ groups, or Cak(C$_0$-C$_6$alkyl) optionally substituted by one to three —R$^{Z1}$ groups.

In embodiment II$_0$, the invention comprises compounds of embodiment 1$_0$ having the structure of formula (II):

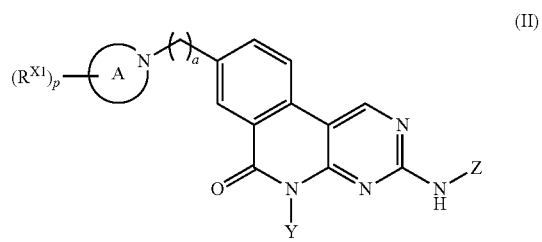

(II)

or a pharmaceutically acceptable salt, prodrug or N-oxide thereof, or solvate or hydrate thereof,
wherein
(a) ring A is

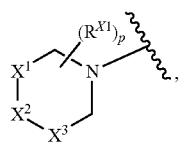

wherein
p is 0, 1, 2, 3 or 4;
X$^1$ is —O—, —S—, —S(O)—, —S(O)$_2$—, —CR$^2$—, —C(R)(R$^{X1}$)—, —C(R$^{X1}$)$_2$—, —N(R)— or —N(R$^{X1}$)—;
X$^2$ is —S—, —S(O)—, —S(O)$_2$—, —CR$^2$—, —C(R)(R$^{X1}$)—, —C(R$^{X1}$)$_2$—, —N(R)— or —N(R$^{X1}$)—; and
X$^3$ is —O—, —S—, —S(O)—, —S(O)$_2$—, —CR$^2$—, —C(R)(R$^{X1}$)—, —C(R$^{X1}$)$_2$—, —N(R)— or —N(R$^{X1}$)—;
(b) ring A is

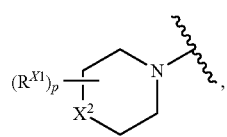

wherein p is 0, 1, 2, 3 or 4;

$X^2$ is —S—, —S(O)—, —S(O)$_2$—, —CR$^2$—, —C(R)(R$^{X1}$)—, —C(R$^{X1}$)$_2$—, —N(R)— or —N(R)—;

(c) ring A is

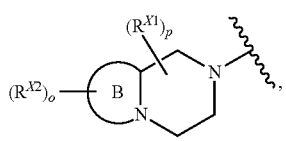

wherein p is 0, 1 or 2;

o is 0, 1 or 2; and ring B is Hca or Het, each comprising a 3-8 membered ring optionally substituted with one or two —R$^{X2}$ groups;

(d) ring A is

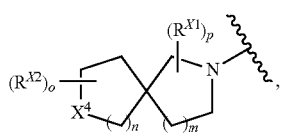

wherein p is 0, 1 or 2;

o is 0, 1 or 2;

n is 0, 1 or 2;

m is 0, 1 or 2; and $X^4$ is —O—, —S—, —S(O)—, —S(O)$_2$—, —CR$^2$—, —C(R)(R$^{X1}$)—, —C(R$^{X1}$)$_2$—, —N(R)— or —N(R$^{X1}$)—;

(e) ring A is

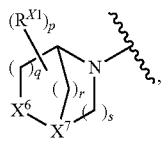

wherein $X^6$ is —O—, —S—, —S(O)—, —S(O)$_2$—, —CR$^2$—, —C(R)(R$^{X1}$)—, —C(R$^{X1}$)$_2$—, —N(R)— or —N(R$^{X1}$)—; and $X^7$ is —CR—, —C(R$^{X1}$)— or —N—;

p is 0, 1 or 2;

q is 0, 1 or 2;

r is 0, 1 or 2; and s is 0, 1 or 2.

In embodiment II$_{0a}$, the compounds are of embodiment II$_0$, wherein a is 0.

In embodiment II$_{0b}$, the compounds are of embodiment II$_0$, wherein a is 1.

In embodiment II$_{0c}$, the compounds are of embodiment II$_0$, wherein Y is any of groups (2a)-(2ww).

In embodiment II$_{0d}$, the compounds are of embodiment II$_0$, wherein Z is any of groups (3a)-(3ccc).

In embodiment I$_1$ of this first aspect, the compounds have structural formula (I):

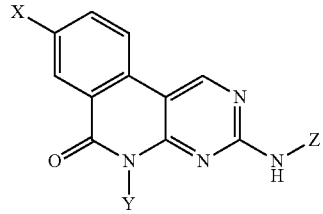

(I)

or a pharmaceutically acceptable salt, prodrug, or N-oxide thereof, or a solvate or hydrate thereof, wherein X is hydrogen, Cak(C$_0$-C$_6$alkyl), Hca(C$_0$-C$_6$alkyl), Ar(C$_0$-C$_6$alkyl) or Het(C$_0$-C$_6$alkyl), wherein Ar, Het, Cak, Hca and the alkyl group is optionally substituted by one to four —R$^{X1}$ groups, wherein each —R$^{X1}$ is independently halogen, cyano, C$_1$-C$_6$alkyl, C$_1$-C$_6$haloalkyl, —C$_1$-C$_6$alkoxy, oxo, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$, —CH$_2$—OP(O)(OR), Ar(C$_0$-C$_6$alkyl), Het(C$_0$-C$_6$alkyl), Cak(C$_0$-C$_6$alkyl) or Hca(C$_0$-C$_6$alkyl), or two —R$^{X1}$ groups taken together, when attached to adjacent atoms, form a Cak, Hca or Het, wherein the Cak Hca and the Het comprise a 3-8 membered ring optionally substituted with one or two —R$^{X2}$ groups, or two —R$^{X1}$ groups taken together, when attached to the same carbon atom, form a Hca, wherein the Hca comprises a 3-8 membered ring optionally substituted with one or two —R$^{X2}$ groups, or two —R$^{X1}$ groups taken together, when attached to non-adjacent atoms, and combined with X, form a bridged Hca optionally substituted with one or two —R$^{X2}$ groups, wherein each —R$^{X2}$ is independently halogen, cyano, nitro, oxo, —OR, —SR, —NR$_2$, —C(O)OR, —C(O)NR$_2$, —C(O)R, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, —N(R)S(O)$_2$R, C$_1$-C$_6$alkyl, or C$_1$-C$_6$haloalkyl;

Y is Cak(C$_0$-C$_6$alkyl) optionally substituted by one or two —R$^{Y1}$ groups;

wherein each —R$^{Y1}$ is independently halogen, cyano, C$_1$-C$_6$alkyl, C$_1$-C$_6$haloalkyl, —C$_1$-C$_6$alkoxy, oxo, —OR, —SR, —NR$_2$, —C(O)R, —C(O)OR, C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR);

Z is C$_1$-C$_6$alkyl or Cak(C$_0$-C$_6$alkyl), each optionally substituted by one to three —R$^{Z1}$ groups;

wherein each —R$^{Z1}$ is independently halogen, cyano, C$_1$-C$_6$alkyl, C$_1$-C$_6$haloalkyl, —C$_1$-C$_6$alkoxy, oxo, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR); and each R is independently hydrogen or C$_1$-C$_6$alkyl, wherein Hca is a 3-15 membered ring or ring system comprising at least one ring, 1-4 O, S, or N atoms, provided no O or S is adjacent to another O or S;

Het is a 5-15 membered aromatic ring or ring system comprising at least one ring and 1-4 O, S, or N atoms, provided no O or S is adjacent to another O or S;

Cak is a 3-8 membered non-aromatic carbocyclic ring or ring system, which may be saturated or partially unsaturated; and Ar is a 6-16 membered aromatic ring or ring system having at least one carbocyclic aromatic ring optionally fused one or more aromatic or non-aromatic rings.

In embodiment $I_2$, the compounds are of embodiment $I_1$, wherein X is hydrogen, Cak($C_0$-$C_6$alkyl) or Hca($C_0$-$C_6$alkyl), wherein each Cak, Hca and alkyl group is optionally substituted by one to three —$R^{X1}$ groups.

In embodiment $I_3$, the compounds are of embodiment $I_1$, wherein X is hydrogen or Hca($C_0$-$C_6$alkyl), wherein each Hca and alkyl group is optionally substituted by one to three —$R^{X1}$ groups.

In embodiment $I_{3a}$, the compounds are of embodiment $I_1$, provided that the compound is not
- 3-(butylamino)-5-(4-hydroxycyclohexyl)-8-(morpholinomethyl)pyrimido[4,5-c]isoquinolin-6(5H)-one;
- 3-(butylamino)-8-(2,6-difluorophenyl)-5-(4-hydroxycyclohexyl)pyrimido[4,5-c]isoquinolin-6(5H)-one; or
- 3-(butylamino)-5-(4-hydroxycyclohexyl)-8-(1-methyl-1H-pyrazol-4-yl)pyrimido[4,5-c]isoquinolin-6(5H)-one.

In embodiment $I_{3b}$, the compounds are of embodiment $I_1$, wherein X is hydrogen, Cak($C_0$-$C_6$alkyl), Hca($C_0$-$C_6$alkyl) or Het($C_0$-$C_6$alkyl, wherein Ar, Het, Cak, Hca and the alkyl group is optionally substituted by one to four —$R^{X1}$ groups, provided that when X is morpholinyl($C_1$alkyl), Z is $C_1$-$C_6$alkyl substituted by one to three —$R^{Z1}$ groups, or Cak($C_0$-$C_6$alkyl) optionally substituted by one to three —$R^{Z1}$ groups.

In embodiment $I_4$, the invention further comprises subgenera of formula (I) in which structural formula (I), X, Y and Z are any group or combinations of groups as defined sections $I^a$-$I^d$ immediately below (e.g., wherein the compound is of structural formula (I) as defined in any of the above embodiments and Z is piperazine optionally substituted with one $R^{X1}$ group, wherein $R^{X1}$ is methyl; or the compound is of formula (Ib), X is group (1jj), Y is group (2r), and Z is group (3h)):

$I^a$—Structural Formula (I) is one of Formulae (Ia)-(If):

(Ia)
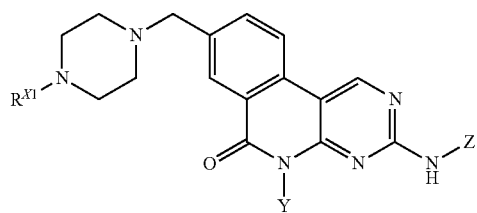

(Ib)
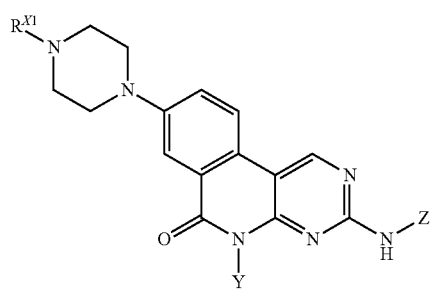

(Ic)
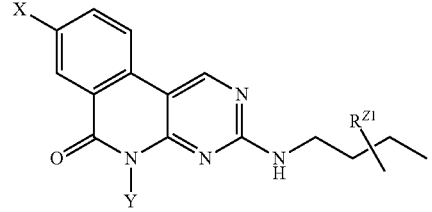

(Id)
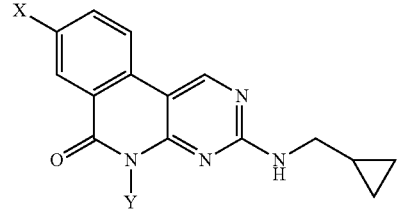

(Ie)
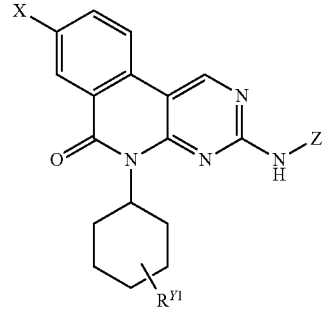

(If)
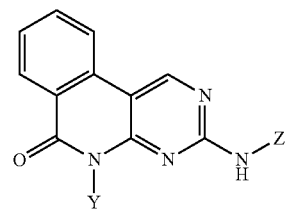

$I^b$—X is Selected from One of the Following Groups (1a)-(1aaa):

(1a) X is hydrogen, Cak($C_0$-$C_6$alkyl), Hca($C_0$-$C_6$alkyl), Ar($C_0$-$C_6$alkyl), Het($C_0$-$C_6$alkyl), wherein Ar, Het, Cak, Hca and the alkyl group is optionally substituted by one to four —$R^{X1}$ groups, wherein
  each —$R^{X1}$ is independently halogen, cyano, $C_1$-$C_6$alkyl, $C_1$-$C_6$haloalkyl, —$C_1$-$C_6$alkoxy, oxo, —OR, —SR, —$NR_2$, —C(O)R, —C(O)OR, —C(O)$NR_2$, —S(O)$_2$$NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$, —$CH_2$—OP(O)(OR), Ar($C_0$-$C_6$alkyl), Het($C_0$-$C_6$alkyl), Cak($C_0$-$C_6$alkyl) or Hca($C_0$-$C_6$alkyl).

(1b) X is Cak($C_0$-$C_6$alkyl), Hca($C_0$-$C_6$alkyl), Ar($C_0$-$C_6$alkyl), Het($C_0$-$C_6$alkyl), wherein Ar, Het, Cak, Hca and the alkyl group is optionally substituted by one to four —$R^{X1}$ groups.

(1c) X is Cak($C_0$-$C_6$alkyl) or Hca($C_0$-$C_6$alkyl), wherein Cak, Hca and the alkyl group is optionally substituted by one to four —$R^{X1}$ groups.

(1d) X is Cak($C_0$-$C_6$alkyl), wherein Cak and the alkyl group is optionally substituted by one to four —$R^{X1}$ groups.

(1e) X is Hca($C_0$-$C_6$alkyl), wherein the Hca and the alkyl group is optionally substituted by one to four —$R^{X1}$ groups.

(1f) X is any of groups (1a)-(1e), wherein
  each —$R^{X1}$ is independently halogen, cyano, $C_1$-$C_6$alkyl, $C_1$-$C_6$haloalkyl, —$C_1$-$C_6$alkoxy, oxo, —OR, —SR, —$NR_2$, —C(O)R, —C(O)OR, —C(O)$NR_2$, —S(O)$_2$$NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$, —$CH_2$—OP(O)(OR), Ar($C_0$-$C_6$alkyl), Het($C_0$-$C_6$alkyl), Cak($C_0$-$C_6$alkyl) or Hca($C_0$-$C_6$alkyl),
  or two —$R^{X1}$ groups taken together, when attached to adjacent atoms, form a Cak, Hca or Het, wherein the Cak Hca and the Het comprise a 3-8 membered ring optionally substituted with one or two —$R^{X2}$ groups,
  or two —$R^{X1}$ groups taken together, when attached to the same carbon atom, form a Hca, wherein the Hca comprises a 3-8 membered ring optionally substituted with one or two —$R^{X2}$ groups,
  or two —$R^{X1}$ groups taken together, when attached to non-adjacent atoms, and combined with X, form a bridged Hca optionally substituted with one or two —$R^{X2}$ groups,
    wherein each —$R^{X2}$ is independently halogen, cyano, nitro, oxo, —OR, —SR, —$NR_2$, —C(O)OR, —C(O)$NR_2$, —C(O)R, —S(O)R, —S(O)$_2$R, —S(O)OR, —S(O)$_2$OR, —S(O)$NR_2$, —S(O)$_2$$NR_2$, —OC(O)R, —OC(O)OR, —OC(O)$NR_2$, —N(R)C(O)R, —N(R)C(O)OR, —N(R)C(O)$NR_2$, —N(R)S(O)R, —N(R)S(O)$_2$R, $C_1$-$C_6$alkyl, or $C_1$-$C_6$haloalkyl.

(1g) X is any of groups (1a)-(1e), wherein
  each —$R^{X1}$ is independently halogen, cyano, $C_1$-$C_6$alkyl, $C_1$-$C_6$haloalkyl, —$C_1$-$C_6$alkoxy, oxo, —OR, —SR, —$NR_2$, —C(O)R, —C(O)OR, —C(O)$NR_2$, —S(O)$_2$$NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$, —$CH_2$—OP(O)(OR), Ar($C_0$-$C_6$alkyl), Het($C_0$-$C_6$alkyl), Cak($C_0$-$C_6$alkyl) or Hca($C_0$-$C_6$alkyl),
  or two —$R^{X1}$ groups taken together, when attached to adjacent atoms, form a Cak, Hca or Het, wherein the Cak Hca and the Het comprise a 3-8 membered ring optionally substituted with one or two —$R^{X2}$ groups,
  or two —$R^{X1}$ groups taken together, when attached to the same carbon atom, form a Hca, wherein the Hca comprises a 3-8 membered ring optionally substituted with one or two —$R^{X2}$ groups.

(1h) X is any of groups (1a)-(1e), wherein
  each —$R^{X1}$ is independently halogen, cyano, $C_1$-$C_6$alkyl, $C_1$-$C_6$haloalkyl, —$C_1$-$C_6$alkoxy, oxo, —OR, —SR, —$NR_2$, —C(O)R, —C(O)OR, —C(O)$NR_2$, —S(O)$_2$$NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$, —$CH_2$—OP(O)(OR), Ar($C_0$-$C_6$alkyl), Het($C_0$-$C_6$alkyl), Cak($C_0$-$C_6$alkyl) or Hca($C_0$-$C_6$alkyl),
  or two —$R^{X1}$ groups taken together, when attached to adjacent atoms, form a Cak, Hca or Het, wherein the Cak Hca and the Het comprise a 3-8 membered ring optionally substituted with one or two —$R^{X2}$ groups.

(1i) X is any of groups (1a)-(1e), wherein
  each —$R^{X1}$ is independently halogen, cyano, $C_1$-$C_6$alkyl, $C_1$-$C_6$haloalkyl, —$C_1$-$C_6$alkoxy, oxo, —OR, —SR, —$NR_2$, —C(O)R, —C(O)OR, —C(O)$NR_2$, —S(O)$_2$$NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$, —$CH_2$—OP(O)(OR), Ar($C_0$-$C_6$alkyl), Het($C_0$-$C_6$alkyl), Cak($C_0$-$C_6$alkyl) or Hca($C_0$-$C_6$alkyl),
  or two —$R^{X1}$ groups taken together, when attached to the same carbon atom, form a Hca, wherein the Hca comprises a 3-8 membered ring optionally substituted with one or two —$R^{X2}$ groups.

(1j) X is any of groups (1a)-(1e), wherein
  each —$R^{X1}$ is independently halogen, cyano, $C_1$-$C_6$alkyl, $C_1$-$C_6$haloalkyl, —$C_1$-$C_6$alkoxy, oxo, —OR, —SR, —$NR_2$, —C(O)R, —C(O)OR, —C(O)$NR_2$, —S(O)$_2$$NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$, —$CH_2$—OP(O)(OR), Ar($C_0$-$C_6$alkyl), Het($C_0$-$C_6$alkyl), Cak($C_0$-$C_6$alkyl) or Hca($C_0$-$C_6$alkyl),
  or two —$R^{X1}$ groups taken together, when attached to non-adjacent atoms, and combined with X, form a bridged Hca optionally substituted with one or two —$R^{X2}$ groups,
    wherein each —$R^{X2}$ is independently halogen, cyano, nitro, oxo, —OR, —SR, —$NR_2$, —C(O)OR, —C(O)$NR_2$, —C(O)R, —S(O)R, —S(O)$_2$R, —S(O)OR, —S(O)$_2$OR, —S(O)$NR_2$, —S(O)$_2$$NR_2$, —OC(O)R, —OC(O)OR, —OC(O)$NR_2$, —N(R)C(O)R, —N(R)C(O)OR, —N(R)C(O)$NR_2$, —N(R)S(O)R, —N(R)S(O)$_2$R, $C_1$-$C_6$alkyl, or $C_1$-$C_6$haloalkyl.

(1k) X is any of groups (1a)-(1e), wherein
  two —$R^{X1}$ groups taken together, when attached to adjacent atoms, form a Cak, Hca or Het, wherein the Cak Hca and the Het comprise a 3-8 membered ring optionally substituted with one or two —$R^{X2}$ groups,
  or two —$R^{X1}$ groups taken together, when attached to the same carbon atom, form a Hca, wherein the Hca comprises a 3-8 membered ring optionally substituted with one or two —$R^{X2}$ groups,
  or two —$R^{X1}$ groups taken together, when attached to non-adjacent atoms, and combined with X, form a bridged Hca optionally substituted with one or two —$R^{X2}$ groups,
    wherein each —$R^{X2}$ is independently halogen, cyano, nitro, oxo, —OR, —SR, —$NR_2$, —C(O)OR, —C(O)$NR_2$, —C(O)R, —S(O)R, —S(O)$_2$R, —S(O)OR, —S(O)$_2$OR, —S(O)$NR_2$, —S(O)$_2$$NR_2$, —OC(O)R, —OC(O)OR, —OC(O)$NR_2$, —N(R)C(O)R, —N(R)C(O)OR, —N(R)C(O)$NR_2$, —N(R)S(O)R, —N(R)S(O)$_2$R, $C_1$-$C_6$alkyl, or $C_1$-$C_6$haloalkyl.

(1l) X is any of groups (1a)-(1e), wherein
  two —$R^{X1}$ groups taken together, when attached to adjacent atoms, form a Cak, Hca or Het, wherein the Cak Hca and the Het comprise a 3-8 membered ring optionally substituted with one or two —$R^{X2}$ groups,
  or two —$R^{X1}$ groups taken together, when attached to the same carbon atom, form a Hca, wherein the Hca comprises a 3-8 membered ring optionally substituted with one or two —$R^{X2}$ groups.

(1m) X is any of groups (1a)-(1e), wherein
  two —$R^{X1}$ groups taken together, when attached to adjacent atoms, form a Cak, Hca or Het, wherein the Cak Hca and the Het comprise a 3-8 membered ring optionally substituted with one or two —$R^{X2}$ groups,
  or two —$R^{X1}$ groups taken together, when attached to non-adjacent atoms, and combined with X, form a bridged Hca optionally substituted with one or two —$R^{X2}$ groups,
    wherein each —$R^{X2}$ is independently halogen, cyano, nitro, oxo, —OR, —SR, —$NR_2$, —C(O)OR, —C(O)$NR_2$, —C(O)R, —S(O)R, —S(O)$_2$R, —S(O)OR, —S(O)$_2$OR, —S(O)$NR_2$, —S(O)$_2$$NR_2$, —OC(O)R, —OC(O)OR, —OC(O)$NR_2$, —N(R)C(O)R, —N(R)

C(O)OR, —N(R)C(O)NR$_2$, —N(R)S(O)R, —N(R)S(O)$_2$R, C$_1$-C$_6$alkyl, or C$_1$-C$_6$haloalkyl.

(1n) X is any of groups (1a)-(1e), wherein
two —R$^{X1}$ groups taken together, when attached to the same carbon atom, form a Hca, wherein the Hca comprises a 3-8 membered ring optionally substituted with one or two —R$^{X2}$ groups,
or two —R$^{X1}$ groups taken together, when attached to non-adjacent atoms, and combined with X, form a bridged Hca optionally substituted with one or two —R$^{X2}$ groups,
wherein each —R$^{X2}$ is independently halogen, cyano, nitro, oxo, —OR, —SR, —NR$_2$, —C(O)OR, —C(O)NR$_2$, —C(O)R, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, —N(R)S(O)$_2$R, C$_1$-C$_6$alkyl, or C$_1$-C$_6$haloalkyl.

(1o) X is any of groups (1a)-(1e), wherein
each —R$^{X1}$ is independently halogen, cyano, C$_1$-C$_6$alkyl, C$_1$-C$_6$haloalkyl, —C$_1$-C$_6$alkoxy, oxo, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$, —CH$_2$—OP(O)(OR), Ar(C$_0$-C$_6$alkyl), Het(C$_0$-C$_6$alkyl), Cak(C$_0$-C$_6$alkyl) or Hca(C$_0$-C$_6$alkyl).

(1p) X is any of groups (1a)-(1e), wherein
two —R$^{X1}$ groups taken together, when attached to adjacent atoms, form a Cak, Hca or Het, wherein the Cak Hca and the Het comprise a 3-8 membered ring optionally substituted with one or two —R$^{X2}$ groups.

(1q) X is any of groups (1a)-(1e), wherein
two —R$^{X1}$ groups taken together, when attached to the same carbon atom, form a Hca, wherein the Hca comprises a 3-8 membered ring optionally substituted with one or two —R$^{X2}$ groups.

(1r) X is any of groups (1a)-(1e), wherein
two —R$^{X1}$ groups taken together, when attached to non-adjacent atoms, and combined with X, form a bridged Hca optionally substituted with one or two —R$^{X2}$ groups,
wherein each —R$^{X2}$ is independently halogen, cyano, nitro, oxo, —OR, —SR, —NR$_2$, —C(O)OR, —C(O)NR$_2$, —C(O)R, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, —N(R)S(O)$_2$R, C$_1$-C$_6$alkyl, or C$_1$-C$_6$haloalkyl.

(1s) X is any of groups (1b)-(1r), wherein
each —R$^{X1}$ is independently halogen, cyano, C$_1$-C$_6$alkyl, C$_1$-C$_6$haloalkyl, —C$_1$-C$_6$alkoxy, oxo, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$, —CH$_2$—OP(O)(OR), Ar(C$_0$-C$_6$alkyl), Het(C$_0$-C$_6$alkyl), Cak(C$_0$-C$_6$alkyl) or Hca(C$_0$-C$_6$alkyl).

(1t) X is any of groups (1b)-(1r), wherein
each —R$^{X1}$ is independently halogen, cyano, C$_1$-C$_6$alkyl, C$_1$-C$_6$haloalkyl, —C$_1$-C$_6$alkoxy, oxo, —OR, —SR, —NR$_2$, —C(O)R, —C(O)OR, —C(O)NR$_2$, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$, —CH$_2$—OP(O)(OR), Ar(C$_0$-C$_6$alkyl), Het(C$_0$-C$_6$alkyl), Cak(C$_0$-C$_6$alkyl) or Hca(C$_0$-C$_6$alkyl).

(1u) X is any of groups (1b)-(1r), wherein
each —R$^{X1}$ is independently halogen, cyano, C$_1$-C$_6$alkyl, C$_1$-C$_6$haloalkyl, —C$_1$-C$_6$alkoxy, oxo, —OR, —SR, —NR$_2$, —C(O)R, —C(O)OR, —C(O)NR$_2$, —OC(O)R, —N(R)C(O)R, —OC(O)OR, —OC(O)NR$_2$, —N(R)C(O)OR, —N(R)C(O)NR$_2$, —N(R)S(O)$_2$R, Ar(C$_0$-C$_6$alkyl), Het(C$_0$-C$_6$alkyl), Cak(C$_0$-C$_6$alkyl) or Hca(C$_0$-C$_6$alkyl).

(1v) X is any of groups (1b)-(1r), wherein
each —R$^{X1}$ is independently halogen, C$_1$-C$_6$alkyl, C$_1$-C$_6$haloalkyl, —C$_1$-C$_6$alkoxy, oxo, —OR, —SR, —NR$_2$, —C(O)R, —C(O)OR, —C(O)NR$_2$, —OC(O)R, —N(R)C(O)R, —OC(O)OR, —OC(O)NR$_2$, —N(R)C(O)OR, —N(R)C(O)NR$_2$, —N(R)S(O)$_2$R, Ar(C$_0$-C$_6$alkyl), Het(C$_0$-C$_6$alkyl), Cak(C$_0$-C$_6$alkyl) or Hca(C$_0$-C$_6$alkyl).

(1w) X is any of groups (1b)-(1r), wherein
each —R$^{X1}$ is independently halogen, cyano, C$_1$-C$_6$alkyl, C$_1$-C$_6$haloalkyl, —C$_1$-C$_6$alkoxy, oxo, —C(O)R, —C(O)OR, —C(O)NR$_2$, —OC(O)R, —N(R)C(O)R, —OC(O)OR, —OC(O)NR$_2$, —N(R)C(O)OR, —N(R)C(O)NR$_2$, —N(R)S(O)$_2$R, Ar(C$_0$-C$_6$alkyl), Het(C$_0$-C$_6$alkyl), Cak(C$_0$-C$_6$alkyl) or Hca(C$_0$-C$_6$alkyl).

(1x) X is any of groups (1b)-(1r), wherein
each —R$^{X1}$ is independently halogen, C$_1$-C$_6$alkyl, C$_1$-C$_6$haloalkyl, oxo, —C(O)R, —C(O)OR, —C(O)NR$_2$, —OC(O)R, —N(R)C(O)R, —OC(O)OR, —OC(O)NR$_2$, —N(R)C(O)OR, —N(R)C(O)NR$_2$, —N(R)S(O)$_2$R, Ar(C$_0$-C$_6$alkyl), Het(C$_0$-C$_6$alkyl), Cak(C$_0$-C$_6$alkyl) or Hca(C$_0$-C$_6$alkyl).

(1y) X is any of groups (1b)-(1r), wherein
each —R$^{X1}$ is independently halogen, C$_1$-C$_6$alkyl, C$_1$-C$_6$haloalkyl, oxo, —C(O)R, —C(O)OR, —C(O)NR$_2$, —N(R)C(O)R, —N(R)C(O)OR, —N(R)C(O)NR$_2$, —N(R)S(O)$_2$R, Ar(C$_0$-C$_6$alkyl), Het(C$_0$-C$_6$alkyl), Cak(C$_0$-C$_6$alkyl) or Hca(C$_0$-C$_6$alkyl).

(1z) X is any of groups (1b)-(1r), wherein
each —R$^{X1}$ is independently halogen, C$_1$-C$_6$alkyl, C$_1$-C$_6$haloalkyl, oxo, —C(O)R, —C(O)OR, —C(O)NR$_2$, —OC(O)R, —OC(O)OR, —OC(O)NR$_2$, Ar(C$_0$-C$_6$alkyl), Het(C$_0$-C$_6$alkyl), Cak(C$_0$-C$_6$alkyl) or Hca(C$_0$-C$_6$alkyl).

(1aa) X is any of groups (1b)-(1r), wherein
each —R$^{X1}$ is independently halogen, C$_1$-C$_6$alkyl, C$_1$-C$_6$haloalkyl, oxo, —C(O)R, —C(O)OR, —C(O)NR$_2$, Ar(C$_0$-C$_6$alkyl), Het(C$_0$-C$_6$alkyl), Cak(C$_0$-C$_6$alkyl) or Hca(C$_0$-C$_6$alkyl).

(1bb) X is any of groups (1b)-(1r), wherein
each —R$^{X1}$ is independently halogen, C$_1$-C$_6$alkyl, C$_1$-C$_6$haloalkyl, oxo, —C(O)OR, Ar(C$_0$-C$_6$alkyl), Het(C$_0$-C$_6$alkyl), Cak(C$_0$-C$_6$alkyl) or Hca(C$_0$-C$_6$alkyl).

(1cc) X is any of groups (1b)-(1r), wherein
each —R$^{X1}$ is independently C$_1$-C$_6$alkyl, C$_1$-C$_6$haloalkyl, oxo, —C(O)OR, Ar(C$_0$-C$_6$alkyl), Het(C$_0$-C$_6$alkyl), Cak(C$_0$-C$_6$alkyl) or Hca(C$_0$-C$_6$alkyl).

(1dd) X is any of groups (1b)-(1r), wherein
each —R$^{X1}$ is independently C$_1$-C$_6$alkyl, C$_1$-C$_6$haloalkyl.

(1ee) X is any of groups (1b)-(1r), wherein
each —R$^{X1}$ is independently oxo, —C(O)OR, Ar(C$_0$-C$_6$alkyl), Het(C$_0$-C$_6$alkyl), Cak(C$_0$-C$_6$alkyl) or Hca(C$_0$-C$_6$alkyl).

(1ff) X is any of groups (1b)-(1r), wherein
each —R$^{X1}$ is independently C$_1$-C$_6$alkyl, C$_1$-C$_6$haloalkyl, Ar(C$_0$-C$_6$alkyl), Het(C$_0$-C$_6$alkyl), Cak(C$_0$-C$_6$alkyl) or Hca(C$_0$-C$_6$alkyl).

(1gg) X is any of groups (1b)-(1r), wherein
each —R$^{X1}$ is independently Cak(C$_0$-C$_6$alkyl) or Hca(C$_0$-C$_6$alkyl).

(1hh) X is any of groups (1b)-(1r), wherein
each —$R^{X1}$ is independently $C_1$-$C_6$alkyl, $C_1$-$C_6$haloalkyl, oxo, —C(O)OR or Hca($C_0$-$C_6$alkyl).
(1ii) X is any of groups (1b)-(1r), wherein
each —$R^{X1}$ is independently $C_1$-$C_6$alkyl, $C_1$-$C_6$haloalkyl, oxo, —C(O)OR or Cak($C_0$-$C_6$alkyl).
(1jj) X is any of groups (1b)-(1r), wherein
each —$R^{X1}$ is independently $C_1$-$C_6$alkyl, $C_1$-$C_6$haloalkyl, —C(O)OR, Cak($C_0$-$C_6$alkyl) or Hca($C_0$-$C_6$alkyl).
(1kk) X is any of groups (1b)-(1jj), wherein —$R^{X1}$ is $C_1$-$C_6$alkyl.
(1ll) X is any of groups (1b)-(1jj), wherein —$R^{X1}$ is $C_1$-$C_6$haloalkyl.
(1mm) X is any of groups (1b)-(1jj), wherein —$R^{X1}$ is oxo.
(1nn) X is any of groups (1b)-(1jj), wherein —$R^{X1}$ is —C(O)OR.
(1oo) X is any of groups (1b)-(1jj), wherein —$R^{X1}$ is Cak($C_0$-$C_6$alkyl).
(1pp) X is any of groups (1b)-(1jj), wherein —$R^{X1}$ is Hca($C_0$-$C_6$alkyl).
(1qq) X is any of groups (1a)-(1pp) or halogen or Hca($C_1$-$C_6$alkyl)-O—.
(1rr) X is any of groups (1a)-(1pp) or halogen.
(1ss) X is any of groups (1a)-(1pp) or Hca($C_1$-$C_6$alkyl)-O—.
(1tt) X is halogen or Hca($C_1$-$C_6$alkyl)-O—.
(1uu) X is halogen.
(1vv) X is Hca($C_1$-$C_6$alkyl)-O—.
(1ww) X is any of groups (1a)-(1vv) wherein each R is independently hydrogen, $C_1$-$C_6$alkyl, $C_1$-$C_6$haloalkyl, Hca($C_0$-$C_6$alkyl), Cak($C_0$-$C_8$alkyl), $C_1$-$C_6$alkyl-CN, —$CH_2C(O)NH_2$ or $C_1$-$C_6$alkyl-OH.
(1xx) X is any of groups (1a)-(1vv) wherein each R is independently hydrogen, $C_1$-$C_6$alkyl, $C_1$-$C_6$haloalkyl, Hca($C_0$-$C_6$alkyl), Cak($C_0$-$C_8$alkyl), $C_1$-$C_6$alkyl-CN, —$CH_2C(O)NH_2$ or $C_1$-$C_6$alkyl-OH.
(1yy) X is any of groups (1a)-(1vv) wherein each R is independently hydrogen, $C_1$-$C_6$alkyl, $C_1$-$C_6$haloalkyl, —$CH_2C(O)NH_2$ or $C_1$-$C_6$alkyl-OH.
(1zz) X is any of groups (1a)-(1vv) wherein each R is independently hydrogen, $C_1$-$C_6$alkyl, Hca($C_0$-$C_6$alkyl) or Cak($C_0$-$C_8$alkyl).
(1aaa) X is any of groups (1a)-(1vv) wherein each R is independently hydrogen or, $C_1$-$C_6$alkyl.

$I^c$—Y is Selected from One of the Following Groups (2a)-(2ww):

(2a) Y is Cak($C_0$-$C_6$alkyl) optionally substituted by one or two —$R^{Y1}$ groups,
wherein each —$R^{Y1}$ is independently halogen, cyano, $C_1$-$C_6$alkyl, $C_1$-$C_6$haloalkyl, —$C_1$-$C_6$alkoxy, oxo, —OR, —SR, —$NR_2$, —C(O)R, —C(O)OR, C(O)$NR_2$, —S(O)$_2NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$ or —$CH_2$—OP(O)(OR).
(2b) Y is Cak($C_0$-$C_6$alkyl) optionally substituted by one —$R^{Y1}$ group;
wherein each —$R^{Y1}$ is independently halogen, cyano, $C_1$-$C_6$alkyl, $C_1$-$C_6$haloalkyl, —$C_1$-$C_6$alkoxy, oxo, —OR, —SR, —$NR_2$, —C(O)R, —C(O)OR, C(O)$NR_2$, —S(O)$_2NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$ or —$CH_2$—OP(O)(OR).
(2c) Y is Cak($C_0$-$C_6$alkyl) optionally substituted by two —$R^{Y1}$ group;
wherein each —$R^{Y1}$ is independently halogen, cyano, $C_1$-$C_6$alkyl, $C_1$-$C_6$haloalkyl, —$C_1$-$C_6$alkoxy, oxo, —OR, —SR, —$NR_2$, —C(O)R, —C(O)OR, C(O)$NR_2$, —S(O)$_2NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$ or —$CH_2$—OP(O)(OR).
(2d) Y is unsubstituted Cak($C_0$-$C_6$alkyl).
(2e) Y is Cak optionally substituted by one or two —$R^{Y1}$ groups,
wherein each —$R^{Y1}$ is independently halogen, cyano, $C_1$-$C_6$alkyl, $C_1$-$C_6$haloalkyl, —$C_1$-$C_6$alkoxy, oxo, —OR, —SR, —$NR_2$, —C(O)R, —C(O)OR, C(O)$NR_2$, —S(O)$_2NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$ or —$CH_2$—OP(O)(OR).
(2f) Y is Cak optionally substituted by one —$R^{Y1}$ group,
wherein each —$R^{Y1}$ is independently halogen, cyano, $C_1$-$C_6$alkyl, $C_1$-$C_6$haloalkyl, —$C_1$-$C_6$alkoxy, oxo, —OR, —SR, —$NR_2$, —C(O)R, —C(O)OR, C(O)$NR_2$, —S(O)$_2NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$ or —$CH_2$—OP(O)(OR).
(2g) Y is Cak optionally substituted by two —$R^{Y1}$ group,
wherein each —$R^{Y1}$ is independently halogen, cyano, $C_1$-$C_6$alkyl, $C_1$-$C_6$haloalkyl, —$C_1$-$C_6$alkoxy, oxo, —OR, —SR, —$NR_2$, —C(O)R, —C(O)OR, C(O)$NR_2$, —S(O)$_2NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$ or —$CH_2$—OP(O)(OR).
(2h) Y is unsubstituted Cak.
(2i) Y is Cak($C_1$alkyl) optionally substituted by one or two —$R^{Y1}$ groups,
wherein each —$R^{Y1}$ is independently halogen, cyano, $C_1$-$C_6$alkyl, $C_1$-$C_6$haloalkyl, —$C_1$-$C_6$alkoxy, oxo, —OR, —SR, —$NR_2$, —C(O)R, —C(O)OR, C(O)$NR_2$, —S(O)$_2NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$ or —$CH_2$—OP(O)(OR).
(2j) Y is Cak($C_1$alkyl) optionally substituted by one —$R^{Y1}$ group;
wherein each —$R^{Y1}$ is independently halogen, cyano, $C_1$-$C_6$alkyl, $C_1$-$C_6$haloalkyl, —$C_1$-$C_6$alkoxy, oxo, —OR, —SR, —$NR_2$, —C(O)R, —C(O)OR, C(O)$NR_2$, —S(O)$_2NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$ or —$CH_2$—OP(O)(OR).
(2k) Y is Cak($C_1$alkyl) optionally substituted by two —$R^{Y1}$ group;
wherein each —$R^{Y1}$ is independently halogen, cyano, $C_1$-$C_6$alkyl, $C_1$-$C_6$haloalkyl, —$C_1$-$C_6$alkoxy, oxo, —OR, —SR, —$NR_2$, —C(O)R, —C(O)OR, C(O)$NR_2$, —S(O)$_2NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$ or —$CH_2$—OP(O)(OR).
(2l) Y is unsubstituted Cak($C_1$alkyl).
(2m) Y is Cak($C_0$-$C_6$alkyl) optionally substituted by one or two —$R^{Y1}$ groups,
wherein each —$R^{Y1}$ is independently halogen, cyano, $C_1$-$C_6$alkyl, $C_1$-$C_6$haloalkyl, —$C_1$-$C_6$alkoxy, oxo, —OR, —SR, —$NR_2$, —C(O)R, —C(O)OR, C(O)$NR_2$, —S(O)$_2NR_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR).

(2n) Y is Cak(C$_0$-C$_6$alkyl) optionally substituted by one or two —R$^{Y1}$ groups,
wherein each —R$^{Y1}$ is independently halogen, C$_1$-C$_6$alkyl, C$_1$-C$_6$haloalkyl, —C$_1$-C$_6$alkoxy, oxo, —OR, —SR, —NR$_2$, —C(O)R, —C(O)OR, C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR).

(2o) Y is Cak(C$_0$-C$_6$alkyl) optionally substituted by one or two —R$^{Y1}$ groups,
wherein each —R$^{Y1}$ is independently halogen, C$_1$-C$_6$alkyl, C$_1$-C$_6$haloalkyl, —C$_1$-C$_6$alkoxy, oxo, —OR, —SR, —NR$_2$, —C(O)R, —C(O)OR, C(O)NR$_2$, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR).

(2p) Y is Cak(C$_0$-C$_6$alkyl) optionally substituted by one or two —R$^{Y1}$ groups,
wherein each —R$^{Y1}$ is independently halogen, C$_1$-C$_6$alkyl, C$_1$-C$_6$haloalkyl, —C$_1$-C$_6$alkoxy, oxo, —OR, —SR, —NR$_2$, —C(O)R, —C(O)OR, C(O)NR$_2$, —OC(O)R, —N(R)C(O)R, —OC(O)OR, —OC(O)NR$_2$, —N(R)C(O)OR, —N(R)C(O)NR$_2$ or —N(R)S(O)$_2$R.

(2q) Y is Cak(C$_0$-C$_6$alkyl) optionally substituted by one or two —R$^{Y1}$ groups,
wherein each —R$^{Y1}$ is independently halogen, C$_1$-C$_6$alkyl, C$_1$-C$_6$haloalkyl, —C$_1$-C$_6$alkoxy, oxo, —OR, —SR, —NR$_2$, —OC(O)R, —N(R)C(O)R, —OC(O)OR, —OC(O)NR$_2$, —N(R)C(O)OR, —N(R)C(O)NR$_2$ or —N(R)S(O)$_2$R.

(2r) Y is Cak(C$_0$-C$_6$alkyl) optionally substituted by one or two —R$^{Y1}$ groups,
wherein each —R$^{Y1}$ is independently halogen, C$_1$-C$_6$alkyl, C$_1$-C$_6$haloalkyl, —C$_1$-C$_6$alkoxy, oxo, —OR, —SR, —NR$_2$, —N(R)C(O)R, —OC(O)OR, —OC(O)NR$_2$, —N(R)C(O)OR, —N(R)C(O)NR$_2$ or —N(R)S(O)$_2$R.

(2s) Y is Cak(C$_0$-C$_6$alkyl) optionally substituted by one or two —R$^{Y1}$ groups,
wherein each —R$^{Y1}$ is independently halogen, C$_1$-C$_6$alkyl, C$_1$-C$_6$haloalkyl, —C$_1$-C$_6$alkoxy, oxo, —OR, —SR, —NR$_2$, —OC(O)NR$_2$ or —N(R)C(O)OR.

(2t) Y is Cak(C$_0$-C$_6$alkyl) optionally substituted by one or two —R$^{Y1}$ groups,
wherein each —R$^{Y1}$ is independently C$_1$-C$_6$alkyl, C$_1$-C$_6$haloalkyl, oxo, —OR, —SR, —NR$_2$, —OC(O)NR$_2$ or —N(R)C(O)OR.

(2u) Y is Cak(C$_0$-C$_6$alkyl) optionally substituted by one or two —R$^{Y1}$ groups,
wherein each —R$^{Y1}$ is independently C$_1$-C$_6$alkyl, oxo, —OR, —NR$_2$, —OC(O)NR$_2$ or —N(R)C(O)OR.

(2v) Y is Cak(C$_0$-C$_6$alkyl) optionally substituted by one —R$^{Y1}$ group, wherein each —R$^{Y1}$ is independently C$_1$-C$_6$alkyl, oxo, —OR, —NR$_2$, —OC(O)NR$_2$ or —N(R)C(O)OR.

(2w) Y is Cak(C$_0$-C$_6$alkyl) optionally substituted by one —R$^{Y1}$ groups, wherein —R$^{Y1}$ is oxo.

(2x) Y is Cak(C$_0$-C$_6$alkyl) optionally substituted by one —R$^{Y1}$ groups, wherein —R$^{Y1}$ is —OR.

(2y) Y is Cak(C$_0$-C$_6$alkyl) optionally substituted by one —R$^{Y1}$ groups, wherein —R$^{Y1}$ is —NR$_2$.

(2z) Y is Cak(C$_0$-C$_6$alkyl) optionally substituted by one —R$^{Y1}$ groups, wherein —R$^{Y1}$ is —OC(O)NR$_2$.

(2aa) Y is Cak(C$_0$-C$_6$alkyl) optionally substituted by one —R$^{Y1}$ groups, wherein —R$^{Y1}$ is —N(R)C(O)OR.

(2bb) Y is Cak(C$_0$-C$_6$alkyl) optionally substituted by one —R$^{Y1}$ group, wherein —R$^{Y1}$ is C$_1$-C$_6$alkyl.

(2cc) Y is Cak(C$_0$-C$_6$alkyl) optionally substituted by two —R$^{Y1}$ groups, wherein each —R$^{Y1}$ is independently C$_1$-C$_6$alkyl, oxo, —OR, —NR$_2$, —OC(O)NR$_2$ or —N(R)C(O)OR.

(2dd) Y is Cak(C$_0$-C$_6$alkyl) optionally substituted by two —R$^{Y1}$ groups, wherein each —R$^{Y1}$ is independently C$_1$-C$_6$alkyl or —N(R)C(O)OR.

(2ee) Y is Cak(C$_0$-C$_6$alkyl) optionally substituted by two —R$^{Y1}$ groups, wherein each —R$^{Y1}$ is independently C$_1$-C$_6$alkyl or —OC(O)NR$_2$.

(2ff) Y is Cak(C$_0$-C$_6$alkyl) optionally substituted by two —R$^{Y1}$ groups, wherein each —R$^{Y1}$ is independently C$_1$-C$_6$alkyl or oxo.

(2gg) Y is Cak(C$_0$-C$_6$alkyl) optionally substituted by two —R$^{Y1}$ groups, wherein each —R$^{Y1}$ is independently C$_1$-C$_6$alkyl or —OR.

(2hh) Y is Cak(C$_0$-C$_6$alkyl) optionally substituted by two —R$^{Y1}$ groups, wherein each —R$^{Y1}$ is independently C$_1$-C$_6$alkyl or —NR$_2$.

(2ii) Y is Cak(C$_0$-C$_6$alkyl) optionally substituted by two —R$^{Y1}$ groups, wherein each —R$^{Y1}$ is independently C$_1$-C$_6$alkyl or —OC(O)NR$_2$.

(2jj) Y is any of groups (2m)-(2ii), wherein Cak(C$_0$-C$_6$alkyl) is Cak.

(2kk) Y is any of groups (2m)-(2ii), wherein Cak(C$_0$-C$_6$alkyl) is Cak(C$_1$alkyl).

(2ll) Y is any of groups (2m)-(2ii), wherein Cak(C$_0$-C$_6$alkyl) is Cak(C$_2$alkyl).

(2mm) Y is any of groups (2a)-(2ll) or Cak(C$_0$-C$_8$alkyl) or Hca(C$_0$-C$_6$alkyl).

(2nn) Y is any of groups (2a)-(2ll) or Cak(C$_0$-C$_8$alkyl).

(2oo) Y is any of groups (2a)-(2ll) or Hca(C$_0$-C$_6$alkyl).

(2pp) Y is Cak(C$_0$-C$_8$alkyl) or Hca(C$_0$-C$_6$alkyl).

(2qq) Y is Cak(C$_0$-C$_8$alkyl).

(2rr) Y is Hca(C$_0$-C$_6$alkyl).

(2ss) Y is any of groups (2a)-(2rr) wherein each R is independently hydrogen, C$_1$-C$_6$alkyl, C$_1$-C$_6$haloalkyl, Hca(C$_0$-C$_6$alkyl), Cak(C$_0$-C$_8$alkyl), C$_1$-C$_6$alkyl-CN, —CH$_2$C(O)NH$_2$ or C$_1$-C$_6$alkyl-OH.

(2tt) Y is any of groups (2a)-(2rr) wherein each R is independently hydrogen, C$_1$-C$_6$alkyl, C$_1$-C$_6$haloalkyl, Hca(C$_0$-C$_6$alkyl), Cak(C$_0$-C$_8$alkyl), C$_1$-C$_6$alkyl-CN, —CH$_2$C(O)NH$_2$ or C$_1$-C$_6$alkyl-OH.

(2uu) Y is any of groups (2a)-(2rr) wherein each R is independently hydrogen, C$_1$-C$_6$alkyl, C$_1$-C$_6$haloalkyl, C$_1$-C$_6$alkyl-CN, —CH$_2$C(O)NH$_2$ or C$_1$-C$_6$alkyl-OH.

(2vv) Y is any of groups (2a)-(2rr) wherein each R is independently hydrogen, C$_1$-C$_6$alkyl, Hca(C$_0$-C$_6$alkyl) or Cak(C$_0$-C$_8$alkyl).

(2ww) Y is any of groups (2a)-(2rr) wherein each R is independently hydrogen or C$_1$-C$_6$alkyl.

I$^d$—Z is Selected from One of the Following Groups (3a)-(3ccc):

(3a) Z is unsubstituted C$_1$-C$_6$alkyl or Cak(C$_0$-C$_6$alkyl).

(3b) Z is C$_1$-C$_6$alkyl or Cak(C$_0$-C$_6$alkyl), each optionally substituted by one to three —R$^{Z1}$ groups,
wherein each —R$^{Z1}$ is independently halogen, cyano, C$_1$-C$_6$alkyl, C$_1$-C$_6$haloalkyl, —C$_1$-C$_6$alkoxy, oxo, —OR, —SR, —NR$_2$, —C(O)R, —C(O)OR, —C(O)NR$_2$, —S(O)$_2$NR$_2$, —S(O)$_2$R, —OC(O)R, —N(R)C (O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR).

(3c) Z is group (3b), wherein C$_1$-C$_6$alkyl and Cak(C$_0$-C$_6$alkyl) are each optionally substituted by one or two —R$^{Z1}$ groups.

(3d) Z is group (3b), wherein C$_1$-C$_6$alkyl and Cak(C$_0$-C$_6$alkyl) are each optionally substituted by two or three —R$^{Z1}$ groups.

(3e) Z is group (3b), wherein C$_1$-C$_6$alkyl and Cak(C$_0$-C$_6$alkyl) are each optionally substituted by one —R$^{Z1}$ group.

(3f) Z is group (3b), wherein C$_1$-C$_6$alkyl and Cak(C$_0$-C$_6$alkyl) are each optionally substituted by two —R$^{Z1}$ groups.

(3g) Z is group (3b), wherein C$_1$-C$_6$alkyl and Cak(C$_0$-C$_6$alkyl) are each optionally substituted by three —R$^{Z1}$ groups.

(3h) Z is any of groups (3b)-(3g), wherein Z is C$_1$-C$_6$alkyl.

(3i) Z is any of groups (3b)-(3g), wherein Z is methyl, ethyl, propyl, butyl or pentyl.

(3j) Z is any of groups (3b)-(3g), wherein Z is methyl, ethyl, propyl or butyl.

(3k) Z is any of groups (3b)-(3g), wherein Z is methyl, ethyl or propyl.

(3l) Z is any of groups (3b)-(3g), wherein Z is methyl or ethyl.

(3m) Z is any of groups (3b)-(3g), wherein Z is methyl or butyl.

(3n) Z is any of groups (3b)-(3g), wherein Z is methyl.

(3o) Z is any of groups (3b)-(3g), wherein Z is butyl.

(3p) Z is any of groups (3b)-(3g), wherein Z is Cak(C$_0$-C$_6$alkyl).

(3q) Z is any of groups (3b)-(3g), wherein Z is Cak.

(3r) Z is any of groups (3b)-(3g), wherein Z is Cak(C$_1$alkyl).

(3s) Z is any of groups (3b)-(3g), wherein Z is Cak(C$_2$alkyl).

(3t) Z is any of groups (3a)-(3s), wherein Cak is cyclopropyl, cyclobutyl, cyclopentyl or cyclohexyl.

(3u) Z is any of groups (3a)-(3s), wherein Cak is cyclopropyl, cyclobutyl or cyclopentyl.

(3v) Z is any of groups (3a)-(3s), wherein Cak is cyclopropyl or cyclobutyl.

(3w) Z is any of groups (3a)-(3s), wherein Cak is cyclopropyl.

(3x) Z is any of groups (3a)-(3s), wherein Cak is cyclobutyl.

(3y) Z is any of groups (3a)-(3s), wherein Cak is cyclopentyl.

(3z) Z is any of groups (3a)-(3s), wherein Cak is cyclohexyl.

(3aa) Z is any of groups (3b)-(3z), wherein each —R$^{Z1}$ is independently halogen, cyano, C$_1$-C$_6$alkyl, C$_1$-C$_6$haloalkyl, —C$_1$-C$_6$alkoxy, oxo, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR).

(3bb) Z is any of groups (3b)-(3z), wherein each —R$^{Z1}$ is independently halogen, cyano, C$_1$-C$_6$alkyl, C$_1$-C$_6$haloalkyl, —C$_1$-C$_6$alkoxy, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR).

(3cc) Z is any of groups (3b)-(3z), wherein each —R$^{Z1}$ is independently halogen, cyano, C$_1$-C$_6$alkyl, C$_1$-C$_6$haloalkyl, —C$_1$-C$_6$alkoxy, —C(O)R, —C(O)OR, —C(O)NR$_2$, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR).

(3dd) Z is any of groups (3b)-(3z), wherein each —R$^{Z1}$ is independently halogen, cyano, C$_1$-C$_6$alkyl, C$_1$-C$_6$haloalkyl, —C$_1$-C$_6$alkoxy, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR).

(3ee) Z is any of groups (3b)-(3z), wherein each —R$^{Z1}$ is independently halogen, cyano, C$_1$-C$_6$alkyl, C$_1$-C$_6$haloalkyl, —C$_1$-C$_6$alkoxy, —OC(O)R, —N(R)C(O)R, —OC(O)OR, —OC(O)NR$_2$, —N(R)C(O)OR, —N(R)C(O)NR$_2$ or —N(R)S(O)$_2$R.

(3ff) Z is any of groups (3b)-(3z), wherein each —R$^{Z1}$ is independently halogen, cyano, C$_1$-C$_6$alkyl, C$_1$-C$_6$haloalkyl, —C$_1$-C$_6$alkoxy, —N(R)C(O)R, —N(R)C(O)OR, —N(R)C(O)NR$_2$ or —N(R)S(O)$_2$R.

(3gg) Z is any of groups (3b)-(3z), wherein each —R$^{Z1}$ is independently halogen, cyano, C$_1$-C$_6$alkyl, C$_1$-C$_6$haloalkyl or —C$_1$-C$_6$alkoxy.

(3hh) Z is any of groups (3b)-(3z), wherein each —R$^{Z1}$ is independently halogen, C$_1$-C$_6$alkyl, C$_1$-C$_6$haloalkyl or —C$_1$-C$_6$alkoxy.

(3ii) Z is any of groups (3b)-(3z), wherein each —R$^{Z1}$ is independently halogen, C$_1$-C$_6$alkyl or C$_1$-C$_6$haloalkyl.

(3jj) Z is any of groups (3b)-(3z), wherein each —R$^{Z1}$ is independently halogen or C$_1$-C$_6$haloalkyl.

(3kk) Z is any of groups (3b)-(3z), wherein each —R$^{Z1}$ is independently halogen.

(3ll) Z is any of groups (3b)-(3z), wherein each —R$^{Z1}$ is independently fluro or chloro.

(3mm) Z is any of groups (3b)-(3z), wherein each —R$^{Z1}$ is chloro.

(3nn) Z is any of groups (3b)-(3z), wherein each —R$^{Z1}$ is fluro.

(3oo) Z is any of groups (3b)-(3z), wherein each —R$^{Z1}$ is independently C$_1$-C$_6$haloalkyl.

(3pp) Z is any of groups (3b)-(3z), wherein each —R$^{Z1}$ is independently fluoromethyl, difluoromethyl or trifluoromethyl.

(3qq) Z is any of groups (3b)-(3z), wherein each —R$^{Z1}$ is independently trifluoromethyl.

(3rr) Z is any of groups (3b)-(3z), wherein each —R$^{Z1}$ is independently C$_1$-C$_6$alkyl.

(3ss) Z is any of groups (3b)-(3z), wherein each —R$^{Z1}$ is independently methyl, ethyl, propyl, butyl or pentyl.

(3tt) Z is any of groups (3b)-(3z), wherein each —R$^{Z1}$ is independently methyl, ethyl, propyl, or butyl.

(3uu) Z is any of groups (3b)-(3z), wherein each —R$^{Z1}$ is independently methyl, ethyl or propyl.

(3vv) Z is any of groups (3b)-(3z), wherein each —R$^{Z1}$ is independently methyl or ethyl.

(3ww) Z is any of groups (3b)-(3z), wherein each —R$^{Z1}$ is independently methyl.

(3xx) Z is any of groups (3b)-(3z), wherein each —R$^{Z1}$ is independently ethyl.

(3yy) Z is any of groups (3a)-(3xx) wherein each R is independently hydrogen, C$_1$-C$_6$alkyl, C$_1$-C$_6$haloalkyl, Hca(C$_0$-C$_6$alkyl), Cak(C$_0$-C$_8$alkyl), C$_1$-C$_6$alkyl-CN, —CH$_2$C(O)NH$_2$ or C$_1$-C$_6$alkyl-OH.

(3zz) Z is any of groups (3a)-(3xx) wherein each R is independently hydrogen, C$_1$-C$_6$alkyl, C$_1$-C$_6$haloalkyl, Hca(C$_0$-C$_6$alkyl), Cak(C$_0$-C$_8$alkyl), C$_1$-C$_6$alkyl-CN, —CH$_2$C(O)NH$_2$ or C$_1$-C$_6$alkyl-OH.

(3aaa) Z is any of groups (3a)-(3xx) wherein each R is independently hydrogen, C$_1$-C$_6$alkyl, C$_1$-C$_6$haloalkyl, C$_1$-C$_6$alkyl-CN, —CH$_2$C(O)NH$_2$ or C$_1$-C$_6$alkyl-OH.

(3bbb) Z is any of groups (3a)-(3xx) wherein each R is independently hydrogen, $C_1$-$C_6$alkyl, Hca($C_0$-$C_6$alkyl) or Cak($C_0$-$C_8$alkyl).

(3ccc) Z is any of groups (3a)-(3xx) wherein each R is independently or $C_1$-$C_6$alkyl.

Particular embodiments of this aspect of the invention comprise compounds of any one of the formulae (I) and (Ia)-(If), each as defined in each of the following rows (or a pharmaceutically acceptable salt, prodrug, or N-oxide thereof, or a solvate or hydrate thereof), wherein each entry is a group number as defined above (e.g., (2h) refers to Y is unsubstituted Cak, and a dash "—" indicates that the variable is as defined in embodiment $I_1$ or defined according to any one of the applicable variable definitions (1a)-(3ccc) [e.g., when Z is a dash, it can be either as defined in any of embodiments $I_1$-$I_4$ or any one of definitions (3a)-(3ccc)]):

| | (I) | X | Y | Z |
|---|---|---|---|---|
| (1)-1 | (Ia) | (1a) | (2a) | (3a) |
| (1)-2 | (Ia) | (1f) | (2d) | (3b) |
| (1)-3 | (Ia) | (1g) | (2e) | (3c) |
| (1)-4 | (Ia) | (1h) | (2h) | (3f) |
| (1)-5 | (Ia) | (1i) | (2i) | (3h) |
| (1)-6 | (Ia) | (1j) | (2l) | (3j) |
| (1)-7 | (Ia) | (1k) | (2m) | (3m) |
| (1)-8 | (Ia) | (1o) | (2r) | (3n) |
| (1)-9 | (Ia) | (1p) | (2v) | (3o) |
| (1)-10 | (Ia) | (1q) | (2aa) | (3p) |
| (1)-11 | (Ia) | (1r) | (2bb) | (3q) |
| (1)-12 | (Ia) | (1v) | (2cc) | (3v) |
| (1)-13 | (Ia) | (1y) | (2ff) | (3w) |
| (1)-14 | (Ia) | (1aa) | (2gg) | (3x) |
| (1)-15 | (Ia) | (1dd) | (2hh) | (3aa) |
| (1)-16 | (Ia) | (1ii) | (2ii) | (3ee) |
| (1)-17 | (Ia) | (1kk) | (2jj) | (3ii) |
| (1)-18 | (Ia) | (1ll) | (2kk) | (3kk) |
| (1)-19 | (Ia) | (1mm) | (2ll) | (3oo) |
| (1)-20 | (Ia) | (1nn) | (2i) | (3rr) |
| (1)-21 | (Ia) | (1oo) | (2l) | (3v) |
| (1)-22 | (Ia) | (1pp) | (2m) | (3w) |
| (1)-23 | (Ia) | (1i) | (2r) | (3x) |
| (1)-24 | (Ia) | (1j) | (2v) | (3aa) |
| (1)-25 | (Ia) | (1k) | (2aa) | (3n) |
| (1)-26 | (Ia) | (1dd) | (2m) | (3aa) |
| (1)-27 | (Ia) | (1ii) | (2r) | (3n) |
| (1)-28 | (Ia) | (1kk) | (2v) | (3o) |
| (1)-29 | (Ia) | (1f) | (2aa) | (3p) |
| (1)-30 | (Ia) | (1g) | (2aa) | (3aa) |
| (1)-31 | (Ia) | (1h) | (2m) | (3n) |
| (1)-32 | (Ia) | (1i) | (2r) | (3o) |
| (1)-33 | (Ia) | (1j) | (2e) | (3p) |
| (1)-34 | (Ia) | (1k) | (2h) | (3m) |
| (1)-35 | (Ia) | (1o) | (2i) | (3n) |
| (1)-36 | (Ia) | (1y) | (2l) | (3o) |
| (1)-37 | (Ia) | (1aa) | (2m) | (3p) |
| (1)-38 | (Ia) | (1dd) | (2m) | (3q) |
| (1)-39 | (Ia) | (1ii) | (2r) | (3v) |
| (1)-40 | (Ia) | (1kk) | (2v) | (3w) |
| (1)-41 | (Ia) | (1r) | (2aa) | (3x) |
| (1)-42 | (Ia) | (1v) | (2m) | (3aa) |
| (1)-43 | (Ia) | (1y) | (2r) | (3n) |
| (1)-44 | (Ia) | (1aa) | (2v) | (3o) |
| (1)-45 | (Ia) | (1dd) | (2aa) | (3p) |
| (1)-46 | (Ia) | (1ii) | (2i) | (3q) |
| (1)-47 | (Ia) | (1i) | (2l) | (3aa) |
| (1)-48 | (Ia) | (1j) | (2m) | (3n) |
| (1)-49 | (Ia) | (1k) | (2r) | (3o) |
| (1)-50 | (Ia) | (1g) | (2v) | (3p) |
| (1)-51 | (Ib) | (1h) | (2aa) | (3b) |
| (1)-52 | (Ib) | (1i) | (2aa) | (3c) |
| (1)-53 | (Ib) | (1j) | (2m) | (3f) |
| (1)-54 | (Ib) | (1k) | (2r) | (3h) |
| (1)-55 | (Ib) | (1o) | (2e) | (3j) |
| (1)-56 | (Ib) | (1i) | (2h) | (3m) |
| (1)-57 | (Ib) | (1j) | (2i) | (3n) |
| (1)-58 | (Ib) | (1k) | (2l) | (3o) |
| (1)-59 | (Ib) | (1o) | (2m) | (3p) |
| (1)-60 | (Ib) | (1p) | (2r) | (3q) |
| (1)-61 | (Ib) | (1q) | (2v) | (3v) |
| (1)-62 | (Ib) | (1r) | (2aa) | (3w) |
| (1)-63 | (Ib) | (1v) | (2aa) | (3x) |
| (1)-64 | (Ib) | (1y) | (2m) | (3aa) |
| (1)-65 | (Ib) | (1aa) | (2r) | (3ee) |
| (1)-66 | (Ib) | (1dd) | (2aa) | (3ii) |
| (1)-67 | (Ib) | (1ii) | (2bb) | (3kk) |
| (1)-68 | (Ib) | (1kk) | (2cc) | (3oo) |
| (1)-69 | (Ib) | (1ll) | (2e) | (3rr) |
| (1)-70 | (Ib) | (1mm) | (2h) | (3a) |
| (1)-71 | (Ib) | (1nn) | (2i) | (3b) |
| (1)-72 | (Ib) | (1oo) | (2l) | (3c) |
| (1)-73 | (Ib) | (1pp) | (2m) | (3f) |
| (1)-74 | (Ib) | (1a) | (2r) | (3h) |
| (1)-75 | (Ib) | (1f) | (2m) | (3j) |
| (1)-76 | (Ib) | (1g) | (2r) | (3m) |
| (1)-77 | (Ib) | (1h) | (2v) | (3n) |
| (1)-78 | (Ib) | (1i) | (2aa) | (3o) |
| (1)-79 | (Ib) | (1j) | (2m) | (3p) |
| (1)-80 | (Ib) | (1k) | (2r) | (3q) |
| (1)-81 | (Ib) | (1o) | (2v) | (3v) |
| (1)-82 | (Ib) | (1y) | (2aa) | (3w) |
| (1)-83 | (Ib) | (1aa) | (2h) | (3x) |
| (1)-84 | (Ib) | (1dd) | (2i) | (3aa) |
| (1)-85 | (Ib) | (1ii) | (2l) | (3ee) |
| (1)-86 | (Ib) | (1kk) | (2m) | (3ii) |
| (1)-87 | (Ib) | (1i) | (2r) | (3kk) |
| (1)-88 | (Ib) | (1j) | (2r) | (3oo) |
| (1)-89 | (Ib) | (1k) | (2v) | (3rr) |
| (1)-90 | (Ib) | (1o) | (2aa) | (3v) |
| (1)-91 | (Ib) | (1y) | (2h) | (3w) |
| (1)-92 | (Ib) | (1aa) | (2i) | (3x) |
| (1)-93 | (Ib) | (1dd) | (2l) | (3aa) |
| (1)-94 | (Ib) | (1ii) | (2m) | (3o) |
| (1)-95 | (Ib) | (1kk) | (2r) | (3p) |
| (1)-96 | (Ib) | (1a) | (2l) | (3q) |
| (1)-97 | (Ib) | (1f) | (2m) | (3v) |
| (1)-98 | (Ib) | (1g) | (2r) | (3w) |
| (1)-99 | (Ib) | (1h) | (2v) | (3x) |
| (1)-100 | (Ib) | (1i) | (2aa) | (3aa) |
| (1)-101 | (Ic) | (1j) | (2e) | (3v) |
| (1)-102 | (Ic) | (1k) | (2h) | (3w) |
| (1)-103 | (Ic) | (1o) | (2i) | (3x) |
| (1)-104 | (Ic) | (1p) | (2l) | (3aa) |
| (1)-105 | (Ic) | (1q) | (2m) | (3b) |
| (1)-106 | (Ic) | (1r) | (2r) | (3c) |
| (1)-107 | (Ic) | (1v) | (2v) | (3f) |
| (1)-108 | (Ic) | (1y) | (2aa) | (3h) |
| (1)-109 | (Ic) | (1aa) | (2aa) | (3j) |
| (1)-110 | (Ic) | (1dd) | (2aa) | (3m) |
| (1)-111 | (Ic) | (1ii) | (2bb) | (3n) |
| (1)-112 | (Ic) | (1kk) | (2cc) | (3o) |
| (1)-113 | (Ic) | (1ll) | (2e) | (3p) |
| (1)-114 | (Ic) | (1mm) | (2r) | (3q) |
| (1)-115 | (Ic) | (1nn) | (2v) | (3v) |
| (1)-116 | (Ic) | (1oo) | (2aa) | (3w) |
| (1)-117 | (Ic) | (1pp) | (2bb) | (3x) |
| (1)-118 | (Ic) | (1y) | (2cc) | (3aa) |
| (1)-119 | (Ic) | (1aa) | (2e) | (3ee) |
| (1)-120 | (Ic) | (1dd) | (2h) | (3ii) |
| (1)-121 | (Ic) | (1ii) | (2i) | (3kk) |
| (1)-122 | (Ic) | (1kk) | (2l) | (3oo) |
| (1)-123 | (Ic) | (1v) | (2m) | (3rr) |
| (1)-124 | (Ic) | (1y) | (2r) | (3aa) |
| (1)-125 | (Ic) | (1aa) | (2v) | (3n) |
| (1)-126 | (Ic) | (1dd) | (2aa) | (3o) |
| (1)-127 | (Ic) | (1ii) | (2bb) | (3p) |
| (1)-128 | (Ic) | (1a) | (2cc) | (3aa) |
| (1)-129 | (Ic) | (1f) | (2ff) | (3a) |
| (1)-130 | (Ic) | (1g) | (2gg) | (3b) |
| (1)-131 | (Ic) | (1h) | (2hh) | (3c) |
| (1)-132 | (Ic) | (1i) | (2ii) | (3f) |
| (1)-133 | (Ic) | (1j) | (2jj) | (3h) |
| (1)-134 | (Ic) | (1k) | (2kk) | (3j) |
| (1)-135 | (Ic) | (1o) | (2ll) | (3m) |

-continued

| | (I) | X | Y | Z |
|---|---|---|---|---|
| (1)-136 | (Ic) | (1f) | (2i) | (3n) |
| (1)-137 | (Ic) | (1g) | (2l) | (3o) |
| (1)-138 | (Ic) | (1h) | (2m) | (3p) |
| (1)-139 | (Ic) | (1i) | (2i) | (3q) |
| (1)-140 | (Ic) | (1j) | (2l) | (3v) |
| (1)-141 | (Ic) | (1k) | (2m) | (3w) |
| (1)-142 | (Ic) | (1o) | (2r) | (3x) |
| (1)-143 | (Ic) | (1h) | (2v) | (3aa) |
| (1)-144 | (Ic) | (1i) | (2aa) | (3ee) |
| (1)-145 | (Ic) | (1j) | (2aa) | (3ii) |
| (1)-146 | (Ic) | (1k) | (2bb) | (3kk) |
| (1)-147 | (Ic) | (1o) | (2cc) | (3oo) |
| (1)-148 | (Ic) | (1p) | (2e) | (3rr) |
| (1)-149 | (Ic) | (1q) | (2h) | (3aa) |
| (1)-150 | (Ic) | (1r) | (2i) | (3n) |
| (1)-151 | (Id) | (1v) | (2l) | (3o) |
| (1)-152 | (Id) | (1y) | (2m) | (3p) |
| (1)-153 | (Id) | (1aa) | (2r) | (3m) |
| (1)-154 | (Id) | (1dd) | (2v) | (3n) |
| (1)-155 | (Id) | (1ii) | (2aa) | (3o) |
| (1)-156 | (Id) | (1kk) | (2bb) | (3p) |
| (1)-157 | (Id) | (1ll) | (2cc) | (3q) |
| (1)-158 | (Id) | (1mm) | (2ff) | (3v) |
| (1)-159 | (Id) | (1nn) | (2gg) | (3w) |
| (1)-160 | (Id) | (1oo) | (2hh) | (3x) |
| (1)-161 | (Id) | (1pp) | (2ii) | (3aa) |
| (1)-162 | (Id) | (1y) | (2jj) | (3aa) |
| (1)-163 | (Id) | (1aa) | (2kk) | (3n) |
| (1)-164 | (Id) | (1dd) | (2ll) | (3o) |
| (1)-165 | (Id) | (1ii) | (2cc) | (3p) |
| (1)-166 | (Id) | (1kk) | (2ff) | (3a) |
| (1)-167 | (Id) | (1f) | (2gg) | (3b) |
| (1)-168 | (Id) | (1g) | (2hh) | (3c) |
| (1)-169 | (Id) | (1h) | (2r) | (3f) |
| (1)-170 | (Id) | (1i) | (2v) | (3h) |
| (1)-171 | (Id) | (1j) | (2aa) | (3j) |
| (1)-172 | (Id) | (1k) | (2bb) | (3m) |
| (1)-173 | (Id) | (1o) | (2cc) | (3n) |
| (1)-174 | (Id) | (1r) | (2ff) | (3o) |
| (1)-175 | (Id) | (1v) | (2l) | (3p) |
| (1)-176 | (Id) | (1y) | (2m) | (3q) |
| (1)-177 | (Id) | (1aa) | (2r) | (3v) |
| (1)-178 | (Id) | (1dd) | (2v) | (3w) |
| (1)-179 | (Id) | (1ii) | (2aa) | (3x) |
| (1)-180 | (Id) | (1kk) | (2m) | (3aa) |
| (1)-181 | (Id) | (1dd) | (2r) | (3ee) |
| (1)-182 | (Id) | (1ii) | (2v) | (3ii) |
| (1)-183 | (Id) | (1kk) | (2aa) | (3kk) |
| (1)-184 | (Id) | (1r) | (2bb) | (3oo) |
| (1)-185 | (Id) | (1v) | (2cc) | (3rr) |
| (1)-186 | (Id) | (1y) | (2m) | (3v) |
| (1)-187 | (Id) | (1aa) | (2r) | (3w) |
| (1)-188 | (Id) | (1dd) | (2v) | (3x) |
| (1)-189 | (Id) | (1ii) | (2aa) | (3aa) |
| (1)-190 | (Id) | (1kk) | (2bb) | (3ee) |
| (1)-191 | (Id) | (1y) | (2cc) | (3o) |
| (1)-192 | (Id) | (1aa) | (2l) | (3p) |
| (1)-193 | (Id) | (1dd) | (2m) | (3a) |
| (1)-194 | (Id) | (1ii) | (2r) | (3b) |
| (1)-195 | (Id) | (1kk) | (2v) | (3v) |
| (1)-196 | (Id) | (1i) | (2aa) | (3w) |
| (1)-197 | (Id) | (1j) | (2bb) | (3x) |
| (1)-198 | (Id) | (1k) | (2cc) | (3aa) |
| (1)-199 | (Id) | (1i) | (2ff) | (3o) |
| (1)-200 | (Id) | (1j) | (2gg) | (3p) |
| (1)-201 | (Ie) | (1k) | (2hh) | (3q) |
| (1)-202 | (Ie) | (1f) | (2ii) | (3v) |
| (1)-203 | (Ie) | (1g) | (2jj) | (3w) |
| (1)-204 | (Ie) | (1h) | (2kk) | (3x) |
| (1)-205 | (Ie) | (1i) | (2ll) | (3aa) |
| (1)-206 | (Ie) | (1j) | (2e) | (3o) |
| (1)-207 | (Ie) | (1k) | (2h) | (3p) |
| (1)-208 | (Ie) | (1o) | (2i) | (3a) |
| (1)-209 | (Ie) | (1p) | (2l) | (3b) |
| (1)-210 | (Ie) | (1q) | (2m) | (3b) |
| (1)-211 | (Ie) | (1r) | (2cc) | (3c) |
| (1)-212 | (Ie) | (1v) | (2ff) | (3f) |
| (1)-213 | (Ie) | (1y) | (2e) | (3h) |
| (1)-214 | (Ie) | (1aa) | (2h) | (3j) |
| (1)-215 | (Ie) | (1dd) | (2i) | (3m) |
| (1)-216 | (Ie) | (1ii) | (2l) | (3n) |
| (1)-217 | (Ie) | (1r) | (2m) | (3o) |
| (1)-218 | (Ie) | (1v) | (2r) | (3p) |
| (1)-219 | (Ie) | (1y) | (2v) | (3q) |
| (1)-220 | (Ie) | (1aa) | (2aa) | (3v) |
| (1)-221 | (Ie) | (1aa) | (2bb) | (3w) |
| (1)-222 | (Ie) | (1dd) | (2cc) | (3x) |
| (1)-223 | (Ie) | (1ii) | (2ff) | (3aa) |
| (1)-224 | (Ie) | (1kk) | (2gg) | (3ee) |
| (1)-225 | (Ie) | (1g) | (2hh) | (3ii) |
| (1)-226 | (Ie) | (1h) | (2ii) | (3kk) |
| (1)-227 | (Ie) | (1i) | (2jj) | (3oo) |
| (1)-228 | (Ie) | (1j) | (2kk) | (3rr) |
| (1)-229 | (Ie) | (1k) | (2ll) | (3m) |
| (1)-230 | (Ie) | (1o) | (2e) | (3n) |
| (1)-231 | (Ie) | (1p) | (2h) | (3o) |
| (1)-232 | (Ie) | (1q) | (2i) | (3p) |
| (1)-233 | (Ie) | (1r) | (2l) | (3q) |
| (1)-234 | (Ie) | (1v) | (2m) | (3v) |
| (1)-235 | (Ie) | (1y) | (2cc) | (3w) |
| (1)-236 | (Ie) | (1aa) | (2ff) | (3x) |
| (1)-237 | (Ie) | (1dd) | (2e) | (3aa) |
| (1)-238 | (Ie) | (1ii) | (2h) | (3o) |
| (1)-239 | (Ie) | (1kk) | (2i) | (3p) |
| (1)-240 | (Ie) | (1ll) | (2l) | (3q) |
| (1)-241 | (Ie) | (1mm) | (2m) | (3v) |
| (1)-242 | (Ie) | (1nn) | (2aa) | (3w) |
| (1)-243 | (Ie) | (1oo) | (2bb) | (3x) |
| (1)-244 | (Ie) | (1pp) | (2cc) | (3aa) |
| (1)-245 | (Ie) | (1r) | (2ff) | (3ee) |
| (1)-246 | (Ie) | (1v) | (2e) | (3ii) |
| (1)-247 | (Ie) | (1y) | (2h) | (3kk) |
| (1)-248 | (Ie) | (1aa) | (2i) | (3oo) |
| (1)-249 | (Ie) | (1f) | (2l) | (3rr) |
| (1)-250 | (Ie) | (1g) | (2m) | (3o) |
| (1)-251 | (If) | (1h) | (2r) | (3p) |
| (1)-252 | (If) | (1i) | (2v) | (3a) |
| (1)-253 | (If) | (1j) | (2aa) | (3b) |
| (1)-254 | (If) | (1k) | (2bb) | (3o) |
| (1)-255 | (If) | (1o) | (2cc) | (3p) |
| (1)-256 | (If) | (1v) | (2ff) | (3q) |
| (1)-257 | (If) | (1y) | (2gg) | (3v) |
| (1)-258 | (If) | (1aa) | (2hh) | (3w) |
| (1)-259 | (If) | (1dd) | (2ii) | (3x) |
| (1)-260 | (If) | (1ii) | (2jj) | (3aa) |
| (1)-261 | (If) | (1r) | (2kk) | (3n) |
| (1)-262 | (If) | (1v) | (2ll) | (3o) |
| (1)-263 | (If) | (1y) | (2cc) | (3p) |
| (1)-264 | (If) | (1aa) | (2ff) | (3q) |
| (1)-265 | (If) | (1dd) | (2gg) | (3v) |
| (1)-266 | (If) | (1ii) | (2hh) | (3w) |
| (1)-267 | (If) | (1kk) | (2e) | (3x) |
| (1)-268 | (If) | (1h) | (2h) | (3aa) |
| (1)-269 | (If) | (1i) | (2i) | (3ee) |
| (1)-270 | (If) | (1j) | (2l) | (3ii) |
| (1)-271 | (If) | (1k) | (2m) | (3kk) |
| (1)-272 | (If) | (1o) | (2d) | (3oo) |
| (1)-273 | (If) | (1p) | (2e) | (3rr) |
| (1)-274 | (If) | (1q) | (2h) | (3v) |
| (1)-275 | (If) | (1r) | (2i) | (3w) |
| (1)-276 | (If) | (1v) | (2l) | (3x) |
| (1)-277 | (If) | (1y) | (2m) | (3aa) |
| (1)-278 | (If) | (1aa) | (2r) | (3m) |
| (1)-279 | (If) | (1dd) | (2v) | (3n) |
| (1)-280 | (If) | (1ii) | (2aa) | (3o) |
| (1)-281 | (If) | (1kk) | (2bb) | (3p) |
| (1)-282 | (If) | (1ll) | (2cc) | (3q) |
| (1)-283 | (If) | (1mm) | (2ff) | (3v) |
| (1)-284 | (If) | (1nn) | (2gg) | (3w) |
| (1)-285 | (If) | (1oo) | (2hh) | (3x) |
| (1)-286 | (If) | (1pp) | (2ii) | (3aa) |
| (1)-287 | (If) | (1r) | (2jj) | (3b) |
| (1)-288 | (If) | (1v) | (2kk) | (3c) |
| (1)-289 | (If) | (1y) | (2ll) | (3f) |

| | (I) | X | Y | Z |
|---|---|---|---|---|
| (1)-290 | (If) | (1aa) | (2cc) | (3h) |
| (1)-291 | (If) | (1dd) | (2ff) | (3j) |
| (1)-292 | (If) | (1ii) | (2gg) | (3m) |
| (1)-293 | (If) | (1kk) | (2hh) | (3n) |
| (1)-294 | (If) | (1aa) | (2h) | (3o) |
| (1)-295 | (If) | (1dd) | (2i) | (3p) |
| (1)-296 | (If) | (1ii) | (2l) | (3q) |
| (1)-297 | (If) | (1r) | (2m) | (3v) |
| (1)-298 | (If) | (1v) | (2v) | (3w) |
| (1)-299 | (If) | (1y) | (2aa) | (3x) |
| (1)-300 | (If) | (1aa) | (2bb) | (3aa) |

In some embodiments, the compound of formulae (I) or (Ia)-(If) is one of the following compounds (or a pharmaceutically acceptable salt, prodrug, or N-oxide thereof, or a solvate or hydrate thereof):

| No. | Structure | Name |
|---|---|---|
| 1 | 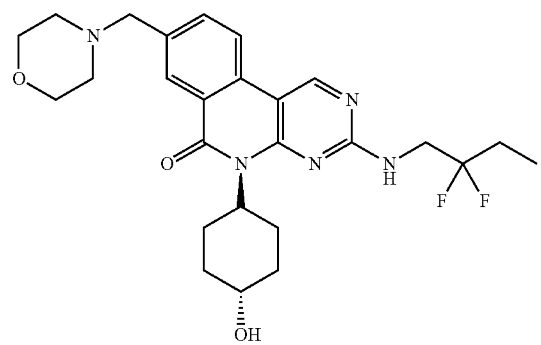 | trans-3-((2,2-Difluorobutyl)amino)-5-(4-hydroxycyclohexyl)-8-(morpholinomethyl)pyrimido[4,5-c]isoquinolin-6(5H)-one |
| 2 | 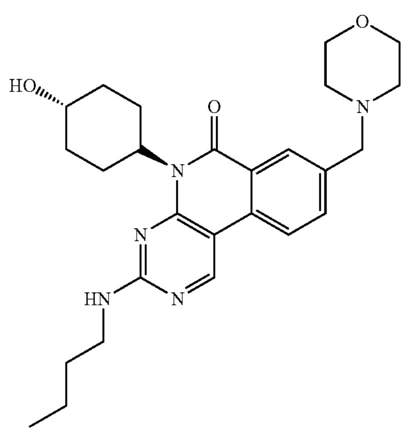 | trans-3-(Butylamino)-5-(4-hydroxycyclohexyl)-8-(morpholinomethyl)pyrimido[4,5-c]isoquinolin-6(5H)-one |
| 3 | 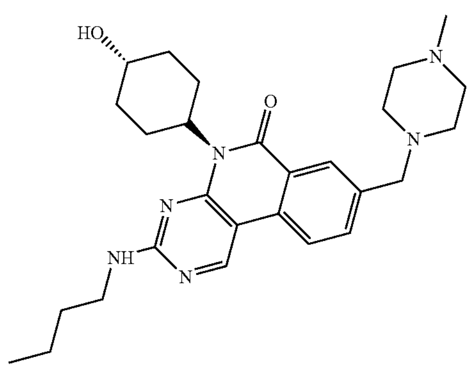 | trans-3-(Butylamino)-5-(4-hydroxycyclohexyl)-8-((4-methylpiperazin-1-yl)methyl)pyrimido[4,5-c]isoquinolin-6(5H)-one |

-continued

| No. | Structure | Name |
|---|---|---|
| 4 | 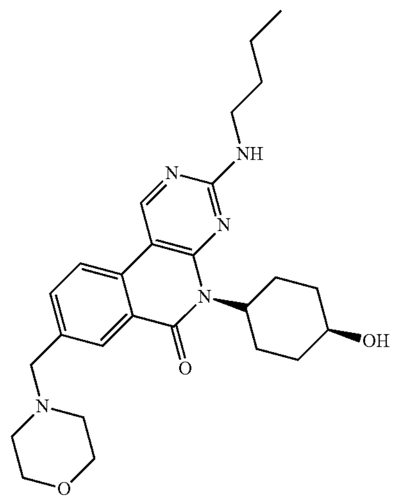 | cis-3-(Butylamino)-5-(4-hydroxycyclohexyl)-8-(morpholinomethyl)pyrimido[4,5-c]isoquinolin-6(5H)-one |
| 5 | 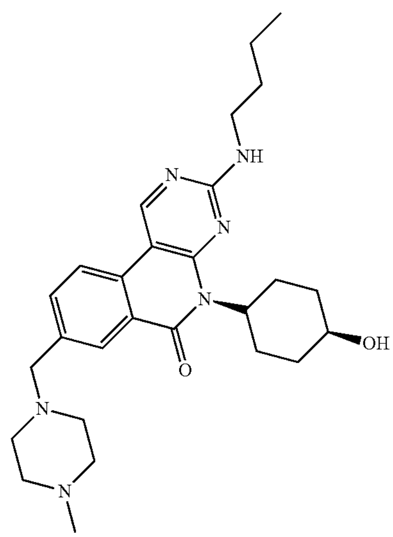 | cis-3-(Butylamino)-5-(4-hydroxycyclohexyl)-8-((4-methylpiperazin-1-yl)methyl)pyrimido[4,5-c]isoquinolin-6(5H)-one |
| 6 | 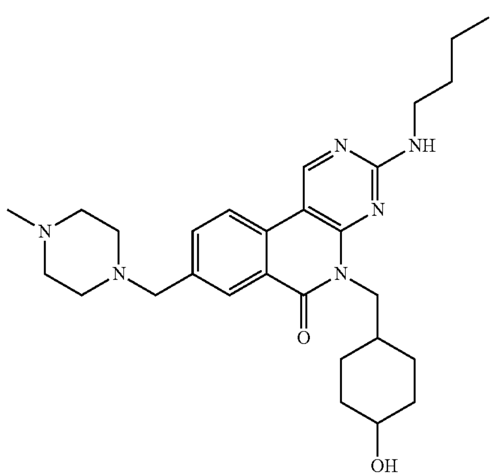 [SMILES: CCCCNc1ncc2c3ccc(CN4CCN(C)CC4)cc3c(=O)n(CC3CCC(O)CC3)c2n1] | 3-(Butylamino)-5-((4-hydroxycyclohexyl)methyl)-8-((4-methylpiperazin-1-yl)methyl)pyrimido[4,5-c]isoquinolin-6(5H)-one |

-continued

| No. | Structure | Name |
|---|---|---|
| 7 | 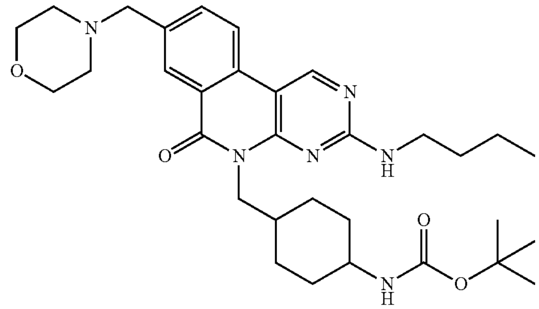 [SMILES: CCCCNc1ncc2c3ccc(CN4CCOCC4)cc3c(=O)n(CC3CCC(NC(=O)OC(C)(C)C)CC3)c2n1] | tert-Butyl (4-((3-(butylamino)-8-(morpholinomethyl)-6-oxopyrimido[4,5-c]isoquinolin-5(6H)-yl)methyl)cyclohexyl)carbamate |
| 8 | 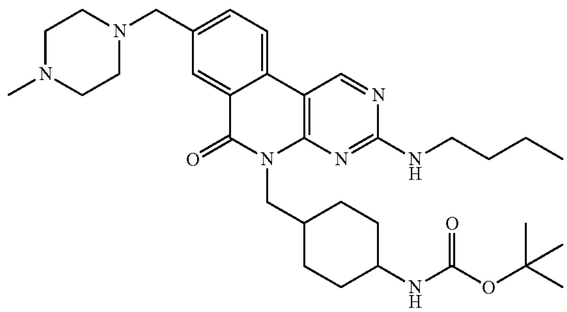 [SMILES: CCCCNc1ncc2c3ccc(CN4CCN(C)CC4)cc3c(=O)n(CC3CCC(NC(=O)OC(C)(C)C)CC3)c2n1] | tert-Butyl (4-((3-(butylamino)-8-((4-methylpiperazin-1-yl)methyl)-6-oxopyrimido[4,5-c]isoquinolin-5(6H)-yl)methyl)cyclohexyl)carbamate |
| 9 | 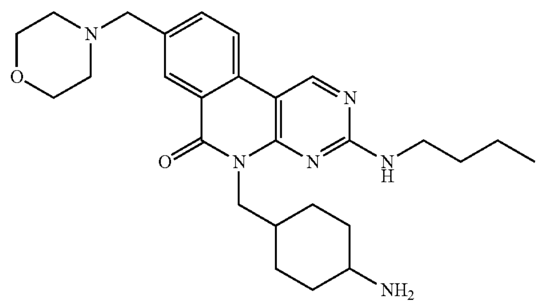 [SMILES: CCCCNc1ncc2c3ccc(CN4CCOCC4)cc3c(=O)n(CC3CCC(N)CC3)c2n1] | 5-((4-Aminocyclohexyl)methyl)-3-(butylamino)-8-(morpholinomethyl)pyrimido[4,5-c]isoquinolin-6(5H)-one |
| 10 | 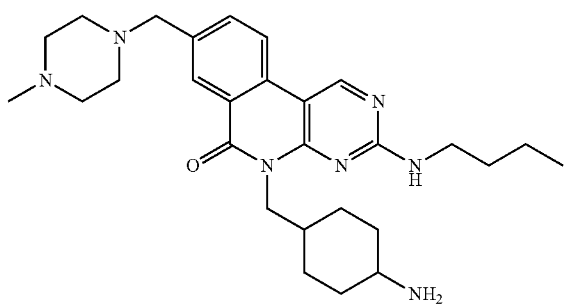 [SMILES: CCCCNc1ncc2c3ccc(CN4CCN(C)CC4)cc3c(=O)n(CC3CCC(N)CC3)c2n1] | 5-((4-Aminocyclohexyl)methyl)-3-(butylamino)-8-((4-methylpiperazin-1-yl)methyl)pyrimido[4,5-c]isoquinolin-6(5H)-one |
| 11 | 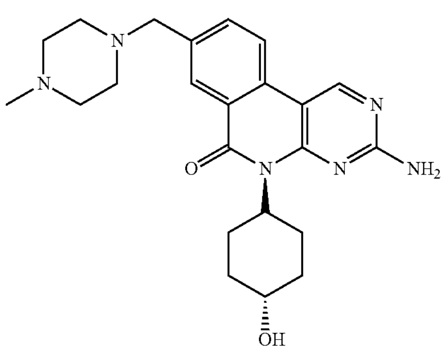 | trans-3-Amino-5-(4-hydroxycyclohexyl)-8-((4-methylpiperazin-1-yl)methyl)pyrimido[4,5-c]isoquinolin-6(5H)-one |

-continued

| No. | Structure | Name |
|---|---|---|
| 12 | 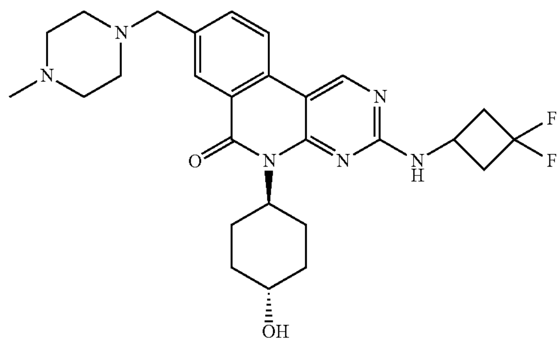 [SMILES: CN1CCN(Cc2ccc3c(c2)c(=O)n([C@H]2CC[C@H](O)CC2)c2nc(NC4CC(F)(F)C4)ncc32)CC1] | trans-3-((3,3-Difluorocyclobutyl)amino)-5-(4-hydroxycyclohexyl)-8-((4-methylpiperazin-1-yl)methyl)pyrimido[4,5-c]isoquinolin-6(5H)-one |
| 13 | 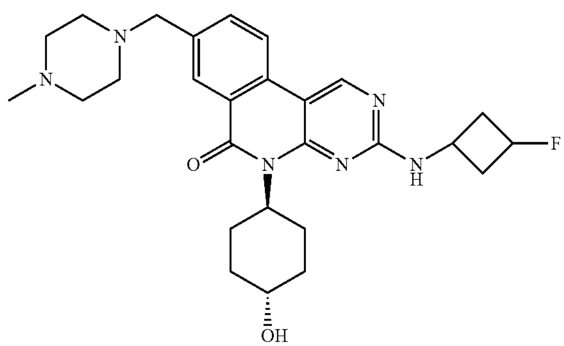 [SMILES: CN1CCN(Cc2ccc3c(c2)c(=O)n([C@H]2CC[C@H](O)CC2)c2nc(NC4CC(F)C4)ncc32)CC1] | trans-3-((3-Fluorocyclobutyl)amino)-5-(4-hydroxycyclohexyl)-8-((4-methylpiperazin-1-yl)methyl)pyrimido[4,5-c]isoquinolin-6(5H)-one |
| 14 | 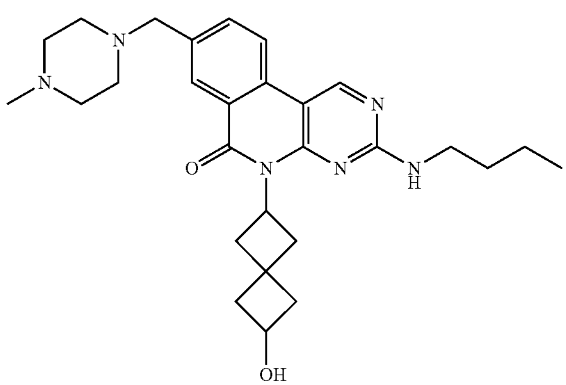 [SMILES: CCCCNc1ncc2c3ccc(CN4CCN(C)CC4)cc3c(=O)n(C3CC4(CC(O)C4)C3)c2n1] | 3-(Butylamino)-5-(6-hydroxyspiro[3.3]heptan-2-yl)-8-((4-methylpiperazin-1-yl)methyl)pyrimido[4,5-c]isoquinolin-6(5H)-one |
| 15 | 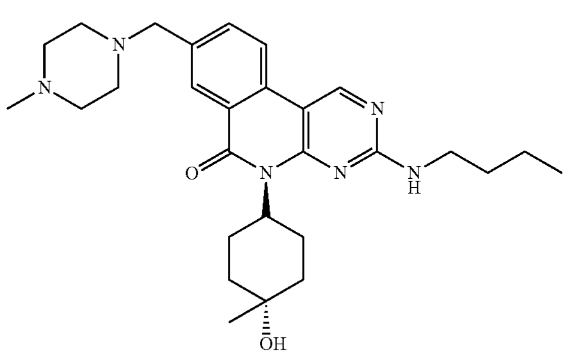 | trans-3-(Butylamino)-5-(4-hydroxy-4-methylcyclohexyl)-8-((4-methylpiperazin-1-yl)methyl)pyrimido[4,5-c]isoquinolin-6(5H)-one |

-continued

| No. | Structure | Name |
|---|---|---|
| 16 | 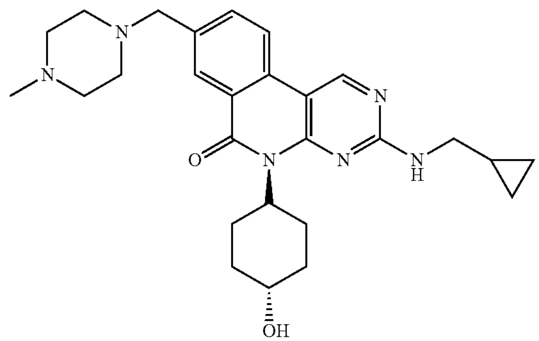 | trans-3-(((Cyclopropylmethyl)amino)-5-(4-hydroxycyclohexyl)-8-((4-methylpiperazin-1-yl)methyl)pyrimido[4,5-c]isoquinolin-6(5H)-one |
| 17 | 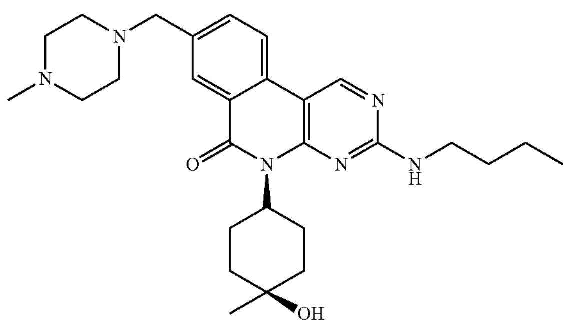 | cis-3-(Butylamino)-5-(4-hydroxy-4-methylcyclohexyl)-8-((4-methylpiperazin-1-yl)methyl)pyrimido[4,5-c]isoquinolin-6(5H)-one |
| 18 | 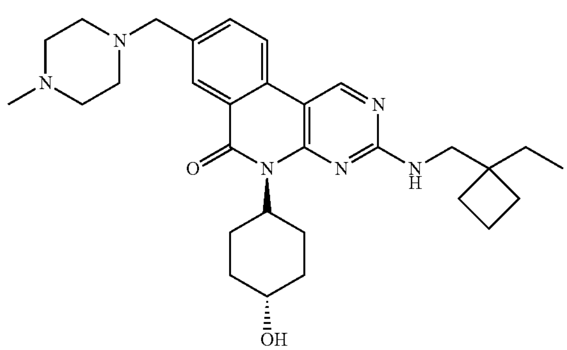 | trans-3-(((1-Ethylcyclobutyl)methyl)amino)-5-(4-hydroxycyclohexyl)-8-((4-methylpiperazin-1-yl)methyl)pyrimido[4,5-c]isoquinolin-6(5H)-one |
| 19 | 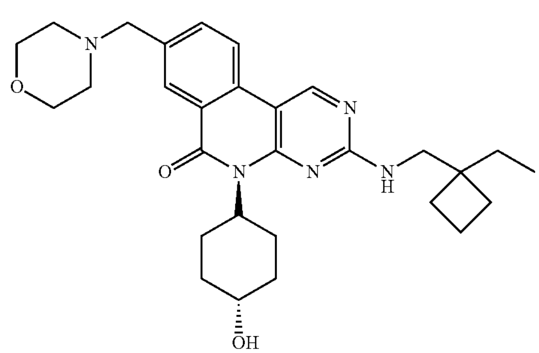 | trans-3-(((1-Ethylcyclobutyl)methyl)amino)-5-(4-hydroxycyclohexyl)-8-(morpholinomethyl)pyrimido[4,5-c]isoquinolin-6(5H)-one |

| No. | Structure | Name |
|---|---|---|
| 20 | 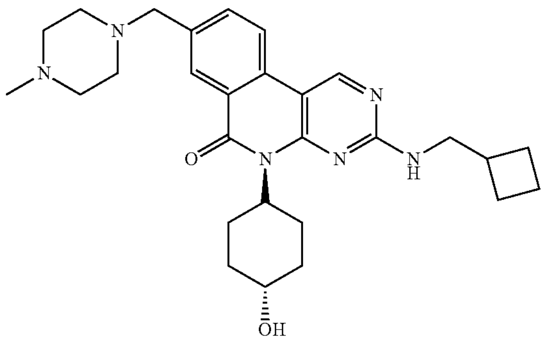 | trans-3-(((1-Ethylcyclobutyl)methyl)amino)-5-(4-hydroxycyclohexyl)-8-(morpholinomethyl)pyrimido[4,5-c]isoquinolin-6(5H)-one |
| 21 | 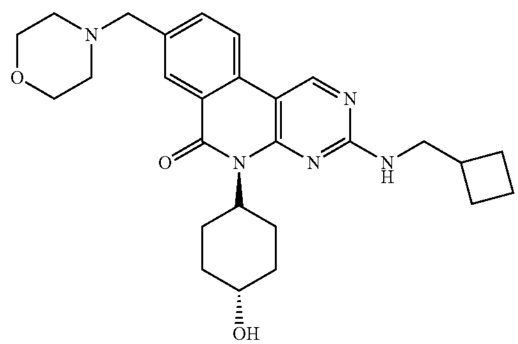 | trans-3-((Cyclobutylmethyl)amino)-5-(4-hydroxycyclohexyl)-8-(morpholinomethyl)pyrimido[4,5-c]isoquinolin-6(5H)-one |
| 22 | 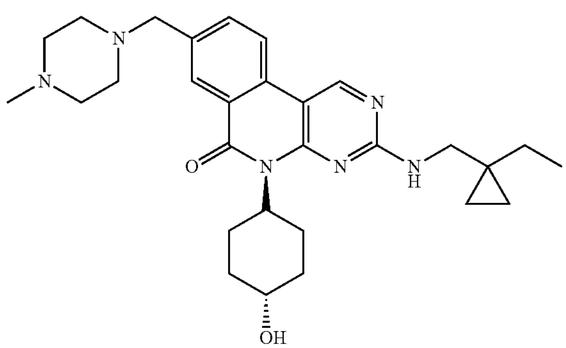 | trans-3-(((1-Ethylcyclopropyl)methyl)amino)-5-(4-hydroxycyclohexyl)-8-((4-methylpiperazin-1-yl)methyl)pyrimido[4,5-c]isoquinolin-6(5H)-one |
| 23 | 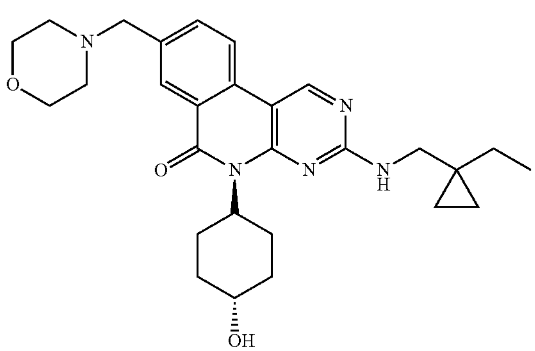 | trans-3-(((1-Ethylcyclopropyl)methyl)amino)-5-((4-hydroxycyclohexyl)-8-(morpholinomethyl)pyrimido[4,5-c]isoquinolin-6(5H)-one |

-continued

| No. | Structure | Name |
|---|---|---|
| 24 | 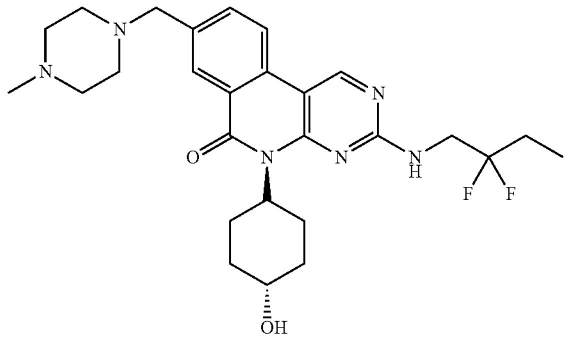 | trans-3-((2,2-Difluorobutyl)amino)-5-(4-hydroxycyclohexyl)-8-((4-methylpiperazin-1-yl)methyl)pyrimido[4,5-c]isoquinolin-6(5H)-one |
| 25 | 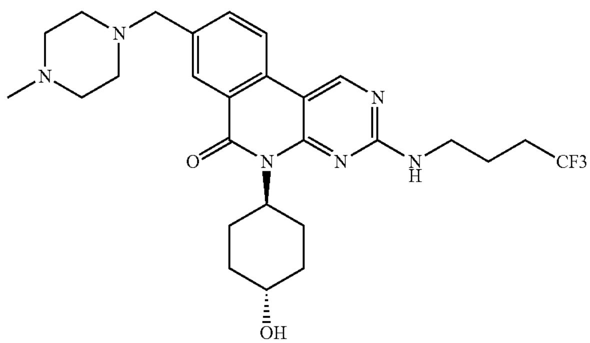 [SMILES: CN1CCN(Cc2ccc3c(c2)c(=O)n([C@H]2CC[C@H](O)CC2)c2nc(NCCCC(F)(F)F)ncc32)CC1] | trans-5-(4-hydroxycyclohexyl)-8-((4-methylpiperazin-1-yl)methyl)-3-((4,4,4-trifluorobutyl)amino)pyrimido-[4,5-c]isoquinolin-6(5H)-one |
| 26 | 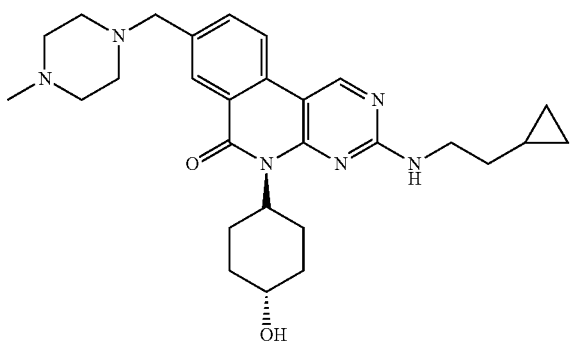 | trans-3-((2-Cyclopropylethyl)amino)-5-(4-hydroxycyclohexyl)-8-((4-methylpiperazin-1-yl)methyl)pyrimido[4,5-c]isoquinolin-6(5H)-one |
| 27 | 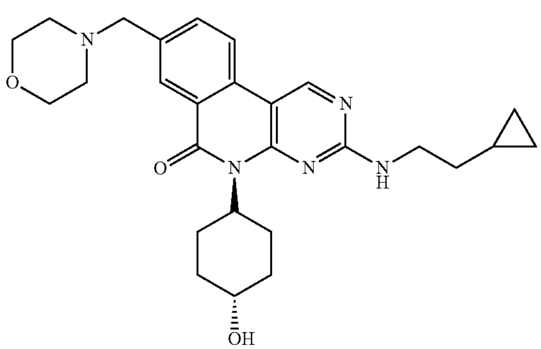 | trans-3-((2-Cyclopropylethyl)amino)-5-(4-hydroxycyclohexyl)-8-(morpholinomethyl)pyrimido[4,5-c]isoquinolin-6(5H)-one |

| No. | Structure | Name |
|---|---|---|
| 28 | 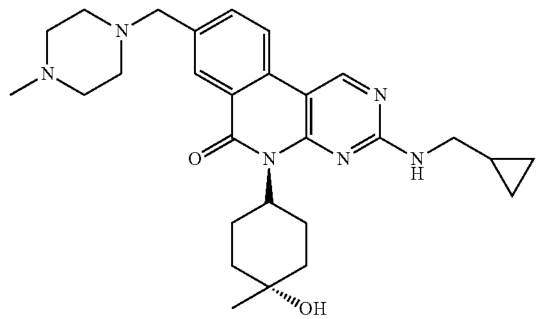 | trans-3-((Cyclopropylmethyl)amino)-5-(4-hydroxy-4-methylcyclohexyl)-8-((4-methylpiperazin-1-yl)methyl)pyrimido[4,5-c]isoquinolin-6(5H)-one |
| 29 | 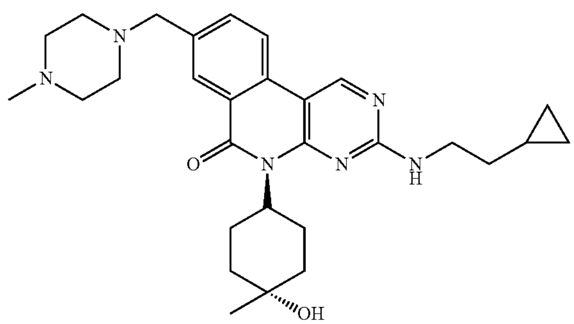 | trans-3-((2-Cyclopropylethyl)amino)-5-(4-hydroxy-4-methylcyclohexyl)-8-((4-methylpiperazin-1-yl)methyl)pyrimido[4,5-c]isoquinolin-6(5H)-one |
| 30 | 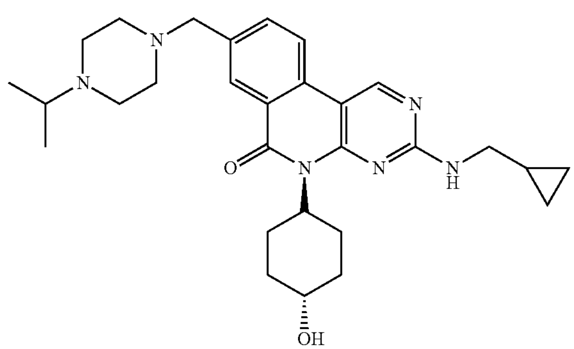 | trans-3-((Cyclopropylmethyl)amino)-5-(4-hydroxycyclohexyl)-8-((4-isopropylpiperazin-1-yl)methyl)pyrimido[4,5-c]isoquinolin-6(5H)-one |
| 31 | 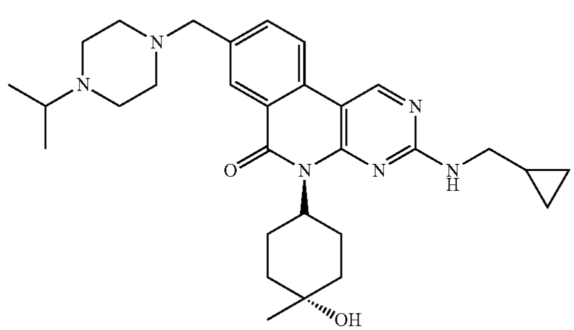 | trans-3-((Cyclopropylmethyl)amino)-5-(4-hydroxy-4-methylcyclohexyl)-8-((4-isopropylpiperazin-1-yl)methyl)pyrimido[4,5-c]isoquinolin-6(5H)-one |

-continued

| No. | Structure | Name |
|---|---|---|
| 32 | 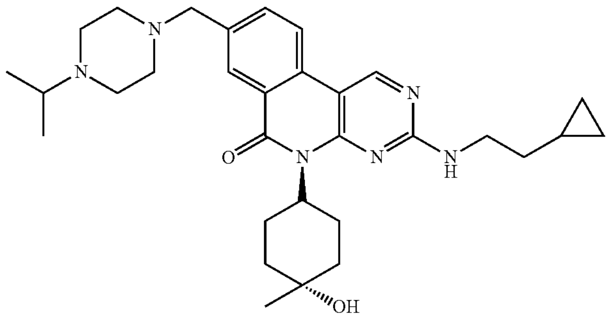 | trans-3-((2-Cyclopropylethyl)amino)-5-(4-hydroxy-4-methylcyclohexyl)-8-((4-isopropylpiperazin-1-yl)methyl)pyrimido[4,5-c]isoquinolin-6(5H)-one |
| 33 | 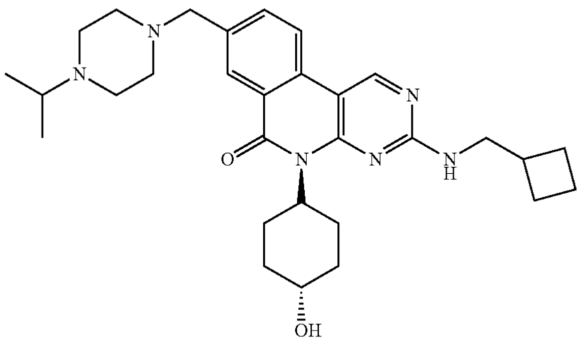 | trans-3-((Cyclobutylmethyl)amino)-5-(4-hydroxycyclohexyl)-8-((4-isopropylpiperazin-1-yl)methyl)pyrimido[4,5-c]isoquinolin-6(5H)-one |
| 34 | 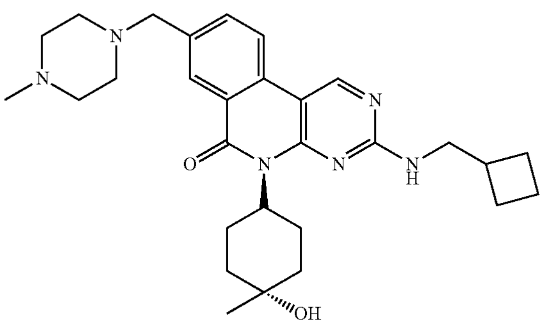 | trans-3-((Cyclobutylmethyl)amino)-5-(4-hydroxy-4-methylcyclohexyl)-8-((4-methylpiperazin-1-yl)methyl)pyrimido[4,5-c]isoquinolin-6(5H)-one |
| 35 | 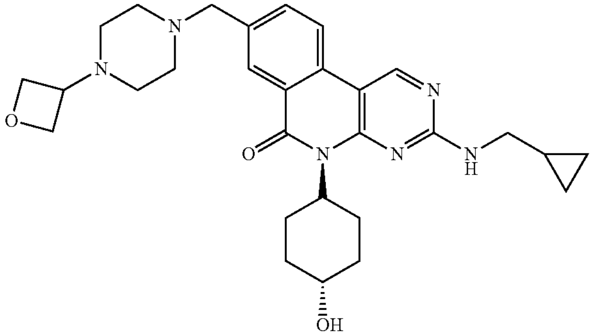 | trans-3-((Cyclopropylmethyl)amino)-5-(4-hydroxycyclohexyl)-8-((4-(oxetan-3-yl)piperazin-1-yl)methyl)pyrimido[4,5-c]isoquinolin-6(5H)-one |

| No. | Structure | Name |
|---|---|---|
| 36 | 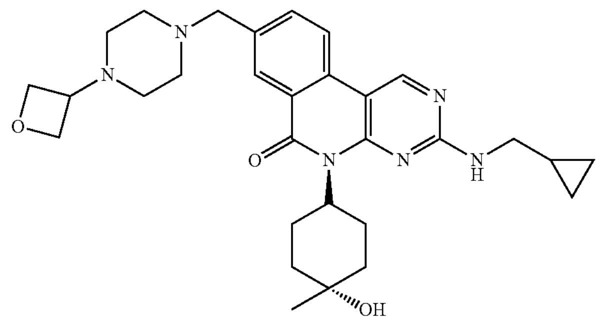 | trans-3-((Cyclopropylmethyl)amino)-5-(4-hydroxy-4-methylcyclohexyl)-8-((4-(oxetan-3-yl)piperazin-1-yl)methyl)pyrimido[4,5-c]isoquinolin-6(5H)-one |
| 37 | 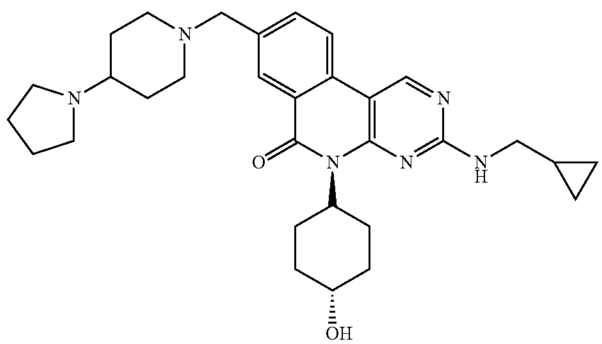 | trans-3-((Cyclopropylmethyl)amino)-5-(4-hydroxycyclohexyl)-8-((4-(pyrrolidin-1-yl)piperidin-1-yl)methyl)pyrimido[4,5-c]isoquinolin-6(5H)-one |
| 38 | 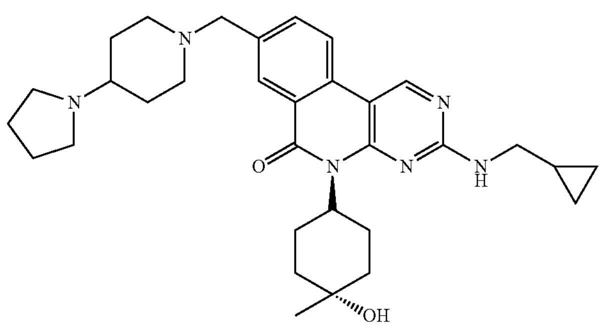 | trans-3-((Cyclopropylmethyl)amino)-5-(4-hydroxy-4-methylcyclohexyl)-8-((4-(pyrrolidin-1-yl)piperidin-1-yl)methyl)pyrimido[4,5-c]isoquinolin-6(5H)-one |
| 39 | 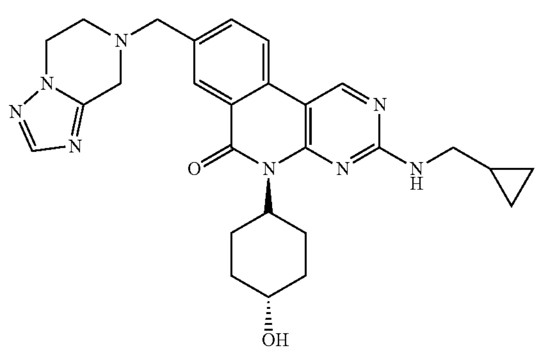 | trans-3-((Cyclopropylmethyl)amino)-8-((5,6-dihydro-[1,2,4]triazolo[1,5-a]pyrazin-7(8H)-yl)methyl)-5-(4-hydroxycyclohexyl)pyrimido[4,5-c]isoquinolin-6(5H)-one |

| No. | Structure | Name |
|---|---|---|
| 40 | 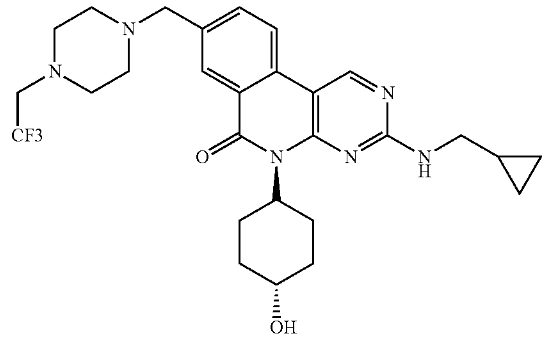 | trans-3-((Cyclopropylmethyl)amino)-5-(4-hydroxycyclohexyl)-8-((4-(2,2,2-trifluoroethyl)piperazin-1-yl)methyl)pyrimido[4,5-c]isoquinolin-6(5H)-one |
| 41 | 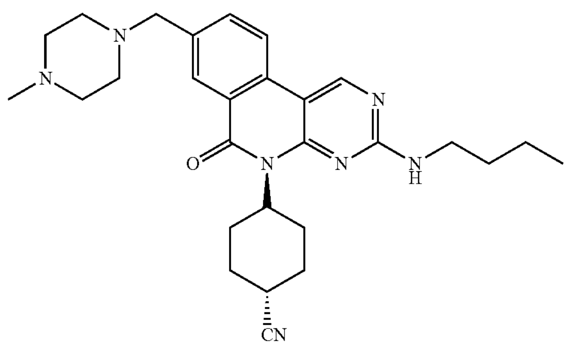 | trans-(3-(butylamino)-8-((4-methylpiperazin-1-yl)methyl)-6-oxopyrimido[4,5-c]isoquinolin-5(6H)-yl)cyclohexane-1-carbonitrile |
| 42 | 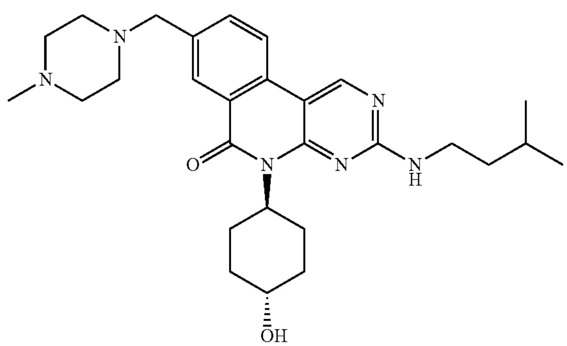 [SMILES: CC(C)CCNc1ncc2c3ccc(CN4CCN(C)CC4)cc3c(=O)n([C@H]3CC[C@H](O)CC3)c2n1] | trans-5-(4-hydroxycyclohexyl)-3-(isopentylamino)-8-((4-methylpiperazin-1-yl)methyl)pyrimido[4,5-c]isoquinolin-6(5H)-one |
| 43 | 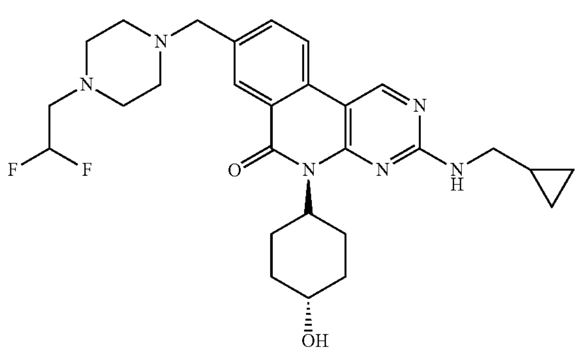 | trans-3-((Cyclopropylmethyl)amino)-8-((4-(2,2-difluoroethyl)piperazin-1-yl)methyl)-5-(4-hydroxycyclohexyl)pyrimido[4,5-c]isoquinolin-6(5H)-one |

-continued

| No. | Structure | Name |
|---|---|---|
| 44 | 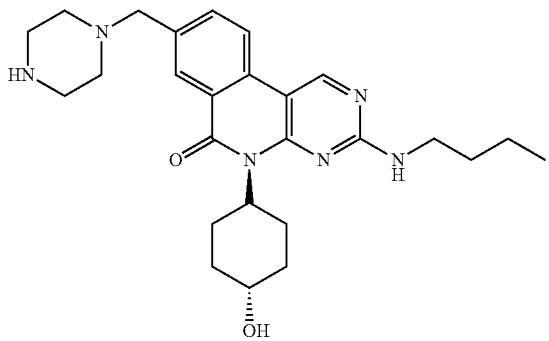 | trans-3-(Butylamino)-5-(4-hydroxycyclohexyl)-8-(piperazin-1-ylmethyl)pyrimido[4,5-c]isoquinolin-6(5H)-one |
| 45 | 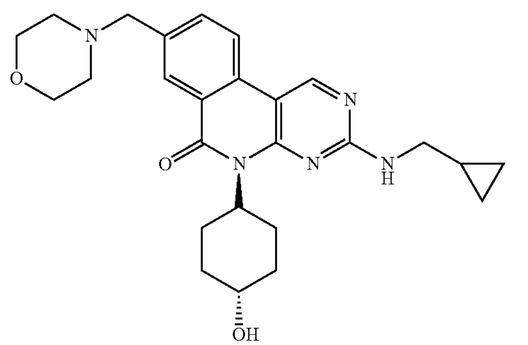 | trans-3-((Cyclopropylmethyl)amino)-5-(4-hydroxycyclohexyl)-8-(morpholinomethyl)pyrimido[4,5-c]isoquinolin-6(5H)-one |
| 46 | 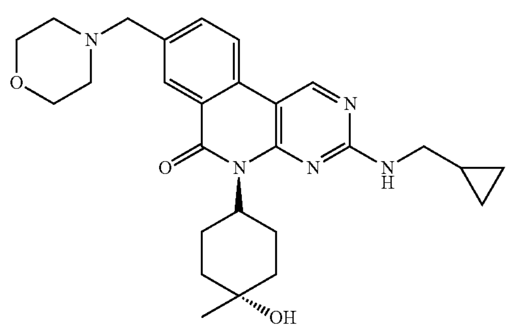 | trans-3-((Cyclopropylmethyl)amino)-5-(4-hydroxy-4-methylcyclohexyl)-8-(morpholinomethyl)pyrimido[4,5-c]isoquinolin-6(5H)-one |
| 47 | 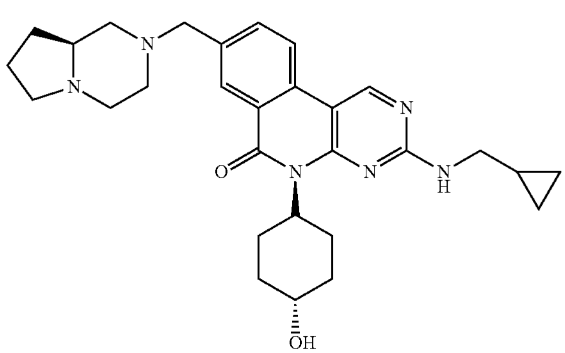 | trans-3-((Cyclopropylmethyl)amino)-8-(((S)-hexahydropyrrolo[1,2-a]pyrazin-2(1H)-yl)methyl)-5-(4-hydroxycyclohexyl)pyrimido[4,5-c]isoquinolin-6(5H)-one |

-continued

| No. | Structure | Name |
|---|---|---|
| 48 | 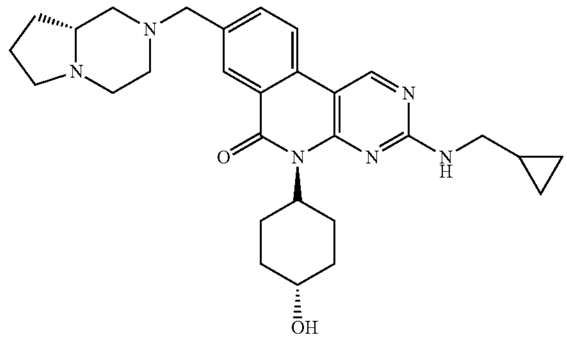 | trans-3-((Cyclopropylmethyl)amino)-8-(((R)-hexahydropyrrolo[1,2-a]pyrazin-2(1H)-yl)methyl)-5-(4-hydroxycyclohexyl)pyrimido[4,5-c]isoquinolin-6(5H)-one |
| 49 | 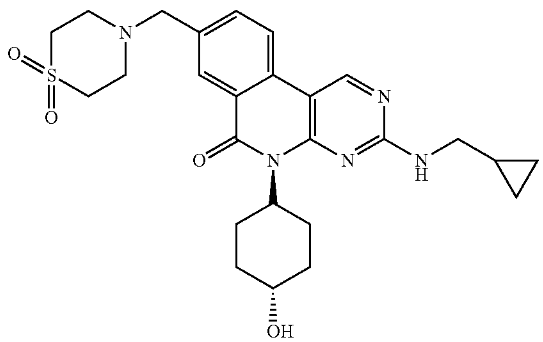 | trans-3-((Cyclopropylmethyl)amino)-8-((1,1-dioxidothiomorpholino)methyl)-5-(4-hydroxycyclohexyl)pyrimido[4,5-c]isoquinolin-6(5H)-one |
| 50 | 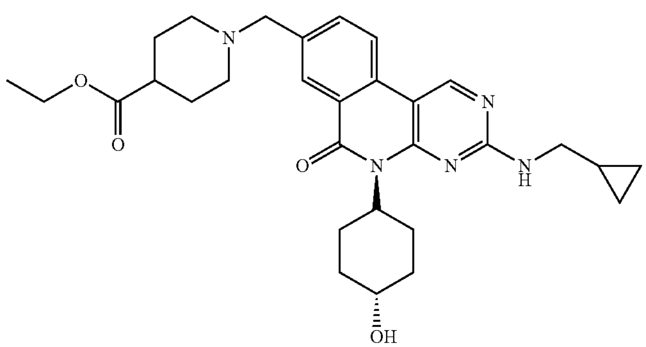 | trans-Ethyl-((3-((Cyclopropylmethyl)amino)-5-(4-hydroxycyclohexyl)-6-oxo-5,6-dihydropyrimido[4,5-c]isoquinolin-8-yl)methyl)piperidine-4-carboxylate |
| 51 | 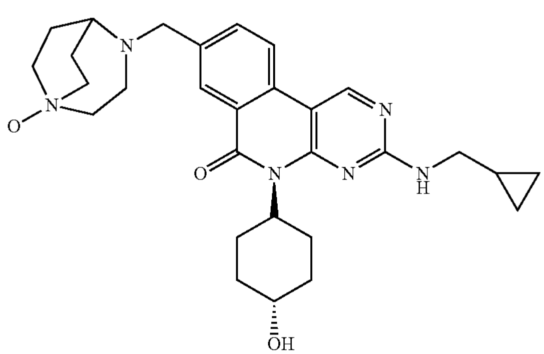 | trans-4-((3-((Cyclopropylmethyl)amino)-5-(4-hydroxycyclohexyl)-6-oxo-5,6-dihydropyrimido[4,5-c]isoquinolin-8-yl)methyl)-1,4-diazabicyclo[3.2.2]nonane 1-oxide |

-continued

| No. | Structure | Name |
|---|---|---|
| 52 | 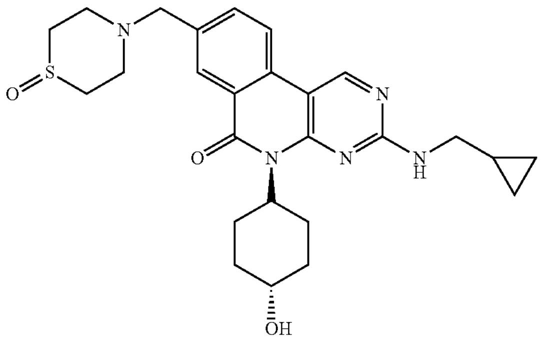 | trans-3-((cyclopropylmethyl)amino)-5-(4-hydroxycyclohexyl)-8-((1-oxidothiomorpholino)methyl)-pyrimido[4,5-c]isoquinolin-6(5H)-one |
| 53 | 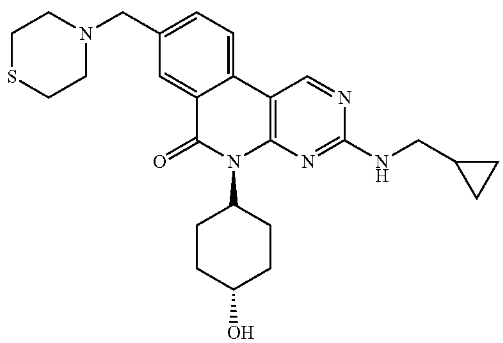 | trans-3-((Cyclopropylmethyl)amino)-5-(4-hydroxycyclohexyl)-8-(thiomorpholinomethyl)pyrimido-[4,5-c]isoquinolin-6(5H)-one |
| 54 | 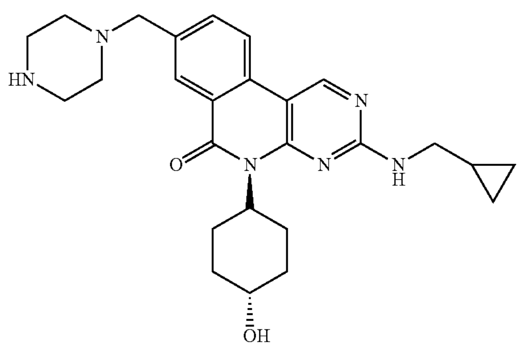 | trans-3-((Cyclopropylmethyl)amino)-5-(4-hydroxycyclohexyl)-8-(piperazin-1-ylmethyl)pyrimido[4,5-c]isoquinolin-6(5H)-one |
| 55 | 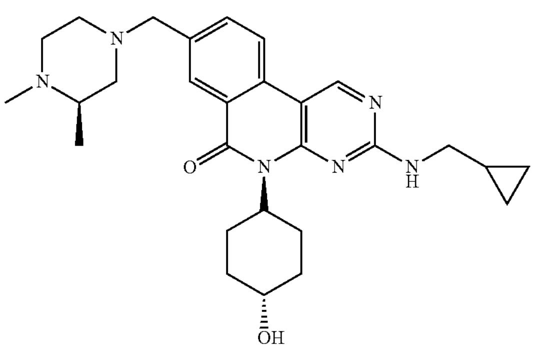 | trans-3-((Cyclopropylmethyl)amino)-8-(((R)-3,4-dimethylpiperazin-1-yl)methyl)-5-(4-hydroxycyclohexyl)pyrimido[4,5-c]isoquinolin-6(5H)-one |

-continued

| No. | Structure | Name |
|---|---|---|
| 56 | 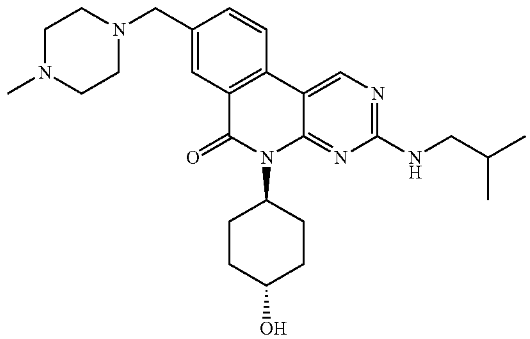 [SMILES: CC(C)CNc1ncc2c3ccc(CN4CCN(C)CC4)cc3c(=O)n([C@H]3CC[C@H](O)CC3)c2n1] | trans-5-(4-Hydroxycyclohexyl)-3-(isobutylamino)-8-((4-methylpiperazin-1-yl)methyl)pyrimido[4,5-c]isoquinolin-6(5H)-one |
| 57 | 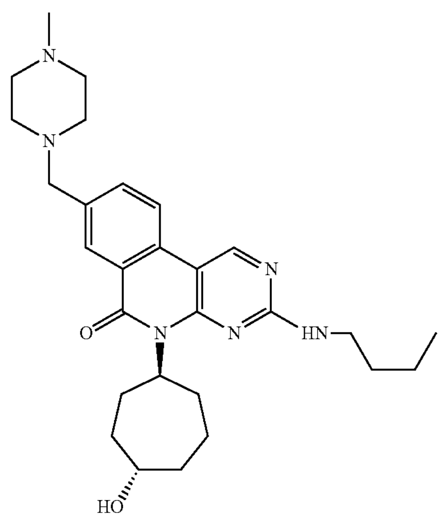 [SMILES: CCCCNc1ncc2c3ccc(CN4CCN(C)CC4)cc3c(=O)n([C@H]3CCC[C@H](O)CC3)c2n1] | 3-(Butylamino)-5-((1S,4S)-4-hydroxycycloheptyl)-8-((4-methylpiperazin-1-yl)methyl)pyrimido[4,5-c]isoquinolin-6(5H)-one |
| 58 | 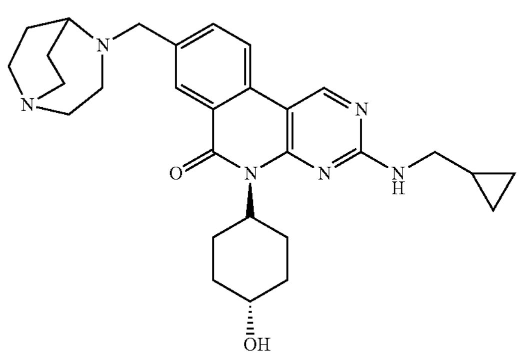 | trans-8-((1,4-Diazabicyclo[3.2.2]nonan-4-yl)methyl)-3-((cyclopropylmethyl)amino)-5-(4-hydroxycyclohexyl)pyrimido[4,5-c]isoquinolin-6(5H)-one |
| 59 | 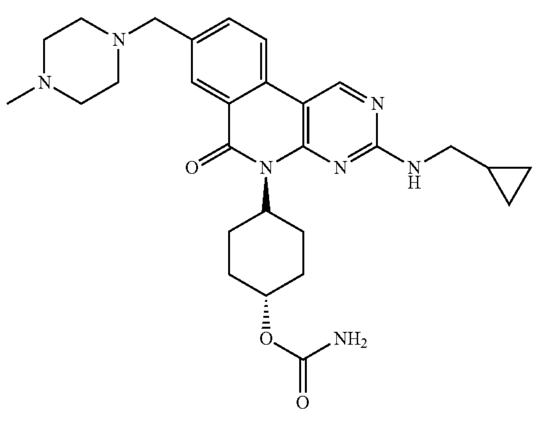 | trans-4-(3-((Cyclopropylmethyl)amino)-8-((4-methylpiperazin-1-yl)methyl)-6-oxopyrimido[4,5-c]isoquinolin-5(6H)-yl)cyclohexyl carbamate |

-continued

| No. | Structure | Name |
|---|---|---|
| 60 | 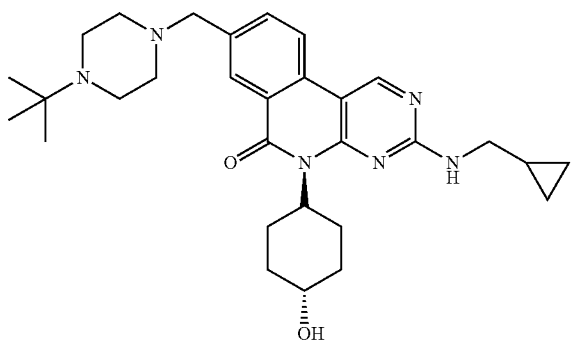 | trans-8-((4-(tert-butyl)piperazin-1-yl)methyl)-3-((cyclopropylmethyl)amino)-5-(4-hydroxycyclohexyl)pyrimido[4,5-c]isoquinolin-6(5H)-one |
| 61 | 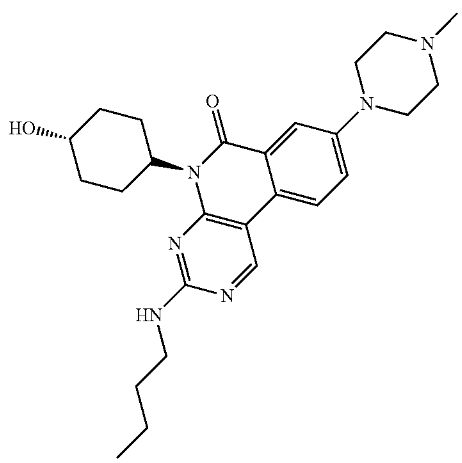 | trans-3-(Butylamino)-5-(4-hydroxycyclohexyl)-8-(4-methylpiperazin-1-yl)pyrimido[4,5-c]isoquinolin-6(5H)-one |
| 62 | 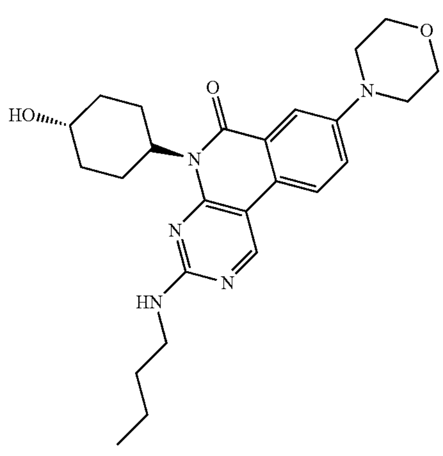 | trans-3-(Butylamino)-5-(4-hydroxycyclohexyl)-8-morpholinopyrimido[4,5-c]isoquinolin-6(5H)-one |

-continued

| No. | Structure | Name |
|---|---|---|
| 63 | 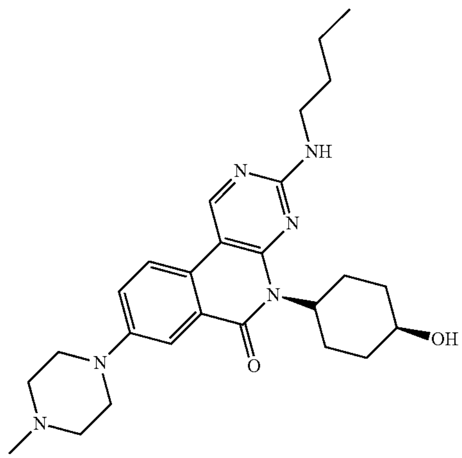 | cis-3-(Butylamino)-5-(4-hydroxycyclohexyl)-8-(4-methylpiperazin-1-yl)pyrimido[4,5-c]isoquinolin-6(5H)-one |
| 64 | 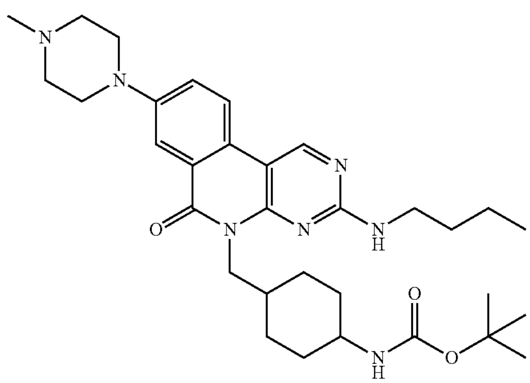 [SMILES: CCCCNc1ncc2c3ccc(N4CCN(C)CC4)cc3c(=O)n(CC3CCC(NC(=O)OC(C)(C)C)CC3)c2n1] | tert-Butyl (4-((3-(Butylamino)-8-(4-methylpiperazin-1-yl)-6-oxopyrimido[4,5-c]isoquinolin-5(6H)-yl)methyl)cyclohexyl)carbamate |
| 65 | 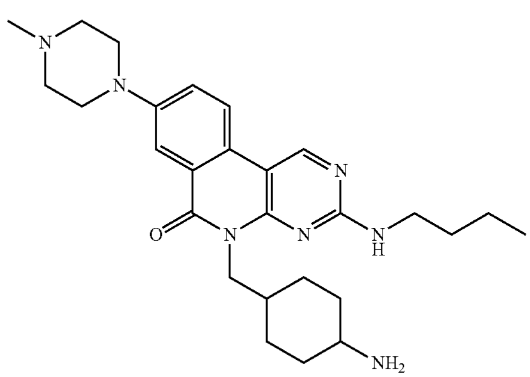 [SMILES: CCCCNc1ncc2c3ccc(N4CCN(C)CC4)cc3c(=O)n(CC3CCC(N)CC3)c2n1] | 5-((4-Aminocyclohexyl)methyl)-3-(butylamino)-8-(4-methylpiperazin-1-yl)pyrimido[4,5-c]isoquinolin-6(5H)-one |

-continued
| No. | Structure | Name |
|---|---|---|
| 66 | 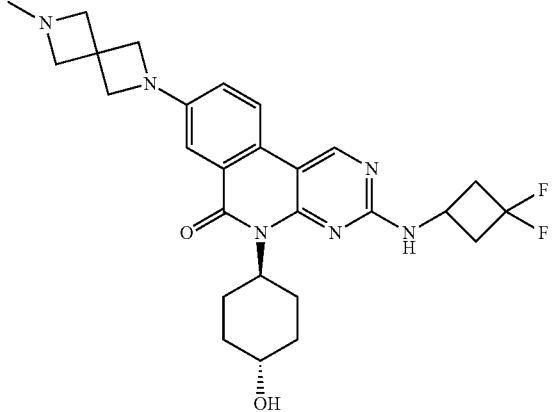 [SMILES: CN1CC2(C1)CN(c1ccc3c(c1)c(=O)n([C@H]1CC[C@H](O)CC1)c1nc(NC4CC(F)(F)C4)ncc31)C2] | trans-3-((3,3-Difluorocyclobutyl)amino)-5-(4-hydroxycyclohexyl)-8-(6-methyl-2,6-diazaspiro[3.3]heptan-2-yl)pyrimido[4,5-c]isoquinolin-6(5H)-one |
| 67 | 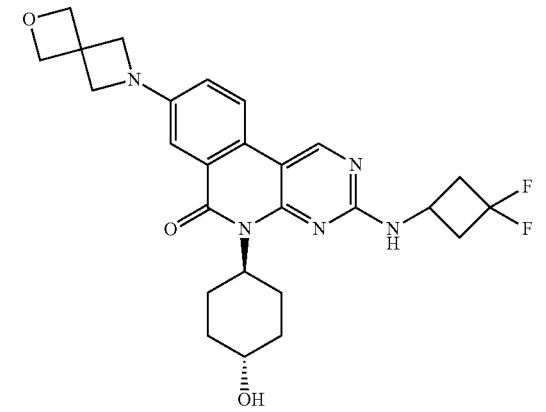 [SMILES: O=c1c2cc(N3CC4(COC4)C3)ccc2c2cnc(NC3CC(F)(F)C3)nc2n1[C@H]1CC[C@H](O)CC1] | trans-3-((3,3-difluorocyclobutyl)amino)-5-(4-hydroxycyclohexyl)-8-(2-oxa-6-azaspiro[3.3]heptan-6-yl)pyrimido[4,5-c]isoquinolin-6(5H)-one |
| 68 | 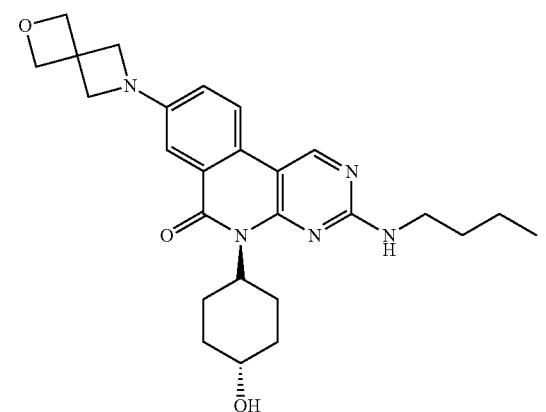 | trans-3-(Butylamino)-5-(4-hydroxycyclohexyl)-8-(2-oxa-6-azaspiro[3.3]heptan-6-yl)pyrimido[4,5-c]isoquinolin-6(5H)-one |

| No. | Structure | Name |
|---|---|---|
| 69 | 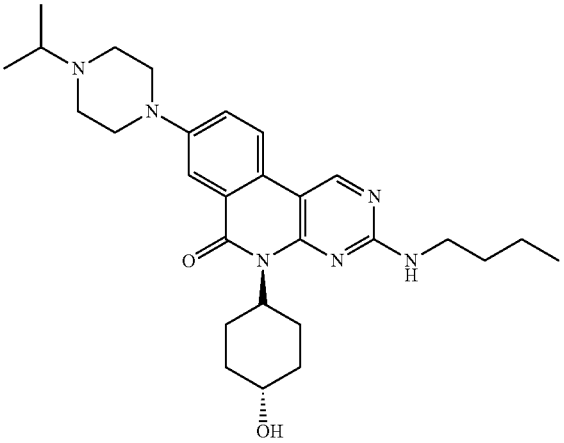 | trans-3-(Butylamino)-5-(4-hydroxycyclohexyl)-8-(4-isopropylpiperazin-1-yl)pyrimido[4,5-c]isoquinolin-6(5H)-one |
| 70 | 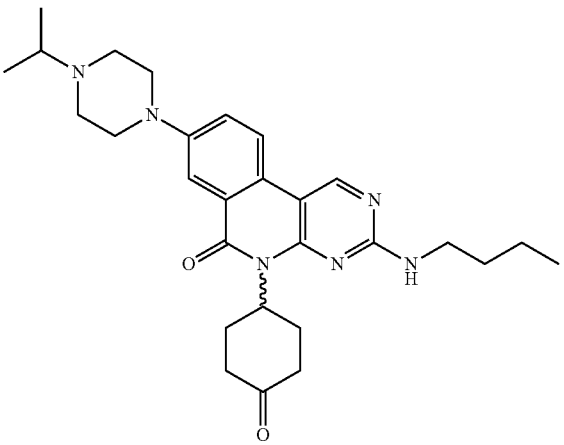 [SMILES: CCCCNc1ncc2c3ccc(N4CCN(C(C)C)CC4)cc3c(=O)n(C3CCC(=O)CC3)c2n1] | 3-(Butylamino)-8-(4-isopropylpiperazin-1-yl)-5-(4-oxocyclohexyl)pyrimido[4,5-c]isoquinolin-6(5H)-one |
| 71 | 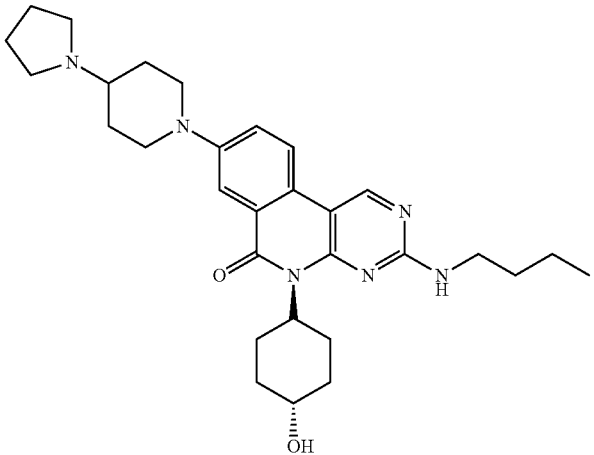 | trans-3-(Butylamino)-5-(4-hydroxycyclohexyl)-8-(4-(pyrrolidin-1-yl)piperidin-1-yl)pyrimido[4,5-c]isoquinolin-6(5H)-one |

| No. | Structure | Name |
|---|---|---|
| 72 | 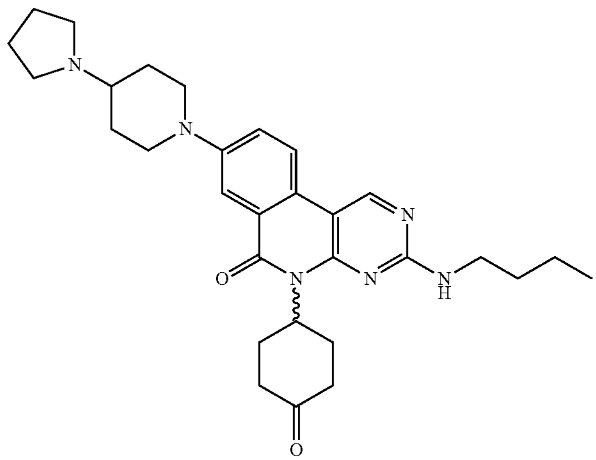 [SMILES: CCCCNc1ncc2c3ccc(N4CCC(N5CCCC5)CC4)cc3c(=O)n(C3CCC(=O)CC3)c2n1] | 3-(Butylamino)-5-(4-oxocyclohexyl)-8-(4-(pyrrolidin-1-yl)piperidin-1-yl)pyrimido[4,5-c]isoquinolin-6(5H)-one |
| 73 | 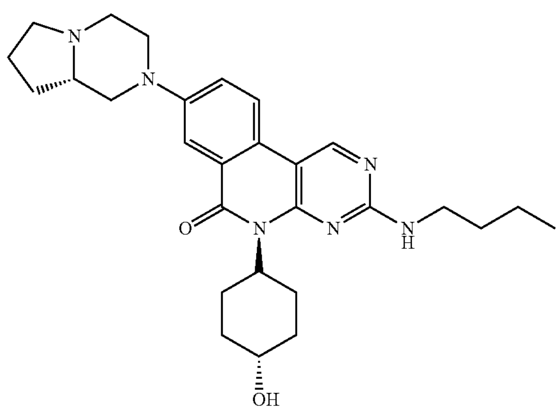 | trans-3-(Butylamino)-8-((S)-hexahydropyrrolo[1,2-a]pyrazin-2(1H)-yl)-5-((1r,4S)-4-hydroxycyclohexyl)pyrimido[4,5-c]isoquinolin-6(5H)-one |
| 74 | 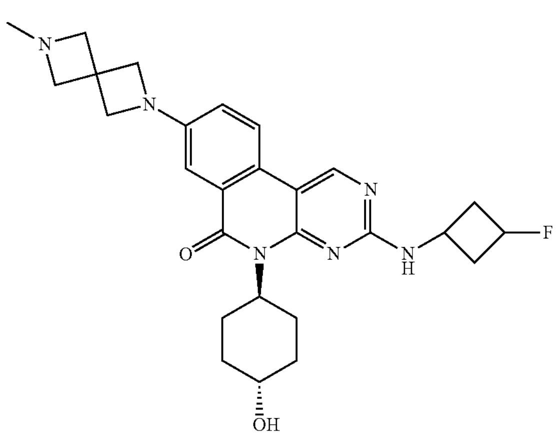 [SMILES: CN1CC2(C1)CN(c1ccc3c(c1)c(=O)n([C@H]1CC[C@H](O)CC1)c1nc(NC4CC(F)C4)ncc31)C2] | trans-3-((3-Fluorocyclobutyl)amino)-5-(4-hydroxycyclohexyl)-8-(6-methyl-2,6-diazaspiro[3.3]heptan-2-yl)pyrimido[4,5-c]isoquinolin-6(5H)-one |

| No. | Structure | Name |
|---|---|---|
| 75 | 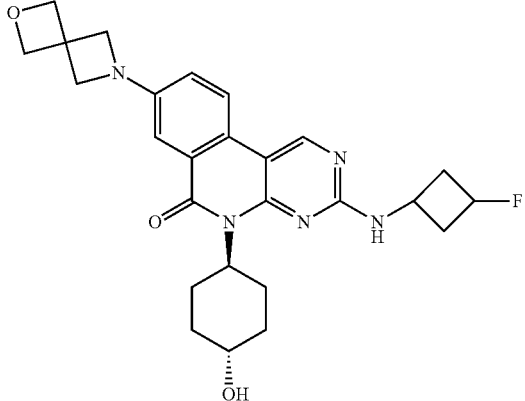 [SMILES: O=c1c2cc(N3CC4(COC4)C3)ccc2c2cnc(NC3CC(F)C3)nc2n1[C@H]1CC[C@H](O)CC1] | trans-3-((3-Fluorocyclobutyl)amino)-5-(4-hydroxycyclohexyl)-8-(2-oxa-6-azaspiro[3.3]heptan-6-yl)pyrimido[4,5-c]isoquinolin-6(5H)-one |
| 76 | 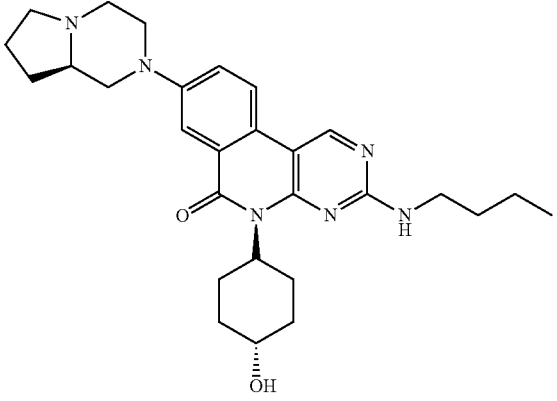 | trans-3-(Butylamino)-8-((R)-hexahydropyrrolo[1,2-a]pyrazin-2(1H)-yl)-5-(4-hydroxycyclohexyl)pyrimido[4,5-c]isoquinolin-6(5H)-one |
| 77 | 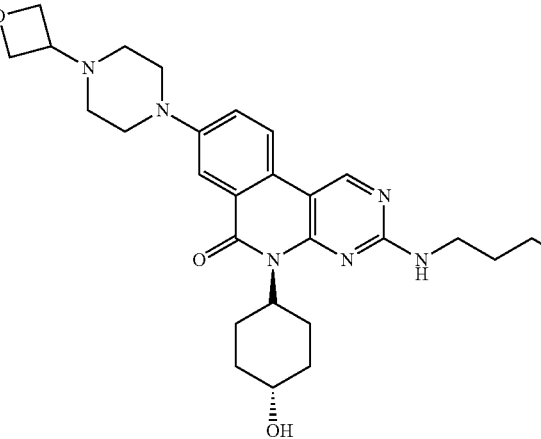 | trans-3-(Butylamino)-5-(4-hydroxycyclohexyl)-8-(4-(oxetan-3-yl)piperazin-1-yl)pyrimido[4,5-c]isoquinolin-6(5H)-one |

-continued

| No. | Structure | Name |
|---|---|---|
| 78 | 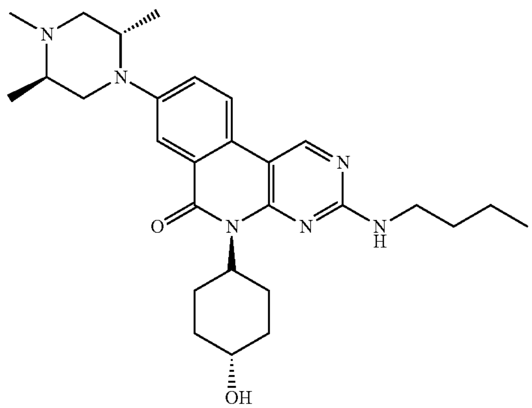 | trans-3-(Butylamino)-5-(4-hydroxycyclohexyl)-8-((2S,5R)-2,4,5-trimethylpiperazin-1-yl)pyrimido[4,5-c]isoquinolin-6(5H)-one |
| 79 | 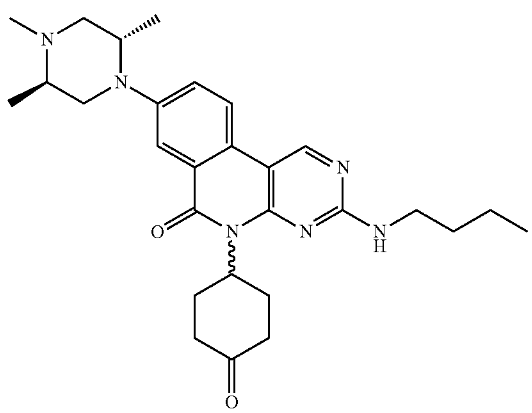 [SMILES: CCCCNc1ncc2c3ccc(N4C[C@@H](C)N(C)C[C@@H]4C)cc3c(=O)n(C3CCC(=O)CC3)c2n1] | 3-(Butylamino)-5-(4-oxocyclohexyl)-8-((2S,5R)-2,4,5-trimethylpiperazin-1-yl)pyrimido[4,5-c]isoquinolin-6(5H)-one |
| 80 | 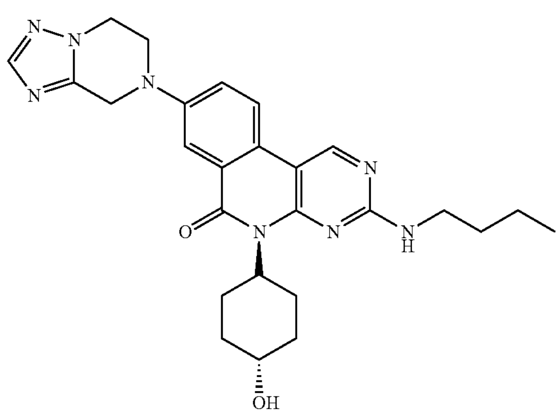 | trans-3-(Butylamino)-8-(5,6-dihydro-[1,2,4]triazolo[1,5-a]pyrazin-7(8H)-yl)-5-(4-hydroxycyclohexyl)pyrimido[4,5-c]isoquinolin-6(5H)-one |

-continued

| No. | Structure | Name |
|---|---|---|
| 81 | 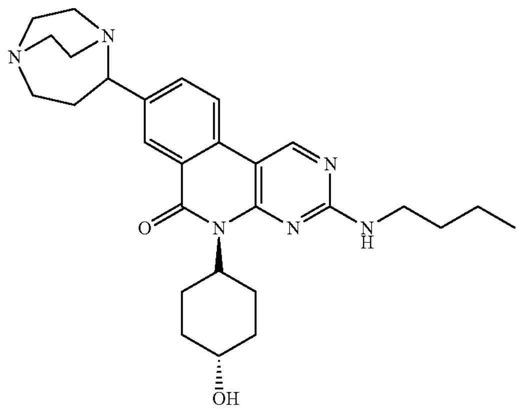 | trans-8-(1,4-Diazabicyclo[3.2.2]nonan-4-yl)-3-(butylamino)-5-(4-hydroxycyclohexyl)pyrimido[4,5-c]isoquinolin-6(5H)-one |
| 82 | 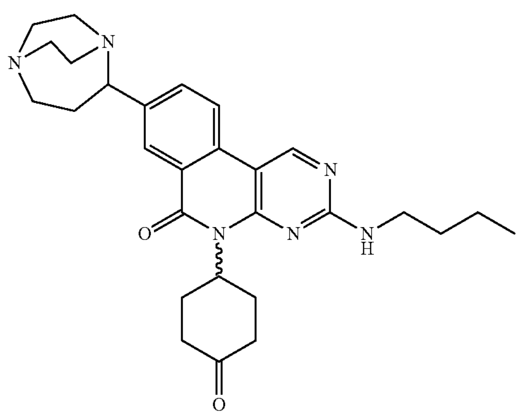 [SMILES: CCCCNc1ncc2c3ccc(C4CCN5CCN4CC5)cc3c(=O)n(C3CCC(=O)CC3)c2n1] | 8-(1,4-Diazabicyclo[3.2.2]nonan-4-yl)-3-(butylamino)-5-(4-oxocyclohexyl)pyrimido[4,5-c]isoquinolin-6(5H)-one |
| 83 | 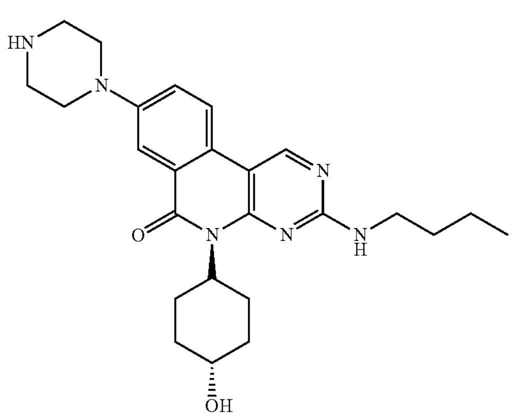 | trans-3-(Butylamino)-5-(4-hydroxycyclohexyl)-8-(piperazin-1-yl)pyrimido[4,5-c]isoquinolin-6(5H)-one |

-continued

| No. | Structure | Name |
|---|---|---|
| 84 | 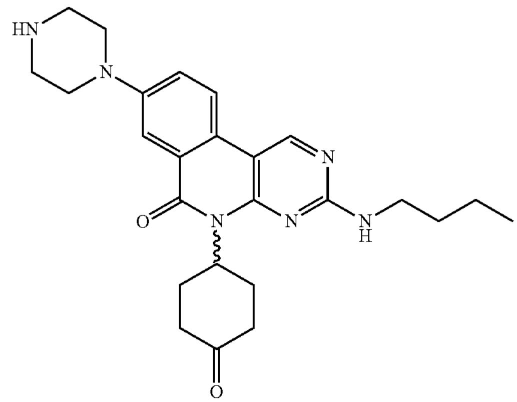 [SMILES: CCCCNc1ncc2c3ccc(N4CCNCC4)cc3c(=O)n(C3CCC(=O)CC3)c2n1] | 3-(Butylamino)-5-(4-oxocyclohexyl)-8-(piperazin-1-yl)pyrimido[4,5-c]isoquinolin-6(5H)-one |
| 85 | 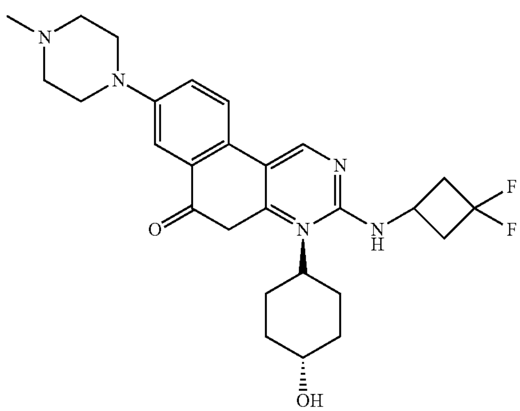 | trans-3-((3,3 Difluorocyclobutyl)amino)-5-(4-hydroxycyclohexyl)-8-(4-methylpiperazin-1-yl)pyrimido[4,5-c]isoquinolin-6(5H)-one |
| 86 | 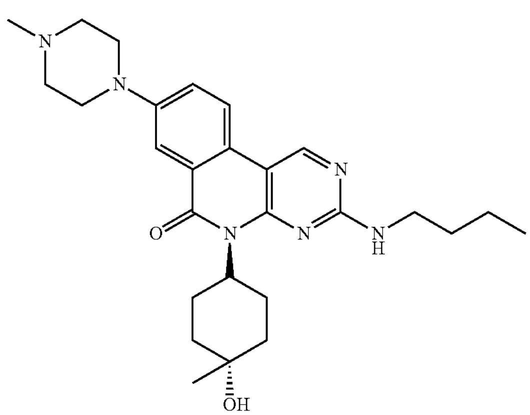 | trans-3-(Butylamino)-5-(4-hydroxy-4-methylcyclohexyl)-8-(4-methylpiperazin-1-yl)pyrimido[4,5-c]isoquinolin-6(5H)-one |

| No. | Structure | Name |
|---|---|---|
| 87 | 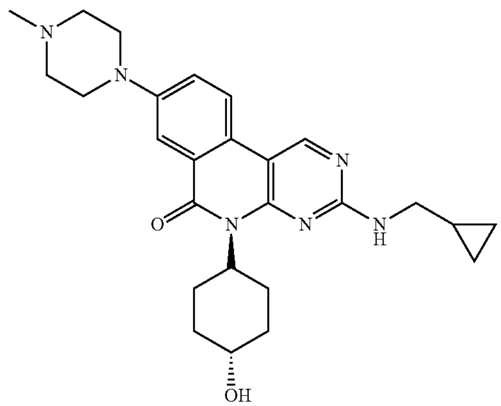 | trans-3-((Cyclopropylmethyl)amino)-5-(4-hydroxycyclohexyl)-8-(4-methylpiperazin-1-yl)pyrimido[4,5-c]isoquinolin-6(5H)-one |
| 88 | 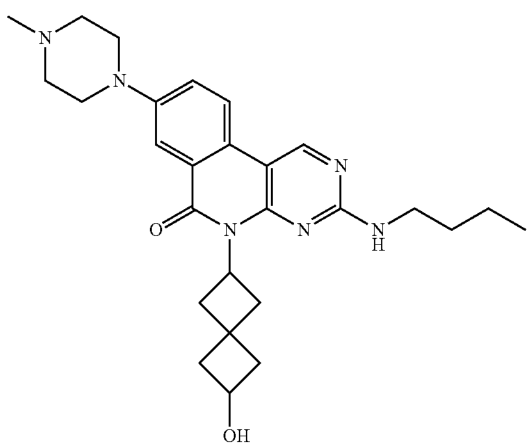 [SMILES: CCCCNc1ncc2c3ccc(N4CCN(C)CC4)cc3c(=O)n(C3CC4(CC(O)C4)C3)c2n1] | 3-(Butylamino)-5-(6-hydroxyspiro[3.3]heptan-2-yl)-8-(4-methylpiperazin-1-yl)pyrimido[4,5-c]isoquinolin-6(5H)-one |
| 89 | 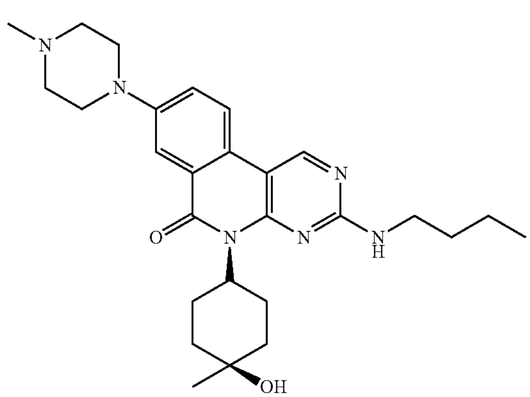 | cis-3-(Butylamino)-5-(4-hydroxy-4-methylcyclohexyl)-8-(4-methylpiperazin-1-yl)pyrimido[4,5-c]isoquinolin-6(5H)-one |

-continued

| No. | Structure | Name |
|---|---|---|
| 90 | 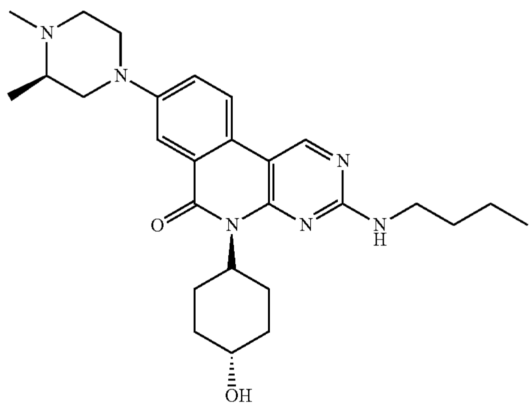 | trans-3-(Butylamino)-8-((R)-3,4-dimethylpiperazin-1-yl)-5-(4-hydroxycyclohexyl)pyrimido[4,5-c]isoquinolin-6(5H)-one |
| 91 | 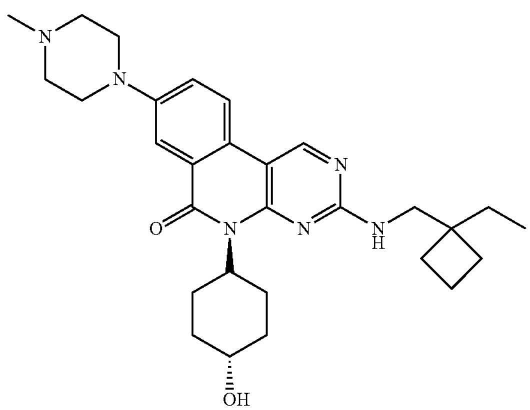 | trans-3-(((1-Ethylcyclobutyl)methyl)amino)-5-(4-hydroxycyclohexyl)-8-(4-methylpiperazin-1-yl)pyrimido[4,5-c]isoquinolin-6(5H)-one |
| 92 | 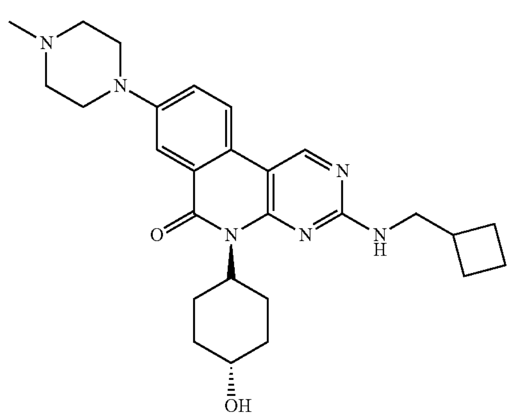 | trans-3-((Cyclobutylmethyl)amino)-5-(4-hydroxycyclohexyl)-8-(4-methylpiperazin-1-yl)pyrimido[4,5-c]isoquinolin-6(5H)-one |

-continued

| No. | Structure | Name |
|---|---|---|
| 93 | 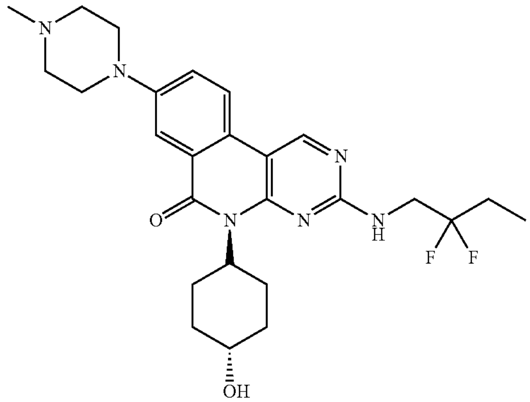 | trans-3-((2,2-Difluorobutyl)amino)-5-(4-hydroxycyclohexyl)-8-(4-methylpiperazin-1-yl)pyrimido[4,5-c]isoquinolin-6(5H)-one |
| 94 | 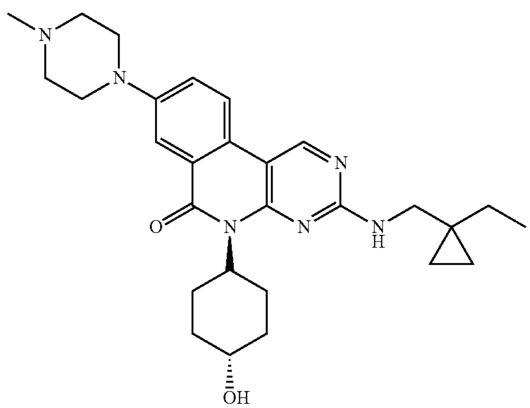 | trans-3-(((1-Ethylcyclopropyl)methyl)amino)-5-(4-hydroxycyclohexyl)-8-(4-methylpiperazin-1-yl)pyrimido[4,5-c]isoquinolin-6(5H)-one |
| 95 | 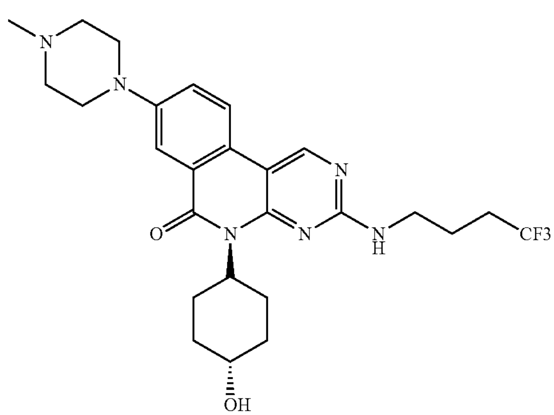 | trans-5-(4-Hydroxycyclohexyl)-8-(4-methylpiperazin-1-yl)-3-((4,4,4-trifluorobutyl)amino)pyrimido-[4,5-c]isoquinolin-6(5H)-one |

-continued

| No. | Structure | Name |
|---|---|---|
| 96 | 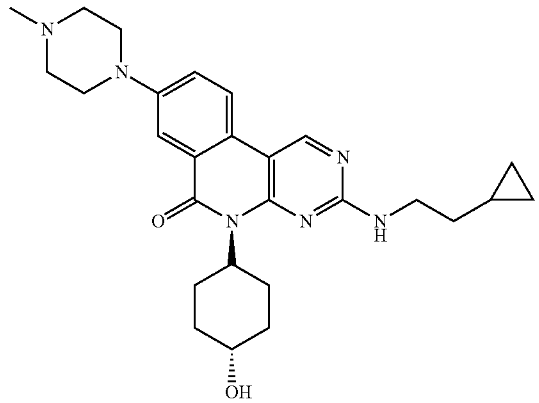 | trans-3-((2-Cyclopropylethyl)amino)-5-(4-hydroxycyclohexyl)-8-(4-methylpiperazin-1-yl)pyrimido[4,5-c]isoquinolin-6(5H)-one |
| 97 | 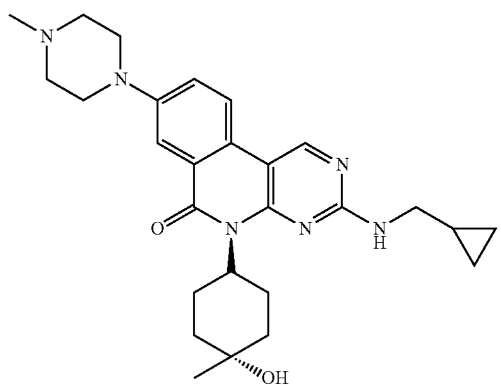 | trans-3-((Cyclopropylmethyl)amino)-5-(4-hydroxy-4-methylcyclohexyl)-8-(4-methylpiperazin-1-yl)pyrimido[4,5-c]isoquinolin-6(5H)-one |
| 98 | 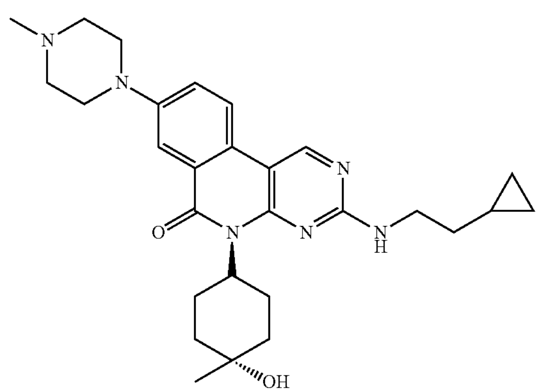 | trans-3-((2-Cyclopropylethyl)amino)-5-(4-hydroxy-4-methylcyclohexyl)-8-(4-methylpiperazin-1-yl)pyrimido[4,5-c]isoquinolin-6(5H)-one |

| No. | Structure | Name |
|---|---|---|
| 99 | 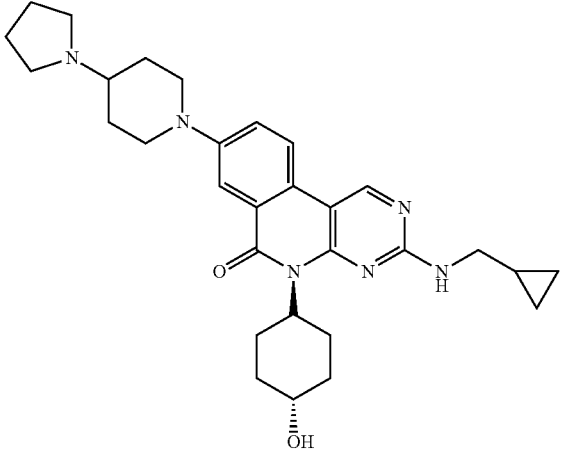 | trans-3-((Cyclopropylmethyl)amino)-5-(4-hydroxycyclohexyl)-8-(4-(pyrrolidin-1-yl)piperidin-1-yl)pyrimido[4,5-c]isoquinolin-6(5H)-one |
| 100 | 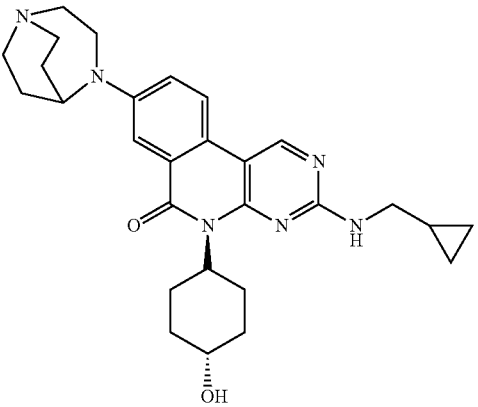 | trans-8-(1,4-diazabicyclo[3.2.2]nonan-4-yl)-3-((cyclopropylmethyl)amino)-5-(4-hydroxycyclohexyl)pyrimido[4,5-c]isoquinolin-6(5H)-one |
| 101 | 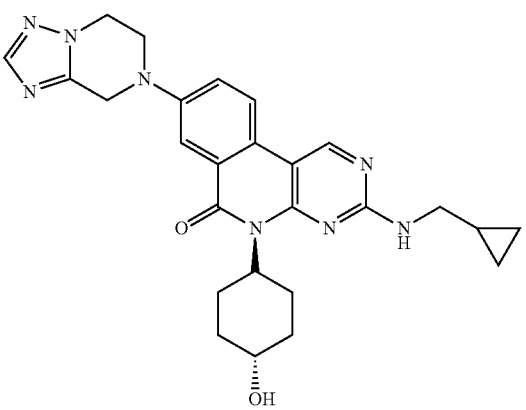 | trans-3-((Cyclopropylmethyl)amino)-8-(5,6-dihydro-[1,2,4]triazolo[1,5-a]pyrazin-7(8H)-yl)-5-(4-hydroxycyclohexyl)pyrimido[4,5-c]isoquinolin-6(5H)-one |

| No. | Structure | Name |
|---|---|---|
| 102 | 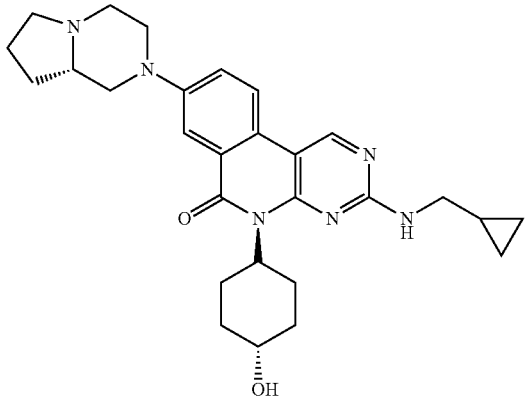 | trans-3-((Cyclopropylmethyl)amino)-8-((S)-hexahydropyrrolo[1,2-a]pyrazin-2(1H)-yl)-5-(4-hydroxycyclohexyl)pyrimido[4,5-c]isoquinolin-6(5H)-one |
| 103 | 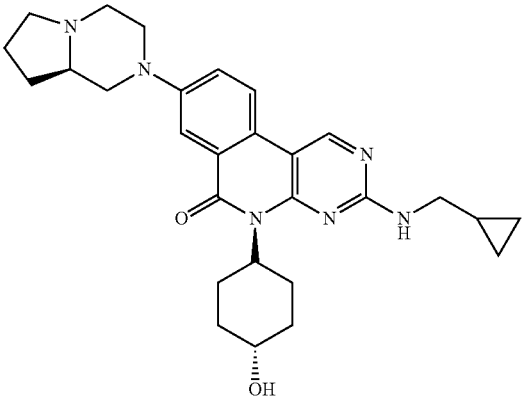 | trans-3-((Cyclopropylmethyl)amino)-8-((R)-hexahydropyrrolo[1,2-a]pyrazin-2(1H)-yl)-5-(4-hydroxycyclohexyl)pyrimido[4,5-c]isoquinolin-6(5H)-one |
| 104 | 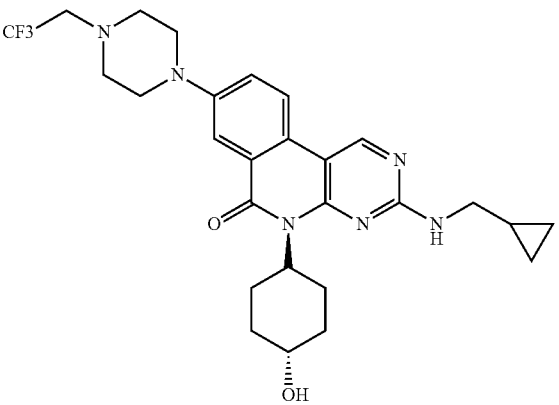 | trans-3-((Cyclopropylmethyl)amino)-5-(4-hydroxycyclohexyl)-8-(4-(2,2,2-trifluoroethyl)piperazin-1-yl)pyrimido[4,5-c]isoquinolin-6(5H)-one |

-continued
| No. | Structure | Name |
|---|---|---|
| 105 | 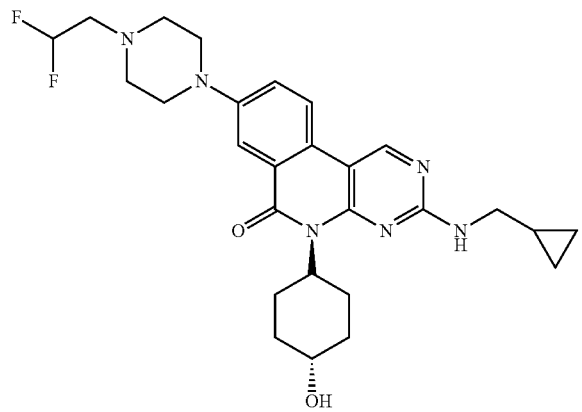 | trans-3-((Cyclopropylmethyl)amino)-8-(4-(2,2-difluoroethyl)piperazin-1-yl)-5-(4-hydroxycyclohexyl)pyrimido[4,5-c]isoquinolin-6(5H)-one |
| 106 | 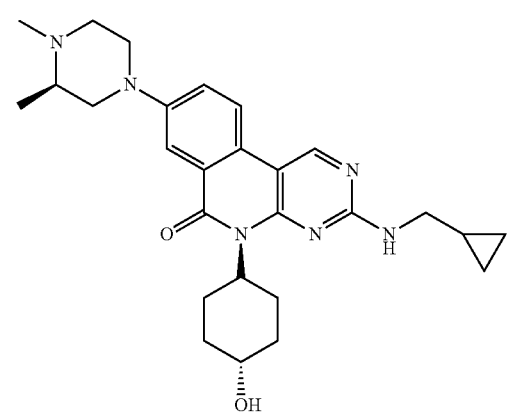 | trans-3-((Cyclopropylmethyl)amino)-8-((R)-3,4-dimethylpiperazin-1-yl)-5-(4-hydroxycyclohexyl)pyrimido[4,5-c]isoquinolin-6(5H)-one |
| 107 | 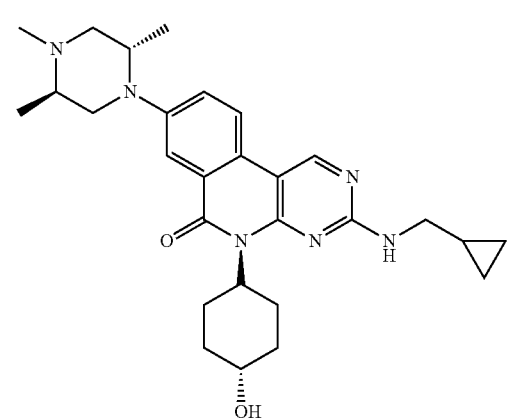 | trans-3-((Cyclopropylmethyl)amino)-5-(4-hydroxycyclohexyl)-8-((2S,5R)-2,4,5-trimethylpiperazin-1-yl)pyrimido[4,5-c]isoquinolin-6(5H)-one |

-continued

| No. | Structure | Name |
|---|---|---|
| 108 | 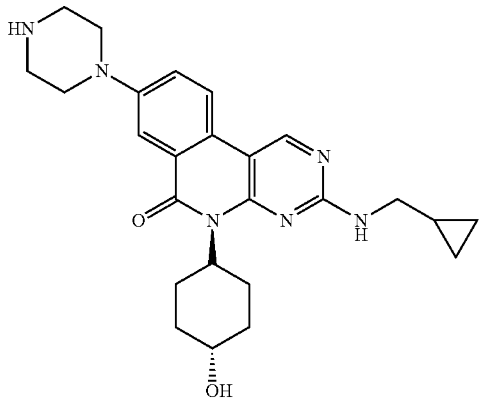 | trans-3-((Cyclopropylmethyl)amino)-5-(4-hydroxycyclohexyl)-8-(piperazin-1-yl)pyrimido[4,5-c]isoquinolin-6(5H)-one |
| 109 | 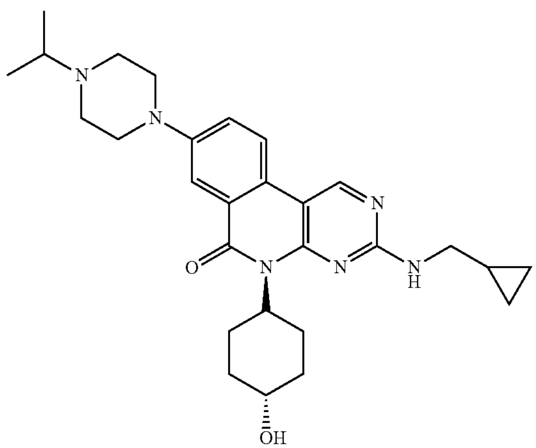 | trans-3-((Cyclopropylmethyl)amino)-5-(4-hydroxycyclohexyl)-8-(4-isopropylpiperazin-1-yl)pyrimido[4,5-c]isoquinolin-6(5H)-one |
| 110 | 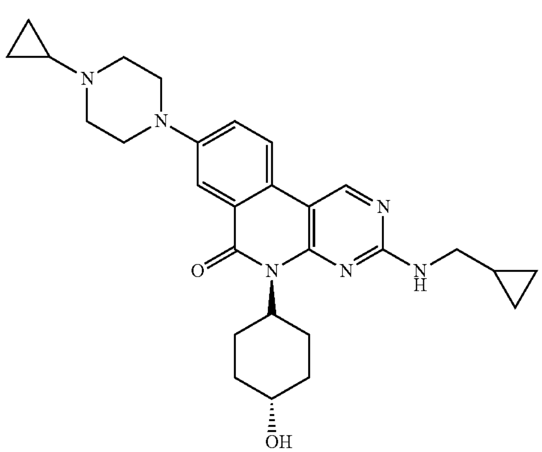 | trans-3-((Cyclopropylmethyl)amino)-8-(4-cyclopropylpiperazin-1-yl)-5-(4-hydroxycyclohexyl)pyrimido[4,5-c]isoquinolin-6(5H)-one |

-continued

| No. | Structure | Name |
|---|---|---|
| 111 | 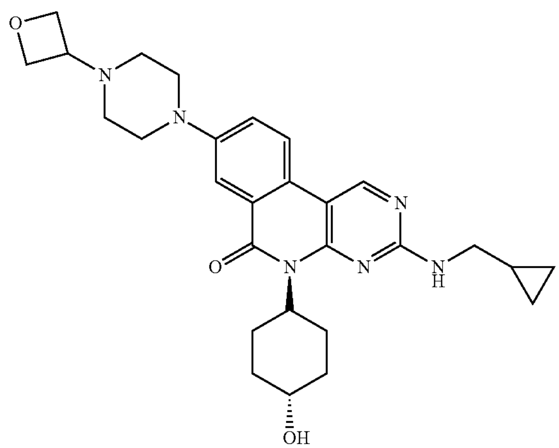 | trans-3-((Cyclopropylmethyl)amino)-5-(4-hydroxycyclohexyl)-8-(4-(oxetan-3-yl)piperazin-1-yl)pyrimido[4,5-c]isoquinolin-6(5H)-one |
| 112 | 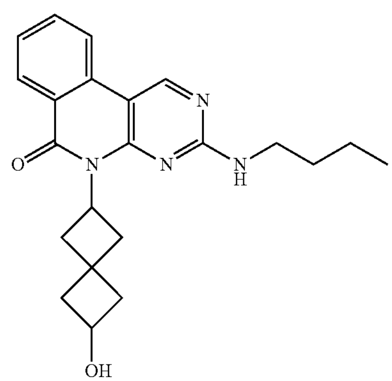 [SMILES: CCCCNc1ncc2c3ccccc3c(=O)n(C3CC4(CC(O)C4)C3)c2n1] | 3-(Butylamino)-5-(6-hydroxyspiro[3.3]heptan-2-yl)pyrimido[4,5-c]isoquinolin-6(5H)-one |
| 113 | 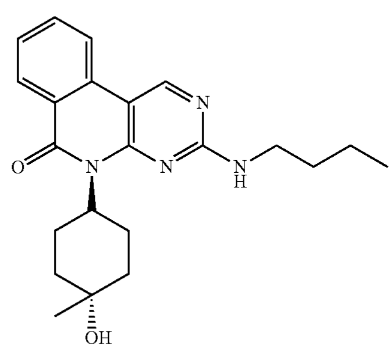 | trans-3-(Butylamino)-5-(4-hydroxy-4-methylcyclohexyl)pyrimido[4,5-c]isoquinolin-6(5H)-one |
| 114 | 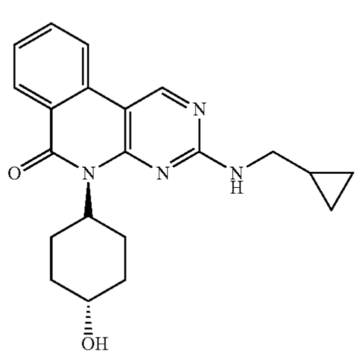 | trans-3-((Cyclopropylmethyl)amino)-5-(4-hydroxycyclohexyl)pyrimido[4,5-c]isoquinolin-6(5H)-one |

-continued

| No. | Structure | Name |
|---|---|---|
| 115 | 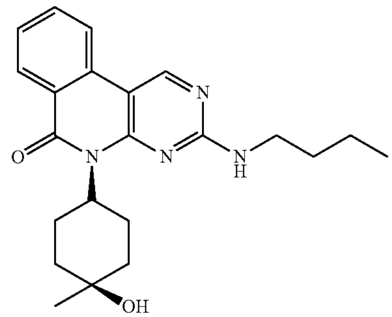 | cis-3-(Butylamino)-5-(4-hydroxy-4-methylcyclohexyl)pyrimido[4,5-c]isoquinolin-6(5H)-one |
| 116 | 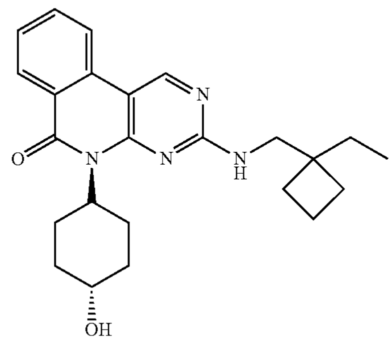 | trans-3-(((1-Ethylcyclobutyl)methyl)amino)-5-(4-hydroxycyclohexyl)pyrimido[4,5-c]isoquinolin-6(5H)-one |
| 117 | 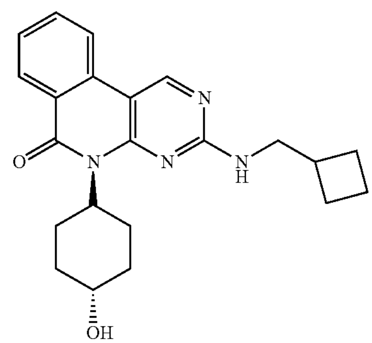 | trans-3-((Cyclobutylmethyl)amino)-5-(4-hydroxycyclohexyl)pyrimido[4,5-c]isoquinolin-6(5H)-one |
| 118 | 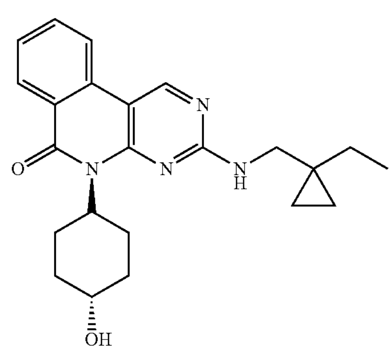 | 3-(((1-Ethylcyclopropyl)methyl)amino)-5-(4-hydroxycyclohexyl)pyrimido[4,5-c]isoquinolin-6(5H)-one |

-continued

| No. | Structure | Name |
|---|---|---|
| 119 | 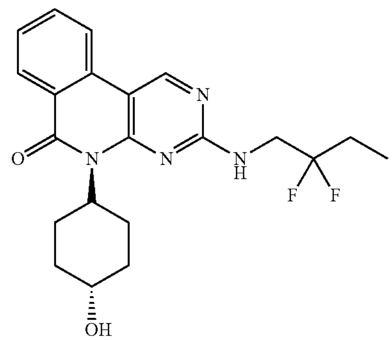 | trans-3-((2,2-difluorobutyl)amino)-5-(4-hydroxycyclohexyl)pyrimido[4,5-c]isoquinolin-6(5H)-one |
| 120 | 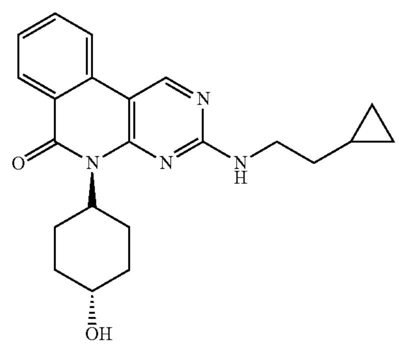 | trans-3-((2-Cyclopropylethyl)amino)-5-(4-hydroxycyclohexyl)pyrimido[4,5-c]isoquinolin-6(5H)-one |
| 121 | 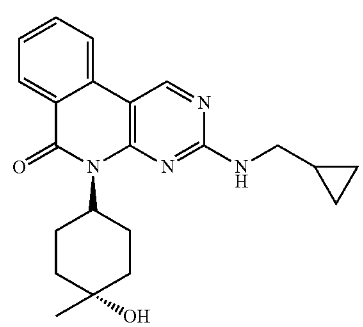 | trans-3-((Cyclopropylmethyl)amino)-5-(4-hydroxy-4-methylcyclohexyl)pyrimido[4,5-c]isoquinolin-6(5H)-one |
| 122 | 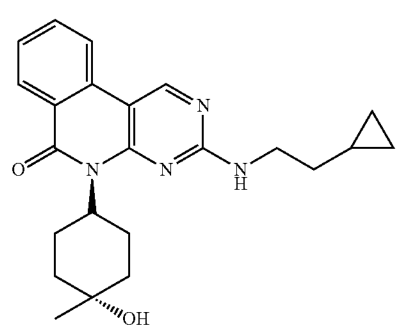 | trans-3-((2-Cyclopropylethyl)amino)-5-(4-hydroxy-4-methylcyclohexyl)pyrimido[4,5-c]isoquinolin-6(5H)-one |

| No. | Structure | Name |
| --- | --- | --- |
| 123 | 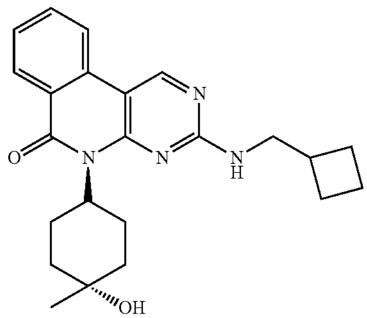 | trans-3-((Cyclobutylmethyl)amino)-5-(4-hydroxy-4-methylcyclohexyl)pyrimido[4,5-c]isoquinolin-6(5H)-one |
| 124 | 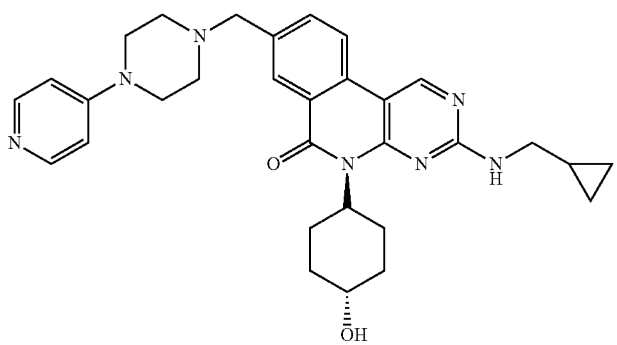 | trans-3-((Cyclopropylmethyl)amino)-5-(4-hydroxycyclohexyl)-8-((4-(pyridin-4-yl)piperazin-1-yl)methyl)pyrimido[4,5-c]isoquinolin-6(5H)-one |
| 125 | 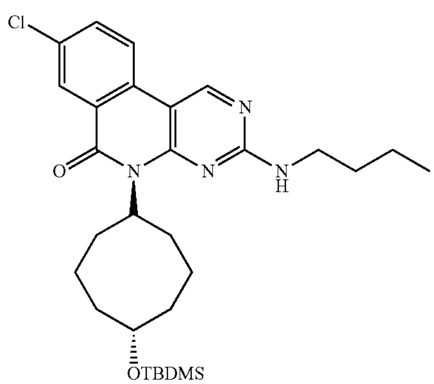 | 3-(Butylamino)-5-((1r,5r)-5-((tert-butyldimethylsilyl)oxy)-cyclooctyl)-8-chloropyrimido[4,5-c]isoquinolin-6(5H)-one |
| 126 | 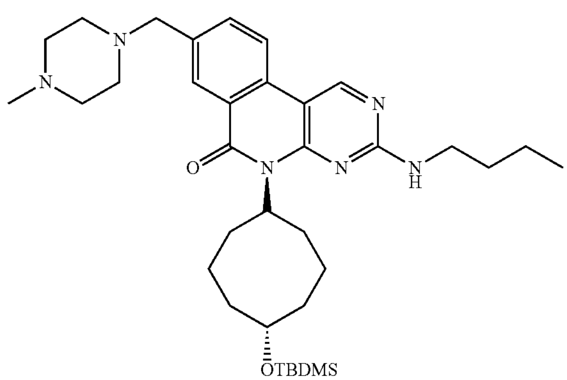 | 3-(Butylamino)-5-((1r,5r)-5-((tert-butyldimethylsilyl)-oxy)cyclooctyl)-8-((4-methylpiperazin-1-yl)methyl)pyrimido[4,5-c]isoquinolin-6(5H)-one |

| No. | Structure | Name |
|---|---|---|
| 127 | 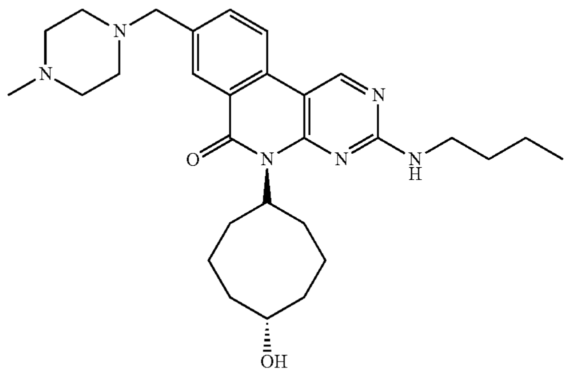 | 3-(Butylamino)-5-((1r,5r)-5-hydroxycyclooctyl)-8-((4-methylpiperazin-1-yl)methyl)pyrimido[4,5-c]isoquinolin-6(5H)-one |
| 128 | 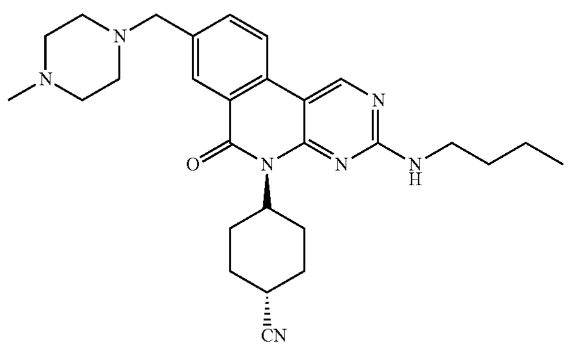 | |
| 129 | 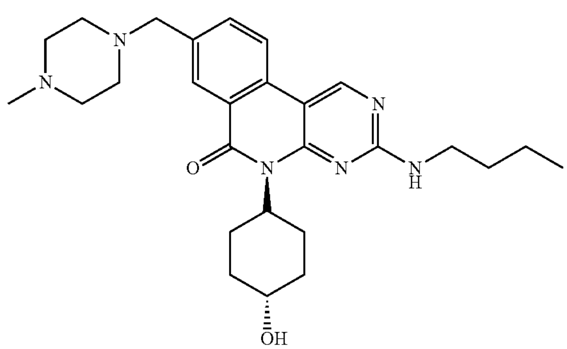 | |
| 130 | 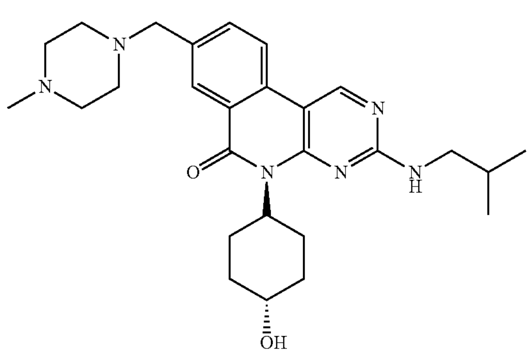 | trans-5-(4-hydroxycyclohexyl)-3-(isobutylamino)-8-((4-methylpiperazin-1-yl)methyl)pyrimido[4,5-c]isoquinolin-6(5H)-one |

| No. | Structure | Name |
|---|---|---|
| 131 | 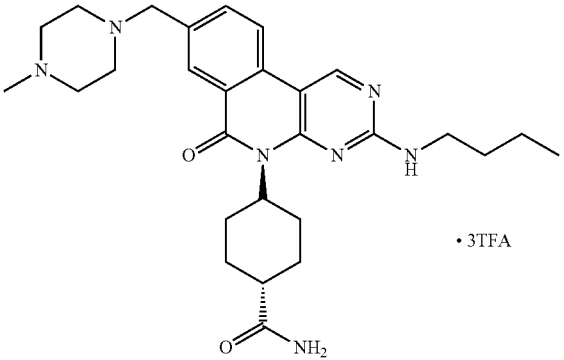 •3TFA | trans-4-(3-(Butylamino)-8-((4-methylpiperazin-1-yl)methyl)-6-oxopyrimido[4,5-c]isoquinolin-5(6H)-yl)cyclohexane-1-carboxamide |
| 132 | 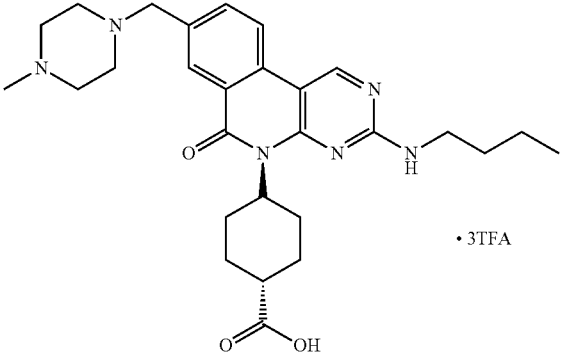 •3TFA | trans-4-(3-(Butylamino)-8-((4-methylpiperazin-1-yl)methyl)-6-oxopyrimido[4,5-c]isoquinolin-5(6H)-yl)cyclohexane-1-carboxylic acid |
| 133 | 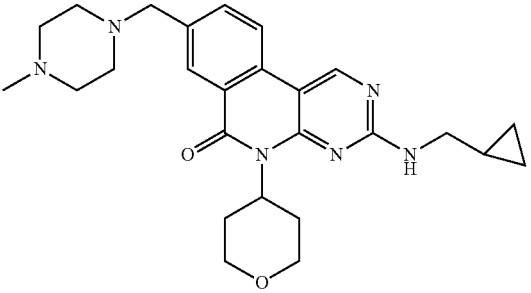 [SMILES: CN1CCN(Cc2ccc3c(c2)c(=O)n(C2CCOCC2)c2nc(NCC4CC4)ncc32)CC1] | |
| 134 | 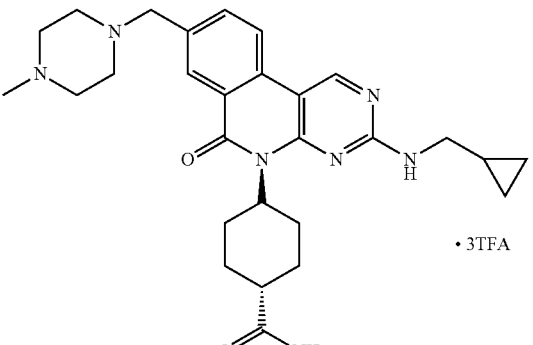 •3TFA | trans-4-(3-((Cyclopropylmethyl)amino)-8-((4-methylpiperazin-1-yl)methyl)-6-oxopyrimido[4,5-c]isoquinolin-5(6H)-yl)cyclohexane-1-carboxamide |

| No. | Structure | Name |
|---|---|---|
| 135 | 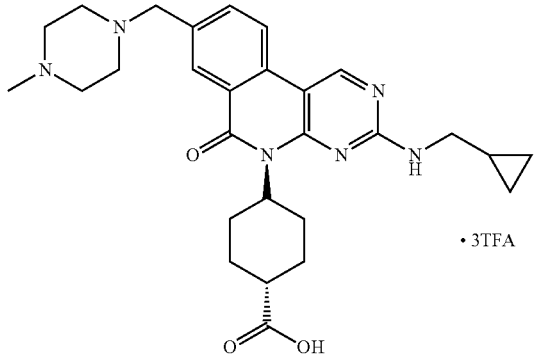 • 3TFA | trans-4-(3-((Cyclopropylmethyl)amino)-8-((4-methylpiperazin-1-yl)methyl)-6-oxopyrimido[4,5-c]isoquinolin-5(6H)-yl)cyclohexane-1-carboxylic acid |
| 136 | 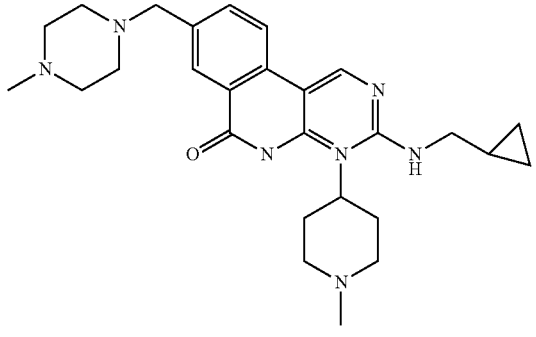 | |
| 137 | 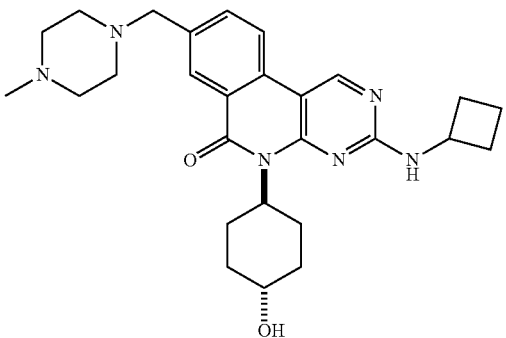 | trans-3-(cyclobutylamino)-5-(4-hydroxycyclohexyl)-8-((4-methylpiperazin-1-yl)methyl)pyrimido[4,5-c]isoquinolin-6(5H)-one |
| 138 | 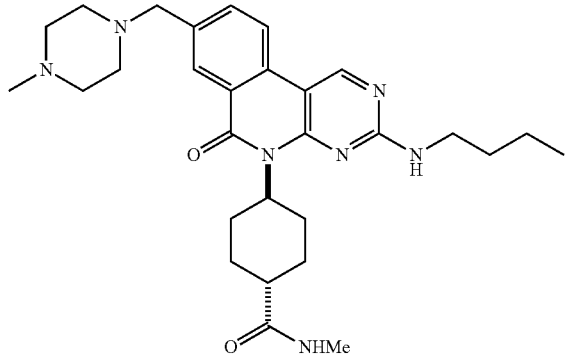 | trans-4-(3-(Butylamino)-8-((4-methylpiperazin-1-yl)methyl)-6-oxopyrimido[4,5-c]isoquinolin-5(6H)-yl)-N-methylcyclohexane-1-carboxamide |

-continued

| No. | Structure | Name |
|---|---|---|
| 139 | 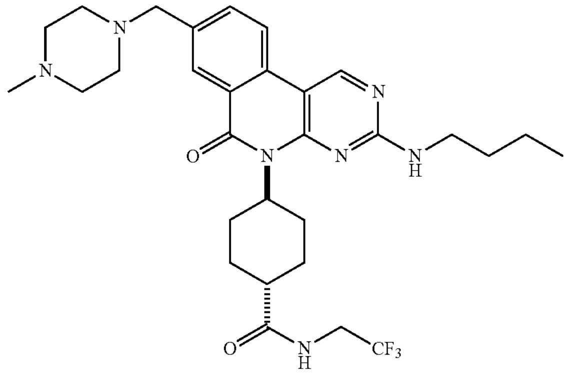 | trans-4-(3-(Butylamino)-8-((4-methylpiperazin-1-yl)methyl)-6-oxopyrimido[4,5-c]isoquinolin-5(6H)-yl)-N-(2,2,2-trifluoroethyl)cyclohexane-1-carboxamide |
| 140 | 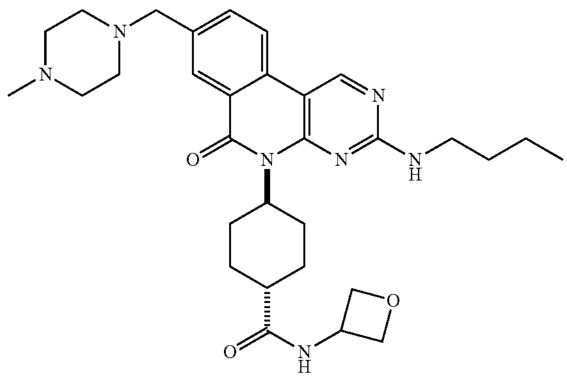 | trans-4-(3-(Butylamino)-8-((4-methylpiperazin-1-yl)methyl)-6-oxopyrimido[4,5-c]isoquinolin-5(6H)-yl)-N-(oxetan-3-yl)cyclohexane-1-carboxamide |
| 141 | · 3HCO$_2$H | trans-4-(3-(Butylamino)-8-((4-methylpiperazin-1-yl)methyl)-6-oxopyrimido[4,5-c]isoquinolin-5(6H)-yl)-N-(cyclopropylmethyl)cyclohexane-1-carboxamide |
| 142 | · 3TFA | trans-4-(3-(Butylamino)-8-((4-methylpiperazin-1-yl)methyl)-6-oxopyrimido[4,5-c]isoquinolin-5(6H)-yl)-N,N-dimethylcyclohexane-1-carboxamide |

-continued

| No. | Structure | Name |
|---|---|---|
| 143 | 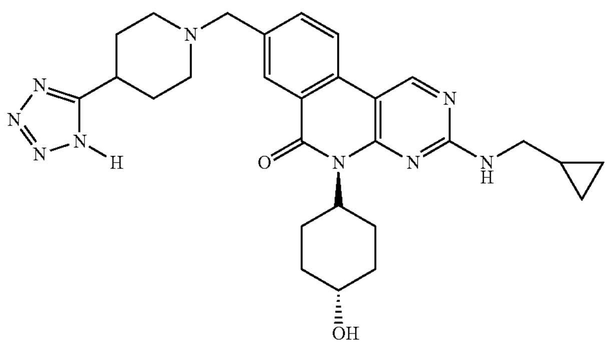 | 8-((4-(1H-tetrazol-5-yl)piperidin-1-yl)methyl)-3-((cyclopropylmethyl)amino)-5-((1s,4s)-4-hydroxycyclohexyl)pyrimido-[4,5-c]isoquinolin-6(5H)-one |
| 144 | 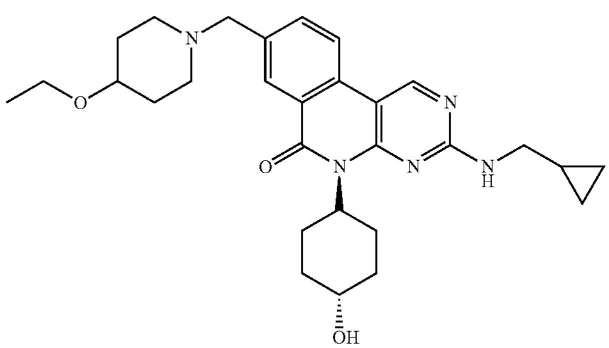 | 3-((cyclopropylmethyl)amino)-8-((4-ethoxypiperidin-1-yl)methyl)-5-((1s,4s)-4-hydroxycyclohexyl)pyrimido-[4,5-c]isoquinolin-6(5H)-one |
| 145 | 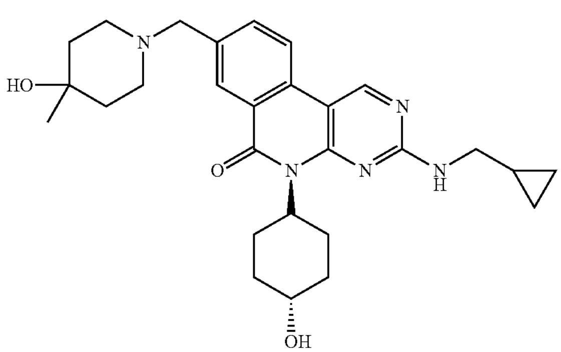 | 3-((cyclopropylmethyl)amino)-8-((4-hydroxy-4-methylpiperidin-1-yl)methyl)-5-((1s,4s)-4-hydroxycyclohexyl)pyrimido-[4,5-c]isoquinolin-6(5H)-one |
| 146 | 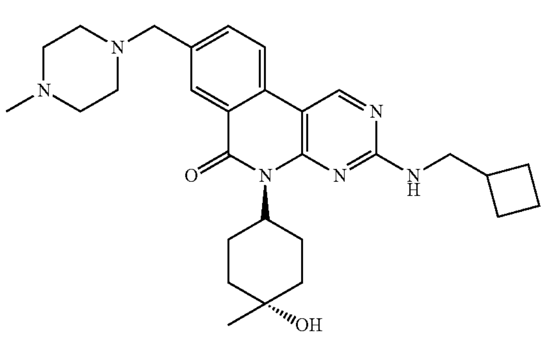 | |

| No. | Structure | Name |
|---|---|---|
| 147 | 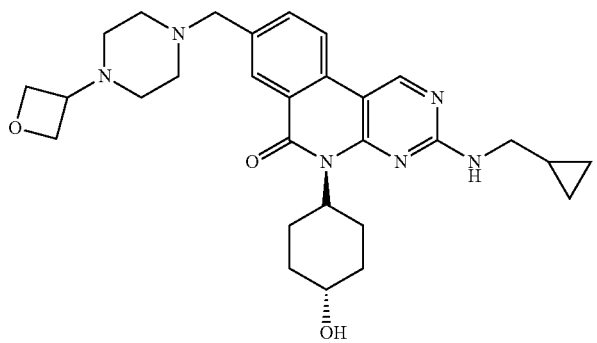 | |
| 148 | 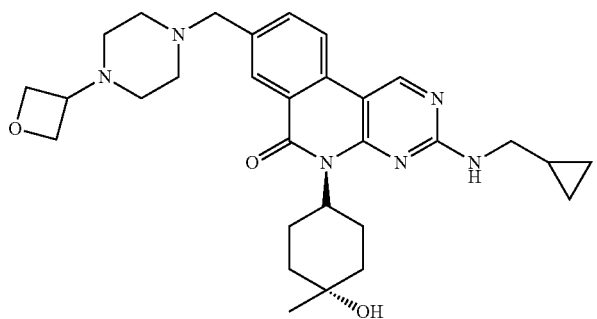 | |
| 149 | 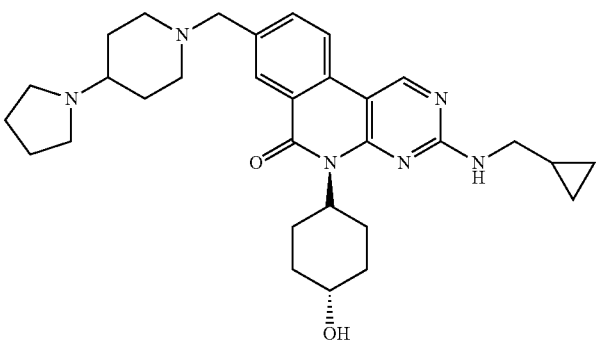 | |
| 150 | 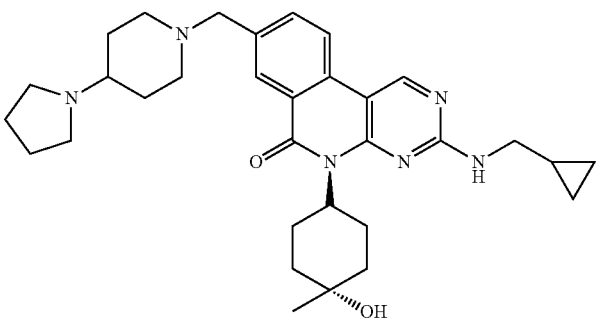 | |

| No. | Structure | Name |
|---|---|---|
| 151 | 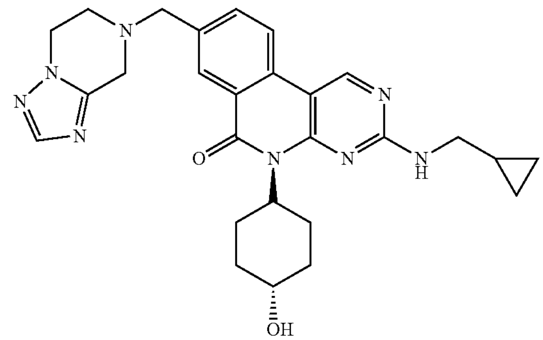 | |
| 152 | 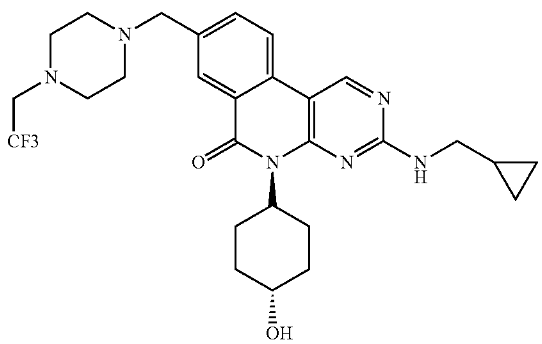 | |
| 153 | 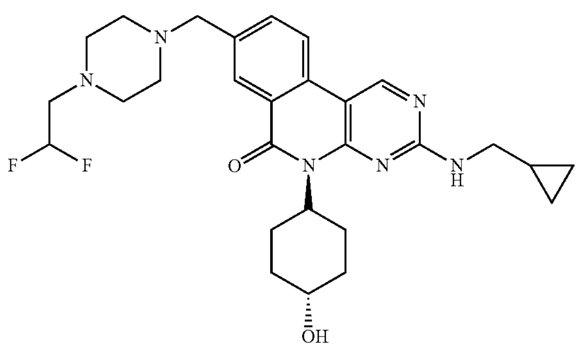 | |
| 154 | 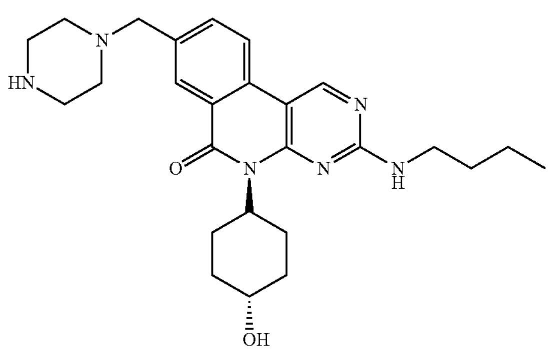 | |

| No. | Structure | Name |
|---|---|---|
| 155 | 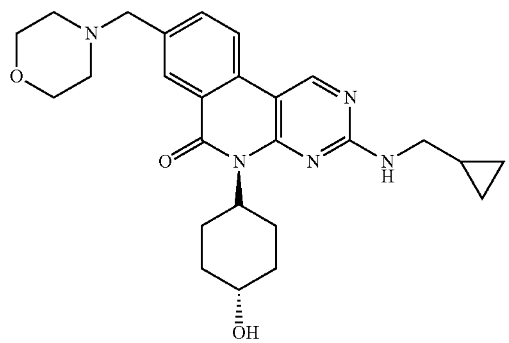 | |
| 156 | 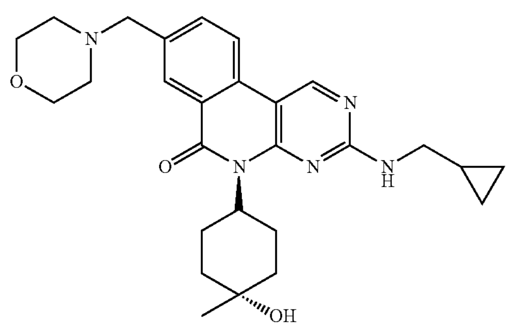 | |
| 157 | 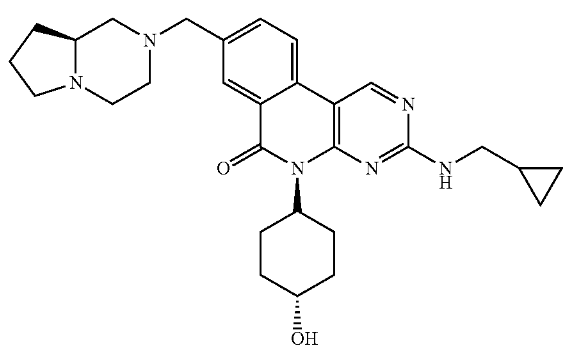 | |
| 158 | 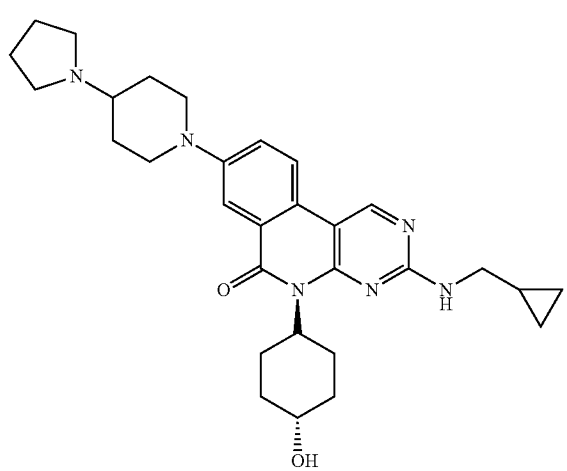 | |

-continued

| No. | Structure | Name |
|---|---|---|
| 159 | 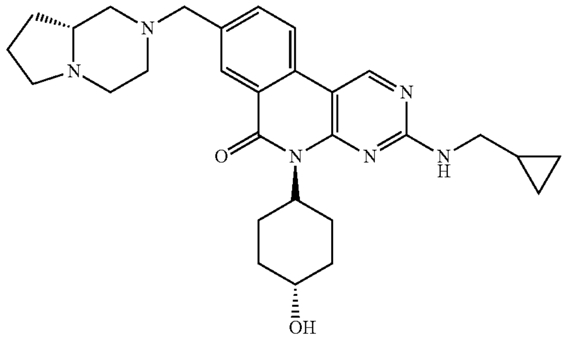 | |
| 160 | 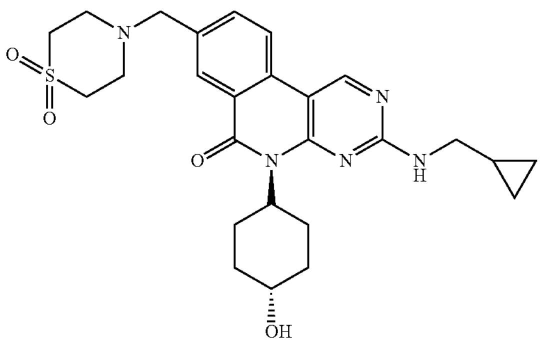 | |
| 161 | 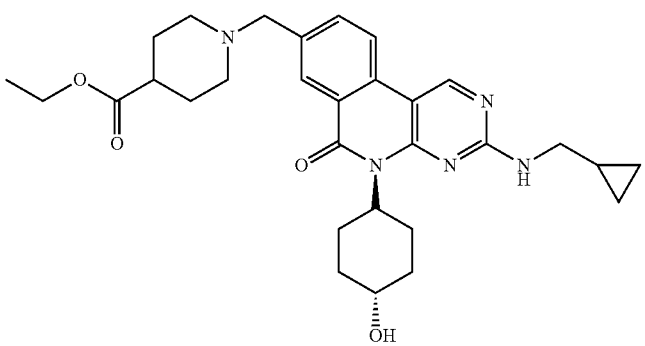 | |
| 162 | 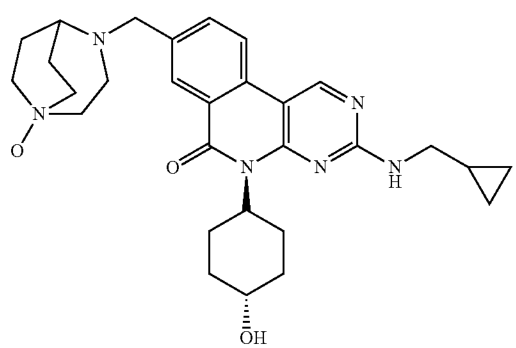 | |

| No. | Structure | Name |
|---|---|---|
| 163 | 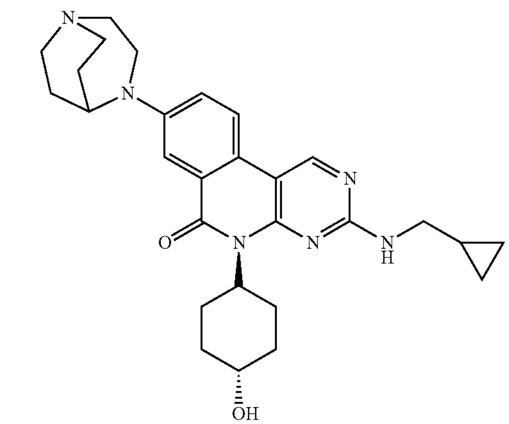 | |
| 164 | 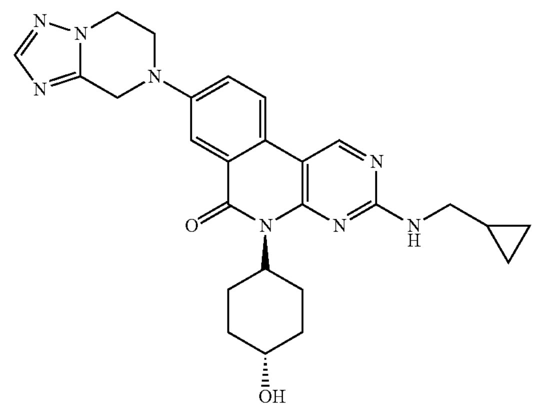 | |
| 165 | 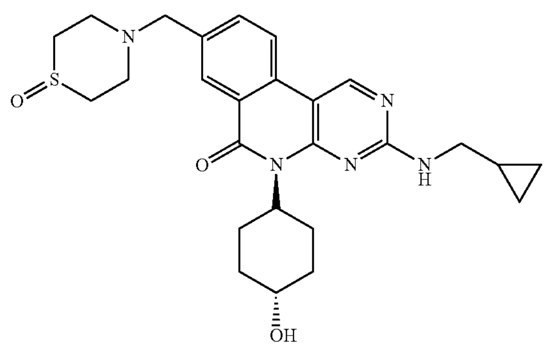 | |
| 166 | 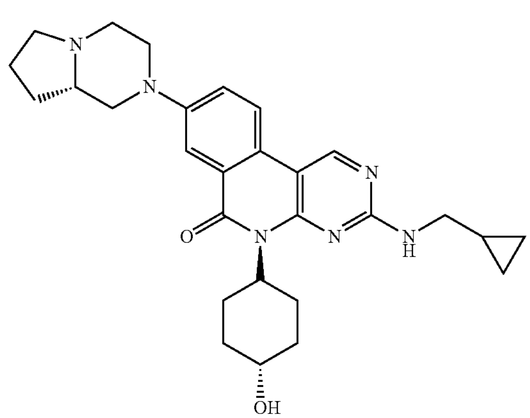 | |

-continued
| No. | Structure | Name |
|---|---|---|
| 167 | 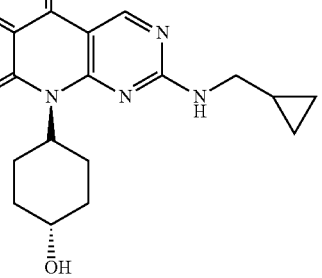 | |
| 168 | 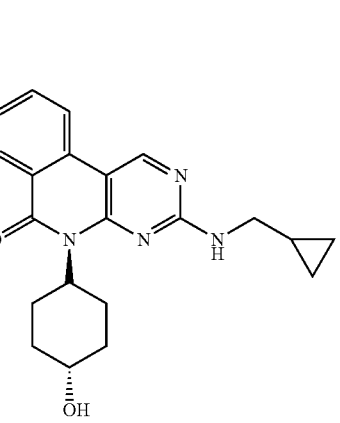 | |
| 169 | 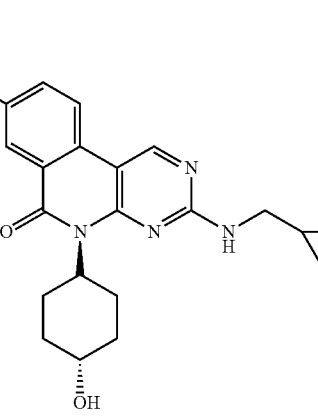 | |
| 170 | 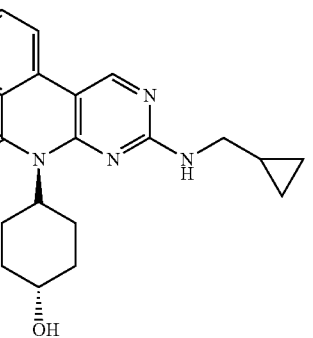 | |

| No. | Structure | Name |
|---|---|---|
| 171 | 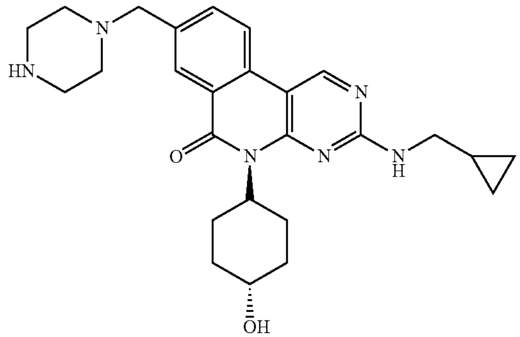 | |
| 172 | 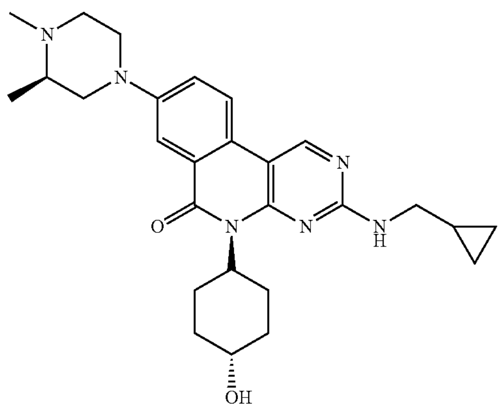 | |
| 173 | 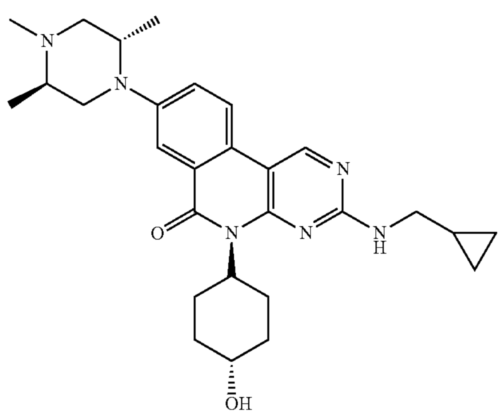 | |
| 174 | 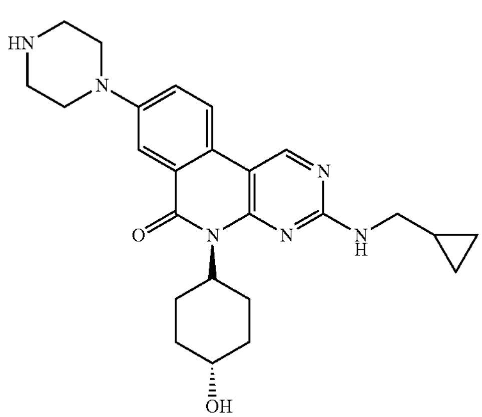 | |

| No. | Structure | Name |
|---|---|---|
| 175 | 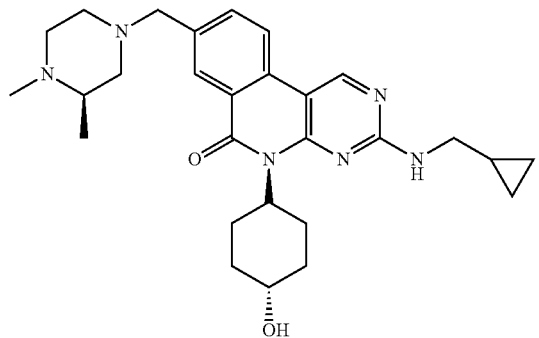 | |
| 176 | 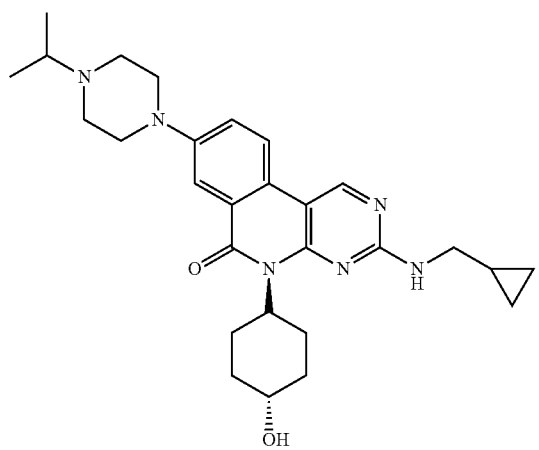 | |
| 177 | 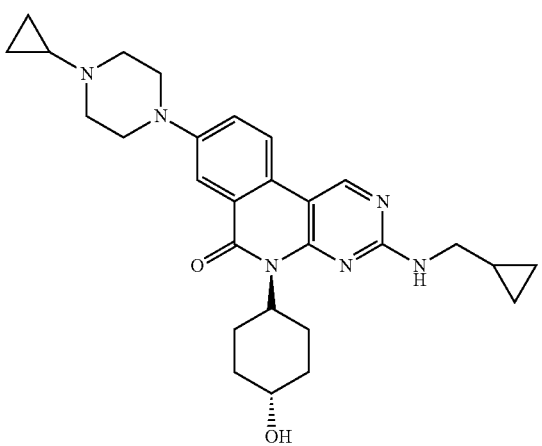 | |

-continued

| No. | Structure | Name |
|---|---|---|
| 178 | 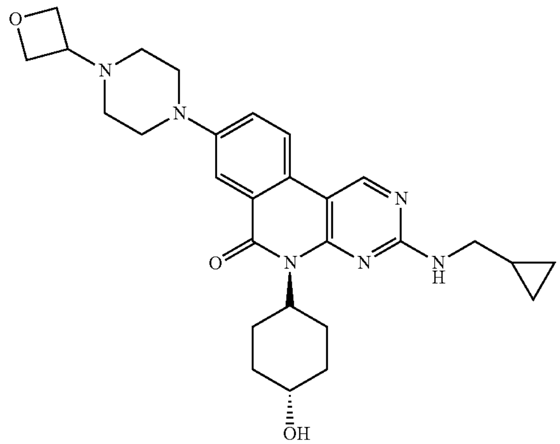 | |
| 179 | 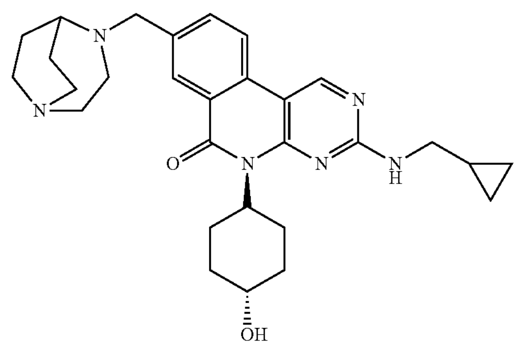 | |
| 180 | 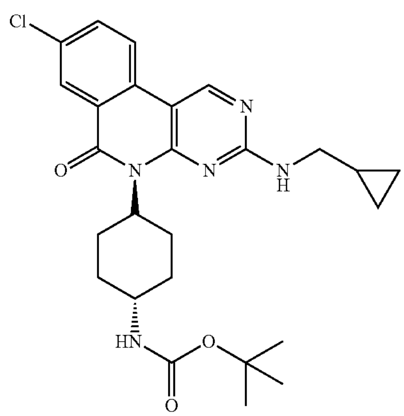 | |
| 181 | 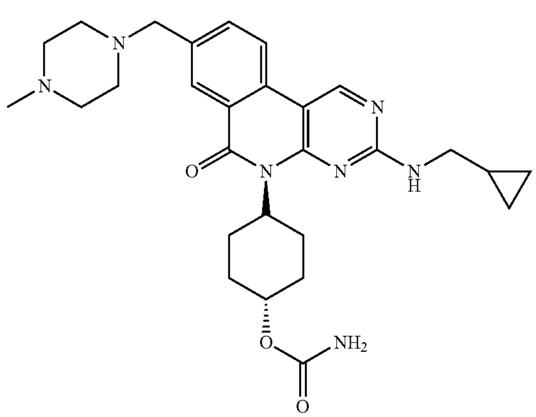 | |

| No. | Structure | Name |
|---|---|---|
| 182 | 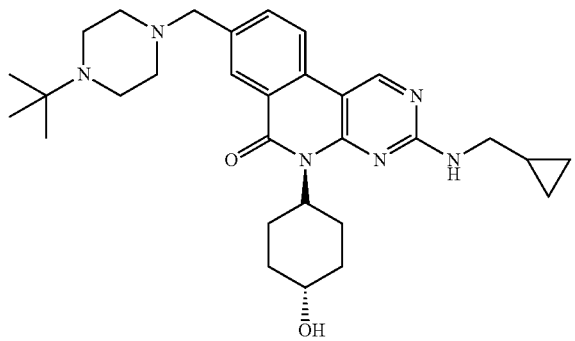 | |
| 183 | 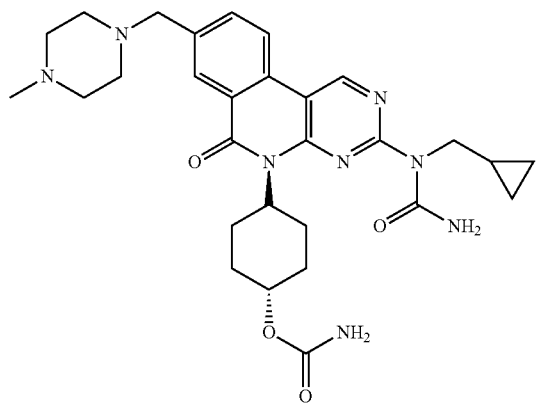 | |
| 184 | 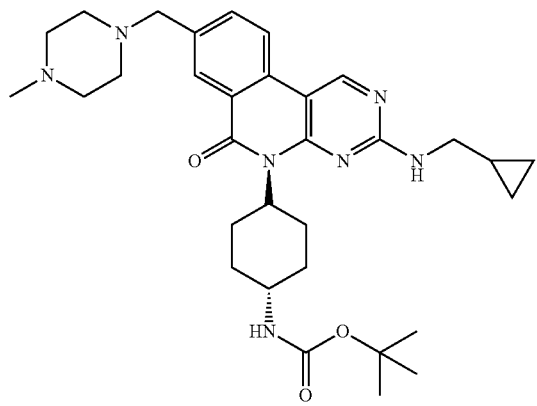 | trans-tert-Butyl (4-(3-((cyclopropylmethyl)amino)-8-((4-methylpiperazin-1-yl)methyl)-6-oxopyrimido[4,5-c]isoquinolin-5(6H)-yl)cyclohexyl)carbamate |
| 185 | 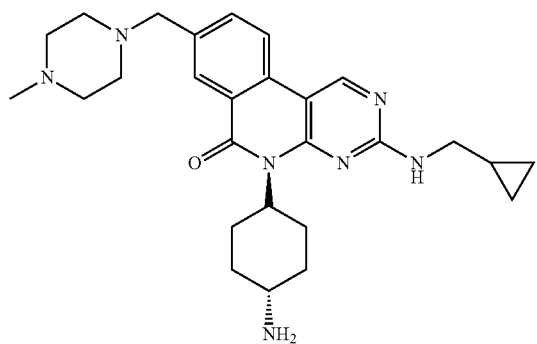 | trans-5-(4-aminocyclohexyl)-3-((cyclopropylmethyl)amino)-8-((4-methylpiperazin-1-yl)methyl)pyrimido[4,5-c]isoquinolin-6(5H)-one |

-continued

| No. | Structure | Name |
|---|---|---|
| 186 | 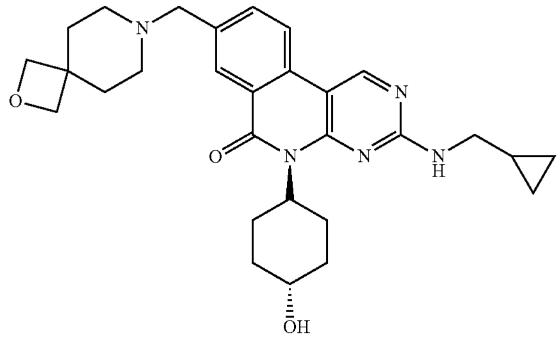 | trans-8-((2-Oxa-7-azaspiro[3.5]nonan-7-yl)methyl)-3-((cyclopropylmethyl)amino)-5-(4-hydroxycyclohexyl)pyrimido-[4,5-c]isoquinolin-6(5H)-one |
| 187 | 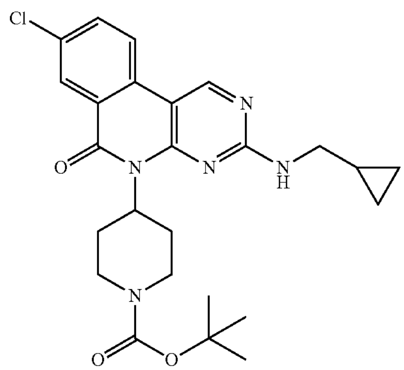 [SMILES: CC(C)(C)OC(=O)N1CCC(n2c(=O)c3cc(Cl)ccc3c3cnc(NCC4CC4)nc32)CC1] | |
| 188 | 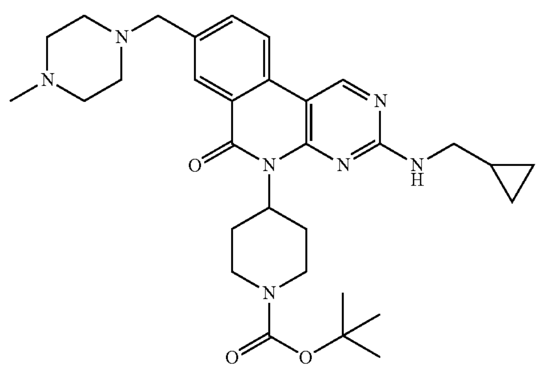 [SMILES: CN1CCN(Cc2ccc3c(c2)c(=O)n(C2CCN(C(=O)OC(C)(C)C)CC2)c2nc(NCC4CC4)ncc32)CC1] | |
| 189 | 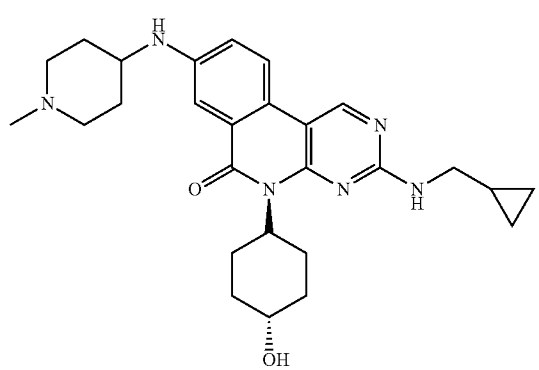 | trans-3-((cyclopropylmethyl)amino)-5-(4-hydroxycyclohexyl)-8-((1-methylpiperidin-4-yl)amino)pyrimido[4,5-c]isoquinolin-6(5H)-one |

-continued

| No. | Structure | Name |
|---|---|---|
| 190 | 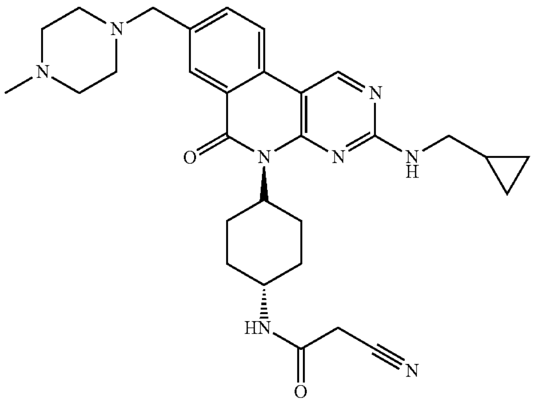 | trans-2-Cyano-N-(4-(3-((cyclopropylmethyl)amino)-8-((4-methylpiperazin-1-yl)methyl)-6-oxopyrimido[4,5-c]isoquinolin-5(6H)-yl)cyclohexyl)acetamide |
| 191 | 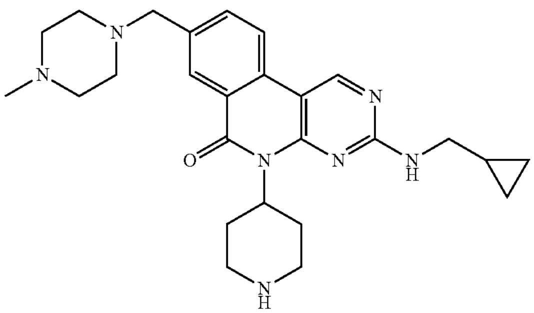 [SMILES: CN1CCN(Cc2ccc3c(c2)c(=O)n(C2CCNCC2)c2nc(NCC4CC4)ncc32)CC1] | |
| 192 | 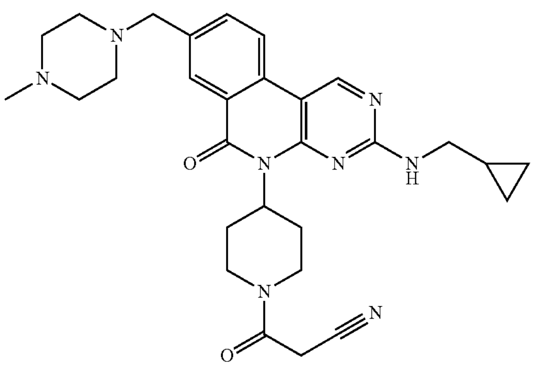 [SMILES: CN1CCN(Cc2ccc3c(c2)c(=O)n(C2CCN(C(=O)CC#N)CC2)c2nc(NCC4CC4)ncc32)CC1] | |
| 193 | 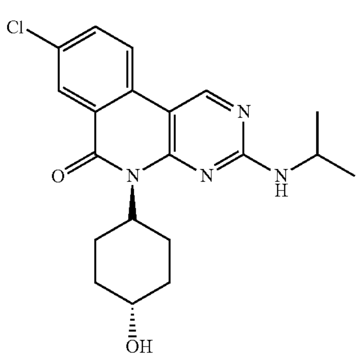 | |

| No. | Structure | Name |
|---|---|---|
| 194 | 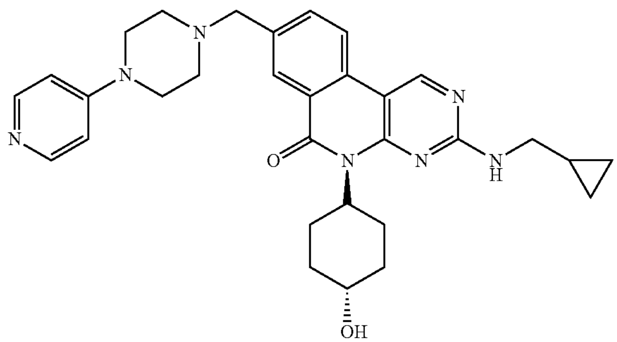 | |
| 195 | 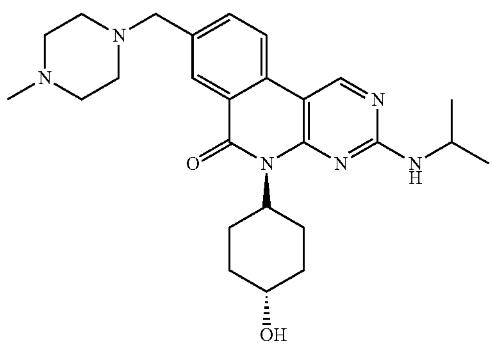 | trans-5-(4-Hydroxycyclohexyl)-3-(isopropylamino)-8-((4-methylpiperazin-1-yl)methyl)pyrimido[4,5-c]isoquinolin-6(5H)-one |
| 196 | 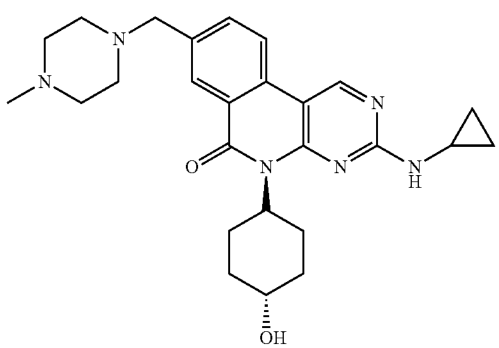 | trans-3-(Cyclopropylamino)-5-(4-hydroxycyclohexyl)-8-((4-methylpiperazin-1-yl)methyl)pyrimido[4,5-c]isoquinolin-6(5H)-one |
| 197 | 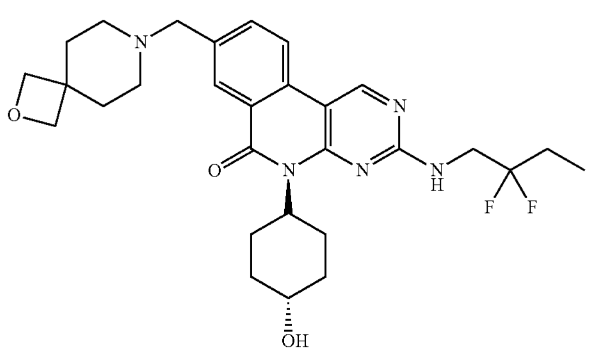 | trans-8-((2-Oxa-7-azaspiro[3.5]nonan-7-yl)methyl)-3-((2,2-difluorobutyl)amino)-5-(4-hydroxycyclohexyl)pyrimido-[4,5-c]isoquinolin-6(5H)-one |

-continued

| No. | Structure | Name |
|---|---|---|
| 198 | 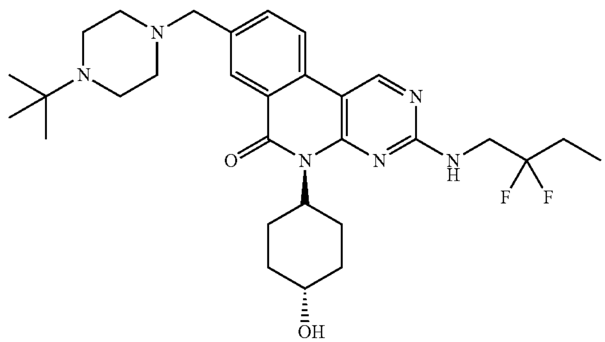 | trans-8-((4-(tert-Butyl)piperazin-1-yl)methyl)-3-((2,2-difluorobutyl)amino)-5-(4-hydroxycyclohexyl)pyrimido-[4,5-c]isoquinolin-6(5H)-one |
| 199 | 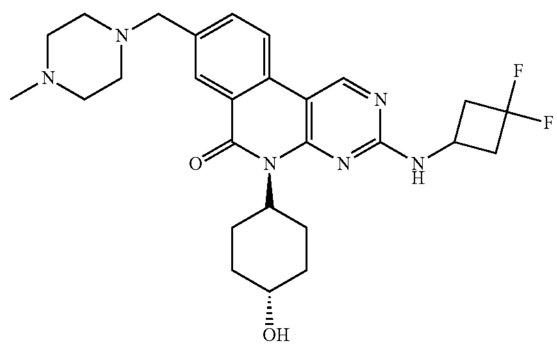 | trans-8-((4-(tert-Butyl)piperazin-1-yl)methyl)-3-((3,3-difluorocyclobutyl)amino)-5-(4-hydroxycyclohexyl)pyrimido-[4,5-c]isoquinolin-6(5H)-one |
| 200 | 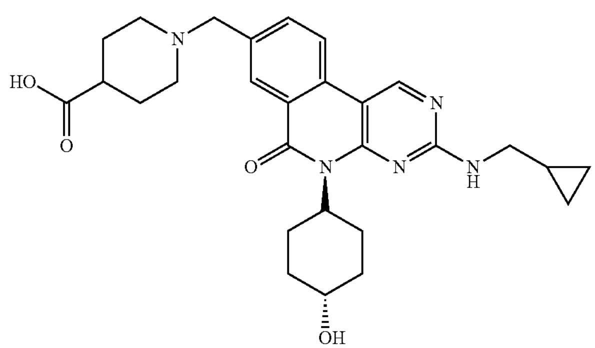 | trans-1-((3-((Cyclopropylmethyl(amino)-5-(4-hydroxycyclohexyl)-6-oxo-5,6-dihydropyrimido[4,5-c]isoquinolin-8-yl)methyl)piperidine-4-carboxylic acid |
| 201 | 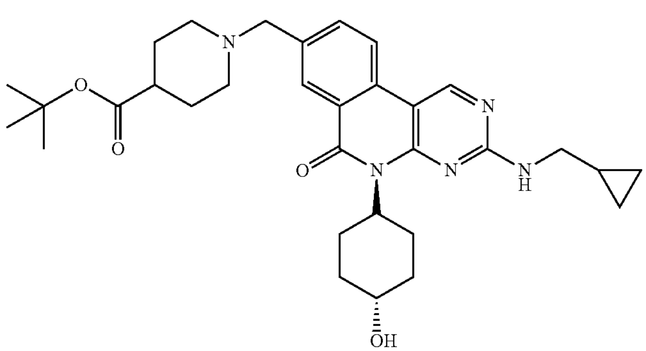 | trans-tert-Butyl 1-((3-((cyclopropylmethyl)amino)-5-(4-hydroxycyclohexyl)-6-oxo-5,6-dihydropyrimido[4,5-c]isoquinolin-8-yl)methyl)piperidine-4-carboxylate |

| No. | Structure | Name |
|---|---|---|
| 202 | 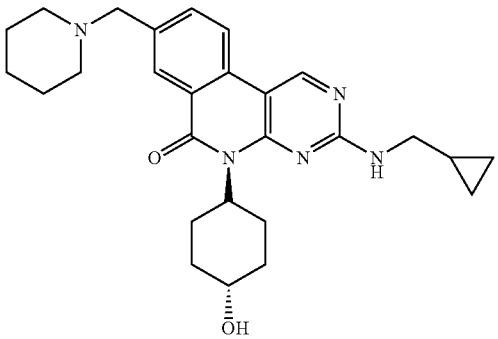 | trans-3-((Cyclopropylmethyl)amino)-5-(4-hydroxycyclohexyl)-8-(piperidin-1-ylmethyl)pyrimido[4,5-c]isoquinolin-6(5H)-one |
| 203 | 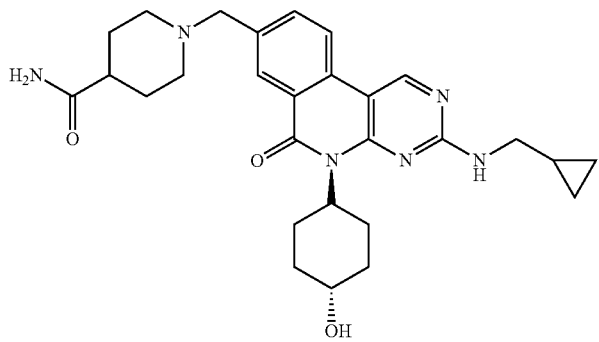 | trans-1-((3-((Cyclopropylmethyl)amino)-5-(4-hydroxycyclohexyl)-6-oxo-5,6-dihydropyrimido[4,5-c]isoquinolin-8-yl)methyl)piperidine-4-carboxamide |
| 204 | 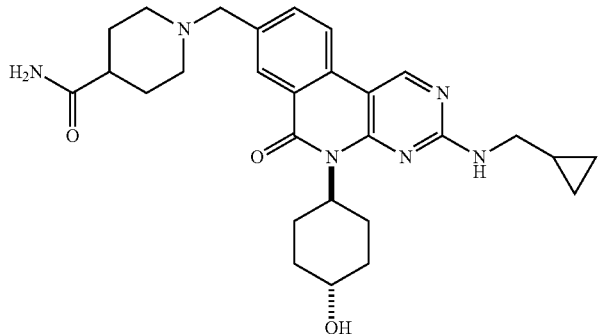 | trans-1-((3-((Cyclopropylmethyl)amino)-5-(4-hydroxycyclohexyl)-6-oxo-5,6-dihydropyrimido[4,5-c]isoquinolin-8-yl)methyl)piperidine-4-carbonitrile |
| 205 | 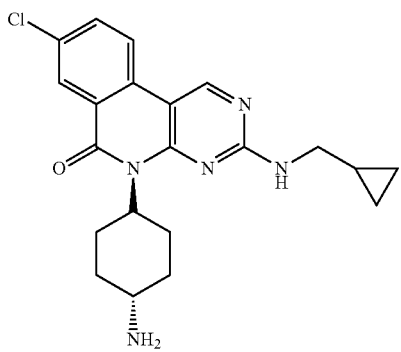 | |

| No. | Structure | Name |
|---|---|---|
| 206 | 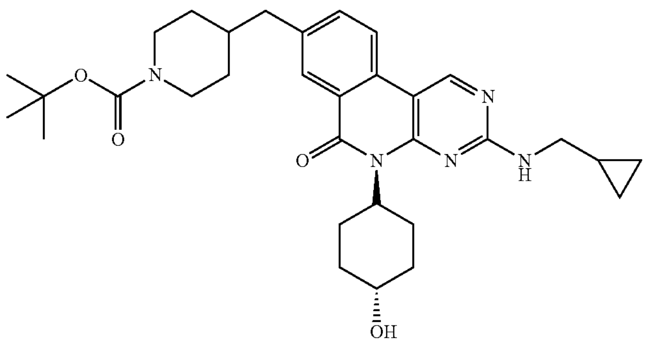 | |
| 207 | 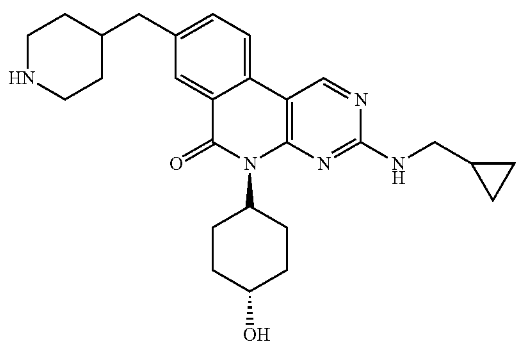 | trans-3-((Cyclopropylmethyl)amino)-5-(4-hydroxycyclohexyl)-8-(piperidin-4-ylmethyl)pyrimido[4,5-c]isoquinolin-6(5H)-one |
| 208 | 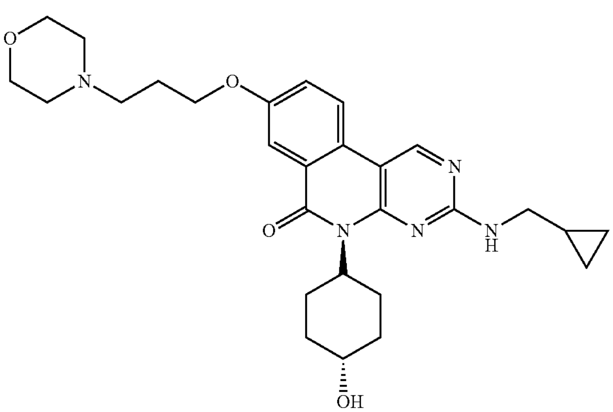 | trans-3-((Cyclopropylmethyl)amino)-5-(4-hydroxycyclohexyl)-8-(3-morpholinopropoxy)pyrimido-[4,5-c]isoquinolin-6(5H)-one |
| 209 | 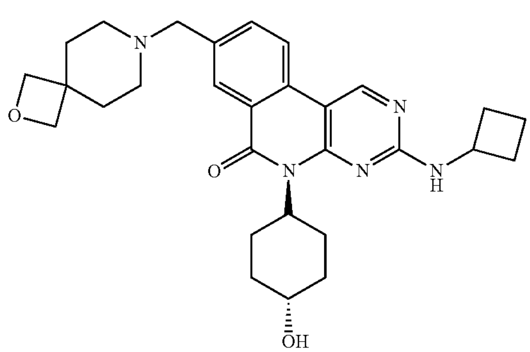 | trans-8-((2-Oxa-7-azaspiro[3.5]nonan-7-yl)methyl)-3-(cyclobutylamino)-5-(4-hydroxycyclohexyl)pyrimido-[4,5-c]isoquinolin-6(5H)-one |

-continued

| No. | Structure | Name |
|---|---|---|
| 210 | 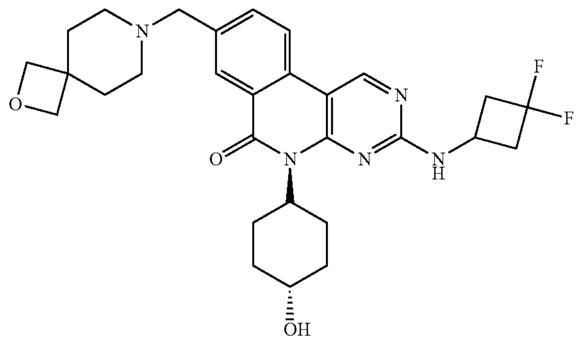 | trans-8-((2-Oxa-7-azaspiro[3.5]nonan-7-yl)methyl)-3-((3,3-difluorocyclobutyl)amino)-5-(4-hydroxycyclohexyl)pyrimido-[4,5-c]isoquinolin-6(5H)-one |
| 211 | 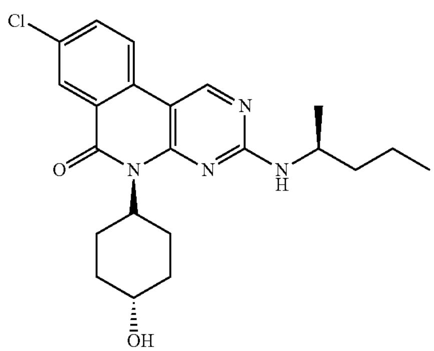 | |
| 212 | 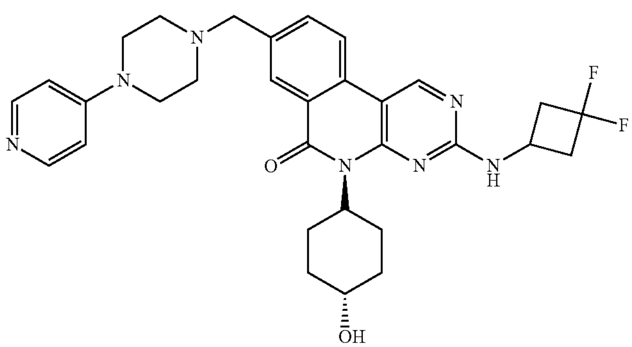 | trans-3-((3,3-Difluorocyclobutyl)amino)-5-(4-hydroxycyclohexyl)-8-((4-(pyridin-4-yl)piperazin-1-yl)methyl)pyrimido[4,5-c]isoquinolin-6(5H)-one |
| 213 | 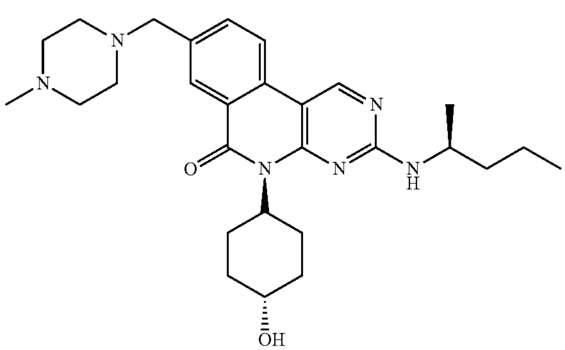 | trans-5-(4-hydroxycyclohexyl)-8-((4-methylpiperazin-1-yl)methyl)-3-(((S)-pentan-2-yl)amino)pyrimido[4,5-c]isoquinolin-6(5H)-one |

| No. | Structure | Name |
|---|---|---|
| 214 | 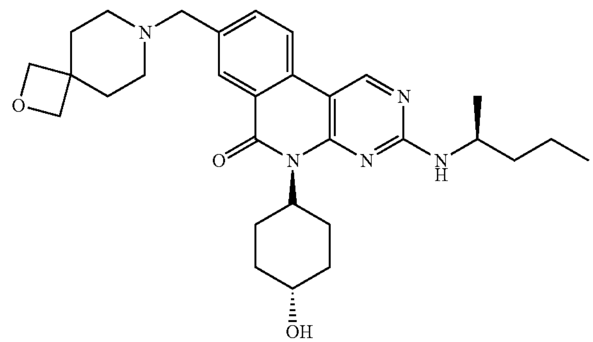 | trans-8-((2-oxa-7-azaspiro[3.5]nonan-7-yl)methyl)-5-(4-hydroxycyclohexyl)-3-(((S)-pentan-2-yl)amino)pyrimido[4,5-c]isoquinolin-6(5H)-one |
| 215 | 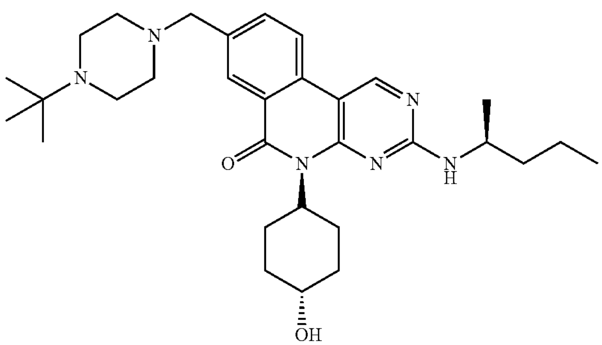 | trans-8-((4-(tert-Butyl)piperazin-1-yl)methyl)-5-(4-hydroxycyclohexyl)-3-(((S)-pentan-2-yl)amino)pyrimido[4,5-c]isoquinolin-6(5H)-one |
| 216 | 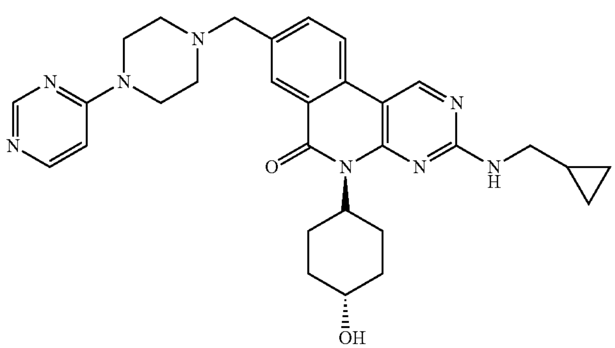 | trans-3-((Cyclopropylmethyl)amino)-5-(4-hydroxycyclohexyl)-8-((4-(pyrimidin-4-yl)piperazin-1-yl)methyl)pyrimido[4,5-c]isoquinolin-6(5H)-one |
| 217 | 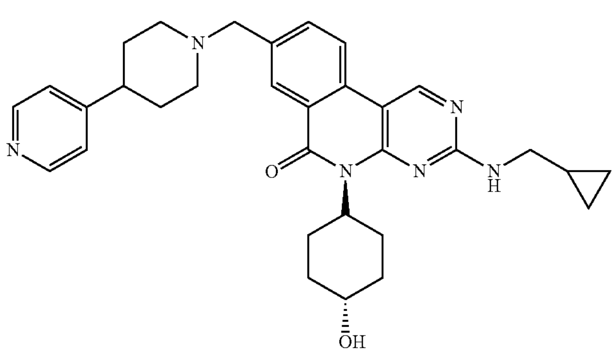 | trans-3-((Cyclopropylmethyl)amino)-5-(4-hydroxycyclohexyl)-8-((4-(pyridin-4-yl)piperidin-1-yl)methyl)pyrimido[4,5-c]isoquinolin-6(5H)-one |

-continued

| No. | Structure | Name |
|---|---|---|
| 218 | 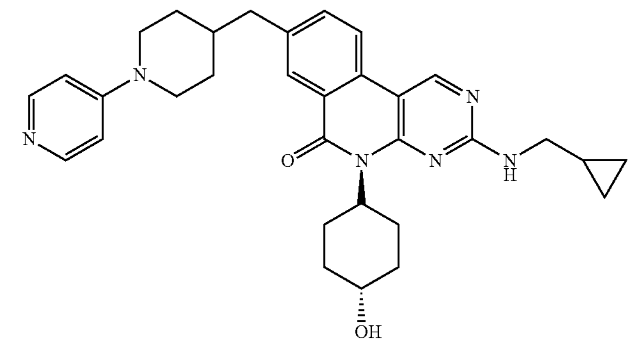 | trans-3-((Cyclopropylmethyl)amino)-5-(4-hydroxycyclohexyl)-8-((1-(pyridin-4-yl)piperidin-4-yl)methyl)pyrimido[4,5-c]isoquinolin-6(5H)-one |
| 219 | 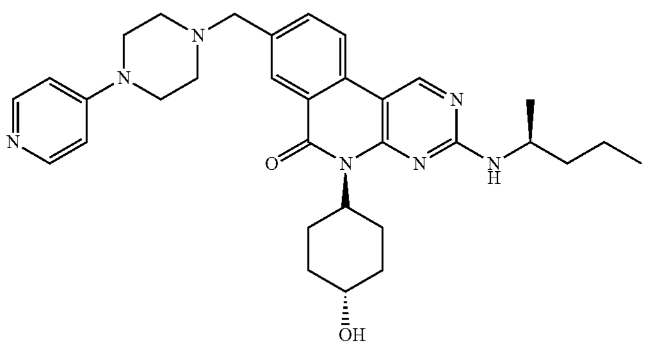 | trans-5-(4-Hydroxycyclohexyl)-3-(((S)-pentan-2-yl)amino)-8-((4-(pyridin-4-yl)piperazin-1-yl)methyl)pyrimido[4,5-c]isoquinolin-6(5H)-one |
| 220 | 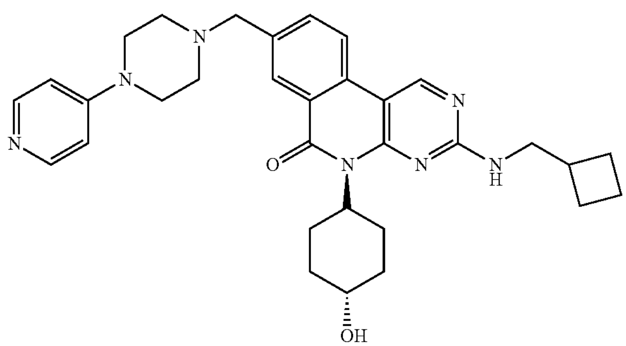 | trans-3-((Cyclobutylmethyl)amino)-5-(4-hydroxycyclohexyl)-8-((4-(pyridin-4-yl)piperazin-1-yl)methyl)pyrimido[4,5-c]isoquinolin-6(5H)-one |
| 221 | 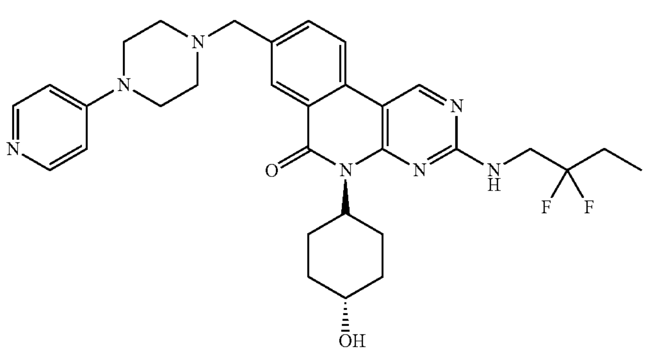 | trans-3-((2,2-Difluorobutyl)amino)-5-(4-hydroxycyclohexyl)-8-((4-(pyridin-4-yl)piperazin-1-yl)methyl)pyrimido[4,5-c]isoquinolin-6(5H)-one |

-continued

| No. | Structure | Name |
|---|---|---|
| 222 | 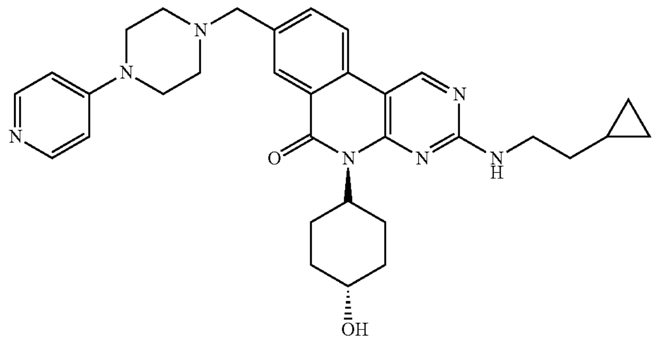 | trans-3-((2-Cyclopropylethyl)amino)-5-(4-hydroxycyclohexyl)-8-((4-(pyridin-4-yl)piperazin-1-yl)methyl)pyrimido[4,5-c]isoquinolin-6(5H)-one |
| 223 | 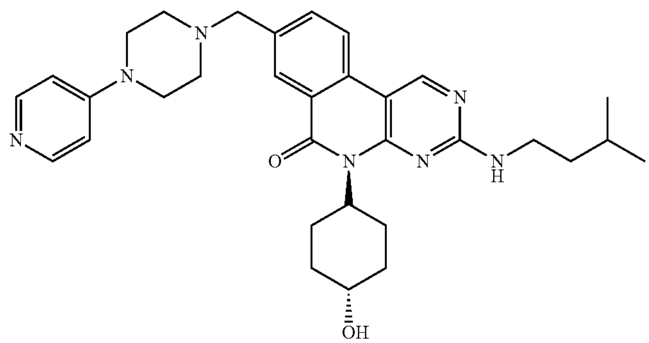 | trans-5-(4-Hydroxycyclohexyl)-3-(isopentylamino)-8-((4-(pyridin-4-yl)piperazin-1-yl)methyl)pyrimido[4,5-c]isoquinolin-6(5H)-one |
| 224 | 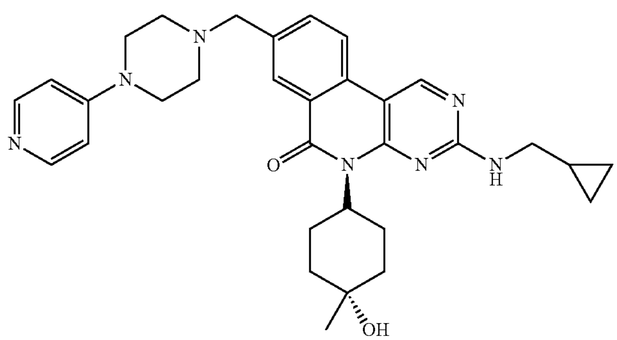 | trans-3-((Cyclopropylmethyl(amino)-5-(4-hydroxy-4-methylcyclohexyl)-8-((4-(pyridin-4-yl)piperazin-1-yl(methyl)pyrimido[4,5-c]isoquinolin-6(5H)-one |
| 225 | 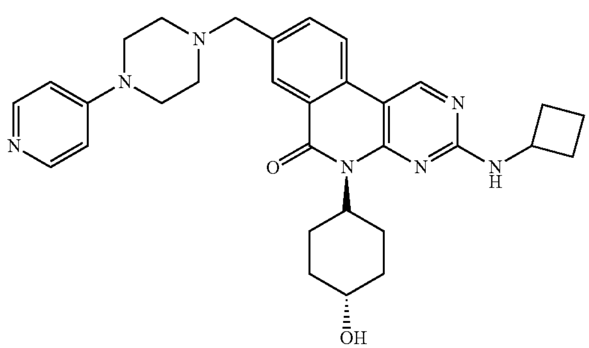 | trans-3-(Cyclobutylamino)-5-(4-hydroxycyclohexyl)-8-((4-(pyridin-4-yl)piperazin-1-yl)methyl)pyrimido[4,5-c]isoquinolin-6(5H)-one |

| No. | Structure | Name |
|---|---|---|
| 226 | 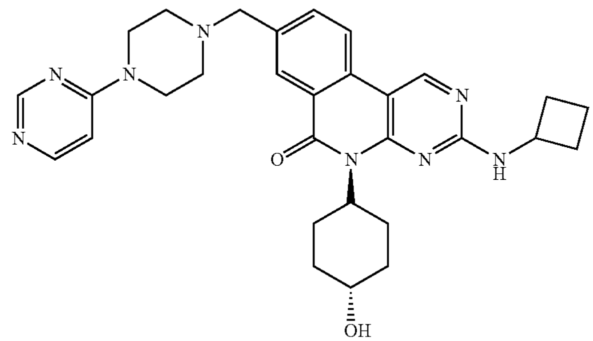 | trans-3-(Cyclobutylamino)-5-(4-hydroxycyclohexyl)-8-((4-(pyrimidin-4-yl)piperazin-1-yl)methyl)pyrimido[4,5-c]isoquinolin-6(5H)-one |
| 227 | 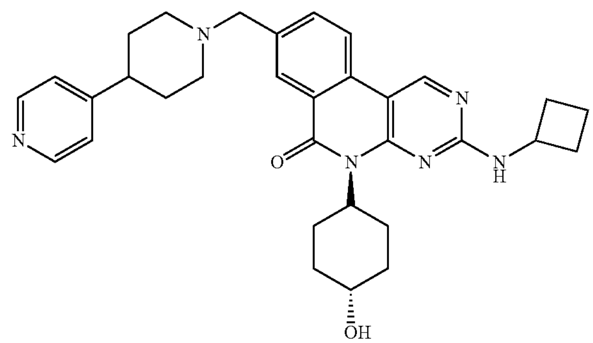 | trans-3-(Cyclobutylamino)-5-(4-hydroxycyclohexyl)-8-((4-(pyridin-4-yl)piperidin-1-yl)methyl)pyrimido[4,5-c]isoquinolin-6(5H)-one |
| 228 | 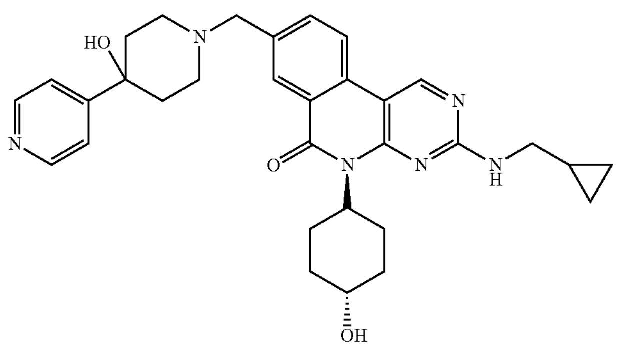 | trans-3-((Cyclopropylmethyl)amino)-8-((4-hydroxy-4-(pyridin-4-yl)piperidin-1-yl)methyl)-5-(4-hydroxycyclohexyl)pyrimido-[4,5-c]isoquinolin-6(5H)-one |
| 229 | 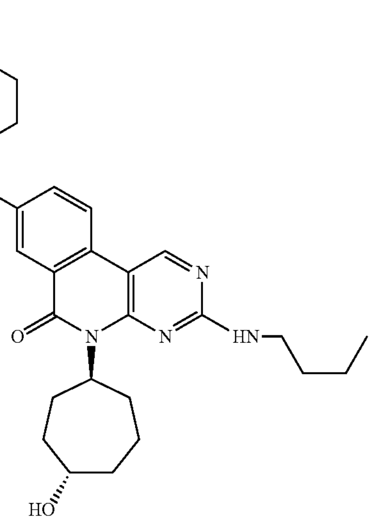 | 3-(butylamino)-5-((1S,4S)-4-hydroxycycloheptyl)-8-((4-methylpiperazin-1-yl)methyl)pyrimido[4,5-c]isoquinolin-6(5H)-one |

-continued

| No. | Structure | Name |
|---|---|---|
| 230 | 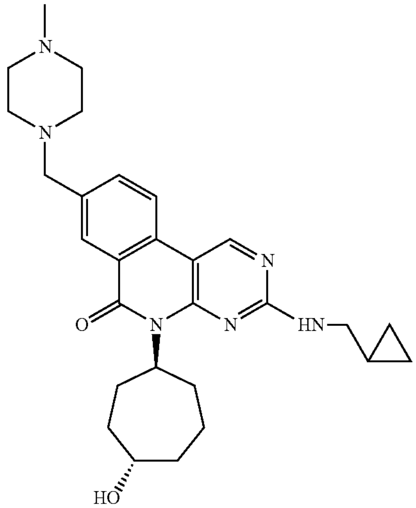 [SMILES: CN1CCN(Cc2ccc3c(c2)c(=O)n([C@H]2CCC[C@H](O)CC2)c2nc(NCC4CC4)ncc32)CC1] | 3-((cyclopropylmethyl)amino)-5-((1S,4S)-4-hydroxycycloheptyl)-8-((4-methylpiperazin-1-yl)methyl)pyrimido[4,5-c]isoquinolin-6(5H)-one |
| 231 | 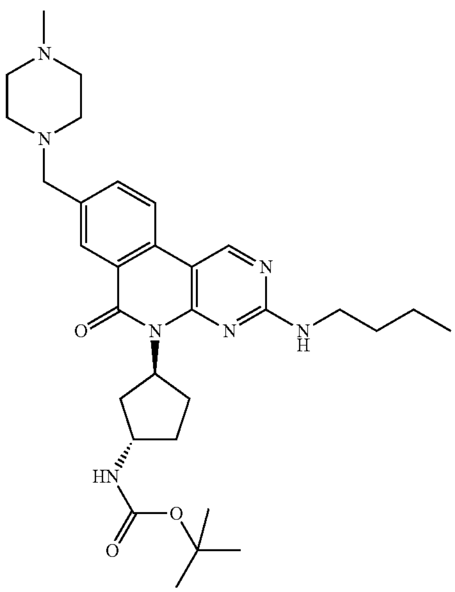 [SMILES: CCCCNc1ncc2c3ccc(CN4CCN(C)CC4)cc3c(=O)n([C@H]3CC[C@H](NC(=O)OC(C)(C)C)C3)c2n1] | tert-butyl ((1S,3S)-3-(3-(butylamino)-8-((4-methylpiperazin-1-yl)methyl)-6-oxopyrimido[4,5-c]isoquinolin-5(6H)-yl)cyclopentyl)carbamate |
| 232 | 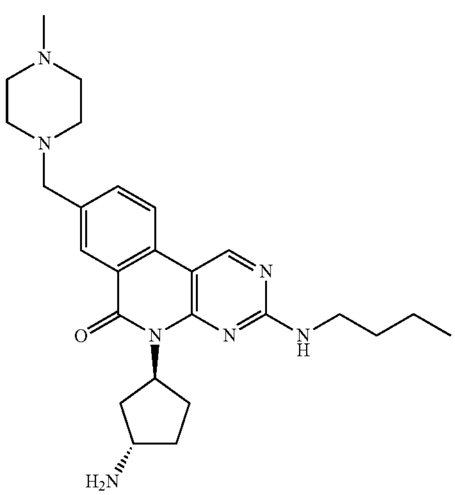 [SMILES: CCCCNc1ncc2c3ccc(CN4CCN(C)CC4)cc3c(=O)n([C@H]3CC[C@H](N)C3)c2n1] | 5-((1S,3S)-3-aminocyclopentyl)-3-(butylamino)-8-((4-methylpiperazin-1-yl)methyl)pyrimido[4,5-c]isoquinolin-6(5H)-one |

-continued
| No. | Structure | Name |
|---|---|---|
| 233 | 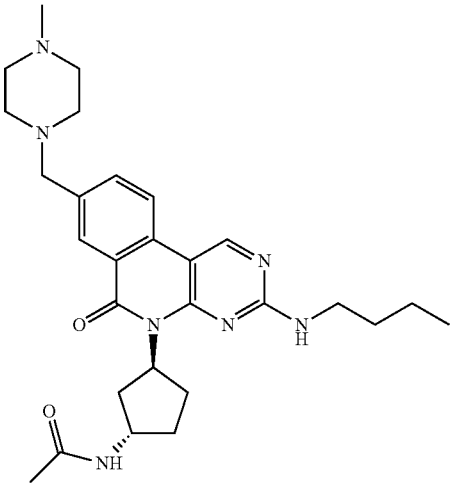 [SMILES: CCCCNc1ncc2c3ccc(CN4CCN(C)CC4)cc3c(=O)n([C@H]3CC[C@H](NC(C)=O)C3)c2n1] | N-((1S,3S)-3-(3-(butylamino)-8-((4-methylpiperazin-1-yl)methyl)-6-oxopyrimido[4,5-c]isoquinolin-5(6H)-yl)cyclopentyl)acetamide |
| 234 | 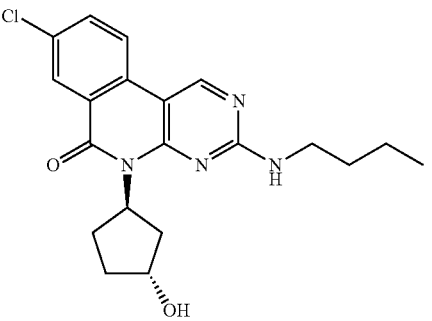 [SMILES: CCCCNc1ncc2c3ccc(Cl)cc3c(=O)n([C@@H]3CC[C@@H](O)C3)c2n1] | 3-(butylamino)-8-chloro-5-((1R,3R)-3-hydroxycyclopentyl)pyrimido[4,5-c]isoquinolin-6(5H)-one |
| 235 | 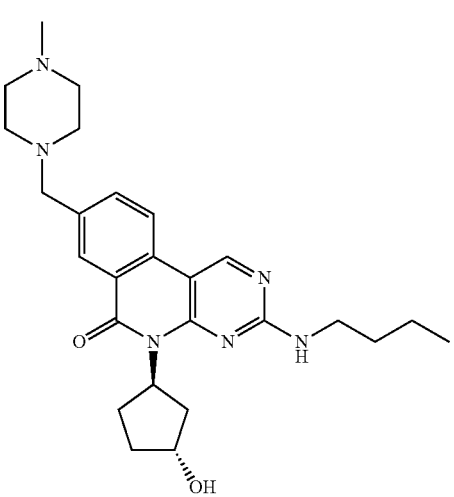 [SMILES: CCCCNc1ncc2c3ccc(CN4CCN(C)CC4)cc3c(=O)n([C@@H]3CC[C@@H](O)C3)c2n1] | 3-(butylamino)-5-((1R,3R)-3-hydroxycyclopentyl)-8-((4-methylpiperazin-1-yl)methyl)pyrimido[4,5-c]isoquinolin-6(5H)-one |

-continued

| No. | Structure | Name |
|---|---|---|
| 236 | 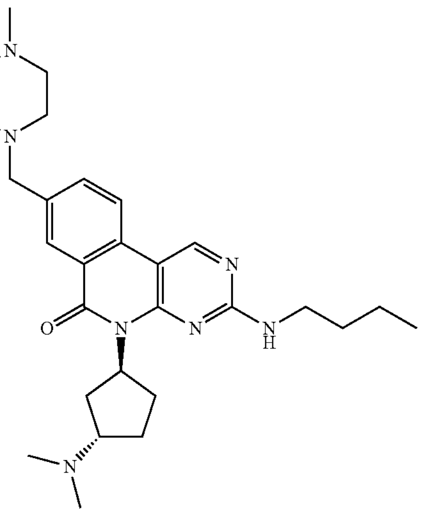 | 3-(butylamino)-5-((1S,3S)-3-(dimethylamino)cyclopentyl)-8-((4-methylpiperazin-1-yl)methyl)pyrimido[4,5-c]isoquinolin-6(5H)-one |
| 237 | 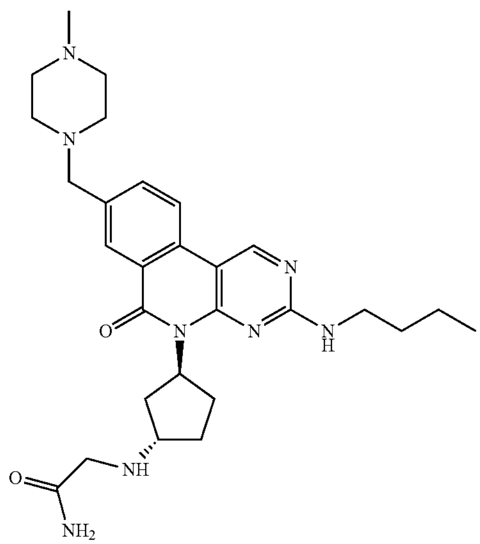 [SMILES: CCCCNc1ncc2c3ccc(CN4CCN(C)CC4)cc3c(=O)n([C@H]3CC[C@H](NCC(N)=O)C3)c2n1] | 2-(((1S,3S)-3-(3-(butylamino)-8-((4-methylpiperazin-1-yl)methyl)-6-oxopyrimido[4,5-c]isoquinolin-5(6H)-yl)cyclopentyl)amino)acetamide |
| 238 | 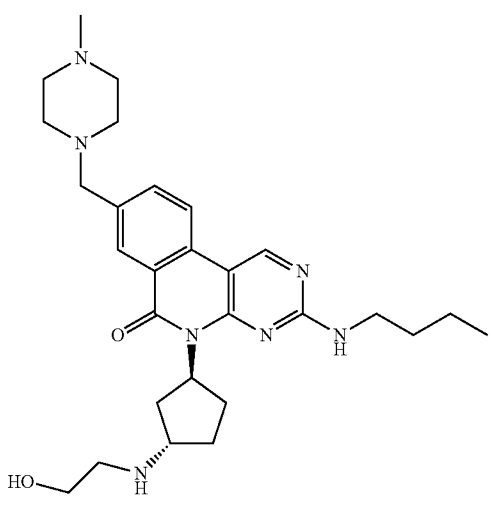 [SMILES: CCCCNc1ncc2c3ccc(CN4CCN(C)CC4)cc3c(=O)n([C@H]3CC[C@H](NCCO)C3)c2n1] | 3-(butylamino)-5-((1S,3S)-3-((2-hydroxyethyl)amino)cyclopentyl)-8-((4-methylpiperazin-1-yl)methyl)pyrimido[4,5-c]isoquinolin-6(5H)-one |

| No. | Structure | Name |
|---|---|---|
| 239 | 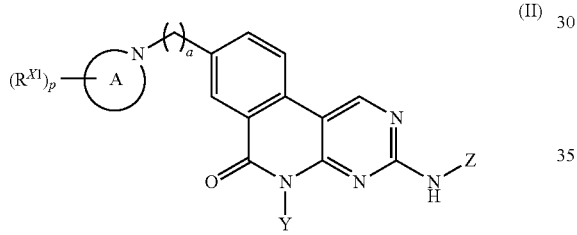 | 1-((1S,3S)-3-(3-(butylamino)-8-((4-methylpiperazin-1-yl)methyl)-6-oxopyrimido[4,5-c]isoquinolin-5(6H)-yl)cyclopentyl)guanidine |

In embodiment Ih of this aspect, the invention comprises compounds having the structure of formula (II):

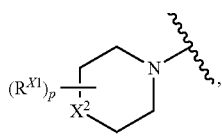   (II)

or a pharmaceutically acceptable salt, prodrug or N-oxide thereof, or solvate or hydrate thereof, wherein ring A is Hca;

a is 0 or 1;

p is 1, 2, 3 or 4; and each —$R^{X1}$ is independently halogen, cyano, $C_1$-$C_6$haloalkyl, —$C_1$-$C_6$alkoxy, oxo, —OR, —SR, —$NR_2$, —C(O)R, —C(O)OR, —C(O)$NR_2$, —S(O)$_2$$NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$, —$CH_2$—OP(O)(OR), Ar($C_0$-$C_6$alkyl), Het($C_0$-$C_6$alkyl), Cak($C_0$-$C_6$alkyl) or Hca($C_0$-$C_6$alkyl).

In embodiment II$_2$ of this aspect, the invention comprises compounds of embodiment II$_1$, wherein (a) ring A is

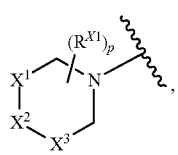

wherein p is 0, 1, 2, 3 or 4;

$X^1$ is —O—, —S—, —S(O)—, —S(O)$_2$—, —$CR^2$—, —C(R)($R^{X1}$)—, —C($R^{X1}$)$_2$—, —N(R)— or —N($R^{X1}$)—;

$X^2$ is —O—, —S—, —S(O)—, —S(O)$_2$—, —$CR^2$—, —C(R)($R^{X1}$)—, —C($R^{X1}$)$_2$—, —N(R)— or —N($R^{X1}$)—; and $X^3$ is —O—, —S—, —S(O)—, —S(O)$_2$—, —$CR^2$—, —C(R)($R^{X1}$)—, —C($R^{X1}$)$_2$—, —N(R)— or —N($R^{X1}$)—;

(b) ring A is

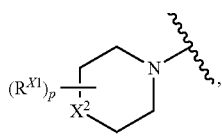

wherein p is 0, 1, 2, 3 or 4;

$X^2$ is —O—, —S—, —S(O)$_2$—, —$CR^2$—, —C(R)($R^{X1}$)—, —C($R^{X1}$)$_2$—, —N(R)— or —N($R^{X1}$)—;

(c) ring A is

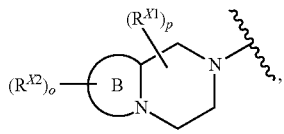

wherein p is 0, 1 or 2;

o is 0, 1 or 2; and ring B is Hca or Het, each comprising a 3-8 membered ring optionally substituted with one or two —$R^{X2}$ groups;

(d) ring A is

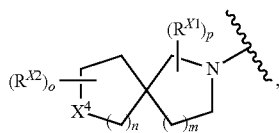

wherein p is 0, 1 or 2;

o is 0, 1 or 2;

n is 0, 1 or 2;

m is 0, 1 or 2; and $X^4$ is —O—, —S—, —S(O)$_2$—, —CR$^2$—, —C(R)(R$^{X1}$)—, —C(R$^{X1}$)$_2$—, —N(R)— or —N(R$^{X1}$)—;

(e) ring A is

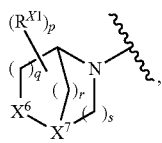

wherein $X^6$ is —O—, —S—, —S(O)—, —S(O)$_2$—, —CR$^2$—, —C(R)(R$^{X1}$)—, —C(R$^{X1}$)$_2$—, —N(R)— or —N(R$^{X1}$)—; and $X^7$ is —CR—, —C(R$^{X1}$)— or —N—;

p is 0, 1 or 2;

q is 0, 1 or 2;

r is 0, 1 or 2; and s is 0, 1 or 2.

In embodiment II$_3$, the compounds are of embodiment I$_1$ or II$_2$, wherein a is 0.

In embodiment II$_4$, the compounds are of embodiment I$_1$ or II$_2$, wherein a is 1.

In embodiment II$_5$, the compounds are of embodiment I$_1$-II$_4$, wherein Y is any of groups (2a)-(2ll).

In embodiment II$_6$, the compounds are of embodiment I$_1$-II$_4$, wherein Z is any of groups (3a)-(3xx).

In embodiment II$_7$, the compounds of the invention are one of formulae (IIa)-(IIj), wherein ring A, ring B, a, p, o, n, m, q, r, s, $X^1$, $X^2$, $X^4$, $X^6$, $X^7$, $R^{X1}$, $R^{X2}$, Y and Z are as defined in embodiments II$_1$-II$_6$ above:

Structural Formula (II) is One of Formulae (IIa)-(IIj):

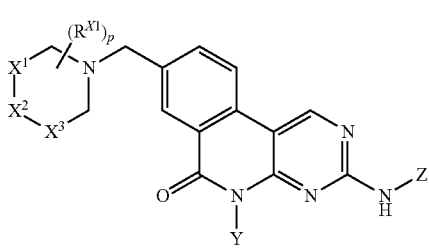

(IIa)

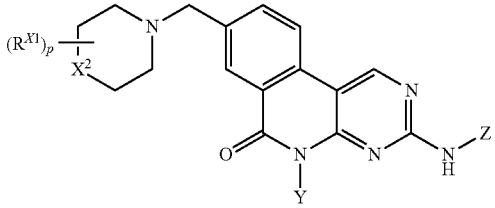

(IIb)

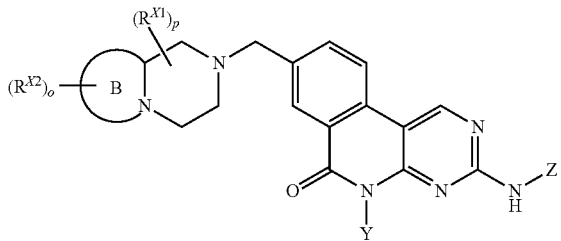

(IIc)

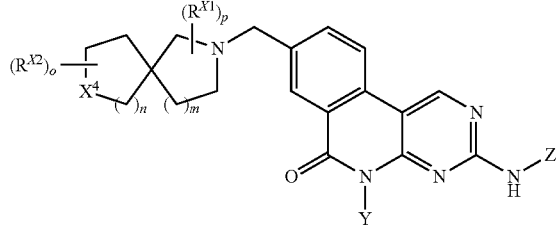

(IId)

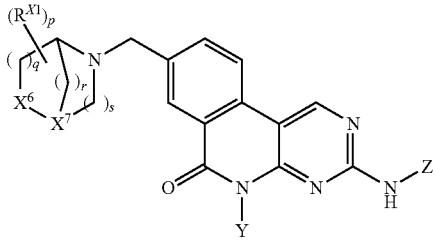

(IIe)

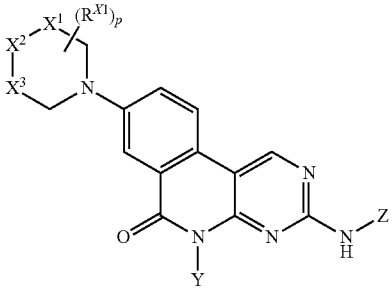

(IIf)

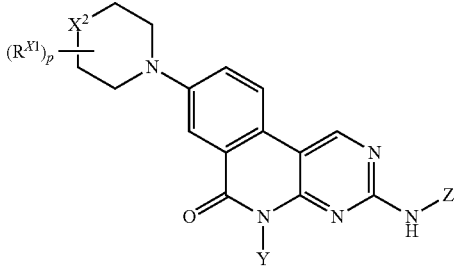

(IIg)

-continued

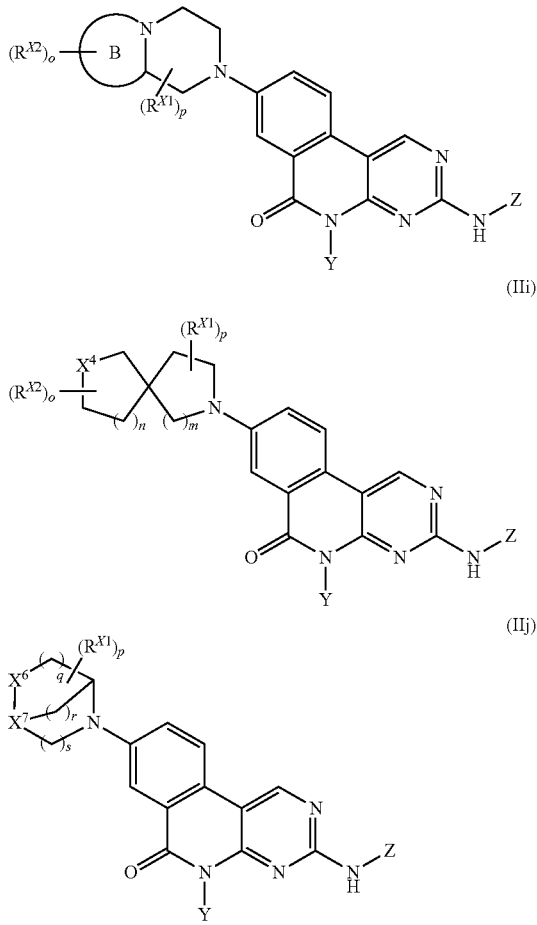

Ring A is Selected from One of the Following Groups (4a)-(4ffff):
(4a) Ring A is

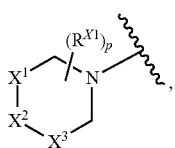

wherein
p is 0, 1, 2, 3 or 4;
$X^1$ is —O—, —S—, —S(O)—, —S(O)$_2$—, —CR$^2$—, —C(R)(R$^{X1}$)—, —C(R$^{X1}$)$_2$—, —N(R)— or —N(R$^{X1}$)—;
$X^2$ is —O—, —S—, —S(O)—, —S(O)$_2$—, —CR$^2$—, —C(R)(R$^{X1}$)—, —C(R$^{X1}$)$_2$—, —N(R)— or —N(R$^{X1}$)—; and
$X^3$ is —O—, —S—, —S(O)—, —S(O)$_2$—, —CR$^2$—, —C(R)(R$^{X1}$)—, —C(R$^{X1}$)$_2$—, —N(R)— or —N(R$^{X1}$)—;

(4b) Ring A is group (4a), wherein
$X^1$ is —O—, —CR$^2$—, —C(R)(R$^{X1}$)—, —C(R$^{X1}$)$_2$—, —N(R)— or —N(R$^{X1}$)—;
$X^2$ is —O—, —CR$^2$—, —C(R)(R$^{X1}$)—, —C(R$^{X1}$)$_2$—, —N(R)— or —N(R$^{X1}$)—; and
$X^3$ is —O—, —CR$^2$—, —C(R)(R$^{X1}$)—, —C(R$^{X1}$)$_2$—, —N(R)— or —N(R$^{X1}$)—.

(4c) Ring A is group (4a), wherein
$X^1$ is —CR$^2$—, —C(R)(R$^{X1}$)— or —C(R$^{X1}$)$_2$;
$X^2$ is —O—, —CR$^2$—, —C(R)(R$^{X1}$)—, —C(R$^{X1}$)$_2$—, —N(R)— or —N(R$^{X1}$)—; and
$X^3$ is —CR$^2$—, —C(R)(R$^{X1}$)— or —C(R$^{X1}$)$_2$—.

(4d) Ring A is group (4a), wherein
$X^1$ is —CR$^2$—, —C(R)(R$^{X1}$)— or —C(R$^{X1}$)$_2$;
$X^2$ is —O—, —S(O)—, —S(O)$_2$—, —N(R)— or —N(R$^{X1}$)—; and
$X^3$ is —CR$^2$—, —C(R)(R$^{X1}$)— or —C(R$^{X1}$)$_2$—.

(4e) Ring A is group (4a), wherein
$X^1$ is —CR$^2$—, —C(R)(R$^{X1}$)— or —C(R$^{X1}$)$_2$;
$X^2$ is —O—, —N(R)— or —N(R$^{X1}$)—; and
$X^3$ is —CR$^2$—, —C(R)(R$^{X1}$)— or —C(R$^{X1}$)$_2$—.

(4f) Ring A is group (4a), wherein
$X^1$ is —CR$^2$—, —C(R)(R$^{X1}$)— or —C(R$^{X1}$)$_2$;
$X^2$ is —S(O)—, —S(O)$_2$—; and
$X^3$ is —CR$^2$—, —C(R)(R$^{X1}$)— or —C(R$^{X1}$)$_2$—.

(4g) Ring A is group (4a), wherein
$X^1$ is —CR$^2$—, —C(R)(R$^{X1}$)— or —C(R$^{X1}$)$_2$;
$X^2$ is —O—; and
$X^3$ is —CR$^2$—, —C(R)(R$^{X1}$)— or —C(R$^{X1}$)$_2$—.

(4h) Ring A is group (4a), wherein
$X^1$ is —CR$^2$—, —C(R)(R$^{X1}$)— or —C(R$^{X1}$)$_2$;
$X^2$ is —N(R)— or —N(R$^{X1}$)—; and
$X^3$ is —CR$^2$—, —C(R)(R$^{X1}$)— or —C(R$^{X1}$)$_2$—.

(4i) Ring A is

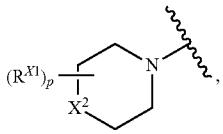

wherein
p is 0, 1, 2, 3 or 4;
$X^2$ is —O—, —S—, —S(O)—, —S(O)$_2$—, —CR$^2$—, —C(R)(R$^{X1}$)—, —C(R$^{X1}$)$_2$—, —N(R)— or —N(R$^{X1}$)—.

(4j) Ring A is group (4i), wherein $X^2$ is —O—, —CR$^2$—, —C(R)(R$^{X1}$)—, —C(R$^{X1}$)$_2$—, —N(R)— or —N(R$^{X1}$)—.
(4k) Ring A is group (4i), wherein $X^2$ is —CR$^2$— or —C(R)(R$^{X1}$)—.
(4l) Ring A is group (4i), wherein $X^2$ is —O—.
(4m) Ring A is group (4i), wherein $X^2$ is —S(O)$_2$—.
(4n) Ring A is group (4i), wherein $X^2$ is —N(R)— or —N(R$^{X1}$)—.
(4o) Ring A is

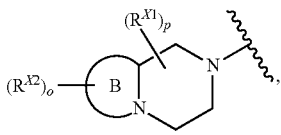

wherein
p is 0, 1 or 2;
o is 0, 1 or 2; and
Ring B is Hca or Het, each comprising a 3-8 membered ring optionally substituted with one or two —R$^{X2}$ groups.

(4p) Ring A is

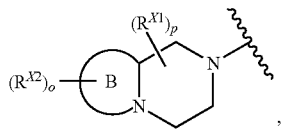

wherein
p is 0, 1 or 2;
o is 0, 1 or 2; and
Ring B is Hca, each comprising a 3-8 membered ring optionally substituted with one or two —$R^{X2}$ groups.
(4q) Ring A is group (4o) or (4p), wherein Hca is a 3-6 membered ring.
(4r) Ring A is group (4o) or (4p), wherein Hca is a 5-6 membered ring.
(4s) Ring A is

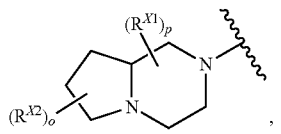

wherein
p is 0, 1 or 2; and
o is 0, 1 or 2.
(4t) Ring A is

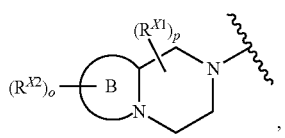

wherein
p is 0, 1 or 2;
o is 0, 1 or 2; and
Ring B is Het, each comprising a 3-8 membered ring optionally substituted with one or two —$R^{X2}$ groups.
(4u) Ring A is group (4t), wherein Het is a 3-6 membered ring.
(4v) Ring A is group (4t), wherein Het is a 5-6 membered ring.
(4w) Ring A is

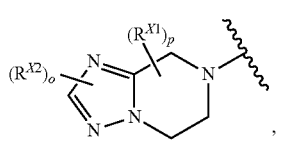

wherein
p is 0, 1 or 2; and
o is 0, 1 or 2.

(4x) Ring A is

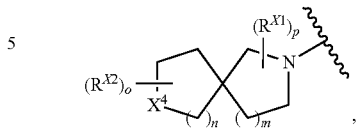

wherein
p is 0, 1 or 2;
o is 0, 1 or 2;
n is 0, 1 or 2;
m is 0, 1 or 2; and
$X^4$ is —O—, —S—, —S(O)—, —S(O)$_2$—, —$CR^2$—, —C(R)($R^{X1}$)—, —C($R^{X1}$)$_2$—, —N(R)— or —N($R^{X1}$)—.
(4y) Ring A is group (4x), wherein $X^4$ is —O—, —S(O)$_2$—, —$CR^2$—, —C(R)($R^{X1}$)—, —C($R^{X1}$)$_2$—, —N(R)— or —N($R^{X1}$)—.
(4z) Ring A is group (4x), wherein $X^4$ is —O—, —S(O)$_2$—, —N(R)— or —N($R^{X1}$)—.
(4aa) Ring A is group (4x), wherein $X^4$ is —O—, —N(R)— or —N($R^{X1}$)—.
(4bb) Ring A is group (4x), wherein $X^4$ is —O—, —$CR^2$—, —C(R)($R^{X1}$)— or —C($R^{X1}$)$_2$—.
(4cc) Ring A is group (4x), wherein $X^4$ is —$CR^2$—, —C(R)($R^{X1}$)—, —C($R^{X1}$)$_2$—, —N(R)— or —N($R^{X1}$)—.
(4dd) Ring A is group (4x), wherein $X^4$ is —S(O)$_2$—, —$CR^2$—, —C(R)($R^{X1}$)— or —C($R^{X1}$)$_2$—.
(4ee) Ring A is group (4x), wherein $X^4$ is —O—.
(4ff) Ring A is group (4x), wherein $X^4$ is —$CR^2$—, —C(R)($R^{X1}$)— or —C($R^{X1}$)$_2$—.
(4gg) Ring A is group (4x), wherein $X^4$ is —N(R)— or —N($R^{X1}$)—.
(4hh) Ring A is any of (4x)-(4gg), wherein
n is 0, 1 or 2; and
m is 0, 1 or 2.
(4ii) Ring A is any of (4x)-(4gg), wherein
n is 0; and
m is 0.
(4jj) Ring A is any of (4x)-(4gg), wherein
n is 1; and
m is 1.
(4kk) Ring A is any of (4x)-(4gg), wherein
n is 0; and
m is 1.
(4ll) Ring A is any of (4x)-(4gg), wherein
n is 1; and
m is 0.
(4mm) Ring A is

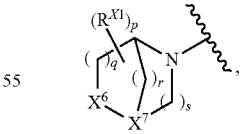

wherein
$X^6$ is —O—, —S—, —S(O)—, —S(O)$_2$—, —$CR^2$—, —C(R)($R^{X1}$)—, —C($R^{X1}$)$_2$—, —N(R)— or —N($R^{X1}$)—; and
$X^7$ is —CR—, —C($R^{X1}$)— or —N—;
p is 0, 1 or 2;
q is 0, 1 or 2;
r is 1 or 2; and
s is 0, 1 or 2.

(4nn) Ring A is group (4mm), wherein $X^6$ is —O—, —S(O)$_2$—, —CR$^2$—, —C(R)(R$^{X1}$)—, —C(R$^{X1}$)$_2$—, —N(R)— or —N(R$^{X1}$)—.

(4oo) Ring A is group (4mm), wherein $X^6$ is —O—, —CR$^2$—, —C(R)(R$^{X1}$)—, —C(R$^{X1}$)$_2$—, —N(R)— or —N(R$^{X1}$)—.

(4pp) Ring A is group (4mm), wherein $X^6$ is —O—, —N(R)— or —N(R$^{X1}$)—.

(4qq) Ring A is group (4mm), wherein $X^6$ is —O.

(4rr) Ring A is group (4mm), wherein $X^6$ is —S(O)$_2$—.

(4ss) Ring A is group (4mm), wherein $X^6$ is —CR$^2$—, —C(R)(R$^{X1}$)— or —C(R$^{X1}$)$_2$—.

(4tt) Ring A is group (4mm), wherein $X^6$ is —N(R)— or —N(R$^{X1}$)—.

(4uu) Ring A is any of groups (4mm)-(4tt), wherein $X^7$ is —CR— or —C(R$^{X1}$)—.

(4vv) Ring A is any of groups (4mm)-(4tt), wherein $X^7$ is —N—.

(4ww) Ring A is any of (4mm)-(4vv), wherein
q is 0, 1 or 2;
r is 1 or 2; and
s is 0, 1 or 2.

(4xx) Ring A is any of (4mm)-(4vv), wherein
q is 0 or 1;
r is 1 or 2; and
s is 0 or 1.

(4yy) Ring A is any of (4mm)-(4vv), wherein
q is 0;
r is 1 or 2; and
s is 0.

(4zz) Ring A is any of (4mm)-(4vv), wherein
q is 1;
r is 1 or 2; and
s is 1.

(4aaa) Ring A is any of (4mm)-(4vv), wherein
q is 0;
r is 1 or 2; and
s is 0.

(4bbb) Ring A is any of (4mm)-(4vv), wherein
q is 1;
r is 1; and
s is 1.

(4ccc) Ring A is any of (4mm)-(4vv), wherein
q is 0;
r is 1 or 2; and
s is 0.

(4ddd) Ring A is any of (4mm)-(4vv), wherein
q is 1;
r is 1; and
s is 1.

(4eee) Ring A is any of (4mm)-(4vv), wherein
q is 1;
r is 2; and
s is 1.

(4fff) Ring A is any of (4mm)-(4vv), wherein
q is 2;
r is 2; and
s is 2.

(4ggg) Ring A is

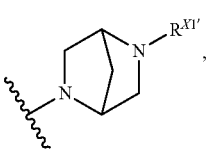

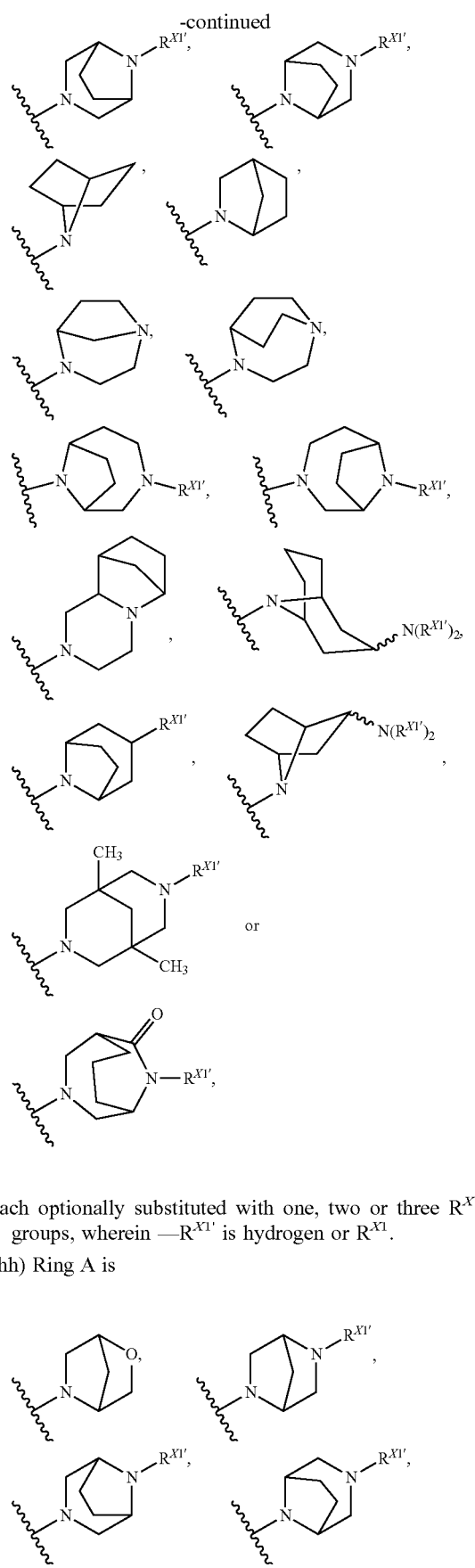

each optionally substituted with one, two or three R$^{X1}$ groups, wherein —R$^{X1'}$ is hydrogen or R$^{X1}$.

(4hhh) Ring A is

-continued

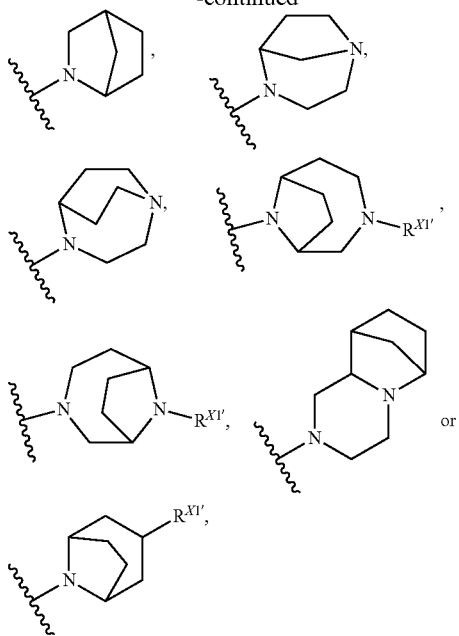

each optionally substituted with one, two or three $R^{X1}$ groups, wherein $-R^{X1'}$ is hydrogen or $R^{X1}$.

(4iii) Ring A is

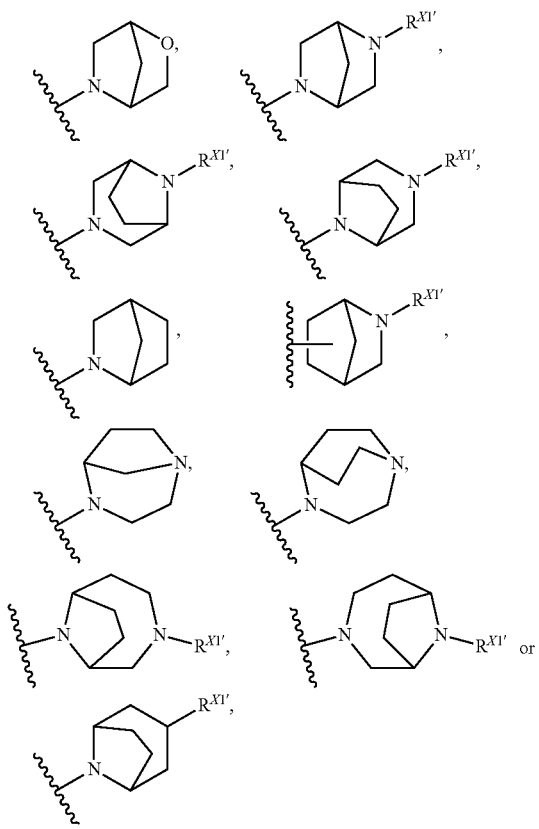

each optionally substituted with one, two or three $R^{X1}$ groups, wherein $-R^{X1'}$ is hydrogen or $R^{X1}$.

(4jjj) Ring A is

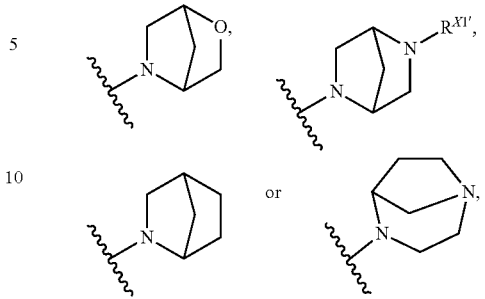

each optionally substituted with one, two or three $R^{X1}$ groups, wherein $-R^{X1'}$ is hydrogen or $R^{X1}$.

(4kkk) Ring A is

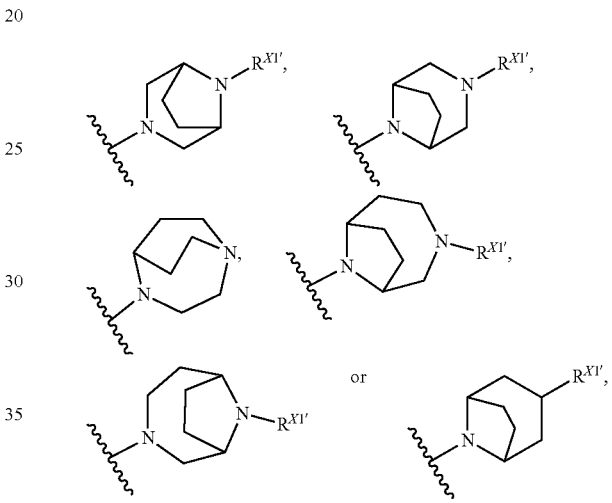

each optionally substituted with one, two or three $R^{X1}$ groups, wherein $-R^{X1'}$ is hydrogen or $R^{X1}$.

(4lll) Ring A is

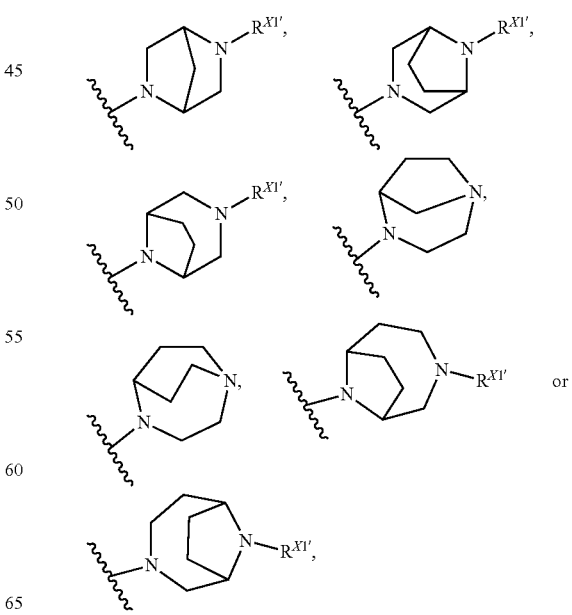

each optionally substituted with one, two or three $R^{X1}$ groups, wherein —$R^{X1'}$ is hydrogen or $R^{X1}$.

(4mmm) Ring A is

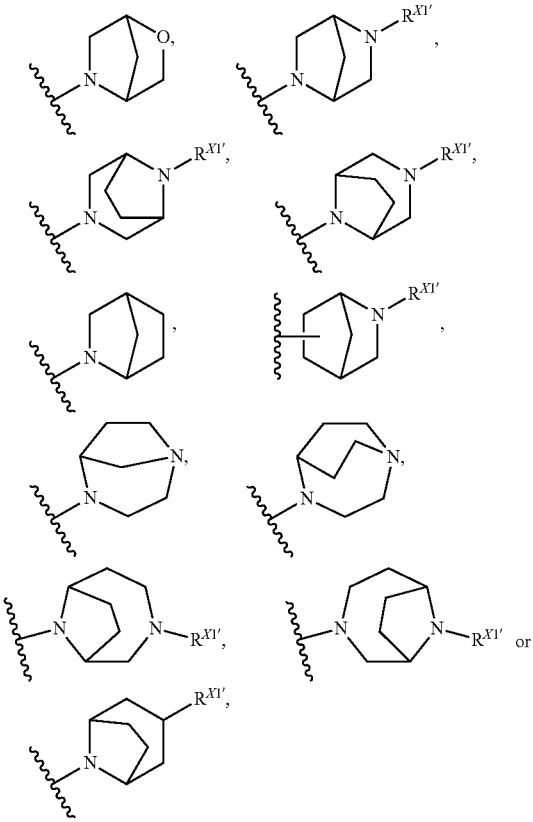

each optionally substituted with one, two or three $R^{X1}$ groups, wherein —$R^{X1'}$ is hydrogen or $R^{X1}$.

(4nnn) Ring A is any of groups (4a)-(4fff), wherein p is 0, 1 or 2.
(4ooo) Ring A is any of groups (4a)-(4fff), wherein p is 0 or 1.
(4ppp) Ring A is any of groups (4a)-(4fff), wherein p is 2.
(4qqq) Ring A is any of groups (4a)-(4fff), wherein p is 1.
(4rrr) Ring A is any of groups (4a)-(4qqq), each —$R^{X1}$ is independently halogen, cyano, $C_1$-$C_6$alkyl, $C_1$-$C_6$haloalkyl, —$C_1$-$C_6$alkoxy, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$, —CH$_2$—OP(O)(OR), Ar($C_0$-$C_6$alkyl), Het($C_0$-$C_6$alkyl), Cak($C_0$-$C_6$alkyl) or Hca($C_0$-$C_6$alkyl).
(4sss) Ring A is any of groups (4a)-(4qqq), each —$R^{X1}$ is independently halogen, cyano, $C_1$-$C_6$alkyl, $C_1$-$C_6$haloalkyl, —$C_1$-$C_6$alkoxy, —C(O)R, —C(O)OR, —C(O)NR$_2$, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$, —CH$_2$—OP(O)(OR), Ar($C_0$-$C_6$alkyl), Het($C_0$-$C_6$alkyl), Cak($C_0$-$C_6$alkyl) or Hca($C_0$-$C_6$alkyl).
(4ttt) Ring A is any of groups (4a)-(4qqq), each —$R^{X1}$ is independently halogen, $C_1$-$C_6$alkyl, $C_1$-$C_6$haloalkyl, —$C_1$-$C_6$alkoxy, —C(O)R, —C(O)OR, —C(O)NR$_2$, —N(R)C(O)R, —N(R)C(O)OR, —N(R)C(O)NR$_2$, —N(R)S(O)$_2$R, —OP(O)(OR)$_2$, —CH$_2$—OP(O)(OR), Ar($C_0$-$C_6$alkyl), Het($C_0$-$C_6$alkyl), Cak($C_0$-$C_6$alkyl) or Hca($C_0$-$C_6$alkyl).
(4uuu) Ring A is any of groups (4a)-(4qqq), each —$R^{X1}$ is independently halogen, cyano, $C_1$-$C_6$haloalkyl, —$C_1$-$C_6$alkoxy, —C(O)R, —C(O)OR, —C(O)NR$_2$, —OC(O)R, —OP(O)(OR)$_2$, —CH$_2$—OP(O)(OR), Ar($C_0$-$C_6$alkyl), Het($C_0$-$C_6$alkyl), Cak($C_0$-$C_6$alkyl) or Hca($C_0$-$C_6$alkyl).
(4vvv) Ring A is any of groups (4a)-(4qqq), each —$R^{X1}$ is independently halogen, cyano, $C_1$-$C_6$haloalkyl, —$C_1$-$C_6$alkoxy, —C(O)R, —C(O)OR, —C(O)NR$_2$, —OC(O)R, —N(R)C(O)R, —OC(O)OR, —OC(O)NR$_2$, —N(R)C(O)OR, —N(R)C(O)NR$_2$, —N(R)S(O)$_2$R, Ar($C_0$-$C_6$alkyl), Het($C_0$-$C_6$alkyl), Cak($C_0$-$C_6$alkyl) or Hca($C_0$-$C_6$alkyl).
(4www) Ring A is any of groups (4a)-(4qqq), each —$R^{X1}$ is independently halogen, cyano, $C_1$-$C_6$haloalkyl, —$C_1$-$C_6$alkoxy, —C(O)R, —C(O)OR, —C(O)NR$_2$, —OC(O)NR$_2$, Ar($C_0$-$C_6$alkyl), Het($C_0$-$C_6$alkyl), Cak($C_0$-$C_6$alkyl) or Hca($C_0$-$C_6$alkyl).
(4xxx) Ring A is any of groups (4a)-(4qqq), each —$R^{X1}$ is independently $C_1$-$C_6$alkyl, $C_1$-$C_6$haloalkyl, —C(O)OR, Ar($C_0$-$C_6$alkyl), Het($C_0$-$C_6$alkyl), Cak($C_0$-$C_6$alkyl) or Hca($C_0$-$C_6$alkyl).
(4yyy) Ring A is any of groups (4a)-(4qqq), each —$R^{X1}$ is independently $C_1$-$C_6$alkyl, $C_1$-$C_6$haloalkyl, Ar($C_0$-$C_6$alkyl), Het($C_0$-$C_6$alkyl), Cak($C_0$-$C_6$alkyl) or Hca($C_0$-$C_6$alkyl).
(4zzz) Ring A is any of groups (4a)-(4qqq), each —$R^{X1}$ is independently Cak($C_0$-$C_6$alkyl) or Hca($C_0$-$C_6$alkyl).
(4aaaa) Ring A is any of groups (4a)-(4qqq), each —$R^{X1}$ is independently Cak($C_0$-$C_6$alkyl).
(4bbbb) Ring A is any of groups (4a)-(4qqq), each —$R^{X1}$ is independently Hca($C_0$-$C_6$alkyl).
(4cccc) Ring A is any of groups (4a)-(4qqq), each —$R^{X1}$ is independently $C_1$-$C_6$alkyl or $C_1$-$C_6$haloalkyl.
(4dddd) Ring A is any of groups (4a)-(4qqq), each —$R^{X1}$ is independently Cak($C_0$-$C_6$alkyl).
(4eeee) Ring A is any of groups (4a)-(4qqq), each —$R^{X1}$ is independently $C_1$-$C_6$haloalkyl.
(4ffff) Ring A is any of groups (4a)-(4fff), wherein p is 0.

Particular embodiments of this aspect of the invention comprise compounds of any one of the formulae (II), and (IIa)-(IIj), each as defined in each of the following rows (or a pharmaceutically acceptable salt, prodrug, or N-oxide thereof, or a solvate or hydrate thereof), wherein each entry is a group number as defined above (e.g., (4ffff) refers to Ring A being any of groups (4a)-(4fff), wherein p is 0, and a dash "—" indicates that the variable is as defined in embodiment II or defined according to any one of the applicable variable definitions (4a)-(4ffff), (2a)-(2ll) and (3a)-(3xx) [e.g., when Ring A is a dash, it can be either as defined in any of embodiments II$_1$-II$_7$ or any one of the applicable definitions (4a)-(4ffff)]):

|  | (II) | Ring A | Y | Z |
|---|---|---|---|---|
| (2)-1 | (IIa) | (4a) | (2a) | (3a) |
| (2)-2 | (IIa) | (4c) | (2d) | (3b) |
| (2)-3 | (IIa) | (4e) | (2e) | (3c) |
| (2)-4 | (IIa) | (4g) | (2h) | (3f) |
| (2)-5 | (IIa) | (4h) | (2i) | (3h) |
| (2)-6 | (IIa) | (4b) | (2l) | (3j) |
| (2)-7 | (IIa) | (4d) | (2m) | (3m) |
| (2)-8 | (IIa) | (4f) | (2r) | (3n) |
| (2)-9 | (IIa) | (4nnn) | (2v) | (3o) |
| (2)-10 | (IIa) | (4ooo) | (2aa) | (3p) |
| (2)-11 | (IIa) | (4ppp) | (2bb) | (3q) |
| (2)-12 | (IIa) | (4qqq) | (2cc) | (3v) |
| (2)-13 | (IIa) | (4ttt) | (2ff) | (3w) |
| (2)-14 | (IIa) | (4vvv) | (2gg) | (3x) |

| (2)- | (II) | Ring A | Y | Z |
|---|---|---|---|---|
| (2)-15 | (IIa) | (4yyy) | (2hh) | (3aa) |
| (2)-16 | (IIa) | (4zzz) | (2ii) | (3ee) |
| (2)-17 | (IIa) | (4cccc) | (2jj) | (3ii) |
| (2)-18 | (IIa) | (4dddd) | (2kk) | (3kk) |
| (2)-19 | (IIa) | (4d) | (2ll) | (3oo) |
| (2)-20 | (IIa) | (4a) | (2i) | (3rr) |
| (2)-21 | (IIa) | (4c) | (2l) | (3v) |
| (2)-22 | (IIa) | (4e) | (2m) | (3w) |
| (2)-23 | (IIa) | (4g) | (2r) | (3x) |
| (2)-24 | (IIa) | (4h) | (2v) | (3aa) |
| (2)-25 | (IIa) | (4nnn) | (2aa) | (3n) |
| (2)-26 | (IIa) | (4cccc) | (2m) | (3aa) |
| (2)-27 | (IIa) | (4vvv) | (2r) | (3n) |
| (2)-28 | (IIa) | (4cccc) | (2v) | (3o) |
| (2)-29 | (IIa) | (4vvv) | (2aa) | (3p) |
| (2)-30 | (IIa) | (4nnn) | (2aa) | (3aa) |
| (2)-31 | (IIb) | (4i) | (2m) | (3n) |
| (2)-32 | (IIb) | (4j) | (2r) | (3o) |
| (2)-33 | (IIb) | (4k) | (2e) | (3p) |
| (2)-34 | (IIb) | (4l) | (2h) | (3m) |
| (2)-35 | (IIb) | (4n) | (2i) | (3n) |
| (2)-36 | (IIb) | (4nnn) | (2l) | (3o) |
| (2)-37 | (IIb) | (4cccc) | (2m) | (3p) |
| (2)-38 | (IIb) | (4j) | (2m) | (3q) |
| (2)-39 | (IIb) | (4k) | (2r) | (3v) |
| (2)-40 | (IIb) | (4l) | (2v) | (3w) |
| (2)-41 | (IIb) | (4n) | (2aa) | (3x) |
| (2)-42 | (IIb) | (4j) | (2m) | (3aa) |
| (2)-43 | (IIb) | (4k) | (2r) | (3n) |
| (2)-44 | (IIb) | (4l) | (2v) | (3o) |
| (2)-45 | (IIb) | (4n) | (2aa) | (3p) |
| (2)-46 | (IIb) | (4nnn) | (2i) | (3q) |
| (2)-47 | (IIb) | (4cccc) | (2l) | (3aa) |
| (2)-48 | (IIb) | (4i) | (2m) | (3n) |
| (2)-49 | (IIb) | (4i) | (2r) | (3o) |
| (2)-50 | (IIb) | (4j) | (2v) | (3p) |
| (2)-51 | (IIb) | (4k) | (2aa) | (3b) |
| (2)-52 | (IIb) | (4l) | (2aa) | (3c) |
| (2)-53 | (IIb) | (4n) | (2m) | (3f) |
| (2)-54 | (IIb) | (4nnn) | (2r) | (3h) |
| (2)-55 | (IIb) | (4cccc) | (2e) | (3j) |
| (2)-56 | (IIb) | (4vvv) | (2h) | (3m) |
| (2)-57 | (IIb) | (4cccc) | (2i) | (3n) |
| (2)-58 | (IIb) | (4l) | (2l) | (3o) |
| (2)-59 | (IIb) | (4n) | (2m) | (3p) |
| (2)-60 | (IIb) | (4nnn) | (2r) | (3q) |
| (2)-61 | (IIc) | (4o) | (2v) | (3v) |
| (2)-62 | (IIc) | (4p) | (2aa) | (3w) |
| (2)-63 | (IIc) | (4s) | (2aa) | (3x) |
| (2)-64 | (IIc) | (4t) | (2m) | (3aa) |
| (2)-65 | (IIc) | (4w) | (2r) | (3ee) |
| (2)-66 | (IIc) | (4p) | (2aa) | (3ii) |
| (2)-67 | (IIc) | (4s) | (2bb) | (3kk) |
| (2)-68 | (IIc) | (4o) | (2cc) | (3oo) |
| (2)-69 | (IIc) | (4o) | (2e) | (3rr) |
| (2)-70 | (IIc) | (4p) | (2h) | (3a) |
| (2)-71 | (IIc) | (4s) | (2i) | (3b) |
| (2)-72 | (IIc) | (4o) | (2l) | (3c) |
| (2)-73 | (IIc) | (4p) | (2m) | (3f) |
| (2)-74 | (IIc) | (4s) | (2r) | (3h) |
| (2)-75 | (IIc) | (4t) | (2m) | (3j) |
| (2)-76 | (IIc) | (4w) | (2r) | (3m) |
| (2)-77 | (IIc) | (4o) | (2v) | (3n) |
| (2)-78 | (IIc) | (4p) | (2aa) | (3o) |
| (2)-79 | (IIc) | (4s) | (2m) | (3p) |
| (2)-80 | (IIc) | (4t) | (2r) | (3q) |
| (2)-81 | (IIc) | (4w) | (2v) | (3v) |
| (2)-82 | (IIc) | (4ooo) | (2aa) | (3w) |
| (2)-83 | (IIc) | (4ppp) | (2h) | (3x) |
| (2)-84 | (IIc) | (4qqq) | (2i) | (3aa) |
| (2)-85 | (IIc) | (4ttt) | (2l) | (3ee) |
| (2)-86 | (IIc) | (4vvv) | (2m) | (3ii) |
| (2)-87 | (IIc) | (4yyy) | (2r) | (3kk) |
| (2)-88 | (IIc) | (4zzz) | (2r) | (3oo) |
| (2)-89 | (IIc) | (4cccc) | (2v) | (3rr) |
| (2)-90 | (IIc) | (4dddd) | (2aa) | (3v) |
| (2)-91 | (IId) | (4x) | (2h) | (3w) |
| (2)-92 | (IId) | (4aa) | (2i) | (3x) |
| (2)-93 | (IId) | (4ee) | (2l) | (3aa) |
| (2)-94 | (IId) | (4ff) | (2m) | (3o) |
| (2)-95 | (IId) | (4gg) | (2r) | (3p) |
| (2)-96 | (IId) | (4jj) | (2l) | (3q) |
| (2)-97 | (IId) | (4ff) | (2m) | (3v) |
| (2)-98 | (IId) | (4gg) | (2r) | (3w) |
| (2)-99 | (IId) | (4jj) | (2v) | (3x) |
| (2)-100 | (IId) | (4ee) | (2aa) | (3aa) |
| (2)-101 | (IId) | (4aa) | (2e) | (3v) |
| (2)-102 | (IId) | (4ee) | (2h) | (3w) |
| (2)-103 | (IId) | (4ff) | (2i) | (3x) |
| (2)-104 | (IId) | (4gg) | (2l) | (3aa) |
| (2)-105 | (IId) | (4jj) | (2m) | (3b) |
| (2)-106 | (IId) | (4ee) | (2r) | (3c) |
| (2)-107 | (IId) | (4ff) | (2v) | (3f) |
| (2)-108 | (IId) | (4gg) | (2aa) | (3h) |
| (2)-109 | (IId) | (4jj) | (2aa) | (3j) |
| (2)-110 | (IId) | (4aa) | (2aa) | (3m) |
| (2)-111 | (IId) | (4nnn) | (2bb) | (3n) |
| (2)-112 | (IId) | (4ooo) | (2cc) | (3o) |
| (2)-113 | (IId) | (4ppp) | (2e) | (3p) |
| (2)-114 | (IId) | (4qqq) | (2r) | (3q) |
| (2)-115 | (IId) | (4ttt) | (2v) | (3v) |
| (2)-116 | (IId) | (4vvv) | (2aa) | (3w) |
| (2)-117 | (IId) | (4yyy) | (2bb) | (3x) |
| (2)-118 | (IId) | (4zzz) | (2cc) | (3aa) |
| (2)-119 | (IId) | (4cccc) | (2e) | (3ee) |
| (2)-120 | (IId) | (4dddd) | (2h) | (3ii) |
| (2)-121 | (IIe) | (4mm) | (2i) | (3kk) |
| (2)-122 | (IIe) | (4ss) | (2l) | (3oo) |
| (2)-123 | (IIe) | (4uu) | (2m) | (3rr) |
| (2)-124 | (IIe) | (4ggg) | (2r) | (3aa) |
| (2)-125 | (IIe) | (4jjj) | (2v) | (3n) |
| (2)-126 | (IIe) | (4lll) | (2aa) | (3o) |
| (2)-127 | (IIe) | (4ss) | (2bb) | (3p) |
| (2)-128 | (IIe) | (4uu) | (2cc) | (3aa) |
| (2)-129 | (IIe) | (4ggg) | (2ff) | (3a) |
| (2)-130 | (IIe) | (4mm) | (2gg) | (3b) |
| (2)-131 | (IIe) | (4ss) | (2hh) | (3c) |
| (2)-132 | (IIe) | (4uu) | (2ii) | (3f) |
| (2)-133 | (IIe) | (4ggg) | (2jj) | (3h) |
| (2)-134 | (IIe) | (4jjj) | (2kk) | (3j) |
| (2)-135 | (IIe) | (4lll) | (2ll) | (3m) |
| (2)-136 | (IIe) | (4mmm) | (2i) | (3n) |
| (2)-137 | (IIe) | (4uu) | (2l) | (3o) |
| (2)-138 | (IIe) | (4ggg) | (2m) | (3p) |
| (2)-139 | (IIe) | (4jjj) | (2i) | (3q) |
| (2)-140 | (IIe) | (4lll) | (2l) | (3v) |
| (2)-141 | (IIe) | (4mmm) | (2m) | (3w) |
| (2)-142 | (IIe) | (4ooo) | (2r) | (3x) |
| (2)-143 | (IIe) | (4ppp) | (2v) | (3aa) |
| (2)-144 | (IIe) | (4qqq) | (2aa) | (3ee) |
| (2)-145 | (IIe) | (4ttt) | (2aa) | (3ii) |
| (2)-146 | (IIe) | (4vvv) | (2bb) | (3kk) |
| (2)-147 | (IIe) | (4yyy) | (2cc) | (3oo) |
| (2)-148 | (IIe) | (4zzz) | (2e) | (3rr) |
| (2)-149 | (IIe) | (4cccc) | (2h) | (3aa) |
| (2)-150 | (IIe) | (4dddd) | (2i) | (3rr) |
| (2)-151 | (IIf) | (4a) | (2l) | (3o) |
| (2)-152 | (IIf) | (4c) | (2m) | (3p) |
| (2)-153 | (IIf) | (4e) | (2r) | (3m) |
| (2)-154 | (IIf) | (4g) | (2v) | (3n) |
| (2)-155 | (IIf) | (4h) | (2aa) | (3o) |
| (2)-156 | (IIf) | (4b) | (2bb) | (3p) |
| (2)-157 | (IIf) | (4d) | (2cc) | (3q) |
| (2)-158 | (IIf) | (4f) | (2ff) | (3v) |
| (2)-159 | (IIf) | (4nnn) | (2gg) | (3w) |
| (2)-160 | (IIf) | (4ooo) | (2hh) | (3x) |
| (2)-161 | (IIf) | (4ppp) | (2ii) | (3aa) |
| (2)-162 | (IIf) | (4qqq) | (2jj) | (3aa) |
| (2)-163 | (IIf) | (4ttt) | (2kk) | (3n) |
| (2)-164 | (IIf) | (4vvv) | (2ll) | (3o) |
| (2)-165 | (IIf) | (4yyy) | (2cc) | (3p) |
| (2)-166 | (IIf) | (4zzz) | (2ff) | (3a) |
| (2)-167 | (IIf) | (4cccc) | (2gg) | (3b) |
| (2)-168 | (IIf) | (4dddd) | (2hh) | (3c) |

-continued

| (II) | Ring A | Y | Z |
|---|---|---|---|
| (2)-169 | (IIf) | (4d) | (2r) | (3f) |
| (2)-170 | (IIf) | (4a) | (2v) | (3h) |
| (2)-171 | (IIf) | (4c) | (2aa) | (3j) |
| (2)-172 | (IIf) | (4e) | (2bb) | (3m) |
| (2)-173 | (IIf) | (4g) | (2cc) | (3n) |
| (2)-174 | (IIf) | (4h) | (2ff) | (3o) |
| (2)-175 | (IIf) | (4nnn) | (2l) | (3p) |
| (2)-176 | (IIf) | (4cccc) | (2m) | (3q) |
| (2)-177 | (IIf) | (4vvv) | (2r) | (3v) |
| (2)-178 | (IIf) | (4cccc) | (2v) | (3w) |
| (2)-179 | (IIf) | (4vvv) | (2aa) | (3x) |
| (2)-180 | (IIf) | (4nnn) | (2m) | (3aa) |
| (2)-181 | (IIg) | (4i) | (2r) | (3ee) |
| (2)-182 | (IIg) | (4j) | (2v) | (3ii) |
| (2)-183 | (IIg) | (4k) | (2aa) | (3kk) |
| (2)-184 | (IIg) | (4l) | (2bb) | (3oo) |
| (2)-185 | (IIg) | (4n) | (2cc) | (3rr) |
| (2)-186 | (IIg) | (4nnn) | (2m) | (3v) |
| (2)-187 | (IIg) | (4cccc) | (2r) | (3w) |
| (2)-188 | (IIg) | (4j) | (2v) | (3x) |
| (2)-189 | (IIg) | (4k) | (2aa) | (3aa) |
| (2)-190 | (IIg) | (4l) | (2bb) | (3ee) |
| (2)-191 | (IIg) | (4n) | (2cc) | (3o) |
| (2)-192 | (IIg) | (4j) | (2l) | (3p) |
| (2)-193 | (IIg) | (4k) | (2m) | (3a) |
| (2)-194 | (IIg) | (4l) | (2r) | (3b) |
| (2)-195 | (IIg) | (4n) | (2v) | (3v) |
| (2)-196 | (IIg) | (4nnn) | (2aa) | (3w) |
| (2)-197 | (IIg) | (4cccc) | (2bb) | (3x) |
| (2)-198 | (IIg) | (4i) | (2cc) | (3aa) |
| (2)-199 | (IIg) | (4i) | (2ff) | (3o) |
| (2)-200 | (IIg) | (4j) | (2gg) | (3p) |
| (2)-201 | (IIg) | (4k) | (2hh) | (3q) |
| (2)-202 | (IIg) | (4l) | (2ii) | (3v) |
| (2)-203 | (IIg) | (4n) | (2jj) | (3w) |
| (2)-204 | (IIg) | (4nnn) | (2kk) | (3x) |
| (2)-205 | (IIg) | (4cccc) | (2ll) | (3aa) |
| (2)-206 | (IIg) | (4vvv) | (2e) | (3o) |
| (2)-207 | (IIg) | (4cccc) | (2h) | (3p) |
| (2)-208 | (IIg) | (4l) | (2i) | (3a) |
| (2)-209 | (IIg) | (4n) | (2l) | (3b) |
| (2)-210 | (IIg) | (4nnn) | (2m) | (3b) |
| (2)-211 | (IIh) | (4o) | (2cc) | (3c) |
| (2)-212 | (IIh) | (4p) | (2ff) | (3f) |
| (2)-213 | (IIh) | (4s) | (2e) | (3h) |
| (2)-214 | (IIh) | (4t) | (2h) | (3j) |
| (2)-215 | (IIh) | (4w) | (2i) | (3m) |
| (2)-216 | (IIh) | (4p) | (2l) | (3n) |
| (2)-217 | (IIh) | (4s) | (2m) | (3o) |
| (2)-218 | (IIh) | (4o) | (2r) | (3p) |
| (2)-219 | (IIh) | (4o) | (2v) | (3q) |
| (2)-220 | (IIh) | (4p) | (2aa) | (3v) |
| (2)-221 | (IIh) | (4s) | (2bb) | (3w) |
| (2)-222 | (IIh) | (4o) | (2cc) | (3x) |
| (2)-223 | (IIh) | (4p) | (2ff) | (3aa) |
| (2)-224 | (IIh) | (4s) | (2gg) | (3ee) |
| (2)-225 | (IIh) | (4t) | (2hh) | (3ii) |
| (2)-226 | (IIh) | (4w) | (2ii) | (3kk) |
| (2)-227 | (IIh) | (4o) | (2jj) | (3oo) |
| (2)-228 | (IIh) | (4p) | (2kk) | (3rr) |
| (2)-229 | (IIh) | (4s) | (2ll) | (3m) |
| (2)-230 | (IIh) | (4t) | (2e) | (3n) |
| (2)-231 | (IIh) | (4nnn) | (2h) | (3o) |
| (2)-232 | (IIh) | (4ooo) | (2i) | (3p) |
| (2)-233 | (IIh) | (4ppp) | (2l) | (3q) |
| (2)-234 | (IIh) | (4qqq) | (2m) | (3v) |
| (2)-235 | (IIh) | (4ttt) | (2cc) | (3w) |
| (2)-236 | (IIh) | (4vvv) | (2ff) | (3x) |
| (2)-237 | (IIh) | (4yyy) | (2e) | (3aa) |
| (2)-238 | (IIh) | (4zzz) | (2h) | (3o) |
| (2)-239 | (IIh) | (4cccc) | (2i) | (3p) |
| (2)-240 | (IIh) | (4dddd) | (2l) | (3q) |
| (2)-241 | (IIi) | (4x) | (2m) | (3v) |
| (2)-242 | (IIi) | (4aa) | (2aa) | (3w) |
| (2)-243 | (IIi) | (4ee) | (2bb) | (3x) |
| (2)-244 | (IIi) | (4ff) | (2cc) | (3aa) |
| (2)-245 | (IIi) | (4gg) | (2ff) | (3ee) |

-continued

| (II) | Ring A | Y | Z |
|---|---|---|---|
| (2)-246 | (IIi) | (4jj) | (2e) | (3ii) |
| (2)-247 | (IIi) | (4ff) | (2h) | (3kk) |
| (2)-248 | (IIi) | (4gg) | (2i) | (3oo) |
| (2)-249 | (IIi) | (4jj) | (2l) | (3rr) |
| (2)-250 | (IIi) | (4ee) | (2m) | (3o) |
| (2)-251 | (IIi) | (4aa) | (2r) | (3p) |
| (2)-252 | (IIi) | (4ee) | (2v) | (3a) |
| (2)-253 | (IIi) | (4ff) | (2aa) | (3b) |
| (2)-254 | (IIi) | (4gg) | (2bb) | (3o) |
| (2)-255 | (IIi) | (4jj) | (2cc) | (3p) |
| (2)-256 | (IIi) | (4ee) | (2ff) | (3q) |
| (2)-257 | (IIi) | (4ff) | (2gg) | (3v) |
| (2)-258 | (IIi) | (4gg) | (2hh) | (3w) |
| (2)-259 | (IIi) | (4jj) | (2ii) | (3x) |
| (2)-260 | (IIi) | (4aa) | (2jj) | (3aa) |
| (2)-261 | (IIi) | (4nnn) | (2kk) | (3n) |
| (2)-262 | (IIi) | (4ooo) | (2ll) | (3o) |
| (2)-263 | (IIi) | (4ppp) | (2cc) | (3p) |
| (2)-264 | (IIi) | (4qqq) | (2ff) | (3q) |
| (2)-265 | (IIi) | (4ttt) | (2gg) | (3v) |
| (2)-266 | (IIi) | (4vvv) | (2hh) | (3w) |
| (2)-267 | (IIi) | (4yyy) | (2e) | (3x) |
| (2)-268 | (IIi) | (4zzz) | (2h) | (3aa) |
| (2)-269 | (IIi) | (4cccc) | (2i) | (3ee) |
| (2)-270 | (IIi) | (4dddd) | (2l) | (3ii) |
| (2)-271 | (IIj) | (4mm) | (2m) | (3kk) |
| (2)-272 | (IIj) | (4ss) | (2d) | (3oo) |
| (2)-273 | (IIj) | (4uu) | (2e) | (3rr) |
| (2)-274 | (IIj) | (4ggg) | (2h) | (3v) |
| (2)-275 | (IIj) | (4jjj) | (2i) | (3w) |
| (2)-276 | (IIj) | (4lll) | (2l) | (3x) |
| (2)-277 | (IIj) | (4ss) | (2m) | (3aa) |
| (2)-278 | (IIj) | (4uu) | (2r) | (3m) |
| (2)-279 | (IIj) | (4ggg) | (2v) | (3n) |
| (2)-280 | (IIj) | (4mm) | (2aa) | (3o) |
| (2)-281 | (IIj) | (4ss) | (2bb) | (3p) |
| (2)-282 | (IIj) | (4uu) | (2cc) | (3q) |
| (2)-283 | (IIj) | (4ggg) | (2ff) | (3v) |
| (2)-284 | (IIj) | (4jjj) | (2gg) | (3w) |
| (2)-285 | (IIj) | (4lll) | (2hh) | (3x) |
| (2)-286 | (IIj) | (4mmm) | (2ii) | (3aa) |
| (2)-287 | (IIj) | (4uu) | (2jj) | (3b) |
| (2)-288 | (IIj) | (4ggg) | (2kk) | (3c) |
| (2)-289 | (IIj) | (4jjj) | (2ll) | (3f) |
| (2)-290 | (IIj) | (4lll) | (2cc) | (3h) |
| (2)-291 | (IIj) | (4mmm) | (2ff) | (3j) |
| (2)-292 | (IIj) | (4ooo) | (2gg) | (3m) |
| (2)-293 | (IIj) | (4ppp) | (2hh) | (3n) |
| (2)-294 | (IIj) | (4qqq) | (2h) | (3o) |
| (2)-295 | (IIj) | (4ttt) | (2i) | (3p) |
| (2)-296 | (IIj) | (4vvv) | (2l) | (3q) |
| (2)-297 | (IIj) | (4yyy) | (2m) | (3v) |
| (2)-298 | (IIj) | (4zzz) | (2v) | (3w) |
| (2)-299 | (IIj) | (4cccc) | (2aa) | (3x) |
| (2)-300 | (IIj) | (4dddd) | (2bb) | (3aa) |

In some embodiments, the compound of formulae (II) or (IIa)-(IIj) is one of the following compounds (or a pharmaceutically acceptable salt, prodrug, or N-oxide thereof, or a solvate or hydrate thereof): 2, 3, 5, 14, 15, 16, 17, 20, 21, 26, 27, 28, 29, 30, 31, 32, 33, 34, 35, 36, 37, 38, 39, 40, 42, 43, 44, 47, 48, 50, 53, 55, 56, 57, 60, 61, 62, 65, 68, 69, 71, 73, 76, 77, 78, 80, 81, 83, 86, 88, 90, 92, 96, 97, 98, 99, 106, 107, 109, 113 or 123.

In embodiment $M_k$ of this aspect, the invention comprises compounds having the structure of formula (III):

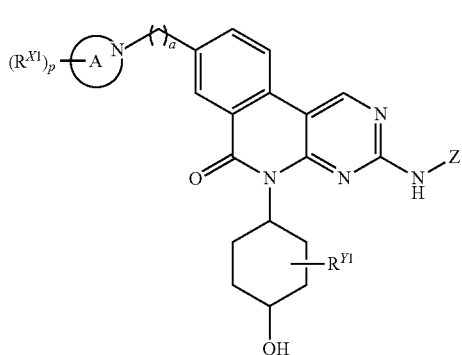
(III)

or a pharmaceutically acceptable salt, prodrug or N-oxide thereof, or solvate or hydrate thereof, wherein
a is 0 or 1;
ring A is

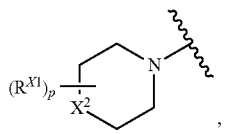
(a)

wherein
p is 0, 1, 2 or 3;
$X^2$ is —O—, —S—, —CR$_2$—, —C(R)(R$^{X1}$)—, —C(R$^{X1}$)$_2$—, —N(R)— or —N(R$^{X1}$)—;

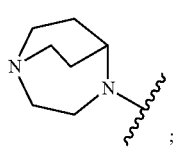
(b)

wherein
p is 0, 1 or 2;
ring B is 5-membered Hca or Het; or

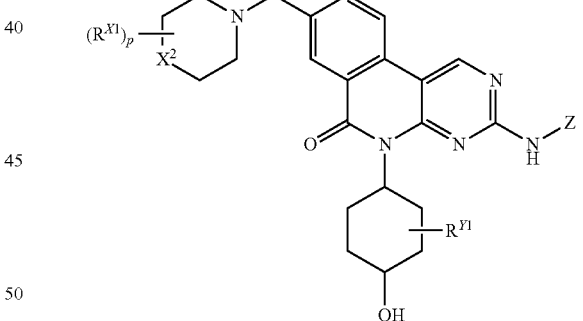
(c)

each —R$^{X1}$ is independently hydrogen, C$_1$-C$_6$alkyl, —C(O)OR, Cak(C$_0$-C$_6$alkyl) or Hca(C$_0$-C$_6$alkyl);
—R$^{Y1}$ is hydrogen or C$_1$-C$_6$alkyl;
Z is C$_1$-C$_6$alkyl or Cak(C$_1$-C$_6$alkyl); and
each R is independently hydrogen or C$_1$-C$_6$alkyl.

In embodiment III$_2$, the compounds are of embodiment I$_1$, wherein a is 0.

In embodiment III$_3$, the compounds are of embodiment I$_1$, wherein a is 1.

In embodiment III$_4$, the compounds are of embodiment I$_1$-II$_3$, wherein ring A is

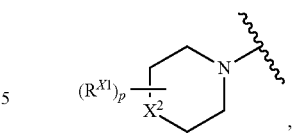

wherein p is 0, 1, 2 or 3; and $X^2$ is —O—, —S—, —CR$_2$—, —C(R)(R$^{X1}$)—, —C(R$^{X1}$)$_2$—, —N(R)— or —N(R$^{X1}$)—.

In embodiment III$_5$, the compounds are of embodiment I$_1$-II$_3$, wherein ring A is

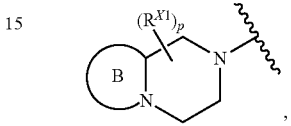

wherein p is 0, 1 or 2; and ring B is 5-membered Hca or Het.

In embodiment III$_6$, the compounds are of embodiment I$_1$-II$_3$, wherein ring A is

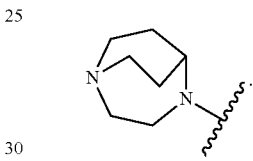

In embodiment III$_7$, the compounds of the invention are of one of formulae (IIIa)-(IIIf), wherein all labels are as defined in any of embodiments III$_1$-III$_6$ above:

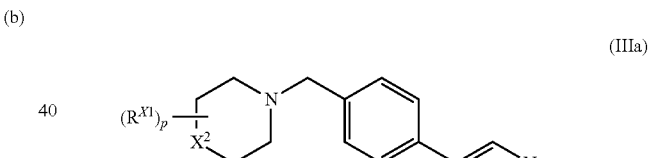
(IIIa)

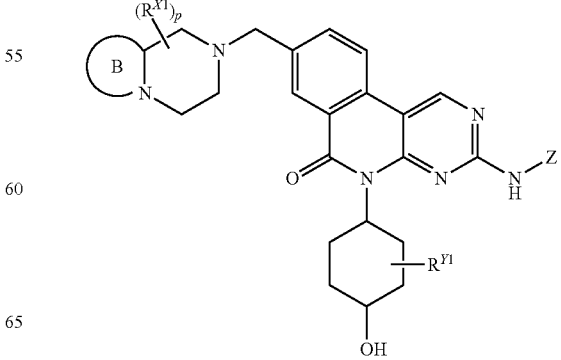
(IIIb)

-continued

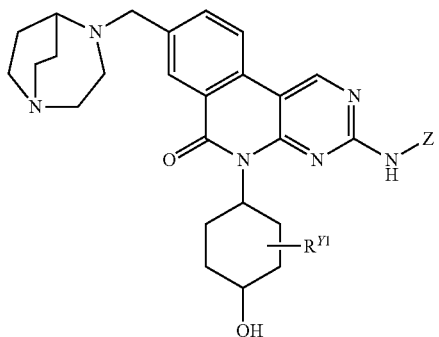
(IIIc)

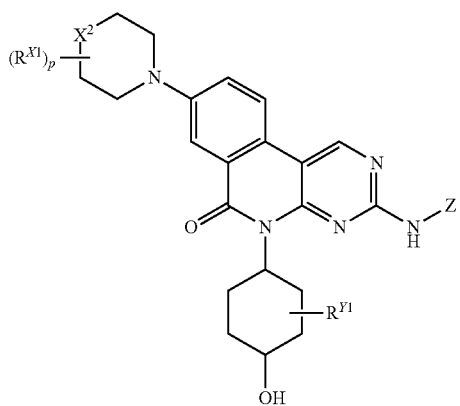
(IIId)

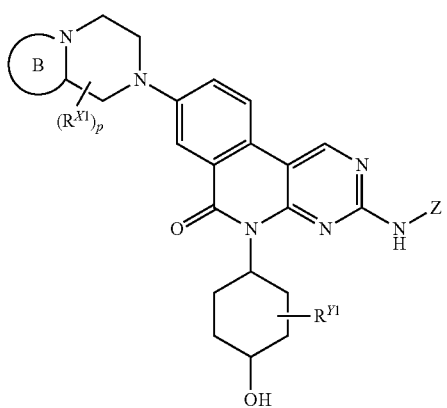
(IIIe)

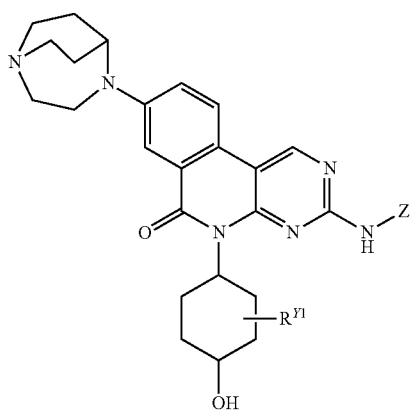
(IIIf)

Particular embodiments of this aspect of the invention comprise compounds of any one of the formulae (III), and (IIIa)-(IIf), each as defined in each of the following rows (or a pharmaceutically acceptable salt, prodrug, or N-oxide thereof, or a solvate or hydrate thereof), wherein each entry is a group number as defined above (e.g., (4ffff) refers to Ring A being any of groups (4a)-(4fff), wherein p is 0, and a dash "—" indicates that the variable is as defined in embodiment III or defined according to any one of the applicable variable definitions (4a)-(4ffff), (2a)-(2ll) and (3a)-(3xx) [e.g., when Ring A is a dash, it can be either as defined in any of embodiments $III_1$-$III_7$ or any one of the applicable definitions (4a)-(4ffff)]):

|  | (III) | Ring A | Z |
|---|---|---|---|
| (3)-1 | (IIIa) | (4i) | (3a) |
| (3)-2 | (IIIa) | (4j) | (3b) |
| (3)-3 | (IIIa) | (4k) | (3c) |
| (3)-4 | (IIIa) | (4l) | (3f) |
| (3)-5 | (IIIa) | (4n) | (3h) |
| (3)-6 | (IIIa) | (4nnn) | (3j) |
| (3)-7 | (IIIa) | (4cccc) | (3m) |
| (3)-8 | (IIIa) | (4j) | (3n) |
| (3)-9 | (IIIa) | (4k) | (3o) |
| (3)-10 | (IIIa) | (4l) | (3p) |
| (3)-11 | (IIIa) | (4n) | (3q) |
| (3)-12 | (IIIa) | (4j) | (3v) |
| (3)-13 | (IIIa) | (4k) | (3w) |
| (3)-14 | (IIIa) | (4l) | (3x) |
| (3)-15 | (IIIa) | (4n) | (3aa) |
| (3)-16 | (IIIa) | (4nnn) | (3ee) |
| (3)-17 | (IIIa) | (4cccc) | (3ii) |
| (3)-18 | (IIIa) | (4i) | (3kk) |
| (3)-19 | (IIIa) | (4i) | (3oo) |
| (3)-20 | (IIIa) | (4j) | (3rr) |
| (3)-21 | (IIIa) | (4k) | (3v) |
| (3)-22 | (IIIa) | (4l) | (3w) |
| (3)-23 | (IIIa) | (4n) | (3x) |
| (3)-24 | (IIIa) | (4nnn) | (3aa) |
| (3)-25 | (IIIa) | (4cccc) | (3n) |
| (3)-26 | (IIIa) | (4vvv) | (3aa) |
| (3)-27 | (IIIa) | (4cccc) | (3n) |
| (3)-28 | (IIIa) | (4l) | (3o) |
| (3)-29 | (IIIa) | (4n) | (3p) |
| (3)-30 | (IIIa) | (4nnn) | (3aa) |
| (3)-31 | (IIIa) | (4i) | (3n) |
| (3)-32 | (IIIa) | (4j) | (3o) |
| (3)-33 | (IIIa) | (4k) | (3p) |
| (3)-34 | (IIIa) | (4l) | (3m) |
| (3)-35 | (IIIa) | (4n) | (3n) |
| (3)-36 | (IIIa) | (4nnn) | (3o) |
| (3)-37 | (IIIa) | (4cccc) | (3p) |
| (3)-38 | (IIIa) | (4j) | (3q) |
| (3)-39 | (IIIa) | (4k) | (3v) |
| (3)-40 | (IIIa) | (4l) | (3w) |
| (3)-41 | (IIIa) | (4n) | (3x) |
| (3)-42 | (IIIa) | (4j) | (3aa) |
| (3)-43 | (IIIa) | (4k) | (3n) |
| (3)-44 | (IIIa) | (4l) | (3o) |
| (3)-45 | (IIIa) | (4n) | (3p) |
| (3)-46 | (IIIa) | (4nnn) | (3q) |
| (3)-47 | (IIIa) | (4cccc) | (3aa) |
| (3)-48 | (IIIa) | (4i) | (3n) |
| (3)-49 | (IIIa) | (4i) | (3o) |
| (3)-50 | (IIIa) | (4j) | (3p) |
| (3)-51 | (IIIb) | (4o) | (3b) |
| (3)-52 | (IIIb) | (4p) | (3c) |
| (3)-53 | (IIIb) | (4s) | (3f) |
| (3)-54 | (IIIb) | (4t) | (3h) |
| (3)-55 | (IIIb) | (4w) | (3j) |
| (3)-56 | (IIIb) | (4p) | (3m) |
| (3)-57 | (IIIb) | (4s) | (3n) |
| (3)-58 | (IIIb) | (4o) | (3o) |
| (3)-59 | (IIIb) | (4o) | (3p) |
| (3)-60 | (IIIb) | (4p) | (3q) |
| (3)-61 | (IIIb) | (4s) | (3v) |
| (3)-62 | (IIIb) | (4o) | (3w) |
| (3)-63 | (IIIb) | (4p) | (3x) |
| (3)-64 | (IIIb) | (4s) | (3aa) |
| (3)-65 | (IIIb) | (4t) | (3ee) |

-continued

| | (III) | Ring A | Z |
|---|---|---|---|
| (3)-66 | (IIIb) | (4w) | (3ii) |
| (3)-67 | (IIIb) | (4o) | (3kk) |
| (3)-68 | (IIIb) | (4p) | (3oo) |
| (3)-69 | (IIIb) | (4s) | (3rr) |
| (3)-70 | (IIIb) | (4t) | (3a) |
| (3)-71 | (IIIb) | (4w) | (3b) |
| (3)-72 | (IIIb) | (4ooo) | (3c) |
| (3)-73 | (IIIb) | (4ppp) | (3f) |
| (3)-74 | (IIIb) | (4qqq) | (3h) |
| (3)-75 | (IIIb) | (4ttt) | (3j) |
| (3)-76 | (IIIb) | (4vvv) | (3m) |
| (3)-77 | (IIIb) | (4yyy) | (3n) |
| (3)-78 | (IIIb) | (4zzz) | (3o) |
| (3)-79 | (IIIb) | (4cccc) | (3p) |
| (3)-80 | (IIIb) | (4ooo) | (3q) |
| (3)-81 | (IIIb) | (4o) | (3v) |
| (3)-82 | (IIIb) | (4p) | (3w) |
| (3)-83 | (IIIb) | (4s) | (3x) |
| (3)-84 | (IIIb) | (4t) | (3aa) |
| (3)-85 | (IIIb) | (4w) | (3ee) |
| (3)-86 | (IIIb) | (4p) | (3ii) |
| (3)-87 | (IIIb) | (4s) | (3kk) |
| (3)-88 | (IIIb) | (4o) | (3oo) |
| (3)-89 | (IIIb) | (4o) | (3rr) |
| (3)-90 | (IIIb) | (4p) | (3v) |
| (3)-91 | (IIIb) | (4s) | (3w) |
| (3)-92 | (IIIb) | (4o) | (3x) |
| (3)-93 | (IIIb) | (4p) | (3aa) |
| (3)-94 | (IIIb) | (4s) | (3o) |
| (3)-95 | (IIIb) | (4t) | (3p) |
| (3)-96 | (IIIb) | (4w) | (3q) |
| (3)-97 | (IIIb) | (4o) | (3v) |
| (3)-98 | (IIIb) | (4p) | (3w) |
| (3)-99 | (IIIb) | (4s) | (3x) |
| (3)-100 | (IIIb) | (4t) | (3aa) |
| (3)-101 | (IIIc) | — | (3v) |
| (3)-102 | (IIIc) | — | (3w) |
| (3)-103 | (IIIc) | — | (3x) |
| (3)-104 | (IIIc) | — | (3aa) |
| (3)-105 | (IIIc) | — | (3b) |
| (3)-106 | (IIIc) | — | (3c) |
| (3)-107 | (IIIc) | — | (3f) |
| (3)-108 | (IIIc) | — | (3h) |
| (3)-109 | (IIIc) | — | (3j) |
| (3)-110 | (IIIc) | — | (3m) |
| (3)-111 | (IIIc) | — | (3n) |
| (3)-112 | (IIIc) | — | (3o) |
| (3)-113 | (IIIc) | — | (3p) |
| (3)-114 | (IIIc) | — | (3q) |
| (3)-115 | (IIIc) | — | (3v) |
| (3)-116 | (IIIc) | — | (3w) |
| (3)-117 | (IIIc) | — | (3x) |
| (3)-118 | (IIIc) | — | (3aa) |
| (3)-119 | (IIIc) | — | (3ee) |
| (3)-120 | (IIIc) | — | (3ii) |
| (3)-121 | (IIIc) | — | (3kk) |
| (3)-122 | (IIIc) | — | (3oo) |
| (3)-123 | (IIIc) | — | (3rr) |
| (3)-124 | (IIIc) | — | (3aa) |
| (3)-125 | (IIIc) | — | (3n) |
| (3)-126 | (IIIc) | — | (3o) |
| (3)-127 | (IIIc) | — | (3p) |
| (3)-128 | (IIIc) | — | (3aa) |
| (3)-129 | (IIIc) | — | (3a) |
| (3)-130 | (IIIc) | — | (3b) |
| (3)-131 | (IIIc) | — | (3c) |
| (3)-132 | (IIIc) | — | (3f) |
| (3)-133 | (IIIc) | — | (3h) |
| (3)-134 | (IIIc) | — | (3j) |
| (3)-135 | (IIIc) | — | (3m) |
| (3)-136 | (IIIc) | — | (3n) |
| (3)-137 | (IIIc) | — | (3o) |
| (3)-138 | (IIIc) | — | (3p) |
| (3)-139 | (IIIc) | — | (3q) |
| (3)-140 | (IIIc) | — | (3v) |
| (3)-141 | (IIIc) | — | (3w) |
| (3)-142 | (IIIc) | — | (3x) |
| (3)-143 | (IIIc) | — | (3aa) |
| (3)-144 | (IIIc) | — | (3ee) |
| (3)-145 | (IIIc) | — | (3ii) |
| (3)-146 | (IIIc) | — | (3kk) |
| (3)-147 | (IIIc) | — | (3oo) |
| (3)-148 | (IIIc) | — | (3rr) |
| (3)-149 | (IIIc) | — | (3aa) |
| (3)-150 | (IIIc) | — | (3n) |
| (3)-151 | (IIId) | (4i) | (3o) |
| (3)-152 | (IIId) | (4j) | (3p) |
| (3)-153 | (IIId) | (4k) | (3m) |
| (3)-154 | (IIId) | (4l) | (3n) |
| (3)-155 | (IIId) | (4n) | (3o) |
| (3)-156 | (IIId) | (4nnn) | (3p) |
| (3)-157 | (IIId) | (4cccc) | (3q) |
| (3)-158 | (IIId) | (4j) | (3v) |
| (3)-159 | (IIId) | (4k) | (3w) |
| (3)-160 | (IIId) | (4l) | (3x) |
| (3)-161 | (IIId) | (4n) | (3aa) |
| (3)-162 | (IIId) | (4j) | (3aa) |
| (3)-163 | (IIId) | (4k) | (3n) |
| (3)-164 | (IIId) | (4l) | (3o) |
| (3)-165 | (IIId) | (4n) | (3p) |
| (3)-166 | (IIId) | (4nnn) | (3a) |
| (3)-167 | (IIId) | (4cccc) | (3b) |
| (3)-168 | (IIId) | (4i) | (3c) |
| (3)-169 | (IIId) | (4i) | (3f) |
| (3)-170 | (IIId) | (4j) | (3h) |
| (3)-171 | (IIId) | (4k) | (3j) |
| (3)-172 | (IIId) | (4l) | (3m) |
| (3)-173 | (IIId) | (4n) | (3n) |
| (3)-174 | (IIId) | (4nnn) | (3o) |
| (3)-175 | (IIId) | (4cccc) | (3p) |
| (3)-176 | (IIId) | (4vvv) | (3q) |
| (3)-177 | (IIId) | (4cccc) | (3v) |
| (3)-178 | (IIId) | (4l) | (3w) |
| (3)-179 | (IIId) | (4n) | (3x) |
| (3)-180 | (IIId) | (4nnn) | (3aa) |
| (3)-181 | (IIId) | (4i) | (3ee) |
| (3)-182 | (IIId) | (4j) | (3ii) |
| (3)-183 | (IIId) | (4k) | (3kk) |
| (3)-184 | (IIId) | (4l) | (3oo) |
| (3)-185 | (IIId) | (4n) | (3rr) |
| (3)-186 | (IIId) | (4nnn) | (3v) |
| (3)-187 | (IIId) | (4cccc) | (3w) |
| (3)-188 | (IIId) | (4j) | (3x) |
| (3)-189 | (IIId) | (4k) | (3aa) |
| (3)-190 | (IIId) | (4l) | (3ee) |
| (3)-191 | (IIId) | (4n) | (3o) |
| (3)-192 | (IIId) | (4j) | (3p) |
| (3)-193 | (IIId) | (4k) | (3a) |
| (3)-194 | (IIId) | (4l) | (3b) |
| (3)-195 | (IIId) | (4n) | (3v) |
| (3)-196 | (IIId) | (4nnn) | (3w) |
| (3)-197 | (IIId) | (4cccc) | (3x) |
| (3)-198 | (IIId) | (4i) | (3aa) |
| (3)-199 | (IIId) | (4i) | (3o) |
| (3)-200 | (IIId) | (4j) | (3p) |
| (3)-201 | (IIIe) | (4o) | (3q) |
| (3)-202 | (IIIe) | (4p) | (3v) |
| (3)-203 | (IIIe) | (4s) | (3w) |
| (3)-204 | (IIIe) | (4t) | (3x) |
| (3)-205 | (IIIe) | (4w) | (3aa) |
| (3)-206 | (IIIe) | (4p) | (3o) |
| (3)-207 | (IIIe) | (4s) | (3p) |
| (3)-208 | (IIIe) | (4o) | (3a) |
| (3)-209 | (IIIe) | (4o) | (3b) |
| (3)-210 | (IIIe) | (4p) | (3b) |
| (3)-211 | (IIIe) | (4s) | (3c) |
| (3)-212 | (IIIe) | (4o) | (3f) |
| (3)-213 | (IIIe) | (4p) | (3h) |
| (3)-214 | (IIIe) | (4s) | (3j) |
| (3)-215 | (IIIe) | (4t) | (3m) |
| (3)-216 | (IIIe) | (4w) | (3n) |
| (3)-217 | (IIIe) | (4o) | (3o) |
| (3)-218 | (IIIe) | (4p) | (3p) |
| (3)-219 | (IIIe) | (4s) | (3q) |

-continued

|       | (III) | Ring A | Z |
|---|---|---|---|
| (3)-220 | (IIIe) | (4t) | (3v) |
| (3)-221 | (IIIe) | (4w) | (3w) |
| (3)-222 | (IIIe) | (4ooo) | (3x) |
| (3)-223 | (IIIe) | (4ppp) | (3aa) |
| (3)-224 | (IIIe) | (4qqq) | (3ee) |
| (3)-225 | (IIIe) | (4ttt) | (3ii) |
| (3)-226 | (IIIe) | (4vvv) | (3kk) |
| (3)-227 | (IIIe) | (4yyy) | (3oo) |
| (3)-228 | (IIIe) | (4zzz) | (3rr) |
| (3)-229 | (IIIe) | (4cccc) | (3m) |
| (3)-230 | (IIIe) | (4ooo) | (3n) |
| (3)-231 | (IIIe) | (4o) | (3o) |
| (3)-232 | (IIIe) | (4p) | (3p) |
| (3)-233 | (IIIe) | (4s) | (3q) |
| (3)-234 | (IIIe) | (4t) | (3v) |
| (3)-235 | (IIIe) | (4w) | (3w) |
| (3)-236 | (IIIe) | (4p) | (3x) |
| (3)-237 | (IIIe) | (4s) | (3aa) |
| (3)-238 | (IIIe) | (4o) | (3o) |
| (3)-239 | (IIIe) | (4o) | (3p) |
| (3)-240 | (IIIe) | (4p) | (3q) |
| (3)-241 | (IIIe) | (4s) | (3v) |
| (3)-242 | (IIIe) | (4o) | (3w) |
| (3)-243 | (IIIe) | (4p) | (3x) |
| (3)-244 | (IIIe) | (4s) | (3aa) |
| (3)-245 | (IIIe) | (4t) | (3ee) |
| (3)-246 | (IIIe) | (4w) | (3ii) |
| (3)-247 | (IIIe) | (4o) | (3kk) |
| (3)-248 | (IIIe) | (4p) | (3oo) |
| (3)-249 | (IIIe) | (4s) | (3rr) |
| (3)-250 | (IIIe) | (4t) | (3o) |
| (3)-251 | (IIIf) | — | (3p) |
| (3)-252 | (IIIf) | — | (3a) |
| (3)-253 | (IIIf) | — | (3b) |
| (3)-254 | (IIIf) | — | (3o) |
| (3)-255 | (IIIf) | — | (3p) |
| (3)-256 | (IIIf) | — | (3q) |
| (3)-257 | (IIIf) | — | (3v) |
| (3)-258 | (IIIf) | — | (3w) |
| (3)-259 | (IIIf) | — | (3x) |
| (3)-260 | (IIIf) | — | (3aa) |
| (3)-261 | (IIIf) | — | (3n) |
| (3)-262 | (IIIf) | — | (3o) |
| (3)-263 | (IIIf) | — | (3p) |
| (3)-264 | (IIIf) | — | (3q) |
| (3)-265 | (IIIf) | — | (3v) |
| (3)-266 | (IIIf) | — | (3w) |
| (3)-267 | (IIIf) | — | (3x) |
| (3)-268 | (IIIf) | — | (3aa) |
| (3)-269 | (IIIf) | — | (3ee) |
| (3)-270 | (IIIf) | — | (3ii) |
| (3)-271 | (IIIf) | — | (3kk) |
| (3)-272 | (IIIf) | — | (3oo) |
| (3)-273 | (IIIf) | — | (3rr) |
| (3)-274 | (IIIf) | — | (3v) |
| (3)-275 | (IIIf) | — | (3w) |
| (3)-276 | (IIIf) | — | (3x) |
| (3)-277 | (IIIf) | — | (3aa) |
| (3)-278 | (IIIf) | — | (3m) |
| (3)-279 | (IIIf) | — | (3n) |
| (3)-280 | (IIIf) | — | (3o) |
| (3)-281 | (IIIf) | — | (3p) |
| (3)-282 | (IIIf) | — | (3q) |
| (3)-283 | (IIIf) | — | (3v) |
| (3)-284 | (IIIf) | — | (3w) |
| (3)-285 | (IIIf) | — | (3x) |
| (3)-286 | (IIIf) | — | (3aa) |
| (3)-287 | (IIIf) | — | (3b) |
| (3)-288 | (IIIf) | — | (3c) |
| (3)-289 | (IIIf) | — | (3f) |
| (3)-290 | (IIIf) | — | (3h) |
| (3)-291 | (IIIf) | — | (3j) |
| (3)-292 | (IIIf) | — | (3m) |
| (3)-293 | (IIIf) | — | (3n) |
| (3)-294 | (IIIf) | — | (3o) |
| (3)-295 | (IIIf) | — | (3p) |
| (3)-296 | (IIIf) | — | (3q) |
| (3)-297 | (IIIf) | — | (3v) |
| (3)-298 | (IIIf) | — | (3w) |
| (3)-299 | (IIIf) | — | (3x) |
| (3)-300 | (IIIf) | — | (3aa) |

In some embodiments, the compound of formulae (III) or (IIIa)-(IIIf) is one of the following compounds (or a pharmaceutically acceptable salt, prodrug, or N-oxide thereof, or a solvate or hydrate thereof): 2, 3, 15, 20, 21, 26, 27, 28, 29, 30, 31, 32, 33, 34, 35, 36, 38, 42, 47, 48, 50, 53, 55, 60, 61, 69, 71, 73, 76, 77, 78, 80, 81, 83, 86, 90, 92, 96, 98 or 113.

In embodiment $IV_1$ of this aspect, the invention comprises compounds having the structure of formula (IV):

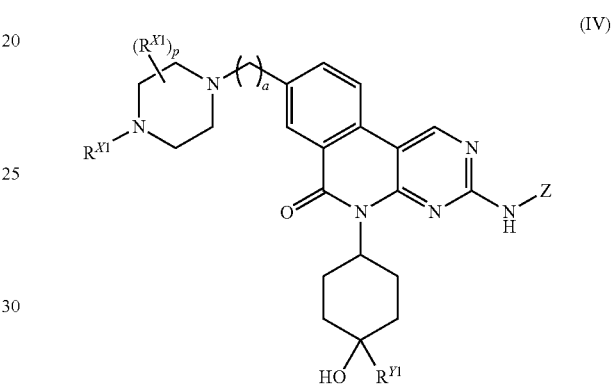

or a pharmaceutically acceptable salt, prodrug or N-oxide thereof, or solvate or hydrate thereof, wherein
a is 0 or 1;
each —$R^{X1}$ is independently hydrogen or $C_1$-$C_6$alkyl;
—$R^{Y1}$ is hydrogen or $C_1$-$C_6$alkyl; and
Z is $C_1$-$C_6$alkyl or Cak($C_1$-$C_6$alkyl).

In embodiment $IV_2$, the compounds are of embodiment $IV_1$, wherein a is 0.

In embodiment $IV_3$, the compounds are of embodiment $IV_1$, wherein a is 1.

In embodiment $IV_4$, the compounds are of any of embodiments $IV_1$-$IV_3$, wherein Z is $C_1$-$C_6$alkyl.

In embodiment $IV_5$, the compounds are of any of embodiments $IV_1$-$IV_3$, wherein Z is Cak($C_1$-$C_6$alkyl).

In some embodiments, the compound of formulae (IV) is one of the following compounds (or a pharmaceutically acceptable salt, prodrug, or N-oxide thereof, or a solvate or hydrate thereof): 15, 29, 32, 33, 34, 60 or 78.

In another aspect, the present invention comprises pharmaceutical compositions comprising a compound according to any one of the preceding aspects of the invention or any embodiment thereof, together with a pharmaceutically acceptable excipient, diluent, or carrier.

In another aspect, the invention comprises the use of a compound described by any one of the preceding aspects of the invention or any embodiment thereof, for the preparation of a medicament for the treatment of medical diseases or conditions that benefit from the inhibition of cytokine signaling. Medical conditions contemplated in this aspect include all diseases and conditions described herein.

The compounds of formulae (I), (Ia)-(If), (II), (IIa)-(IIj), (III), (IIIa)-(IIIf) and (IV) described above are useful as tyrosine kinase inhibitors. Tyrosine kinases are characterized by a conserved sequence within the kinase domain and adhesion molecule-like extracellular domains. Tyrosine kinases regulate a number of biological processes, including cell proliferation/survival, cell adhesion and migration, blood clot stabilization, and regulation of inflammatory cytokine release. Genetic or experimental alteration of tyrosine kinase function, specifically of the TAM (Tyro 3, Axl and Mer) receptor family, can contribute to a number of disease states, including coagulopathy, autoimmune disease, retinitis pigmentosa, and cancer. Thus, tyrosine kinases, specifically the TAM (Tyro 3, Axl and Mer) receptor family play a role in oncogenic mechanisms as family members are overexpressed in a spectrum of human cancers and have prognostic significance in some. In one aspect the present compounds are selective for one or more tyrosine kinase. For example, exemplary compounds inhibit on of more of the TAM (Tyro 3, Axl and Mer) receptor family. In certain examples, the present compounds inhibit Mer from about 5-fold less potently to about equipotently with Axl. In other examples, the present compounds inhibit Mer selectively over Axl.

In particular, the present compounds can be use to treat disorders, such as pulmonary hypertension, chronic renal disease, acute renal disease, wound healing, arthritis, osteoporosis, kidney disease, congestive heart failure, ulcers, ocular disorders, corneal wounds, diabetic nephropathy, impaired neurological function, Alzheimer's disease, atherosclerosis, peritoneal and sub-dermal adhesion, kidney fibrosis, lung fibrosis, including idiopathic pulmonary fibrosis, and liver fibrosis, hepatitis B, hepatitis C, alcohol-induced hepatitis, cancer, haemochromatosis, primary biliary cirrhosis, restenosis, retroperitoneal fibrosis, mesenteric fibrosis, endometriosis, keloids, cancer, abnormal bone function, inflammatory disorders, scarring and photoaging of the skin.

Particular proliferative diseases that can be treated with the present compounds include those selected from a benign or malignant tumor, carcinoma of the brain, kidney, liver, adrenal gland, bladder, breast, stomach, gastric tumors, ovaries, colon, rectum, prostate, pancreas, lung, vagina or thyroid, sarcoma, glioblastomas, multiple myeloma or gastrointestinal cancer, especially colon carcinoma or colorectal adenoma or a tumor of the neck and head, an epidermal hyperproliferation, melanoma, psoriasis, prostate hyperplasia, a neoplasia, a neoplasia of epithelial character, leukemias and lymphomas, a mammary carcinoma or a leukemia. Other diseases include Cowden syndrome, Lhermitte-Dudos disease and Bannayan-Zonana syndrome, or diseases in which the PI3K/PKB pathway is aberrantly activated.

The compounds described herein also include isotopically labeled compounds where one or more atoms have an atomic mass different from the atomic mass conventionally found in nature. Examples of isotopes that may be incorporated into the compounds disclosed herein include, but are not limited to, $^2H$, $^3H$, $^{11}C$, $^{13}C$, $^{14}C$, $^{15}N$, $^{18}O$, $^{17}O$, $^{18}F$, etc. Thus, the disclosed compounds may be enriched in one or more of these isotopes relative to the natural abundance of such isotope. As is known to those of skill in the art, such isotopically enriched compounds are useful for a variety of purposes. For example, substitution with heavier isotopes such as deuterium ($^2H$) may afford certain therapeutic advantages that result from greater metabolic stability. Substitution with positron emitting isotopes, such as 18F can be useful in Positron Emission Tomography (PET) studies. By way of example, deuterium ($^2H$) has a natural abundance of about 0.015%. Accordingly, for approximately every 6,500 hydrogen atoms occurring in nature, there is one deuterium atom. Specifically contemplated herein are compounds enriched in deuterium at one or more positions. Thus, deuterium containing compounds of the disclosure have deuterium at one or more positions (as the case may be) in an abundance of greater than 0.015%.

In another aspect, the invention comprises combination therapies for the treatment of cancer, including both pre-malignant and malignant neoplasms. In this aspect, the invention comprises a method of treating cancer comprising administering to a subject a compound disclosed herein in conjunction with a therapeutic treatment of cancer. In some embodiments of the invention, the compounds disclosed herein are used in combination of standard of care antiproliferative treatments of cancer. The amount of a compound disclosed herein for use in the combination therapy is an amount sufficient to inhibit one or more of the TAM (Tyro 3, Axl and Mer) receptor family. Treatment with the present compounds thus blocks the ability of cancer stem cells to recapitulate a tumor destroyed by treatment with standard of care. Efficacy of treatment can be determined by any art recognized method generally empolyed for the particular cancer being treated and includes, for example, retardation, inhibition, or regression of tumor growth.

Reference to "combination therapy" and treatment with a compound dislcosed herein "in conjunction with" another therapeutic treatment means that the compound and other therapeutic treatment can be administered simultaneously or sequentially such that the resultant treatment is more efficacious than either treatment alone.

One embodiment of treating cancer in a subject comprises administering to a subject in need thereof an amount described above of a compound disclosed herein in combination with the administration of a therapeutically effective amount of one or more chemotherapeutic agents, wherein the one or more chemotherapeutic agents is selected from the group consisting of antimetabolites, alkylating agents, coordination compounds, platinum complexes, DNA cross-linking compounds, inhibitors of transcription enzymes, tyrosine kinase inhibitors, protein kinase inhibitors, topoisomerase inhibitors, DNA minor-groove binding compounds, vinca alkyloids, taxanes, antitumor antibiotics, hormones, aromatase inhibitors, enzymes, growth factor receptors antibodies, cytokines, cell surface markers antibodies, HDAC inhibitors, HSP 90 inhibitors, BCL-2 inhibitors, B-raf inhibitors, MEK inhibitors, mTOR inhibitors, proteasome inhibitors and monoclonal antibodies.

Among the BCL-2 inhibitors useful in the invention is ABT-199.

Another embodiment of methods for treating a subject comprises administering to the subject an amount (as described above) of a compound disclosed herein in combination with the administration of a therapeutically effective amount of one or more chemotherapeutic agents, the one or more chemotherapeutic agents being independently selected from the group consisting of mechlorothamine, cyclophosphamide, ifosfamide, melphalan, chlorambucil, ethyleneimines, methylmelamines, procarbazine, dacarbazine, temozolomide, busulfan, carmustine, lomustine, methotrexate, fluorouracil, capecitabine, cytarabine, gemcitabine, cytosine arabinoside, mecaptopurine, fludarabine, cladribine, thioguanine, azathioprine, vinblastine, vincristine, paclitaxel, docetaxel, colchicine, actinomycin D, daunorubicin, bleomycin, L-asparaginase, cisplatin, carboplatin, oxaliplatin, prednisone, dexamethasone, amino glutethimide, formestane, anastrozole, hydroxyprogesterone caproate, medroxyprogesterone, tamoxifen, amsacrine, mitoxantrone, topotecan, irinotecan, camptothecin, afatinib, axitinib, bosutinib, bortezomib, carfilzomib, cabozantinib, cediranib, crizotinib, dasatinib, dabrafenib, evorolimus, ibrutinib, LDK378, LGX818, MEK162, regorafenib, ruxolitinib, selumetinib, sorafenib, trametinib, vemurafenib, erlotinib, gefitinib, imatinib, lapatinib, lestaurtinib, nilotinib, palbociclib, pazopanib, pomatinib, semaxanib, sirolimus, sunitinib, temsirolimus, vatalanib, vandetanib, anti Her2 antibodies, interferon-α, interferon-γ, interleukin 2, GM CSF, anti CTLA 4 antibodies, rituximab, anti CD33 antibodies, MGCD0103, vorinostat, 17-AAG, thalidomide, lenalidomide, rapamycin, CCI-779, doxorubicine, gemcitabine, melphalan, NPI052, gemtuzumab, alemtuzumab, cetuximab, ibritumomab tiuxaetan, tositumomab, iodine-131 tositumomab, trastuzumab, ado-trastuzumab emtansine, obinutuzumab, bevacizumab, rituximab, and anti-TRAIL death receptor antibodies.

In particular, the presently disclosed compounds are useful in combination with immunooncology agents, such as checkpoint inhibitors. Examples of such agents include anti-CTLA 4 agents, anti-PD1 and anti PD-L1 agents. Among the CTLA 4 antibodies that can be used in the present invention is ipilimumab, marketed as YERVOY® by Bristol-Myers Squibb.

Other checkpoint pathway inhibitors include PD-1 inhibitors, such as nivolumab and lambrolizumab, and PD-L1 inhibitors, such as pembrolizumab, MEDI-4736 and MPDL3280A/RG7446. Additional checkpoint inhibitors for combination with the compounds disclosed herein include, Anti-LAG-3 agents, such as BMS-986016 (MDX-1408).

Further chemotherapeutic agents for combination with the presently disclosed TAM receptor family inhibitors include Anti-SLAMF7 agents, such as the humanized monoclonal antibody elotuzumab (BMS-901608), anti-KIR agents, such as the anti-KIR monoclonal antibody lirilumab (BMS-986015), and anti-CD137 agents, such as the fully human monoclonal antibody urelumab (BMS-663513).

The following table displays exemplary cancers treatable in the combination therapies of the invention and the therapeutic drug and/or other treatment for use with the compounds disclosed herein:

| Cancer | Drug or Treatment |
| --- | --- |
| Glioma | lomustine, temozolide and/or radiation |
| hepatocellular carcinoma | sorafenib, regorafenib |
| myelodysplastic syndromes | decitabine or azacytidine |
| pancreatic cancer | Gemcitabine |
| ovarian cancer, such as epithelial ovarian carcinoma | carboplatin, cisplatin, doxorubicin, gemcitabine, paclitaxel |
| breast cancer | Trastuzumab |
| basal and squamous skin carcinomas | 5-fluorouracil, imiquimod, photodynamic therapy (e.g. with 5-aminolevulinic acid), |
| head and neck carcinoma | bleomycin, cisplatin, cetuximab, docetaxel, fluorouracil, methotrexate |
| triple negative breast cancer | Paclitaxel |
| Prostate | abiraterone, enzalutamide |

In another aspect, the invention comprises a method of determining and measuring the ability of the compounds disclosed herein to inhibit TAM (Tyro 3, Axl and Mer) receptor family, in order to identify cancers and, more specifically, tumors. In one embodiment, neoplasms susceptible to such combination therapy can be identified by testing for TAM (Tyro 3, Axl and Mer) receptor family activity using techniques known to those skilled in the art. Optionally in this embodiment, where the tested compound is found to inhibit on or more of the TAM (Tyro 3, Axl and Mer) receptor family in the tested neoplasm, the compound is subsequently used in a combination therapy for treatment of the neoplasm, as described herein.

Definitions

The names of the chemical structures disclosed herein are generated from the structures by ChemDraw Profession version 16.

Terms used herein may be preceded and/or followed by a single dash, "—", or a double dash, "=", to indicate the bond order of the bond between the named substituent and its parent moiety; a single dash indicates a single bond and a double dash indicates a double bond or a pair of single bonds in the case of a spiro-substituent. In the absence of a single or double dash it is understood that a single bond is formed between the substituent and its parent moiety; further, substituents are intended to be read "left to right" unless a dash indicates otherwise. For example, arylalkyl, arylalkyl-, and alkylaryl indicate the same functionality.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety can refer to a monovalent radical (e.g. $CH_3$—$CH_2$—), in some circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene). All atoms are understood to have their normal number of valences for bond formation (i.e., 4 for carbon, 3 for N, 2 for O, and 2, 4, or 6 for S, depending on the oxidation state of the S). Nitrogens in the presently disclosed compounds can be hypervalent, e.g., an N-oxide or tetrasubstituted ammonium salt. On occasion a moiety may be defined, for example, as $(A)_a$-B—, wherein a is 0 or 1. In such instances, when a is 0 the moiety is B- and when a is 1 the moiety is A-B—.

As used herein, the term "alkyl" includes alkyl, alkenyl and alkynyl groups of a designed number of carbon atoms, such as 1 to 6 carbons (i.e., inclusive of 1 and 6), 1 to 6 carbons, 1 to 3 carbons, or 1, 2, 3, 4, 5 or 6. The term "$C_m$-$C_n$alkyl" means an alkyl group having from m to n carbon atoms (i.e., inclusive of m and n). The term "$C_m$-$C_n$alkyl" means an alkyl group having from m to n carbon atoms. For example, "$C_1$-$C_6$alkyl" is an alkyl group having from one to six carbon atoms. Alkyl and alkyl groups may be straight or branched and depending on context, may be a monovalent radical or a divalent radical (i.e., an alkylene group). In the case of an alkyl or alkyl group having zero carbon atoms (i.e., "$C_0$alkyl"), the group is simply a single covalent bond if it is a divalent radical or is a hydrogen atom if it is a monovalent radical. For example, the moiety "—($C_0$-$C_6$alkyl)-Ar" signifies connection of an optionally substituted aryl through a single bond or an alkylene bridge having from 1 to 6 carbons. Examples of "alkyl" include, for example, methyl, ethyl, propyl, isopropyl, butyl, iso-, sec- and tert-butyl, pentyl, hexyl, heptyl, 3-ethylbutyl, 3-hexenyl and propargyl. If the number of carbon atoms is not specified, the subject "alkyl" or "alkyl" moiety has from 1 to 6 carbons.

The term "haloalkyl" is an alkyl group substituted with one or more halogen atoms, e.g. F, Cl, Br and I. A more specific term, e.g., "fluoroalkyl" is an alkyl group substituted with one or more fluorine atoms. Examples of "fluoroalkyl" include fluoromethyl, difluoromethyl, trifluoromethyl, pentafluoroethyl, hexafluoroisopropyl and the like. In certain embodiments of the compounds disclosed herein, each haloalkyl is a fluoroalkyl.

The term "aryl" or "Ar" represents an aromatic ring system having a single ring (e.g., phenyl) which is optionally fused to other aromatic hydrocarbon rings or non-aromatic hydrocarbon rings. "Aryl" includes ring systems having multiple condensed rings or 6-16 members, in which at least one is carbocyclic and aromatic, (e.g., 1,2,3,4-tetrahydronaphthyl, naphthyl). Examples of aryl groups include phenyl, 1-naphthyl, 2-naphthyl, indanyl, indenyl, dihydronaphthyl, fluorenyl, tetralinyl, and 6,7,8,9-tetrahydro-5H-benzo[a]cycloheptenyl. In certain examples, aryl groups include those having a first carbocyclic, aromatic ring fused to an aromatic or aliphatic heterocycle, for example, 2,3-dihydrobenzofuranyl. The aryl groups herein are unsubstituted or, when specified as "optionally substituted", can unless stated otherwise be substituted in one or more substitutable positions with various groups, as described below.

The term "heteroaryl" or "Het" refers to an aromatic ring system containing 5-15 members and at least one heteroatom selected from nitrogen, oxygen and sulfur in an aromatic ring. Heteroaryl groups will have 1-4 O, S, or N atoms, provided no O or S is adjacent to another O or S. Most commonly, the heteroaryl groups will have 1, 2, 3, or 4 heteroatoms. The heteroaryl may be fused to one or more non-aromatic ring, for example, cycloalkyl or heterocycloalkyl rings, wherein the cycloalkyl (Cak) and heterocycloalkyl (Hca) rings are described herein. In one embodiment of the present compounds the heteroaryl group is bonded to the remainder of the structure through an atom in a heteroaryl group aromatic ring. In another embodiment, the heteroaryl group is bonded to the remainder of the structure through a non-aromatic ring atom. Examples of heteroaryl groups include, for example, pyridyl, pyrimidinyl, quinolinyl, benzothienyl, indolyl, indolinyl, pyridazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, benzo[1,4]oxazinyl, triazolyl, tetrazolyl, isothiazolyl, naphthyridinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. Preferred heteroaryl groups include pyridyl, pyrimidinyl, quinolinyl, indolyl, pyrrolyl, furanyl, thienyl and imidazolyl, pyrazolyl, indazolyl, thiazolyl and benzothiazolyl. In certain embodiments, each heteroaryl is selected from pyridyl, pyrimidinyl, pyridazinyl, pyrazinyl, imidazolyl, isoxazolyl, pyrazolyl, oxazolyl, thiazolyl, furanyl, thienyl, pyrrolyl, oxadiazolyl, thiadiazolyl, triazolyl, tetrazolyl, isothiazolyl, pyridinyl-N-oxide, pyrrolyl N-oxide, pyrimidinyl N-oxide, pyridazinyl N-oxide, pyrazinyl N-oxide, imidazolyl N-oxide, isoxazolyl N-oxide, oxazolyl N-oxide, thiazolyl N-oxide, pyrrolyl N-oxide, oxadiazolyl N-oxide, thiadiazolyl N-oxide, triazolyl N-oxide, and tetrazolyl N-oxide. Preferred heteroaryl groups include pyridyl, pyrimidyl, quinolinyl, indolyl, pyrrolyl, furanyl, thienyl, imidazolyl, pyrazolyl, indazolyl, thiazolyl and benzothiazolyl. The heteroaryl groups herein are unsubstituted or, when specified as "optionally substituted", can unless stated otherwise be substituted in one or more substitutable positions with various groups, as described below.

The term "heterocycloalkyl" or "Hca" refers to a non-aromatic ring or ring system containing at least one heteroatom that is preferably selected from nitrogen, oxygen and sulfur, wherein said heteroatom is in a non-aromatic ring. The heterocycloalkyl may have 1-4 O, S, or N atoms, provided no O or S is adjacent to another O or S. The heterocycloalkyl may have 1, 2, 3 or 4 heteroatoms. The heterocycloalkyl may be saturated (i.e., a heterocycloalkyl) or partially unsaturated (i.e., a heterocycloalkenyl). Heterocycloalkyl includes monocyclic groups of three to eight annular atoms as well as bicyclic and polycyclic ring systems, including bridged and fused systems, wherein each ring includes three to eight annular atoms, or the ring system includes 3-15 members. The heterocycloalkyl ring is optionally fused to other heterocycloalkyl rings and/or non-aromatic hydrocarbon rings and/or phenyl rings. In certain embodiments, the heterocycloalkyl groups have from 3 to 8 members in a single ring. In other embodiments, heterocycloalkyl groups have 5 or 6 members in a single ring. In some embodiments, the heterocycloalkyl groups have 3, 4, 5, 6, 7 or 8 members in a single ring. Examples of heterocycloalkyl groups include, for example, azabicyclo[2.2.2]octyl (in each case also "quinuclidinyl" or a quinuclidine derivative), azabicyclo[3.2.1]octyl, 2,5-diazabicyclo[2.2.1]heptyl, morpholinyl, thiomorpholinyl, thiomorpholinyl S-oxide, thiomorpholinyl S,S-dioxide, 2-oxazolidonyl, piperazinyl, homopiperazinyl, piperazinonyl, pyrrolidinyl, azepanyl, azetidinyl, pyrrolinyl, tetrahydropyranyl, piperidinyl, tetrahydrofuranyl, tetrahydrothienyl, 3,4-dihydroisoquinolin-2(1H)-yl, isoindindionyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, imidazolidonyl, tetrahydrothienyl S-oxide, tetrahydrothienyl S,S-dioxide and homothiomorpholinyl S-oxide. Especially desirable heterocycloalkyl groups include morpholinyl, 3,4-dihydroisoquinolin-2(1H)-yl, tetrahydropyranyl, piperidinyl, aza-bicyclo[2.2.2]octyl, γ-butyrolactonyl (i.e., an oxo-substituted tetrahydrofuranyl), γ-butryolactamyl (i.e., an oxo-substituted pyrrolidine), pyrrolidinyl, piperazinyl, azepanyl, azetidinyl, thiomorpholinyl, thiomorpholinyl S,S-dioxide, 2-oxazolidonyl, imidazolidonyl, isoindolindionyl, piperazinonyl. The heterocycloalkyl groups herein are unsubstituted or, when specified as "optionally substituted", can unless stated otherwise be substituted in one or more substitutable positions with various groups, as described below.

The term "cycloalkyl" or "Cak" refers to a non-aromatic carbocyclic ring or ring system, which may be saturated (i.e., a cycloalkyl) or partially unsaturated (i.e., a cycloalkenyl). The cycloalkyl ring optionally fused to or otherwise attached (e.g., spiro or bridged systems) to other cycloalkyl rings. Certain examples of cycloalkyl groups present in the disclosed compounds have from 3 to 8 members in a single ring, such as having 5 or 6 members in a single ring. In some embodiments, the cycloalkyl groups have 3, 4, 5, 6, 7 or 8 members in a single ring. Examples of cycloalkyl groups include, for example, cyclohexyl, cyclopentyl, cyclobutyl, cyclopropyl, tetrahydronaphthyl and bicyclo[2.2.1]heptane. The cycloalkyl groups herein are unsubstituted or, when specified as "optionally substituted", may be substituted in one or more substitutable positions with various groups.

The term "ring system" encompasses monocycles, as well as fused, spiro and/or bridged polycycles.

The term "fused" as used herein refers to a cyclic moiety formed by two adjacent atoms and two available substitutable positions on those atoms. Each of the rings in the fused system is independently aromatic or non-aromatic. For example, a moiety such as

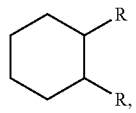

wherein two R groups attached to the adjacent atoms form a fused-Cak group, which includes compounds such as

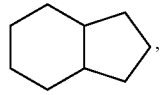

where the fused-cyclopentyl group is formed from the two R groups attached to the parent cyclohexyl ring by two single bonds. Similarly, a fused-Hca group can be formed, including such compounds as

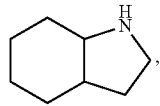

where the fused pyrrolidinyl ring is formed from the two R groups attached to the parent cyclohexyl ring by two single bonds.

The term "spiro" as used herein refers to a cyclic moiety formed by an atom and two available substitutable positions on that same atom. For example, a moiety such as

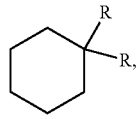

wherein two R groups attached to the same atom form a spiro-Cak group, which includes compounds such as

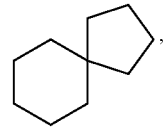

where the spiro-cyclopentyl group is formed from the two R groups attached to the parent cyclohexyl ring by two single bonds. Similarly, a spiro-Hca group can be formed, including such compounds as

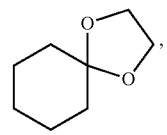

where the spiro-1,3-dioxolanyl ring is formed from the two R groups attached to the parent cyclohexyl ring by two single bonds.

The term "bridged" as used herein refers to a cyclic moiety formed by two non-adjacent atoms and two available substitutable positions on those atoms. For example, a moiety such as

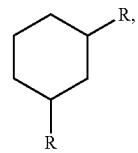

wherein two R groups attached to the adjacent atoms form a fused-Cak group, which includes compounds such as

where the bridged portion is formed from the two R groups attached to the parent cyclohexyl ring by two single bonds. Similarly, a bridged-Hca group can be formed, including such compounds as

where the bridged portion is formed from the two R groups attached to the parent cyclohexyl ring by two single bonds.

The term "oxa" means a divalent oxygen radical in a chain, sometimes designated as —O—.

The term "oxo" means a doubly bonded oxygen, sometimes designated as =O or for example in describing a carbonyl "C(O)" may be used to show an oxo substituted carbon.

The term "electron withdrawing group" means a group that withdraws electron density from the structure to which it is attached than would a similarly-attached hydrogen atom. For example, electron withdrawing groups can be selected from the group consisting of halo (e.g., fluoro, chloro, bromo, and iodo), cyano, —($C_1$-$C_4$ fluoroalkyl), —O—($C_1$-$C_4$ fluoroalkyl), —C(O)—($C_0$-$C_4$alkyl), —C(O)O—($C_0$-$C_4$alkyl), —C(O)N($C_0$-$C_4$alkyl)($C_0$-$C_4$alkyl), —S(O)$_2$O—($C_0$-$C_4$alkyl), $NO_2$ and —C(O)-Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group.

The term "substituted," when used to modify a specified group or radical, means that one or more hydrogen atoms of the specified group or radical are each, independently of one another, replaced with the same or different substituent groups as defined below, unless specified otherwise.

Substituent groups for substituting for hydrogens on saturated carbon atoms in the specified group or radical are, unless otherwise specified, —$R^{60}$, halo, —$O^-M^+$, =O, —$OR^{70}$, —$SR^{70}$, —$S^-M^+$, =S, —$NR^{80}R^{80}$, =$NR^{70}$, =N—$OR^{70}$, trihalomethyl, —$CF_3$, —CN, —OCN, —SCN, —NO, —$NO_2$, =$N_2$, —$N_3$, —$SO_2R^{70}$, —$SO_2O^-M^+$, —$SO_2OR^{70}$, —$OSO_2R^{70}$, —$OSO_2O^-M^+$, —$OSO_2OR^{70}$, —P(O)($O^-$)$_2$($M^+$)$_2$, —P(O)($OR^{70}$)$O^-M^+$, —P(O)($OR^{70}$)$_2$, —C(O)$R^{70}$, —C(S)$R^{70}$, —C($NR^{70}$)$R^{70}$, —$CO_2^-M^+$, —C(O)$OR^{70}$, —C(S)$OR^{70}$, —C(O)$NR^{80}R^{80}$, —C($NR^{70}$)$NR^{80}R^{80}$, —OC(O)$R^{70}$, —OC(S)$R^{70}$, —OC(O)$O^-M^+$, —OC(O)$OR^{70}$, —OC(S)$OR^{70}$, —$NR^{70}$C(O)$R^{70}$, —$NR^{70}$C(S)$R^{70}$, —$NR^{70}CO_2^-M^+$, —$NR^{70}CO_2R^{70}$, —$NR^{70}$C(S)$OR^{70}$, —$NR^{70}$C(O)$NR^{80}R^{80}$, —$NR^{70}$C($NR^{70}$)$R^{70}$ and —$NR^{70}$C($NR^{70}$)$NR^{80}R^{80}$. Each $R^{60}$ is independently selected from the group consisting of alkyl, heteroalkyl, cycloalkyl, heterocycloalkyl, heterocycloalkylalkyl, cycloalkylalkyl, aryl, arylalkyl, heteroaryl and heteroarylalkyl, each of which is optionally substituted with 1, 2, 3, 4 or 5 groups selected from the group consisting of halo, —$O^-M^+$, =O, —$OR^{71}$, —$SR^{71}$, —$S^-M^+$, =S, —$NR^{81}R^{81}$, =$NR^{71}$, =N—$OR^{71}$, trihalomethyl, —$CF_3$, —CN, —OCN, —SCN, —NO, —$NO_2$, =$N_2$, —$N_3$, —$SO_2R^{71}$, —$SO_2O^-M^+$, —$SO_2OR^{71}$, —$OSO_2R^{71}$, —$OSO_2O^-M^+$, —$OSO_2OR^{71}$, —P(O)($O^-$)$_2$($M^+$)$_2$, —P(O)($OR^{71}$)$O^-M^+$, —P(O)($OR^{71}$)$_2$, —C(O)$R^{71}$, —C(S)$R^{71}$, —C($NR^{71}$)$R^{71}$, —C(O)$O^-M^+$, —C(O)$OR^{71}$, —C(S)$OR^{71}$, —C(O)$NR^{81}R^{81}$, —C($NR^{71}$)$NR^{81}R^{81}$, —OC(O)$R^{71}$, —OC(S)$R^{71}$, —OC(O)$O^-M^+$, —OC(O)$OR^{71}$, —OC(S)$OR^{71}$, —$NR^{71}$C(O)$R^{71}$, —$NR^{71}$C(S)$R^{71}$, —$NR^{71}CO_2^-M^+$, —$NR^{71}CO_2R^{71}$, —$NR^{71}$C(S)$OR^{71}$, —$NR^{71}$C(O)$NR^{81}R^{81}$, —$NR^{71}$C($NR^{71}$)$R^{71}$ and —$NR^{71}$C($NR^{71}$)$NR^{81}R^{81}$. Each $R^{70}$ is independently hydrogen or $R^{60}$; each $R^{80}$ is independently $R^{70}$ or alternatively, two $R^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$alkyl substitution; and each $M^+$ is a counter ion with a net single positive charge. Each $R^{71}$ is independently hydrogen or $R^{61}$, in which $R^{61}$ is alkyl, heteroalkyl, cycloalkyl, heterocycloalkyl, heterocycloalkylalkyl, cycloalkylalkyl, aryl, arylalkyl, heteroaryl and heteroarylalkyl, each of which is optionally substituted with 1, 2, 3, 4 or 5 groups selected from the group consisting of halo, —$O^-M^+$, =O, —$OR^{72}$, —$SR^{72}$, —$S^-M^+$, =S, —$NR^{82}R^{82}$, =$NR^{72}$, =N—$OR^{72}$, trihalomethyl, —$CF_3$, —CN, —OCN, —SCN, —NO, —$NO_2$, =$N_2$, —$N_3$, —$SO_2R^{71}$, —$SO_2O^-M^+$, —$SO_2OR^{72}$, —$OSO_2O^-M^+$, —$OSO_2OR^{72}$, —P(O)($O^-$)$_2$($M^+$)$_2$, —P(O)($OR^{72}$)$O^-M^+$, —P(O)($OR^{72}$)$_2$, —C(O)$R^{72}$, —C(S)$R^{72}$, —C($NR^{72}$)$R^{72}$, —C(O)$O^-M^+$, —C(O)$OR^{72}$, —C(S)$OR^{72}$, —C(O)$NR^{82}R^{82}$, —C($NR^{72}$)$NR^{82}R^{82}$, —OC(O)$R^{72}$, —OC(S)$R^{72}$, —OC(O)$O^-M^-$, —OC(O)$OR^{72}$, —OC(S)$OR^{72}$, —$NR^{72}$C(O)$R^{72}$, —$NR^{72}$C(S)$R^{72}$, —$NR^{72}CO_2^-M^+$, —$NR^{72}CO_2R^{72}$, —$NR^{72}$C(S)$OR^{72}$, —$NR^{72}$C(O)$NR^{82}R^{82}$, —$NR^{72}$C($NR^{72}$)$R^{72}$ and —$NR^{72}$C($NR^{72}$)$NR^{82}R^{82}$; and each $R^{81}$ is independently $R^{71}$ or alternatively, two $R^{81}$s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution. Each $R^{72}$ is independently hydrogen, ($C_1$-$C_6$alkyl) or ($C_1$-$C_6$fluoroalkyl); each $R^{82}$ is independently $R^{72}$ or alternatively, two $R^{82}$s, taken together with the nitrogen atom to which they are bonded, form a 5-, 6- or 7-membered heterocycloalkyl which may optionally include 1, 2, 3 or 4 of the same or different additional heteroatoms selected from the group consisting of O, N and S, of which N may have —H or $C_1$-$C_3$alkyl substitution. Each $M^+$ may independently be, for example, an alkali ion, such as $K^+$, $Na^+$, $Li^+$; an ammonium ion, such as $^+N(R^{60})_4$; or an alkaline earth ion, such as $[Ca^{2+}]_{0.5}$, $[Mg^{2+}]_{0.5}$, or $[Ba^{2+}]_{0.5}$ ("subscript 0.5 means e.g. that one of the counter ions for such divalent alkali earth ions can be an ionized form of a presently disclosed compound and the other a typical counter ion such as chloride, or two ionized presently disclosed molecules can serve as counter ions for such divalent alkali earth ions, or a doubly ionized compound can serve as the counter ion for such divalent alkali earth ions). As specific examples, —$NR^{80}R^{80}$ is meant to include —$NH_2$, —NH-alkyl, N-pyrrolidinyl, N-piperazinyl, 4-methyl-piperazin-1-yl and N-morpholinyl.

Substituent groups for hydrogens on unsaturated carbon atoms in "substituted" alkene, alkyne, aryl and heteroaryl groups are, unless otherwise specified, —$R^{60}$, halo, —$O^-M^+$, —$OR^{70}$, —$SR^{70}$, —$S^-M^+$, —$NR^{80}R^{80}$, trihalomethyl, —$CF_3$, —CN, —OCN, —SCN, —NO, —$NO_2$, —$N_3$, —$SO_2R^{70}$, —$SO_3^-M^+$, —$SO_3R^{70}$, —$OSO_2R^{70}$, —$OSO_3^-M^+$, —$OSO_3R^{70}$, —$PO_3^{-2}(M^+)_2$, —P(O)($OR^{70}$)$O^-M^+$, —P(O)($OR^{70}$)$_2$, —C(O)$R^{70}$, —C(S)$R^{70}$, —C($NR^{70}$)$R^{70}$, —$CO_2^-M^+$, —$CO_2R^{70}$, —C(S)$OR^{70}$, —C(O)$NR^{80}R^{80}$, —C($NR^{70}$)$NR^{80}R^{80}$, —OC(O)$R^{70}$, —OC(S)$R^{70}$, —$OCO_2^-M^+$, —$OCO_2R^{70}$, —OC(S)$OR^{70}$, —$NR^{70}$C(O)$R^{70}$, —$NR^{70}$C(S)$R^{70}$, —$NR^{70}CO_2^-M^+$, —$NR^{70}CO_2R^{70}$, —$NR^{70}$C(S)$OR^{70}$, —$NR^{70}$C(O)$NR^{80}R^{80}$, —$NR^{70}$C($NR^{70}$)$R^{70}$ and —$NR^{70}$C($NR^{70}$)$NR^{80}R^{80}$, where $R^{60}$, $R^{70}$, $R^{80}$ and $M^+$ are as previously defined.

Substituent groups for hydrogens on nitrogen atoms in "substituted" heteroalkyl and heterocycloalkyl groups are, unless otherwise specified, —$R^{60}$, —$O^-M^+$, —$OR^{70}$, —$SR^{70}$, —$S^-M^+$, —$NR^{80}R^{80}$, trihalomethyl, —$CF_3$, —CN, —NO, —$NO_2$, —S(O)$_2R^{70}$, —S(O)$_2O^-M^+$, —S(O)$_2OR^{70}$, —OS(O)$_2R^{70}$, —OS(O)$_2O^-M^+$, —OS(O)$_2OR^{70}$, —P(O)($O^-$)$_2$($M^+$)$_2$, —P(O)($OR^{70}$)$O^-M^+$, —P(O)($OR^{70}$)($OR^{70}$), —C(O)$R^{70}$, —C(S)$R^{70}$, —C($NR^{70}$)$R^{70}$, —C(O)$OR^{70}$, —C(S)$OR^{70}$, —C(O)$NR^{80}R^{80}$, —C($NR^{70}$)$NR^{80}R^{80}$, —OC(O)—$R^{70}$, —OC(S)$R^{70}$, —OC(O)$OR^{70}$, —OC(S)$OR^{70}$, —$NR^{70}$C(O)$R^{70}$, —$NR^{70}$C(S)$R^{70}$, —$NR^{70}$C(O)$OR^{70}$, —$NR^{70}$C(S)$OR^{70}$, —$NR^{70}$C(O)$NR^{80}R^{80}$, —$NR^{70}$C($NR^{70}$)$R^{70}$ and —$NR^{70}$C($NR^{70}$)$NR^{80}R^{80}$, where $R^{60}$, $R^{70}$, $R^{80}$ and $M^+$ are as previously defined.

In certain embodiments of the compounds disclosed herein, a group that is substituted has 1, 2, 3, or 4 substituents, 1, 2, or 3 substituents, 1 or 2 substituents, or 1 substituent.

In certain embodiments, substituent groups on "substituted" alkyl, cycloalkyl, heterocycloalkyl, aryl and heteroaryl groups are -halo, —OH, —O—($C_1$-$C_4$alkyl), —O—($C_1$-$C_4$haloalkyl), —N($C_0$-$C_4$ alkyl)($C_0$-$C_4$alkyl), —SH, —S(O)$_{0-2}$—($C_1$-$C_4$alkyl), —($C_1$-$C_4$alkyl), —($C_1$-$C_4$haloalkyl), —C(O)—($C_0$-$C_4$alkyl), —C(O)N($C_0$-$C_4$alkyl)($C_0$-$C_4$alkyl), —N($C_0$-$C_4$alkyl)C(O)($C_0$-$C_4$alkyl) ($C_0$-$C_4$alkyl), —C(O)O—($C_0$-$C_4$alkyl), —OC(O)—($C_0$-$C_4$alkyl), S(O)$_2$—O($C_0$-$C_4$alkyl), and —NO$_2$, in which no alkyl is further substituted.

The compounds disclosed herein can also be provided as pharmaceutically acceptable salts. The term "pharmaceutically acceptable salts" or "a pharmaceutically acceptable salt thereof" refer to salts prepared from pharmaceutically acceptable non-toxic acids or bases including inorganic acids and bases and organic acids and bases. If the compound is basic, salts may be prepared from pharmaceutically acceptable non-toxic acids. Such salts may be, for example, acid addition salts of at least one of the following acids: benzenesulfonic acid, citric acid, α-glucoheptonic acid, D-gluconic acid, glycolic acid, lactic acid, malic acid, malonic acid, mandelic acid, phosphoric acid, propanoic acid, succinic acid, sulfuric acid, tartaric acid (d, l, or dl), tosic acid (toluenesulfonic acid), valeric acid, palmitic acid, pamoic acid, sebacic acid, stearic acid, lauric acid, acetic acid, adipic acid, carbonic acid, 4-chlorobenzenesulfonic acid, ethanedisulfonic acid, ethylsuccinic acid, fumaric acid, galactaric acid (mucic acid), D-glucuronic acid, 2-oxoglutaric acid, glycerophosphoric acid, hippuric acid, isethionic acid (ethanolsulfonic acid), lactobionic acid, maleic acid, 1,5-naphthalene-disulfonic acid, 2-naphthalene-sulfonic acid, pivalic acid, terephthalic acid, thiocyanic acid, cholic acid, n-dodecyl sulfate, 3-hydroxy-2-naphthoic acid, 1-hydroxy-2-naphthoic acid, oleic acid, undecylenic acid, ascorbic acid, (+)-camphoric acid, d-camphorsulfonic acid, dichloroacetic acid, ethanesulfonic acid, formic acid, hydriodic acid, hydrobromic acid, hydrochloric acid, methanesulfonic acid, nicotinic acid, nitric acid, orotic acid, oxalic acid, picric acid, L-pyroglutamic acid, saccharine, salicylic acid, gentisic acid, and/or 4-acetamidobenzoic acid.

The compounds described herein can also be provided in prodrug form. "Prodrug" refers to a derivative of an active compound (drug) that undergoes a transformation under the conditions of use, such as within the body, to release the active drug. Prodrugs are frequently, but not necessarily, pharmacologically inactive until converted into the active drug. Prodrugs are typically obtained by masking a functional group in the drug believed to be in part required for activity with a progroup (defined below) to form a promoiety which undergoes a transformation, such as cleavage, under the specified conditions of use to release the functional group, and hence the active drug. The cleavage of the promoiety can proceed spontaneously, such as by way of a hydrolysis reaction, or it can be catalyzed or induced by another agent, such as by an enzyme, by light, by acid, or by a change of or exposure to a physical or environmental parameter, such as a change of temperature. The agent can be endogenous to the conditions of use, such as an enzyme present in the cells to which the prodrug is administered or the acidic conditions of the stomach, or it can be supplied exogenously. A wide variety of progroups, as well as the resultant promoieties, suitable for masking functional groups in the active drugs to yield prodrugs are well-known in the art. For example, a hydroxyl functional group can be masked as a sulfonate, ester or carbonate promoiety, which can be hydrolyzed in vivo to provide the hydroxyl group. An amino functional group can be masked as an amide, carbamate, imine, urea, phosphenyl, phosphoryl or sulfenyl promoiety, which can be hydrolyzed in vivo to provide the amino group. A carboxyl group can be masked as an ester (including silyl esters and thioesters), amide or hydrazide promoiety, which can be hydrolyzed in vivo to provide the carboxyl group. Specific examples of suitable progroups and their respective promoieties will be apparent to those of skill in the art.

The compounds disclosed herein can also be provided as N-oxides.

The presently disclosed compounds, salts, prodrugs and N-oxides can be provided, for example, in solvate or hydrate form.

One of ordinary skill in the art of medicinal chemistry also will appreciate that the disclosed structures are intended to include isotopically enriched forms of the present compounds. As used herein "isotopes" includes those atoms having the same atomic number but different mass numbers. As is known to those of skill in the art, certain atoms, such as hydrogen occur in different isotopic forms. For example, hydrogen includes three isotopic forms, protium, deuterium and tritium. As will be apparent to those of skill in the art upon consideration of the present compounds, certain compounds can be enriched at a given position with a particular isotope of the atom at that position. For example, compounds having a fluorine atom, may be synthesized in a form enriched in the radioactive fluorine isotope $^{18}$F. Similarly, compounds may be enriched in the heavy isotopes of hydrogen: deuterium and tritium; and similarly can be enriched in a radioactive isotope of carbon, such as $^{13}$C. Such isotopic variant compounds undergo different metabolic pathways and can be useful, for example, in studying the ubiquitination pathway and its role in disease.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" an enzyme with a compound includes the administration of a compound described herein to an individual or patient, such as a human, as well as, for example, introducing a compound into a sample containing a cellular or purified preparation containing the enzyme.

As used herein, the terms "individual," "patient," or "subject" are used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

In certain embodiments, a therapeutically effective amount can be an amount suitable for (1) preventing the disease; for example, preventing a disease, condition or disorder in an individual who may be predisposed or otherwise susceptible to the disease, condition or disorder but does not yet experience or display the pathology or symptomatology of the disease;

(2) inhibiting the disease; for example, inhibiting a disease, condition or disorder in an individual who is experiencing or displaying the pathology or symptomatology of the disease, condition or disorder; or (3) ameliorating the disease (including a symptom thereof); for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used here, the terms "treatment" and "treating" means (i) ameliorating the referenced disease state, condition, or disorder (or a symptom thereof), such as, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease or symptom thereof; or (ii) eliciting the referenced biological effect (e.g., modulation or inhibition of one or more of the TAM (Tyro 3, Axl and Mer) receptor family).

Manifestation of amelioration of a disease condition by inhibiting one or more of the TAM (Tyro 3, Axl and Mer) receptor family may require the concomitant or sequential administration of additional therapeutic agents, such as antineoplastic agents in the case of cancer, or antiretroviral agents in the case of viral diseases. For example, administration of inhibitors of one or more of the TAM (Tyro 3, Axl and Mer) receptor family for the treatment of cancer does not always produce a direct antitumor effect when used as a single agent. However, when combined with chemotherapeutic drugs (antineoplastic) the antitumor effect observed is higher than the sum of effects of each agent alone.

As used herein, the terms "catalytic pocket", "catalytic site", "active site" collectively and indistinctly refer to a region of the enzyme that contains amino acid residues responsible for the substrate binding (charge, hydrophobicity, steric hindrance) and catalytic amino acid residues which act as proton donors or acceptors or are responsible for binding a cofactor and participate in the catalysis of a chemical reaction.

As used herein, the phrase "pharmaceutically acceptable salt" refers to both pharmaceutically acceptable acid and base addition salts and solvates. Such pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—$(CH_2)_n$—COOH where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

Pharmaceutical Formulations and Dosage Forms

The compounds of structural formulae (I)-(IV) can be administered, for example, orally, topically, parenterally, by inhalation or spray or rectally in dosage unit formulations containing one or more pharmaceutically acceptable carriers, diluents or excipients. The term parenteral as used herein includes percutaneous, subcutaneous, intravascular (e.g., intravenous), intramuscular, or intrathecal injection or infusion techniques and the like.

Pharmaceutical compositions can be made using the presently disclosed compounds. For example, in one embodiment, a pharmaceutical composition includes a pharmaceutically acceptable carrier, diluent or excipient, and a compound as described above with reference to structural formulae (I)-(IV).

In the pharmaceutical compositions disclosed herein, one or more compounds of structural formulae (I)-(IV) may be present in association with one or more pharmaceutically acceptable carriers, diluents or excipients, and, if desired, other active ingredients. The pharmaceutical compositions containing compounds of structural formulae (I)-(IV) may be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any suitable method for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by suitable techniques to delay disintegration and absorption in the gastrointestinal tract and thereby provide a sustained action over a longer period. For example, a time delay material such as glyceryl monostearate or glyceryl distearate can be employed.

Formulations for oral use can also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use can also be presented as lozenges.

Aqueous suspensions contain the active materials in admixture with excipients suitable for the manufacture of aqueous suspensions. Such excipients can be suspending agents, for example sodium carboxymethylcellulose, methylcellulose, hydropropylmethylcellulose, sodium alginate, polyvinylpyrrolidone, gum tragacanth and gum acacia; dispersing or wetting agents such as a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

In some embodiments, the pharmaceutically acceptable carrier, diluent, or excipient is not water. In other embodiments, the water comprises less than 50% of the composition. In some embodiments, compositons comprising less than 50% water have at least 1%, 2%, 3%, 4% or 5% water. In other embodiments, the water content is present in the composition in a trace amount.

In some embodiments, the pharmaceutically acceptable carrier, diluent, or excipient is not alcohol. In other embodiments, the alcohol comprises less than 50% of the composition. In some embodiments, compositons comprising less than 50% alcohol have at least 1%, 2%, 3%, 4% or 5% alcohol. In other embodiments, the alcohol content is present in the composition in a trace amount.

Syrups and elixirs can be formulated with sweetening agents, for example glycerol, propylene glycol, sorbitol, glucose or sucrose. Such formulations can also contain a demulcent, a preservative, flavoring, and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils can be employed as a solvent or suspending medium. For this purpose any bland fixed oil can be employed including synthetic mono- or diglycerides. In addition, fatty acids such as oleic acid find use in the preparation of injectables.

Compounds of structural formulae (I)-(IV) can also be administered in the form of suppositories, e.g., for rectal administration of the drug. These compositions can be prepared by mixing the compound with a suitable non-irritating excipient that is solid at ordinary temperatures but liquid at the rectal temperature and will therefore melt in the rectum to release the drug. Such materials include cocoa butter and polyethylene glycols.

Compounds of structural formula (I)-(IV) can also be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds can vary according to, for example, the particular use for which the treatment is made, the manner of administration of the compound, the health and condition of the patient, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds described herein can also be formulated in combination with one or more additional active ingredients which can include any pharmaceutical agent such as anti-viral agents, vaccines, antibodies, immune enhancers, immune suppressants, anti-inflammatory agents and the like.

EXAMPLES

General Synthetic Methodologies

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry," Plenum Press, London and New York 1973, in T. W. Greene and P. G. M. Wuts, "Protective Groups in Organic Synthesis," Third edition, Wiley, New York 1999, in "The Peptides"; Volume 3 (editors: E. Gross and J. Meienhofer), Academic Press, London and New York 1981, in "Methoden der organischen Chemie," Houben-Weyl, 4.sup.th edition, Vol. 15/1, Georg Thieme Verlag, Stuttgart 1974, in H.-D. Jakubke and H. Jescheit, "Aminosauren, Peptide, Proteine," Verlag Chemie, Weinheim, Deerfield Beach, and Basel 1982, and/or in Jochen Lehmann, "Chemie der Kohlenhydrate: Monosaccharide and Derivate," Georg Thieme Verlag, Stuttgart 1974. The protecting groups may be removed at a convenient subsequent stage using methods known from the art.

The compounds disclosed herein can be made using procedures familiar to the person of ordinary skill in the art and as described herein. For example, compounds of structural formula (I) can be prepared according to Schemes 1-3, or analogous synthetic schemes.

One of skill in the art can adapt the reaction sequences of Schemes 1-3 to fit the desired target molecule. Of course, in certain situations one of skill in the art will use different reagents to affect one or more of the individual steps or to use protected versions of certain of the substituents. Additionally, one skilled in the art would recognize that compounds of structural formulae (I)-(IV) can be synthesized using different routes altogether.

Compounds suitable for use in the presently disclosed pharmaceutical compositions include compounds described herein. These compounds can be made according to the general schemes described above, for example using a procedure similar to that described below in the Examples.

The following examples are intended to further illustrate certain embodiments and are not intended to limit the scope of the presently disclosed compounds.

EXAMPLES

Example 1: Synthesis and Characterization

Scheme 1: General Synthesis 1

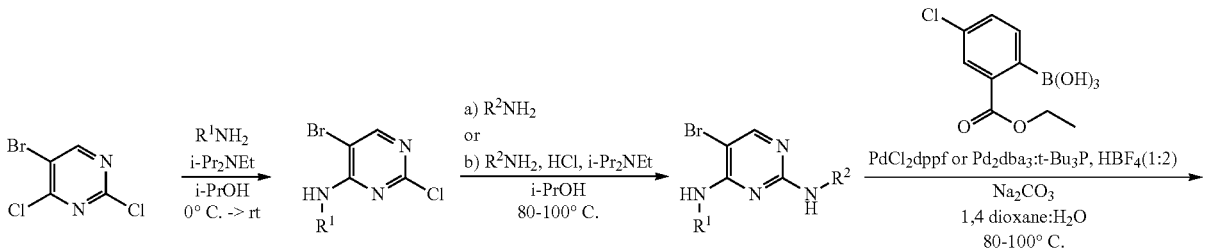

-continued
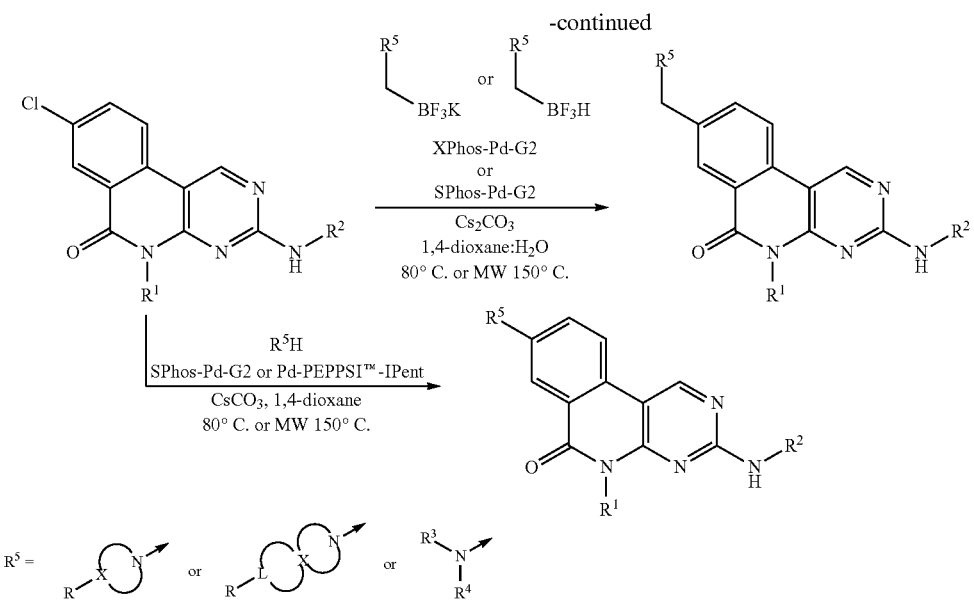
Scheme 2: General Synthesis 2
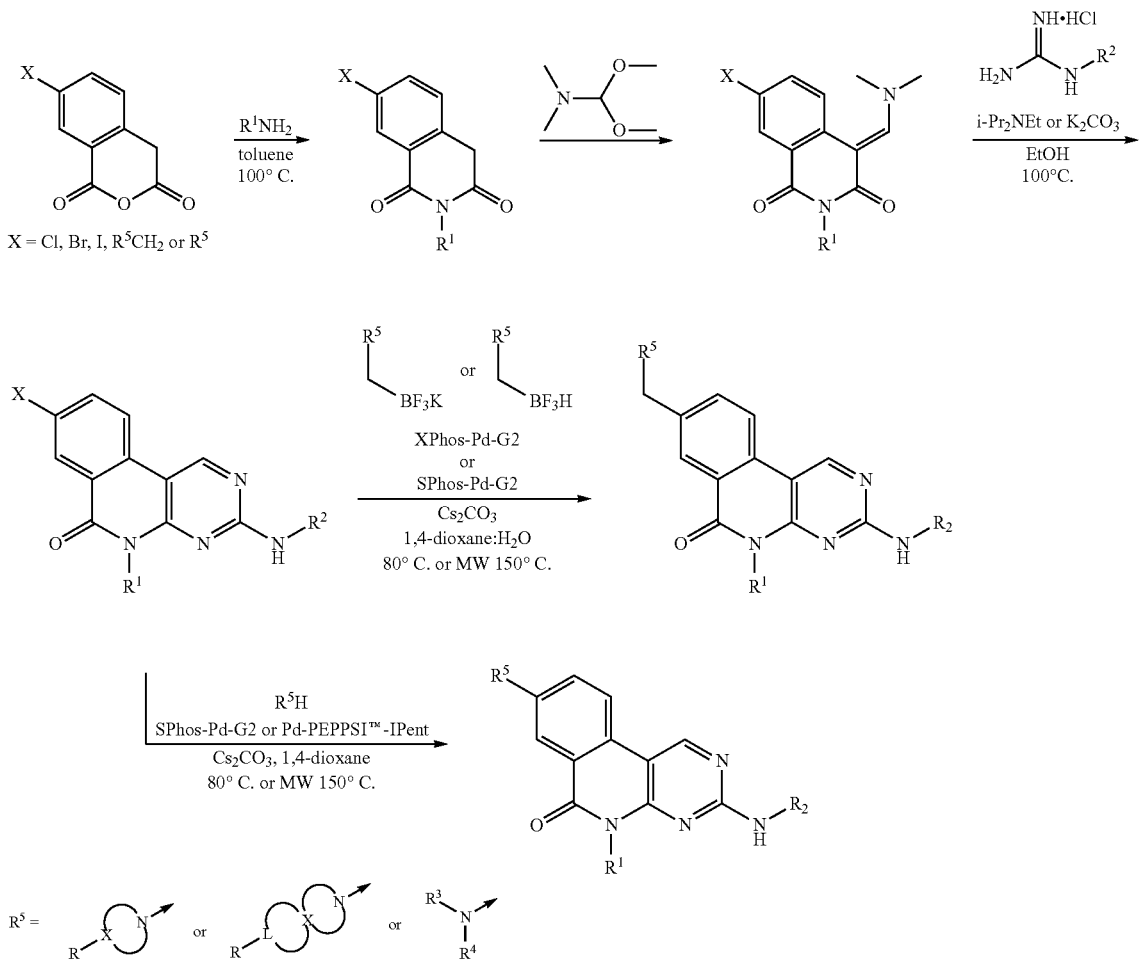

Scheme 3: General Synthesis 3

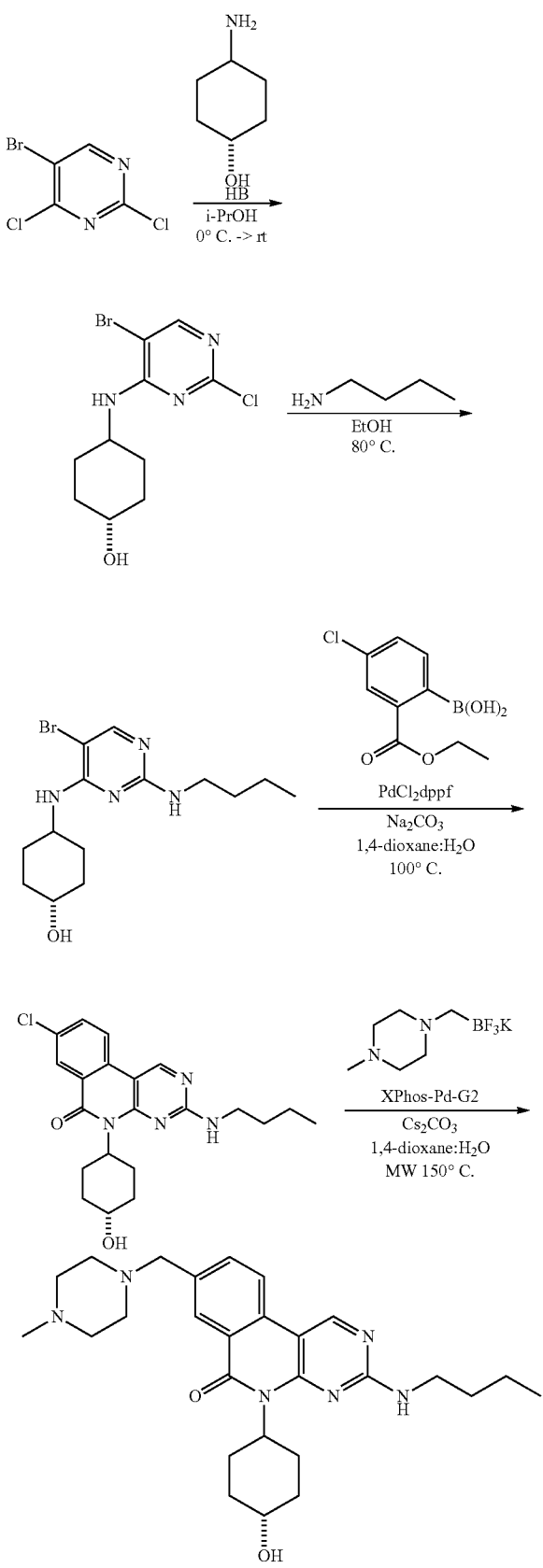

General Procedure for the Preparation of 3-(alkylamino)-8-chloro-5-(4-alky)pyrimido[4,5-c]isoquinolin-6(5H)-ones is Described in the Preparation of trans-3-(butylamino)-8-chloro-5-(4-hydroxycyclohexyl)pyrimido[4,5-c]isoquinolin-6(5H)-one trans-3-(Butylamino)-8-chloro-5-(4-hydroxycyclohexyl)pyrimido[4,5-c]isoquinolin-6(5H)-one

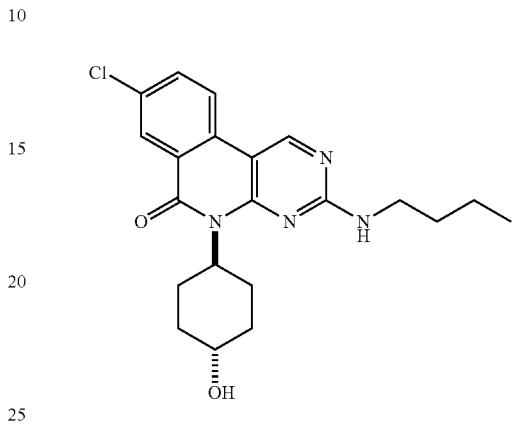

A two-neck round-bottom flask was charged with trans-4-((5-bromo-2-(butylamino)pyrimidin-4-yl)amino)cyclohexan-1-ol (1.1 g, 3.20 mmol), 4-chloro-2-ethoxycarbonylphenylboronic acid (1.25 g, 5.47 mmol), Na₂CO₃ (1.22 g, 11.5 mmol), 1,4-dioxane (30 mL), water (10 mL) and a stir bar. One of the reaction flask necks was fitted with a three-way stopcock attached reflux condenser and closed other neck with a rubber septum. Aargon filled balloon was attached to stopcock and degassing was done by evacuating air from the closed reaction system under vacuum and subsequently back filled with argon while stirring the reaction contents. Heating with an oil bath was also initiated simultaneously during the degassing procedure. Following three cycles of degassing in the space of 15 minutes and oil bath temperature at 35° C., PdCl₂(dppf) (0.26 g, 0.32 mmol) was added to stirred heterogeneous mixture through rubber septum stoppered neck. Rubber septum was fitted back to reaction flask after the catalyst addition, degassing cycle repeated (3 times, 15 minutes) and the stirred reaction mixture was heated further to 100° C. under argon. Initial red heterogeneous reaction mixture transformed to dark biphasic solution upon heating at 90° C. (oil-bath) under argon for 14 h. LC/MS analysis of reaction mixture aliquot indicated unreacted trans-44(5-bromo-2-(butylamino)pyrimidin-4-yl)amino)cyclohexan-1-ol (11.89%) still present. Upon no change in the peak composition of reaction mixture after 22 h of heating, hot dark reaction mixture suction filtered through sintered glass funnel loaded with Celite® (14 g) and reaction flask was rinsed with 1,4-dioxane (2×25 mL) and filtered. The filter cake was further washed with additional 1,4-dioxane (30 mL) until no material was detected by silica gel TLC plate analysis. Resulting homogenous brown filtrate (120 mL) was concentrated by rotary evaporator under vacuum to dryness. The crude dark solid was diluted with EtOAc/THF (150 mL/75 mL), water (75 mL), stirred at room temperature for 20 min, transferred to separatory funnel and aqueous layer was separated. Subsequently, organic layer was washed with saturated aq. NaCl solution (20 mL) and separated organic layer. Previously separated aq. layer was further extracted with EtOAc/THF (150 mL/75 mL) and washed with aq. NaCl solution (20 mL). Combined organic layers were dried over anhydrous MgSO$_4$, filtered and concentrated by rotary evaporator under vacuum. The dark crude solid thus obtained was dissolved in 4% MeOH/CH$_2$Cl$_2$ (30 mL), adsorbed on silica gel (22 g) and purified by by flash chromatography [Combiflash Torrent® with RediSep® silica gel column 40 g and eluted with 30-50-70% EtOAc/hexane solvent gradient]. Upon analyzing off-white solid obtained after concentrating fractions eluted with 50-70% EtOAc/hexane indicated mixture of trans-4-((5-bromo-2-(butylamino)pyrimidin-4-yl)amino)cyclohexan-1-ol (12%) and trans-3-(butylamino)-8-chloro-5-(4-hydroxycyclohexyl)pyrimido[4,5-c]isoquinolin-6(5H)-one (87%). Subsequently, above solid was heated in EtOAc/hexane (25 mL/6 mL), cooled to room temperature, solution filtered and dried to obtain 800 mg of trans-3-(butylamino)-8-chloro-5-(4-hydroxycyclohexyl)pyrimido[4,5-c]isoquinolin-6(5H)-one (LC/MS: purity 98%).

$^1$H NMR (400 MHz, DMSO-d$_6$) δ 9.22 (s, 1H), 8.33 (d, J=8.7 Hz, 1H), 8.10 (d, J=2.5 Hz, 1H), 7.82 (br s, 0.7H), 7.76 (dd, J=8.7, 2.4 Hz, 1H), 7.62 (br s, 0.3H), 5.37 (br s, 1H), 4.65 (d, J=4.2 Hz, 1H), 3.49 (br s, 1H), 3.34 (q, J=6.8 Hz, 2H), 2.72 (br s, 2H), 1.95 (d, J=9.6 Hz, 2H), 1.60-1.51 (m, 4H), 1.44-1.22 (m, 4H), 0.91 (t, J=7.3 Hz, 3H). LCMS: Purity 98%, MS (m/e) 401 (MH$^+$).

cis-3-(Butylamino)-8-chloro-5-(4-hydroxycyclohexyl)pyrimido[4,5-c]isoquinolin-6(5H)-one

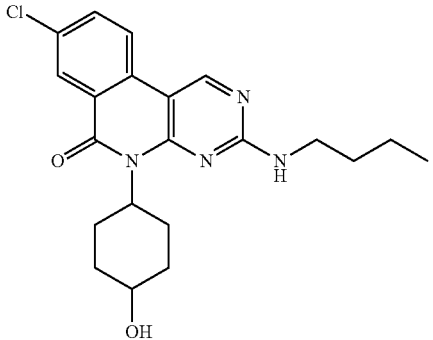 [SMILES: CCCCNc1ncc2c3ccc(Cl)cc3c(=O)n(C3CCC(O)CC3)c2n1]

$^1$H NMR (400 MHz, DMSO-d$_6$) δ 9.21 (s, 1H), 8.33 (d, J=8.7 Hz, 1H), 8.11 (d, J=2.4 Hz, 1H), 7.76 (dd, J=8.7, 2.4 Hz, 1H), 7.72 (br s, 0.7H) 7.52 (br s, 0.3H), 5.39 (s, 1H), 4.33 (app d, J=1.8 Hz, 1H), 3.92-3.86 (m, 1H), 3.41 (br s, 1H), 3.11 (br s, 2H), 1.81 (d, J=13.0 Hz, 2H), 1.54 (p, J=7.9, 7.3 Hz, 4H), 1.41-1.27 (m, 4H), 0.89 (t, J=7.3 Hz, 3H). LCMS: Purity 97%, MS (m/e) 401 (MH$^+$).

3-(Butylamino)-8-chloro-5-((4-hydroxycyclohexyl)methyl)pyrimido[4,5-c]isoquinolin-6(5H)-one

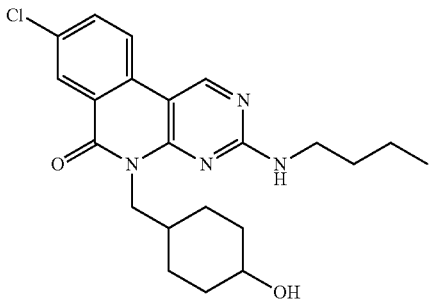 [SMILES: CCCCNc1ncc2c3ccc(Cl)cc3c(=O)n(CC3CCC(O)CC3)c2n1]

$^1$H NMR (400 MHz, DMSO-d$_6$) δ 9.23 (s, 1H), 8.37 (d, J=8.7 Hz, 1H), 8.13 (d, J=2.3 Hz, 1H), 7.84 (t, J=6.0 Hz, 1H), 7.79 (dd, J=8.7, 2.4 Hz, 1H), 4.44 (d, J=4.5 Hz, 1H), 4.20 (d, J=6.9 Hz, 2H), 3.37-3.28 (overlapped m, 3H), 1.90-1.74 (app m 3H), 1.60-1.50 (m, 4H), 1.36 (p, J=7.4 Hz, 2H), 1.19-0.94 (m, 4H), 0.91 (t, J=7.3 Hz, 3H). LCMS: Purity 98%, MS (m/e) 415 (MH$^+$).

tert-Butyl-(4-((3-(butylamino)-8-chloro-6-oxopyrimido[4,5-c]isoquinolin-5(6H)-yl)methyl)cyclohexyl)carbamate

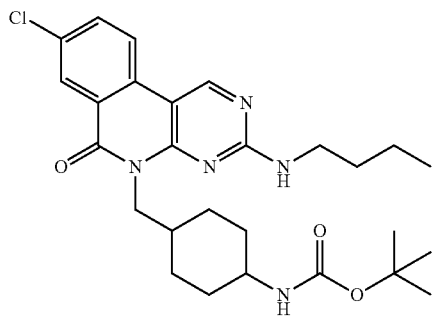 [SMILES: CCCCNc1ncc2c3ccc(Cl)cc3c(=O)n(CC3CCC(NC(=O)OC(C)(C)C)CC3)c2n1]

$^1$H NMR (400 MHz, DMSO-d$_6$) δ 9.23 (s, 1H), 8.36 (d, J=8.7 Hz, 1H), 8.12 (d, J=2.0 Hz, 1H), 7.90-7.81 (m, 1H), 7.78 (dd, J=8.7, 2.4 Hz, 1H), 6.63 (d, J=7.7 Hz, 1H), 4.19 (d, J=6.4 Hz, 2H), 3.32 (overlapped m, 2H), 3.13 (br s, 1H), 1.80 (br s, 1H), 1.72 (d, J=10.7 Hz, 2H), 1.62-1.51 (m, 4H), 1.33 (overlapped s, 11H), 1.15-0.99 (m, 4H), 0.92 (t, J=7.4 Hz, 3H). LCMS: Purity 96%, MS (m/e) 515 (MH$^+$).

trans-3-Amino-8-chloro-5-(4-hydroxycyclohexyl)pyrimido[4,5-c]isoquinolin-6(5H)-one

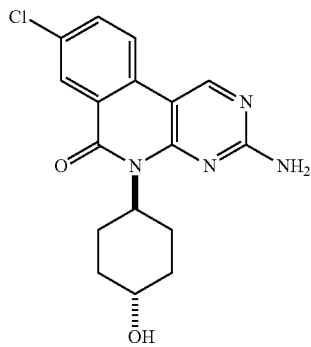

$^1$H NMR (400 MHz, DMSO-d$_6$) δ 9.22 (s, 1H), 8.34 (d, J=8.9 Hz, 1H), 8.10 (d, J=2.4 Hz, 1H), 7.75 (d, J=2.4 Hz, 1H), 7.15 (s, 2H), 5.38 (s, 1H), 4.60 (d, J=4.4 Hz, 1H), 3.56 (s, 1H), 2.71 (s, 2H), 1.93 (d, J=10.6 Hz, 2H), 1.53 (d, J=10.7 Hz, 2H), 1.29 (q, J=13.7 Hz, 2H). LCMS: Purity 99%, MS (m/e) 345 (MH$^+$).

203

3-(Butylamino)-8-chloro-5-(6-hydroxyspiro[3.3]heptan-2-yl)pyrimido[4,5-c]isoquinolin-6(5H)-one

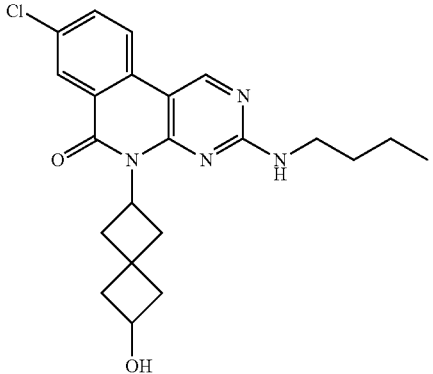 [SMILES: CCCCNc1ncc2c3ccc(Cl)cc3c(=O)n(C3CC4(CC(O)C4)C3)c2n1]

$^1$H NMR (400 MHz, DMSO-d$_6$) δ 9.19 (s, 1H), 8.29 (d, J=8.7 Hz, 1H), 8.07 (d, J=2.4 Hz, 1H), 7.77 (br s, 0.7H), 7.74 (dd, J=8.7, 2.3 Hz, 1H), 7.58 (br s, 0.3H), 5.65 (p, J=9.0 Hz, 1H), 4.93 (d, J=6.2 Hz, 1H), 4.07-3.93 (m, 1H), 3.41-3.29 (m, 2H), 3.20-3.19 (m, 2H), 2.48-2.38 (m, 1H), 2.31-2.18 (m, 3H), 1.90 (ddd, J=11.3, 7.7, 4.1 Hz, 2H), 1.55 (t, J=7.3 Hz, 2H), 1.44-1.31 (m, 2H), 0.92 (t, J=7.6 Hz, 3H).). LCMS: Purity 97%, MS (m/e) 413 (MH$^+$).

trans-3-(Butylamino)-8-chloro-5-(4-hydroxy-4-methylcyclohexyl)pyrimido[4,5-c]isoquinolin-6(5H)-one

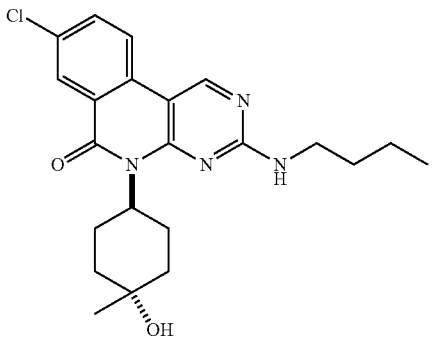

$^1$H NMR (400 MHz, DMSO-d$_6$) δ 9.23 (s, 1H), 8.33 (d, J=9.0 Hz, 1H), 8.11 (d, J=2.4 Hz, 1H), 7.81 (s, 0.7H), 7.76 (dd, J=8.7, 2.3 Hz, 1H), 7.56 (s, 0.3H), 5.46 (br s, 1H), 4.42 (s, 1H), 3.35 (app q, J=6.8 Hz, 2H), 2.76-2.69 (app m, 2H), 1.67 (d, J=10.9 Hz, 2H), 1.60-1.46 (m, 6H), 1.35 (q, J=7.3 Hz, 2H), 1.28 (s, 3H), 0.90 (t, J=7.3 Hz, 3H). LCMS: Purity 97%, MS (m/e) 415 (MH$^+$).

204 trans-8-Chloro-3-((cyclopropylmethyl)amino)-5-(4-hydroxycyclohexyl)pyrimido[4,5-c]isoquinolin-6(5H)-one

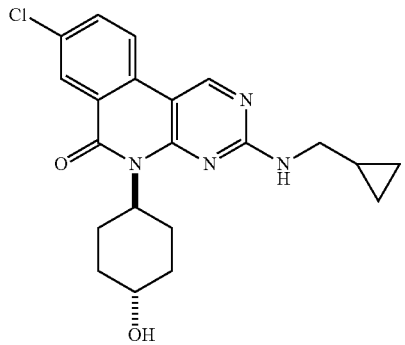

$^1$H NMR (400 MHz, DMSO-d$_6$) δ 9.24 (s, 1H), 8.34 (d, J=8.8 Hz, 1H), 8.11 (d, J=2.3 Hz, 1H), 7.94-7.86 (m, 1H), 7.77 (dd, J=8.7, 2.4 Hz, 1H), 5.37 (br s, 1H), 4.65 (app d, J=4.3 Hz, 1H), 3.75-3.42 (br s, 1H), 3.25 (t, J=6.5 Hz, 2H), 2.74 (br s, 2H), 1.94 (app d, J=13.7 Hz, 2H), 1.57 (d, J=11.1 Hz, 2H), 1.37-1.25 (q, J=13.3 Hz, 2H), 1.15-1.05 (m, 1H), 0.45 (q, J=5.2 Hz, 2H), 0.25 (q, J=4.9 Hz, 2H). LCMS: Purity 99%, MS (m/e) 399 (MH$^+$).

cis-3-(Butylamino)-8-chloro-5-(4-hydroxy-4-methylcyclohexyl)pyrimido[4,5-c]isoquinolin-6(5H)-one

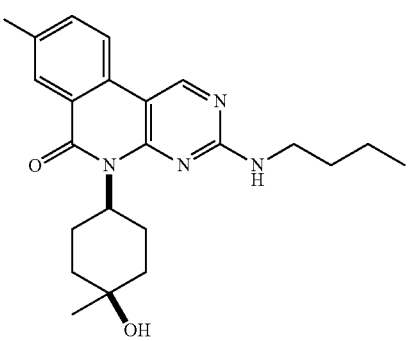

LCMS: Purity 98%, MS (m/e) 415 (MH$^+$).

trans-8-Chloro-3-(((1-ethylcyclobutyl)methyl)amino)-5-(4-hydroxycyclohexyl)pyrimido[4,5-c]isoquinolin-6(5H)-one

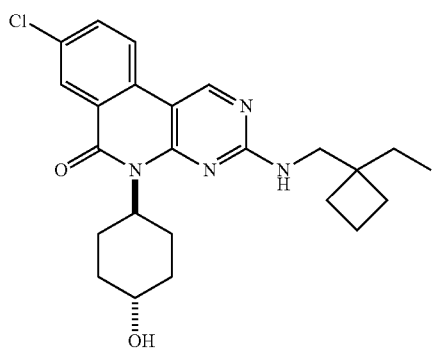

$^1$H NMR (400 MHz, DMSO-d$_6$) δ 9.23 (s, 1H), 8.34 (d, J=8.8 Hz, 1H), 8.09 (d, J=2.4 Hz, 1H), 7.82 (br s, 0.7H), 7.76

(dd, J=8.7, 2.4 Hz, 1H), 7.53 (br s, 0.3H), 5.42 (br s, 1H), 4.66 (d, J=4.2 Hz, 1H), 3.52-3.42 (m, 3H), 2.70 (br s, 2H), 1.95-1.75 (m, 6H), 1.79 (app q, J=6.9 Hz, 2H), 1.70-1.48 (m, 4H), 1.36-1.25 (m, 2H), 0.85 (t, J=7.4 Hz, 3H). LCMS: Purity 98%, MS (m/e) 441(MH$^+$).

trans-8-Chloro-3-((cyclobutylmethyl)amino)-5-(4-hydroxycyclohexyl)pyrimido[4,5-c]isoquinolin-6(5H)-one

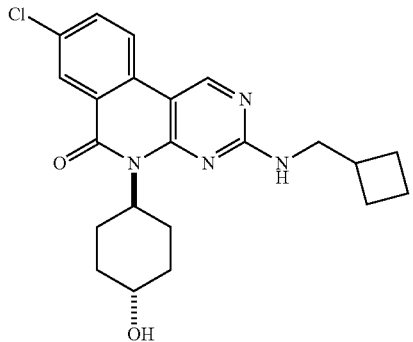

$^1$H NMR (400 MHz, DMSO-d$_6$) δ 9.21 (s, 1H), 8.33 (d, J=8.8 Hz, 1H), 8.10 (d, J=2.4 Hz, 1H), 7.87 (app s, 0.7H), 7.76 (d, J=8.8, 2.4 Hz, 1H), 7.64 (br s, 0.3H), 5.37 (br s, 1H), 4.66 (d, J=4.4 Hz, 1H), 3.49 (br s, 1H), 3.40 (t, J=6.6 Hz, 2H), 2.90-2.52 (m, 3H), 2.10-1.89 (m, 4H), 1.84 (p, J=6.8, 6.3 Hz, 2H), 1.74 (q, J=8.1 Hz, 2H), 1.57 (app d, J=11.4 Hz, 2H), 1.30 (app q, J=14.0 Hz, 2H). LCMS: Purity 98%, MS (m/e) 413 (MH$^+$).

trans-8-Chloro-3-(((1-ethylcyclopropyl)methyl)amino)-5-(4-hydroxycyclohexyl)pyrimido[4,5-c]isoquinolin-6(5H)-one

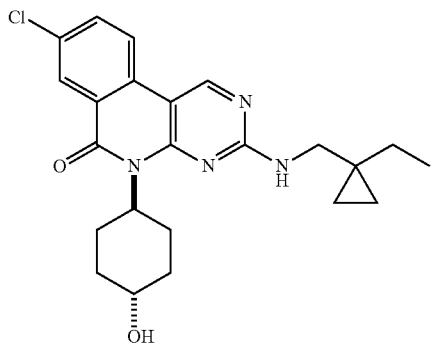

$^1$H NMR (400 MHz, DMSO-d$_6$) δ 9.25-9.20 (m, 1H), 8.33 (d, J=8.7 Hz, 1H), 8.09 (d, J=2.3 Hz, 1H), 7.81 (br s, 0.7H), 7.76 (dd, J=8.7, 2.4 Hz, 1H), 7.60 (br s, 0.3H), 5.41 (br s, 1H), 4.65 (d, J=4.1 Hz, 1H), 3.52 (br s, 1H), 3.39 (app t, J=7.0 Hz, 2H), 2.72 (br s, 2H), 1.94 (d, J=10.7 Hz, 2H), 1.55 (d, J=10.4 Hz, 2H), 1.36-1.26 (m, 4H), 0.91 (t, J=7.4 Hz, 3H), 0.49-0.43 (app m, 2H), 0.29-0.22 (m, 2H). LCMS: Purity 98%, MS (m/e) 427 (MH$^+$).

trans-8-Chloro-3-((2,2-difluorobutyl)amino)-5-(4-hydroxycyclohexyl)pyrimido[4,5-c]isoquinolin-6(5H)-one

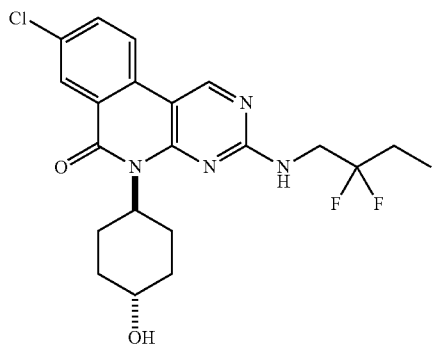

$^1$H NMR (400 MHz, DMSO-d$_6$) δ 9.30 (s, 1H), 8.37 (d, J=8.7 Hz, 1H), 8.12 (d, J=2.4 Hz, 1H), 8.09 (br s, 0.7H), 7.97 (br s, 0.3H), 7.80 (dd, J=8.7, 2.4 Hz, 1H), 5.38 (s, 1H), 4.65 (s, 1H), 3.93-3.82 (app m, 2H), 3.51 (s, 1H), 2.72 (br s, 2H), 2.01-1.83 (m, 4H), 1.56 (d, J=10.5 Hz, 2H), 1.30 (q, J=11.5 Hz, 2H), 0.99 (t, J=7.5 Hz, 3H). LCMS: Purity 98%, MS (m/e) 437 (MH$^+$).

trans-8-Chloro-3-((2-cyclopropylethyl)amino)-5-(4-hydroxycyclohexyl)pyrimido[4,5-c]isoquinolin-6(5H)-one

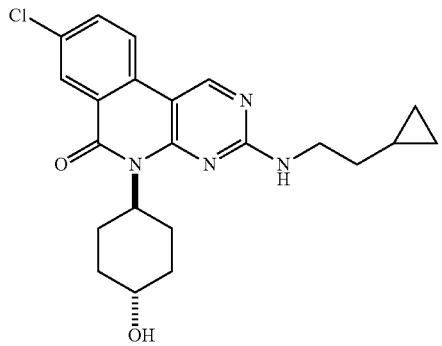

$^1$H NMR (400 MHz, DMSO-d$_6$) δ 9.21 (s, 1H), 8.33 (d, J=8.7 Hz, 1H), 8.10 (d, J=2.3 Hz, 1H), 7.80 (s, 0.7H), 7.76 (dd, J=8.7, 2.4 Hz, 1H), 7.63 (s, 0.3H), 5.37 (br s, 1H), 4.64 (d, J=4.2 Hz, 1H), 3.52 (br s, 1H), 3.43 (q, J=6.5 Hz, 2H), 2.73 (br s, 2H), 1.95 (d, J=11.1 Hz, 2H), 1.58 (d, J=10.7 Hz, 2H), 1.48 (q, J=7.2 Hz, 2H), 1.30 (q, J=10.7 Hz, 2H), 0.81-0.66 (m, 1H), 0.41 (app d, J=7.7 Hz, 2H), 0.06 (app d, J=5.0 Hz, 2H). LCMS: Purity 99%, MS (m/e) 413 (MH$^+$).

207 trans-8-Chloro-3-((cyclopropylmethyl)amino)-5-(4-hydroxy-4-methylcyclohexyl)pyrimido[4,5-c]isoquinolin-6(5H)-one

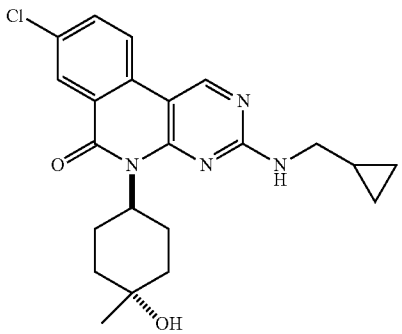

LCMS: Purity 99%, MS (m/e) 413 (MH+).

trans-8-Chloro-3-((2-cyclopropylethyl)amino)-5-(4-hydroxy-4-methylcyclohexyl)pyrimido[4,5-c]isoquinolin-6(5H)-one

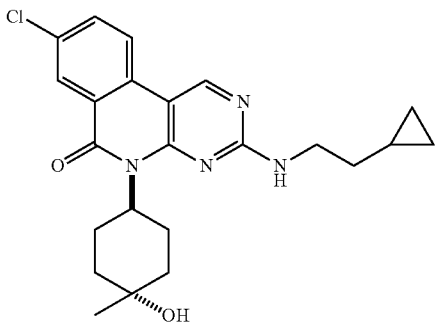

$^1$H NMR (400 MHz, DMSO-d$_6$) δ 9.22 (s, 1H), 8.33 (d, J=8.8 Hz, 1H), 8.11 (d, J=2.3 Hz, 1H), 7.79 (br s, 0.7H), 7.76 (dd, J=8.6, 2.4 Hz, 1H), 7.53 (br s, 03H), 5.44 (br s, 1H), 4.41 (br s, 1H), 3.43 (q, J=6.3 Hz, 2H), 2.80-2.68 (app m, 2H), 1.67 (app d, J=8.8 Hz, 2H), 1.58-1.42 (m, 6H), 1.29 (s, 3H), 0.80-0.67 (m, 1H), 0.45-0.35 (m, 2H), 0.06 (q, J=5.0 Hz, 2H). LCMS: Purity 99%, MS (m/e) 427 (MH+).

trans-8-Chloro-3-((cyclobutylmethyl)amino)-5-(4-hydroxy-4-methylcyclohexyl)pyrimido[4,5-c]isoquinolin-6(5H)-one

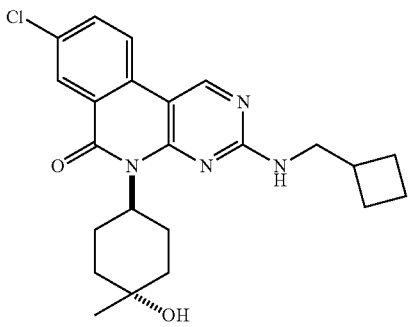

208

$^1$H NMR (400 MHz, DMSO-d$_6$) δ 9.21 (s, 1H), 8.32 (d, J=8.8 Hz, 1H), 8.11 (d, J=2.4 Hz, 1H), 7.84 (br s, 0.7H), 7.75 (dd, J=8.7, 2.3 Hz, 1H), 7.57 (br s 0.3H), 5.44 (br s, 1H), 4.43 (s, 1H), 3.41 (t, J=6.5 Hz, 2H), 2.69 (s, 2H), 2.65-2.52 (m, 1H), 2.06-1.93 (m, 2H), 1.90-1.77 (m, 2H), 1.70 (dd, J=20.6, 11.8 Hz, 4H), 1.58-1.41 (m, 4H), 1.28 (s, 3H). LCMS: Purity 98%, MS (m/e) 427 (MH+).

trans-8-Chloro-5-(4-hydroxycyclohexyl)pyrimido[4,5-c]isoquinolin-6(5H)-one $^1$H NMR (400 MHz, DMSO-d$_6$) δ 9.77 (s, 1H), 9.11 (s, 1H), 8.66 (d, J=8.8 Hz, 1H), 8.25 (d, J=2.3 Hz, 1H), 7.97 (dd, J=8.6, 2.3 Hz, 1H), 5.47 (br s, 1H), 4.63 (d, J=4.5 Hz, 1H), 3.59-3.46 (m, 1H), 2.70 (dd, J=27.3, 15.3 Hz, 2H), 1.95 (d, J=10.7 Hz, 2H), 1.62 (d, J=11.2 Hz, 2H), 1.40-1.25 (m, 2H). LCMS: Purity 96%, MS (m/e) 330 (MH+).

General procedure for the preparation of 3-(alkylamino)-5-(substituedalkyl)-8-((substitutedamino)methyl)pyrimido[4,5-c]isoquinolin-6(5H)-ones is described in the preparation of trans-3-(butylamino)-5-(4-hydroxycyclohexyl)-8-(4-methylpiperazin-1-yl)methyl)pyrimido[4,5-c]isoquinolin-6(5H)-one.

The crude concentrate obtained after processing end reaction mixture was purified by preparative HPLC (reverse phase column, CH$_3$CN:H$_2$O as eluting solvent containing either formic acid or CF$_3$COOH as a modifier) or silica gel flash column chromatography to provide corresponding product as salt/solvates or free base respectively.

trans-3-(Butylamino)-5-(4-hydroxycyclohexyl)-8-(4-methylpiperazin-1-yl)methyl)pyrimido[4,5-c]isoquinolin-6(5H)-one

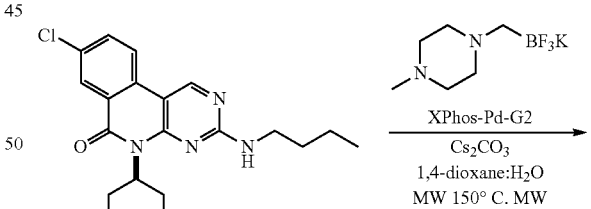

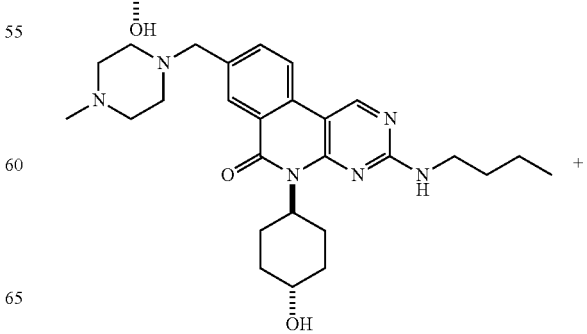

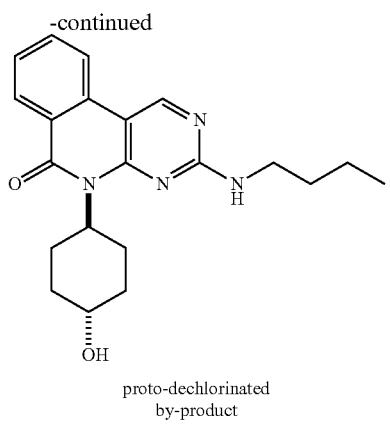

proto-dechlorinated
by-product

A microwave vial was charged with trans-3-(butylamino)-8-chloro-5-(4-hydroxycyclohexyl)pyrimido[4,5-c]isoquinolin-6(5H)-one (125 mg, 0.31 mmol), potassium 1-methyl-4-trifluoroboratomethyl piperazine (97 mg, 0.44 mmol), Cs$_2$CO$_3$ (300 mg, 0.94 mmol), XPhos-Pd-G2 (9 mg, 0.011 mmol), 1,4-dioxane (3 mL), water (0.3 mL) and a stirbar. After bubbling nitrogen through suspension for 3 min, reaction mixture was capped and heated in a microwave at 150° C. for 45 min. LC/MC analysis reaction aliquot indicated described trans-3-(butylamino)-5-(4-hydroxycyclohexyl)-8-((4-methylpiperazin-1-yl)methyl)pyrimido[4,5-c]isoquinolin-6(5H)-one (AUC 70%) and proto-dechlorinated by-product [trans-3-(butylamino)-5-(4-hydroxycyclohexyl) pyrimido[4,5-c]isoquinolin-6(5H)-one (AUC 16%)] with complete consumption of trans-3-(butylamino)-8-chloro-5-(4-hydroxycyclohexyl)pyrimido[4,5-c]isoquinolin-6(5H)-one. At this stage, pale yellow heterogeneous reaction mixture was diluted with THF (3 mL) and filtered through Celite®. Upon rinsing microwave vial with additional amount of THF (2×5 mL), flitering through Celite® homogeneous yellow filtrate was dried over MgSO$_4$, filtered and concentrated to dryness. The crude concentrated semi-solid was dissolved in 5% 7N NH$_3$ MeOH/CH$_2$Cl$_2$ (12 mL), adsorbed on silica gel (4 g), dried and purified by flash chromatography [Combiflash Torrent® with RediSep® silica gel column 12 g and eluted with 30-50% 5% 7N NH$_3$ MeOH in CH$_2$Cl$_2$:CH$_2$Cl$_2$ solvent gradient]. Solid that was obtained upon concentrating product fractions was heated in EtOAc (6 mL), cooled to room temperature and filtered to provide desired trans-3-(butylamino)-5-(4-hydroxycyclohexyl)-8-(4-methylpiperazin-1-yl)methyl)pyrimido[4,5-c]isoquinolin-6(5H)-one (78 mg) as a white solid. $^1$H NMR (400 MHz, Methanol-d$_4$) δ 9.04 (s, 1H), 8.19 (s, 1H), 8.11 (d, J=8.4 Hz, 1H), 7.69 (dd, J=8.3, 1.9 Hz, 1H), 5.68-5.31 (m, 1H), 3.68 (app dd, J=11.4, 4.4 Hz, 1H), 3.61 (s, 2H), 3.45 (t, J=7.2 Hz, 2H), 3.10-2.70 (br s, 2H), 2.53-2.48 (m, 8H), 2.26 (s, 3H), 2.09 (app d, J=11.1 Hz, 2H), 1.72-1.62 (m, 4H), 1.47 (app dt, J=15.3, 8.8 Hz, 4H), 0.99 (t, J=7.3 Hz, 3H). LCMS: Purity 99%, MS (m/e) 479 (MH$^+$).

trans-3-(Butylamino)-5-(4-hydroxycyclohexyl)pyrimido[4,5-c]isoquinolin-6(5H)-one

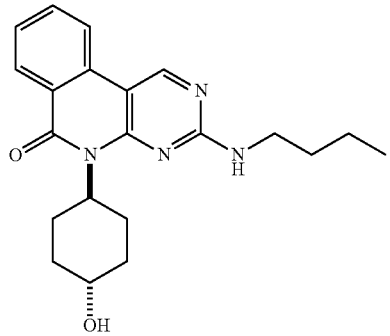

$^1$H NMR (400 MHz, DMSO-d$_6$) δ 9.22 (s, 1H), 8.29 (d, J=8.0 Hz, 1H), 8.18 (d, J=7.8 Hz, 1H), 7.72 (t, J=8.3 Hz, 1H), 7.54 (br s, 1H), 7.45 (t, J=7.6 Hz, 1H), 5.39 (s, 1H), 4.64 (app d, J=4.3 Hz, 1H), 3.50 (s, 1H), 3.35 (q, J=6.7 Hz, 2H), 2.76 (s, 2H), 1.95 (d, J=13.0 Hz, 2H), 1.69-1.46 (m, 4H), 1.46-1.18 (m, 4H), 0.91 (t, J=7.3 Hz, 3H). LCMS: Purity 98%, MS (m/e) 367 (MH$^+$).

trans-3-(Butylamino)-5-(4-hydroxycyclohexyl)-8-(morpholinomethyl)pyrimido[4,5-c]isoquinolin-6(5H)-one

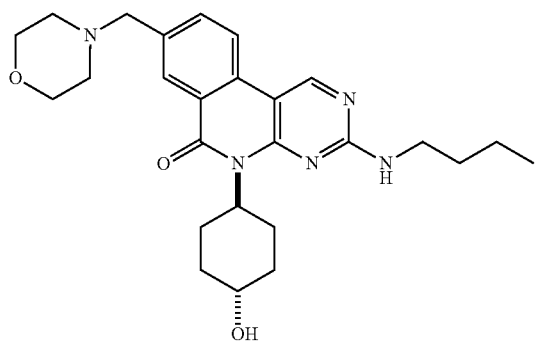

$^1$H NMR (400 MHz, Methanol-d$_4$) δ 9.09 (s, 1H), 8.24 (app d, J=1.9 Hz, 1H), 8.17 (d, J=8.3 Hz, 1H), 7.74 (dd, J=8.3, 1.9 Hz, 1H), 5.75-5.42 (br s, 1H), 3.74-3.70 (m, 1H), 3.69 (t, J=4.7 Hz, 4H), 3.63 (s, 2H), 3.47 (t, J=7.2 Hz, 2H), 3.09-2.71 (br s, 2H), 2.48 (t, J=4.7 Hz, 4H), 2.10 (app d, J=11.6 Hz, 2H), 1.79-1.58 (m, 4H), 1.58-1.36 (m, 4H), 1.00 (t, J=7.4 Hz, 3H). LCMS: Purity 98%, MS (m/e) 479 (MH$^+$).

211 cis-3-(Butylamino)-5-(4-hydroxycyclohexyl)-8-(morpholinomethyl)pyrimido[4,5-c]isoquinolin-6(5H)-one

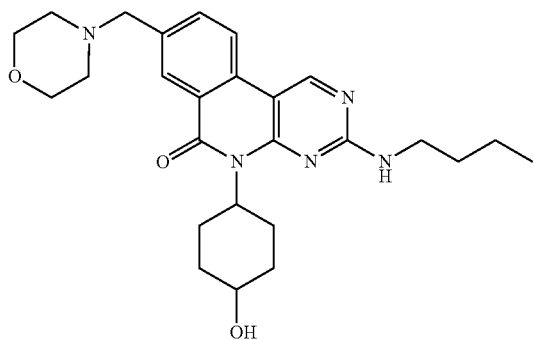 [SMILES: CCCCNc1ncc2c3ccc(CN4CCOCC4)cc3c(=O)n(C3CCC(O)CC3)c2n1]

$^1$H NMR (400 MHz, Methanol-$d_4$) δ 9.06 (s, 1H), 8.23 (d, J=1.4 Hz, 1H), 8.14 (d, J=8.3 Hz, 1H), 7.72 (dd, J=8.4, 1.9 Hz, 1H), 5.51 (br s, 1H), 4.05 (app s, 1H), 3.69 (app t, J=4.7 Hz, 4H), 3.61 (s, 2H), 3.59-3.39 (br s, 2H), 3.28-3.06 (br s, 2H), 2.47 (app t, J=4.7 Hz, 4H), 1.97 (d, J=14.0 Hz, 2H), 1.78-1.54 (m, 4H), 1.46 (app td, J=14.6, 14.1, 7.1 Hz, 4H), 0.98 (t, J=7.4 Hz, 3H). LCMS: Purity 97%, MS (m/e) 479 (MH$^+$).

cis-3-(Butylamino)-5-(4-hydroxycyclohexyl)-8-((4-methylpiperazin-1-yl)methyl)pyrimido[4,5-c]isoquinolin-6(5H)-one

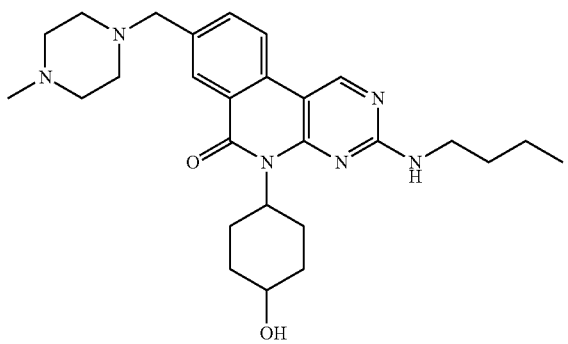 [SMILES: CCCCNc1ncc2c3ccc(CN4CCN(C)CC4)cc3c(=O)n(C3CCC(O)CC3)c2n1]

$^1$H NMR (400 MHz, Methanol-$d_4$) δ 9.06 (s, 1H), 8.22 (s, 1H), 8.14 (d, J=8.4 Hz, 1H), 7.70 (d, J=8.4 Hz, 1H), 5.68-5.28 (m, 1H), 4.05 (s, 1H), 3.63 (s, 2H), 3.51 (br s, 2H), 3.23-3.16 (m, 2H), 2.64-2.34 (br s, 8H), 2.26 (s, 3H), 1.97 (d, J=12.6 Hz, 2H), 1.75-1.58 (m, 4H), 1.51-1.40 (m, 4H), 0.98 (t, J=7.3 Hz, 3H). LCMS: Purity 97%, MS (m/e) 479 (MH$^+$).

212

3-(Butylamino)-5-((4-hydroxycyclohexyl)methyl)-8-(4-methylpiperazin-1-yl)methyl)pyrimido[4,5-c]isoquinolin-6(5H)-one

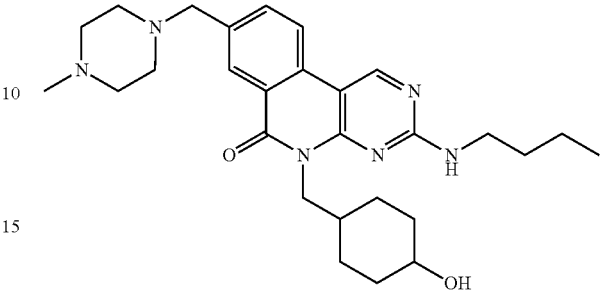

$^1$H NMR (400 MHz, Methanol-$d_4$) δ 9.09 (s, 1H), 8.25 (d, J=1.7 Hz, 1H), 8.19 (d, J=8.4 Hz, 1H), 7.74 (dd, J=8.3, 1.9 Hz, 1H), 4.33 (d, J=7.5 Hz, 2H), 3.65 (s, 2H), 3.54-3.41 (m, 3H), 2.61-2.44 (m, 8H), 2.28 (s, 3H), 2.0-1.92 (app m, 3H), 1.67 (app td, J=15.0, 14.2, 7.2 Hz, 4H), 1.46 (app dt, J=15.0, 7.4 Hz, 2H), 1.31-1.09 (m, 4H), 0.99 (t, J=7.4 Hz, 3H). LCMS: Purity 97%, MS (m/e) 479 (MH$^+$).

tert-Butyl (4-((3-(butylamino)-8-(morpholinomethyl)-6-oxopyrimido[4,5-c]isoquinolin-5(6H)-yl)methyl)cyclohexyl)carbamate

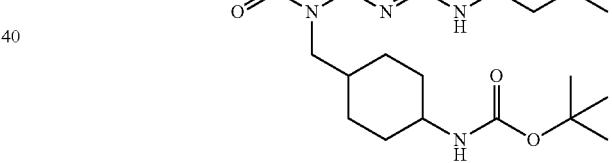

LCMS: Purity 98%, MS (m/e) 579 (MH$^+$).

tert-Butyl (4-((3-(butylamino)-8-((4-methylpiperazin-1-yl)methyl)-6-oxopyrimido[4,5-c]isoquinolin-5(6H)-yl)methyl)cyclohexyl)carbamate

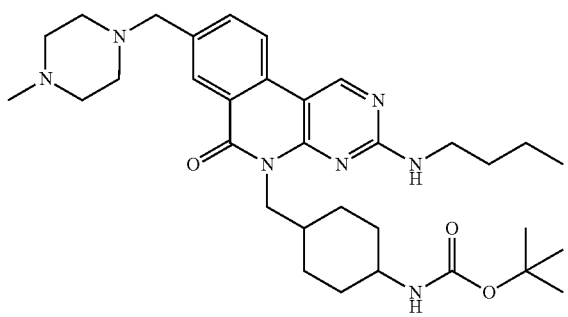 [SMILES: CCCCNc1ncc2c3ccc(CN4CCN(C)CC4)cc3c(=O)n(CC3CCC(NC(=O)OC(C)(C)C)CC3)c2n1]

¹H NMR (400 MHz, Methanol-d₄) δ 9.10 (s, 1H), 8.25 (s, 1H), 8.19 (d, J=8.4 Hz, 1H), 7.74 (dd, J=8.3, 1.9 Hz, 1H), 4.35 (d, J=6.9 Hz, 2H), 3.65 (s, 2H), 3.45 (t, J=7.2 Hz, 2H), 2.87-2.32 (m, 8H), 2.27 (s, 3H), 2.06-1.75 (m, 4H), 1.75-1.54 (m, 4H), 1.48-1.39 (m, 2H), 1.40 (s, 9H), 1.31-1.19 (app m, 2H), 1.09 (q, J=15.4, 14.0 Hz, 2H), 0.99 (t, J=7.5 Hz, 3H). LCMS: Purity 98%, MS (m/e) 592 (MH⁺).

trans-3-Amino-5-(4-hydroxycyclohexyl)-8-((4-methylpiperazin-1-yl)methyl)pyrimido[4,5-c]isoquinolin-6(5H)-one

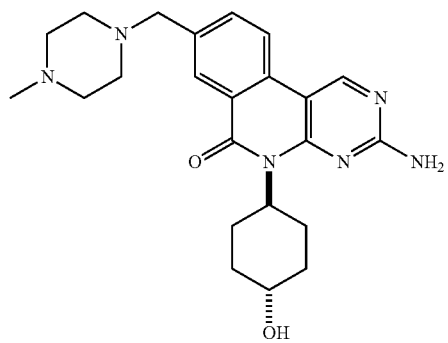

¹H NMR (400 MHz, Methanol-d₄) δ 9.09 (s, 1H), 8.22 (d, J=1.7 Hz, 1H), 8.16 (d, J=8.3 Hz, 1H), 7.72 (dd, J=8.3, 1.9 Hz, 1H), 5.57 (br s, 1H), 3.80-3.67 (app m, 1H), 3.64 (s, 2H), 2.94-2.70 (br m, 2H), 2.59-2.39 (br m, 8H), 2.27 (s, 3H), 2.08 (d, J=11.7 Hz, 2H), 1.67 (d, J=11.0 Hz, 2H), 1.55-1.40 (m, 2H). LCMS: Purity 97%, MS (m/e) 423 (MH⁺).

trans-3-((3,3-Difluorocyclobutyl)amino)-5-(4-hydroxycyclohexyl)-8-((4-methylpiperazin-1-yl)methyl)pyrimido[4,5-c]isoquinolin-6(5H)-one triformate salt or solvate

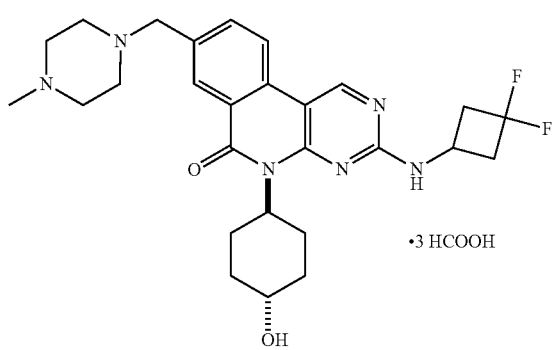

¹H NMR (300 MHz, Methanol-d₄) δ 9.17 (s, 1H), 8.27 (s, 1H), 8.22 (d, J=8.4 Hz, 1H), 7.75 (d, J=8.4 Hz, 1H), 5.56 (br s, 1H), 4.36 (br s, 1H), 3.77 (s, 2H), 3.72 (br s, 1H), 3.35-3.29 (m, 4H), 3.06-3.02 (m, 4H), 2.88 (s, 3H), 2.86-2.65 (m, 8H), 2.14-2.10 (m, 2H), 1.72-1.68 (m, 2H), 1.56-1.47 (m, 2H). LCMS: Purity 99%, MS (m/e) 513 (MH⁺-3 HCOOH).

trans-3-((3-Fluorocyclobutyl)amino)-5-(4-hydroxycyclohexyl)-8-((4-methylpiperazin-1-yl)methyl)pyrimido[4,5-c]isoquinolin-6(5H)-one triformate salt or solvate

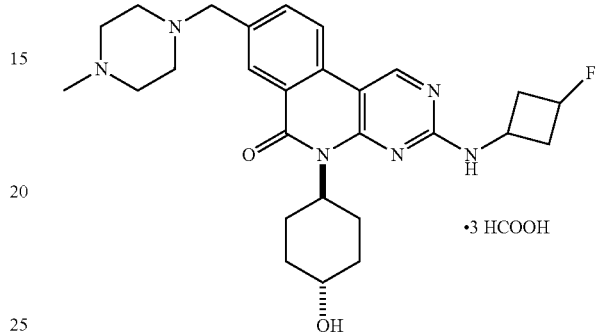

¹H NMR (300 MHz, Methanol-d₄) δ 9.13 (s, 1H), 8.28 (s, 1H), 8.21 (d, J=8.4 Hz, 1H), 7.77 (d, J=8.4 Hz, 1H), 5.52 (br s, 1H), 5.35-5.16 (m, 1H), 4.65 (br s, 1H), 3.84 (s, 2H), 3.73 (br s, 1H), 3.30-3.28 (m, 6H), 2.89 (s, 3H), 2.86-2.45 (m, 1H), 2.13-2.09 (m, 2H), 1.72-1.68 (m, 2H), 1.54-1.46 (m, 2H). LCMS: Purity 99%, MS (m/e) 495 (MH⁺-3 HCOOH).

3-(Butylamino)-5-(6-hydroxyspiro[3.3]heptan-2-yl)-8-((4-methylpiperazin-1-yl)methyl)pyrimido[4,5-c]isoquinolin-6(5H)-one

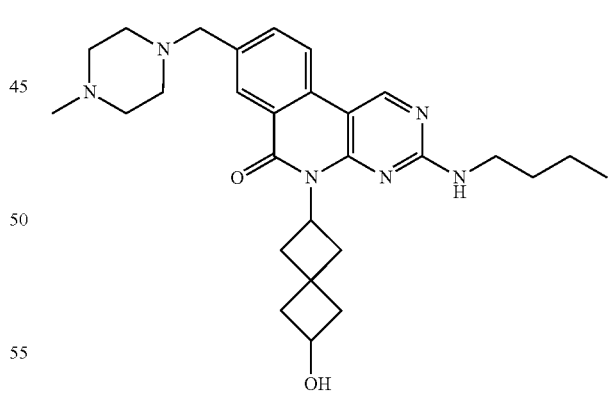

¹H NMR (400 MHz, Methanol-d₄) δ 8.99 (s, 1H), 8.15 (s, 1H), 8.06 (d, J=8.4 Hz, 1H), 7.66 (d, J=8.3 Hz, 1H), 5.76 (p, J=8.9 Hz, 1H), 4.16 (q, J=7.2 Hz, 1H), 3.60 (s, 2H), 3.44 (t, J=7.2 Hz, 2H), 3.17 (br s, 2H), 2.60-2.31 (br m, 12H), 2.26 (s, 3H), 2.08-1.97 (m, 2H), 1.64 (dt, J=14.5, 7.3 Hz, 2H), 1.46 (p, J=7.2 Hz, 2H), 0.99 (t, J=7.3 Hz, 3H). LCMS: Purity 99%, MS (m/e) 491 (MH⁺).

215

3-(Butylamino)-5-(6-hydroxyspiro[3.3]heptan-2-yl)pyrimido[4,5-c]isoquinolin-6(5H)-one

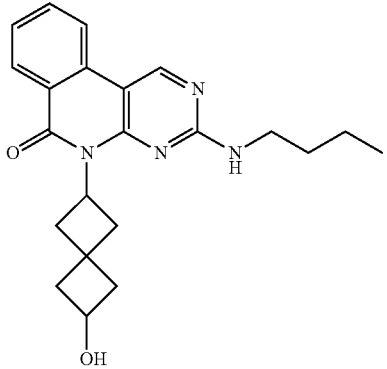 [SMILES: CCCCNc1ncc2c3ccccc3c(=O)n(C3CC4(CC(O)C4)C3)c2n1]

$^1$H NMR (400 MHz, DMSO-d$_6$) δ 9.23 (s, 1H), 8.28 (d, J=8.4 Hz, 1H), 8.17 (d, J=9.1 Hz, 1H), 7.79-7.65 (m, 2H), 7.45 (t, J=7.6 Hz, 1H), 5.69 (p, J=9.0 Hz, 1H), 4.93 (d, J=6.3 Hz, 1H), 4.01 (dq, J=14.8, 7.7, 7.3 Hz, 1H), 3.43-3.32 (m, 2H), 3.25-3.08 (m, 2H), 2.99 (br s, 1H), 2.39-2.12 (m, 3H), 2.01-1.81 (m, 2H), 1.70-1.49 (m, 2H), 1.49-1.29 (m, 2H), 0.93 (d, J=7.0 Hz, 3H). LCMS: Purity 95%, MS (m/e) 379 (MH$^+$).

trans-3-(Butylamino)-5-(4-hydroxy-4-methylcyclohexyl)-8-((4-methylpiperazin-1-yl)methyl)pyrimido[4,5-c]isoquinolin-6(5H-one

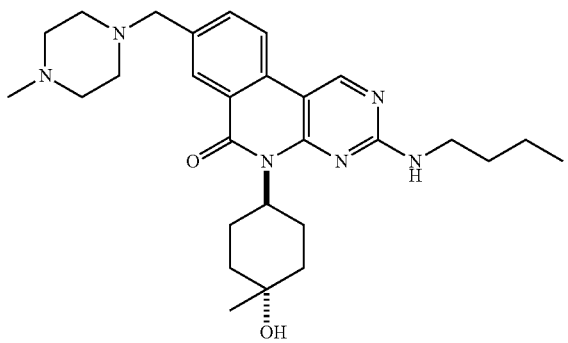

$^1$H NMR (400 MHz, Methanol-d$_4$) δ 9.07 (s, 1H), 8.21 (d, J=1.6 Hz, 1H), 8.14 (d, J=8.4 Hz, 1H), 7.71 (dd, J=8.3, 1.9 Hz, 1H), 5.65 (app br s, 1H), 3.63 (s, 2H), 3.47 (t, J=7.1 Hz, 2H), 2.88 (app qt, J=12.6 Hz, 2H), 2.62-2.41 (br s, 8H), 2.27 (s, 3H), 1.82 (d, J=12.2 Hz, 2H), 1.74-1.57 (m, 6H), 1.47 (app q, J=7.2 Hz, 2H)), 1.44 (s, 3H), 0.99 (t, J=7.3 Hz, 3H). LCMS: Purity 99%, MS (m/e) 493 (MH$^+$).

216 trans-3-(Butylamino)-5-(4-hydroxy-4-methylcyclohexyl)pyrimido[4,5-c]isoquinolin-6(5H)-one

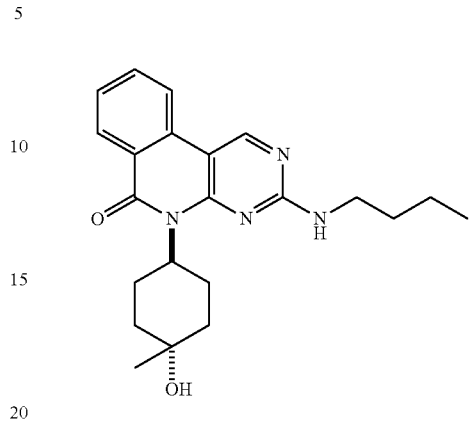

$^1$H NMR (400 MHz, DMSO-d$_6$) δ 9.23 (s, 1H), 8.29 (d, J=8.1 Hz, 1H), 8.19 (d, J=8.0 Hz, 1H), 7.72 (app t, J=7.6 Hz, 2H), 7.45 (app t, J=7.6 Hz, 1H), 5.46 (s, 1H), 4.41 (s, 1H), 3.36 (q, J=6.8 Hz, 2H), 2.91-2.57 (m, 2H), 1.67 (d, J=12.4 Hz, 2H), 1.63-1.44 (m, 6H), 1.35 (q, J=7.3 Hz, 2H), 1.29 (s, 3H), 0.91 (t, J=7.3 Hz, 3H). LCMS: Purity 95%, MS (m/e) 381 (MH$^+$).

trans-3-((Cyclopropylmethyl)amino)-5-(4-hydroxycyclohexyl)-8-((4-methylpiperazin-1-yl)methyl)pyrimido[4,5-c]isoquinolin-6(5H)-one

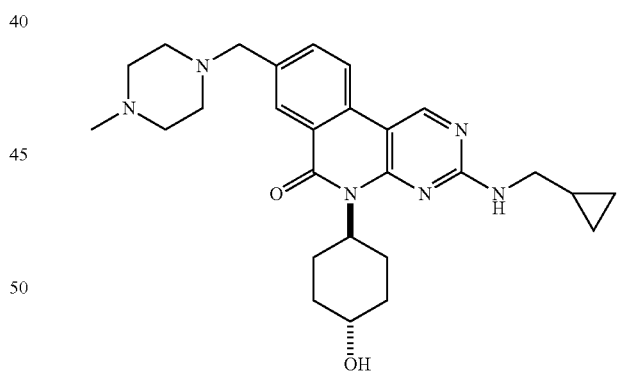

$^1$H NMR (400 MHz, Methanol-d$_4$) δ 9.05 (s, 1H), 8.20 (d, J=1.5 Hz, 1H), 8.12 (d, J=8.3 Hz, 1H), 7.69 (dd, J=8.3, 1.9 Hz, 1H), 5.54 (br s, 1H), 3.71 (tt, J=10.2, 4.2 Hz, 1H), 3.62 (s, 2H), 3.34 (d, J=6.9 Hz, 2H), 2.99-2.72 (br s, 2H), 2.68-2.35 (br s, 8H), 2.26 (s, 3H), 2.09 (d, J=11.3 Hz, 2H), 1.68 (d, J=11.5 Hz, 2H), 1.48 (q, J=13.3 Hz, 2H), 1.22-1.12 (m, 1H), 0.59-0.50 (m, 2H), 0.31 (q, J=4.8 Hz, 2H). LCMS: Purity 98%, MS (m/e) 477 (MH$^+$).

217 trans-3-((Cyclopropylmethyl)amino)-5-(4-hydroxy-cyclohexyl)pyrimido[4,5-c]isoquinolin-6(5H)-one

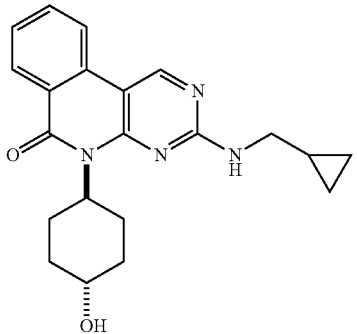

$^1$H NMR (400 MHz, DMSO-$d_6$) δ 9.24 (s, 1H), 8.29 (d, J=7.8 Hz, 1H), 8.18 (d, J=8.2 Hz, 1H), 7.81 (br s, 0.7H), 7.73 (t, J=7.6 Hz, 1H), 7.66 (br s, 0.3H), 7.45 (t, J=7.9 Hz, 1H), 5.40 (s, 1H), 4.65 (s, 1H), 3.75-3.42 (br, 1H), 3.25 (t, J=6.3 Hz, 2H), 2.80 (br s, 2H), 1.95 (app d, J=11.8 Hz, 2H), 1.55 (d, J=11.1 Hz, 2H), 1.31 (q, J=13.3 Hz, 2H), 1.20 (app br s, 1H), 0.45 (q, J=5.2 Hz, 2H), 0.25 (q, J=4.8 Hz, 2H). LCMS: Purity 94%, MS (m/e) 365 (MH$^+$).

218 cis-3-(Butylamino)-5-(4-hydroxy-4-methylcyclohexyl)pyrimido[4,5-c]isoquinolin-6(5H)-one

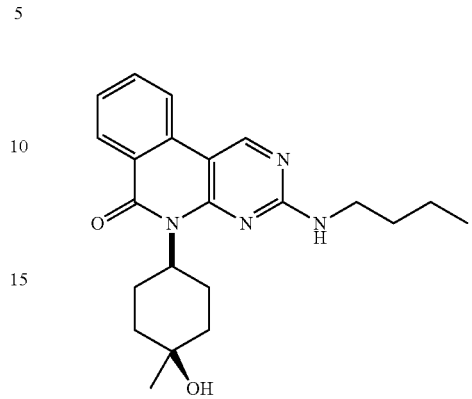

$^1$H NMR (400 MHz, DMSO-$d_6$) δ 9.21 (s, 1H), 8.28 (d, J=8.1 Hz, 1H), 8.19 (d, J=8.1 Hz, 1H), 7.72 (t, J=7.6 Hz, 1H), 7.66-7.57 (m, 1H), 7.45 (t, J=7.6 Hz, 1H), 5.37 (s, 1H), 4.00 (s, 1H), 3.39 (br s, 2H), 3.22-2.85 (m, 2H), 1.69 (d, J=12.9 Hz, 2H), 1.54 (dt, J=14.7, 7.2 Hz, 2H), 1.46-1.27 (m, 6H), 1.14 (s, 3H), 0.89 (q, J=7.1 Hz, 3H). LCMS: Purity 95%, MS (m/e) 381 (MH$^+$).

cis-3-(Butylamino)-5-(4-hydroxy-4-methylcyclohexyl)-8-((4-methylpiperazin-1-yl)methyl)pyrimido[4,5-c]isoquinolin-6(5H)-one

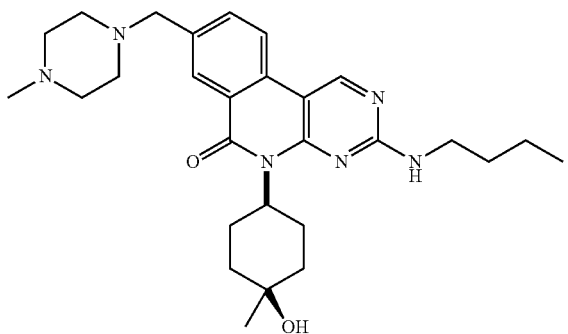

$^1$H NMR (400 MHz, Methanol-$d_4$) δ 9.05 (s, 1H), 8.21 (s, 1H), 8.12 (d, J=8.1 Hz, 1H), 7.69 (dd, J=8.4, 2.0 Hz, 1H), 5.47 (s, 1H), 3.61 (s, 2H), 3.49 (br s, 2H), 3.20 (br s, 2H), 2.69-2.30 (s, 8H), 2.26 (s, 3H), 1.83 (d, J=13.4 Hz, 2H), 1.69-1.52 (m, 4H), 1.51-1.41 (m, 4H), 1.25 (s, 3H), 0.98 (t, J=7.3 Hz, 3H). LCMS: Purity 99%, MS (m/e) 493 (MH$^+$).

trans-3-(((1-Ethylcyclobutyl)methyl)amino)-5-(4-hydroxycyclohexyl)-8-((4-methylpiperazin-1-yl)methyl)pyrimido[4,5-c]isoquinolin-6(5H)-one

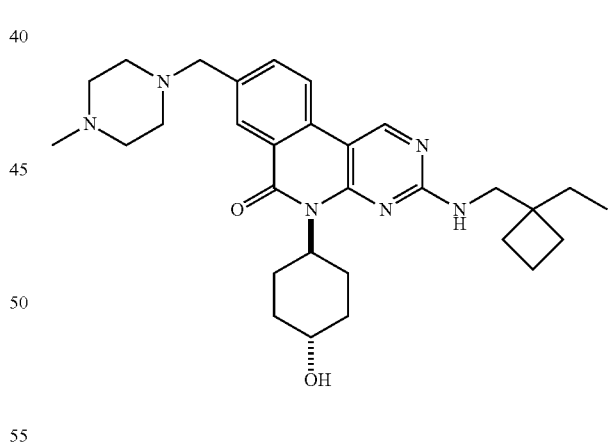

$^1$H NMR (400 MHz, Methanol-$d_4$) δ 9.09 (m, 1H), 8.21 (s, 1H), 8.15 (d, J=8.3 Hz, 1H), 7.71 (dd, J=8.3, 2.1 Hz, 1H), 5.60 (br s, 1H), 3.74-3.66 (m, 1H), 3.63 (s, 2H), 3.58 (s, 2H), 3.00-2.72 (br s, 2H), 2.2.7-2.33 (br s, 8H), 2.27 (s, 3H), 2.09 (d, J=11.7 Hz, 2H), 1.94-1.88 (m 4H), 1.85-1.75 (m, 2H), 1.68 (d, J=12.1 Hz, 2H), 1.61 (q, J=7.1, 6.6 Hz, 2H), 1.48 (q, J=12.0 Hz, 2H), 0.93 (t, J=7.2 Hz, 3H). LCMS: Purity 99%, MS (m/e) 519 (MH$^+$).

219 trans-3-(((1-Ethylcyclobutyl)methyl)amino)-5-(4-hydroxycyclohexyl)-8-(morpholinomethyl)pyrimido[4,5-c]isoquinolin-6(5H)-one

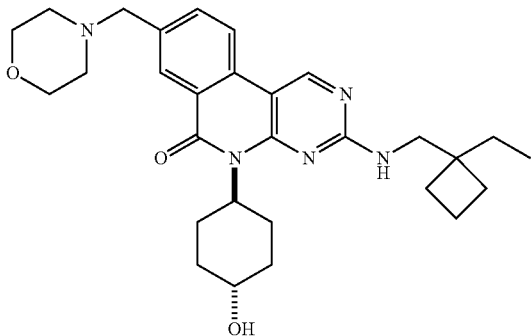

LCMS: Purity 99%, MS (m/e) 506 (MH+).

trans-3-(((1-Ethylcyclobutyl)methyl)amino)-5-(4-hydroxycyclohexyl)pyrimido[4,5-c]isoquinolin-6(5H)-one

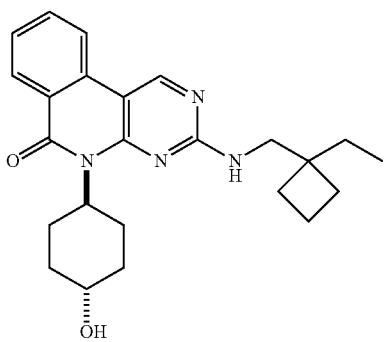

$^1$H NMR (400 MHz, DMSO-$d_6$) δ 9.24 (s, 1H), 8.30 (d, J=8.1 Hz, 1H), 8.18 (d, J=7.9 Hz, 1H), 7.72 (t, J=8.3 Hz, 1H), 7.66-7.61 (app m, 1H), 7.45 (t, J=8.0 Hz, 1H), 5.43 (br s, 1H), 4.65 (s, 1H), 3.60-3.45 (unresolved m, 3H), 2.97-2.58 (br s, 2H), 1.99-1.75 (m, 6H), 1.84-1.75 (m, 2H), 1.70-1.48 (m, 4H), 1.36-1.25 (m, 2H), 0.86 (t, J=7.4 Hz, 3H). LCMS: Purity 96%, MS (m/e) 407 (MH+).

trans-3-(((1-Ethylcyclobutyl)methyl)amino)-5-(4-hydroxycyclohexyl)-8-(morpholinomethyl)pyrimido[4,5-c]isoquinolin-6(5H)-one

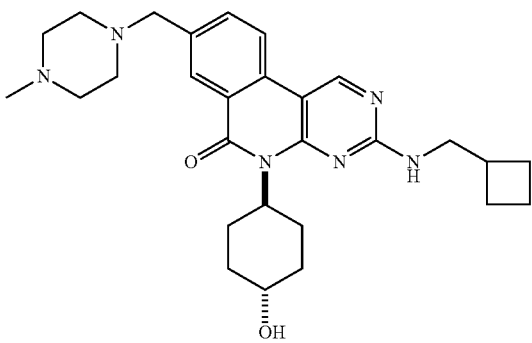

220

$^1$H NMR (400 MHz, Methanol-$d_4$) δ 9.06 (s, 1H), 8.21 (s, 1H), 8.13 (d, J=8.4 Hz, 1H), 7.70 (dd, J=8.3, 1.9 Hz, 1H), 5.56 (br s, 1H), 3.76-3.64 (m, 1H), 3.63 (s, 2H), 3.50 (d, J=7.1 Hz, 2H), 3.09-2.76 (br s, 2H), 2.69 (p, J=7.6 Hz, 1H), 2.58-2.35 (br s, 8H), 2.27 (s, 3H), 2.19-2.06 (m, 4H), 2.01-1.89 (m, 2H), 1.82 (dt, J=18.4, 8.4 Hz, 2H), 1.69 (d, J=11.2 Hz, 2H), 1.48 (qd, J=12.9, 12.5, 3.5 Hz, 2H). LCMS: Purity 98%, MS (m/e) 490 (MH+).

trans-3-((Cyclobutylmethyl)amino)-5-(4-hydroxycyclohexyl)-8-(morpholinomethyl)pyrimido[4,5-c]isoquinolin-6(5H)-one

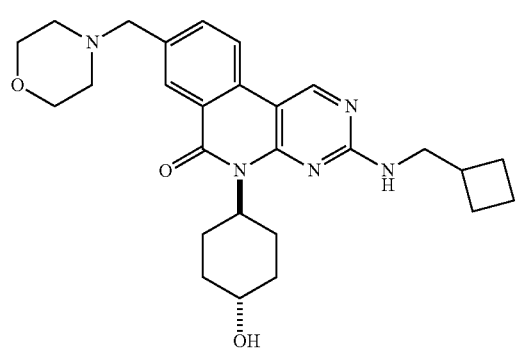

LCMS: Purity 99%, MS (m/e) 478 (MH+).

trans-3-((Cyclobutylmethyl)amino)-5-(4-hydroxycyclohexyl)pyrimido[4,5-c]isoquinolin-6(5H)-one

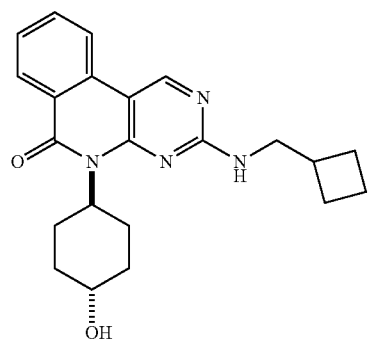

$^1$H NMR (400 MHz, DMSO-$d_6$) δ 9.22 (s, 1H), 8.29 (d, J=8.3 Hz, 1H), 8.19 (d, J=8.2 Hz, 1H), 7.84-7.75 (br s m, 1H), 7.73 (t, J=8.3 Hz, 1H), 7.45 (t, J=7.9 Hz, 1H), 5.39 (br s, 1H), 4.65 (s, 1H), 3.49 (br s, 1H), 3.41 (t, J=6.5 Hz, 2H), 2.85-2.70 (br s, 2H), 2.68-2.56 (m, 1H), 2.07-1.92 (m, 4H), 1.87 (p, J=6.9, 6.3 Hz, 2H), 1.74 (q, J=7.9 Hz, 2H), 1.58 (d, J=14.7 Hz, 2H), 1.37-1.28 (m, 2H). LCMS: Purity 97%, MS (m/e) 379 (MH+).

221 trans-3-(((1-Ethylcyclopropyl)methyl)amino)-5-(4-hydroxycyclohexyl)-8-((4-methylpiperazin-1-yl)methyl)pyrimido[4,5-c]isoquinolin-6(5H)-one

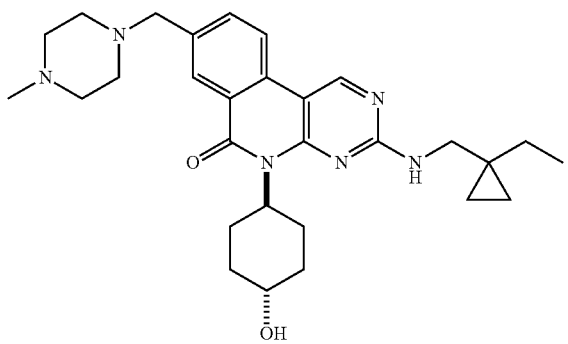

$^1$H NMR (400 MHz, Methanol-$d_4$) δ 9.08 (s, 1H), 8.21 (s, 1H), 8.14 (d, J=8.9 Hz, 1H), 7.71 (d, J=8.2 Hz, 1H), 5.59 (br s, 1H), 3.77-3.66 (m, 1H), 3.63 (s, 2H), 3.48 (s, 2H), 2.87 (br s, 2H), 2.51 (br s, 8H), 2.27 (s, 3H), 2.09 (d, J=12.0 Hz, 2H), 1.68 (d, J=11.9 Hz, 2H), 1.52-1.41 (app m, 4H), 0.99 (app t, J=14.4 Hz, 3H), 0.51 (s, 2H), 0.36 (s, 2H). LCMS: Purity 99%, MS (m/e) 505 (MH$^+$).

trans-3-(((1-Ethylcyclopropyl)methyl)amino)-5-((4-hydroxycyclohexyl)-8-(morpholinomethyl)pyrimido[4,5-c]isoquinolin-6(5H)-one

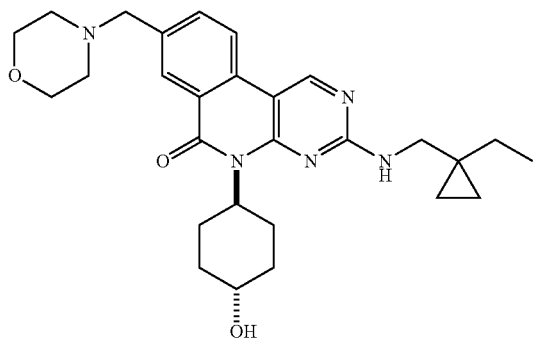

LCMS: Purity 99%, MS (m/e) 492 (MH$^+$).

3-(((1-Ethyl cyclopropyl)methyl)amino)-5-(4-hydroxycyclohexyl)pyrimido[4,5-c]isoquinolin-6(5H)-one

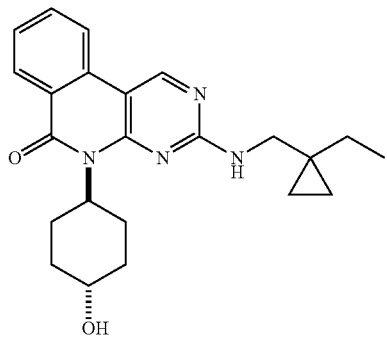

222

$^1$H NMR (400 MHz, DMSO-$d_6$) δ 9.23 (s, 1H), 8.29 (d, J=8.1 Hz, 1H), 8.18 (d, J=7.8 Hz, 1H), 7.72 (overlapped t, J=7.6 Hz, 2H), 7.45 (t, J=7.6 Hz, 1H), 5.43 (s, 1H), 4.65 (s, 1H), 3.50 (br s, 1H), 3.40 (app d, J=5.3 Hz, 2H), 2.73 (br s, 2H), 1.95 (d, J=10.8 Hz, 2H), 1.55 (d, J=11.9 Hz, 2H), 1.36-1.26 (m, 4H), 0.92 (t, J=7.3 Hz, 3H), 0.46 (app t, J=2.7 Hz, 2H), 0.27-0.24 (app m, 2H). LCMS: Purity 97%, MS (m/e) 393 (MH$^+$).

trans-3-((2,2-Difluorobutyl)amino)-5-(4-hydroxycyclohexyl)-8-((4-methylpiperazin-1-yl)methyl)pyrimido[4,5-c]isoquinolin-6(5H)-one

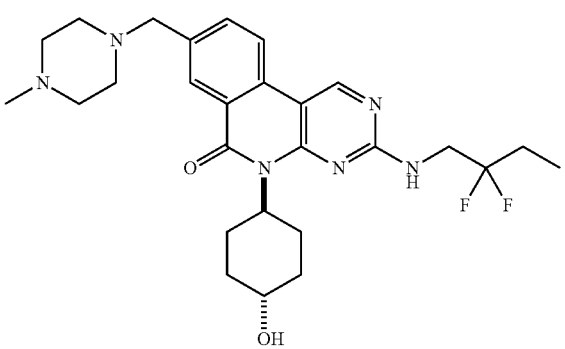

$^1$H NMR (400 MHz, Methanol-$d_4$) δ 9.15 (s, 1H), 8.23 (s, 1H), 8.18 (d, J=8.4 Hz, 1H), 7.74 (d, J=8.4 Hz, 1H), 5.56 (br s, 1H), 3.96 (t, J=13.9 Hz, 2H), 3.75-3.69 (app m, 1H), 3.64 (s, 2H), 3.00-2.78 (br s, 2H), 2.72-2.35 (br s, 8H), 2.27 (s, 3H), 2.09 (d, J=11.5 Hz, 2H), 1.97 (dq, J=16.4, 8.1 Hz, 2H), 1.69 (d, J=12.1 Hz, 2H), 1.48 (app qt, J=12.1 Hz, 2H), 1.08 (t, J=7.5 Hz, 3H). LCMS: Purity 99%, MS (m/e) 515 (MH$^+$).

trans-3-((2,2-Difluorobutyl)amino)-5-(4-hydroxycyclohexyl)-8-(morpholinomethyl)pyrimido[4,5-c]isoquinolin-6(5H)-one

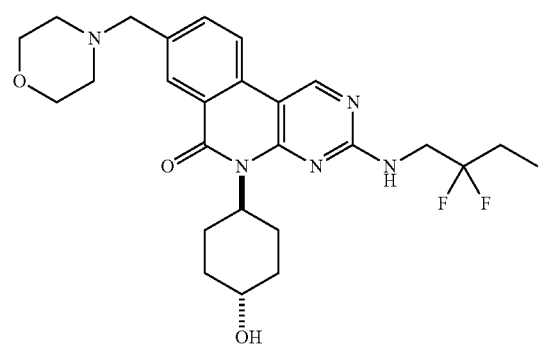

LCMS: Purity 99%, MS (m/e) 502 (MH$^+$).

223 trans-3-((2,2-difluorobutyl)amino)-5-(4-hydroxycyclohexyl)pyrimido[4,5-c]isoquinolin-6(5H)-one

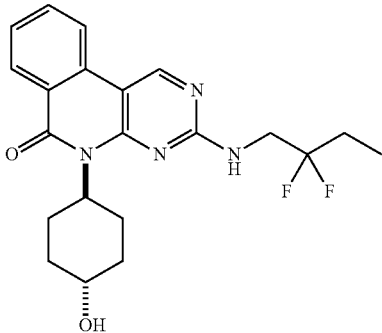

$^1$H NMR (400 MHz, DMSO-d$_6$) δ 9.30 (s, 1H), 8.33 (d, J=8.1 Hz, 1H), 8.20 (d, J=7.7 Hz, 1H), 8.02 (br s, 1H), 7.75 (t, J=7.6 Hz, 1H), 7.49 (t, J=7.6 Hz, 1H), 5.38 (br s, 1H), 4.64 (s, 1H), 3.95-3.82 (app m, 2H), 3.89 (br s, 1H), 2.76 (br s, 2H), 2.03-1.84 (m, 4H), 1.56 (d, J=10.9 Hz, 2H), 1.31 (q, J=11.1 Hz, 2H), 0.99 (t, J=7.5 Hz, 3H). LCMS: Purity 97%, MS (m/e) 403 (MI-1$^+$).

trans-5-(4-hydroxycyclohexyl)-8-((4-methylpiperazin-1-yl)methyl)-3-((4,4,4-trifluorobutyl)amino)pyrimido[4,5-c]isoquinolin-6(5H)-one triformate salt or solvate

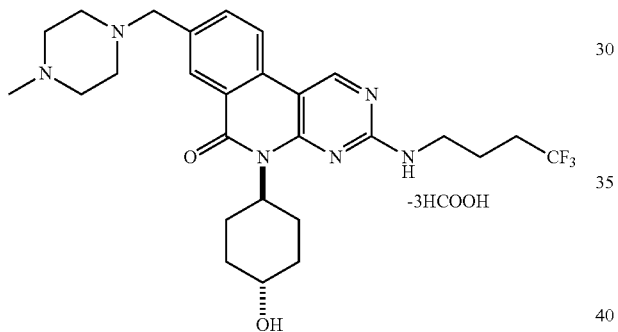

$^1$H NMR (300 MHz, Methanol-d$_4$) δ 9.13 (s, 1H), 8.46 (br s, 1H), 8.25 (s, 1H), 8.20 (d, J=7.8 Hz, 1H), 7.74 (d, J=7.8 Hz, 1H), 5.53 (br s, 1H), 3.71 (s, 3H), 3.55 (t, J=6.9 Hz, 2H), 3.29 (br s, 2H), 2.93 (br s, 6H), 2.78-2.63 (m, 4H), 2.60 (s, 2H), 2.33-2.24 (m, 2H), 2.12-2.08 (m, 2H), 1.95-1.93 (m, 2H), 1.72-1.68 (m, 2H), 1.54-1.46 (m, 2H). LCMS: Purity 99%, MS (m/e) 533 (MH$^+$-3HCOOH).

trans-3-((2-Cyclopropylethyl)amino)-5-(4-hydroxycyclohexyl)-8-((4-methylpiperazin-1-yl)methyl)pyrimido[4,5-c]isoquinolin-6(5H)-one

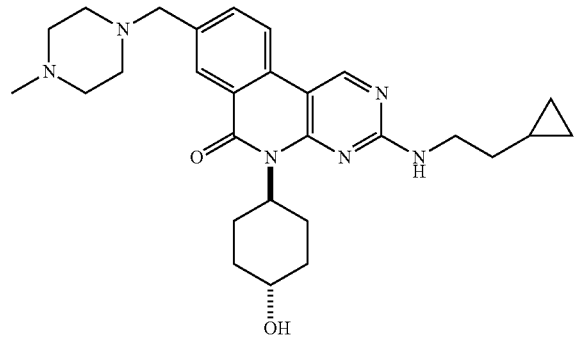

$^1$H NMR (400 MHz, Methanol-d$_4$) δ 9.08 (s, 1H), 8.22 (s, 1H), 8.15 (d, J=8.3 Hz, 1H), 7.71 (d, J=8.3 Hz, 1H), 5.57 (br s, 1H), 3.71 (dq, J=11.0, 5.7, 4.6 Hz, 1H), 3.63 (s, 2H), 3.56 (t, J=7.3 Hz, 2H), 2.91 (br s, 2H), 2.51 (br s, 8H), 2.27 (s, 3H), 2.10 (d, J=11.2 Hz, 2H), 1.69 (d, J=12.2 Hz, 2H), 1.62-1.42 (overlapped m, 4H), 0.79 (app dq, J=14.4, 7.4 Hz, 1H), 0.49 (app d, J=8.2 Hz, 2H), 0.12 (app d, J=4.9 Hz, 2H). LCMS: Purity 99%, MS (m/e) 491 (MH$^+$).

trans-3-((2-Cyclopropylethyl)amino)-5-(4-hydroxycyclohexyl)-8-(morpholinomethyl)pyrimido[4,5-c]isoquinolin-6(5H)-one

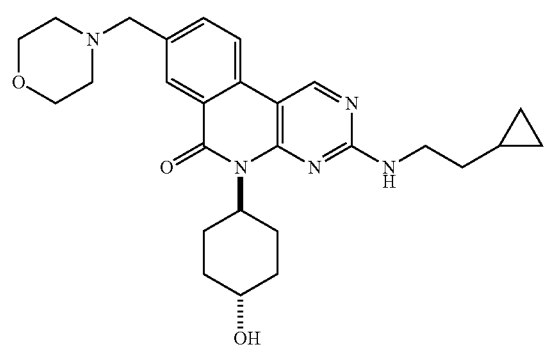

LCMS: Purity 99%, MS (m/e) 478 (MH$^+$).

trans-3-((2-Cyclopropylethyl)amino)-5-(4-hydroxycyclohexyl)pyrimido[4,5-c]isoquinolin-6(5H)-one

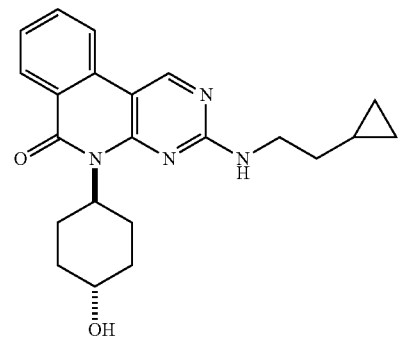

$^1$H NMR (400 MHz, DMSO-d$_6$) δ 9.22 (s, 1H), 8.29 (d, J=8.1 Hz, 1H), 8.18 (d, J=7.8 Hz, 1H), 7.72 (t, J=8.2 Hz, 1H), 7.55 (br s, 1H), 7.45 (t, J=7.6 Hz, 1H), 5.39 (br s, 1H), 4.64 (d, J=4.1 Hz, 1H), 3.53 (br s, 1H), 3.44 (q, J=6.4 Hz, 2H), 2.77 (br s, 2H), 1.96 (d, J=10.1 Hz, 2H), 1.58 (d, J=10.7 Hz, 2H), 1.48 (q, J=7.2 Hz, 2H), 1.33 (q, J=10.7 Hz, 2H), 0.82-0.67 (m, 1H), 0.42 (q, J=4.8 Hz, 2H), 0.07 (dt, J=5.0, 2.6 Hz, 2H). LCMS: Purity 97%, MS (m/e) 379 (MH$^+$).

225 trans-3-((Cyclopropylmethyl)amino)-5-(4-hydroxy-4-methylcyclohexyl)-8-((4-methylpiperazin-1-yl)methyl)pyrimido[4,5-c]isoquinolin-6(5H)-one

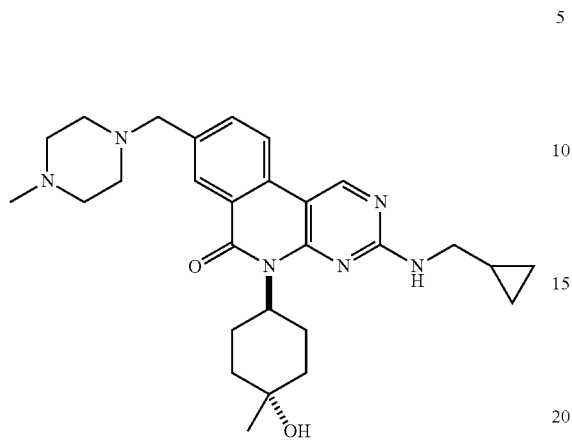

$^1$H NMR (400 MHz, Methanol-d$_4$) δ 9.08 (s, 1H), 8.21 (s, 1H), 8.14 (d, J=8.4 Hz, 1H), 7.71 (d, J=8.3 Hz, 1H), 5.63 (br s, 1H), 3.63 (s, 2H), 3.35 (d, J=6.7 Hz, 2H), 2.89 (app qt, J=13.0 Hz, 2H), 2.51 (br s, 8H), 2.27 (s, 3H), 1.82 (d, J=12.7 Hz, 2H), 1.70 (d, J=12.8 Hz, 2H), 1.60 (d, J=12.8 Hz, 2H), 1.44 (s, 3H), 1.17 (tt, J=13.8, 7.0 Hz, 1H), 0.53 (dt, J=7.5, 4.9 Hz, 2H), 0.30 (d, J=4.5 Hz, 2H). LCMS: Purity 99%, MS (m/e) 491 (MH$^+$).

trans-3-((Cyclopropylmethyl)amino)-5-(4-hydroxy-4-methylcyclohexyl)pyrimido[4,5-c]isoquinolin-6(5H)-one

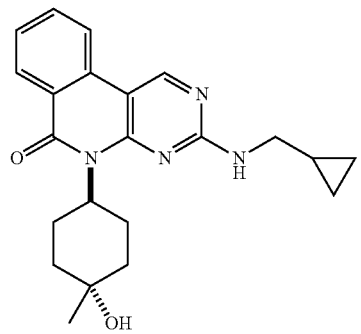

$^1$H NMR (400 MHz, DMSO-d$_6$) δ 9.25 (s, 1H), 8.30 (d, J=8.1 Hz, 1H), 8.19 (d, J=8.0 Hz, 1H), 7.81 (br s, 1H), 7.73 (t, J=7.6 Hz, 1H), 7.46 (t, J=7.9 Hz, 1H), 5.46 (br s, 1H), 4.41 (s, 1H), 3.26 (t, J=6.4 Hz, 2H), 2.75 (app br s, 2H), 1.68 (d, J=12.4 Hz, 2H), 1.56-1.48 (m, 4H), 1.30 (s, 3H), 1.12-1.08 (app m, 1H), 0.44 (app q, J=5.6 Hz, 2H), 0.24 (app q, J=5.1 Hz, 2H).). LCMS: Purity 99%, MS (m/e) 379 (MH$^+$).

226 trans-3-((2-Cyclopropylethyl)amino)-5-(4-hydroxy-4-methylcyclohexyl)-8-((4-methylpiperazin-1-yl)methyl)pyrimido[4,5-c]isoquinolin-6(5H)-one

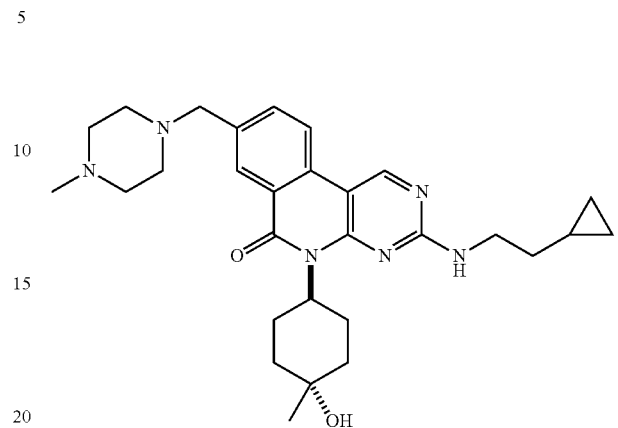

$^1$H NMR (400 MHz, DMSO-d$_6$) δ 9.19 (s, 1H), 8.23 (d, J=8.4 Hz, 1H), 8.08 (s, 1H), 7.66 (br s, 0.7H), 7.62 (d, J=8.4 Hz, 1H), 7.41 (br s, 0.3H), 5.45 (br s, 1H), 4.39 (s, 1H), 3.52 (s, 2H), 3.42 (q, J=6.3 Hz, 2H), 3.30-3.24 (m, 1H), 2.74 (app d, J=11.6 Hz, 2H), 2.35 (s, 3H), 2.30 (s, 3H), 2.11 (s, 3H), 1.66 (d, J=10.0 Hz, 2H), 1.58-1.43 (m, 6H), 1.29 (s, 3H), 0.72 (td, J=13.7, 13.2, 5.8 Hz, 1H), 0.39 (app dtd, J=7.7, 5.6, 3.1 Hz, 2H), 0.05 (app d, J=4.6 Hz, 2H). LCMS: Purity 99%, MS (m/e) 505 (MH$^+$).

trans-3-((2-Cyclopropylethyl)amino)-5-(4-hydroxy-4-methylcyclohexyl)pyrimido[4,5-c]isoquinolin-6(5H)-one

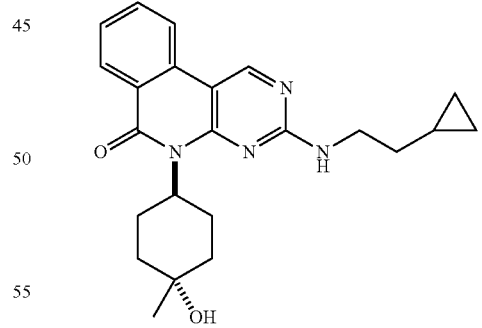

$^1$H NMR (400 MHz, DMSO-d$_6$) δ 9.23 (s, 1H), 8.29 (d, J=8.1 Hz, 1H), 8.19 (d, J=8.0 Hz, 1H), 7.73 (overlapped t, J=7.6 Hz, 2H), 7.45 (t, J=7.6 Hz, 1H), 5.46 (br s, 1H), 4.41 (s, 1H), 3.44 (q, J=6.4 Hz, 2H), 2.84-2.71 (m, 2H), 1.68 (app d, J=10.6 Hz, 2H), 1.59-1.43 (m, 6H), 1.30 (s, 3H), 0.80-0.68 (m, 1H), 0.45-0.36 (m, 2H), 0.06 (q, J=5.2 Hz, 2H). LCMS: Purity 95%, MS (m/e) 393 (MH$^+$).

227 trans-3-((Cyclopropylmethyl)amino)-5-(4-hydroxy-cyclohexyl)-8-((4-isopropylpiperazin-1-yl)methyl)pyrimido[4,5-c]isoquinolin-6(5H)-one

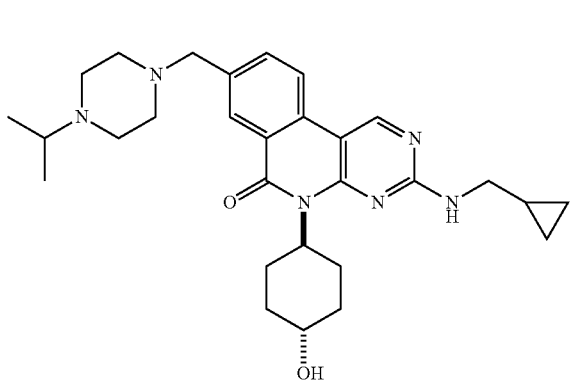

$^1$H NMR (400 MHz, Methanol-$d_4$) δ 9.09 (d, J=1.8 Hz, 1H), 8.23 (s, 1H), 8.16 (d, J=8.3 Hz, 1H), 7.72 (d, J=8.3 Hz, 1H), 5.57 (br s, 1H), 3.71 (tt, J=10.2, 4.2 Hz, 1H), 3.63 (s, 2H), 3.35 (d, J=6.5 Hz, 2H), 2.90 (br s, 2H), 2.67-2.55 (m, 9H), 2.10 (d, J=12.4 Hz, 2H), 1.69 (d, J=12.4 Hz, 2H), 1.48 (q, J=12.4 Hz, 2H), 1.25-1.14 (m, 1H), 1.07 (dd, J=6.6, 1.9 Hz, 6H), 0.54 (app q, J=5.5, 4.8 Hz, 2H), 0.31 (app q, J=4.8 Hz, 2H). LCMS: Purity 97%, MS (m/e) 505 (MH$^+$).

trans-3-((Cyclopropylmethyl)amino)-5-(4-hydroxy-4-methylcyclohexyl)-8-((4-isopropylpiperazin-1-yl)methyl)pyrimido[4,5-c]isoquinolin-6(5H)-one

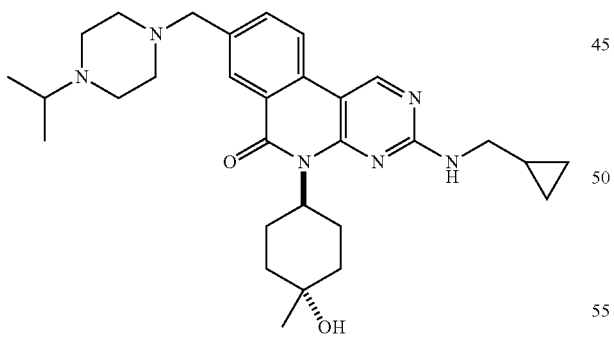

$^1$H NMR (400 MHz, Methanol-$d_4$) δ 9.09 (s, 1H), 8.22 (s, 1H), 8.15 (d, J=8.1 Hz, 1H), 7.72 (d, J=8.3 Hz, 1H), 5.63 (s, 1H), 3.63 (s, 2H), 3.35 (d, J=6.5 Hz, 2H), 2.89 (app m, 2H), 2.69-2.57 (m, 9H), 1.82 (d, J=12.3 Hz, 2H), 1.75-1.57 (m, 4H), 1.44 (s, 3H), 1.25-1.14 (app m, 1H), 1.06 (d, J=6.5 Hz, 6H), 0.54 (app q, J=5.5, 4.8 Hz, 2H), 0.30 (app q, J=5.0 Hz, 2H). LCMS: Purity 98%, MS (m/e) 519 (MH$^+$).

228 trans-3-((2-Cyclopropylethyl)amino)-5-(4-hydroxy-4-methylcyclohexyl)-8-((4-isopropylpiperazin-1-yl)methyl)pyrimido[4,5-c]isoquinolin-6(5H)-one

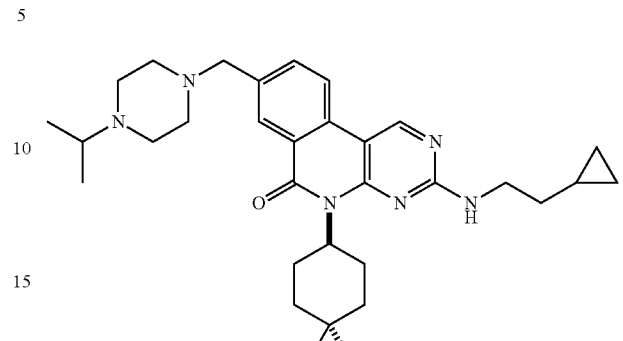

LCMS: Purity 97%, MS (m/e) 533 (MH$^+$).

trans-3-((Cyclobutylmethyl)amino)-5-(4-hydroxycyclohexyl)-8-((4-isopropylpiperazin-1-yl)methyl)pyrimido[4,5-c]isoquinolin-6(5H)-one

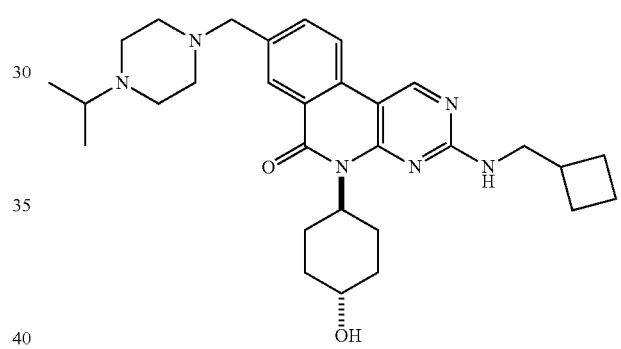

LCMS: Purity 99%, MS (m/e) 519 (MH$^+$).

trans-3-((Cyclobutylmethyl)amino)-5-(4-hydroxy-4-methylcyclohexyl)-8-((4-methylpiperazin-1-yl)methyl)pyrimido[4,5-c]isoquinolin-6(5H)-one

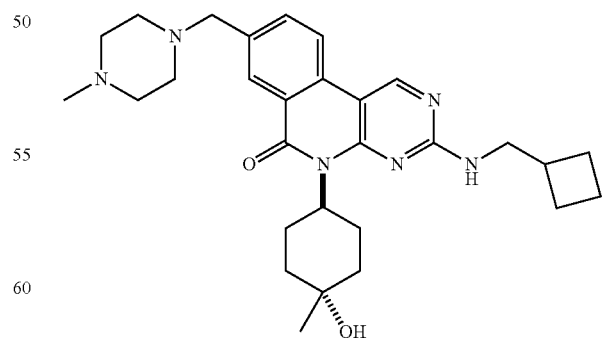

$^1$H NMR (400 MHz, DMSO-$d_6$) δ 9.19 (s, 1H), 8.23 (d, J=8.3 Hz, 1H), 8.08 (s, 1H), 7.72 (br s, 0.7H), 7.62 (d, J=8.3 Hz, 1H), 7.47 (br s, 0.3H), 5.45 (br s, 1H), 4.40 (s, 1H), 3.52 (s, 2H), 3.40 (t, J=6.4 Hz, 2H), 3.27 (app d, J=2.7 Hz, 1H), 2.72-2.56 (m, 4H), 2.35 (br s, 3H), 2.30 (br s, 3H), 2.11 (s, 3H), 2.04-1.93 (m, 2H), 1.89-1.77 (m, 2H), 1.76-1.60 (m, 4H), 1.57-1.46 (m, 4H), 1.28 (s, 3H). LCMS: Purity 99%, MS (m/e) 505 (MH+).

trans-3-((Cyclobutylmethyl)amino)-5-(4-hydroxy-4-methylcyclohexyl)pyrimido[4,5-c]isoquinolin-6(5H)-one

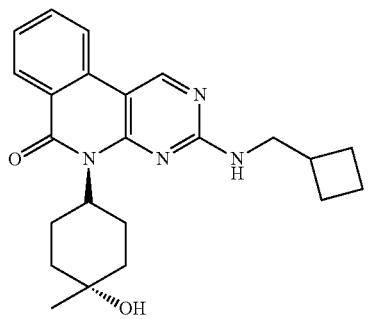

$^1$H NMR (400 MHz, DMSO-d$_6$) δ 9.23 (s, 1H), 8.29 (d, J=8.2 Hz, 1H), 8.19 (d, J=7.9 Hz, 1H), 7.74 (br s, 1H), 7.72 (t, J=7.6 Hz, 1H), 7.45 (t, J=7.6 Hz, 1H), 5.46 (br s, 1H), 4.42 (s, 1H), 3.42 (t, J=6.5 Hz, 2H), 2.74 (app m, 2H), 2.60 (p, J=7.3 Hz, 1H), 2.07-1.94 (m, 2H), 1.84 (dt, J=14.1, 6.7 Hz, 2H), 1.80-1.70 (m, 4H), 1.56-1.50 (m, 4H), 1.29 (s, 3H). LCMS: Purity 95%, MS (m/e) 393 (MH+).

trans-3-((Cyclopropylmethyl)amino)-5-(4-hydroxycyclohexyl)-8-((4-(pyridin-4-yl)piperazin-1-yl)methyl)pyrimido[4,5-c]isoquinolin-6(5H)-one

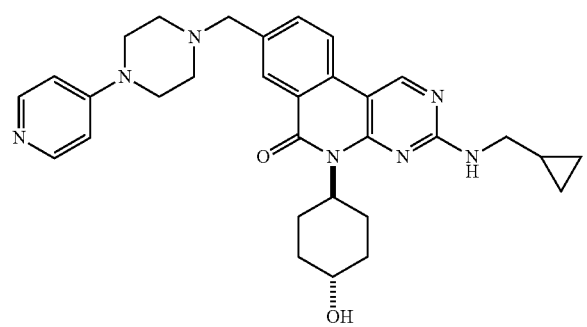

$^1$H NMR (400 MHz, Methanol-d$_4$) δ 9.10 (s, 1H), 8.26 (d, J=1.3 Hz, 1H), 8.17 (d, J=8.3 Hz, 1H), 8.09 (dd, J=5.2, 1.7 Hz, 2H), 7.76 (dd, J=8.3, 1.9 Hz, 1H), 6.82 (dd, J=5.2, 1.7 Hz, 2H), 5.58 (br s, 1H), 3.75-3.71 (m, 1H), 3.68 (s, 2H), 3.41 (app t, J=5.0 Hz, 4H), 3.38-3.33 (m, 2H), 2.92 (br s, 2H), 2.61 (t, J=5.1 Hz, 4H), 2.14-2.04 (m, 2H), 1.70 (d, J=11.3 Hz, 2H), 1.56-1.39 (m, 2H), 1.22-1.12 (m, 1H), 0.59-0.44 (m, 2H), 0.31 (app q, J=4.7 Hz, 2H). LCMS: Purity 98%, MS (m/e) 540 (MH+).

trans-3-((Cyclopropylmethyl)amino)-5-(4-hydroxycyclohexyl)-8-((4-(oxetan-3-yl)piperazin-1-yl)methyl)pyrimido[4,5-c]isoquinolin-6(5H)-one

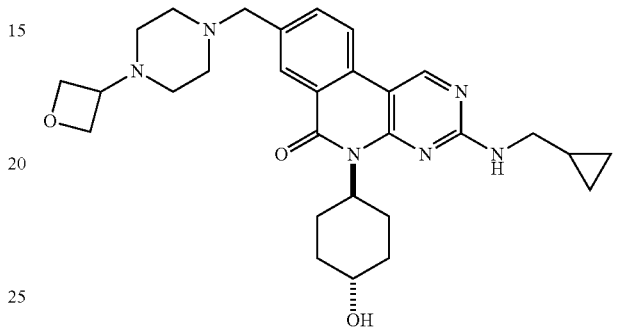

$^1$H NMR (400 MHz, DMSO-d$_6$) δ 9.20 (s, 1H), 8.23 (d, J=8.4 Hz, 1H), 8.08 (s, 1H), 7.77 (s, 1H), 7.63 (d, J=8.3 Hz, 1H), 5.37 (br s, 1H), 4.63 (s, 1H), 4.48 (t, J=6.5 Hz, 2H), 4.37 (t, J=6.5 Hz, 2H), 3.55 (s, 2H), 3.41-3.33 (m, 2H), 3.25-3.22 (app m, 2H), 2.76 (br s, 2H), 2.39 (br s, 4H), 2.24 (br s, 4H), 1.94 (app d, J=13.5 Hz, 2H), 1.54 (app s, 2H), 1.30 (q, J=12.1, 11.3 Hz, 2H), 1.15-1.15 (m, 1H), 0.44 (d, J=7.8 Hz, 2H), 0.23 (app d, J=5.0 Hz, 2H). LCMS: Purity 99%, MS (m/e) 519 (MH+).

trans-3-((Cyclopropylmethyl)amino)-5-(4-hydroxy-4-methylcyclohexyl)-8-((4-(oxetan-3-yl)piperazin-1-yl)methyl)pyrimido[4,5-c]isoquinolin-6(5H)-one

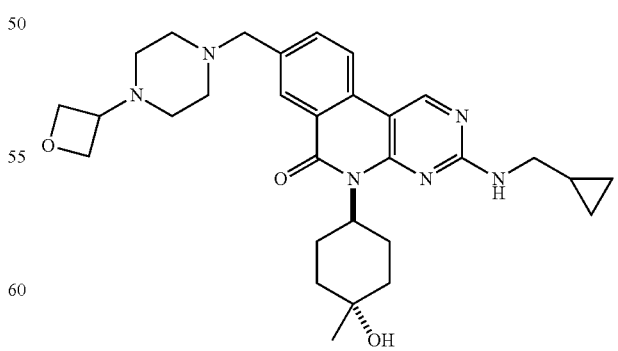

LCMS: Purity 99%, MS (m/e) 533 (MH+).

231 trans-3-((Cyclopropylmethyl)amino)-5-(4-hydroxy-cyclohexyl)-8-((4-(pyrrolidin-1-yl)piperidin-1-yl)methyl)pyrimido[4,5-c]isoquinolin-6(5H)-one

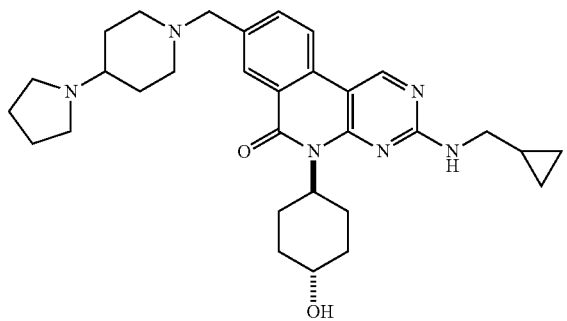

¹H NMR (400 MHz, Methanol-d₄) δ 9.10 (s, 1H), 8.20 (s, 1H), 8.16 (d, J=8.3 Hz, 1H) 7.73 (d, J=8.3 Hz, 1H), 5.56 (br s, 1H), 3.72 (m, 1H), 3.60 (s, 2H), 3.35 (d, J=6.8 Hz, 2H), 2.92 (d, J=11.2 Hz, 4H), 2.61 (s, 4H), 2.12-2.01 (m, 5H), 1.93 (d, J=12.3 Hz, 2H), 1.79 (s, 4H), 1.69 (d, J=11.3 Hz, 2H), 1.60-1.43 (app m, 4H), 1.18 (br s, 1H), 0.58-0.49 (m, 2H), 0.31 (app d, J=5.1 Hz, 2H). LCMS: Purity 97%, MS (m/e) 531 (MH⁺).

trans-3-((Cyclopropylmethyl)amino)-5-(4-hydroxy-4-methylcyclohexyl)-8-((4-(pyrrolidin-1-yl)piperidin-1-yl)methyl)pyrimido[4,5-c]isoquinolin-6(5H)-one

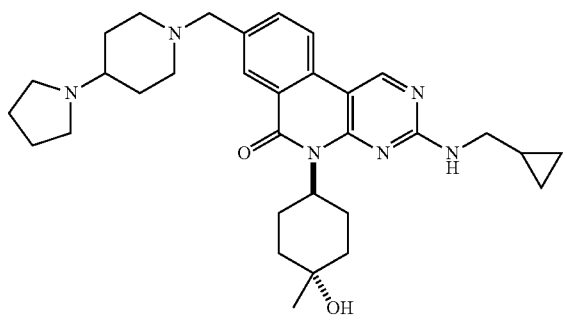

LCMS: Purity 98%, MS (m/e) 545 (MH⁺).

trans-3-((Cyclopropylmethyl)amino)-8-((5,6-dihydro-[1,2,4]triazolo[1,5-a]pyrazin-7(8H)-yl)methyl)-5-(4-hydroxycyclohexyl)pyrimido[4,5-c]isoquinolin-6(5H)-one

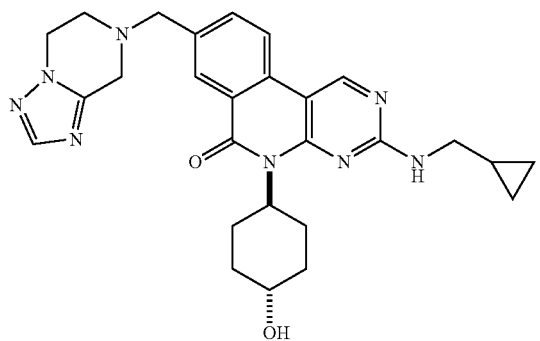

232

¹H NMR (400 MHz, DMSO-d₆) δ 9.22 (s, 1H), 8.28 (d, J=8.4 Hz, 1H), 8.15 (s, 1H), 7.87 (s, 1H), 7.87 (br s, 0.6H), 7.72 (d, J=8.2 Hz, 1H), 7.64 (br s, 0.3H), 5.37 (br s, 1H), 4.63 (s, 1H), 4.09 (t, J=4.9 Hz, 2H), 4.00 (tt, J=1.6, 0.9 Hz, 1H), 3.85 (s, 2H), 3.70 (s, 2H), 3.50 (br s, 1H), 3.30-3.22 (m, 2H), 2.96 (t, J=5.6 Hz, 2H), 2.76 (br s, 1H), 1.94 (d, J=12.7 Hz, 2H), 1.56 (app d, J=11.1 Hz, 2H), 1.30 (q, J=11.2 Hz, 2H), 1.10 (m, 1H), 0.44 (d, J=7.8 Hz, 2H), 0.24 (d, J=4.9 Hz, 2H). LCMS: Purity 97%, MS (m/e) 501 (MH⁺).

trans-3-((Cyclopropylmethyl)amino)-5-(4-hydroxycyclohexyl)-8-((4-(2,2,2-trifluoroethyl)piperazin-1-yl)methyl)pyrimido[4,5-c]isoquinolin-6(5H)-one

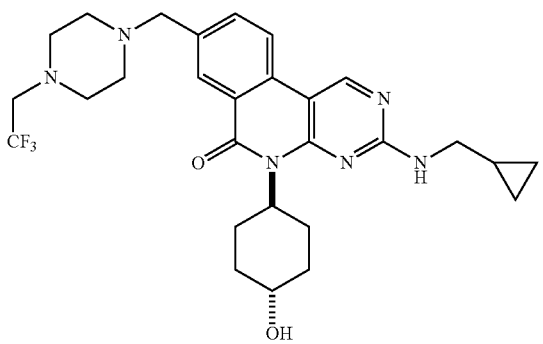

¹H NMR (400 MHz, DMSO-d₆) δ 9.20 (s, 1H), 8.23 (d, J=8.3 Hz, 1H), 8.08 (s, 1H), 7.77 (s, 1H), 7.62 (d, J=8.2 Hz, 1H), 5.38 (s, 1H), 4.63 (s, 1H), 3.54 (app s, 3H), 3.32-3.20 (m, 2H), 3.11 (q, J=10.4 Hz, 2H), 2.76 (br s, 2H), 2.60 (s, 4H), 2.37 (s, 4H), 1.94 (app d, J=9.7 Hz, 2H), 1.55 (app d, J=8.6 Hz, 2H), 1.30 (q, J=11.8 Hz, 2H), 1.10 (app br s, 1H), 0.44 (app d, J=7.8 Hz, 2H), 0.24 (app d, J=4.4 Hz, 2H). ¹⁹F NMR (376 MHz, DMSO-d₆) δ −67.84 (t, J=10.1 Hz). LCMS: Purity 98%, MS (m/e) 545 (MH⁺).

trans-(3-(butylamino)-8-((4-methylpiperazin-1-yl)methyl)-6-oxopyrimido[4,5-c]isoquinolin-5(6H)-yl)cyclohexane-1-carbonitrile tris trifluoroacetic acid salt or solvate

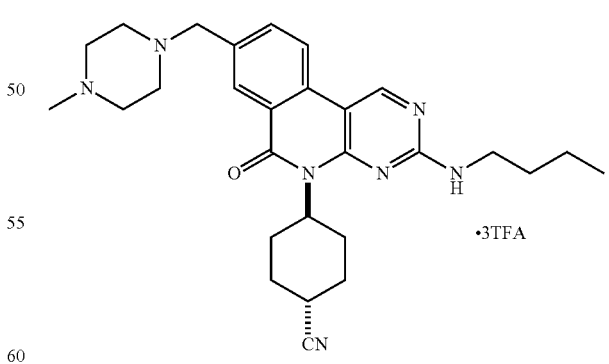

¹H NMR (300 MHz, Methanol-d₄) δ 9.12 (s, 1H), 8.29 (s, 1H), 8.20 (d, J=8.1 Hz, 1H), 7.75 (d, J=8.1 Hz, 1H), 5.52 (br s, 1H), 3.81 (s, 2H), 3.51 (br s, 2H), 3.36-3.24 (m, 5H), 2.89 (s, 3H), 2.85-2.65 (m, 6H), 2.32-2.29 (m, 2H), 1.83-1.68 (m, 6H), 1.52-1.45 (m, 2H), 1.02 (t, J=7.5 Hz, 3H). LCMS: Purity 98%, MS (m/e) 488 (MH⁺-3TFA).

233 trans-5-(4-hydroxycyclohexyl)-3-(isopentylamino)-
8-((4-methylpiperazin-1-yl)methyl)pyrimido[4,5-c]
isoquinolin-6(5H)-one triformate salt or solvate

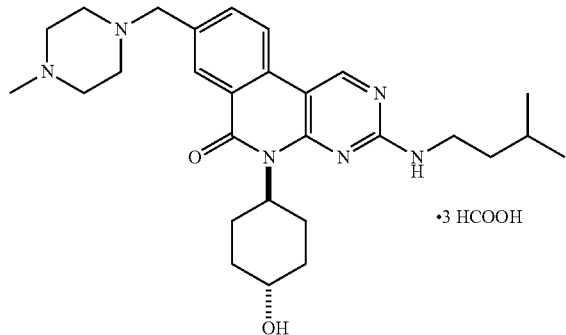

LCMS: Purity 99%, MS (m/e) 493 (MH⁺-3 HCOOH).

trans-3-((Cyclopropylmethyl)amino)-8-((4-(2,2-dif-
luoroethyl)piperazin-1-yl)methyl)-5-(4-hydroxycy-
clohexyl)pyrimido[4,5-c]isoquinolin-6(5H)-one

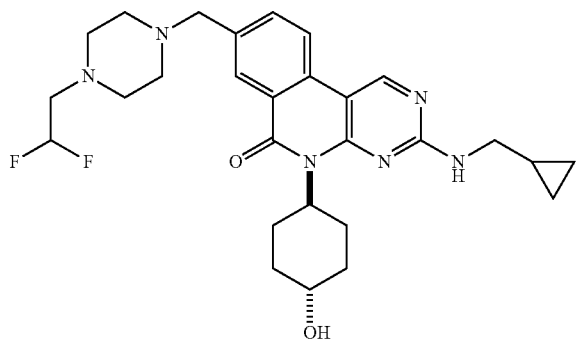

LCMS: Purity 98%, MS (m/e) 527 (MH⁺).

trans-3-((Cyclopropylmethyl)amino)-5-(4-hydroxy-
cyclohexyl)-8-(morpholinomethyl)pyrimido[4,5-c]
isoquinolin-6(5H)-one

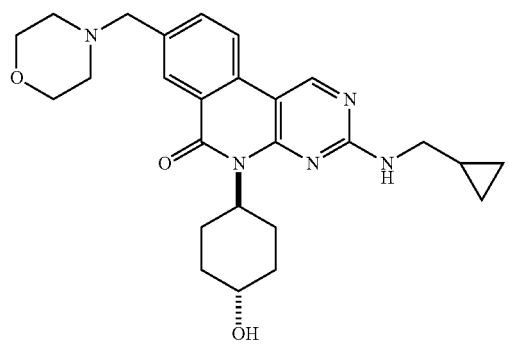

LCMS: Purity 97%, MS (m/e) 464 (MH⁺).

234 trans-3-((Cyclopropylmethyl)amino)-5-(4-hydroxy-
4-methylcyclohexyl)-8-(morpholinomethyl)pyrimido
[4,5-c]isoquinolin-6(5H)-one

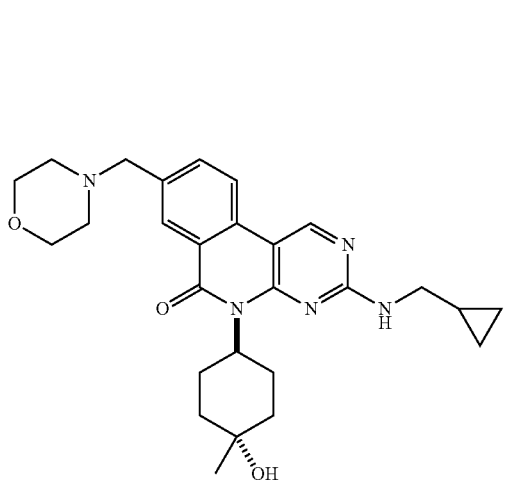

$^1$H NMR (400 MHz, Methanol-$d_4$) δ 9.10 (s, 1H), 8.23 (s, 1H), 8.17 (d, J=8.4 Hz, 1H), 7.74 (dd, J=8.4, 1.8 Hz, 1H), 5.64 (br s, 1H), 3.70 (t, J=4.6 Hz, 4H), 3.63 (s, 2H), 3.36 (d, J=7.0 Hz, 2H), 2.90 (qt, J=11.9 Hz, 2H), 2.48 (t, J=4.6 Hz, 4H), 1.83 (d, J=12.2 Hz, 2H), 1.70 (td, J=13.1, 3.9 Hz, 2H), 1.62 (d, J=11.2 Hz, 2H), 1.45 (s, 3H), 1.25-1.15 (m, 1H), 0.59-0.49 (m, 2H), 0.31 (q, J=5.1 Hz, 2H). LCMS: Purity 99%, MS (m/e) 478 (MH⁺).

trans-3-((Cyclopropylmethyl)amino)-8-((S)-hexahy-
dropyrrolo[1,2-a]pyrazin-2(1H)-yl)methyl)-5-(4-
hydroxycyclohexyl)pyrimido[4,5-c]isoquinolin-6
(5H)-one

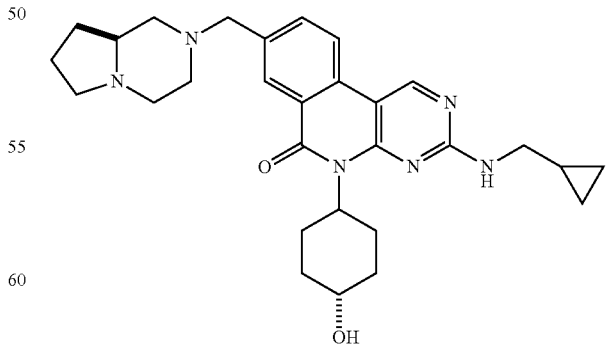

LCMS: Purity 97%, MS (m/e) 503 (MH⁺).

235 trans-3-((Cyclopropylmethyl)amino)-8-(((R)-hexa-hydropyrrolo[1,2-a]pyrazin-2(1H)-yl)methyl)-5-(4-hydroxycyclohexyl)pyrimido[4,5-c]isoquinolin-6(5H)-one

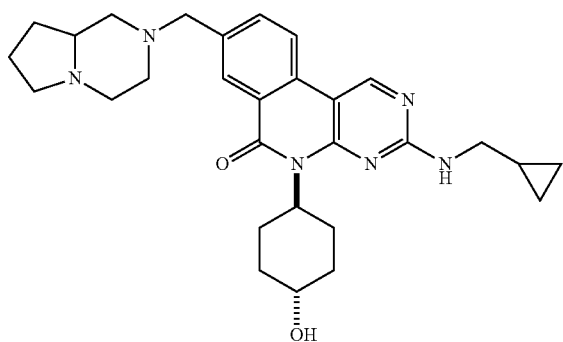

LCMS: Purity 96%, MS (m/e) 503 (MH$^+$).

trans-3-((Cyclopropylmethyl)amino)-8-((1,1-dioxi-dothiomorpholino)methyl)-5-(4-hydroxycyclohexyl)pyrimido[4,5-c]isoquinolin-6(5H)-one

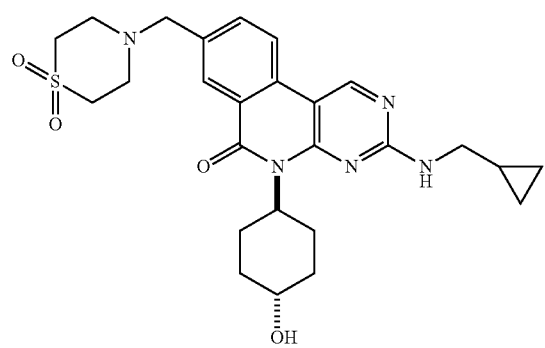

$^1$H NMR (400 MHz, DMSO-d$_6$) δ 9.23 (s, 1H), 8.27 (d, J=8.4 Hz, 1H), 8.12 (s, 1H), 7.80 (br s, 0.7H), 7.70 (dd, J=8.3, 1.9 Hz, 1H), 7.65 (br s, 0.3H), 5.38 (br s, 1H), 4.64 (s, 1H), 3.77 (s, 2H), 3.51 (br s, 1H), 3.27-3.23 (app m, 3H), 3.09 (t, J=4.6 Hz, 4H), 2.88 (app d, J=5.5 Hz, 4H), 2.76 (br s, 1H), 1.95 (d, J=10.8 Hz, 2H), 1.56 (d, J=9.9 Hz, 2H), 1.30 (q, J=11.0 Hz, 2H), 1.11 (app br s, 1H), 0.45 (d, J=7.6 Hz, 2H), 0.25 (q, J=5.1 Hz, 2H). LCMS: Purity 96%, MS (m/e) 512 (MH$^+$).

236 trans-Ethyl 1-((3-((Cyclopropylmethyl)amino)-5-(4-hydroxycyclohexyl)-6-oxo-5,6-dihydropyrimido[4,5-c]isoquinolin-8-yl)methyl)piperidine-4-carboxylate

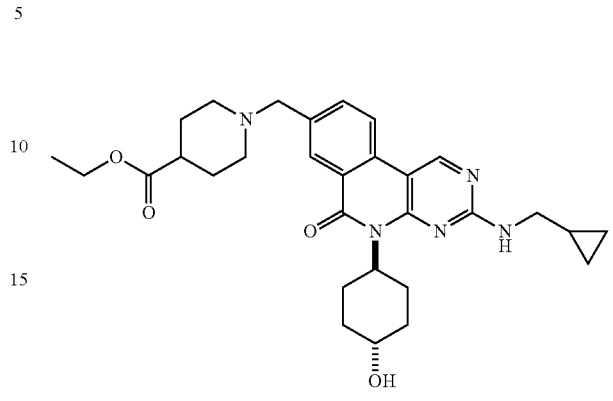

$^1$H NMR (400 MHz, Methanol-d$_4$) δ 9.11 (s, 1H), 8.22 (s, 1H), 8.17 (s, J=8.3 Hz, 1H), 7.73 (dd, J=8.3, 1.9 Hz, 1H), 5.57 (br s, 1H), 4.11 (q, J=7.1 Hz, 2H), 3.76-3.67 (m, 1H), 3.63 (s, 2H), 3.36 (d, J=6.8 Hz, 2H), 2.88 (app d, J=11.5 Hz, 4H), 2.34 (ddt, J=11.1, 8.1, 4.0 Hz, 1H), 2.13 (dd, J=19.4, 10.4 Hz, 4H), 1.89 (d, J=10.6 Hz, 2H), 1.80-1.66 (m, 4H), 1.56-1.41 (app m, 2H), 1.23 (t, J=7.1 Hz, 3H), 1.21-1.15 (m, 1H), 0.55 (app ddd, J=8.0, 5.8, 4.4 Hz, 2H), 0.32 (q, J=5.1 Hz, 2H). LCMS: Purity 96%, MS (m/e) 534 (MH$^+$).

trans-3-((Cyclopropylmethyl)amino)-5-(4-hydroxy-cyclohexyl)-8-(thiomorpholinomethyl)pyrimido[4,5-c]isoquinolin-6(5H)-one

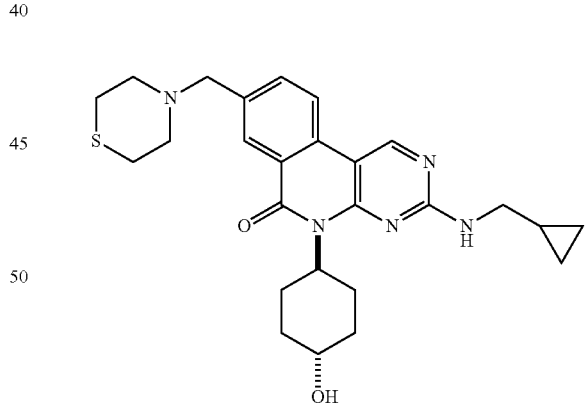

$^1$H NMR (400 MHz, DMSO-d$_6$) δ 9.21 (s, 1H), 8.24 (d, J=8.3 Hz, 1H), 8.08 (s, 1H), 7.78 (br s, 0.7H), 7.64 (app dd, J=8.2, 1.9 Hz, 1.3H), 5.39 (br s, 1H), 4.64 (s, 1H), 3.58 (s, 2H), 3.51 (br s, 1H), 3.27 (t, J=6.4 Hz, 2H), 2.76 (br s, 2H), 2.61 (app q, J=6.4 Hz, 8H), 1.95 (d, J=9.9 Hz, 2H), 1.56 (d, J=9.6 Hz, 2H), 1.30 (q, J=11.2 Hz, 2H), 1.11 (app br s, 1H), 0.44 (dd, J=7.7, 4.8 Hz, 2H), 0.24 (q, J=4.9 Hz, 2H). LCMS: Purity 97%, MS (m/e) 480 (MH$^+$).

237 trans-3-((Cyclopropylmethyl)amino)-8-(((R)-3,4-dimethylpiperazin-1-yl)methyl)-5-(4-hydroxycyclohexyl)pyrimido[4,5-c]isoquinolin-6(5H)-one

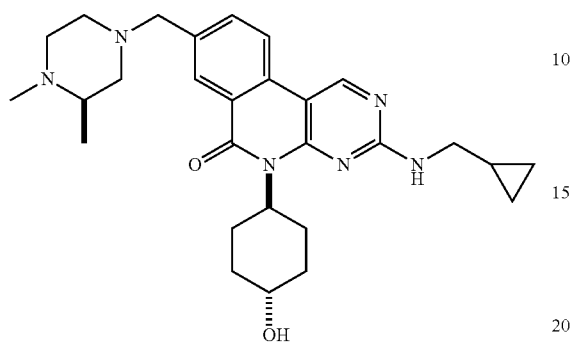

$^1$H NMR (400 MHz, Methanol-$d_4$) δ 9.10 (s, 1H), 8.23 (s, 1H), 8.17 (d, J=8.3 Hz, 1H), 7.73 (dd, J=8.3, 1.9 Hz, 1H), 5.57 (br s, 1H), 3.78-3.67 (m, 1H), 3.62 (s, 2H), 3.36 (d, J=6.7 Hz, 2H), 3.10-2.85 (br s, 2H), 2.83-2.71 (m, 3H), 2.42-2.22 (m, 6H), 2.10 (d, J=10.6 Hz, 2H), 1.94 (t, J=10.8 Hz, 1H), 1.70 (d, J=11.0 Hz, 2H), 1.51 (d, J=10.6 Hz, 2H), 1.11 (m, 1H), 1.04 (d, J=6.3 Hz, 3H), 0.54 (app ddd, J=8.0, 5.8, 4.4 Hz, 2H), 0.32 (q, J=4.9 Hz, 2H). LCMS: Purity 97%, MS (m/e) 491 (MH$^+$).

trans-5-(4-Hydroxycyclohexyl)-3-(isobutylamino)-8-((4-methylpiperazin-1-yl)methyl)pyrimido[4,5-c]isoquinolin-6(5H)-one

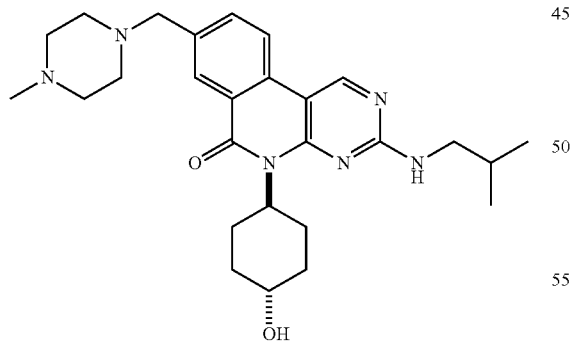

$^1$H NMR (300 MHz, Methanol-$d_4$) δ 9.09 (s, 1H), 8.22 (s, 1H), 8.16 (d, J=8.1 Hz, 1H), 7.72 (d, J=8.1 Hz, 1H), 5.53 (br s, 1H), 3.72 (br s, 1H), 3.64 (s, 2H), 3.29 (br s, 4H), 2.89 (br s, 2H), 2.52 (br s, 8H), 2.27 (s, 3H), 2.12-1.98 (m, 3H), 1.71-1.67 (m, 2H), 1.55-1.46 (m, 2H), 1.01 (d, J=6.6 Hz, 6H). LCMS: Purity 98%, MS (m/e) 479 (MH$^+$).

238

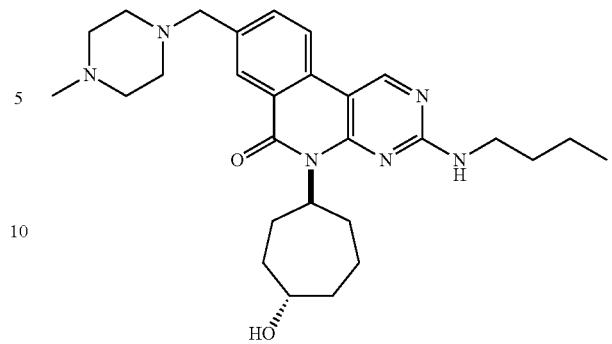

3-(Butylamino)-5-((1S,4S)-4-hydroxycycloheptyl)-8-((4-methylpiperazin-1-yl)methyl)pyrimido[4,5-c]isoquinolin-6(5H)-one LCMS: Purity 97%, MS (m/e) 492 (MH$^+$).

trans-8-((1,4-Diazabicyclo[3.2.2]nonan-4-yl)methyl)-3-((cyclopropylmethyl)amino)-5-(4-hydroxycyclohexyl)pyrimido[4,5-c]isoquinolin-6(5H)-one

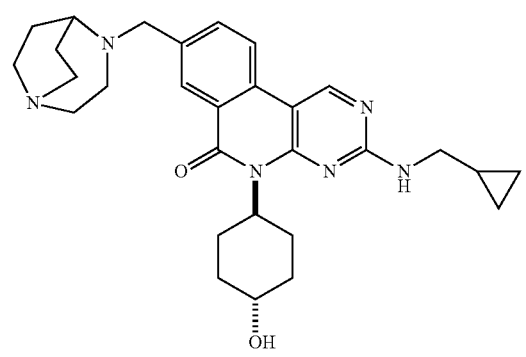

$^1$H NMR (400 MHz, Methanol-$d_4$) δ 9.09 (s, 1H), 8.24 (s, 1H), 8.15 (d, J=8.3 Hz, 1H), 7.77 (d, J=8.3 Hz, 1H), 5.57 (br s, 1H), 3.80 (s, 2H), 3.79-3.69 (app m, 2H), 3.35 (app d, J=8.5 Hz, 2H), 3.03-2.79 (m, 8H), 2.80 (t, J=5.6 Hz, 2H), 2.10 (d, J=11.2 Hz, 2H), 2.03-1.98 (m, 2H), 1.70 (d, J=11.3 Hz, 2H), 1.62 (tt, J=9.6, 5.1 Hz, 2H), 1.48 (qd, J=13.7, 3.3 Hz, 2H). 1.28-1.16 (m, 1H), 0.55 (app dt, J=7.5, 5.0 Hz, 2H), 0.31 (q, J=5.1 Hz, 2H). LCMS: Purity 98%, MS (m/e) 503 (MH$^+$).

trans-8-((4-(tert-butyl)piperazin-1-yl)methyl)-3-((cyclopropylmethyl)amino)-5-(4-hydroxycyclohexyl)pyrimido[4,5-c]isoquinolin-6(5H)-one

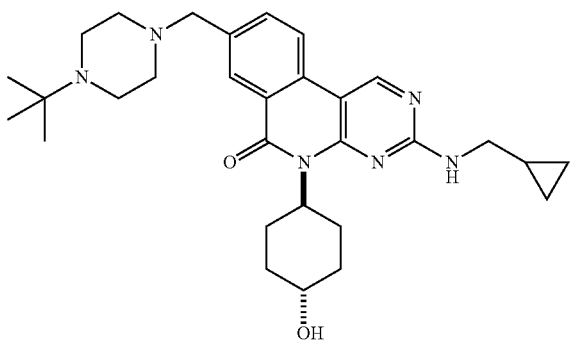

¹H NMR (400 MHz, Methanol-d₄) δ 9.10 (s, 1H), 8.23 (s, 1H), 8.17 (d, J=8.3 Hz, 1H), 7.73 (dd, J=8.3, 1.8 Hz, 1H), 5.58 (br s, 1H), 3.76-3.68 (m, 1H), 3.64 (s, 2H), 3.36 (d, J=6.8 Hz, 2H), 3.10-2.80 (br s, 2H), 2.67 (s, 4H), 2.55 (s, 4H), 2.10 (d, J=11.3 Hz, 2H), 1.70 (d, J=11.1 Hz, 2H), 1.49 (qd, J=13.7, 3.3 Hz, 2H), 1.09 (s, 9H), 0.54 (app dt, J=7.5, 5.0 Hz, 2H), 0.31 (q, J=4.9 Hz, 2H). LCMS: Purity 98%, MS (m/e) 519 (MH⁺).

5-((4-Aminocyclohexyl)methyl)-3-(butylamino)-8-((4-methylpiperazin-1-yl)methyl)pyrimido[4,5-c]isoquinolin-6(5H)-one

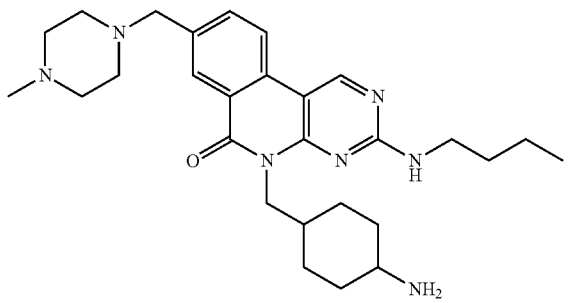 [SMILES: CCCCNc1ncc2c3ccc(CN4CCN(C)CC4)cc3c(=O)n(CC3CCC(N)CC3)c2n1]

tert-Butyl (4-((3-(butylamino)-8-((4-methylpiperazin-1-yl)methyl)-6-oxopyrimido[4,5-c]isoquinolin-5(6H)-yl)methyl)cyclohexyl)carbamate (70 mg, 0.118 mmol) was stirred in 4.0 N HCl in 1,4-dioxane (3 mL) and MeOH (2 mL) at room temperature. After 2 h, reaction mixure was concentrated to dryness, upon analyzing by LC/MS which indicated complete consumption of tert-butyl (4-((3-(butylamino)-8-((4-methylpiperazin-1-yl)methyl)-6-oxopyrimido[4,5-c]isoquinolin-5(6H)-yl)methyl)cyclohexyl)carbamate to desired 5-((4-aminocyclohexyl)methyl)-3-(butylamino)-8-((4-methylpiperazin-1-yl)methyl)pyrimido[4,5-c]isoquinolin-6(5H)-one, neutralized with aq. NaHCO₃, suction filtered and dried. Thus collected off-white solid (78 mg) upon heating in MeOH (7 mL), was polish filtered. The resulting off-white solid thus obtained after concentration of filtreate was heated in EA (7 mL), cooled to room temperature, filtered, washed with water on the funnel and dried to provide 5-((4-aminocyclohexyl)methyl)-3-(butylamino)-8-((4-methylpiperazin-1-yl)methyl)pyrimido[4,5-c]isoquinolin-6(5H)-one (38 mg) as a white solid. ¹H NMR (400 MHz, Methanol-d₄) δ 9.07 (s, 1H), 8.23 (s, 1H), 8.16 (d, J=8.4 Hz, 1H), 7.72 (d, J=8.4 Hz, 1H), 4.32 (d, J=7.2 Hz, 2H), 3.64 (s, 2H), 3.44 (t, J=7.2 Hz, 2H), 2.52-2.38 (m, 9H), 2.27 (d, J=1.8 Hz, 3H), 1.97 (app s, 1H), 1.87 (d, J=12.1 Hz, 2H), 1.73-1.61 (m, 4H), 1.46 (p, J=7.3 Hz, 2H), 1.24 (q, J=12.4 Hz, 2H), 1.05 (app q, J=12.7 Hz, 2H), 0.99 (t, J=7.3 Hz, 3H). LCMS: Purity 99%, MS (m/e) 492 (MH⁺).

5-((4-Aminocyclohexyl)methyl)-3-(butylamino)-8-(morpholinomethyl)pyrimido[4,5-c]isoquinolin-6(5H)-one

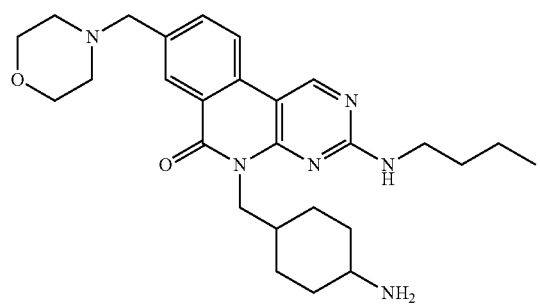 [SMILES: CCCCNc1ncc2c3ccc(CN4CCOCC4)cc3c(=O)n(CC3CCC(N)CC3)c2n1]

5-((4-Aminocyclohexyl)methyl)-3-(butylamino)-8-(morpholinomethyl)pyrimido[4,5-c]isoquinolin-6(5H)-one was prepared analogous to the preparation of 5-((4-aminocyclohexyl)methyl)-3-(butylamino)-8-((4-methylpiperazin-1-yl)methyl)pyrimido[4,5-c]isoquinolin-6(5H)-one from tert-butyl (4-((3-(butylamino)-8-(morpholinomethyl)-6-oxopyrimido[4,5-c]isoquinolin-5(6H)-yl)methyl)cyclohexyl)carbamate. LCMS: Purity 98%, MS (m/e) 479 (MH⁺).

trans-3-(Butylamino)-5-(4-hydroxycyclohexyl)-8-(piperazin-1-ylmethyl)pyrimido[4,5-c]isoquinolin-6(5H)-one

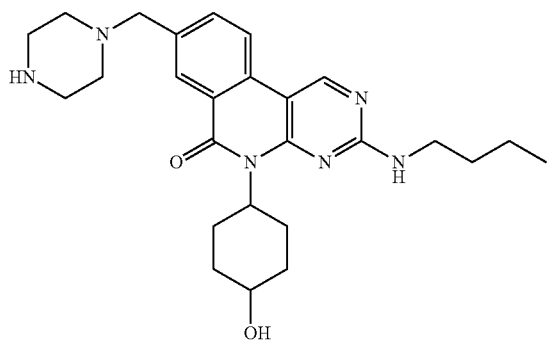 [SMILES: CCCCNc1ncc2c3ccc(CN4CCNCC4)cc3c(=O)n(C3CCC(O)CC3)c2n1]

Analogous to the preparation of trans-3-(butylamino)-5-(4-hydroxycyclohexyl)-8-((4-methylpiperazin-1-yl)methyl)pyrimido[4,5-c]isoquinolin-6(5H)-one, trans-tert-butyl 4-((3-(butylamino)-5-(4-hydroxycyclohexyl)-6-oxo-5,6-dihydropyrimido[4,5-c]isoquinolin-8-yl)methyl)piperazine-1-carboxylate was prepared and hydrolysed similar to the preparation of 5-((4-aminocyclohexyl)methyl)-3-(butylamino)-8-((4-methylpiperazin-1-yl)methyl)pyrimido[4,5-c]isoquinolin-6(5H)-one. The crude concentrated semi-solid obtained after concentration of reaction solution was dissolved in 7% 7N NH$_3$ MeOH/CH$_2$Cl$_2$ (16 mL), adsorbed on silica gel (4 g), dried, purified by flash chromatography [Combiflash Torrent® with RediSep® silica gel column 12 g and eluted with 30-100% 10% 7N NH$_3$ MeOH in CH$_2$Cl$_2$: CH$_2$Cl$_2$ solvent gradient]. Upon concentrating product fractions, the resulting solid (purity 98%) was heated in EtOAc (10 mL), cooled to room temperature, filtered and dried to provide trans-3-(butylamino)-5-(4-hydroxycyclohexyl)-8-(piperazin-1-ylmethyl)pyrimido[4,5-c]isoquinolin-6(5H)-one as a white solid. $^1$H NMR (400 MHz, DMSO-d$_6$) δ 9.19 (s, 1H), 8.23 (d, J=8.3 Hz, 1H), 8.08 (s, 1H), 7.70 (s, 0.7H), 7.63 (dd, J=8.3, 1.9 Hz, 1H), 7.51 (s, 0.3H), 5.38 (br s, 1H), 4.64 (s, 1H), 3.50 (app s, 3H), 3.39-3.27 (m, 3H), 2.76 (br s, 2H), 2.66 (t, J=4.9 Hz, 4H), 2.27 (s, 4H), 1.94 (app d, J=9.7 Hz, 2H), 1.56 (app dt, J=14.1, 6.6 Hz, 4H), 1.44-1.23 (m, 4H), 0.91 (t, J=7.3 Hz, 3H). LCMS: Purity 99%, MS (m/e) 465 (MH$^+$).

trans-4-((3-((Cyclopropylmethyl)amino)-5-(4-hydroxycyclohexyl)-6-oxo-5,6-dihydropyrimido[4,5-c]isoquinolin-8-yl)methyl)-1,4-diazabicyclo[3.2.2]nonane 1-oxide

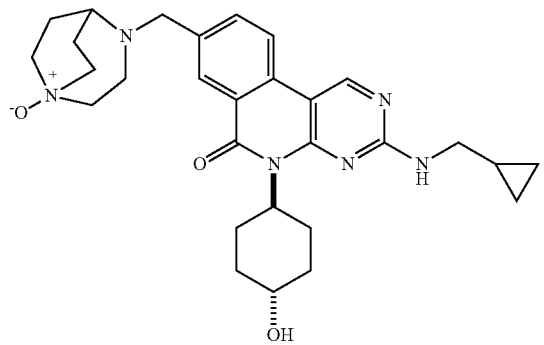

A microwave vial was charged with trans-3-(butylamino)-8-chloro-5-(4-hydroxycyclohexyl)pyrimido[4,5-c]isoquinolin-6(5H)-one (100 mg, 0.25 mmol), ((1,4-diazabicyclo[3.2.2]nonan-4-ium-4-yl)methyl)trifluoroborate (73 mg, 0.35 mmol), Cs$_2$CO$_3$ (245 mg, 0.74 mmol), SPhos-Pd-G2 (5 mg, 0.007 mmol), 1,4-dioxane (3 mL), water (0.3 mL) and a stirbar. After bubbling nitrogen through suspension for 3 min, reaction mixture was capped and heated in a microwave for 45 min at 150° C. Pale yellow heterogeneous reaction mixture was diluted with THF (3 mL) and filtered through Celite®. Upon rinsing microwave vial with additional amount of THF (2×5 mL), flitering through Celite®, homogeneous yellow filtrate was dried over MgSO$_4$, filtered and concentrated to dryness. The crude concentrated semi-solid was dissolved in 5% 7N NH$_3$ MeOH/CH$_2$Cl$_2$ (12 mL) and adsorbed on silica gel (4 g). The resulting material was dried by slow stream of house nitrogen and purified by flash chromatography [Combiflash Torrent® with RediSep® silica gel column 12 g and eluted with 30-50-100% 10% 7N NH$_3$ MeOH in CH$_2$Cl$_2$:CH$_2$Cl$_2$ solvent gradient. Major peak on chromatogram was identified by LC/MS as an oxidized product of trans-8-((1,4-diazabicyclo[3.2.2]nonan-4-yl)methyl)-3-((cyclopropylmethyl)amino)-5-(4-hydroxycyclohexyl)pyrimido[4,5-c]isoquinolin-6(5H)-one. The resulting white solid obtained after concentration of major peak fractions heated in EtOAc (9 mL), cooled to room temperature, filtered to provide trans-4-((3-((cyclopropylmethyl)amino)-5-(4-hydroxycyclohexyl)-6-oxo-5,6-dihydropyrimido[4,5-c]isoquinolin-8-yl)methyl)-1,4-diazabicyclo[3.2.2]nonane 1-oxide (62 mg, purity 99%). $^1$H NMR (400 MHz, Methanol-d$_4$) δ 9.10 (s, 1H), 8.27 (s, 1H), 8.16 (d, J=8.3 Hz, 1H), 7.76 (dd, J=8.3, 1.9 Hz, 1H), 5.58 (br s, 1H), 3.80 (s, 2H), 3.73-3.65 (m, 5H), 3.45-3.27 (m, 4H), 3.09 (t, J=5.6 Hz, 1H), 2.96 (app t, J=5.6 Hz, 4H), 2.37-2.30 (m, 2H), 2.11-2.02 (m, 4H), 1.69 (d, J=11.5 Hz, 2H), 1.55-1.41 (app m, 2H), 1.21-1.12 (m, 1H), 0.54 (ddd, J=8.0, 5.8, 4.4 Hz, 2H), 0.31 (q, J=5.1 Hz, 2H). LCMS: Purity 99%, MS (m/e) 519 (MH$^+$).

trans-3-((cyclopropylmethyl)amino)-5-(4-hydroxycyclohexyl)-8-((1-oxidothiomorpholino)methyl)pyrimido[4,5-c]isoquinolin-6(5H)-one

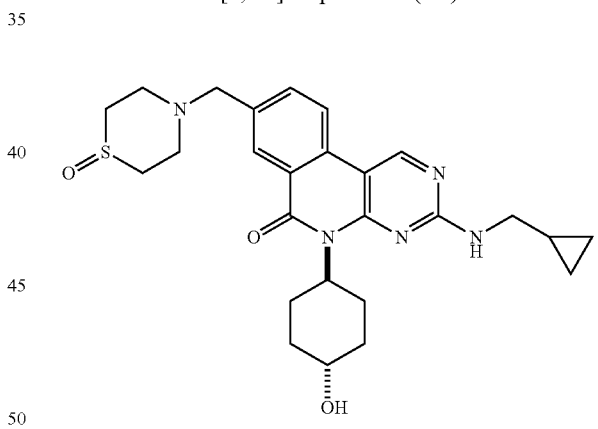

trans-3-((Cyclopropylmethyl)amino)-5-(4-hydroxycyclohexyl)-8-((1-oxidothiomorpholino)methyl)pyrimido[4,5-c]isoquinolin-6(5H)-one was obtained after following reaction and work-up procedures analogous to the preparation of trans-4-((3-((Cyclopropylmethyl)amino)-5-(4-hydroxycyclohexyl)-6-oxo-5,6-dihydropyrimido[4,5-c]isoquinolin-8-yl)methyl)-1,4-diazabicyclo[3.2.2]nonane 1-oxide. $^1$H NMR (400 MHz, DMSO-d$_6$) δ 9.22 (s, 1H), 8.26 (d, J=8.3 Hz, 1H), 8.12 (s, 1H), 7.79 (br s, 0.6H), 7.67 (dd, J=8.2, 1.9 Hz, 1.4H), 5.39 (br s, 1H), 4.64 (s, 1H), 3.66 (s, 2H), 3.50 (br s, 1H), 3.27-3.23 (m, 3H), 2.93-2.80 (m, 4H), 2.79-2.67 (m, 3H), 2.62 (app dd, J=9.6, 5.3 Hz, 2H), 1.95 (d, J=11.9 Hz, 2H), 1.57 (d, J=11.9 Hz, 2H), 1.30 (q, J=11.2 Hz, 2H), 1.11 (app br s, 1H), 0.48 (ddd, J=8.0, 5.8, 4.4 Hz, 2H), 0.25 (q, J=4.7 Hz, 2H). LCMS: Purity 99%, MS (m/e) 496 (MH$^+$).

trans-3-((Cyclopropylmethyl)amino)-5-(4-hydroxy-cyclohexyl)-8-(piperazin-1-ylmethyl)pyrimido[4,5-c]isoquinolin-6(5H)-one

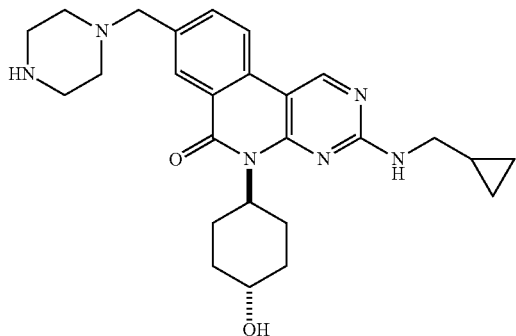

trans-tert-Butyl 4-((3-(cyclopropylamino)-5-(4-hydroxy-cyclohexyl)-6-oxo-5,6-dihydropyrimido[4,5-c]isoquinolin-8-yl)methyl)piperazine-1-carboxylate (170 mg), prepared in the similar manner to the preparation of trans-3-(butylamino)-5-(4-hydroxycyclohexyl)-8-((4-methylpiperazin-1-yl)methyl)pyrimido[4,5-c]isoquinolin-6(5H)-one, was stirred in conc. HCl (3 mL), THF (3 mL) and EtOH (3 mL) for 36 h. Upon removing volatiles from reaction solution, the concentrate was cooled in ice-bath, basified with solid $K_2CO_3$, warmed to room temperature, diluted with $CH_2Cl_2$ (75 mL) and sepearated the organic layer. Upon further extraction of aqueous layer with $CH_2Cl_2$ (75 mL×2), combined organic layers were stirred over anhydrous $Na_2SO_4$, filtered and concentrated. The crude viscous liquid was purified by flash chromatography [Combiflash Torrent® with RediSep® silica gel column 12 g and eluted with 50-100% 10% 7N $NH_3$ MeOH in $CH_2Cl_2:CH_2Cl_2$ solvent gradient]. Upon concentrating product fractions, the resulting white solid was heated in EtOAc (10 mL), cooled to room temperature, filtered and dried provide trans-3-((cyclopropylmethyl)amino)-5-(4-hydroxycyclohexyl)-8-(piperazin-1-ylmethyl)pyrimido[4,5-c]isoquinolin-6(5H)-one (120 mg). $^1$H NMR (400 MHz, DMSO-$d_6$) δ 9.21 (s, 1H), 8.24 (d, J=8.3 Hz, 1H), 8.08 (s, 1H), 7.77 (s, 0.7H), 7.64 (dd, J=8.3, 1.9 Hz, 1.3H), 5.39 (brs, 1H), 4.64 (s, 1H), 3.51 (app s, 3H), 3.25 (t, J=6.4 Hz, 2H), 2.77 (br s, 2H), 2.66 (t, J=4.8 Hz, 4H), 2.28 (s, 4H), 1.95 (d, J=10.9 Hz, 2H), 1.56 (d, J=10.6 Hz, 2H), 1.30 (q, J=11.2 Hz, 2H), 1.11 (m, 1H), 0.44 (ddd, J=8.0, 5.8, 4.4 Hz, 2H), 0.24 (q, J=4.9 Hz, 2H). LCMS: Purity 97%, MS (m/e) 463 (MH$^+$).

trans-4-(3-((Cyclopropylmethyl)amino)-8-((4-methylpiperazin-1-yl)methyl)-6-oxopyrimido[4,5-c]isoquinolin-5(6H)-yl)cyclohexyl carbamate

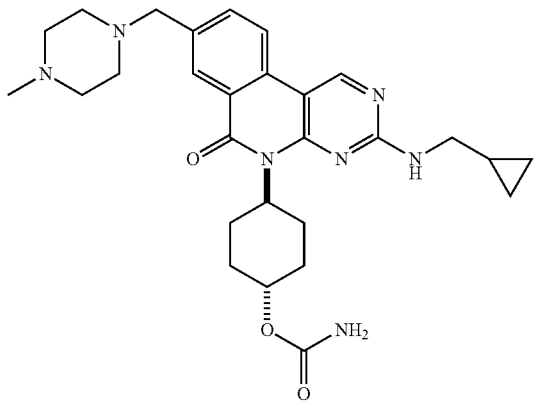

Trichloroacetyl isocyanate (25 µL, 40 mg, 0.21 m period of 3 min to a stirred heterogeneous solution of trans-3-((cyclopropylmethyl)amino)-5-(4-hydroxycyclohexyl)-8-((4-methylpiperazin-1-yl)methyl)pyrimido[4,5-c]isoquinolin-6(5H)-one (100 mg, 0.21 mmol) in anhydrous $CH_2Cl_2$ at −78° C. under argon. The resulting pale yellow homogeneous solution was stirred for 2 h and warmed to room temperature. LC/MS analysis after 2 h indicated complete consumption of trans-3-((cyclopropylmethyl)amino)-5-(4-hydroxycyclohexyl)-8-((4-methylpiperazin-1-yl)methyl)pyrimido[4,5-c]isoquinolin-6(5H)-one. At this stage, reaction mixture was quenched with MeOH (4 mL) and concentrated to dryness. The resulting solid was stirred in MeOH (6 mL) and $K_2CO_3$ (116 mg, 0.83 mmol) at room temperature. After 2 h, heterogeneous reaction mixture was concentrated to dryness, diluted with water (10 mL) and filtered. Thus collected white solid after drying was purified by flash chromatography [Combiflash Torrent® with RediSep® silica gel column 12 g and eluted with 30-70% 7% 7N $NH_3$ MeOH in $CH_2Cl_2:CH_2Cl_2$ solvent gradient] and obtained trans-4-(3-((cyclopropylmethyl)amino)-8-((4-methylpiperazin-1-yl)methyl)-6-oxopyrimido[4,5-c]isoquinolin-5(6H)-yl)cyclohexyl carbamate as a white solid. $^1$H NMR (400 MHz, DMSO-$d_6$) δ 9.22 (s, 1H), 8.25 (d, J=8.1 Hz, 1H), 8.09 (s, 1H), 7.81 (br s, 1H), 7.65 (dd, J=8.3, 1.9 Hz, 1H), 6.43 (br s, 2H), 5.42 (br s, 1H), 4.54 (br s, 1H), 4.00 (br s, 1H), 3.54 (s, 2H), 3.31-3.22 (m, 2H), 2.84 (br s, 2H), 2.36-2.31 (overlapped br s, 8H), 2.13 (s, 3H), 2.05 (app d, J=10.2 Hz, 2H), 1.64 (app s, 2H), 1.43 (app q, J=12.1 Hz, 2H), 1.16-1.07 (m, 1H), 0.45 (q, J=5.5 Hz, 2H), 0.25 (q, J=6.1, 5.6 Hz, 2H). LCMS: Purity 99%, MS (m/e) 520 (MH$^+$).

General procedure for the preparation of 3-((alkylamino)-8-((cycloaminomethyl)-5-4-alkyl)pyrimido[4,5-c]isoquinolin-6(5H)-one is described in the preparation of trans-3-(butylamino)-5-(4-hydroxycyclohexyl)-8-((4-methylpiperazin-1-yl)methyl)pyrimido[4,5-c]isoquinolin-6(5H)-one Preparation of aminomethyltrifluoroborates: (JOC 2008, 73, 2052-2057, JOC 2011, 76, 2762-2769). Aminomethyltrifluoroborates which are not available commerically were prepared according to literature procedure. Trifluoro((4-isopropylpiperazin-1-ium-1-yl)methyl)borate preparation describes reaction procedure and isolation of synthesized respective aminomethyltrifluoroborates represented below.

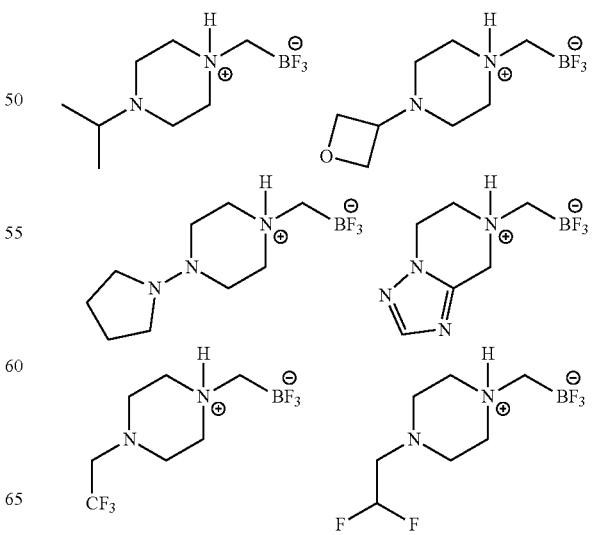

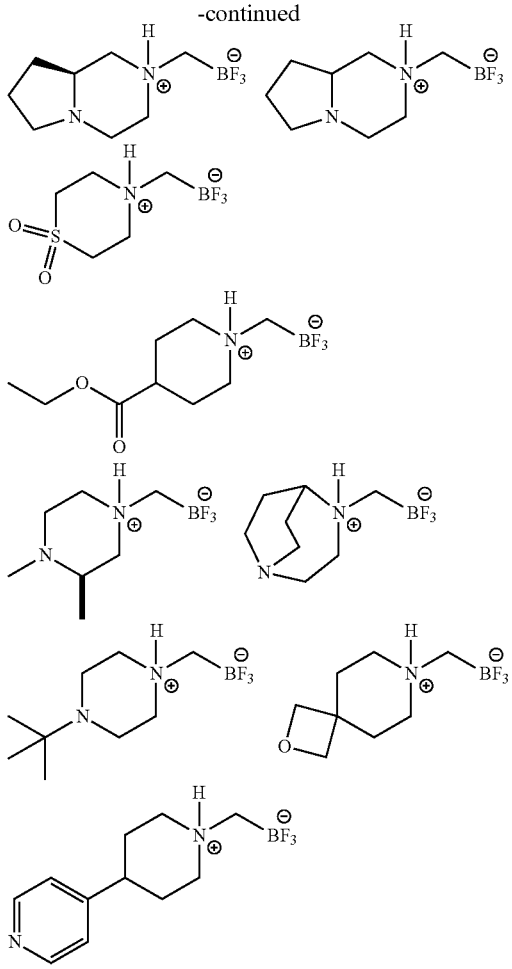

Trifluoro((4-isopropylpiperazin-1-ium-1-yl)methyl)borate

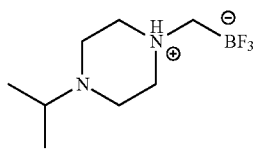

A mixture of potassium(bromomethyl)trifluoroborate (1.28 g, 6.37 mmol) and N-isopropylpiperazine (0.84 g, 6.55 mol) was stirred in dry THF (20 ml) at 70° C. overnight under argon, cooled to room temperature and concentrated to dryness. The resulting white solid was stirred again at 70° C. in dry acetone (75 mL) under argon for 3 h. Upon filtering heterogeneous slurry through Celite®, filtrate was concentrated to drynesss, heated in acetone (3 mL), diluted with dry Et$_2$O (15 mL) and heated at 30° C. for 20 min, and cooled to room temperature. The resulting off-white crystalline solid was filtered through a fritted Teflon tube under nitrogen and dried under high vauum to provide trifluoro((4-isopropylpiperazin-1-ium-1-yl)methyl)borate (1.0 g). $^1$H NMR (400 MHz, Acetonitrile-d$_3$) δ 6.10 (s, 1H), 3.48 (d, J=12.6 Hz, 2H), 2.92 (app t, J=10.7 Hz, 4H), 2.74 (hept, J=6.6 Hz, 1H), 2.53 (app t, J=12.9 Hz, 2H), 2.12 (s, 2H), 1.02 (d, J=6.6 Hz, 6H). $^{19F}$ NMR (376 MHz, Acetonitrile-d$_3$) δ −142.02 (q, J=47.3 Hz).

General procedure for the preparation of 3-((alkylamino)-5-(substitutedalkyl)-8-(substitutedaminyl)pyrimido[4,5-c]isoquinolin-6(5H)-ones is described in the preparation of trans-3-(butylamino)-5-(4-hydroxycyclohexyl)-8-(4-methylpiperazin-1-yl)pyrimido[4,5-c]isoquinolin-6(5H)-one.

The crude concentrate obtained after processing end reaction mixture was purified by preparative HPLC (reverse phase column, CH$_3$CN:H$_2$O as eluting solvent containing either formic acid or CF$_3$COOH as a modifier) or silica gel flash column chromatography to provide corresponding product as salt/solvates or free base respectively.

Procedure-A: trans-3-(Butylamino)-5-(4-hydroxycyclohexyl)-8-(4-methylpiperazin-1-yl)pyrimido[4,5-c]isoquinolin-6(5H)-one

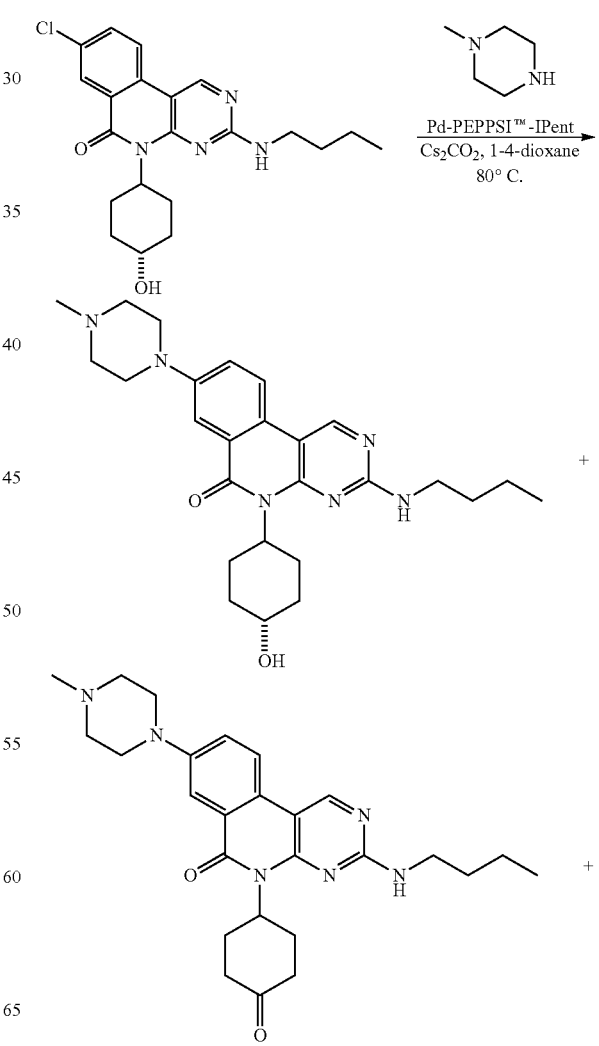

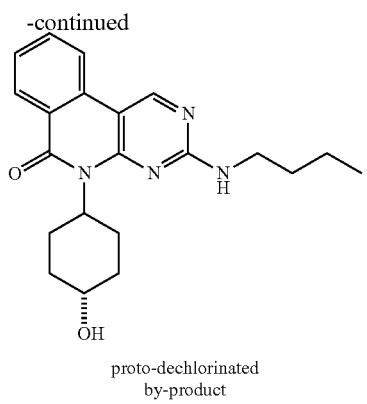

proto-dechlorinated
by-product trans-3-(Butylamino)-8-chloro-5-(4-hydroxycyclohexyl)pyrimido[4,5-c]isoquinolin-6(5H)-one (200 mg, 0.49 mmol), N-methylpiperazine (80 mg, 0.79 mmol), Cs₂CO₃ (320 mg, 0.98 mmol), Pd-PEPPSI™-IPent (40 mg, 0.05 mmol) and a stir bar were transferred to a screw-capped vial (20 mL). The vial was sealed with a cap containing PTFE septum and air was removed from vial by vacuum. Dry 1,4-Dioxane (4 mL) was added to vial under vacuum by a syringe. Air was removed from the closed reaction system by vacuum, back filled with argon while stirring the reaction contents. After 3-4 cycles of repeated degassing cycles, reaction mixture was stirred at 80° C. and progress was monitored by LC/MS. Initial reaction mixture turned to yellow after 30 min of heating and eventually to an organge. After 5 h, LC/MS analysis of reaction aliquot indicated the desired trans-3-(butylamino)-5-(4-hydroxycyclohexyl)-8-(4-methylpiperazin-1-yl)pyrimido[4,5-c]isoquinolin-6(5H)-one (AUC 66%) formation along with proto-dechlorinated by-product [trans-3-(butylamino)-5-(4-hydroxycyclohexyl)pyrimido[4,5-c]isoquinolin-6(5H)-one (AUC 14%] and 3-(butylamino)-8-(4-methylpiperazin-1-yl)-5-(4-oxocyclohexyl)pyrimido[4,5-c]isoquinolin-6(5H)-one (AUC 9%) with complete consumption of trans-3-(butylamino)-8-chloro-5-(4-hydroxycyclohexyl)pyrimido[4,5-c]isoquinolin-6(5H)-one At this stage, orange heterogeneous reaction mixture was diluted with THF (3 mL) and filtered through Celite®. Upon rinsing vial with additional amount of THF (2×5 mL), flitering through Celite®, homogeneous yellow filtrate was concentrated to dryness. The crude concentrated semi-solid was dissolved in 5% 7N NH₃ MeOH/CH₂Cl₂ (12 mL), adsorbed on silica gel (10 g), dried and purified by flash chromatography [Combiflash Torrent® with RediSep® silica gel column 12 g (pre-conditioned with CH₂Cl₂) and eluted with 30-70% CH₂Cl₂:7% 7N NH₃ MeOH in CH₂Cl₂ solvent gradient. Off-white solid obtained upon concentrating product fractions was heated in EtOAc (6 mL), cooled to room temperature and filtered to provide desired trans-3-(butylamino)-5-(4-hydroxycyclohexyl)-8-((4-methylpiperazin-1-yl)methyl)pyrimido[4,5-c]isoquinolin-6(5H)-one (113 mg) as a off-white solid. ¹H NMR (400 MHz, Methanol-d₄) δ 8.98 (s, 1H), 8.06 (d, J=9.0 Hz, 1H), 7.71 (d, J=2.4 Hz, 1H), 7.46 (dd, J=8.9, 2.8 Hz, 1H), 5.58 (br s, 1H), 3.75-3.68 (m, 1H), 3.46 (t, J=7.2 Hz, 2H), 3.36-3.29 (app m, 4H), 2.91 (br s, 2H), 2.65 (t, J=5.1 Hz, 4H), 2.37 (s, 3H), 2.10 (d, J=11.6 Hz, 2H), 1.73-1.60 (m, 4H), 1.53-1.42 (app m, 4H), 1.00 (t, J=7.4 Hz, 3H). LCMS: Purity 97%, MS (m/e) 465 (MH⁺).

Procedure-B: trans-3-(Butylamino)-5-(4-hydroxycyclohexyl)-8-(4-methylpiperazin-1-yl)pyrimido[4,5-c]isoquinolin-6(5H)-one

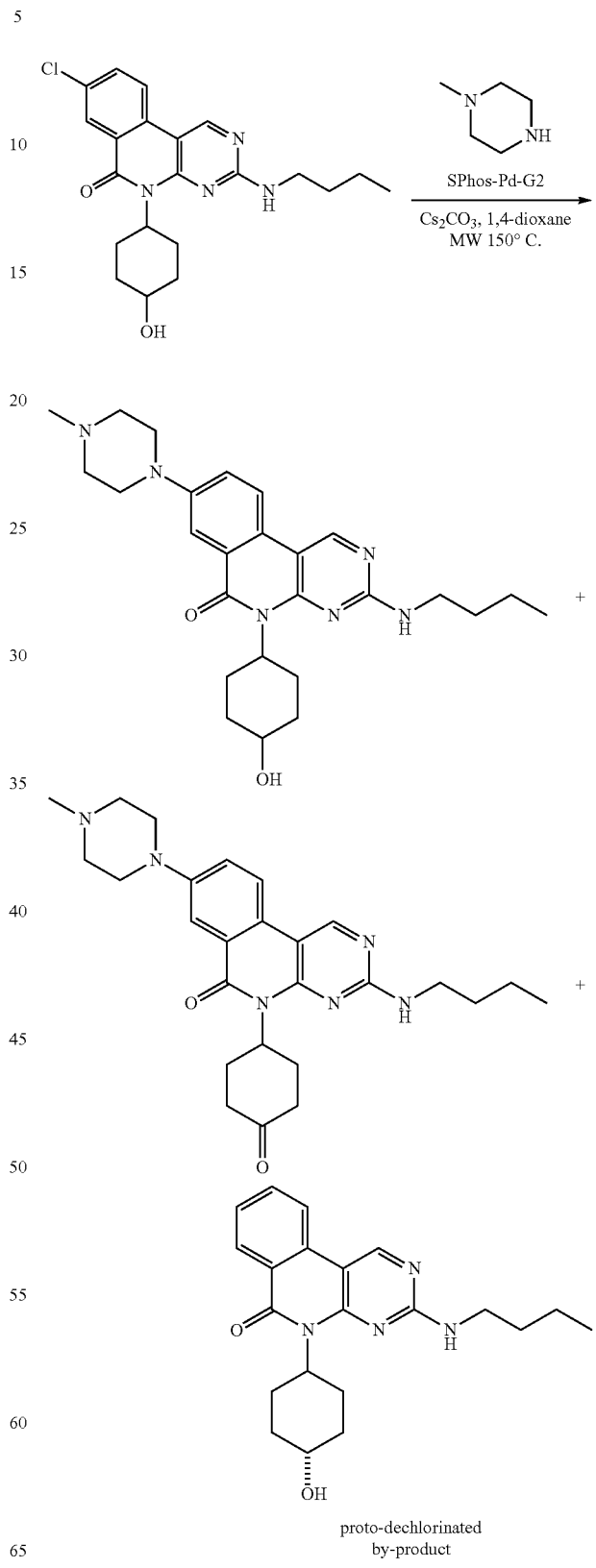

proto-dechlorinated
by-product trans-3-(Butylamino)-8-chloro-5-(4-hydroxycyclohexyl)pyrimido[4,5-c]isoquinolin-6(5H)-one (100 mg, 0.25 mmol), N-methylpiperazine (75 mg, 0.75 mmol), Cs$_2$CO$_3$ (163 mg, 0.50 mmol), SPhos-Pd-G2 (18 mg, 0.025 mmol) and a stir bar were transferred to a microwave vial. The vial was tightly capped with a rubber septum and air was removed from vial by vacuum. Dry 1,4-Dioxane (4 mL) was added to vial under vacuum by a syringe. Air was removed from the closed reaction system by vacuum, back filled with argon while stirring the reaction contents. After 3-4 cycles of repeated degassing cycles, reaction mixture was heated in a microwave at 150° C. for 60 min. LC/MS analysis of reaction aliquot indicated partial consumption trans-3-(butylamino)-8-chloro-5-(4-hydroxycyclohexyl)pyrimido[4,5-c]isoquinolin-6(5H)-one (AUC 24%). At this stage additional amounts of N-methylpiperazine (75 mg, 0.75 mmol), Cs$_2$CO$_3$ (163 mg, 0.50 mmol) and SPhos-Pd-G2 (18 mg, 0.025 mmol) were transferred to previously heated above reaction mixture and heated again in microwave at 150° C. for 45 min. LC/MS analysis of reaction aliquot indicated the desired trans-3-(butylamino)-5-(4-hydroxycyclohexyl)-8-(4-methylpiperazin-1-yl)pyrimido[4,5-c]isoquinolin-6(5H)-one (AUC 46%) formation along with proto-dechlorinated by-product [trans-3-(butylamino)-5-(4-hydroxycyclohexyl)pyrimido[4,5-c]isoquinolin-6(5H)-one (AUC 24%] and 3-(butylamino)-8-(4-methylpiperazin-1-yl)-5-(4-oxocyclohexyl)pyrimido[4,5-c]isoquinolin-6(5H)-one (AUC 12%) with complete consumption of trans-3-(butylamino)-8-chloro-5-(4-hydroxycyclohexyl)pyrimido[4,5-c]isoquinolin-6(5H)-one. At this stage, dark heterogeneous reaction mixture was diluted with THF (3 mL) and filtered through Celite®. Upon rinsing microwave vial with additional amount of THF (2×3 mL), flitering through Celite®, homogeneous yellow filtrate was concentrated to dryness. The crude concentrated semi-solid was dissolved in 5% 7N NH$_3$ MeOH/CH$_2$Cl$_2$ (12 mL), adsorbed on silica gel (10 g), dried and purified by flash chromatography [Combiflash Torrent® with RediSep® silica gel column 12 g (pre-conditioned with CH$_2$Cl$_2$) and eluted with 30-70% CH$_2$Cl$_2$:7% 7N NH$_3$ MeOH in CH$_2$Cl$_2$ solvent gradient. Off-white solid obtained upon concentrating product fractions was heated in EtOAc (6 mL), cooled to room temperature and filtered to provide desired trans-3-(butylamino)-5-(4-hydroxycyclohexyl)-8-((4-methylpiperazin-1-yl)methyl)pyrimido[4,5-c]isoquinolin-6(5H)-one (38 mg, purity 98%) as a off-white solid. $^1$H NMR (400 MHz, Methanol-d$_4$) δ 8.98 (s, 1H), 8.06 (d, J=9.0 Hz, 1H), 7.71 (d, J=2.4 Hz, 1H), 7.46 (dd, J=8.9, 2.8 Hz, 1H), 5.58 (br s, 1H), 3.75-3.68 (m, 1H), 3.46 (t, J=7.2 Hz, 2H), 3.36-3.29 (app m, 4H), 2.91 (br s, 2H), 2.65 (t, J=5.1 Hz, 4H), 2.37 (s, 3H), 2.10 (d, J=11.6 Hz, 2H), 1.73-1.60 (m, 4H), 1.53-1.42 (app m, 4H), 1.00 (t, J=7.4 Hz, 3H). LCMS: Purity 99%, MS (m/e) 465 (MH$^+$).

trans-3-(Butylamino)-5-(4-hydroxycyclohexyl)-8-morpholinopyrimido[4,5-c]isoquinolin-6(5H)-one

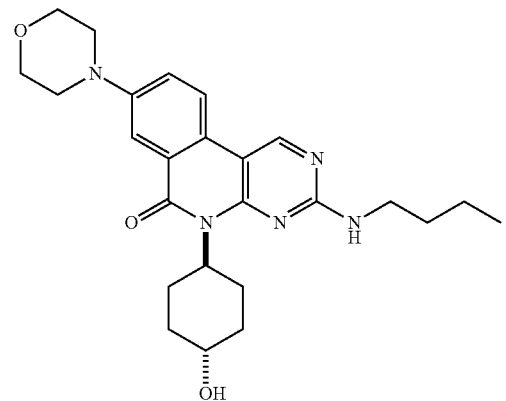

$^1$H NMR (400 MHz, Methanol-d$_4$) δ 9.00 (s, 1H), 8.08 (d, J=9.0 Hz, 1H), 7.72 (d, J=2.7 Hz, 1H), 7.47 (dd, J=8.9, 2.8 Hz, 1H), 5.58 (br s, 1H), 3.90-3.83 (m, 4H), 3.75-3.68 (m, 1H), 3.46 (t, J=7.2 Hz, 2H), 3.29-3.21 (m, 4H), 2.91 (br s, 2H), 2.10 (d, J=11.8 Hz, 2H), 1.74-1.60 (m, 4H), 1.53-1.42 (app m, 4H), 1.00 (t, J=7.3 Hz, 3H). LCMS: Purity 95%, MS (m/e) 452 (MH$^+$).

cis-3-(Butylamino)-5-(4-hydroxycyclohexyl)-8-(4-methylpiperazin-1-yl)pyrimido[4,5-c]isoquinolin-6(5H)-one

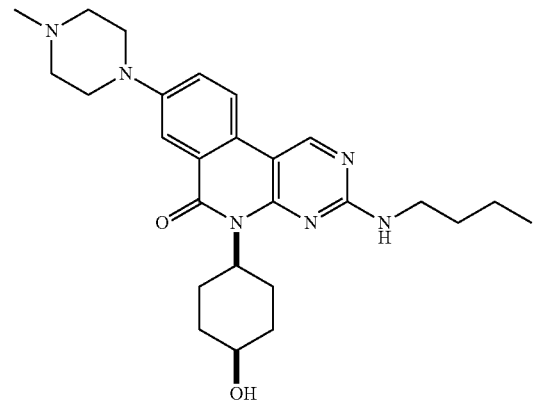

$^1$H NMR (400 MHz, Methanol-d$_4$) δ 8.98 (s, 1H), 8.06 (d, J=8.9 Hz, 1H), 7.73 (d, J=2.8 Hz, 1H), 7.46 (dd, J=8.9, 2.8 Hz, 1H), 5.54 (br s, 1H), 4.09-4.03 (app m, 1H), 3.50 (s, 2H), 3.36-3.29 (app m, 4H), 3.26-3.15 (app m, 2H), 2.69-2.61 (app m, 4H), 2.36 (s, 3H), 1.98 (d, J=14.2 Hz, 2H), 1.75-1.58 (m, 4H), 1.53-1.42 (app m, 4H), 0.98 (t, J=7.4 Hz, 3H). LCMS: Purity 97%, MS (m/e) 401 (MH$^+$).

251 tert-Butyl (4-((3-(Butylamino)-8-(4-methylpiperazin-1-yl)-6-oxopyrimido[4,5-c]isoquinolin-5(6H)-yl)methyl)cyclohexyl)carbamate

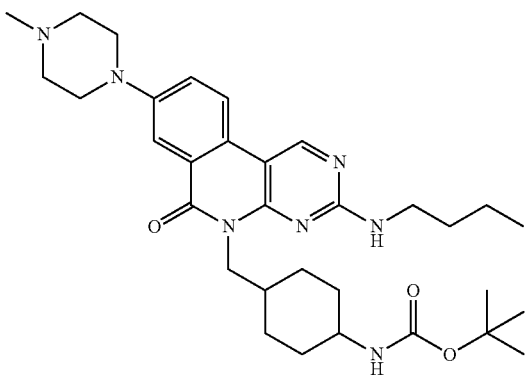 [SMILES: CCCCNc1ncc2c3ccc(N4CCN(C)CC4)cc3c(=O)n(CC3CCC(NC(=O)OC(C)(C)C)CC3)c2n1]

$^1$H NMR (400 MHz, DMSO-d$_6$) δ 9.13 (s, 1H), 8.18 (d, J=8.9 Hz, 1H), 7.58 (d, J=2.7 Hz, 1H), 7.50 (br s, 1H), 7.49 (dd, J=9.0, 2.8 Hz, 1H), 6.63 (d, J=8.4 Hz, 1H), 4.22 (d, J=6.9 Hz, 2H), 3.26-3.18 (m, 3H), 3.16-3.13 (br s, 1H), 2.22 (s, 3H), 1.81-1.70 (m, 3H), 1.61-1.49 (m, 4H), 1.33 (s, 9H), 1.15-0.97 (m, 4H), 0.91 (t, J=7.3 Hz, 3H). LCMS: Purity 98%, MS (m/e) 578 (MH$^+$).

trans-3-((3,3-Difluorocyclobutyl)amino)-5-(4-hydroxycyclohexyl)-8-(6-methyl-2,6-diazaspiro[3.3]heptan-2-yl)pyrimido[4,5-c]isoquinolin-6(5H)-one triformic acid salt or solvate

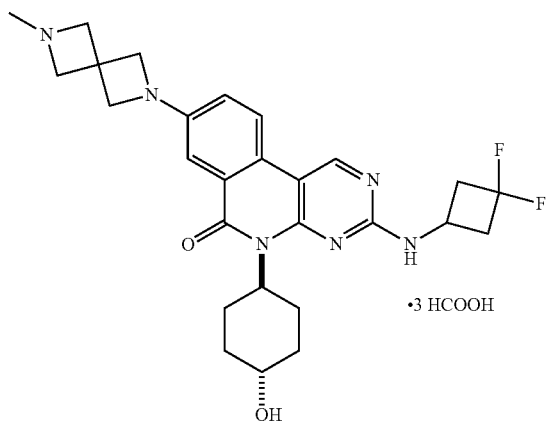

$^1$H NMR (300 MHz, Methanol-d$_4$) δ 9.03 (s, 1H), 8.10 (d, J=9.0 Hz, 1H), 7.28 (s, 1H), 7.01 (d, J=9.0 Hz, 1H), 5.52 (br s, 1H), 4.57-4.53 (m, 2H), 4.30-4.26 (m, 4H), 4.20 (brs, 2H), 4.14 (brs, 2H), 3.04 (m, 2H), 3.01 (s, 3H), 2.91-2.82 (m, 2H), 2.78-2.63 (m, 3H), 2.14-2.10 (m, 2H), 1.72-1.67 (m, 2H), 1.51-1.47 (m, 2H). LCMS: Purity 99%, MS (m/e) 511 (MH$^+$-3HCOOH).

trans-3-((3,3-difluorocyclobutyl)amino)-5-(4-hydroxycyclohexyl)-8-(2-oxa-6-azaspiro[3.3]heptan-6-yl)pyrimido[4,5-c]isoquinolin-6(5H)-one triformic acid salt or solvate

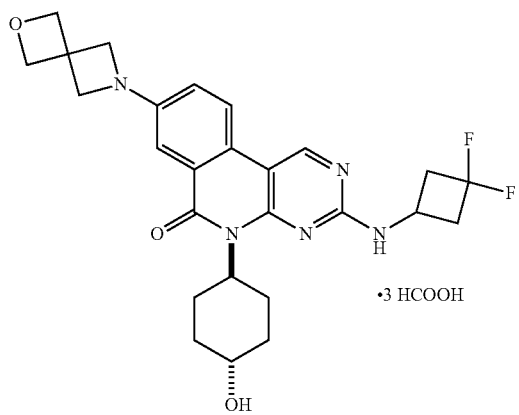

LCMS: Purity 99%, MS (m/e) 498 (MH$^+$-3HCOOH).

trans-3-(Butylamino)-5-(4-hydroxycyclohexyl)-8-(2-oxa-6-azaspiro[3.3]heptan-6-yl)pyrimido[4,5-c]isoquinolin-6(5H)-one

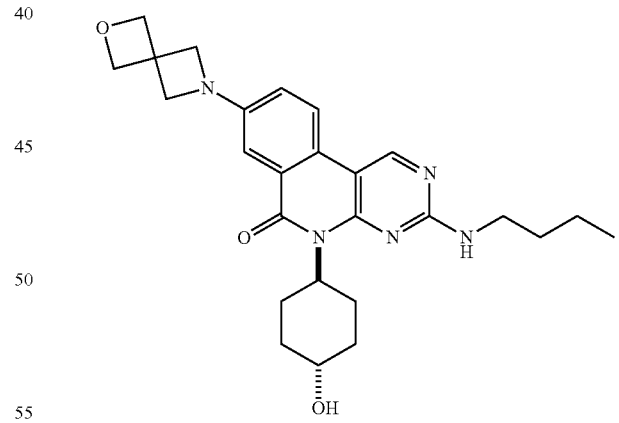

$^1$H NMR (400 MHz, DMSO-d$_6$) δ 9.09 (s, 1H), 8.12 (d, J=8.7 Hz, 1H), 7.47 (s, 1H), 7.10 (d, J=2.5 Hz, 1H), 6.91 (dd, J=8.7, 2.6 Hz, 1H), 5.39 (br s, 1H), 4.72 (s, 4H), 4.62 (s, 1H), 4.07 (s, 4H), 4.03-4.00 (app s, 1H), 3.49 (app s, 1H), 3.35-3.31 (hidden m, 1H), 2.98-2.58 (br s, 2H), 1.94 (d, J=10.7 Hz, 2H), 1.58-1.51 (app m, 4H), 1.43-1.21 (m, 4H), 0.91 (t, J=7.3 Hz, 3H). LCMS: Purity 98%, MS (m/e) 464 (MH$^+$).

253 trans-3-(Butylamino)-5-(4-hydroxycyclohexyl)-8-(4-isopropylpiperazin-1-yl)pyrimido[4,5-c]isoquinolin-6(5H)-one

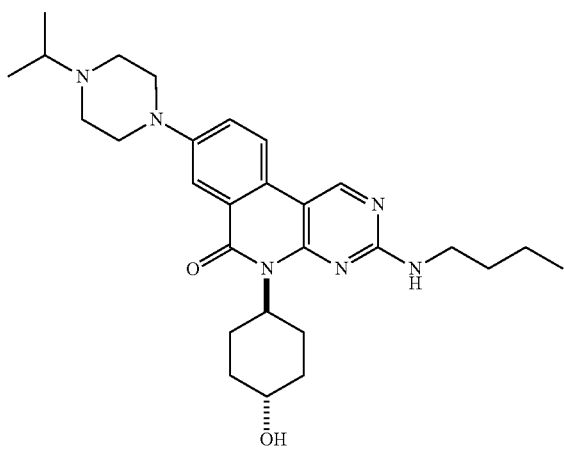

$^1$H NMR (400 MHz, Methanol-$d_4$) δ 9.00 (s, 1H), 8.09 (d, J=8.9 Hz, 1H), 7.74 (d, J=2.5 Hz, 1H), 7.49 (dd, J=8.9, 2.8 Hz, 1H), 5.59 (br s, 1H), 3.75-3.68 (m, 1H), 3.46 (t, J=7.2 Hz, 2H), 3.42-3.31 (app m, 4H), 2.99-2.92 (app m, 7H), 2.10 (d, J=10.9 Hz, 2H), 1.71-1.63 (app m, 4H), 1.54-1.42 (m, 4H), 1.22 (d, J=6.5 Hz, 6H), 1.00 (t, J=7.4 Hz, 3H). LCMS: Purity 99%, MS (m/e) 493 (MH$^+$).

3-(Butylamino)-8-(4-isopropylpiperazin-1-yl)-5-(4-oxocyclohexyl)pyrimido[4,5-c]isoquinolin-6(5H)-one

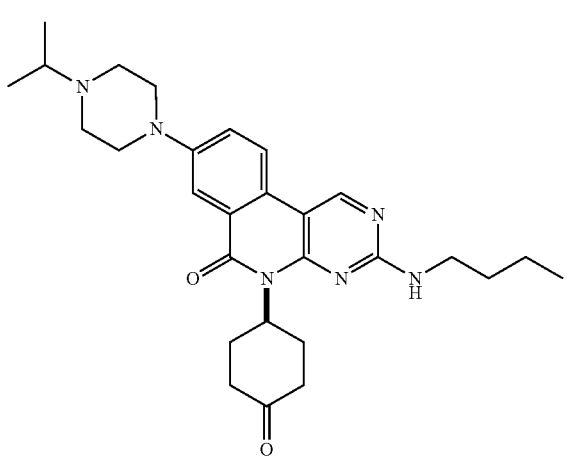

LCMS: Purity 99%, MS (m/e) 491 (MH$^+$).

254 trans-3-(Butylamino)-5-(4-hydroxycyclohexyl)-8-(4-(pyrrolidin-1-yl)piperidin-1-yl)pyrimido[4,5-c]isoquinolin-6(5H)-one

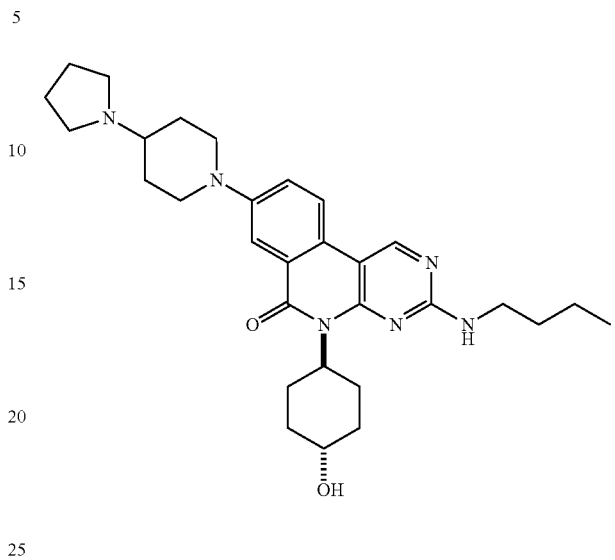

$^1$H NMR (400 MHz, DMSO-$d_6$) δ 9.10 (s, 1H), 8.11 (d, J=9.2 Hz, 1H), 7.55 (d, J=2.5 Hz, 1H), 7.50 (b s, 0.7H), 7.45 (dd, J=8.9, 2.7 Hz, 1.3H), 5.39 (br s, 1H), 4.62 (s, 1H), 3.69 (d, J=12.8 Hz, 2H), 3.49 (br s, 1H), 3.33-3.32 (m, 3H), 3.27 (app s, 4H), 2.79 (app t, J=11.2 Hz, 3H), 2.13-2.09 (app m, 1H), 1.91 (app br s, 4H), 1.68-1.62 (m, 4H), 1.56-1.50 (m, 6H), 1.42-1.24 (m, 4H), 0.90 (t, J=7.3 Hz, 3H). LCMS: Purity 99%, MS (m/e) 519 (MH$^+$).

3-(Butylamino)-5-(4-oxocyclohexyl)-8-(4-(pyrrolidin-1-yl)piperidin-1-yl)pyrimido[4,5-c]isoquinolin-6(5H)-one

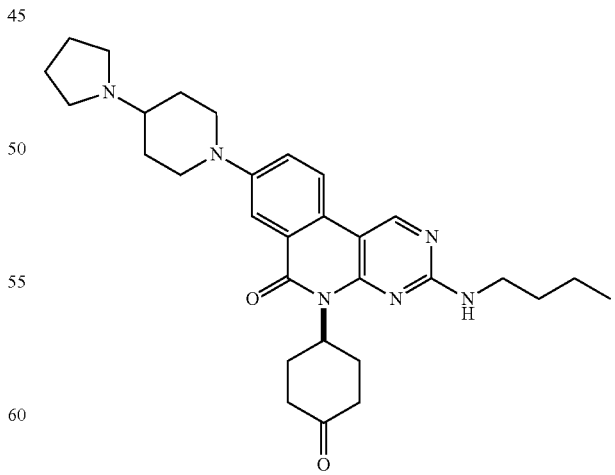

LCMS: Purity 98%, MS (m/e) 517 (MH$^+$).

255 trans-3-(Butylamino)-8-((S)-hexahydropyrrolo[1,2-a]pyrazin-2(1H)-yl)-5-((1r,4S)-4-hydroxycyclohexyl)pyrimido[4,5-c]isoquinolin-6(5H)-one

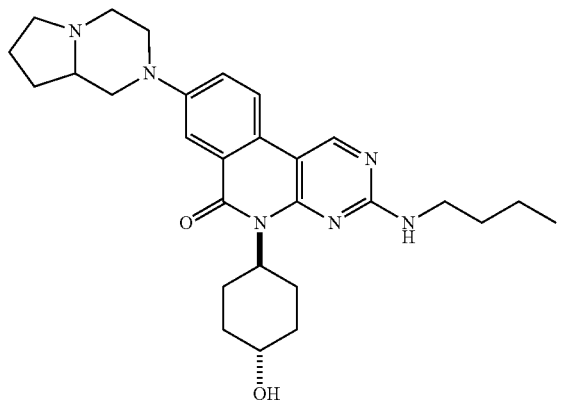

$^1$H NMR (400 MHz, Methanol-$d_4$) δ 8.95 (s, 1H), 8.01 (d, J=9.0 Hz, 1H), 7.69 (d, J=2.4 Hz, 1H), 7.44 (dd, J=8.9, 2.7 Hz, 1H), 5.56 (br s, 1H), 3.89 (app d, J=10.2 Hz, 1H), 3.79-3.65 (m, 2H), 3.44 (t, J=7.2 Hz, 2H), 3.22-3.08 (m, 2H), 2.93 (app td, J=11.8, 3.2 Hz, 3H), 2.59 (t, J=10.1 Hz, 1H), 2.42 (td, J=11.3, 3.3 Hz, 1H), 2.29-2.21 (m, 2H), 2.09 (d, J=11.0 Hz, 2H), 2.04-1.92 (m, 1H), 1.92-1.79 (m, 2H), 1.69-1.61 (m, 4H), 1.57-1.41 (m, 5H) 0.99 (t, J=7.4 Hz, 3H). LCMS: Purity 98%, MS (m/e) 491 (MH$^+$).

trans-3-((3-Fluorocyclobutyl)amino)-5-(4-hydroxycyclohexyl)-8-(6-methyl-2,6-diazaspiro[3.3]heptan-2-yl)pyrimido[4,5-c]isoquinolin-6(5H)-one triformic acid salt or solvate

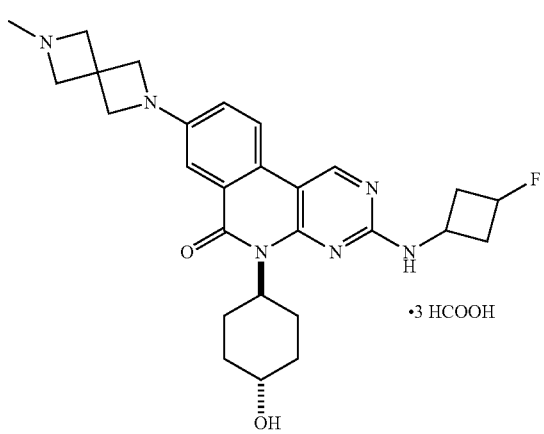

$^1$H NMR (300 MHz, Methanol-$d_4$) δ 8.95 (s, 1H), 9.49 (br s, 1H), 8.02 (d, J=8.7 Hz, 1H), 7.22 (s, 1H), 6.96 (d, J=8.7 Hz, 1H), 5.53 (br s, 1H), 5.36-5.14 (m, 1H), 4.60 (m, 1H),

256

4.31 (brs, 4H), 4.12 (brs, 4H), 3.73 (m, 1H), 2.88 (s, 3H), 2.68-2.39 (m, 4H), 2.12-2.09 (m, 2H), 1.68-1.65 (m, 2H), 1.51-1.46 (m, 2H). LCMS: Purity 99%, MS (m/e) 493 (MH$^+$-3HCOOH).

trans-3-((3-Fluorocyclobutyl)amino)-5-(4-hydroxycyclohexyl)-8-(2-oxa-6-azaspiro[3.3]heptan-6-yl)pyrimido[4,5-c]isoquinolin-6(5H)-one tris trifluoroacetic acid salt or solvate

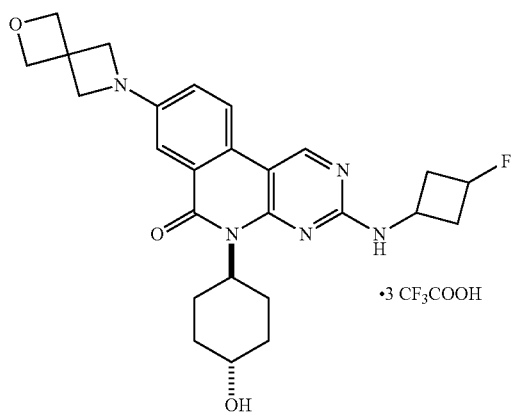

$^1$H NMR (300 MHz, Methanol-$d_4$) δ 8.95 (s, 1H), 9.49 (br s, 1H), 8.03 (d, J=8.7 Hz, 1H), 7.27 (s, 1H), 6.97 (d, J=8.7 Hz, 1H), 5.53 (br s, 1H), 5.36-5.14 (m, 1H), 4.88 (brs, 4H), 4.80 (m, 1H), 4.64 (m, 1H), 4.16 (brs, 3H), 3.79 (m, 2H), 2.85 (m, 2H), 2.66 (brs, 2H), 2.60-2.42 (m, 2H), 2.15-2.11 (m, 2H), 1.74-1.71 (m, 2H), 1.52-1.47 (m, 2H).

LCMS: Purity 99%, MS (m/e) 480 (MH$^+$-3TFA).

trans-3-(Butylamino)-8-((R)-hexahydropyrrolo[1,2-a]pyrazin-2(1H)-yl)-5-(4-hydroxycyclohexyl)pyrimido[4,5-c]isoquinolin-6(5H)-one

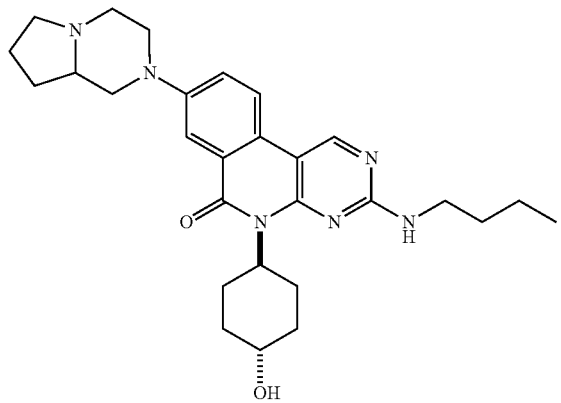

LCMS: Purity 99%, MS (m/e) 491 (MH$^+$).

257 trans-3-(Butylamino)-5-(4-hydroxycyclohexyl)-8-(4-(oxetan-3-yl)piperazin-1-yl)pyrimido[4,5-c]isoquinolin-6(5H)-one

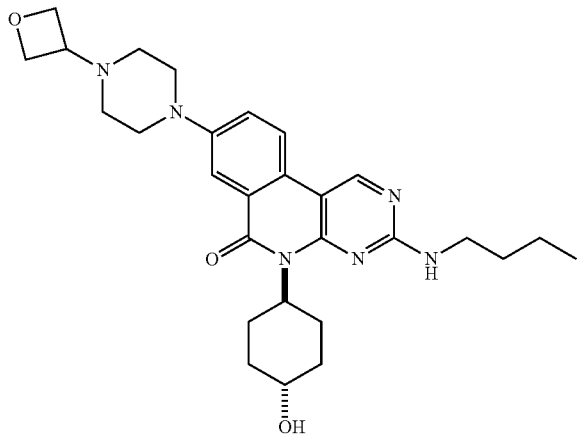

¹H NMR (400 MHz, DMSO-d₆) δ 9.12 (s, 1H), 8.14 (d, J=8.9 Hz, 1H), 7.56 (d, J=2.5 Hz, 1H), 7.52 (s, 0.7H), 7.47 (dd, J=9.0, 2.8 Hz, 1H), 7.36 (s, 0.3H), 5.40 (br s, 1H), 4.62 (s, 1H), 4.56 (t, J=6.5 Hz, 2H), 4.46 (t, J=6.1 Hz, 2H), 3.53-3.38 (m, 2H), 3.38-3.32 (app m, 2H), 3.25-3.22 (m, 4H), 2.76 (br s, 2H), 2.46-2.38 (m, 4H), 1.94 (d, J=11.0 Hz, 2H), 1.62-1.51 (m, 4H), 1.43-1.23 (m, 4H), 0.91 (t, J=7.3 Hz, 3H). LCMS: Purity 99%, MS (m/e) 507 (MH⁺).

trans-3-(Butylamino)-5-(4-hydroxycyclohexyl)-8-((2S,5R)-2,4,5-trimethylpiperazin-1-yl)pyrimido[4,5-c]isoquinolin-6(5H)-one

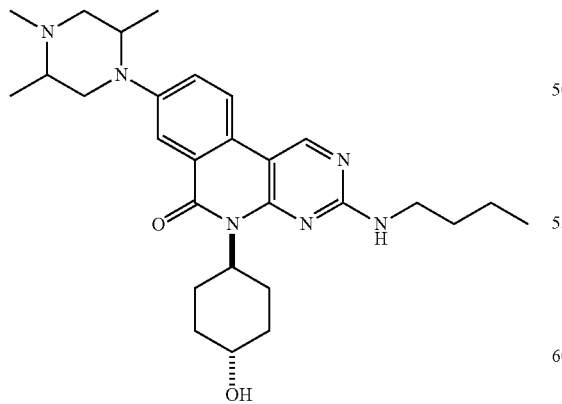

¹H NMR (400 MHz, Methanol-d₄) δ 8.96 (s, 1H), 8.03 (d, J=9.0 Hz, 1H), 7.67 (d, J=2.3 Hz, 1H), 7.44 (dd, J=8.9, 2.8 Hz, 1H), 5.57 (br s, 1H), 3.75-3.72 (app m, 1H), 3.67 (d, J=11.9 Hz, 2H), 3.45 (t, J=7.2 Hz, 2H), 2.90 (br s, 2H), 2.60 (t, J=11.5 Hz, 2H), 2.50-2.42 (app m, 2H), 2.37 (s, 3H), 2.10 (d, J=10.7 Hz, 2H), 1.70-1.62 (app m, 4H), 1.53-1.39 (m, 4H), 1.23 (d, J=6.2 Hz, 6H), 0.99 (t, J=7.4 Hz, 3H). LCMS: Purity 99%, MS (m/e) 493 (MH⁺).

258

3-(Butylamino)-5-(4-oxocyclohexyl)-8-((2S,5R)-2,4,5-trimethylpiperazin-1-yl)pyrimido[4,5-c]isoquinolin-6(5H)-one

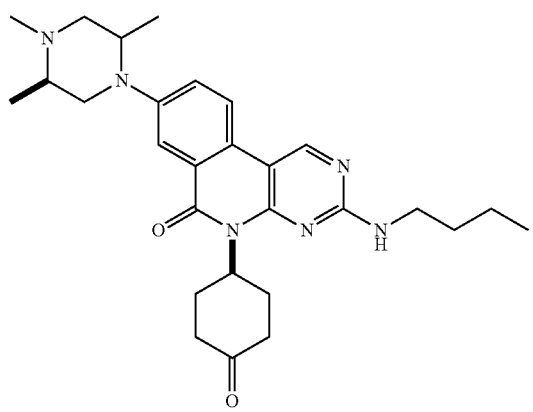

LCMS: Purity 97%, MS (m/e) 401 (MH⁺).

trans-3-(Butylamino)-8-(5,6-dihydro-[1,2,4]triazolo[1,5-a]pyrazin-7(8H)-yl)-5-(4-hydroxycyclohexyl)pyrimido[4,5-c]isoquinolin-6(5H)-one

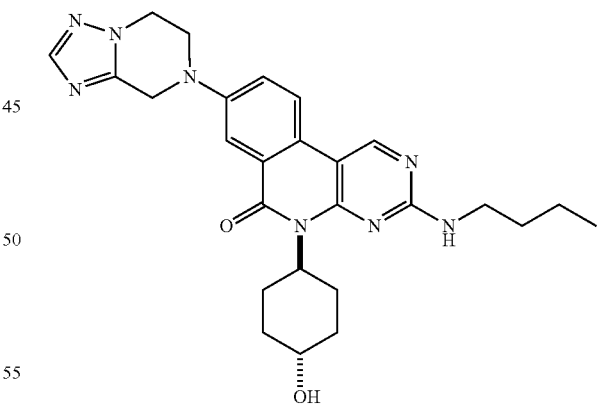

¹H NMR (400 MHz, Methanol-d₄) δ 9.01 (s, 1H), 8.16 (d, J=9.1 Hz, 1H), 7.99 (s, 1H), 7.87 (d, J=3.0 Hz, 1H), 7.64 (dd, J=9.0, 2.7 Hz, 1H), 5.54 (br s, 1H), 4.68 (s, 2H), 4.37 (t, J=5.2 Hz, 2H), 3.99 (t, J=5.2 Hz, 2H), 3.78-3.68 (m, 1H), 3.56-3.44 (m, 2H), 2.11 (d, J=11.4 Hz, 2H), 1.73-1.66 (m, 5H), 1.53-1.44 (m, 5H), 1.01 (t, J=7.4 Hz, 3H). LCMS: Purity 99%, MS (m/e) 489 (MH⁺).

259 trans-8-(1,4-Diazabicyclo[3.2.2]nonan-4-yl)-3-(butylamino)-5-(4-hydroxycyclohexyl)pyrimido[4,5-c]isoquinolin-6(5H)-one

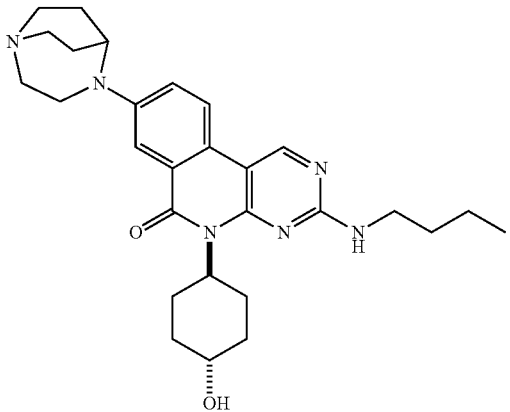

¹H NMR (400 MHz, DMSO-d₆) δ 9.07 (s, 1H), 8.08 (d, J=8.9 Hz, 1H), 7.43 (d, J=2.9 Hz, 1H), 7.35 (br s, 0.7H), 7.28 (dd, J=9.1, 2.9 Hz, 1H), 7.07 (br s, 0.3H), 5.40 (br s, 1H), 4.62 (s, 1H), 4.09 (s, 1H), 3.56 (t, J=5.7 Hz, 2H), 3.50 (br s, 1H), 2.99-2.89 (m, 4H), 2.85-2.78 (m, 4H), 2.02-1.93 (m 4H), 1.70-1.63 (m, 2H), 1.55 (app p, J=7.4 Hz, 4H), 1.43-1.22 (m, 4H), 0.91 (t, J=7.3 Hz, 3H). LCMS: Purity 99%, MS (m/e) 491 (MH⁺).

8-(1,4-Diazabicyclo[3.2.2]nonan-4-yl)-3-(butylamino)-5-(4-oxocyclohexyl)pyrimido[4,5-c]isoquinolin-6(5H)-one

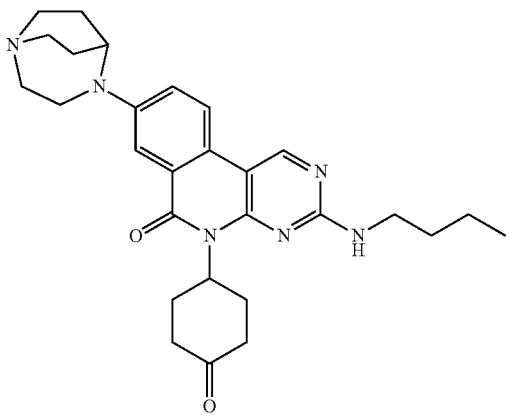 [SMILES: CCCCNc1ncc2c3ccc(N4CCN5CCC4CC5)cc3c(=O)n(C3CCC(=O)CC3)c2n1]

LCMS: Purity 97%, MS (m/e) 489

260 trans-3-((3,3-Difluorocyclobutyl)amino)-5-(4-hydroxycyclohexyl)-8-(4-methylpiperazin-1-yl)pyrimido[4,5-c]isoquinolin-6(5H)-one triformate salt or solvate

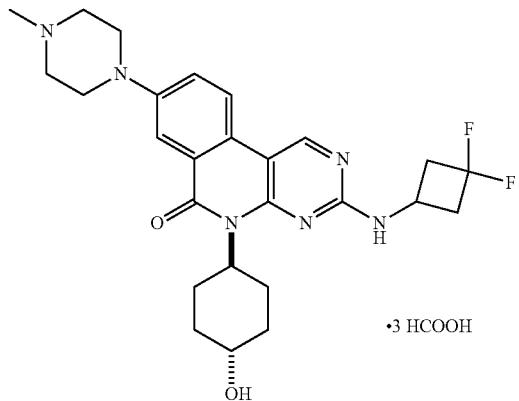

¹H NMR (300 MHz, Methanol-d₄) δ 9.09 (s, 1H), 8.19 (d, J=9.0 Hz, 1H), 7.80 (s, 1H), 7.57 (d, J=9.0 Hz, 1H), 5.56 (br s, 1H), 4.35 (m, 1H), 3.99 (m, 2H), 3.76-3.74 (m, 4H), 3.12-3.02 (m, 6H), 2.99 (s, 3H), 2.89 (br s, 2H), 2.74-2.64 (m, 2H), 2.14-2.10 (m, 2H), 1.72-1.68 (m, 2H), 1.51-1.47 (m, 2H). LCMS: Purity 98%, MS (m/e) 499 (MH⁺-3HCOOH).

trans-3-(Butylamino)-5-(4-hydroxy-4-methylcyclohexyl)-8-(4-methylpiperazin-1-yl)pyrimido[4,5-c]isoquinolin-6(5H)-one

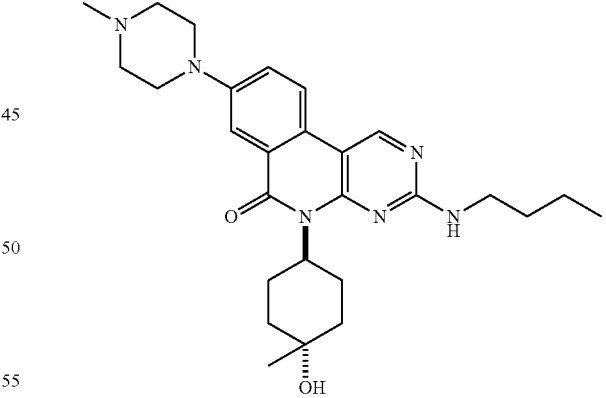

¹H NMR (400 MHz, DMSO-d₆) δ 9.12 (s, 1H), 8.14 (d, J=8.9 Hz, 1H), 7.56 (d, J=2.6 Hz, 1H), 7.50 (br s, 0.7H), 7.46 (dd, J=9.0, 2.7 Hz, 1H), 7.07 (br s, 0.3H), 5.48 (br s, 1H), 4.40 (s, 1H), 3.35-3.30 (m, 1H), 3.27 (s, 1H), 3.21 (t, J=4.9 Hz, 4H), 2.74 (app q, J=12.9 Hz, 2H), 2.45 (t, J=4.9 Hz, 4H), 2.21 (s, 3H), 1.66 (d, J=12.3 Hz, 2H), 1.61-1.43 (m, 6H), 1.42-1.26 (m, 2H), 1.35 (h, J=7.3 Hz, 1H), 0.90 (t, J=7.3 Hz, 3H). LCMS: Purity 97%, MS (m/e) 479 (MH⁺).

261 trans-3-((Cyclopropylmethyl)amino)-5-(4-hydroxy-cyclohexyl)-8-(4-methylpiperazin-1-yl)pyrimido[4,5-c]isoquinolin-6(5H)-one

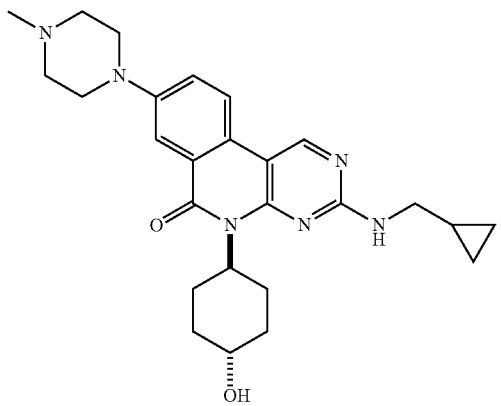

$^1$H NMR (400 MHz, Methanol-$d_4$) δ 9.12 (s, 1H), 8.13 (d, J=8.9 Hz, 1H), 7.58 (br s, 1H) 7.56 (d, J=2.6 Hz, 1H), 7.45 (dd, J=9.0, 2.8 Hz, 1H), 5.39 (br s, 1H), 4.61 (s, 1H), 3.50 (s, 1H), 3.26-3.15 (m, 6H), 2.75 (br s, 2H), 2.44 (app t, J=5.0 Hz, 4H), 2.20 (s, 3H), 1.98-1.89 (m, 2H), 1.53 (d, J=10.6 Hz, 2H), 1.29 (q, J=13.0 Hz, 2H), 1.14-1.10 (m, 1H), 0.47-0.38 (m, 2H), 0.23 (q, J=4.8 Hz, 2H). LCMS: Purity 99%, MS (m/e) 463 (MH$^+$).

3-(Butylamino)-5-(6-hydroxyspiro[3.3]heptan-2-yl)-8-(4-methylpiperazin-1-yl)pyrimido[4,5-c]isoquinolin-6(5H)-one

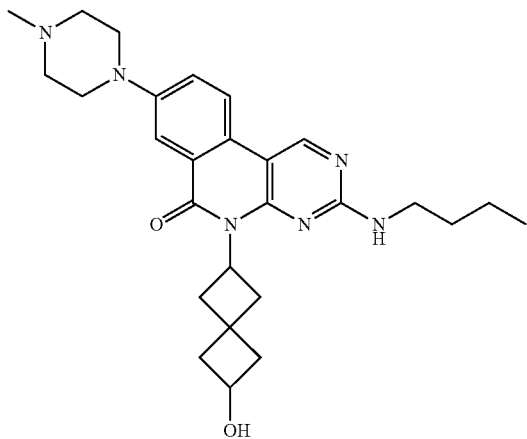 [SMILES: CCCCNc1ncc2c3ccc(N4CCN(C)CC4)cc3c(=O)n(C3CC4(CC(O)C4)C3)c2n1]

$^1$H NMR (400 MHz, DMSO-$d_6$) δ 9.10 (s, 1H), 8.11 (d, J=9.0 Hz, 1H), 7.54 (d, J=2.6 Hz, 1H), 7.47 (br s, 1H), 7.44 (dd, J=9.0, 2.7 Hz, 1H), 5.73 (p, J=9.1 Hz, 1H), 4.92 (s, 1H), 4.00 (dt, J=13.5, 5.6 Hz, 1H), 3.39-3.33 (app m, 2H), 3.20 (t, J=5.1 Hz, 4H), 3.10 (br s, 2H), 2.45 (t, J=5.1 Hz, 4H), 2.42-2.41 (m, 2H), 2.29 (br s, 2H), 2.21 (s, 3H), 1.95-1.85 (m, 2H), 1.54 (dt, J=14.0, 6.7 Hz, 2H), 1.36 (app q, J=11.0, 7.4 Hz, 2H), 0.91 (t, J=7.2 Hz, 3H). LCMS: Purity 96%, MS (m/e) 477 (MH$^+$).

262 cis-3-(Butylamino)-5-(4-hydroxy-4-methylcyclohexyl)-8-(4-methylpiperazin-1-yl)pyrimido[4,5-c]isoquinolin-6(5H)-one

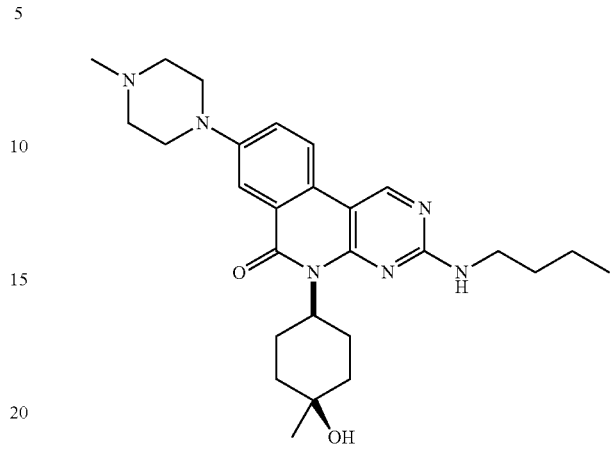

$^1$H NMR (400 MHz, Methanol-$d_4$) δ 8.98 (s, 1H), 8.06 (d, J=8.9 Hz, 1H), 7.73 (d, J=2.7 Hz, 1H), 7.46 (dd, J=8.9, 2.8 Hz, 1H), 5.52 (br s, 1H), 3.48 (br s, J=7.7 Hz, 2H), 3.32 (app m, J=5.2 Hz, 4H), 3.25-3.12 (br s, 2H), 2.69-2.61 (m, 4H), 2.36 (s, 3H), 1.84 (d, J=13.0 Hz, 2H), 1.69-1.55 (m, 4H), 1.51-1.42 (m, 4H), 1.26 (s, 3H), 0.98 (t, J=7.4 Hz, 3H). LCMS: Purity 99%, MS (m/e) 479 (MH$^+$).

trans-3-(Butylamino)-8-((R)-3,4-dimethylpiperazin-1-yl)-5-(4-hydroxycyclohexyl)pyrimido[4,5-c]isoquinolin-6(5H)-one

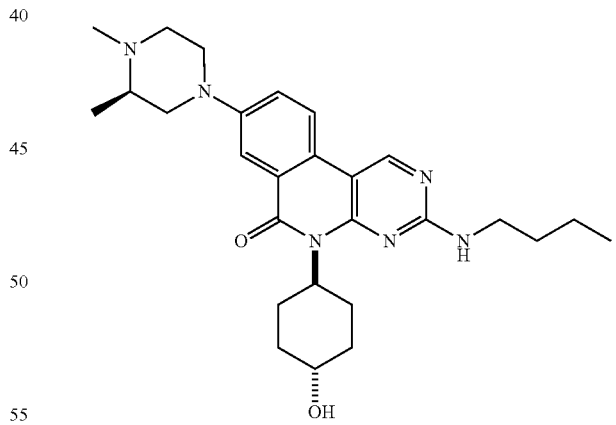

$^1$H NMR (400 MHz, Methanol-$d_4$) δ 8.95 (s, 1H), 8.02 (d, J=9.0 Hz, 1H), 7.68 (d, J=2.5 Hz, 1H), 7.43 (dd, J=8.9, 2.7 Hz, 1H), 5.56 (br s, 1H), 3.73-3.60 (m, 3H), 3.44 (t, J=7.2 Hz, 2H), 3.01-2.87 (m, 4H), 2.56 (dd, J=12.0, 10.2 Hz, 1H), 2.46 (td, J=12.6, 12.0, 3.2 Hz, 1H), 2.36 (s, 3H), 2.35-2.31 (m, 1H), 2.09 (d, J=11.1 Hz, 2H), 1.72-1.59 (m, 4H), 1.52-1.42 (m, 4H), 1.19 (d, J=6.3 Hz, 3H), 0.99 (t, J=7.3 Hz, 3H). LCMS: Purity 98%, MS (m/e) 479 (MH$^+$).

263 trans-3-(((1-Ethylcyclobutyl)methyl)amino)-5-(4-hydroxycyclohexyl)-8-(4-methylpiperazin-1-yl)pyrimido[4,5-c]isoquinolin-6(5H)-one

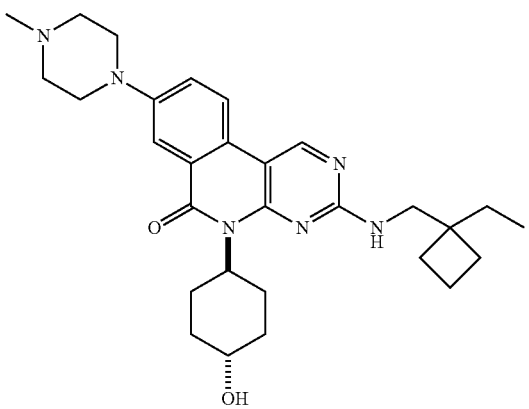

LCMS: Purity 98%, MS (m/e) 505 (MH⁺).

trans-3-((Cyclobutylmethyl)amino)-5-(4-hydroxycyclohexyl)-8-(4-methylpiperazin-1-yl)pyrimido[4,5-c]isoquinolin-6(5H)-one

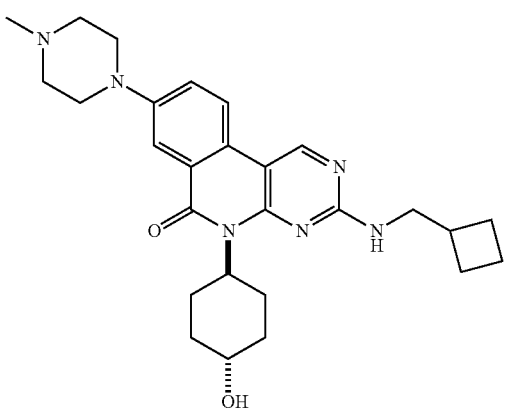

¹H NMR (400 MHz, Methanol-d₄) δ 8.98 (s, 1H), 8.06 (d, J=9.0 Hz, 1H), 7.71 (d, J=2.0 Hz, 1H), 7.46 (dd, J=8.9, 2.8 Hz, 1H), 5.58 (br s, 1H), 3.74-3.67 (m, 1H), 3.50 (d, J=7.1 Hz, 2H), 3.33-3.31 (overlapped m, 4H), 2.91 (br s, 2H), 2.73-2.65 (app m, 1H), 2.66-2.64 (app m, 4H), 2.37 (s, 3H), 2.19-2.06 (m, 4H), 1.99-1.89 (m, 2H), 1.86-1.78 (m, 2H), 1.69 (d, J=11.2 Hz, 2H), 1.48 (app qd, J=13.3, 12.9, 3.4 Hz, 2H). LCMS: Purity 98%, MS (m/e) 477 (MH⁺).

264 trans-3-((2,2-Difluorobutyl)amino)-5-(4-hydroxycyclohexyl)-8-(4-methylpiperazin-1-yl)pyrimido[4,5-c]isoquinolin-6(5H)-one

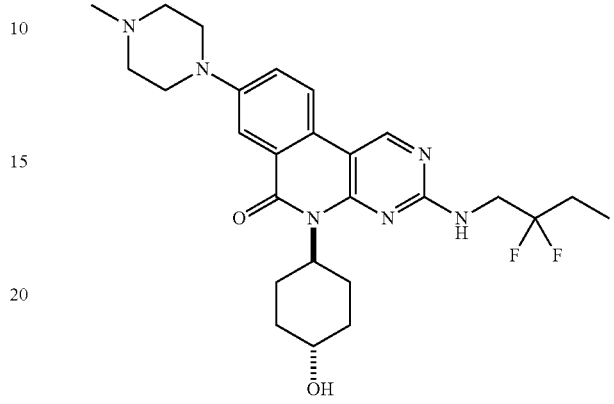

¹H NMR (400 MHz, DMSO-d₆) δ 9.18 (s, 1H), 8.18 (d, J=9.0 Hz, 1H), 7.80 (br s, 1H), 7.56 (d, J=2.6 Hz, 1H), 7.48 (dd, J=8.9, 2.7 Hz, 1H), 5.40 (br s, 1H), 4.62 (s, 1H), 3.86 (td, J=14.0, 6.5 Hz, 2H), 3.52 (br s, 1H), 3.23-3.21 (app m, 4H), 2.75 (br s, 2H), 2.47-2.45 (overlapped m, 4H), 2.21 (s, 3H), 2.00-1.85 (m, 4H), 1.53 (d, J=10.9 Hz, 2H), 1.30 (q, J=10.9 Hz, 2H), 0.99 (t, J=7.5 Hz, 3H). LCMS: Purity 98%, MS (m/e) 501 (MH⁺).

trans-3-(((1-Ethylcyclopropyl)methyl)amino)-5-(4-hydroxycyclohexyl)-8-(4-methylpiperazin-1-yl)pyrimido[4,5-c]isoquinolin-6(5H)-one

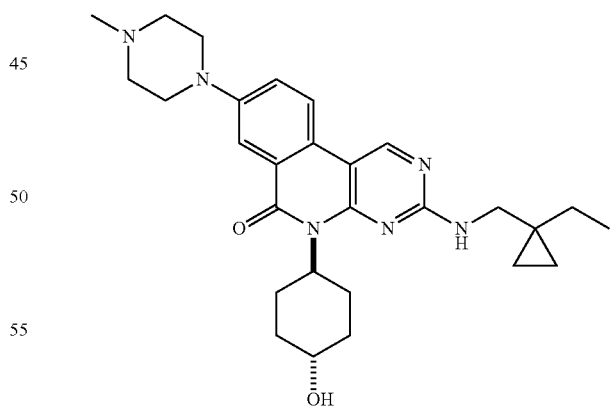

¹H NMR (400 MHz, DMSO-d₆) δ 9.12 (s, 1H), 8.14 (d, J=9.0 Hz, 1H), 7.55 (d, J=2.6 Hz, 1H), 7.46 (app dd, J=8.9, 2.6 Hz, 2H), 5.44 (br s, 1H), 4.63 (s, 2H), 3.51 (br s, 1H), 3.37 (d, J=6.2 Hz, 2H), 3.24-3.16 (m, 4H), 2.74 (br s, 2H), 2.47-2.45 (overlapped m, 4H), 2.21 (s, 3H), 1.94 (d, J=11.3 Hz, 2H), 1.53 (d, J=12.0 Hz, 2H), 1.36-1.26 (m, 4H), 0.91 (t, J=7.3 Hz, 3H), 0.45 (app s, 2H), 0.28-0.21 (app m, 2H). LCMS: Purity 99%, MS (m/e) 491 (MH⁺).

265 trans-5-(4-Hydroxycyclohexyl)-8-(4-methylpiper-azin-1-yl)-3-((4,4,4-trifluorobutyl)amino)pyrimido[4,5-c]isoquinolin-6(5H)-one triformic acid salt or solvate

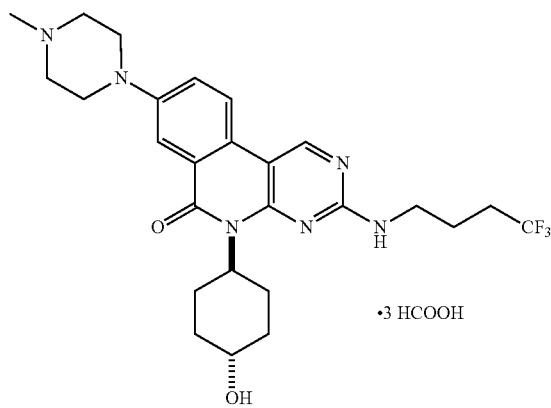

¹H NMR (300 MHz, Methanol-d₄) δ 9.03 (s, 1H), 8.42 (br s, 1H), 8.12 (d, J=7.8 Hz, 1H), 7.75 (s, 1H), 7.51 (d, J=7.8 Hz, 1H), 5.53 (br s, 1H), 3.71 (m, 1H), 3.55 (t, J=7.2 Hz, 2H), 3.43 (m, 4H), 3.02 (m, 4H), 2.78-2.68 (m, 2H), 2.64 (s, 3H), 2.33-2.24 (m, 2H), 2.13-2.08 (m, 2H), 1.98-1.91 (m, 2H), 1.72-1.68 (m, 2H), 1.51-1.46 (m, 2H). LCMS: Purity 98%, MS (m/e) 519 (MH⁺-3HCOOH).

trans-3-((2-Cyclopropylethyl)amino)-5-(4-hydroxy-cyclohexyl)-8-(4-methylpiperazin-1-yl)pyrimido[4,5-c]isoquinolin-6(5H)-one

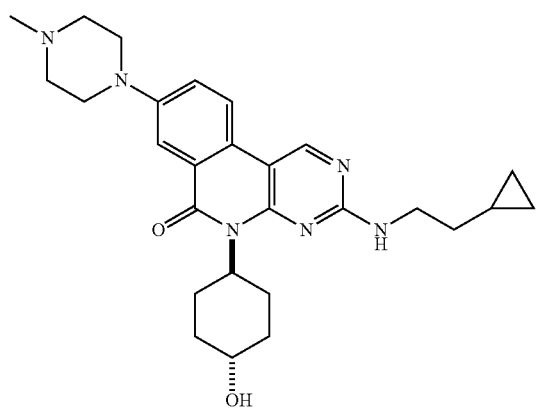

¹H NMR (400 MHz, Methanol-d₄) δ 8.97 (s, 1H), 8.04 (d, J=8.9 Hz, 1H), 7.71 (d, J=2.6 Hz, 1H), 7.45 (dd, J=8.9, 2.7 Hz, 1H), 5.57 (br s, 1H), 3.72 (ddd, J=15.2, 7.4, 4.2 Hz, 1H), 3.55 (t, J=7.2 Hz, 2H), 3.32-3.31 (overlapped m, 4H), 2.91 (br s 2H), 2.65 (t, J=5.1 Hz, 4H), 2.37 (s, 3H), 2.10 (d, J=11.2 Hz, 2H), 1.69 (d, J=11.1 Hz, 2H), 1.56 (q, J=7.1 Hz, 2H), 1.53-1.44 (app m, 2H), 0.86-0.76 (m, 1H), 0.49 (dt, J=8.0, 5.0 Hz, 2H), 0.12 (q, J=5.0 Hz, 2H). LCMS: Purity 98%, MS (m/e) 477 (MH⁺).

266 trans-3-((Cyclopropylmethyl)amino)-5-(4-hydroxy-4-methylcyclohexyl)-8-(4-methylpiperazin-1-yl)pyrimido[4,5-c]isoquinolin-6(5H)-one

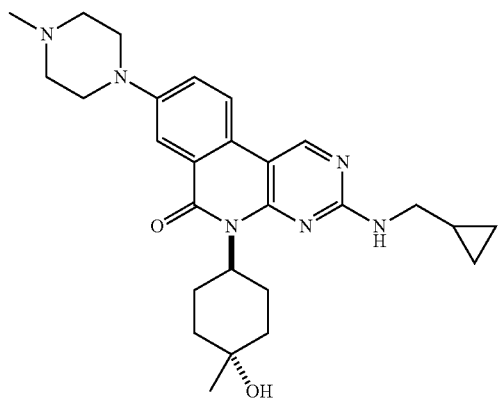

¹H NMR (400 MHz, Methanol-d₄) δ 9.01 (s, 1H), 8.08 (d, J=8.9 Hz, 1H), 7.72 (d, J=2.7 Hz, 1H), 7.48 (dd, J=8.9, 2.8 Hz, 1H), 5.65 (br s, 1H), 3.36-3.33 (overlapped m, 4H), 2.91 (dd, J=24.4, 12.4 Hz, 2H), 2.65 (t, J=5.1 Hz, 4H), 2.37 (s, 3H), 1.83 (d, J=12.2 Hz, 2H), 1.70 (td, J=13.3, 3.8 Hz, 2H), 1.61 (d, J=11.4 Hz, 2H), 1.45 (s, 3H), 1.20-1.14 (m, 2H), 0.54 (ddd, J=8.0, 5.8, 4.4 Hz, 2H), 0.30 (q, J=5.0 Hz, 2H). LCMS: Purity 99%, MS (m/e) 477 (MH⁺).

trans-3-((2-Cyclopropylethyl)amino)-5-(4-hydroxy-4-methylcyclohexyl)-8-(4-methylpiperazin-1-yl)pyrimido[4,5-c]isoquinolin-6(5H)-one

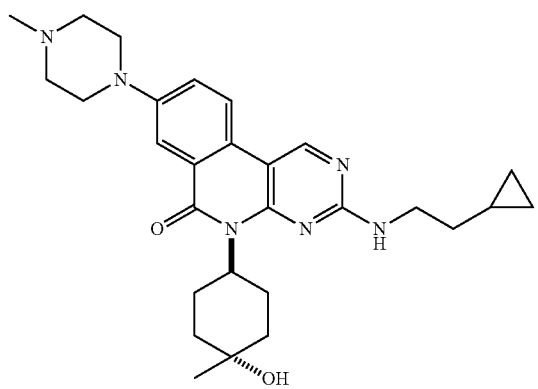

¹H NMR (400 MHz, DMSO-d₆) δ 9.13 (s, 1H), 8.14 (d, J=8.9 Hz, 1H), 7.56 (d, J=2.7 Hz, 1H), 7.46 (overlapped dd, J=9.0, 2.7 Hz, 1H), 5.48 (br s, 1H), 4.40 (s, 1H), 3.44-3.39 (m, 2H), 3.28 (app s, 1H), 3.24-3.17 (m, 4H), 2.75 (app dd, J=25.8, 14.2 Hz, 2H), 2.46-2.44 (overlapped m, 4H), 2.21 (s, 3H), 1.67 (d, J=12.1 Hz, 2H), 1.58-1.42 (m, 6H), 1.29 (s, 3H), 0.80-0.68 (m, 1H), 0.40 (dt, J=8.0, 5.0 Hz, 2H), 0.06 (q, J=5.3 Hz, 2H). LCMS: Purity 99%, MS (m/e) 491 (MH⁺).

267 trans-3-((Cyclopropylmethyl)amino)-5-(4-hydroxy-cyclohexyl)-8-(4-(pyrrolidin-1-yl)piperidin-1-yl)pyrimido[4,5-c]isoauinolin-6(5H)-one

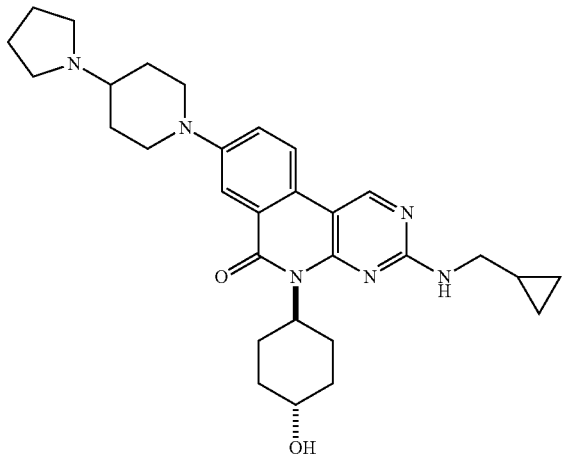

$^1$H NMR (400 MHz, DMSO-d$_6$) δ 9.12 (s, 1H), 8.13 (d, J=8.9 Hz, 1H), 7.56 (d, J=2.7 Hz, 1H), 7.46 (dd, J=9.0, 2.8 Hz, 1H), 5.40 (br s, 1H), 4.62 (s, 1H), 3.69 (dd, J=12.3, 4.7 Hz, 2H), 3.51 (br s, 1H), 3.27 (app s, 1H), 3.22 (d, J=12.0 Hz, 2H), 2.79 (app t, J=11.2 Hz, 3H), 2.15-2.10 (app m, 1H), 1.97-1.90 (m, 4H), 1.65 (app s, 4H), 1.57-1.44 (m, 4H), 1.30 (q, J=11.5 Hz, 2H), 1.15-1.07 (m, 1H), 0.43 (dt, J=8.0, 5.0 Hz, 2H), 0.24 (q, J=5.0 Hz, 2H). LCMS: Purity 96%, MS (m/e) 517 (MH$^+$).

trans-8-(1,4-diazabicyclo[3.2.2]nonan-4-yl)-3-((cyclopropylmethyl)amino)-5-(4-hydroxycyclohexyl)pyrimido[4,5-c]isoquinolin-6(5H)-one

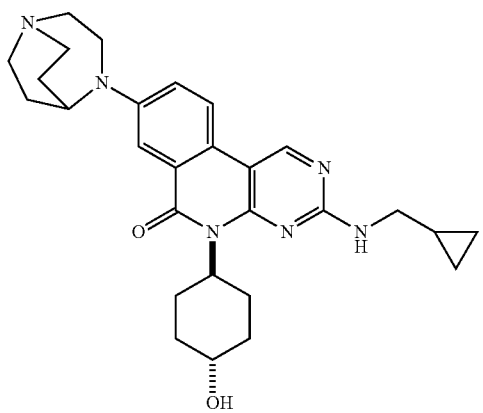

$^1$H NMR (400 MHz, DMSO-d$_6$) δ 9.08 (s, 1H), 8.08 (d, J=9.0 Hz, 1H), 7.48 (br s, 1H), 7.43 (d, J=2.8 Hz, 1H), 7.28 (dd, J=9.1, 2.9 Hz, 1H), 5.40 (br s, 1H), 4.62 (s, 1H), 4.09 (s, 1H), 3.56 (t, J=5.8 Hz, 2H), 3.50 (br s, 1H), 3.22 (d, J=6.6 Hz, 2H), 2.99-2.89 (m, 4H), 2.85-2.78 (m, 4H), 2.02-1.93 (m, 4H), 1.70-1.63 (m, 2H), 1.53 (d, J=11.7 Hz, 2H), 1.30 (q, J=11.0 Hz, 2H), 1.13-1.04 (m, 1H), 0.43 (dt, J=8.0, 5.0 Hz, 2H), 0.24 (q, J=5.0 Hz, 2H). LCMS: Purity 97%, MS (m/e) 401 (MH$^+$).

268 trans-3-((Cyclopropylmethyl)amino)-8-(5,6-dihydro-[1,2,4]triazolo[1,5-a]pyrazin-7(8H)-yl)-5-(4-hydroxycyclohexyl)pyrimido[4,5-c]isoquinolin-6(5H)-one

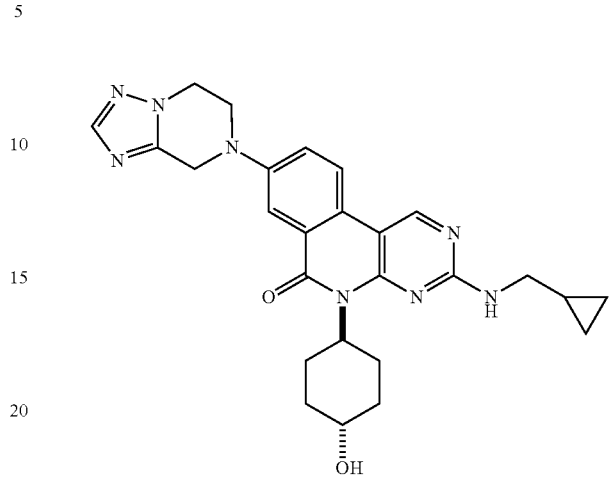

$^1$H NMR (400 MHz, DMSO-d$_6$) δ 9.17 (s, 1H), 8.23 (d, J=8.8 Hz, 1H), 7.97 (s, 1H), 7.69 (d, J=2.8 Hz, 1H), 7.65 (dd, J=9.1, 2.9 Hz, 1H), 7.63 (overlapped s, 1H), 5.41 (br s, 1H), 4.62 (app s, 3H), 4.26 (t, J=5.4 Hz, 2H), 3.95-3.87 (t, J=5.4 Hz, 2H), 3.51 (br s, 1H), 3.24 (t, J=6.2 Hz, 2H), 2.88 (br s, 2H), 1.95 (d, J=10.5 Hz, 2H), 1.55 (d, J=9.4 Hz, 2H), 1.31 (q, J=11.0 Hz, 2H), 1.17-1.11 (m, 1H), 0.44 (dt, J=8.0, 5.0 Hz, 2H), 0.24 (q, J=5.0 Hz, 2H). LCMS: Purity 97%, MS (m/e) 487 (MH$^+$).

trans-3-((Cyclopropylmethyl)amino)-8-((S)-hexahydropyrrolo[1,2-a]pyrazin-2(1H)-yl)-5-(4-hydroxycyclohexyl)pyrimido[4,5-c]isoquinolin-6(5H)-one

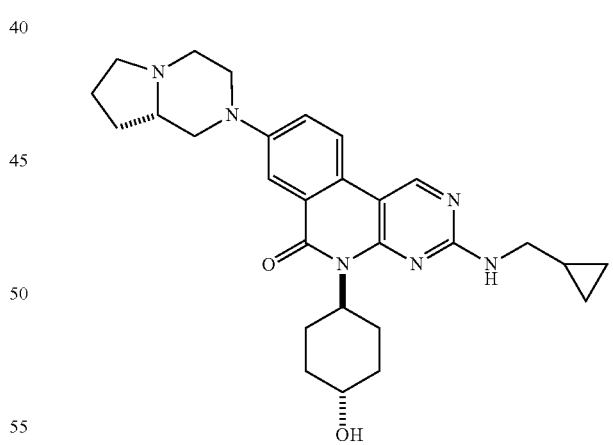

H NMR (400 MHz, Methanol-d$_4$) δ 9.00 (s, 1H), 8.07 (d, J=9.0 Hz, 1H), 7.73 (d, J=2.3 Hz, 1H), 7.49 (dd, J=8.9, 2.8 Hz, 1H), 5.58 (br s, 1H), 3.93 (d, J=10.5 Hz, 1H), 3.82-3.67 (m, 2H), 3.34 (app d, J=6.8 Hz, 2H), 3.23-3.09 (m, 2H), 2.95 (app td, J=11.8, 3.3 Hz, 3H), 2.61 (t, J=10.9 Hz, 1H), 2.44 (td, J=11.4, 3.3 Hz, 1H), 2.29-2.22 (m, 2H), 2.10 (d, J=11.3 Hz, 2H), 1.99-1.93 (m, 1H), 1.93-1.79 (m, 2H), 1.69 (d, J=11.5 Hz, 2H), 1.61-1.42 (m, 3H), 1.20-1.14 (m, 1H), 0.54 (ddd, J=8.0, 5.8, 4.4 Hz, 2H), 0.30 (q, J=5.0 Hz, 2H). LCMS: Purity 97%, MS (m/e) 489 (MH$^+$).

269 trans-3-((Cyclopropylmethyl)amino)-8-((R)-hexahydropyrrolo[1,2-a]pyrazin-2(1H)-yl)-5-(4-hydroxycyclohexyl)pyrimido[4,5-c]isoquinolin-6(5H)-one

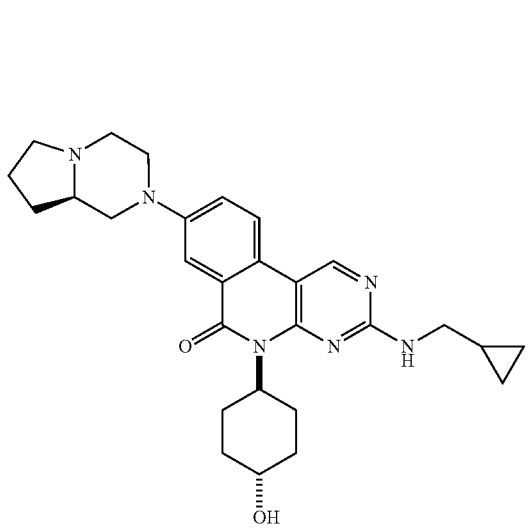

LCMS: Purity 97%, MS (m/e) 489 (MH+).

trans-3-((Cyclopropylmethyl)amino)-5-(4-hydroxycyclohexyl)-8-(4-(2,2,2-trifluoroethyl)piperazin-1-yl)pyrimido[4,5-c]isoquinolin-6(5H)-one

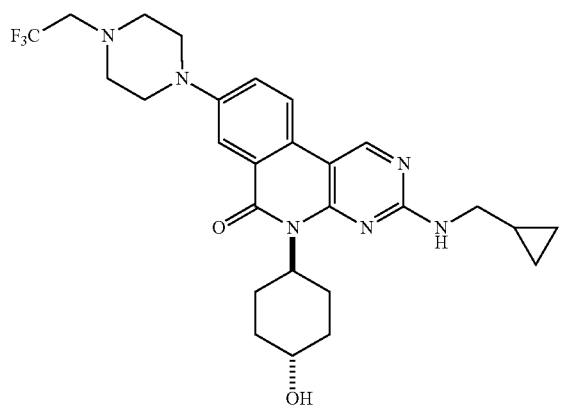

$^1$H NMR (400 MHz, DMSO-d$_6$) δ 9.13 (s, 1H), 8.15 (d, J=8.9 Hz, 1H), 7.62 (br s, 1H), 7.56 (d, J=2.7 Hz, 1H), 7.47 (dd, J=9.0, 2.8 Hz, 1H), 5.40 (br s, 1H), 4.62 (s, 1H), 3.51 (br s, 1H), 3.31-3.17 (app m, 8H), 2.78 (app t, J=5.1 Hz, 6H), 1.94 (d, J=10.6 Hz, 2H), 1.54 (d, J=10.3 Hz, 2H), 1.30 (q, J=11.0 Hz, 2H), 1.17-1.11 (m, 1H), 0.43 (dt, J=8.0, 5.0 Hz, 2H), 0.23 (q, J=5.0 Hz, 2H). LCMS: Purity 97%, MS (m/e) 531(MH+).

270 trans-3-((Cyclopropylmethyl)amino)-8-(4-(2,2-difluoroethyl)piperazin-1-yl)-5-(4-hydroxycyclohexyl)pyrimido[4,5-c]isoquinolin-6(5H)-one

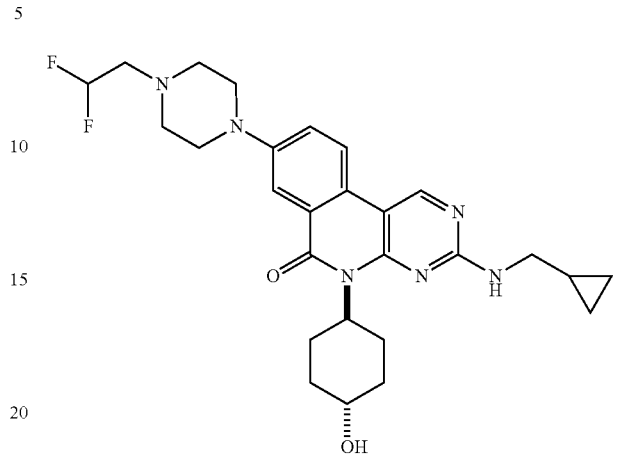

$^1$H NMR (400 MHz, DMSO-d$_6$) δ 9.13 (s, 1H), 8.14 (d, J=8.9 Hz, 1H), 7.60 (br s, 1H), 7.56 (d, J=2.7 Hz, 1H), 7.46 (dd, J=9.0, 2.8 Hz, 1H), 6.17 (tt, J=55.7, 4.3 Hz, 1H), 5.40 (br s, 1H), 4.62 (s, 1H), 3.51 (app br s, 1H), 3.28-3.17 (m, 6H), 2.78 (app td, J=15.7, 4.3 Hz, 4H), 2.69 (app t, J=4.8 Hz, 4H), 1.94 (d, J=10.6 Hz, 2H), 1.54 (d, J=10.3 Hz, 2H), 1.30 (q, J=11.0 Hz, 2H), 1.17-1.11 (m, 1H), 0.43 (dt, J=8.0, 5.0 Hz, 2H), 0.23 (q, J=5.0 Hz, 2H). $^{19}$F NMR (376 MHz, DMSO-d$_6$) δ −118.56 (dt, J=55.8, 15.7 Hz). LCMS: Purity 97%, MS (m/e) 513 (MH+).

trans-3-((Cyclopropylmethyl)amino)-8-((R)-3,4-dimethylpiperazin-1-yl)-5-(4-hydroxycyclohexyl)pyrimido[4,5-c]isoquinolin-6(5H)-one

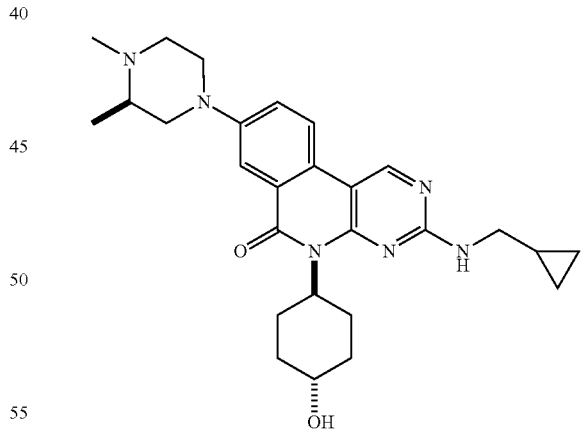

$^1$H NMR (400 MHz, Methanol-d$_4$) δ 8.98 (s, 1H), 8.05 (d, J=9.0 Hz, 1H), 7.69 (d, J=2.4 Hz, 1H), 7.46 (dd, J=9.0, 2.8 Hz, 1H), 5.57 (br s, 1H), 3.78-3.61 (m, 3H), 3.34 (app d, J=6.9 Hz, 2H), 3.03-2.88 (m, 3H), 2.56 (dd, J=12.0, 10.2 Hz, 1H), 2.46 (td, J=12.6, 12.0, 3.2 Hz, 1H), 2.36 (s, 3H), 2.35-2.31 (m, 1H), 2.10 (d, J=11.4 Hz, 2H), 1.69 (d, J=11.1 Hz, 2H), 1.48 (q, J=11.6, 10.5 Hz, 2H), 1.20-1.14 (m, 1H), 1.19 (overlapped app d, J=6.3 Hz, 4H), 0.54 (ddd, J=8.0, 5.8, 4.4 Hz, 2H), 0.30 (q, J=5.0 Hz, 2H). LCMS: Purity 97%, MS (m/e) 477 (MH+).

271 trans-3-((Cyclopropylmethyl)amino)-5-(4-hydroxy-cyclohexyl)-8-((2S,5R)-2,4,5-trimethylpiperazin-1-yl)pyrimido[4,5-c]isoquinolin-6(5H)-one

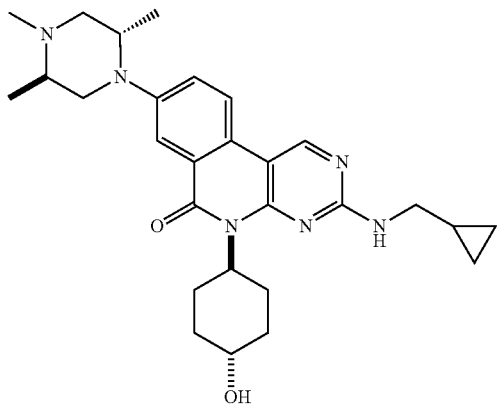

$^1$H NMR (400 MHz, DMSO-d$_6$) δ 9.13 (s, 1H), 8.13 (d, J=8.9 Hz, 1H), 7.58 (br s, 1H), 7.53 (d, J=2.7 Hz, 1H), 7.47 (dd, J=9.0, 2.8 Hz, 1H), 5.42 (br s, 1H), 4.62 (s, 1H), 3.63 (d, J=11.4 Hz, 2H), 3.50 (br s, 1H), 3.23 (d, J=6.6 Hz, 2H), 2.75 (br s, 2H), 2.43 (t, J=11.3 Hz, 2H), 2.29-2.22 (m, 2H), 2.18 (s, 3H), 1.94 (d, J=11.5 Hz, 2H), 1.54 (d, J=10.8 Hz, 2H), 1.30 (q, J=10.9 Hz, 2H), 1.08 (overlapped d, J=6.1 Hz, 7H), 0.43 (dt, J=8.0, 5.0 Hz, 2H), 0.23 (q, J=5.0 Hz, 2H). LCMS: Purity 98%, MS (m/e) 491 (MH$^+$).

272 trans-3-((Cyclopropylmethyl)amino)-8-(4-cyclopropylpiperazin-1-yl)-5-(4-hydroxycyclohexyl)pyrimido[4,5-c]isoquinolin-6(5H)-one

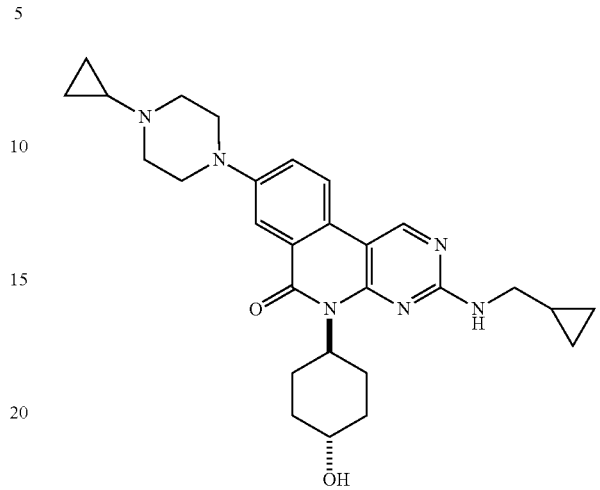

$^1$H NMR (400 MHz, DMSO-d$_6$) δ 9.13 (s, 1H), 8.14 (d, J=8.9 Hz, 1H), 7.55 (d, J=2.7 Hz, 1H), 7.58 (br s, 1H), 7.46 (dd, J=9.0, 2.8 Hz, 1H), 5.42 (s, 1H), 4.62 (s, 1H), 3.52 (br s, 1H), 3.23 (t, J=6.4 Hz, 2H), 3.20-3.12 (m, 4H), 2.75 (br s, 2H), 2.73-2.63 (m, 4H), 1.94 (d, J=11.7 Hz, 2H), 1.72-1.60 (m, 1H), 1.54 (d, J=10.5 Hz, 2H), 1.30 (q, J=11.4 Hz, 2H), 1.20-1.02 (m, 1H), 0.52-0.37 (m, 4H), 0.34 (dt, J=6.9, 4.0 Hz, 2H), 0.24 (q, J=4.9 Hz, 2H). LCMS: Purity 97%, MS (m/e) 489 (MH$^+$).

trans-3-((Cyclopropylmethyl)amino)-5-(4-hydroxy-cyclohexyl)-8-(4-isopropylpiperazin-1-yl)pyrimido[4,5-c]isoquinolin-6(5H)-one

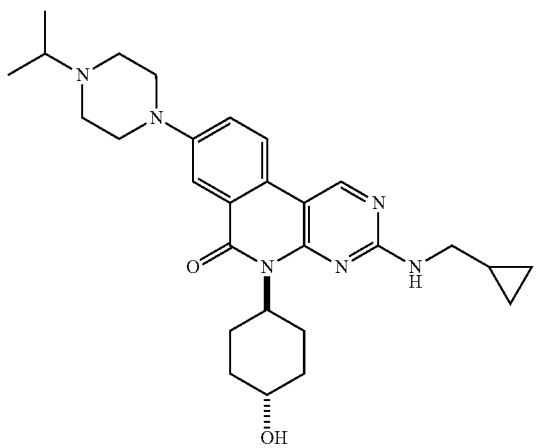

$^1$H NMR (400 MHz, DMSO-d$_6$) δ 9.13 (s, 1H), 8.14 (d, J=8.9 Hz, 1H), 7.58 (br s, 1H), 7.54 (d, J=2.8 Hz, 1H), 7.45 (dd, J=9.0, 2.8 Hz, 1H), 5.73 (br s, 1H), 4.62 (s, 1H), 3.51 (br s, 1H), 3.27-3.15 (m, 6H), 2.75 (br s, 2H), 2.69 (p, J=6.7 Hz, 1H) 2.59-2.54 (m, 4H), 1.94 (d, J=11.1 Hz, 2H), 1.54 (d, J=11.4 Hz, 2H), 1.30 (q, J=11.3 Hz, 2H), 1.17-1.06 (m, 1H), 0.99 (d, J=6.5 Hz, 6H), 0.43 (dt, J=8.0, 5.0 Hz, 2H), 0.23 (q, J=5.0 Hz, 2H). LCMS: Purity 97%, MS (m/e) 491 (MH$^+$).

trans-3-((Cyclopropylmethyl)amino)-5-(4-hydroxy-cyclohexyl)-8-(4-(oxetan-3-yl)piperazin-1-yl)pyrimido[4,5-c]isoquinolin-6(5H)-one

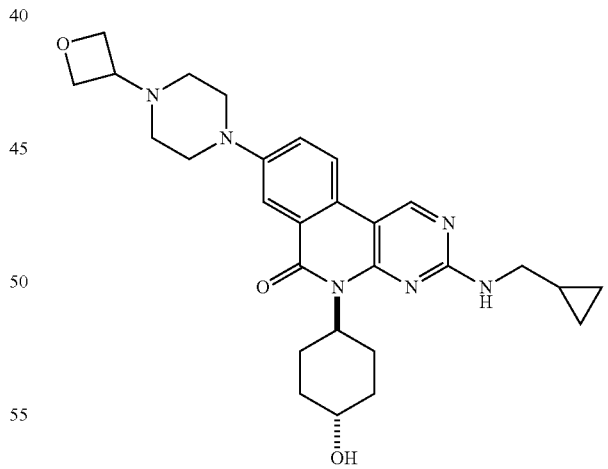

$^1$H NMR (400 MHz, DMSO-d$_6$) δ 9.13 (s, 1H), 8.15 (d, J=8.9 Hz, 1H), 7.62 (br s, 1H), 7.56 (d, J=2.7 Hz, 1H), 7.47 (dd, J=9.0, 2.8 Hz, 1H), 5.40 (br s, 1H), 4.63 (s, 1H), 4.56 (t, J=6.5 Hz, 2H), 4.46 (t, J=6.1 Hz, 2H), 3.52 (br s, 1H), 3.44 (p, J=6.5 Hz, 1H), 3.27-3.19 (m, 6H), 2.77 (br s, 2H), 2.45-2.37 (m, 4H), 1.94 (d, J=11.4 Hz, 2H), 1.54 (d, J=11.8 Hz, 2H), 1.30 (q, J=11.5 Hz, 2H), 1.21-0.95 (m, 1H), 0.43 (dt, J=8.0, 5.0 Hz, 2H), 0.24 (q, J=5.0 Hz, 2H). LCMS: Purity 97%, MS (m/e) 505 (MH$^+$).

5-((4-Aminocyclohexyl)methyl)-3-(butylamino)-8-(4-methylpiperazin-1-yl)pyrimido[4,5-c]isoquinolin-6(5H)-one

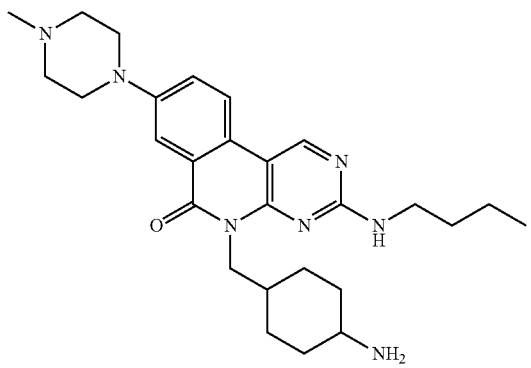 [SMILES: CCCCNc1ncc2c3ccc(N4CCN(C)CC4)cc3c(=O)n(CC3CCC(N)CC3)c2n1]

5-((4-Aminocyclohexyl)methyl)-3-(butylamino)-8-(4-methylpiperazin-1-yl)pyrimido[4,5-c]isoquinolin-6(5H)-one was prepared by the acid hydrolysis of tert-butyl (4-((3-(butylamino)-8-(4-methylpiperazin-1-yl)-6-oxopyrimido[4,5-c]isoquinolin-5(6H)-yl)methyl)cyclohexyl)carbamate analogous to the preparation of 5-((4-aminocyclohexyl)methyl)-3-(butylamino)-8-((4-methylpiperazin-1-yl)methyl)pyrimido[4,5-c]isoquinolin-6(5H)-one. ¹H NMR (400 MHz, Methanol-d₄) δ 8.98 (s, 1H), 8.08 (d, J=8.8 Hz, 1H), 7.73 (d, J=2.6 Hz, 1H), 7.48 (dd, J=9.0, 2.6 Hz, 1H), 4.33 (d, J=7.3 Hz, 2H), 3.48-3.39 (m, 2H), 3.36-3.29 (hidden m, 4H), 2.65 (t, J=5.0 Hz, 4H), 2.61-2.58 (m, 1H), 2.37 (s, 3H), 2.01-1.86 (m, 1H), 1.99 (d, J=14.5 Hz, 2H), 1.73-1.59 (m, 4H), 1.46 (p, J=7.4 Hz, 2H), 1.28-1.17 (m, 2H), 1.12-0.95 (m, 5H). LCMS: Purity 98%, MS (m/e) 478 (MH⁺).

trans-3-(Butylamino)-5-(4-hydroxycyclohexyl)-8-(piperazin-1-yl)pyrimido[4,5-c]isoquinolin-6(5H)-one

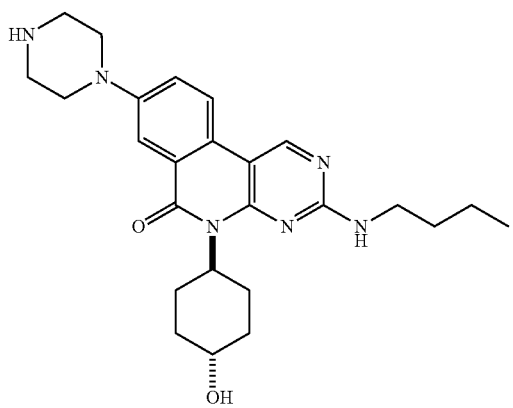

Analogous to the preparation of trans-3-(Butylamino)-5-(4-hydroxycyclohexyl)-8-(piperazin-1-ylmethyl)pyrimido[4,5-c]isoquinolin-6(5H)-one, trans-3-(butylamino)-5-(4-hydroxycyclohexyl)-8-(piperazin-1-yl)pyrimido[4,5-c]isoquinolin-6(5H)-one was obtained after acidic hydrolysis of trans-tert-butyl 4-(3-(butylamino)-5-(4-hydroxycyclohexyl)-6-oxo-5,6-dihydropyrimido[4,5-c]isoquinolin-8-yl)piperazine-1-carboxylate. The crude reaction mixture was purified by preparative HPLC on reverse phase column by CH₃CN:H₂O an an eluting solvent containing formic acid modifier. Upon neutralizing concentrated fraction with aq. NaHCO₃, the resulting white solid was collected by filtration and suction dried to obtain trans-3-(butylamino)-5-(4-hydroxycyclohexyl)-8-(piperazin-1-yl)pyrimido[4,5-c]isoquinolin-6(5H)-one. ¹H NMR (400 MHz, DMSO-d₆) δ 9.12 (s, 1H), 8.14 (d, J=8.8 Hz, 1H), 7.54 (d, J=2.7 Hz, 1H), 7.50 (br s, 0.7H), 7.45 (dd, J=9.0, 2.7 Hz, 1H), 7.07 (br s, 0.3H), 5.40 (br s, 1H), 4.63 (s, 1H), 3.50 (s, 1H), 3.34-3.39 (app m, 2H), 3.12 (t, J=5.1 Hz, 4H), 2.85 (t, J=4.9 Hz, 4H), 2.74 (br s, 2H), 1.94 (d, J=12.1 Hz, 2H), 1.60-1.51 (m, 4H), 1.40-1.21 (m, 4H), 0.91 (t, J=7.3 Hz, 3H). LCMS: Purity 99%, MS (m/e) 451 (MH⁺).

3-(Butylamino)-5-(4-oxocyclohexyl)-8-(piperazin-1-yl)pyrimido[4,5-c]isoquinolin-6(5H)-one

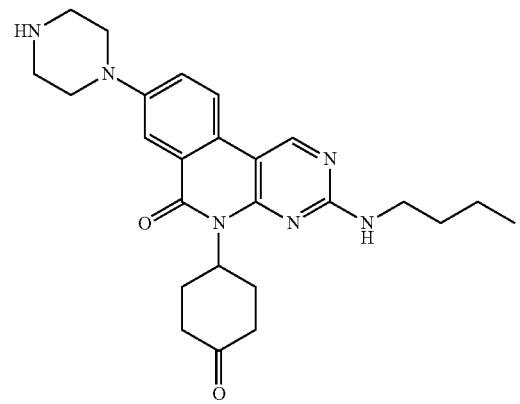 [SMILES: CCCCNc1ncc2c3ccc(N4CCNCC4)cc3c(=O)n(C3CCC(=O)CC3)c2n1]

LCMS: Purity 97%, MS (m/e) 449 (MH⁺).

trans-3-((Cyclopropylmethyl)amino)-5-(4-hydroxycyclohexyl)-8-(piperazin-1-yl)pyrimido[4,5-c]isoquinolin-6(5H)-one

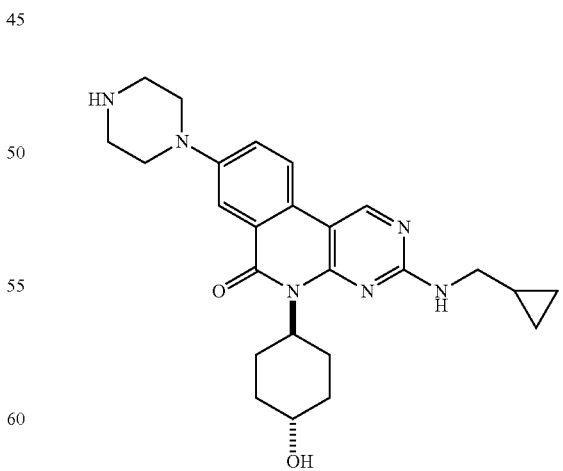

Analogous to the preparation of trans-3-(butylamino)-5-(4-hydroxycyclohexyl)-8-(piperazin-1-yl)pyrimido[4,5-c]isoquinolin-6(5H)-one, trans-3-((cyclopropylmethyl)amino)-5-(4-hydroxycyclohexyl)-8-(piperazin-1-yl)

pyrimido[4,5-c]isoquinolin-6(5H)-one was obtained after acidic hydrolysis of trans-tert-butyl 4-(3-((cyclopropylmethyl)amino)-5-(4-hydroxycyclohexyl)-6-oxo-5,6-dihydropyrimido[4,5-c]isoquinolin-8-yl)piperazine-1-carboxylate. $^1$H NMR (400 MHz, DMSO-$d_6$) δ 9.12 (s, 1H), 8.14 (d, J=9.0 Hz, 1H), 7.57 (br s, 1H), 7.54 (d, J=2.7 Hz, 1H), 7.45 (dd, J=8.9, 2.8 Hz, 1H), 5.40 (br s, 1H), 4.62 (s, 1H), 3.51 (br s, 1H), 3.23 (t, J=6.3 Hz, 2H), 3.15-3.07 (m, 4H), 2.88-2.77 (m, 6H), 2.41 Sapp br s, 1H), 1.94 (d, J=11.4 Hz, 2H), 1.54 (d, J=11.8 Hz, 2H), 1.30 (q, J=11.4 Hz, 2H), 1.17-1.06 (m, 1H), 0.43 (dt, J=8.0, 5.0 Hz, 2H), 0.23 (q, J=5.0 Hz, 2H). LCMS: Purity 98%, MS (m/e) 449 (MH$^+$).

trans-4-((5-Bromo-2-chloropyrimidin-4-yl)amino)cyclohexan-1-ol

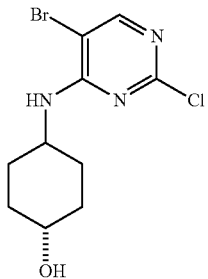

i-Pr$_2$NEt (15 mL, 11 g, 86.6 mmol) was added to a stirring ice-salt bath cooled solution of 5-bromo-2,4-dichloropyrimidine (10 g, 43.9 mmol) in i-PrOH (20 mL) over a period of 20 min. Subsequently, a solution of trans-4-aminocyclohexan-1-ol (5 g, 43.4 mmol) dissolved in i-PrOH (25 mL) was added over a period of 2 h. Upon complete addition of trans-4-aminocyclohexan-1-ol, reaction mixture was maintained at the same temperature for additional period (2 h) and allowed to warm to room temperature. After 18 h, reaction solution was concentrated under reduced pressure, diluted with aq. NaHCO$_3$ and extracted into EtOAc (3×100 mL). Combined organic layers were washed with water (75 mL), aq. NaCl (70 mL), stirred over MgSO$_4$, and fitered through Celite®. Upon concentrating filtrate, the resulting pale yellow crystalline solid (12G) was stirred in 20% EtOAc/hexanes (60 mL) at 90° C. for 20 min, cooled to room temperature and suction filtered. The crystalline white solid on the funnel was further washed with 20% EtOAc/hexanes (15 mL) to provide trans-4-((5-bromo-2-chloropyrimidin-4-yl)amino)cyclohexan-1-ol (9 g). $^1$H NMR (400 MHz, DMSO-$d_6$) δ 8.20 (s, 1H), 7.19 (d, J=8.2 Hz, 1H), 4.55 (d, J=4.5 Hz, 1H), 3.84 (tdt, J=11.9, 8.1, 4.1 Hz, 1H), 3.36 (app ddt, J=15.0, 10.8, 4.2 Hz, 1H), 1.82 (app d, J=12.4 Hz, 2H), 1.74 (app d, J=12.5 Hz, 2H)., 1.50 (app qd, J=12.9, 3.3 Hz, 2H), 1.21 (app qd, J=13.3, 3.4 Hz, 2H). LCMS: Purity 99%, MS (m/e) 307 (MH$^+$).

trans-4-(((5-Bromo-2-chloropyrimidin-4-yl)amino)methyl)cyclohexan-1-ol

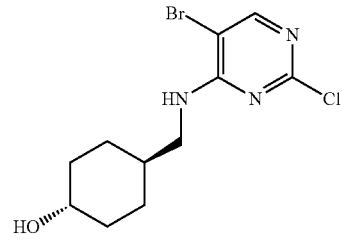 [SMILES: O[C@H]1CC[C@H](CNc2nc(Cl)ncc2Br)CC1]

trans-(4-Aminomethyl)cyclohexan-1-ol (2.0 g, 12 mmol) was added all at once to a stirring heterogeneous mixture of 5-bromo-2,4-dichloropyrimidine (3.85 g, 16.9 mmol), Na$_2$CO$_3$ (2.6 g, 24.5 mmol) in 2-propanol (10 mL) and water (10 mL). After stirring heterogeneous reaction mixture at room temperature for 18 h, reaction mixture was concentrated and diluted with water (30 mL) followed by EtOAc (150 mL). Upon separating organic layer and further extraction of aqueous layer with EtOAc (2×100 mL), combined organic layers were washed with water (30 mL), saturated aq. NaCl solution (30 mL), dried over MgSO$_4$, filtered and concentrated under reduced pressure. Subsequent purification of crude concentrate by silica gel flash column chromatography [Combiflash Torrent® with RediSep® silica gel column 80 g and eluted with 30-50% EtOAc/hexanes solvent gradient], concentrating the desired product fractions, the resulting white solid was heated in 20% EtOAc/hexanes (15 mL) for 5 min, cooled to room temperature, filtered and dried to obtain trans-4-(((5-bromo-2-chloropyrimidin-4-yl)amino)methyl)cyclohexan-1-ol (1.6 g, 41%) $^1$H NMR (400 MHz, DMSO-$d_6$) δ 8.19 (s, 1H), 7.65 (t, J=5.8 Hz, 1H), 4.44 (s, 1H), 3.33 (overlapped m 1H), 3.19 (t, J=6.5 Hz, 2H), 1.79 (d, J=12.3, 3.1 Hz, 2H), 1.62 (d, J=12.3 Hz, 2H), 1.58-1.45 (m, 1H), 1.13-0.99 (m, 2H), 0.99-0.81 (m, 2H). LCMS: Purity 97%, MS (m/e) 321 (MH$^+$).

trans-tert-Butyl (4-(((5-bromo-2-chloropyrimidin-4-yl)amino)methyl)cyclohexyl)carbamate

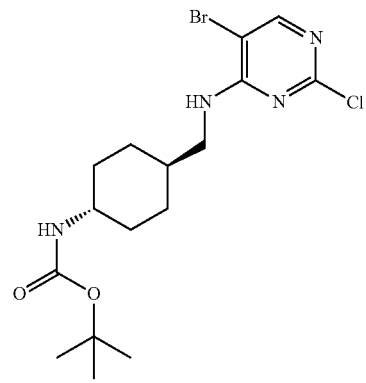 [SMILES: CC(C)(C)OC(=O)N[C@H]1CC[C@H](CNc2nc(Cl)ncc2Br)CC1]

trans-tert-Butyl (4-(((5-bromo-2-chloropyrimidin-4-yl)amino)methyl)cyclohexyl)carbamate was obtained in an analogous manner to the preparation of trans-4-(((5-bromo-2-chloropyrimidin-4-yl)amino)methyl)cyclohexan-1-ol. $^1$H NMR (400 MHz, DMSO-$d_6$) δ 8.20 (s, 1H), 7.67 (t, J=5.8

Hz, 1H), 6.64 (d, J=8.0 Hz, 1H), 3.18 (t, J=6.4 Hz, 2H), 3.14-3.08 (m, 1H)., 1.74 (d, J=11.0 Hz, 2H), 1.64 (d, J=12.2 Hz, 2H), 1.56-1.47 (m, 1H), 1.35 (s, 9H), 1.07 (q, J=12.1, 11.5 Hz, 2H), 0.93 (q, J=12.4, 11.5 Hz, 2H). LCMS: Purity 99%, MS (m/e) 419 (MH+).

trans-4-((2-Amino-5-bromopyrimidin-4-yl)amino) cyclohexan-1-ol

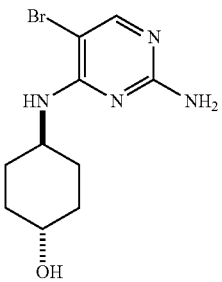

trans-4-aminocyclohexan-1-ol (1.6 g, 13.8 mmol), 5-bromo-2,4-dichloropyrimidine (2.5 g, 11.9 mmol) and i-Pr₂NEt (3.1 mL, 2.3 g, 17.7 mmol) in 2-propanol were stirred in a sealed tube at 100° C. After 16 h, reaction mixture was cooled to room temperature, concentrated and purified silica gel flash column chromatography [Combiflash Torrent® with RediSep® silica gel column 40 g and eluted with 0-5% MeOH/CH₂Cl₂ solvent gradient] to obtain off-white solid of trans-4-((2-Amino-5-bromopyrimidin-4-yl)amino)cyclohexan-1-ol (2.1 g). ¹H NMR (400 MHz, DMSO-d₆) δ 7.84 (s, 1H), 6.61 (s, 2H), 6.44 (d, J=8.3 Hz, 1H), 4.55 (s, 1H), 3.94-3.84 (m, 1H), 3.38-3.33 (app m, 1H), 1.82 (d, J=11.6 Hz, 2H), 1.74 (d, J=10.3 Hz, 2H), 1.44 (q, J=11.6, 10.1 Hz, 2H), 1.23-1.07 (m, 2H). LCMS: Purity 99%, MS (m/e) 287 (MH+).

6-((5-Bromo-2-chloropyrimidin-4-yl)amino)spiro [3.3]heptan-2-ol

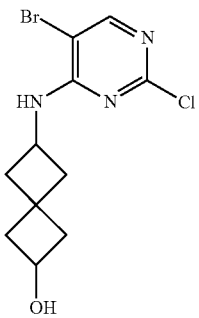 [SMILES: OC1CC2(C1)CC(Nc1nc(Cl)ncc1Br)C2]

tert-Butyl (6-hydroxyspiro[3.3]heptan-2-yl)carbamate (2.0 g, 8.79 mmol) in EtOAc (50 mL) was treated 4.0 N HCl in dioxane (20 mL, 80 mmol) at room temperature and stirred under nitrogen 2 h. Upon concentrating heterogeneous reaction, the resulting 6-aminospiro[3.3]heptan-2-ol hydrochloride was sitrrred in 2-propanol (10 mL)/water (10 mL) at 0° C., treated with solid Na₂CO₃ (2.8 g, 26.40 mmol) followed by 5-bromo-2,4-dichloropyrimidine (3.4 g, 14.9 mmol) portion-wise over a period of 20 min under nitrogen and allowed to warm to room tempeurature. After overnight, reaction mixture was concentrated and diluted with water (30 mL)/EtOAc (150 mL). Upon separating organic layer and further extraction of aqueous layer with EtOAc (2×100 mL), combined organic layers were washed with water (30 mL), saturated aq. NaCl solution (30 mL), dried over MgSO₄, filtered and concentrated under reduced pressure. Subsequent purification of crude visclous liquid by silica gel column chromatography [Combiflash Torrent® with RediSep® silica gel column 80 g and eluted with 30-50-70% EtOAc/hexanes solvent gradient] provided 6-((5-Bromo-2-chloropyrimidin-4-yl)amino)spiro[3.3]heptan-2-ol. ¹H NMR (400 MHz, DMSO-d₆) δ 8.21 (s, 1H), 7.69 (d, J=7.2 Hz, 1H), 4.33 (app h, J=8.1 Hz, 2H), 3.94 (p, J=7.3 Hz, 1H), 2.42-2.32 (m, 1H), 2.30-2.24 (m, 1H), 2.23-2.09 (m, 4H), 1.81 (ddd, J=13.5, 10.8, 7.7 Hz, 2H). LCMS: Purity 99%, MS (m/e) 318 (MH+).

trans-4-((5-Bromo-2-chloropyrimidin-4-yl)amino)-1-methylcyclohexan-1-ol

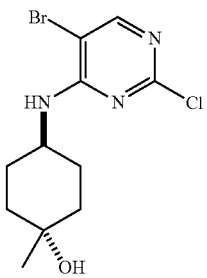

trans-4-((5-Bromo-2-chloropyrimidin-4-yl)amino)-1-methylcyclohexan-1-ol was obtained as a white solid after following analogous reaction procedure and isolation described for trans-4-((5-bromo-2-chloropyrimidin-4-yl) amino)cyclohexan-1-ol. ¹H NMR (400 MHz, DMSO-d₆) δ 8.21 (d, J=0.8 Hz, 1H), 7.20 (d, J=8.3 Hz, 1H), 4.30 (br s, 1H), 3.96-3.82 (m, 1H), 1.71-1.49 (m, 6H), 1.42 (td, J=12.7, 4.9 Hz, 2H), 1.15 (s, 3H). LCMS: Purity 99%, MS (m/e) 320 (MH+).

cis-4-((5-Bromo-2-chloropyrimidin-4-yl)amino)-1-methylcyclohexan-1-ol

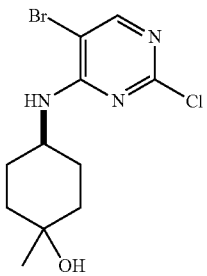

cis-4-((5-Bromo-2-chloropyrimidin-4-yl)amino)-1-methylcyclohexan-1-ol was prepared analogous to trans-4-((5-bromo-2-chloropyrimidin-4-yl)amino)cyclohexan-1-ol to obtain a white solid. ¹H NMR (400 MHz, DMSO-d₆) δ 8.20 (d, J=0.8 Hz, 1H), 7.21 (d, J=8.1 Hz, 1H), 4.03 (s, 1H), 3.87-3.83 (app m, 1H), 1.87-1.77 (m, 2H), 1.59-1.48 (m, 4H), 1.35 (td, J=14.5, 13.8, 4.2 Hz, 2H), 1.10 (s, 3H). LCMS: Purity 98%, MS (m/e) 320 (MH⁺).

trans-4-((5-Bromo-2-(butylamino)pyrimidin-4-yl)amino)cyclohexan-1-ol

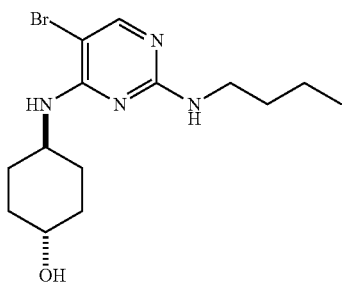

A solution of trans-4-((5-bromo-2-chloropyrimidin-4-yl)amino)cyclohexan-1-ol (6.3 g, 20.5 mmol), n-butylamine (6.1 mL, 4.5 g, 61.5 mmol) and ethanol (10 ml) was stirred and heated in a sealed tube at 90° C. After 16 h, pale yellow reaction solution was cooled to room temperature and progress of reaction was analyzed by LC/MS which indicated complete consumption of trans-4-((5-bromo-2-chloropyrimidin-4-yl)amino)cyclohexan-1-ol to trans-4-((5-bromo-2-(butylamino)pyrimidin-4-yl)amino)cyclohexan-1-ol quantitatively. The crude yellow semi-solid obtained after concentration of reaction solution was diluted with diluted with aq. NaHCO₃ (30 ml) and extracted into EtOAc (3×75 mL). Combined organic layers were washed with water (35 mL), aq. NaCl (30 mL), stirred over MgSO₄, and fitered through Celite®. Upon concentrating filtrate, the resulting pale yellow crystalline solid (8G) was purified by silica gel flash column chromatography [Combiflash Torrent® with RediSep® silica gel column 80 g and eluted with 30-65% EtOAc/hexanes solvent gradient] and obtained trans-4-((5-bromo-2-(butylamino)pyrimidin-4-yl)amino)cyclohexan-1-ol (5.9 g) as a white solid. ¹H NMR (400 MHz, DMSO-d₆) δ 7.76 (s, 1H), 6.70 (s, 1H), 5.98 (s, 1H), 4.52 (d, J=4.4 Hz, 1H), 3.89-3.78 (m, 1H), 3.41-3.32 (m, 1H), 3.14 (q, J=6.9 Hz, 2H), 1.86-1.77 (m, 4H), 1.51-1.33 (m, 4H), 1.33-1.24 (m, 2H), 1.24-1.11 (m, 2H), 0.87 (t, J=7.3 Hz, 3H). LCMS: Purity 98%, MS (m/e) 344 (MH⁺).

The following compounds were prepared and isolated by the reaction of respective amine and corresponding 5-bromo-4-amino(substituted)pyrimidines in similar manner to trans-4-((5-bromo-2-(butylamino)pyrimidin-4-yl)amino)cyclohexan-1-ol trans-4-(((5-Bromo-2-(butylamino)pyrimidin-4-yl)amino)methyl)cyclohexan-1-ol

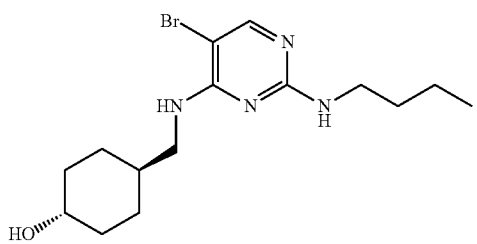 [SMILES: CCCCNc1ncc(Br)c(NC[C@H]2CC[C@H](O)CC2)n1]

¹H NMR (400 MHz, DMSO-d₆) δ 7.74 (s, 1H), 6.66 (br s, 2H), 4.44 (d, J=4.4 Hz, 1H), 3.36-3.22 (m, 1H), 3.13 (app q, J=6.7 Hz, 4H), 1.84-1.75 (m, 2H), 1.63 (d, J=11.9 Hz, 2H), 1.53 (ddt, J=11.4, 7.7, 4.1 Hz, 1H), 1.44 (p, J=7.4 Hz, 2H), 1.27 (dq, J=14.4, 7.3 Hz, 2H), 1.13-0.97 (m, 2H), 0.97-0.84 (app m, 5H). LCMS: Purity 99%, MS (m/e) 357 (MH⁺).

trans-4-((5-Bromo-2-((cyclopropylmethyl)amino)pyrimidin-4-yl)amino)cyclohexan-1-ol

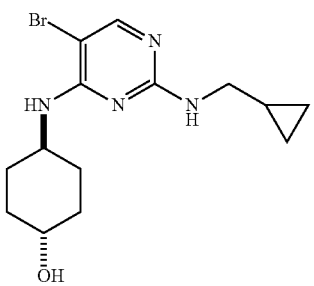

¹H NMR (400 MHz, DMSO-d₆) δ 7.77 (s, 1H), 6.76 (s, 1H), 5.99 (app d, J=7.5 Hz, 1H), 4.52 (d, J=4.5 Hz, 1H), 3.88-3.74 (m, 1H), 3.41-3.22 (m, 1H), 3.04 (t, J=6.4 Hz, 2H), 1.80 (t, J=12.5 Hz, 4H), 1.48-1.32 (m, 2H), 1.26-1.12 (m, 2H), 1.05-0.96 (m, 1H), 0.41-0.30 (m, 2H), 0.16 (q, J=4.9 Hz, 2H). LCMS: Purity 97%, MS (m/e) 341 (MH⁺).

trans-4-((5-Bromo-2-(((1-ethylcyclobutyl)methyl)amino)pyrimidin-4-yl)amino)cyclohexan-1-ol

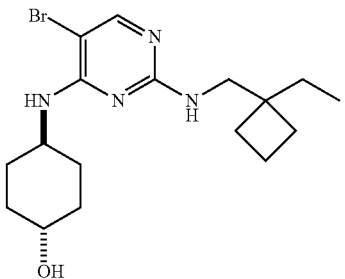

¹H NMR (400 MHz, DMSO-d₆) δ 7.76 (s, 1H), 6.74 (br s, 1H), 5.99 (br s, 1H), 4.52 (d, J=4.4 Hz, 1H), 3.91-3.84 (m, 1H), 3.43-3.32 (m, 1H), 3.28 (d, J=6.4 Hz, 2H), 1.88-1.67 (m, 8H), 1.57 (app qd, J=8.2, 7.6, 2.6 Hz, 2H), 1.47-1.32 (m, 4H), 1.25-1.10 (m, 2H), 0.79 (t, J=7.4 Hz, 3H). LCMS: Purity 99%, MS (m/e) 384 (MH⁺).

281 trans-4-((5-Bromo-2-((cyclopropylmethyl)amino)pyrimidin-4-yl)amino)-1-methylcyclohexan-1-ol

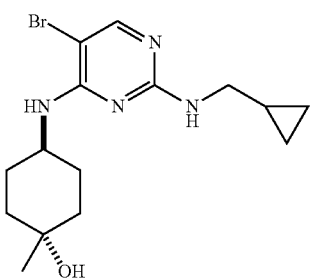

$^1$H NMR (400 MHz, DMSO-$d_6$) δ 7.78 (s, 1H), 6.75 (br s, 1H), 6.04 (d, J=8.0 Hz, 1H), 4.26 (s, 1H), 3.94-3.86 (m, 1H), 3.03 (t, J=6.4 Hz, 2H), 1.70 (app d, J=7.8 Hz, 2H), 1.58-1.34 (m, 6H), 1.14 (s, 3H), 1.06-0.93 (m, 1H), 0.41-0.31 (m, 2H), 0.15 (q, J=4.8 Hz, 2H). LCMS: Purity 99%, MS (m/e) 355 (MH$^+$).

trans-tert-butyl-4-((5-bromo-2-(butylamino)pyrimidin-4-yl)amino)methyl)cyclohexyl)carbamate

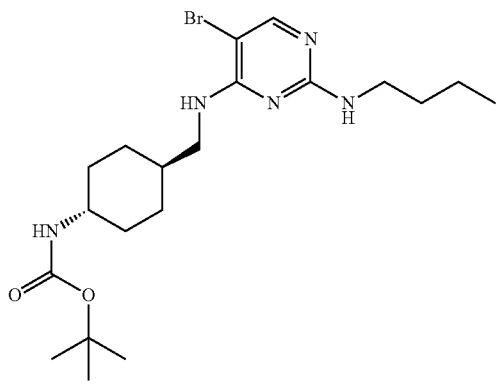 [SMILES: CCCCNc1ncc(Br)c(NC[C@H]2CC[C@H](NC(=O)OC(C)(C)C)CC2)n1]

trans-tert-butyl-4-((5-bromo-2-(butylamino)pyrimidin-4-yl)amino)methyl)cyclohexyl)carbamate was prepared analogous to the preparation of trans-4-((5-bromo-2-(butylamino)pyrimidin-4-yl)amino)cyclohexan-1-ol. The resulting white solid obtained after reaction solution concentration followed by treating with aq. NaHCO$_3$ was filtered. trans-tert-Butyl-4-(((5-bromo-2-(butylamino)pyrimidin-4-yl)amino)methyl)cyclohexyl)carbamate thus obtained was used in next step with no further purification. $^1$H NMR (400 MHz, DMSO-$d_6$) δ 7.75 (s, 1H), 6.65 (app br d, J=8.1 Hz, 3H), 3.13 (app q, J=6.7 Hz, 5H), 1.74 (d, J=10.9 Hz, 2H), 1.66 (d, J=12.8 Hz, 2H), 1.56-1.49 (m, 1H), 1.49-1.38 (m, 2H), 1.35 (s, 9H), 1.32-1.19 (app m, 2H), 1.06 (q, J=11.8 Hz, 2H), 0.97-0.82 (app m, 5H). LCMS: Purity 98%, MS (m/e) 457 (MH$^+$).

282 trans-4-((5-Bromo-2-(butylamino)pyrimidin-4-yl)amino)-1-methylcyclohexan-1-ol

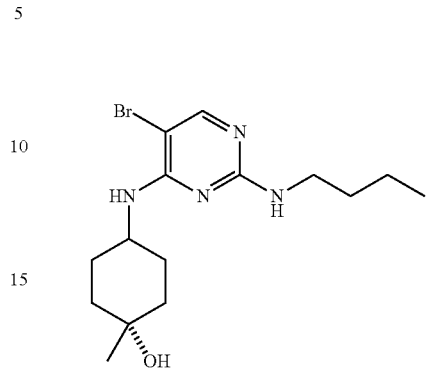

trans-4-((5-Bromo-2-(butylamino)pyrimidin-4-yl)amino)-1-methylcyclohexan-1-ol was prepared and purified analogous to the preparation of trans-tert-butyl-4-(((5-bromo-2-(butylamino)pyrimidin-4-yl)amino)methyl)cyclohexyl)carbamate. $^1$H NMR (400 MHz, DMSO-$d_6$) δ 7.77 (s, 1H), 6.70 (br s, 1H), 6.02 (d, J=7.2 Hz, 1H), 4.26 (s, 1H), 3.89 (app br s, 1H), 3.14 (q, J=6.6 Hz, 2H), 1.78-1.67 (m, 2H), 1.58-1.47 (m, 4H), 1.47-1.34 (m, 4H), 1.27 (h, J=7.3 Hz, 2H), 1.14 (s, 3H), 0.86 (t, J=7.3 Hz, 3H). LCMS: Purity 98%, MS (m/e) 358 (MH$^+$).

cis-4-((5-Bromo-2-(butylamino)pyrimidin-4-yl)amino)-1-methylcyclohexan-1-ol

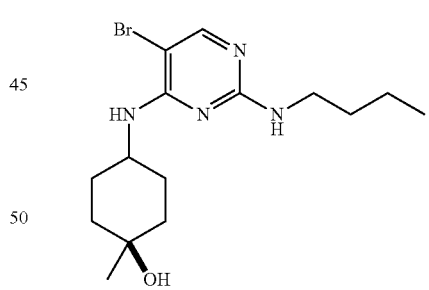

cis-4((5-Bromo-2-(butylamino)pyrimidin-4-yl)amino)-1-methylcyclohexan-1-ol was prepared and isolated analogously to the preparation of trans-tert-butyl-4-(((5-bromo-2-(butylamino)pyrimidin-4-yl)amino)methyl)cyclohexyl)carbamate. $^1$H NMR (400 MHz, DMSO-$d_6$) δ 7.77 (s, 1H), 6.69 (br s, 1H), 5.90 (s, 1H), 4.02 (s, 1H), 3.85-3.76 (m, 1H), 3.14 (q, J=6.6 Hz, 2H), 1.74-1.64 (m, 2H), 1.63-1.51 (m, 4H), 1.51-1.38 (m, 4H), 1.27 (h, J=7.3 Hz, 2H), 1.09 (s, 3H), 0.86 (t, J=7.3 Hz, 3H). LCMS: Purity 96%, MS (m/e) 358 (MH$^+$).

trans-4-((5-Bromo-2-((cyclobutylmethyl)amino)pyrimidin-4-yl)amino)cyclohexan-1-ol

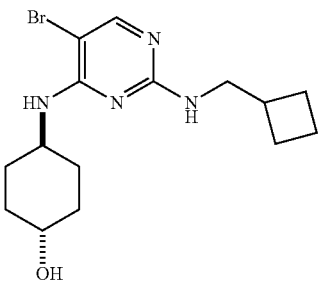

A solution of trans-4-((5-bromo-2-chloropyrimidin-4-yl)amino)cyclohexan-1-ol (2.0 g, 6.5 mmol), cyclobutylmethanamine hydrochloride (2.0 g, 16.4 mmol), i-Pr$_2$NEt (8.5 mL, 6.3 g, 48.9 mmol) and ethanol (10 ml) was stirred and heated in a sealed tube at 90° C. till complete consumption of trans-4-((5-bromo-2-chloropyrimidin-4-yl)amino)cyclohexan-1-ol. Upon completion of reaction, reaction solution was processed and isolated in an identical manner as described in the preparation of trans-4-((5-bromo-2-(butylamino)pyrimidin-4-yl)amino)cyclohexan-1-ol. $^1$H NMR (400 MHz, DMSO-d$_6$) δ 7.76 (s, 1H), 6.72 (br s, 1H), 5.99 (br s, 1H), 4.52 (d, J=4.2 Hz, 1H), 3.86-3.77 (m, 1H), 3.37 (app tt, J=10.7, 3.6 Hz, 2H), 3.20 (t, J=6.5 Hz, 2H), 1.98-1.90 (m, 2H), 1.83-1.76 (m, 6H), 1.71-1.58 (m, 2H), 1.45-1.35 (m, 2H), 1.26-1.11 (m, 2H). LCMS: Purity 99%, MS (m/e) 356 (MH$^+$).

The following analogs were also prepared analogous to the preparation of trans-4-((5-bromo-2-((cyclobutylmethyl)amino)pyrimidin-4-yl)amino)cyclohexan-1-ol from corresponding amine hydrochloride salts and 5-bromo-4-amino(substituted)pyrimidines trans-4-((5-Bromo-2-(((1-ethylcyclopropyl)methyl)amino)pyrimidin-4-yl)amino)cyclohexan-1-ol

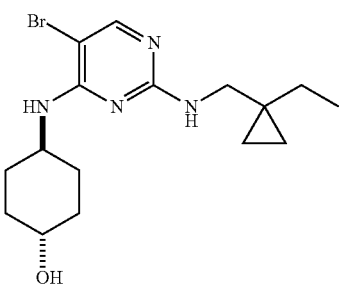

$^1$H NMR (400 MHz, DMSO-d$_6$) δ 7.75 (s, 1H), 6.67 (br s, 1H), 5.99 (br s, 1H), 4.52 (d, J=4.4 Hz, 1H), 3.91-3.81 (m, 1H), 3.40-3.32 (m, 1H), 3.18 (d, J=5.9 Hz, 2H), 1.80 (app t, J=12.2 Hz, 4H), 1.40 (qd, J=13.6, 12.3, 3.4 Hz, 2H), 1.27 (q, J=7.4 Hz, 2H), 1.23-1.11 (m, 2H), 0.87 (t, J=7.3 Hz, 3H), 0.42-0.34 (m, 2H), 0.20-0.13 (m, 2H). LCMS: Purity 99%, MS (m/e) 370 (MH$^+$).

trans-4-((5-Bromo-2-((2,2-difluorobutyl)amino)pyrimidin-4-yl)amino)cyclohexan-1-ol

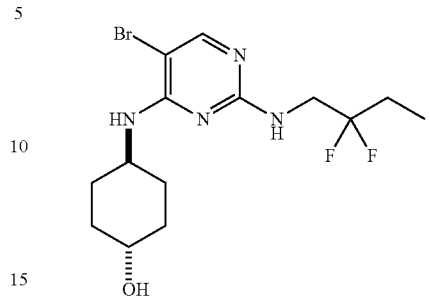

$^1$H NMR (400 MHz, DMSO-d$_6$) δ 7.82 (s, 1H), 7.02 (br s, 1H), 6.15 (d, J=8.3 Hz, 1H), 4.53 (d, J=4.5 Hz, 1H), 3.91-3.78 (m, 1H), 3.68 (td, J=14.2, 6.6 Hz, 2H), 3.36 (tq, J=11.1, 4.2 Hz, 1H), 1.94-1.74 (m, 6H), 1.49-1.33 (m, 2H), 1.26-1.11 (m, 2H), 0.94 (t, J=7.5 Hz, 3H). $^{19}$F NMR (376 MHz, DMSO-d$_6$) δ -103.62 (app q, J=14.5 Hz). LCMS: Purity 97%, MS (m/e) 380 (MH$^+$).

trans-4-((5-Bromo-2-((2-cyclopropylethyl)amino)pyrimidin-4-yl)amino)cyclohexan-1-ol

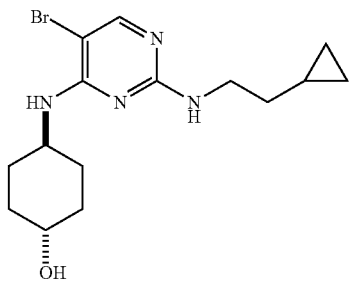

$^1$H NMR (400 MHz, DMSO-d$_6$) δ 7.76 (s, 1H), 6.71 (br s, 1H), 5.98 (br s, 1H), 4.53 (d, J=4.3 Hz, 1H), 3.88-3.79 (m, 1H), 3.43-3.26 (m, 1H), 3.26-3.16 (app m, 2H), 1.87-1.77 (m, 4H), 1.47-1.32 (m, 4H), 1.19 (qd, J=14.2, 13.0, 3.7 Hz, 2H), 0.74-0.59 (m, 1H), 0.37 (q, J=5.1 Hz, 2H), 0.01 (q, J=4.8 Hz, 2H). LCMS: Purity 99%, MS (m/e) 356 (MH$^+$).

trans-4-((5-Bromo-2-((2-cyclopropylethyl)amino)pyrimidin-4-yl)amino)-1-methylcyclohexan-1-ol

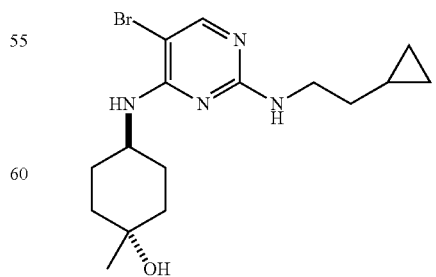

$^1$H NMR (400 MHz, DMSO-d$_6$) δ 7.77 (s, 1H), 6.69 (br s, 1H), 6.02 (d, J=7.9 Hz, 1H), 4.26 (s, 1H), 3.96-3.86 (m,

1H), 3.26-3.16 (app m, 2H), 1.70 (br s, 2H), 1.59-1.31 (m, 8H), 1.14 (s, 3H), 0.69-0.63 (m, 1H), 0.42-0.32 (m, 2H), 0.00 (q, J=4.8 Hz, 2H). LCMS: Purity 99%, MS (m/e) 370 (MH+).

General Scheme for the Preparation of 3-heteroaryl-2,2'-bipyridine:

Catalyst 1: Pd(PPh$_3$)$_4$ or Pd$_2$(dba)$_3$/2-dicyclohexylphosphino-2',6'-dimethoxybiphenyl (SPhos) or Pd(OAc)$_2$/2-dicyclohexylphosphino-2',6'-dimethoxybiphenyl (SPhos) or Pd$_2$(dba)$_3$/2-dicyclohexylphosphino-2',6'-dimethoxybiphenyl (Xphos), Pd(OAc)$_2$/2-dicyclohexylphosphino-2',6'-dimethoxybiphenyl (Xphos) or Chloro(2-dicyclohexylphosphino-2',6'-dimethoxy-1,1'-biphenyl)[2-(2'-amino-1,1'-biphenyl)]palladium(II) (SPhos-Pd-G2) or Chloro(2-dicyclohexylphosphino-2',4'-6'-triisopropyl-1,1'-biphenyl)[2-2'-amino-1,1'-biphenyl)]palladium(II) (XPhos-Pd-G2) or Pd$_2$(dba)$_3$/sodium 2'-dicyclohexylphosphino-2,6-dimethoxy-1,1'-biphenyl-3-sulfonate hydrate or Pd(OAc)$_2$/sodium 2'-dicyclohexylphosphino-2,6-dimethoxy-1,1'-biphenyl-3-sulfonate hydrate Catalyst 2: Pd(PPh$_3$)$_4$ or Pd$_2$(dba)$_3$/2-dicyclohexylphosphino-2',6'-dimethoxybiphenyl (SPhos) or Pd(OAc)$_2$/2-dicyclohexylphosphino-2',6'-dimethoxybiphenyl (SPhos) or Pd$_2$(dba)$_3$/2-dicyclohexylphosphino-2',6'-dimethoxybiphenyl (Xphos), Pd(OAc)$_2$/2-dicyclohexylphosphino-2',6'-dimethoxybiphenyl (Xphos) or Chloro(2-dicyclohexylphosphino-2',6'-dimethoxy-1,1'-biphenyl)[2-(2'-amino-1,1'-biphenyl)]palladium(II) (SPhos-Pd-G2) or Chloro(2-dicyclohexylphosphino-2',4'-6'-triisopropyl-1,1'-biphenyl)[2-2'-amino-1,1'-biphenyl)]palladium(II) (XPhos-Pd-G2)

LC/MS: rt (Method A or Method B)

Method A: Column: Luna 5□mC8 (100×4.6 mm), Flow rate 1.0 mL/min, Mobile phase: A: H$_2$O 0.05% TFA, B: CH$_3$CN 0.05% TFA Method B: Column: Gemini 5□mC18 (100×4.6 mm), Flow rate 1.5 mL/min, Mobile phase: A: H$_2$O 0.05% HCOOH, B: CH$_3$CN 0.05% HCOOH 3-((3,3-difluorocyclobutyl)amino)-5-(trans-4-hydroxycyclohexyl)-8-(6-methyl-2,6-diazaspiro[3.3]heptan-2-yl)pyrimido[4,5-c]isoquinolin-6(5H)-one

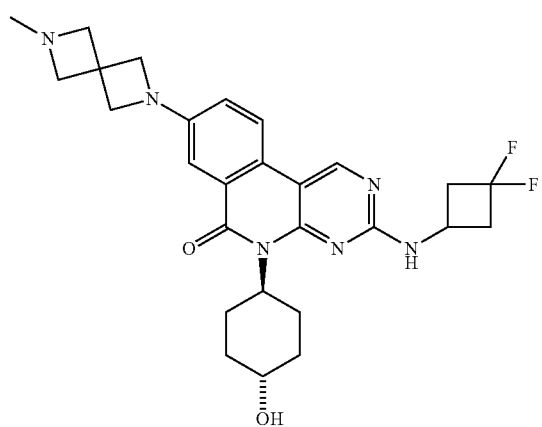 [SMILES: CN1CC2(C1)CN(c1ccc3c(c1)c(=O)n([C@H]1CC[C@H](O)CC1)c1nc(NC4CC(F)(F)C4)ncc31)C2]

LCMS: rt 3.17 min (B), MS (m/e) 511 MH+.
$^1$H NMR (300 MHz, Methanol-d$_4$) δ 9.03 (s, 1H), 8.10 (d, J=9.0 Hz, 1H), 7.28 (s, 1H), 7.01 (d, J=9.0 Hz, 1H), 5.52 (br s, 1H), 4.57-4.53 (m, 2H), 4.30-4.26 (m, 4H), 4.20 (brs, 2H), 4.14 (brs, 2H), 3.04 (m, 2H), 3.01 (s, 3H), 2.91-2.82 (m, 2H), 2.78-2.63 (m, 3H), 2.14-2.10 (m, 2H), 1.72-1.67 (m, 2H), 1.51-1.47 (m, 2H).

3-((3,3-difluorocyclobutyl)amino)-5-(trans-4-hydroxycyclohexyl)-8-(2-oxa-6-azaspiro[3.3]heptan-6-yl)pyrimido[4,5-c]isoquinolin-6(5H)-one

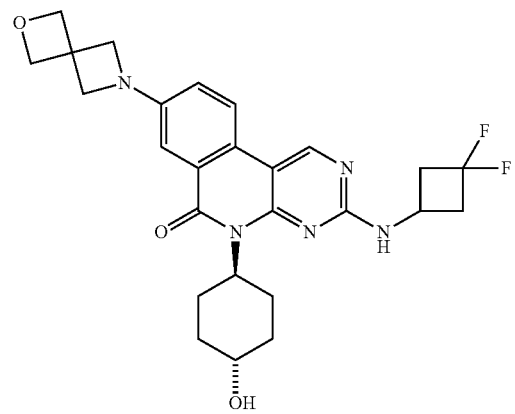 [SMILES: O=c1c2cc(N3CC4(COC4)C3)ccc2c2cnc(NC3CC(F)(F)C3)nc2n1[C@H]1CC[C@H](O)CC1]

LCMS: rt 5.13 min (B), MS (m/e) 498 MH+.

3-((3-fluorocyclobutyl)amino)-5-(trans-4-hydroxycyclohexyl)-8-(6-methyl-2,6-diazaspiro[3.3]heptan-2-yl)pyrimido[4,5-c]isoquinolin-6(5H)-one

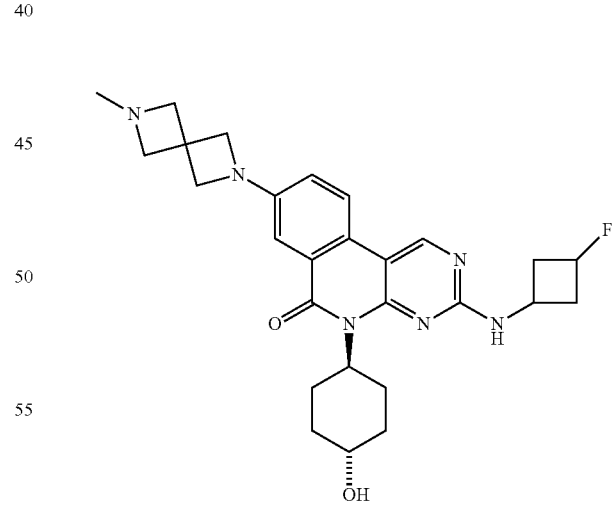

LCMS: rt 4.30 min (A), MS (m/e) 493 MH+.
$^1$H NMR (300 MHz, Methanol-d$_4$) δ 8.95 (s, 1H), 9.49 (br s, 1H), 8.02 (d, J=8.7 Hz, 1H), 7.22 (s, 1H), 6.96 (d, J=8.7 Hz, 1H), 5.53 (br s, 1H), 5.36-5.14 (m, 1H), 4.60 (m, 1H), 4.31 (brs, 4H), 4.12 (brs, 4H), 3.73 (m, 1H), 2.88 (s, 3H), 2.68-2.39 (m, 4H), 2.12-2.09 (m, 2H), 1.68-1.65 (m, 2H), 1.51-1.46 (m, 2H).

287

3-((3-fluorocyclobutyl)amino)-5-(trans-4-hydroxy-cyclohexyl)-8-(2-oxa-6-azaspiro[3.3]heptan-6-yl)pyrimido[4,5-c]isoquinolin-6(5H)-one

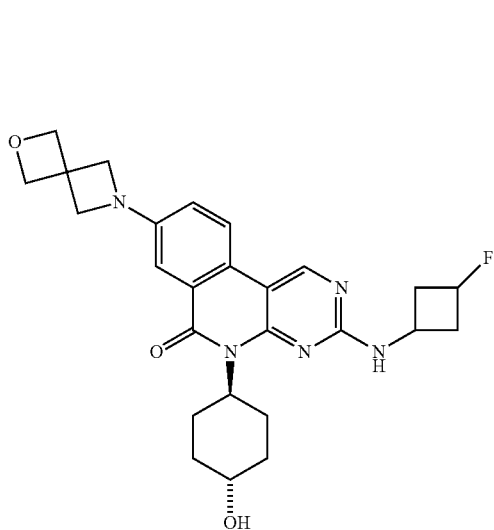 [SMILES: O=c1c2cc(N3CC4(COC4)C3)ccc2c2cnc(NC3CC(F)C3)nc2n1[C@H]1CC[C@H](O)CC1]

LCMS: rt 5.35 min (A), MS (m/e) 480 MH$^+$.

$^1$H NMR (300 MHz, Methanol-d$_4$) δ 8.95 (s, 1H), 9.49 (br s, 1H), 8.03 (d, J=8.7 Hz, 1H), 7.27 (s, 1H), 6.97 (d, J=8.7 Hz, 1H), 5.53 (br s, 1H), 5.36-5.14 (m, 1H), 4.88 (brs, 4H), 4.80 (m, 1H), 4.64 (m, 1H), 4.16 (brs, 3H), 3.79 (m, 2H), 2.85 (m, 2H), 2.66 (brs, 2H), 2.60-2.42 (m, 2H), 2.15-2.11 (m, 2H), 1.74-1.71 (m, 2H), 1.52-1.47 (m, 2H).

3-((3,3-difluorocyclobutyl)amino)-5-(trans-4-hydroxycyclohexyl)-8-(4-methylpiperazin-1-yl)pyrimido[4,5-c]isoquinolin-6(5H)-one

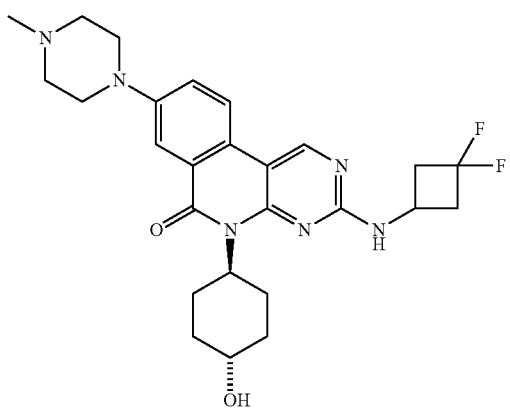 [SMILES: CN1CCN(c2ccc3c(c2)c(=O)n([C@H]2CC[C@H](O)CC2)c2nc(NC4CC(F)(F)C4)ncc32)CC1]

LCMS: rt 4.66 min (A), MS (m/e) 499 MH$^+$.

$^1$H NMR (300 MHz, Methanol-d$_4$) δ 9.09 (s, 1H), 8.19 (d, J=9.0 Hz, 1H), 7.80 (s, 1H), 7.57 (d, J=9.0 Hz, 1H), 5.56 (br s, 1H), 4.35 (m, 1H), 3.99 (m, 2H), 3.76-3.74 (m, 4H), 3.12-3.02 (m, 6H), 2.99 (s, 3H), 2.89 (br s, 2H), 2.74-2.64 (m, 2H), 2.14-2.10 (m, 2H), 1.72-1.68 (m, 2H), 1.51-1.47 (m, 2H).

288

5-(Trans-4-hydroxycyclohexyl)-8-(4-methylpiperazin-1-yl)-3-((4,4,4-trifluorobutyl)amino)pyrimido[4,5-c]isoquinolin-6(5H)-one

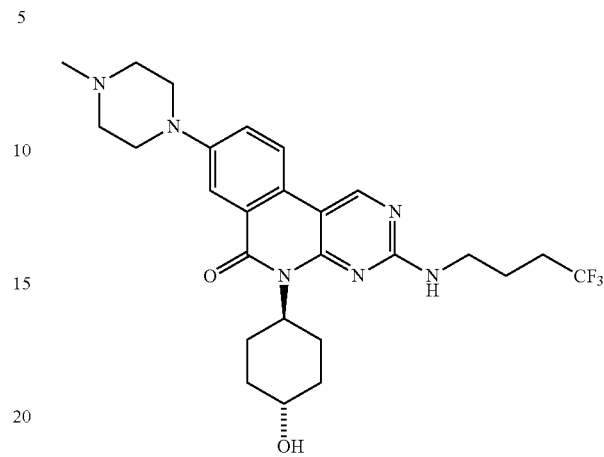

LCMS: rt 3.19 min (A), MS (m/e) 519 MH$^+$.

$^1$H NMR (300 MHz, Methanol-d$_4$) δ 9.03 (s, 1H), 8.42 (br s, 1H), 8.12 (d, J=7.8 Hz, 1H), 7.75 (s, 1H), 7.51 (d, J=7.8 Hz, 1H), 5.53 (br s, 1H), 3.71 (m, 1H), 3.55 (t, J=7.2 Hz, 2H), 3.43 (m, 4H), 3.02 (m, 4H), 2.78-2.68 (m, 2H), 2.64 (s, 3H), 2.33-2.24 (m, 2H), 2.13-2.08 (m, 2H), 1.98-1.91 (m, 2H), 1.72-1.68 (m, 2H), 1.51-1.46 (m, 2H).

3-((3,3-difluorocyclobutyl)amino)-5-((trans-4-hydroxycyclohexyl)-8-((4-methylpiperazin-1-yl)methyl)pyrimido[4,5-c]isoquinolin-6(5H)-one

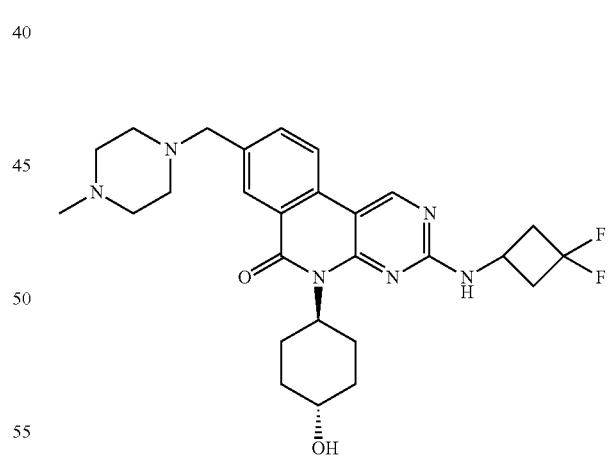

LCMS: rt 3.03 min (B), MS (m/e) 513 MH$^+$.

$^1$H NMR (300 MHz, Methanol-d$_4$) δ 9.17 (s, 1H), 8.27 (s, 1H), 8.22 (d, J=8.4 Hz, 1H), 7.75 (d, J=8.4 Hz, 1H), 5.56 (br s, 1H), 4.36 (br s, 1H), 3.77 (s, 2H), 3.72 (br s, 1H), 3.35-3.29 (m, 4H), 3.06-3.02 (m, 4H), 2.88 (s, 3H), 2.86-2.65 (m, 8H), 2.14-2.10 (m, 2H), 1.72-1.68 (m, 2H), 1.56-1.47 (m, 2H).

289

3-((3-fluorocyclobutyl)amino)-5-((trans-4-hydroxy-cyclohexyl)-8-((4-methylpiperazin-1-yl)methyl)pyrimido[4,5-c]isoquinolin-6(5H)-one

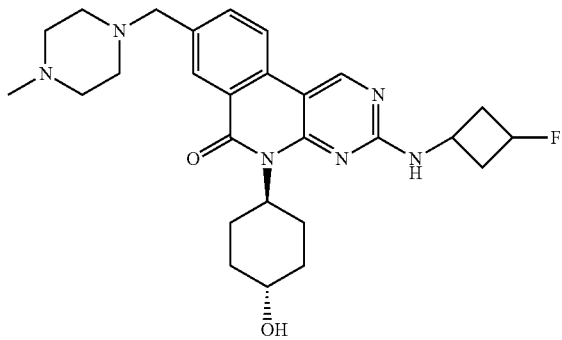 [SMILES: CN1CCN(Cc2ccc3c(c2)c(=O)n([C@H]2CC[C@H](O)CC2)c2nc(NC4CC(F)C4)ncc32)CC1]

LCMS: rt 2.85 min (B), MS (m/e) 495 MH$^+$.

$^1$H NMR (300 MHz, Methanol-d$_4$) δ 9.13 (s, 1H), 8.28 (s, 1H), 8.21 (d, J=8.4 Hz, 1H), 7.77 (d, J=8.4 Hz, 1H), 5.52 (br s, 1H), 5.35-5.16 (m, 1H), 4.65 (br s, 1H), 3.84 (s, 2H), 3.73 (br s, 1H), 3.30-3.28 (m, 6H), 2.89 (s, 3H), 2.86-2.45 (m, 1H), 2.13-2.09 (m, 2H), 1.72-1.68 (m, 2H), 1.54-1.46 (m, 2H).

290 trans-4-(3-(butylamino)-8-((4-methylpiperazin-1-yl)methyl)-6-oxopyrimido[4,5-c]isoquinolin-5(6H)-yl)cyclohexane-1-carbonitrile

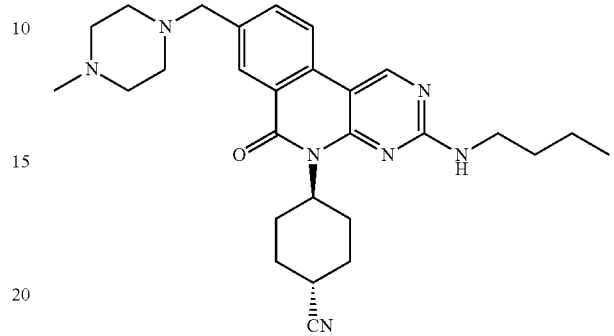

LCMS: rt 5.43 min (A), MS (m/e) 488 MH$^+$.

$^1$H NMR (300 MHz, Methanol-d$_4$) δ 9.12 (s, 1H), 8.29 (s, 1H), 8.20 (d, J=8.1 Hz, 1H), 7.75 (d, J=8.1 Hz, 1H), 5.52 (br s, 1H), 3.81 (s, 2H), 3.51 (br s, 2H), 3.36-3.24 (m, 5H), 2.89 (s, 3H), 2.85-2.65 (m, 6H), 2.32-2.29 (m, 2H), 1.83-1.68 (m, 6H), 1.52-1.45 (m, 2H), 1.02 (t, J=7.5 Hz, 3H).

5-((Trans-4-hydroxycyclohexyl)-8-((4-methylpiperazin-1-yl)methyl)-3-((4,4,4-trifluorobutyl)amino)pyrimido[4,5-c]isoquinolin-6(5H)-one

5-((trans-4-hydroxycyclohexyl)-3-(isopentylamino)-8-((4-methylpiperazin-1-yl)methyl)pyrimido[4,5-c]isoquinolin-6(5H)-one

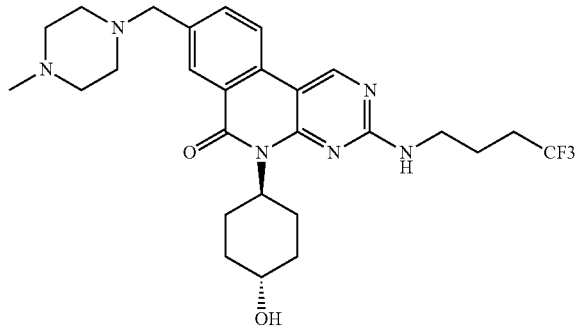 [SMILES: CN1CCN(Cc2ccc3c(c2)c(=O)n([C@H]2CC[C@H](O)CC2)c2nc(NCCCC(F)(F)F)ncc32)CC1]

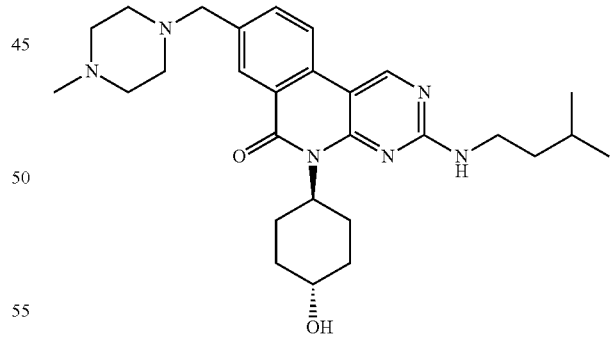

LCMS: rt 3.17 min (B), MS (m/e) 533 MH$^+$.

$^1$H NMR (300 MHz, Methanol-d$_4$) δ 9.13 (s, 1H), 8.46 (br s, 1H), 8.25 (s, 1H), 8.20 (d, J=7.8 Hz, 1H), 7.74 (d, J=7.8 Hz, 1H), 5.53 (br s, 1H), 3.71 (s, 3H), 3.55 (t, J=6.9 Hz, 2H), 3.29 (br s, 2H), 2.93 (br s, 6H), 2.78-2.63 (m, 4H), 2.60 (s, 2H), 2.33-2.24 (m, 2H), 2.12-2.08 (m, 2H), 1.95-1.93 (m, 2H), 1.72-1.68 (m, 2H), 1.54-1.46 (m, 2H).

LCMS: rt 3.28 min (B), MS (m/e) 493 MH$^+$.

$^1$H NMR (300 MHz, Methanol-d$_4$) δ 9.09 (s, 1H), 8.31 (br s, 1H), 8.24 (s, 1H), 8.18 (d, J=8.1 Hz, 1H), 7.73 (d, J=8.1 Hz, 1H), 5.54 (br s, 1H), 3.74 (s, 2H), 3.71 (br s, 1H), 3.50 (t, J=7.5 Hz, 2H), 3.20 (br s, 4H), 2.86 (br s, 2H), 2.80 (s, 3H), 2.74 (br s, 4H), 2.12-2.08 (m, 2H), 1.76-1.42 (m, 8H), 1.01 (d, J=6.6 Hz, 6H).

5-(trans-4-hydroxycyclohexyl)-3-(isobutylamino)-8-((4-methylpiperazin-1-yl)methyl)pyrimido[4,5-c]isoquinolin-6(5H)-one

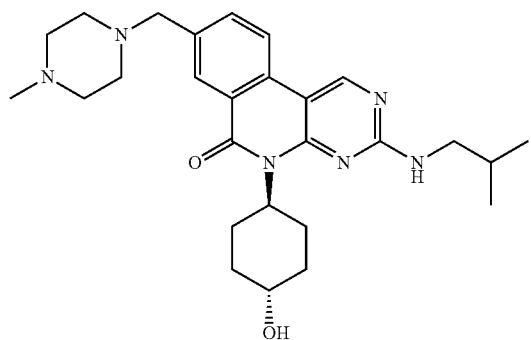 [SMILES: CC(C)CNc1ncc2c3ccc(CN4CCN(C)CC4)cc3c(=O)n([C@H]3CC[C@H](O)CC3)c2n1]

LCMS: rt 4.33 min (A), MS (m/e) 479 MH⁺.

¹H NMR (300 MHz, Methanol-d₄) δ 9.09 (s, 1H), 8.22 (s, 1H), 8.16 (d, J=8.1 Hz, 1H), 7.72 (d, J=8.1 Hz, 1H), 5.53 (br s, 1H), 3.72 (br s, 1H), 3.64 (s, 2H), 3.29 (br s, 4H), 2.89 (br s, 2H), 2.52 (br s, 8H), 2.27 (s, 3H), 2.12-1.98 (m, 3H), 1.71-1.67 (m, 2H), 1.55-1.46 (m, 2H), 1.01 (d, J=6.6 Hz, 6H).

Preparation of aminomethyltrifluoroborates: (JOC 2008, 73, 2052-2057, JOC 2011, 76, 2762-2769). Aminomethyltrifluoroborates which are not available commerically were prepared according to literature procedure. Trifluoro((4-isopropylpiperazin-1-ium-1-yl)methyl)borate preparation describes reaction procedure and isolation of synthesized respective aminomethyltrifluoroborates represented below.

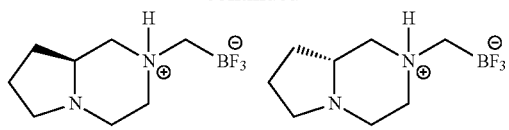

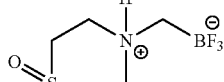

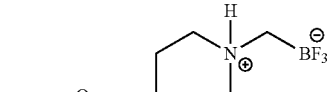

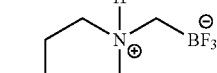

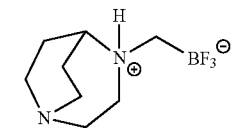

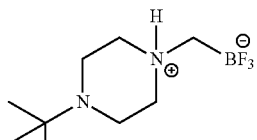

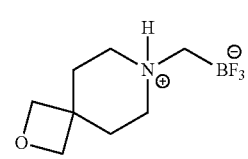

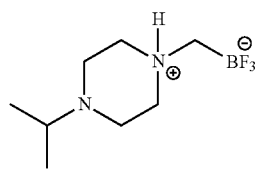

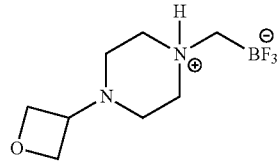

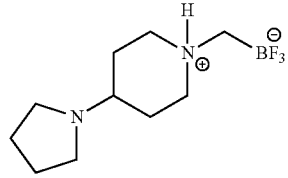

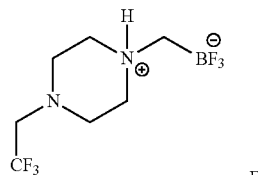

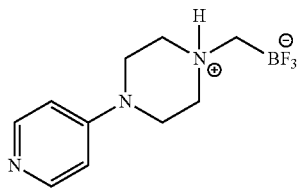

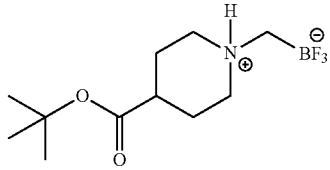

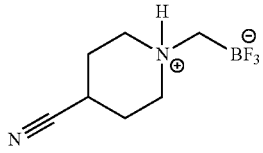

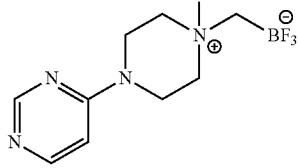

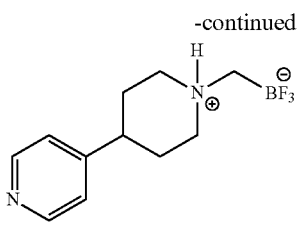

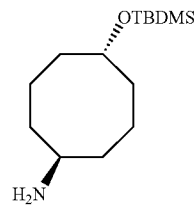

Example 2: Synthesis of (1r,5r)-5-((tert-Butyldimethylsilyl)oxy)cyclooctan-1-amine (5)

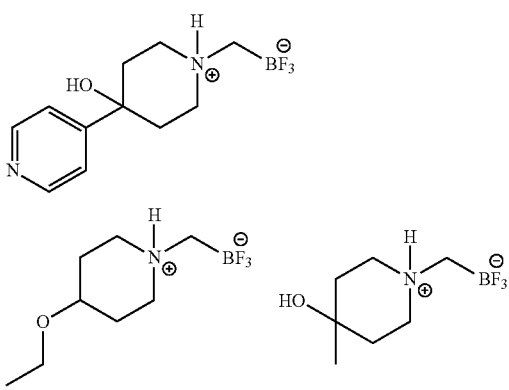

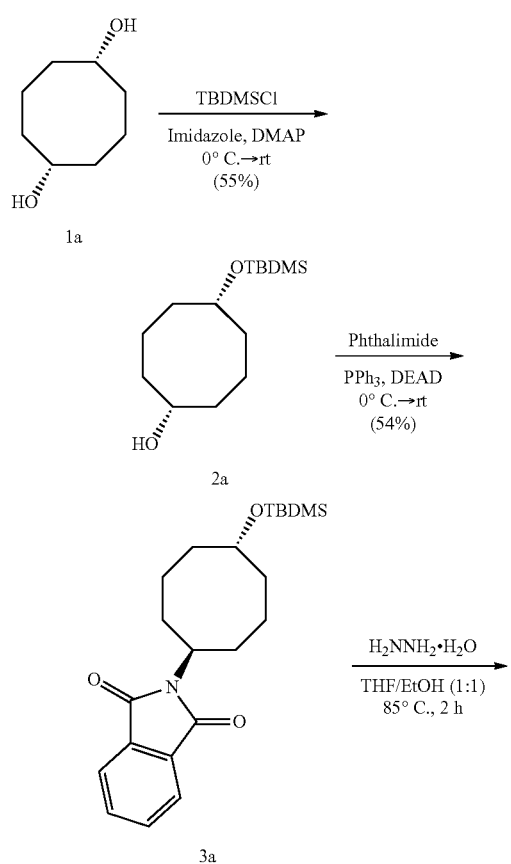

Step 1-1: Synthesis of (1s,5s)-5-((tert-Butyldimethylsilyl)oxy)cyclooctan-1-ol (2a)

To an ice-cold solution of (1s,5s)-cyclooctane-1,5-diol (10 g, 69.3 mmol) in THF (200 mL), imidazole (6.6 g, 97 mmol), tert-butylchlorodimethylsilane (10.5 g, 69.7 mmol) and DMAP (30 mg, 24.6 μmol) were added successively (Plettenburg, O. et al. PCT Int. Appl. WO2008077551). A white precipitate was observed and the reaction mixture was allowed to stir and warm up to room temperature over 18 h. LC/MS traces show no starting material, and hence the reaction mixture was poured over ice-water (100 mL). The layers were separated, aqueous layer extracted with ethyl acetate (3×50 mL) and the combined organic layer was dried (MgSO$_4$), filtered and concentrated to give a colorless oil. Column chromatography purification using 10-20% ethyl acetate/hexanes as the eluent provided 9.9 g (55%) of a colorless oil. $^1$H NMR (400 MHz, Chloroform-d) δ 3.88-3.73 (m, 2H), 1.91-1.59 (m, 10H), 1.47-1.35 (m, 2H), 0.88 (s, 9H), 0.03 (s, 6H). MS m/e: 259 (M+H)$^+$.

Step 2: Synthesis of 2-((1r,5r)-5-((tert-Butyldimethylsilyl)oxy)cyclooctyl)isoindoline-1,3-dione (3a)

To an ice-cold solution of (1s,5s)-5-((tert-butyldimethylsilyl)oxy)cyclooctan-1-ol (2a, 0.5 g, 1.9 mmol), phthalimide (0.31 g, 2.1 mmol) and triphenylphosphine (0.57 g, 2.2 mmol) in THF (10 mL), diethyl azodicaboxylate (40% wt. in toluene, 0.95 mL, 0.36 g, 2.1 mmol) was added dropwise (Inoue, T. et al. PCT Int. Appl. WO2007077949). The resulting colorless reaction mixture was allowed to stir and warm up to room temperature overnight. LC/MS traces show starting material has been consumed. The reaction mixture was then concentrated and purified by column chromatography, eluting with neat hexanes initially and increasing the polarity to 20% ethyl acetate/hexanes, to provide 407 mg (54%) of 2-((1r,5r)-5-((tert-butyldimethylsilyl)oxy)cyclooctyl)-isoindoline-1,3-dione (3a) as a white solid. $^1$H NMR (400 MHz, Chloroform-d) δ 7.82-7.77 (m, 2H), 7.70-7.65 (m, 2H), 4.37 (tt, J=11.2, 2.8 Hz, 1H), 3.90 (td, J=7.2, 4.2 Hz, 1H), 2.30 (dddd, J=14.1, 11.0, 8.2, 4.4 Hz, 2H), 1.85-1.62 (m, 10H), 0.90 (s, 9H), 0.07 (s, 6H). MS m/e: 388 (M+H)$^+$.

Step 3: Synthesis of (1r,5r)-5-((tert-Butyldimethylsilyl)oxy)cyclooctan-1-amine (4a)

A solution of 2-((1r,5r)-5-((tert-butyldimethylsilypoxy)cyclooctyl)-isoindoline-1,3-dione (3a, 0.4 g, 1.0 mmol), hydrazine hydrate (64%, 0.5 mL, 0.33 g, 10.3 mmol) in THF/EtOH (1:1) solution was allowed to stir at 85° C. for 12 h (Inoue, T. et al. PCT Int. Appl. WO2007077949). The resulting reaction mixture was then concentrated, diluted with dichloromethane (20 mL) and extracted with 1N NaOH solution (3×10 mL) to give 0.26 g (98%) of (1r,5r)-5-((tert-butyldimethylsilyl)oxy)cyclooctan-1-amine (4a) as a colorless oil upon drying (MgSO$_4$), filtration and concentration. $^1$H NMR (400 MHz, Chloroform-d) δ 3.79 (septet, J=3.9 Hz, 1H), 2.95 (tt, J=9.4, 3.3 Hz, 1H), 1.80-1.52 (m, 10H), 1.45-1.36 (m, 2H), 0.88 (s, 9H), 0.03 (s, 6H). MS m/e: 258 (M+H)$^+$.
Example 3: Synthesis of 3-(Butylamino)-5-((1r,5r)-5-hydroxycyclooctyl)-8-((4-methylpiperazin-1-yl)methyl)pyrimido[4,5-c]isoquinolin-6(5H)-one (127
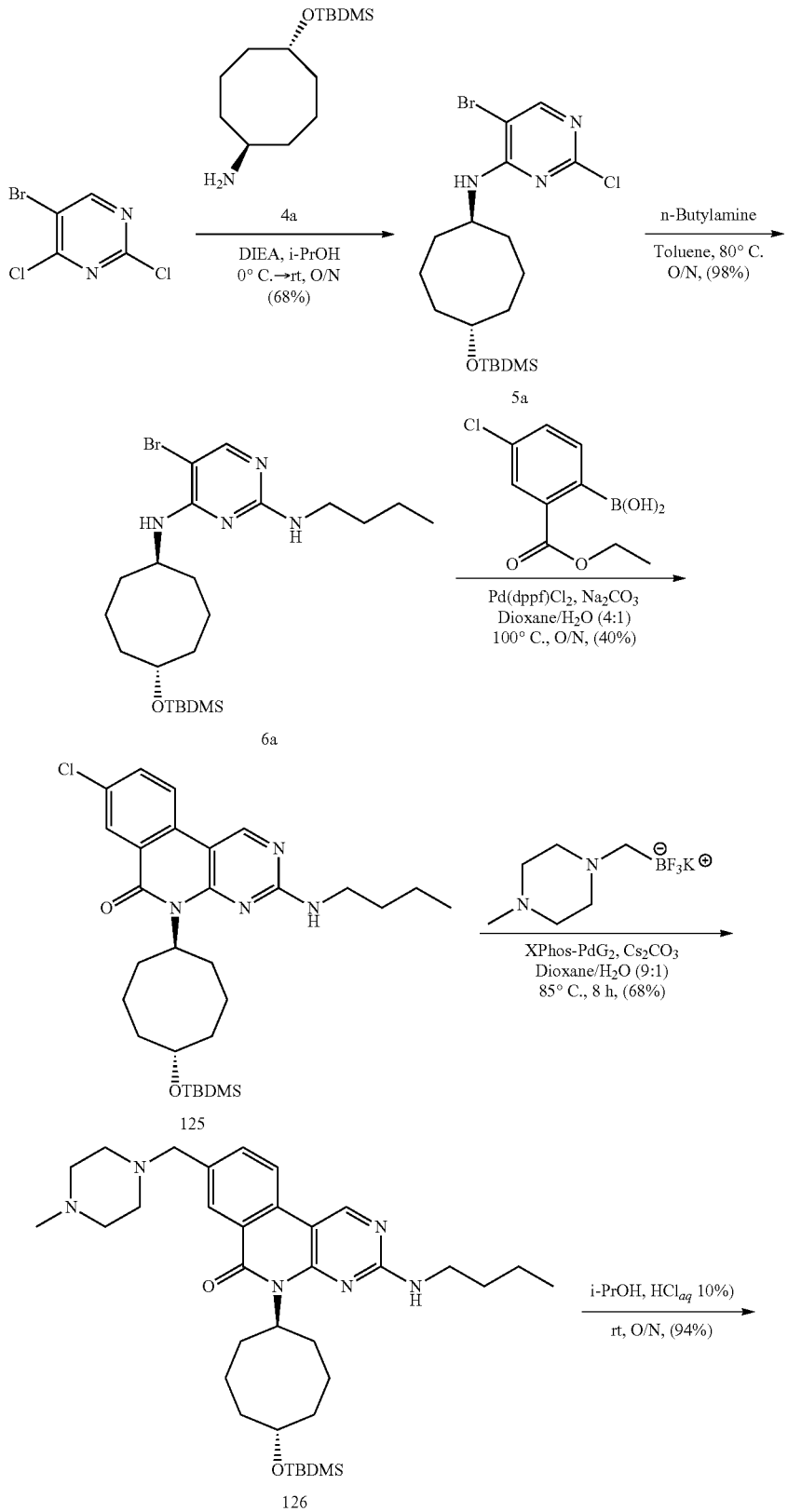

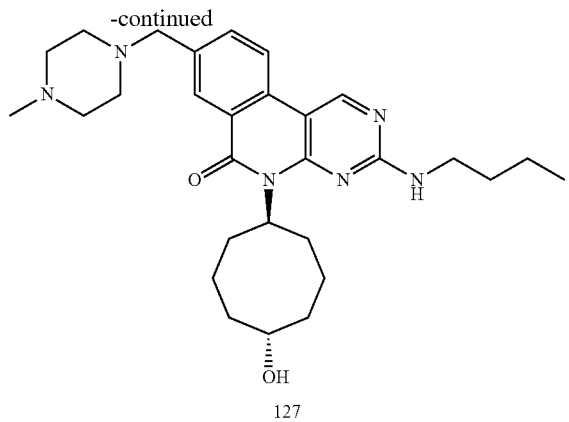

127

Step 2-1: Synthesis of 5-Bromo-N-((1r,5r)-5-((tert-butyldimethylsilyl)oxy)cyclooctyl)-2-chloropyrimidin-4-amine (5a)

To an ice-cold solution of 5-bromo-2,4-dichloropyrimidine (0.215 g, 0.94 mmol) and N,N-diisopropylethylamine (0.22 mL, 0.16 g, 1.3 mmol) in isopropanol (5 mL), (1r,5r)-5-((tert-butyldimethylsilyl)oxy)cyclooctan-1-amine (4a, 260 mg, 1.0 mmol) was added dropwise (Zhang, W. et al. J. Med. Chem. 2014, 57(16), 7031). The resulting reaction mixture was allowed to stir and warm up to room temperature overnight, concentrated, diluted with ethyl acetate (20 mL) and water (20 mL). The layers were separated and the aqueous solution was extracted with ethyl acetate (3×10 mL) and the combined organic layer was dried (MgSO$_4$), filtered and concentrated to give a yellow oil. Column chromatography purification using 0-20% ethyl acetate/hexanes as the eluent provided 0.286 g (68%) of 5-bromo-N-((1r,5r)-5-((tert-butyldimethylsilyl)oxy)-cyclooctyl)-2-chloropyrimidin-4-amine (5a) as a colorless oil. $^1$H NMR (400 MHz, Chloroform-d) δ 8.08 (s, 1H), 5.39 (d, J=7.7 Hz, 1H), 4.25-4.17 (m, 1H), 3.87-3.81 (m, 1H), 1.99-1.92 (m, 2H), 1.80-1.75 (m, 6H), 1.65-1.54 (m, 4H), 0.89 (s, 9H), 0.05 (s, 6H). MS m/e: 448 (M+H)$^+$.

Step 2-2: Synthesis of 5-Bromo-N$^2$-butyl-N$^4$-((1r,5r)-5-((tert-butyldimethylsilyl)oxy)cyclooctyl)pyrimidine-2,4-diamine (6a)

A solution of 5-bromo-N-((1r,5r)-5-((tert-butyldimethylsilyl)oxy)-cyclooctyl)-2-chloropyrimidin-4-amine (5a, 0.286 g, 0.64 mmol) and n-butylamine (0.65 mL, 0.48 g, 6.6 mmol) in toluene (10 mL) was allowed to stir at 80° C. under N$_2$ atmosphere for 12 h (Zhang, W. et al. J. Med. Chem. 2013, 56(23), 9683). LC/MS traces indicated less than 50% of starting material was consumed, and hence additional amounts (1 mL, 2×2 mL) of n-butylamine were added with continued heating until only the product was detected by LC/MS traces. The resulting reaction mixture was concentrated, diluted with ethyl acetate (30 mL) and brine (20 mL) and the layers were separated. The organic layer was washed with brine (2×10 mL), dried (MgSO$_4$), filtered and concentrated to provide 0.30 g (98%) of 5-bromo-N$^2$-butyl-N$^4$-((1r,5r)-5-((tert-butyldimethylsilyl)oxy)cyclooctyl)pyrimidine-2,4-diamine (6a. $^1$H NMR (400 MHz, Chloroform-d) δ 7.82 (s, 1H), 5.00 (d, J=7.8 Hz, 1H), 4.88 (s, 1H), 4.21-4.14 (m, 1H), 3.83-3.77 (m, 1H), 3.33 (td, J=7.1, 5.8 Hz, 2H), 1.98-1.89 (m, 2H), 1.80-1.70 (m, 6H), 1.65-1.48 (m, 6H), 1.44-1.35 (m, 2H), 0.93 (t, J=7.3 Hz, 3H), 0.88 (s, 9H), 0.05 (s, 6H). MS m/e: 485 (M+H)$^+$.

Step 2-3: Synthesis of 3-(Butylamino)-5-((1r,5r)-5-((tert-butyldimethylsilyl)oxy)cyclooctyl)-8-chloropyrimido[4,5-c]isoquinolin-6(5H)-one (125)

The orange degassed (3×) solution of 5-bromo-N$^2$-butyl-N$^4$-((1r,5r)-5-((tert-butyldimethylsilyl)oxy)cyclooctyl)pyrimidine-2,4-diamine (6a, 0.3 g, 0.62 mmol), 4-chloro-2-ethoxycarbonylphenylboronic acid (0.215 g, 0.94 mmol), Pd(dppf)Cl$_2$ (55 mg, 67 µmol), Na$_2$CO$_3$ (0.2 g, 1.9 mmol) in dioxane/H$_2$O (4:1, 20 mL) was allowed to stir at 100° C. under N$_2$ atmosphere for 19 h. Additional amounts of boronic acid (2×100 mg), palladium catalyst (2×25 mg) and Na$_2$CO$_3$ were added and the reaction mixture was allowed to stir at 100° C. overnight. The reaction mixture was cooled down to room temperature, concentrated and diluted with dichloromethane and water. The layers were separated and the aqueous layer was extracted with dichloromethane (3×20 mL). The combined organic layer was dried (MgSO$_4$), filtered and concentrated to provide a black residue. Column chromatography purification using 0-20% ethyl acetate/hexanes as the eluent provided 0.135 g (40%) of 3-(butylamino)-5-((1r,5r)-5-((tert-butyldimethylsilyl)oxy)cyclooctyl)-8-chloropyrimido[4,5-c]isoquinolin-6(5H)-one (125) as a white solid. $^1$H NMR (400 MHz, Chloroform-d) δ 8.95 (s, 1H), 8.36 (d, J=19.8 Hz, 1H), 7.94 (d, J=8.7 Hz, 1H), 7.61 (dd, J=8.6, 2.4 Hz, 1H), 3.88 (s, 1H), 3.53 (q, J=6.8 Hz, 2H), 2.70-2.54 (m, 2H), 1.95-1.64 (m, 13H), 1.47 (q, J=7.7 Hz, 2H), 0.98 (t, J=7.5 Hz, 3H), 0.91 (s, 9H), 0.07 (s, 6H). MS m/e: 543 (M+H)$^+$.

Step 2-4: Synthesis of 3-(Butylamino)-5-((1r,5r)-5-((tert-butyldimethylsilyl)oxy)cyclooctyl)-8-((4-methylpiperazin-1-yl)methyl)pyrimido[4,5-c]isoquinolin-6(5H)-one (126)

A degassed (3×) solution of 3-(butylamino)-5-((1r,5r)-5-((tert-butyldimethylsilyl)oxy)cyclooctyl)-8-chloropyrimido[4,5-c]isoquinolin-6(5H)-one (7, 0.13 g, 0.24 mmol), potassium 1-methyl-4-trifluoroboratomethylpiperzine (0.08 g, 0.36 mmol), XPhos Palladacycle G2 (0.02 g, 0.25 mmol), Cs$_2$CO$_3$ (0.235 g, 0.72 mmol) in dioxane/H$_2$O (9:1, 10 mL) was allowed to stir at 85° C. under N$_2$ atmosphere for 8 h. Since starting material was still present (LC/MS traces), additional amounts of the borate (0.16 g), palladium catalyst (0.02 g), and Cs$_2$CO$_3$ (0.235 g) were added to the cooled down reaction mixture, vessel degassed (3×), and the reaction mixture was allowed to stir at 85° C. overnight. The reaction mixture was cooled down to room temperature, concentrated and diluted with dichloromethane (20 mL) and water (20 mL). The layers were separated and the aqueous layer was extracted with dichloromethane (3×10 mL) and the combined organic layer was dried (MgSO$_4$), filtered and concentrated to provide a brown residue. Column chromatography purification using 0-10% methanol/dichloromethane as the eluent provided, upon trituration with hexanes, 0.101 g (68%) of 3-(butylamino)-5-((1r,5r)-5-((tert-butyldimethylsilyl)oxy)cyclooctyl)-8-((4-methylpiperazin-1-yl)methyl)pyrimido[4,5-c]isoquinolin-6(5H)-one (126) as a white solid. $^1$H NMR (400 MHz, Chloroform-d) δ 8.99 (s, 1H), 8.30 (d, J=22.7 Hz, 1H), 7.97 (d, J=8.3 Hz, 1H), 7.69 (dd, J=8.2, 1.9 Hz, 1H), 5.92 (s, 1H), 5.68 (s, 1H). 5.37 (s, 1H), 3.88 (s, 1H), 3.61 (s, 2H), 3.52 (p, J=6.4, 6.0 Hz, 2H), 2.74-2.35 (m, 9H), 2.28 (s, 3H), 1.97-1.64 (m, 12H), 1.47 (dq, J=14.2, 7.1 Hz, 2H), 0.89 (t, J=7.4 Hz, 3H), 0.91 (s, 9H), 0.07 (s, 6H). MS m/e: 621 (M+H)$^+$.

Step 2-5: Synthesis of of 3-(Butylamino)-5-((1r,5r)-5-hydroxycyclooctyl)-8-((4-methylpiperazin-1-yl)methyl)pyrimido[4,5-c]isoquinolin-6(5H)-one (127)

A solution of 3-(butylamino)-5-((1r,5r)-5-((tert-butyldimethylsilyl)oxy)cyclooctyl)-8-((4-methylpiperazin-1-yl)methyl)pyrimido[4,5-c]isoquinolin-6(5H)-one (126, 0.075 g, 0.12 mmol) in a mixture of i-PrOH (0.5 mL) and 10% HCl aqueous solution (0.5 mL) was allowed to stir at room temperature overnight (Plettenburg, O. et al. PCT Int. Appl. WO2008077551). LC/MS traces indicated only product was present, and hence the reaction mixture was concentrated to provide, upon trituration with ethyl ether, 62 mg (94%) of 3-(butylamino)-5-((1r,5r)-5-hydroxycyclooctyl)-8-((4-methylpiperazin-1-yl)methyl)pyrimido[4,5-c]isoquinolin-6(5H)-one (127) as a white solid. $^1$H NMR (400 MHz, Methanol-d$_4$) δ 9.20 (s, 1H), 8.50 (d, J=27.6 Hz, 1H), 8.32 (d, J=8.3 Hz, 1H), 8.04 (dd, J=8.2, 1.9 Hz, 1H), 5.75 (d, J=50.9 Hz, 1H), 4.37 (s, 2H), 3.90 (s, 2H), 3.81-3.35 (m, 9H), 2.98 (s, 3H), 2.75-2.52 (m, 2H), 2.03-1.68 (m, 13H), 1.60-1.44 (m, 2H), 1.02 (t, J=7.4 Hz, 3H). MS m/e: 507 (M+H)$^+$.

Synthesis of 143

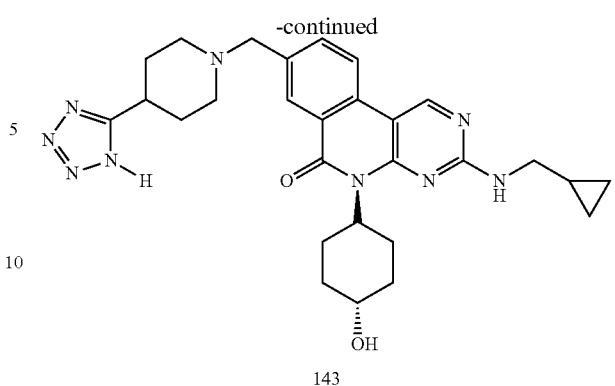

143

Synthesis of 8-((4-(1H-tetrazol-5-yl)piperidin-1-yl)methyl)-3-((cyclopropylmethyl)amino)-5-((1s,4s)-4-hydroxycyclohexyl)pyrimido[4,5-c]isoquinolin-6(5H)-one (143)

To a solution of 1-((3-((cyclopropylmethyl)amino)-5-((1s,4s)-4-hydroxycyclohexyl)-6-oxo-5,6-dihydropyrimido[4,5-c]isoquinolin-8-yl)methyl)piperidine-4-carbonitrile (0.1 g, 0.21 mmol) in DMF (2 mL), was added NH$_4$Cl (0.107 g, 2.0 mmol) at room temperature followed by NaN$_3$ (0.078 g, 1.2 mmol) and a drop of acetic acid. The resulting reaction mixture was stirred at room temperature for over night. Crude reaction mixture was diluted with few drops of water and the resulting white solid was filtered off to get the desired product in 45% yield. $^1$H NMR (300 MHz, DMSO-d$_6$) δ 8.98 (s, 1H), 8.02 (d, J=8.2 Hz, 1H), 7.90 (d, J=1.7 Hz, 1H), 7.62-7.49 (m, 1H), 7.44 (dd, J=8.3, 1.9 Hz, 1H), 5.15 (s, 1H), 3.41 (s, 4H), 2.86-2.53 (m, 5H), 1.96 (td, J=11.1, 10.6, 2.5 Hz, 2H), 1.71 (dd, J=10.2, 5.9 Hz, 4H), 1.63-1.41 (m, 1H), 1.32 (d, J=11.4 Hz, 2H), 1.07 (d, J=12.7 Hz, 2H), 0.87 (d, J=9.3 Hz, 1H), 0.35-0.11 (m, 2H), 0.01 (q, J=3.1, 1.7 Hz, 2H). MS m/e: 530 (M+H)$^+$.

Synthesis of 144 & 145

Synthesis of 3-((cyclopropylmethyl)amino)-8-((4-ethoxypiperidin-1-yl)methyl)-5-((1s,4s)-4-hydroxycyclohexyl)pyrimido[4,5-c]isoquinolin-6(5H)-one (144)

See General Experimental Procedure from Sekhar's Experimental Section

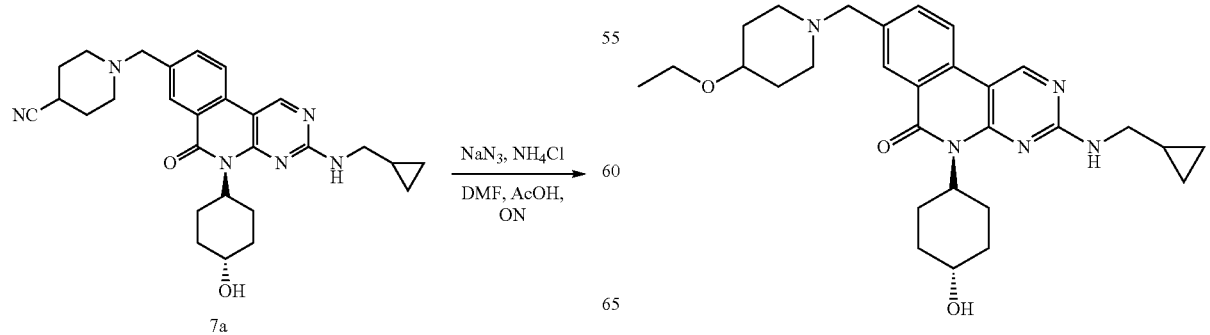

¹H NMR (300 MHz, DMSO-d₆) δ 8.99 (s, 1H), 8.02 (d, J=8.4 Hz, 1H), 7.85 (d, J=1.8 Hz, 1H), 7.55 (s, 1H), 7.42 (dd, J=8.3, 1.9 Hz, 1H), 5.17 (s, 1H), 4.42 (d, J=4.8 Hz, 1H), 3.31 (s, 3H), 3.18 (q, J=7.0 Hz, 2H), 3.04 (d, J=7.4 Hz, 3H), 2.64-2.36 (m, 4H), 1.85 (t, J=10.6 Hz, 2H), 1.78-1.66 (m, 2H), 1.64-1.48 (m, 2H), 1.42-1.26 (m, 2H), 1.28-0.95 (m, 4H), 0.84 (t, J=7.0 Hz, 3H), 0.29-0.15 (m, 2H), 0.10-0.02 (m, 2H). MS m/e: 506 (M+H)⁺.

Synthesis of 3-((cyclopropylmethyl)amino)-8-((4-hydroxy-4-methylpiperidin-1-yl)methyl)-5-((1s,4s)-4-hydroxycyclohexyl)pyrimido[4,5-c]isoquinolin-6(5H)-one (145)

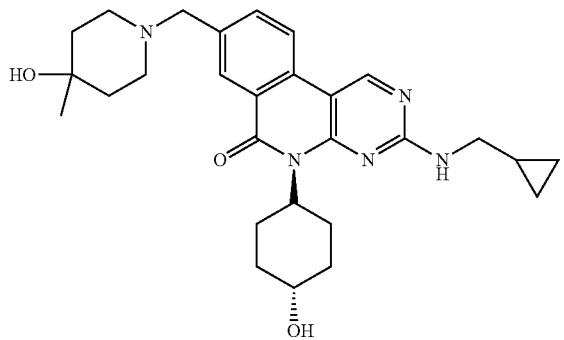

¹H NMR (300 MHz, DMSO-d₆) δ 8.99 (s, 1H), 8.01 (d, J=8.3 Hz, 1H), 7.86 (s, 1H), 7.54 (s, 1H), 7.41 (dd, J=8.3, 1.9 Hz, 1H), 5.16 (s, 1H), 4.41 (s, 1H), 3.83 (d, J=4.4 Hz, 1H), 3.78 (t, J=7.1 Hz, 1H), 3.31 (s, 2H), 3.07-2.96 (m, 3H), 2.55 (s, 2H), 2.14 (s, 4H), 1.75 (s, 1H), 1.33 (s, 2H), 1.22 (t, J=5.5 Hz, 4H), 1.09 (d, J=12.2 Hz, 1H), 0.93 (t, J=7.1 Hz, 1H), 0.86 (s, 3H), 0.29-0.16 (m, 2H), 0.02 (d, J=5.2 Hz, 2H). MS m/e: 492 (M+H)⁺.

trans-tert-Butyl (4-(3-((cyclopropylmethyl)amino)-8-((4-methylpiperazin-1-yl)methyl)-6-oxopyrimido[4,5-c]isoquinolin-5(6H)-yl)cyclohexyl)carbamate (184)

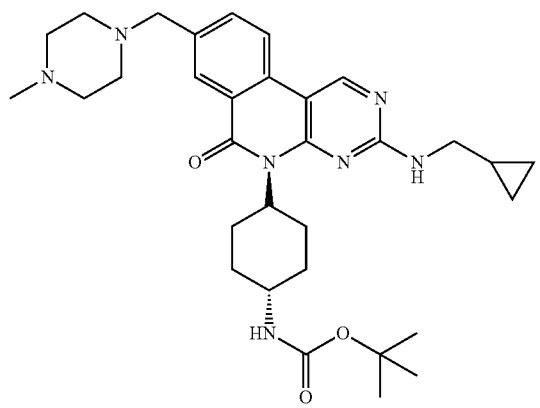

¹H NMR (400 MHz, DMSO-d₆) δ 9.21 (s, 1H), 8.24 (d, J=8.3 Hz, 1H), 8.19-8.01 (m, 1H), 7.78 (s, 1H), 7.64 (dd, J=8.3, 1.8 Hz, 1H), 6.79 (d, J=7.8 Hz, 1H), 5.36 (s, 1H), 3.54 (s, 2H), 3.28-3.21 (m, 2H), 2.98-2.66 (m, 3H), 2.45-2.17 (m, 8H), 2.13 (s, 3H), 1.89 (app d, J=11.8 Hz, 2H), 1.63-1.52 (app m, 2H), 1.38 (s, 10H), 1.18-1.06 (m, 1H), 0.67-0.38 (m, 2H), 0.38-0.13 (m, 2H). LCMS: Purity 96%, MS (m/e) 576 (MH⁺).

trans-8-((2-Oxa-7-azaspiro[3.5]nonan-7-yl)methyl)-3-((cyclopropylmethyl)amino)-5-(4-hydroxycyclohexyl)pyrimido[4,5-c]isoquinolin-6(5H)-one (186)

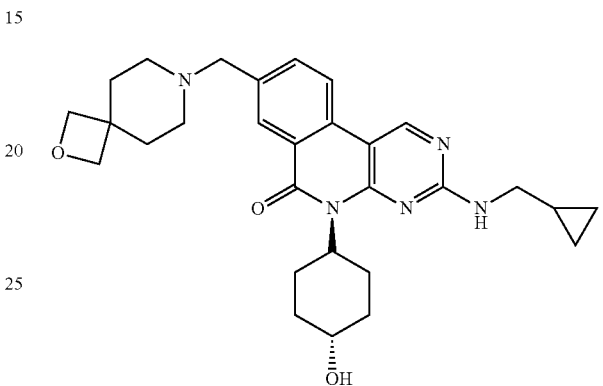

¹H NMR (400 MHz, Methanol-d₄) δ 9.11 (s, 1H), 8.22 (d, J=1.8 Hz, 1H), 8.17 (d, J=8.3 Hz, 1H), 7.72 (dd, J=8.3, 1.9 Hz, 1H), 5.58 (s, 1H), 4.41 (s, 4H), 3.79-3.65 (m, 1H), 3.59 (s, 2H), 3.36 (d, J=6.8 Hz, 2H), 2.92 (br s, 2H), 2.40 (br s, 4H), 2.10 (d, J=12.2 Hz, 2H), 1.89 (t, J=5.3 Hz, 4H), 1.70 (d, J=12.1 Hz, 2H), 1.49 (q, J=12.6, 11.8 Hz, 2H), 1.34-1.07 (m, 1H), 0.70-0.49 (m, 2H), 0.42-0.07 (m, 2H). LCMS: Purity 96%, MS (m/e) 504 (MH⁺).

trans-5-(4-Hydroxycyclohexyl)-3-(isopropylamino)-8-((4-methylpiperazin-1-yl)methyl)pyrimido[4,5-c]isoquinolin-6(5H)-one (195)

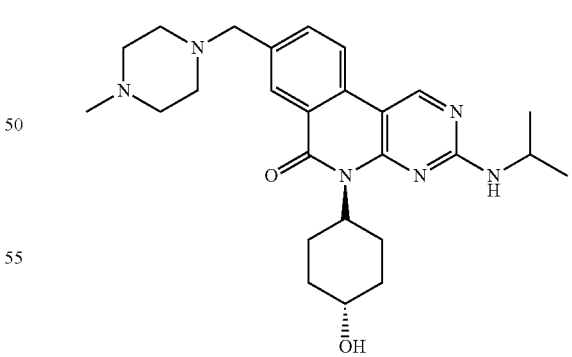

¹H NMR (400 MHz, Methanol-d₄) δ 9.10 (s, 1H), 8.23 (d, J=1.9 Hz, 1H), 8.16 (d, J=8.3 Hz, 1H), 7.73 (dd, J=8.3, 1.9 Hz, 1H), 5.58 (s, 1H), 4.20 (dt, J=13.9, 7.2 Hz, 1H), 3.71 (td, J=10.8, 5.3 Hz, 1H), 3.65 (s, 2H), 2.90 (s, 2H), 2.52 (s, 8H), 2.28 (s, 3H), 2.10 (d, J=11.6 Hz, 2H), 1.70 (d, J=12.3 Hz, 2H), 1.48 (q, J=12.9 Hz, 2H), 1.31 (d, J=6.5 Hz, 6H). LCMS: Purity 98%, MS (m/e) 465 (MH⁺).

303 trans-3-(Cyclopropylamino)-5-(4-hydroxycyclohexyl)-8-((4-methylpiperazin-1-yl)methyl)pyrimido[4,5-c]isoquinolin-6(5H)-one (196)

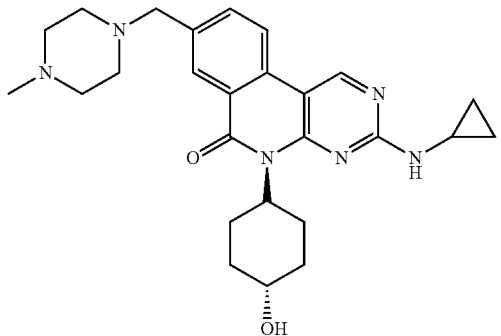

$^1$H NMR (400 MHz, Methanol-d$_4$) δ 9.11 (s, 1H), 8.29-8.22 (m, 1H), 8.18 (d, J=8.3 Hz, 1H), 7.74 (dd, J=8.3, 1.9 Hz, 1H), 5.54 (d, J=44.7 Hz, 1H), 3.78-3.67 (m, 1H), 3.65 (s, 2H), 2.98 (s, 2H), 2.81 (tt, J=7.1, 3.8 Hz, 1H), 2.53 (s, 8H), 2.28 (s, 3H), 2.10 (d, J=11.7 Hz, 2H), 1.70 (d, J=11.7 Hz, 2H), 1.60-1.40 (m, 2H), 0.93-0.78 (m, 2H), 0.69-0.53 (m, 2H). LCMS: Purity 95%, MS (m/e) 463 (MH$^+$).

trans-5-(4-hydroxycyclohexyl)-3-(isobutylamino)-8-((4-methylpiperazin-1-yl)methyl)pyrimido[4,5-c]isoquinolin-6(5H)-one (130)

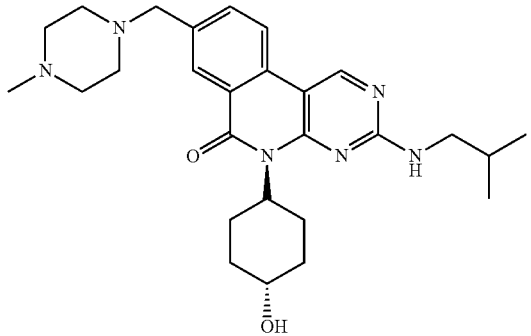

LCMS: Purity 98%, MS (m/e) 479 (MH$^+$).

trans-3-(cyclobutylamino)-5-(4-hydroxycyclohexyl)-8-((4-methylpiperazin-1-yl)methyl)pyrimido[4,5-c]isoquinolin-6(5H)-one (137)

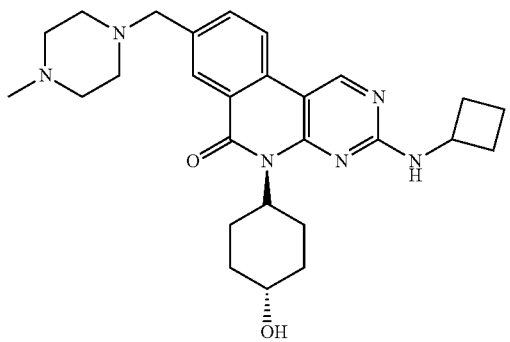

$^1$H NMR (400 MHz, DMSO-d$_6$) δ 9.21 (s, 1H), 8.24 (d, J=8.3 Hz, 1H), 8.09 (d, J=1.8 Hz, 1H), 8.05-7.90 (m, 1H),

304

7.64 (dd, J=8.3, 1.8 Hz, 1H), 5.38 (br s, 1H), 4.66 (s, 1H), 4.33 (s, 1H), 3.53 (s, 2H), 2.98-2.61 (m, 2H), 2.39-2.22 (m, 11H), 2.13 (s, 3H), 2.10-1.88 (m, 4H), 1.72 (s, 2H), 1.55 (s, 2H), 1.32 (q, J=12.1, 11.6 Hz, 2H). LCMS: Purity 98%, MS (m/e) 477 (MH$^+$).

trans-8-((2-Oxa-7-azaspiro[3.5]nonan-7-yl)methyl)-3-((2,2-difluorobutypamino)-5-(4-hydroxycyclohexyl)pyrimido[4,5-c]isoquinolin-6(5H)-one (197)

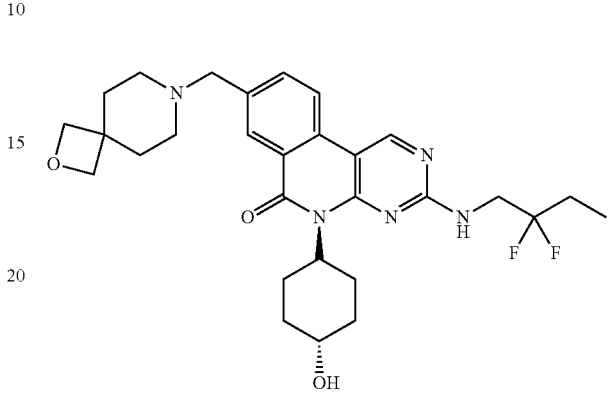

LCMS: Purity 98%, MS (m/e) 542 (MH$^+$).

trans-8-((4-(tert-Butyl)piperazin-1-yl)methyl)-3-((2,2-difluorobutyl)amino)-5-(4-hydroxycyclohexyl)pyrimido[4,5-c]isoquinolin-6(5H)-one (198)

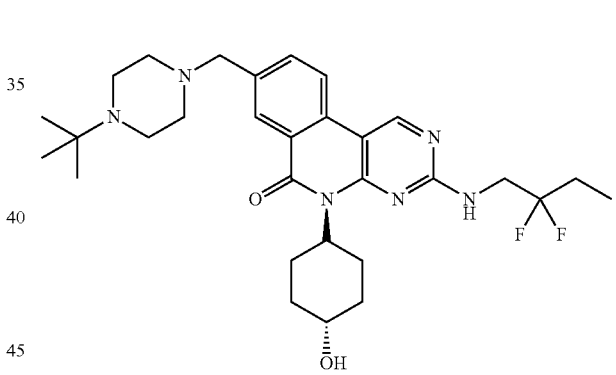

LCMS: Purity 98%, MS (m/e) 557 (MH$^+$).

trans-8-((4-(tert-Butyppiperazin-1-yl)methyl)-3-((3,3-difluorocyclobutyl)amino)-5-(4-hydroxycyclohexyl)pyrimido[4,5-c]isoquinolin-6(5H)-one (199)

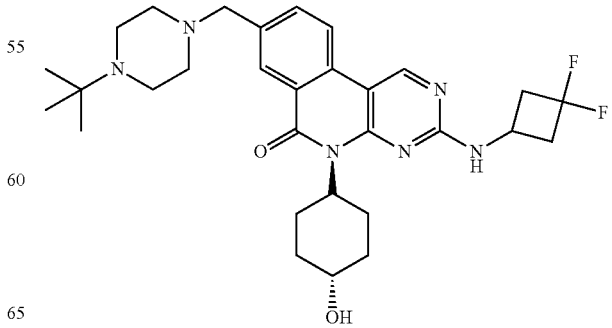

305

$^1$H NMR (400 MHz, Methanol-$d_4$) δ 9.15 (s, 1H), 8.25 (s, 1H), 8.20 (d, J=8.4 Hz, 1H), 7.74 (dd, J=8.3, 1.8 Hz, 1H), 5.52 (s, 1H), 4.35 (br s, 1H), 3.73 (dt, J=11.1, 6.5 Hz, 1H), 3.65 (s, 2H), 3.15-2.78 (m, 4H), 2.79-2.38 (m, 10H), 2.12 (d, J=12.2 Hz, 2H), 1.70 (d, J=12.2 Hz, 2H), 1.49 (q, J=10.6 Hz, 2H), 1.09 (s, 9H). LCMS: Purity 95%, MS (m/e) 555 (MH$^+$).

trans-tert-Butyl 1-((3-((cyclopropylmethyl)amino)-5-(4-hydroxycyclohexyl)-6-oxo-5,6-dihydropyrimido[4,5-c]isoquinolin-8-yl)methyl)piperidine-4-carboxylate (201)

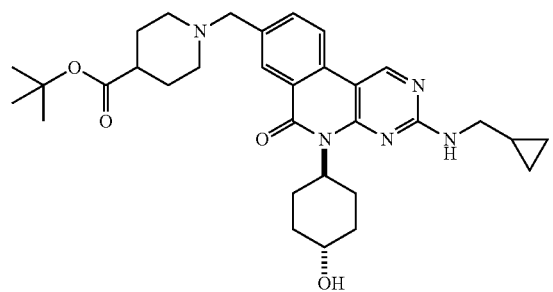

$^1$H NMR (400 MHz, Methanol-$d_4$) δ 9.11 (s, 1H), 8.22 (s, 1H), 8.17 (d, J=8.4 Hz, 1H), 7.74 (dd, J=8.4, 1.9 Hz, 1H), 5.58 (s, 1H), 3.77-3.68 (app m, 1H), 3.63 (s, 2H), 3.36 (d, J=6.8 Hz, 2H), 3.06-2.74 (m, 3H), 2.31-2.19 (m, 1H), 2.15-2.06 (m, 5H), 1.89-1.80 (m, 4H), 1.79-1.64 (m, 4H), 1.53-1.44 (m, 2H), 1.43 (s, 9H), 1.29-1.08 (m, 1H), 0.67-0.48 (m, 2H), 0.31 (q, J=4.9 Hz, 2H). LCMS: Purity 96%, MS (m/e) 562 (MH$^+$).

trans-3-((Cyclopropylmethyl)amino)-5-(4-hydroxycyclohexyl)-8-(piperidin-1-ylmethyl)pyrimido[4,5-c]isoquinolin-6(5H)-one (202)

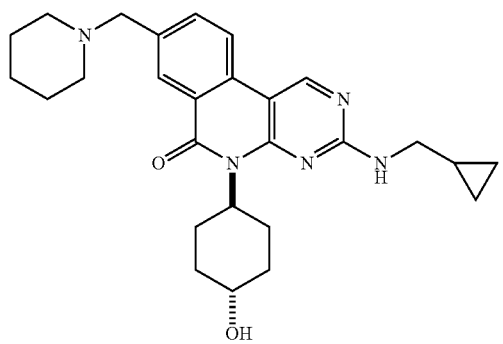

LCMS: Purity 97%, MS (m/e) 462 (MH$^+$).

306 trans-1-((3-((Cyclopropylmethyl)amino)-5-(4-hydroxycyclohexyl)-6-oxo-5,6-dihydropyrimido[4,5-c]isoquinolin-8-yl)methyl)piperidine-4-carbonitrile (204)

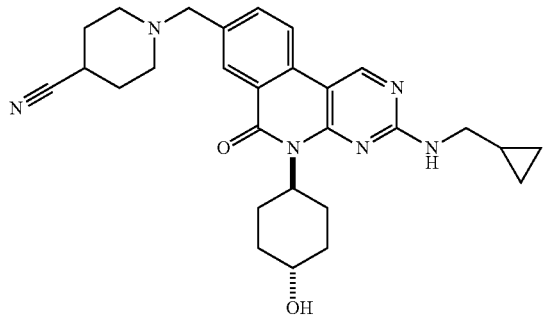

$^1$H NMR (400 MHz, Methanol-$d_4$) δ 9.11 (s, 1H), 8.22 (s, 1H), 8.17 (d, J=8.3 Hz, 1H), 7.73 (dd, J=8.3, 1.9 Hz, 1H), 5.53 (br s, 1H), 3.77-3.68 (m, 1H), 3.64 (s, 2H), 3.36 (d, J=6.8 Hz, 2H), 3.06-2.60 (m, 5H), 2.38 (app s, 2H), 2.10 (app d, J=12.4 Hz, 2H), 2.00-1.92 (m, 2H), 1.86-1.78 (m, 2H), 1.70 (d, J=12.5 Hz, 2H), 1.54-1.43 (m, 2H), 1.29-1.08 (m, 1H), 0.63-0.46 (m, 2H), 0.41-0.23 (m, 2H). LCMS: Purity 97%, MS (m/e) 487 (MH$^+$).

trans-8-((2-Oxa-7-azaspiro[3.5]nonan-7-yl)methyl)-3-(cyclobutylamino)-5-(4-hydroxycyclohexyl)pyrimido[4,5-c]isoquinolin-6(5H)-one (209)

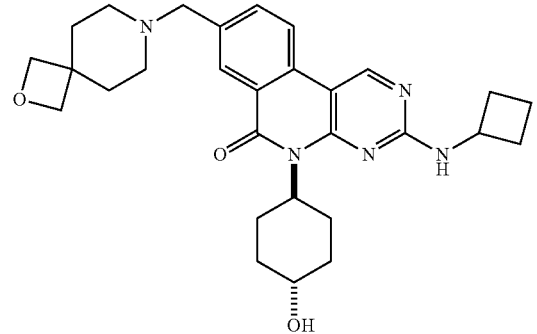

LCMS: Purity 97%, MS (m/e) 504 (MH$^+$).

trans-8-((2-Oxa-7-azaspiro[3.5]nonan-7-yl)methyl)-3-((3,3-difluorocyclobutyl)amino)-5-(4-hydroxycyclohexyl)pyrimido[4,5-c]isoquinolin-6(5H)-one (210)

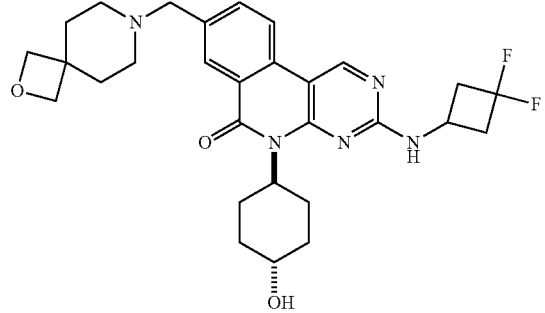

LCMS: Purity 97%, MS (m/e) 540 (MH$^+$).

307 trans-3-((3,3-Difluorocyclobutyl)amino)-5-(4-hydroxycyclohexyl)-8-((4-(pyridin-4-yl)piperazin-1-yl)methyl)pyrimido[4,5-c]isoquinolin-6(5H)-one (212)

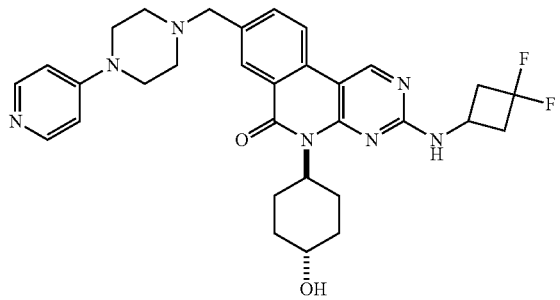

LCMS: Purity 96%, MS (m/e) 576 (MH$^+$).

trans-5-(4-hydroxycyclohexyl)-8-((4-methylpiperazin-1-yl)methyl)-3-(((S)-pentan-2-yl)amino)pyrimido[4,5-c]isoquinolin-6(5H)-one (213)

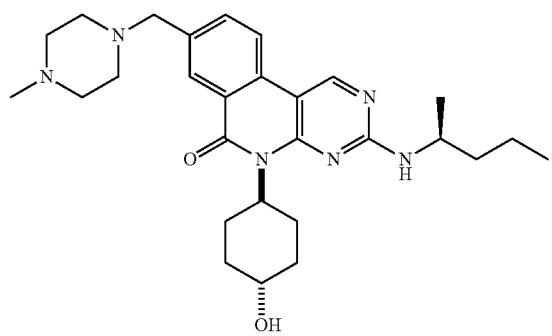

LCMS: Purity 94%, MS (m/e) 493 (MH$^+$).

trans-8-((2-oxa-7-azaspiro[3.5]nonan-7-yl)methyl)-5-(4-hydroxycyclohexyl)-3-(((S)-pentan-2-yl)amino)pyrimido[4,5-c]isoquinolin-6(5H)-one (214)

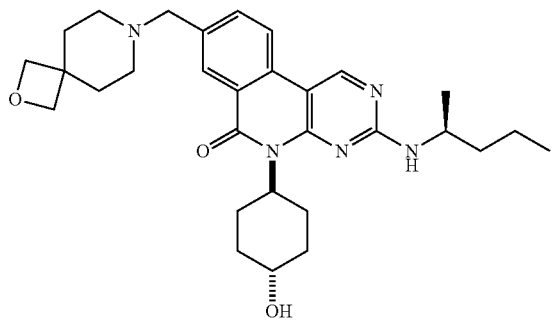

LCMS: Purity 94%, MS (m/e) 520 (MH$^+$).

308 trans-8-((4-(tert-Butyl)piperazin-1-yl)methyl)-5-(4-hydroxycyclohexyl)-3-(((S)-pentan-2-yl)amino)pyrimido[4,5-c]isoquinolin-6(5H)-one (215)

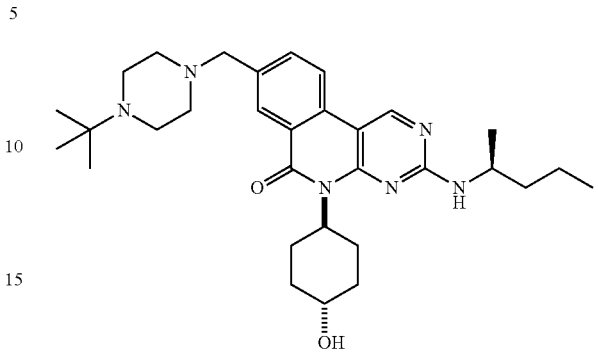

LCMS: Purity 94%, MS (m/e) 535 (MH$^+$).

trans-3-((Cyclopropylmethyl)amino)-5-(4-hydroxycyclohexyl)-8-((4-(pyrimidin-4-yl)piperazin-1-yl)methyl)pyrimido[4,5-c]isoquinolin-6(5H)-one (216)

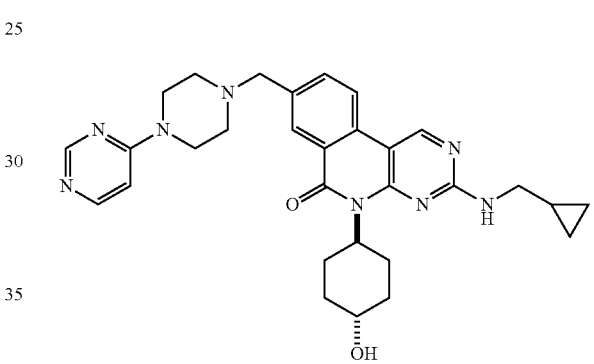

$^1$H NMR (400 MHz, Methanol-d$_4$) δ 9.11 (s, 1H), 8.43 (dd, J=1.2, 0.7 Hz, 1H), 8.27 (d, J=1.7 Hz, 1H), 8.19 (d, J=8.3 Hz, 1H), 8.09 (dd, J=6.5, 0.7 Hz, 1H), 7.77 (dd, J=8.3, 1.9 Hz, 1H), 6.75 (dd, J=6.5, 1.3 Hz, 1H), 5.53 (br s, 1H), 3.79-3.70 (m, 5H), 3.69 (s, 2H), 3.36 (d, J=6.9 Hz, 2H), 2.92 (br s, 2H), 2.56 (t, J=5.1 Hz, 4H), 2.10 (d, J=12.0 Hz, 2H), 1.70 (d, J=12.5 Hz, 2H), 1.49 (q, J=12.3, 11.1 Hz, 2H), 1.32-1.10 (m, 1H), 0.63-0.49 (m, 2H), 0.38-0.25 (m, 2H). LCMS: Purity 97%, MS (m/e) 541 (MH$^+$).

trans-3-((Cyclopropylmethyl)amino)-5-(4-hydroxycyclohexyl)-8-((4-(pyridin-4-yl)piperidin-1-yl)methyl)pyrimido[4,5-c]isoquinolin-6(5H)-one (217)

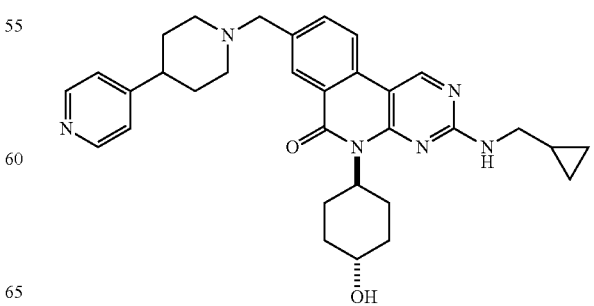

¹H NMR (400 MHz, Methanol-d₄) δ 9.11 (s, 1H), 8.47-8.36 (m, 2H), 8.26 (s, 1H), 8.18 (d, J=8.3 Hz, 1H), 7.76 (dd, J=8.4, 1.9 Hz, 1H), 7.41-7.16 (m, 2H), 5.58 (s, 1H), 3.76-3.70 (m, 1H), 3.69 (s, 2H), 3.36 (d, J=6.8 Hz, 2H), 3.05 (d, J=11.5 Hz, 2H), 2.92 (br s, 2H), 2.62 (app ddt, J=11.5, 8.6, 4.4 Hz, 1H), 2.22 (td, J=11.9, 3.3 Hz, 2H), 2.10 (d, J=11.9 Hz, 2H), 1.94-1.74 (m, 4H), 1.70 (d, J=11.9 Hz, 2H), 1.49 (app q, J=12.2, 11.0 Hz, 2H), 1.35-1.08 (m, 1H), 0.62-0.47 (m, 2H), 0.45-0.22 (m, 2H). LCMS: Purity 97%, MS (m/e) 539 (MH⁺).

trans-5-(4-Hydroxycyclohexyl)-3-(((S)-pentan-2-yl)amino)-8-((4-(pyridin-4-yl)piperazin-1-yl)methyl)pyrimido[4,5-c]isoquinolin-6(5H)-one (219)

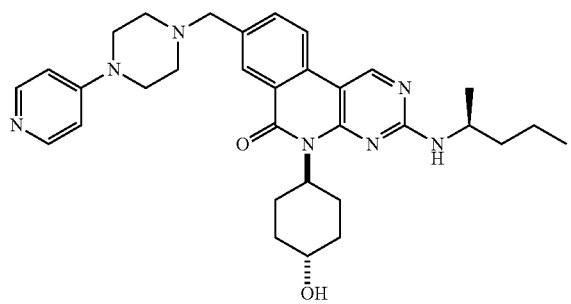

¹H NMR (400 MHz, Methanol-d₄) δ 9.10 (s, 1H), 8.26 (s, 1H), 8.18 (d, J=8.3 Hz, 1H), 8.10 (dd, J=5.2, 1.7 Hz, 2H), 7.77 (dd, J=8.3, 1.9 Hz, 1H), 6.82 (dd, J=5.3, 1.4 Hz, 2H), 5.58 (br s, 1H), 4.15 (app td, J=15.0, 14.1, 7.4 Hz, 1H), 3.75-3.71 (m, 1H), 3.69 (s, 2H), 3.42 (t, J=5.1 Hz, 4H), 2.90 (br s, 2H), 2.61 (t, J=5.1 Hz, 4H), 2.10 (d, J=12.6 Hz, 2H), 1.70 (app d, J=13.0 Hz, 4H), 1.58-1.41 (m, 4H), 1.28 (d, J=6.5 Hz, 3H), 0.97 (t, J=7.2 Hz, 3H). LCMS: Purity 97%, MS (m/e) 556 (MH⁺).

trans-3-((Cyclobutylmethyl)amino)-5-(4-hydroxycyclohexyl)-8-((4-(pyridin-4-yl)piperazin-1-yl)methyl)pyrimido[4,5-c]isoquinolin-6(5H)-one (220)

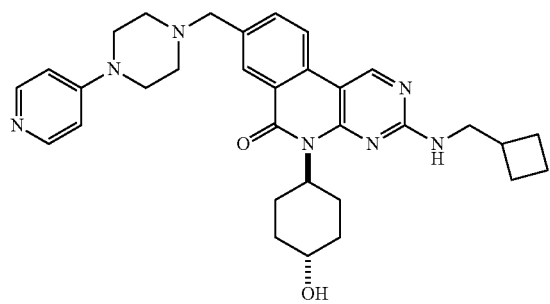

LCMS: Purity 97%, MS (m/e) 554 (MH⁺).

trans-3-((2,2-Difluorobutyl)amino)-5-(4-hydroxycyclohexyl)-8-((4-(pyridin-4-yl)piperazin-1-yl)methyl)pyrimido[4,5-c]isoquinolin-6(5H)-one (221)

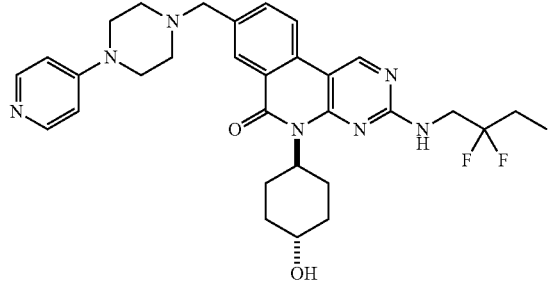

LCMS: Purity 97%, MS (m/e) 578 (MH⁺).

trans-3-((2-Cyclopropylethyl)amino)-5-(4-hydroxycyclohexyl)-8-((4-(pyridin-4-yl)piperazin-1-yl)methyl)pyrimido[4,5-c]isoquinolin-6(5H)-one (222)

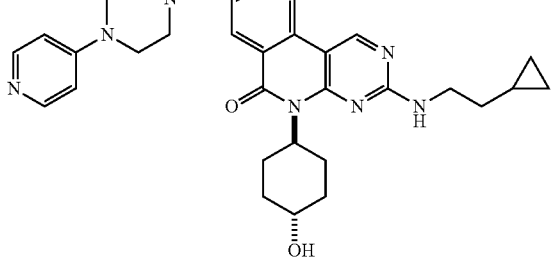

LCMS: Purity 97%, MS (m/e) 554 (MH⁺).

trans-5-(4-Hydroxycyclohexyl)-3-(isopentylamino)-8-((4-(pyridin-4-yl)piperazin-1-yl)methyl)pyrimido[4,5-c]isoquinolin-6(5H)-one (223)

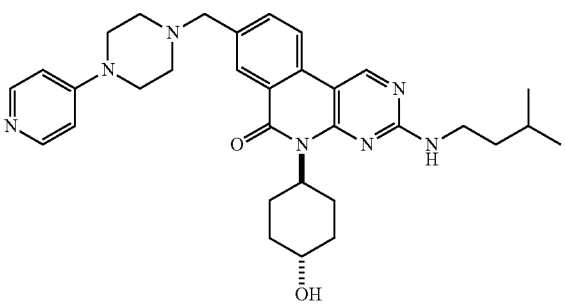

LCMS: Purity 97%, MS (m/e) 555 (MH⁺).

311 trans-3-((Cyclopropylmethyl)amino)-5-(4-hydroxy-4-methylcyclohexyl)-8-((4-(pyridin-4-yl)piperazin-1-yl)methyl)pyrimido[4,5-c]isoquinolin-6(5H)-one (224)

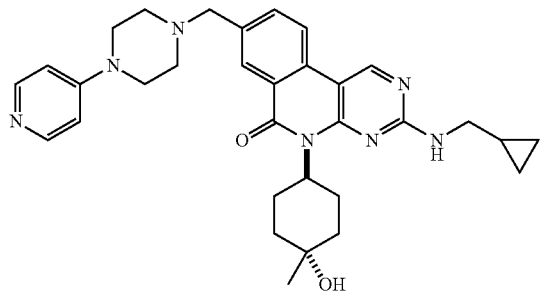

LCMS: Purity 97%, MS (m/e) 554 (MH⁺).

trans-3-(Cyclobutylamino)-5-(4-hydroxycyclohexyl)-8-((4-(pyridin-4-yl)piperazin-1-yl)methyl)pyrimido[4,5-c]isoquinolin-6(5H)-one (225)

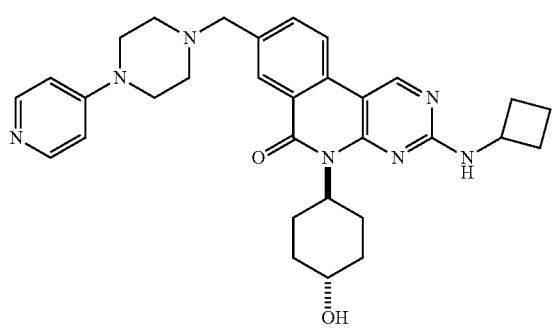

LCMS: Purity 98%, MS (m/e) 540 (MH⁺).

trans-3-(Cyclobutylamino)-5-(4-hydroxycyclohexyl)-8-((4-(pyrimidin-4-yl)piperazin-1-yl)methyl)pyrimido[4,5-c]isoquinolin-6(5H)-one (226)

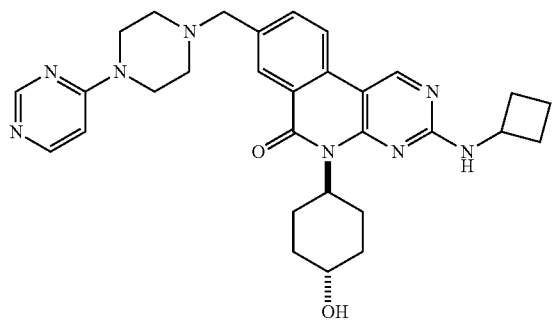

LCMS: Purity 99%, MS (m/e) 541 (MH⁺).

312 trans-3-(Cyclobutylamino)-5-(4-hydroxycyclohexyl)-8-((4-(pyridin-4-yl)piperidin-1-yl)methyl)pyrimido[4,5-c]isoquinolin-6(5H)-one (227)

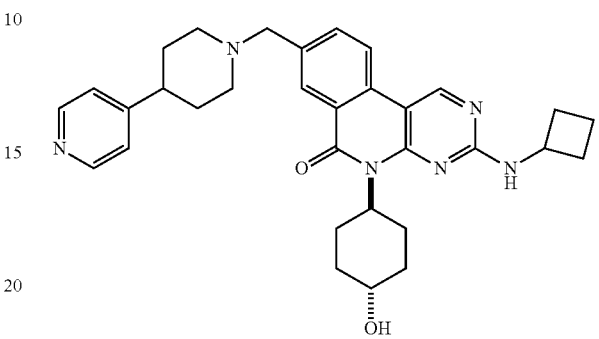

LCMS: Purity 97%, MS (m/e) 539 (MH⁺).

trans-3-((Cyclopropylmethyl)amino)-8-((4-hydroxy-4-(pyridin-4-yl)piperidin-1-yl)methyl)-5-(4-hydroxycyclohexyl)pyrimido[4,5-c]isoquinolin-6(5H)-one (228)

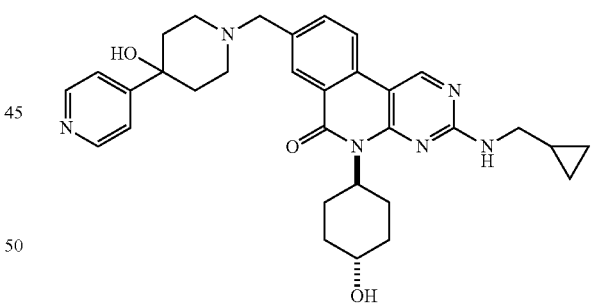

¹H NMR (400 MHz, DMSO-d₆) δ 9.22 (s, 1H), 8.57-8.42 (app m, 2H), 8.26 (d, J=8.3 Hz, 1H), 8.13 (d, J=1.6 Hz, 1H), 7.78 (s, 1H), 7.69 (dd, J=8.3, 1.8 Hz, 1H), 7.52-7.40 (app m, 2H), 5.38 (br s, 1H), 5.04 (s, 1H), 4.64 (br s, 1H), 3.62 (s, 2H), 3.52 (br s, 1H), 3.25 (t, J=6.4 Hz, 2H), 2.77 (br s, 2H), 2.71-2.55 (m, 2H), 2.43 (app d, J=11.0 Hz, 2H), 1.99-1.87 (m, 4H), 1.61-1.49 (m, 4H), 1.46-1.22 (m, 2H), 1.22-1.01 (m, 1H), 0.54-0.35 (m, 2H), 0.35-0.14 (m, 2H). LCMS: Purity 98%, MS (m/e) 555 (MH⁺).

trans-3-((Cyclopropylmethyl)amino)-5-(4-hydroxy-cyclohexyl)-8-((1-(pyridin-4-yl)piperidin-4-yl)methyl)pyrimido[4,5-c]isoquinolin-6(5H)-one (218)
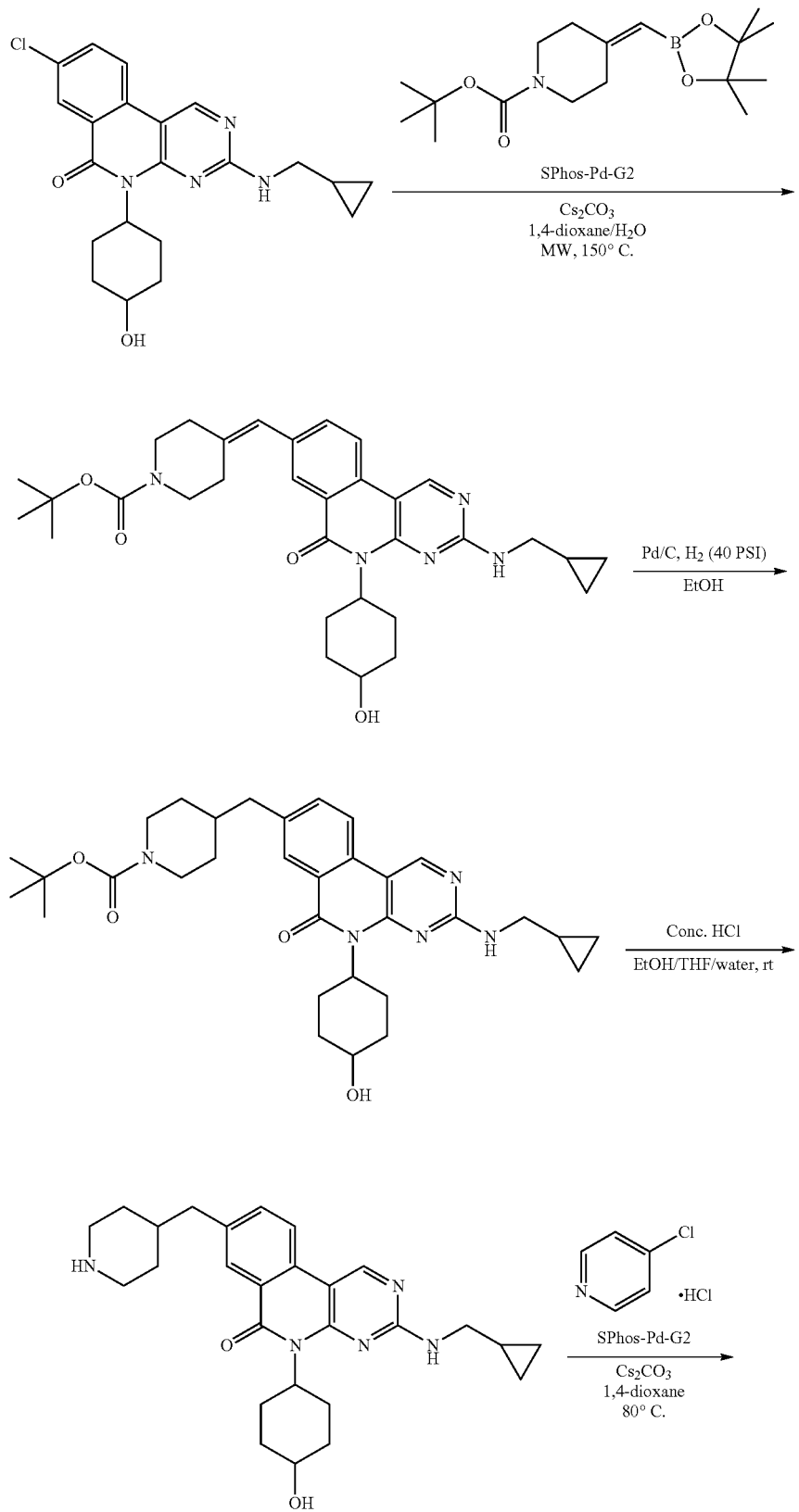

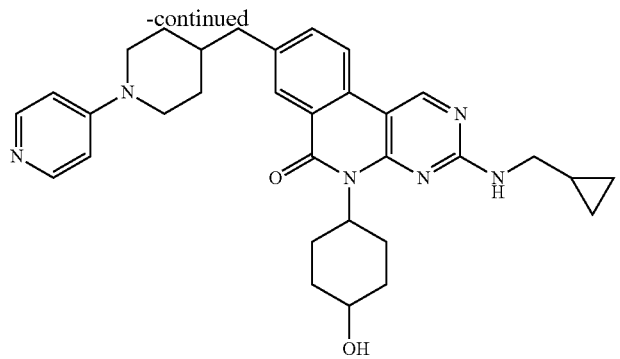

trans-3-((Cyclopropylmethyl)amino)-5-(4-hydroxycyclohexyl)-8-(piperidin-4-ylmethyl)pyrimido[4,5-c]isoquinolin-6(5H)-one (75 mg, 0.16 mmol), 4-chloropyridine hydrochloride (34 mg, 0.23 mmol), $Cs_2CO_3$ (150 mg, 0.46 mmol), SPhos-Pd-G2 (6 mg, 0.008 mmol) and dry 1,4-dioxane (4 mL) were transferred successively to a Teflon screw capped vial (18 mg, 0.025 mmol) containing a stir bar. Air was removed from the closed reaction system by vacuum, back filled with argon while stirring the reaction contents. After three repeated degassing cycles, reaction mixture was stirred at 80° C. After 6 h, dark reaction mixture was cooled to room temperature and analyzed the progress of reaction. LC/MS analysis of reaction aliquot indicated complete consumption of trans-3-((cyclopropylmethyl)amino)-5-(4-hydroxycyclohexyl)-8-(piperidin-4-ylmethyppyrimido[4,5-c]isoquinolin-6(5H)-one. Subsequently, dark heterogeneous reaction mixture was diluted with THF (10 mL) and filtered through Celite®. Reaction vial was further rinsed with THF (10 mL) and filtered through Celite®. Upon concentrating the combined homogeneous filtrates, the crude concentrated semi-solid was dissolved in 5% 7N $NH_3$ $MeOH/CH_2Cl_2$ (6 mL), adsorbed on silica gel, dried and purified by flash chromatography [Combiflash with RediSep® silica gel column 12 g (pre-conditioned with $CH_2Cl_2$) and eluted with 0-5% 7N $NH_3$ MeOH in $CH_2Cl_2$:$CH_2Cl_2$ solvent gradient. Off-white solid obtained upon concentrating product fractions was stirred in EtOAc (3 mL), sonicated and filtered. The resulting off-white solid was dried to provide trans-3-((cyclopropylmethyl)amino)-5-(4-hydroxycyclohexyl)-8-((1-(pyridin-4-yl)piperidin-4-yl)methyl)pyrimido[4,5-c]isoquinolin-6(5H)-one (62 mg). $^1$H NMR (400 MHz, Methanol-$d_4$) δ 9.09 (s, 1H), 8.13 (d, J=8.3 Hz, 1H), 8.10 (s, 1H), 8.08-8.01 (app m, 2H), 7.60 (dd, J=8.3, 1.9 Hz, 1H), 6.83-6.73 (app m, 2H), 5.58 (br s, 1H), 3.98 (d, J=13.2 Hz, 2H), 3.81-3.62 (m, 1H), 3.36 (d, J=6.8 Hz, 2H), 3.08-2.79 (app m, 3H), 2.71 (d, J=7.2 Hz, 2H), 2.10 (d, J=11.9 Hz, 2H), 1.96-1.86 (m, 1H), 1.78-1.66 (app m, 5H), 1.49 (app q, J=11.2, 10.7 Hz, 2H), 1.41-1.13 (m, 3H), 0.65-0.46 (m, 2H), 0.42-0.25 (m, 2H). LCMS: Purity 98%, MS (m/e) 539 (MH$^+$).

trans-3-((Cyclopropylmethyl)amino)-5-(4-hydroxycyclohexyl)-8-(piperidin-4-ylmethyl)pyrimido[4,5-c]isoquinolin-6(5H)-one (207)

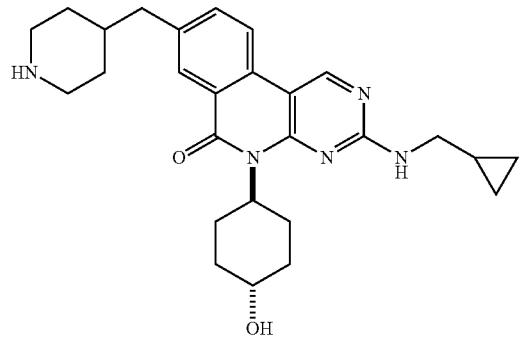

A microwave vial (35 mL) containing a stir bar was charged with trans-8-chloro-3-((cyclopropylmethyl)amino)-5-(4-hydroxycyclohexyl)pyrimido[4,5-c]isoquinolin-6(5H)-one (300 mg, 0.75 mmol), tert-butyl 4-((4,4,5,5-tetramethyl-1,3,2-dioxaborolan-2-yl)methylene)piperidine-1-carboxylate (310 mg, 0.96 mmol), SPhos-Pd-G2 (16 mg, 0.02 mmol), $Cs_2CO_3$ (610 mg, 1.87 mmol), 1,4-dioxane (18 mL) and water (2 mL) successively. The resulting heterogeneous suspension was degassed by bubbling nitrogen for 10 min, capped and heated at 150° C. in microwave for 90 min. At this stage, LC/MS of the reaction aliquot indicated 15% unreacted trans-8-chloro-3-((cyclopropylmethyl)amino)-5-(4-hydroxycyclohexyl)pyrimido[4,5-c]isoquinolin-6(5H)-one. Subsequently, additional amounts of tert-butyl 4-((4,4,5,5-tetramethyl-1,3,2-dioxaborolan-2-yl)methylene)piperidine-1-carboxylate (100 mg), SPhos-Pd-G2 (7 mg) and $Cs_2CO_3$ (1.87 mmol) were added to reaction mixture, degassed by nitrogen and stoppered. Upon heating at 150° C. in the microwave for 1 h, LC/MS of the reaction aliquot indicated the complete consumption of trans-8-chloro-3-((cyclopropylmethyl)amino)-5-(4-hydroxycyclohexyl)pyrimido[4,5-c]isoquinolin-6(5H)-one, dark reaction mixture was diluted with THF (15 mL) filtered through Celite®. The Celite® pad was further washed with THF rinses (2×10 ml) of reaction vial. Combined filtrates were stirred over anhydrous $MgSO_4$ for 15 min, filtered and concentrated. The resulting semi-solid crude concentrate was diluted with $CH_2Cl_2$ (4 mL), adsorbed on silica gel, purified by flash column chromatography [Combiflash with RediSep® silica gel column 40 g (pre-conditioned with 50% EtOAc/hexanes) and eluted with 50-100% EtOAc/hexanes solvent gradient). Thus obtained semi white solid of trans-tert-butyl 4-((3-((cyclopropylmethyl)amino)-5-(4-hydroxycyclohexyl)-6-oxo-5,6-dihydropyrimido[4,5-c]isoquinolin-8-yl)methylene)piperidine-1-carboxylate (380 mg) was hydrogenated over Pd/C (30 mg, 10 wt. % loading, Degussa type E101 NE/W) at 40 PSI for 2 days in EtOH in a par vessel on a par shaker. The reaction mixture was filtered through Celite®, concentrated, adsorbed on silica gel after dissolving in 3% 7N $NH_3$ MeOH in $CH_2Cl_2$, dried, purified by flash chromatography [Combiflash with RediSep® silica gel column 12 g (pre-conditioned with $CH_2Cl_2$) and eluted with 0-3% 7N $NH_3$ MeOH in $CH_2Cl_2$:$CH_2Cl_2$ solvent gradient] and obtained trans-tert-butyl 4-((3-((cyclopropylmethyl)amino)-5-(4-hydroxycyclohexyl)-6-oxo-5,6-dihydropyrimido[4,5-c]isoquinolin-8-yl)methyl)piperidine-1-carboxylate (340 mg) as a white solid.

trans-tert-butyl 4-((3-((cyclopropylmethyl)amino)-5-(4-hydroxycyclohexyl)-6-oxo-5,6-dihydropyrimido[4,5-c]isoquinolin-8-yl)methyl)piperidine-1-carboxylate (300 mg) was stirred in a solution of conc. HCl (2 mL), THF (4 mL), EtOH (2 mL) and water (3 mL) at room temperature. After 2 d, reaction mixture was concentrated, cooled in ice-bath, basified with solid $Na_2CO_3$ and warmed to room temperature. The resulting semi-suspension was extracted into 0.5% MeOH/$CH_2Cl_2$ (5×75 mL) and the combined organic layers were dried over anhydrous $Na_2SO_4$, filtered and concentrated. The crude concentrate was dissolved in 10% 7N $NH_3$ MeOH/$CH_2Cl_2$, adsorbed onto silica gel, dried, purified by flash chromatography [Combiflash with RediSep® silica gel column 24 g and eluted with 0-10% 7N $NH_3$ MeOH in $CH_2Cl_2$:$CH_2Cl_2$ solvent gradient] and obtained trans-3-((cyclopropylmethyl)amino)-5-(4-hydroxycyclohexyl)-8-(piperidin-4-ylmethyl)pyrimido[4,5-c]isoquinolin-6(5H)-one as a white solid (182 mg). $^1$H NMR (400 MHz, Methanol-$d_4$) δ 9.08 (s, 1H), 8.11 (d, J=8.3 Hz, 1H), 8.07 (s, 1H), 7.57 (dd, J=8.3, 1.9 Hz, 1H), 5.58 (br s, 1H), 3.75-3.67 (app m, 1H), 3.35 (d, J=6.8 Hz, 2H), 3.01 (app dt, J=12.5, 3.2 Hz, 2H), 2.91 (br s, 2H), 2.67 (d, J=7.1 Hz, 2H), 2.54 (td, J=12.5, 2.6 Hz, 2H), 2.10 (d, J=12.1 Hz, 2H), 1.87-1.57 (m, 5H), 1.57-1.34 (m, 2H), 1.28-1.15 (m, 3H), 0.62-0.47 (m, 2H), 0.31 (app q, J=4.8 Hz, 2H). LCMS: Purity 97%, MS (m/e) 462 (MH$^+$).

trans-3-((Cyclopropylmethyl)amino)-5-(4-hydroxycyclohexyl)-8-((1-methylpiperidin-4-yl)amino)pyrimido[4,5-c]isoquinolin-6(5H)-one (189)

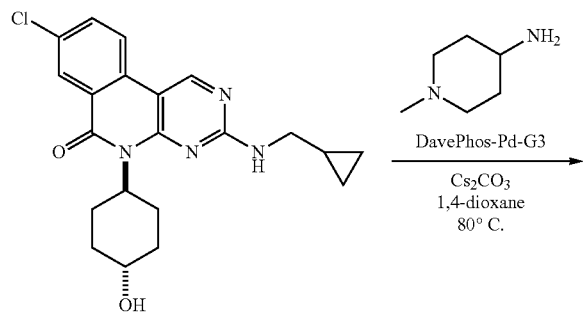

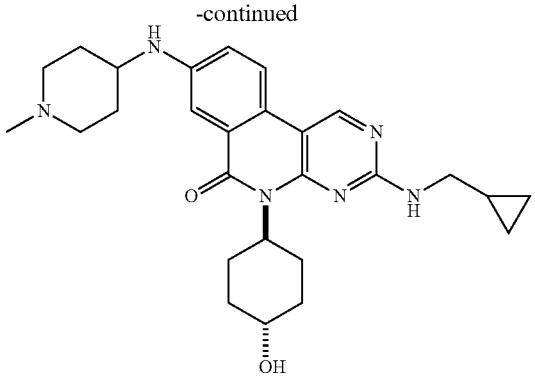

trans-8-Chloro-3-((cyclopropylmethyl)amino)-5-(4-hydroxycyclohexyl)pyrimido[4,5-c]isoquinolin-6(5H)-one (100 mg, 025 mmol), 4-amino-1-methylpiperidine (60 mg, 0.52 mmol), $Cs_2CO_3$ (163 mg, 0.50 mmol), DavePhos-Pd-G3 (20 mg, 26 mmol) and dry 1,4-dioxane (4 mL) were transferred successively to a Teflon stoppered vial (18 mg, 0.025 mmol) containing a stir bar. Air was removed from the closed reaction system by vacuum, back filled with argon while stirring the reaction contents. After three degassing cycles, reaction mixture was heated at 80° C. under argon atmosphere for 4 h. LC/MS analysis of reaction aliquot indicated complete consumption of trans-8-Chloro-3-((cyclopropylmethyl)amino)-5-(4-hydroxycyclohexyl)pyrimido[4,5-c]isoquinolin-6(5H)-one resulting in the quantitative formation of product after 4 h. Subsequently, dark heterogeneous reaction mixture was diluted with THF (10 mL) and filtered through Celite®. Upon rinsing the reaction vial with additional THF (10 mL) followed by filtration through Celite®, combined homogeneous filtrates were concentrated. The resulting dark semi-solid was dissolved in 5% 7N $NH_3$ MeOH/$CH_2Cl_2$ (12 mL), adsorbed on silica gel (10 g), dried and purified by flash chromatography [Combiflash with RediSep® silica gel column 12 g (pre-conditioned with $CH_2Cl_2$) and eluted with 0-5% 7N $NH_3$ MeOH in $CH_2Cl_2$:$CH_2Cl_2$ solvent gradient. Off-white solid obtained upon concentrating product fractions was stirred in EtOAc (3 mL), sonicated, filtered and suction dried. Thus collected off-white solid was further dried under high vacuum and obtained trans-3-((cyclopropylmethyl)amino)-5-(4-hydroxycyclohexyl)-8-((1-methylpiperidin-4-yl)amino)pyrimido[4,5-c]isoquinolin-6(5H)-one (63 mg). $^1$H NMR (400 MHz, DMSO-$d_6$) δ 9.04 (s, 1H), 8.00 (d, J=8.8 Hz, 1H), 7.43 (s, 1H), 7.24 (d, J=2.1 Hz, 1H), 7.06 (dd, J=8.8, 2.6 Hz, 1H), 5.95 (d, J=7.8 Hz, 1H), 5.39 (s, 1H), 4.62 (d, J=4.3 Hz, 1H), 3.52 (s, 1H), 3.22 (t, J=6.4 Hz, 3H), 3.02-2.62 (m, 3H), 2.16 (s, 3H), 2.12-1.75 (m, 6H), 1.56-1.24 m, 7H), 1.15-1.05 (m, 1H), 0.51-0.33 (m, 2H), 0.23 (dt, J=5.9, 4.4 Hz, 2H). LCMS: Purity 96%, MS (m/e) 477 (MH$^+$).

319 trans-3-((Cyclopropylmethyl)amino)-5-(4-hydroxy-cyclohexyl)-8-(3-morpholinopropoxy)pyrimido[4,5-c]isoquinolin-6(5H)-one (208)

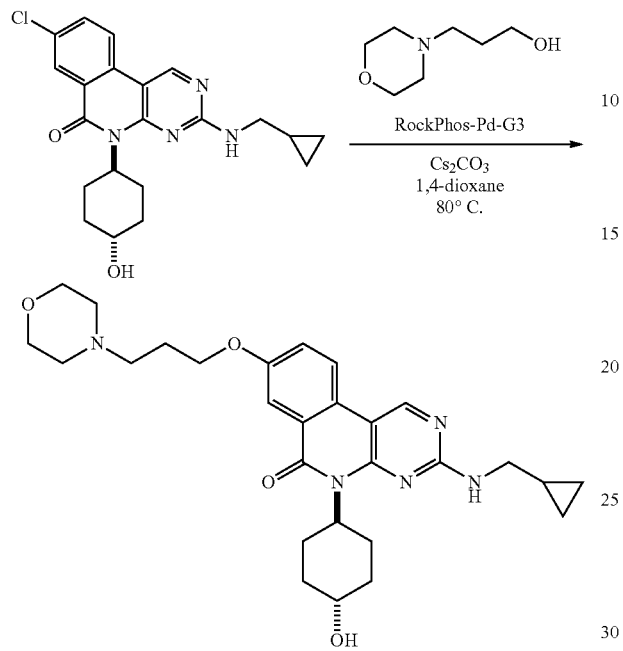

trans-8-Chloro-3-((cyclopropylmethyl)amino)-5-(4-hydroxycyclohexyl)pyrimido[4,5-c]isoquinolin-6(5H)-one (100 mg, 025 mmol), 3-morpholinopropanol (72 mg, 0.49 mmol), $Cs_2CO_3$ (160 mg, 0.49 mmol), RockPhos-Pd-G3 (6 mg, 0.006 mmol) and dry 1,4-dioxane (4 mL) were transferred successively to a Teflon stoppered vial containing a stir bar. Air was removed from the closed reaction system by vacuum, back filled with argon while stirring the reaction contents. After 3-4 cycles of repeated degassing cycles, reaction mixture was heated at 80° C. LC/MS analysis of reaction aliquot indicated complete consumption of trans-8-chloro-3-((cyclopropylmethyl)amino)-5-(4-hydroxycyclohexyl)pyrimido[4,5-c]isoquinolin-6(5H)-one resulting in the quantitative formation of product after 24 h. Reaction mixture was diluted with THF (5 mL) and filtered through Celite®. Upon rinsing reaction vial further with THF (5 mL) followed by filtration through Celite®, combined homogeneous filtrates were concentrated under reduced pressure. The resulting the crude concentrate was dissolved in 5% 7N $NH_3$ MeOH/$CH_2Cl_2$ (12 mL), adsorbed on silica gel (10 g), dried and purified by flash chromatography [Combiflash with RediSep® silica gel column 12 g (pre-conditioned with $CH_2Cl_2$) and eluted with 0-5% 7N $NH_3$ MeOH in $CH_2Cl_2$:$CH_2Cl_2$ solvent gradient. Pale yellow solid thus obtained after concentrating product fractions was stirred in EtOAc (3 mL), sonicated, filtered and dried to provide 78 mg of trans-3-((cyclopropylmethyl)amino)-5-(4-hydroxycyclohexyl)-8-(3-morpholinopropoxy)pyrimido[4,5-c]isoquinolin-6(5H)-one. LCMS: Purity 98%, MS (m/e) 508 ($MH^+$).

320 trans-5-(4-aminocyclohexyl)-3-((cyclopropylmethyl)amino)-8-((4-methylpiperazin-1-yl)methyl)pyrimido[4,5-c]isoquinolin-6(5H)-one (185)

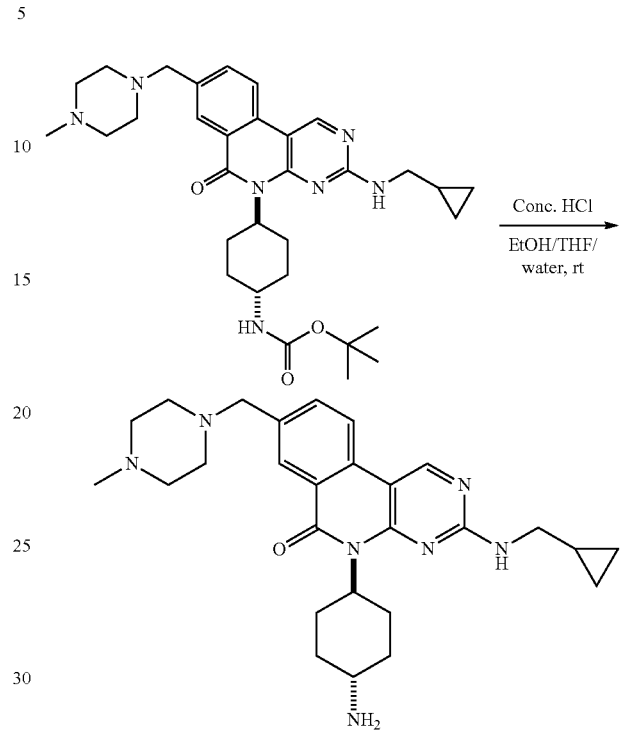

trans-tert-Butyl (4-(3-((cyclopropylmethyl)amino)-8-((4-methylpiperazin-1-yl)methyl)-6-oxopyrimido[4,5-c]isoquinolin-5(6H)-yl)cyclohexyl)carbamate (500 mg), was stirred in conc. HCl (3 mL), THF (3 mL), EtOH (3 mL) and water (2 mL). After 36 h, LC/MS analysis of reaction aliquot indicated partial (50%) progress, additional conc. HCl (3 mL), EtOH (2 mL) and water (3 mL) were added to reaction mixture and allowed to stir at room temperature for 3 days (90% conversion). Upon removing volatiles from reaction solution, the concentrate was cooled in ice-bath, basified with solid $Na_2CO_3$ and warmed to room temperature. The resulting white solid was collected by filtration, washed with water, suction dried and purified by flash chromatography [Combiflash with RediSep® silica gel column 12 g and eluted with 0-5% 7N $NH_3$ MeOH in $CH_2Cl_2$:$CH_2Cl_2$ solvent gradient]. Upon concentrating product fractions, the resulting white solid was stirred in EtOAc (6 mL), filtered and dried provide trans-5-(4-aminocyclohexyl)-3-((cyclopropylmethyl)amino)-8-((4-methylpiperazin-1-yl)methyl)pyrimido[4,5-c]isoquinolin-6(5H)-one (280 mg). $^1$H NMR (400 MHz, Methanol-$d_4$) δ 9.08 (s, 1H), 8.22 (d, J=2.0 Hz, 1H), 8.15 (d, J=8.3 Hz, 1H), 7.71 (dd, J=8.3, 1.9 Hz, 1H), 5.55 (d, J=17.1 Hz, 1H), 3.63 (s, 2H), 3.35 (d, J=6.9 Hz, 2H), 3.01-2.75 (m, 3H), 2.51 (s, 9H), 2.27 (s, 3H), 2.06 (app d, J=12.4 Hz, 2H), 1.79-1.60 (m, 2H), 1.40 (qd, J=12.9, 3.6 Hz, 2H), 1.29-0.93 (m, 1H), 0.65-0.45 (m, 2H), 0.44-0.13 (m, 2H). LCMS: Purity 98%, MS (m/e) 476 ($MH^+$).

trans-2-Cyano-N-(4-(3-((cyclopropylmethyl)amino)-8-((4-methylpiperazin-1-yl)methyl)-6-oxopyrimido[4,5-c]isoquinolin-5(6H)-yl)cyclohexyl)acetamide (190)

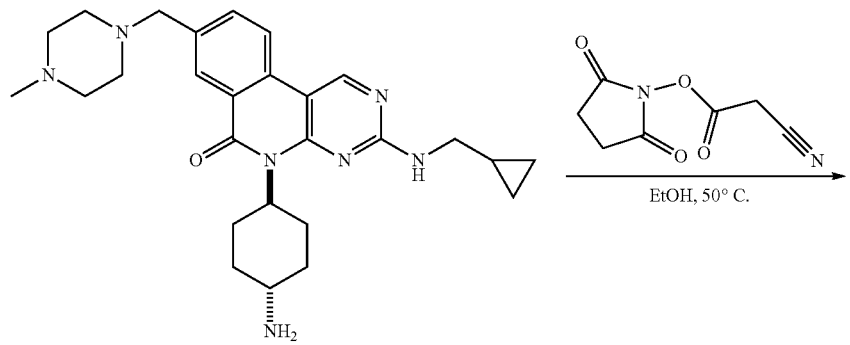

trans-5-(4-Aminocyclohexyl)-3-((cyclopropylmethyl)amino)-8-((4-methylpiperazin-1-yl)methyl)pyrimido[4,5-c]isoquinolin-6(5H)-one (25 mg, 52 mmol) and succinimidyl cyanoacetate (10 mg, 55 mmol) were stirred in EtOH at 50° C. under nitrogen overnight. Reaction mixture was concentrated and purified by flash chromatography [Combiflash with RediSep® silica gel column 12 g (pre-conditioned with $CH_2Cl_2$) and eluted with 0-7% 7N $NH_3$ MeOH in $CH_2Cl_2$: $CH_2Cl_2$ solvent gradient) to obtain trans-2-Cyano-N-(4-(3-((cyclopropylmethyl)amino)-8-((4-methylpiperazin-1-yl)methyl)-6-oxopyrimido[4,5-c]isoquinolin-5(6H)-yl)cyclohexyl)acetamide (18 mg) as a white solid. $^1$H NMR (400 MHz, DMSO-$d_6$) δ 9.22 (s, 1H), 8.27-8.19 (m, 2H), 8.10 (d, J=1.8 Hz, 1H), 7.80 (s, 1H), 7.65 (dd, J=8.4, 1.8 Hz, 1H), 5.39 (s, 1H), 3.70-3.54 (app m, 4H), 3.29-3.22 (m, 1H), 2.99-2.72 (br m, 3H), 2.42-2.20 (m, 8H), 2.13 (s, 3H), 1.95 (d, J=12.1 Hz, 2H), 1.71-1.52 (m, 3H), 1.46-1.25 (m, 2H), 1.19-1.05 (m, 1H), 0.46 (d, J=7.7 Hz, 2H), 0.26 (d, J=4.9 Hz, 2H). LCMS: Purity 97%, MS (m/e) 543 (MH$^+$).

trans-1-((3-((Cyclopropylmethyl)amino)-5-(4-hydroxycyclohexyl)-6-oxo-5,6-dihydropyrimido[4,5-c]isoquinolin-8-yl)methyl)piperidine-4-carboxamide (203)

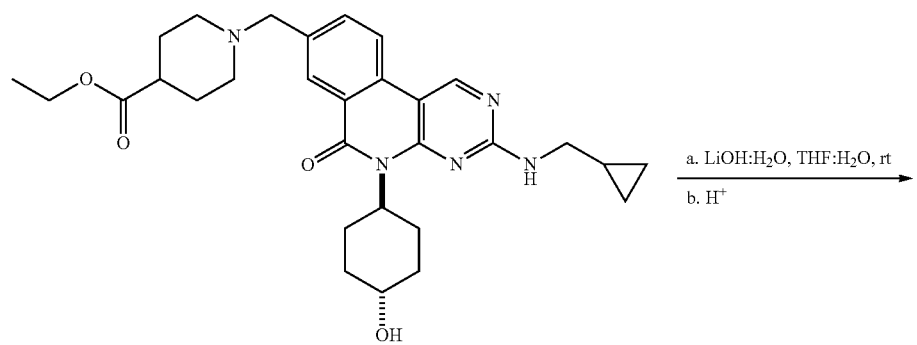

-continued

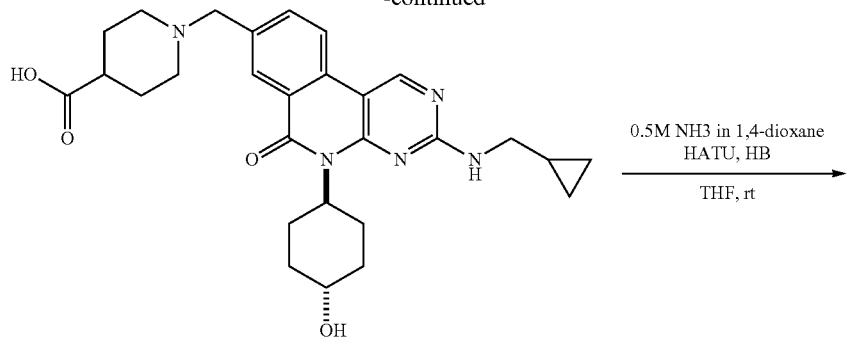

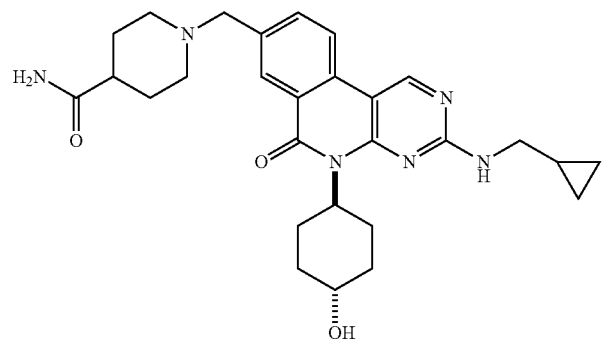

i-Pr$_2$NEt (0.08 mL, 58 mg, 0.57 mmol) followed by 0.5 M NH$_3$ in 1,4-dioxane (1.48 mL, 0.74 mmol) were added successively to a stirring suspension of trans-1-((3-((cyclopropylmethyl)amino)-5-(4-hydroxycyclohexyl)-6-oxo-5,6-dihydropyrimido[4,5-c]isoquinolin-8-yl)methyl)piperidine-4-carboxylic acid (75 mg, 0.15 mmol) and HATU (84 mg, 0.22 mmol) in THF (5 mL), under nitrogen. After 14 h, reaction mixture was concentrated, diluted with water and filtered. Thus collected solid upon suction drying was dissolved in 5% 7N NH$_3$ MeOH/CH$_2$Cl$_2$, adsorbed on silica gel, dried and purified by flash silica gel column chromatography [Combiflash with RediSep® silica gel column 4 g (pre-conditioned with CH$_2$Cl$_2$) and eluted with 0-7% 7N NH$_3$ MeOH in CH$_2$Cl$_2$:CH$_2$Cl$_2$ solvent gradient) and obtained trans-1-((3-((cyclopropylmethyl)amino)-5-(4-hydroxycyclohexyl)-6-oxo-5,6-dihydropyrimido[4,5-c]isoquinolin-8-yl)methyl)piperidine-4-carboxamide as a white solid (38 mg) $^1$H NMR (400 MHz, Methanol-d$_4$) δ 9.11 (s, 1H), 8.22 (d, J=1.6 Hz, 1H), 8.17 (d, J=8.3 Hz, 1H), 7.74 (dd, J=8.3, 1.9 Hz, 1H), 5.58 (s, 1H), 3.83-3.66 (m, 1H), 3.63 (s, 2H), 3.36 (d, J=6.8 Hz, 2H), 3.07-2.80 (app m, 3H), 2.26-2.18 m, 1H), 2.14-2.04 2.09 (m, 4H), 1.88-1.56 (m, 6H), 1.62-1.36 (m, 2H), 1.36-1.09 (m, 1H), 0.60-0.44 (m, 2H), 0.44-0.19 (m, 2H). LCMS: Purity 97%, MS (m/e) 505 (MH$^+$).

trans-1-((3-(((Cyclopropylmethyl)amino)-5-(4-hydroxycyclohexyl)-6-oxo-5,6-dihydropyrimido[4,5-c]isoquinolin-8-yl)methyl)piperidine-4-carboxylic acid (200)

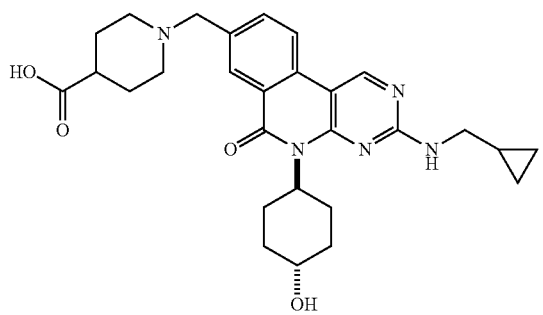

trans-ethyl 1-((3-(((Cyclopropylmethyl)amino)-5-(4-hydroxycyclohexyl)-6-oxo-5,6-dihydropyrimido[4,5-c]isoquinolin-8-yl)methyl)piperidine-4-carboxylate (160 mg, 0.3 mmol) and LiOH.H$_2$O (25 mg, 0.59 mmol) was stirred in THF (2 mL) and water (1 mL) at room temperature. LC/MS analysis of reaction aliquot indicated quantitative conversion of ester to acid after 4 h. Subsequently, reaction mixture was concentrated under reduce pressure and acidified with 1N aq. HCl to pH 7.0. The resulting homogeneous solution was extracted into EtOAc (3×30 mL). Combined organic layers were dried over anhydrous Na$_2$SO$_4$, polish filtered and concentrated. The resulting white solid was diluted with water, stirred, filtered, dried and obtained trans-1-((3-((cyclopropylmethyl)amino)-5-(4-hydroxycyclohexyl)-6-oxo-5,6-dihydropyrimido[4,5-c]isoquinolin-8-yl)methyl)piperidine-4-carboxylic acid (114 mg) $^1$H NMR (400 MHz, DMSO-d$_6$) δ 9.21 (s, 1H), 8.24 (d, J=8.3 Hz, 1H), 8.08 (d, J=1.8 Hz, 1H), 7.77 (s, 1H), 7.64 (dd, J=8.3, 1.9 Hz, 1H), 5.41 (s, 1H), 4.63 (s, 1H), 4.02 (s, 1H), 3.53 (s, 2H), 3.21-3.22 (app m, 4H), 2.85-2.64 (m, 2H), 2.20-2.13 (m, 1H), 2.02-1.89 (m, 4H), 1.80-1.69 (m, 2H), 1.60-1.47 (m, 4H), 1.38-1.23 (m, 2H), 1.14-1.07 (m, 1H), 0.44 (dt, J=8.2, 2.9 Hz, 2H), 0.37-0.12 (m, 2H). LCMS: Purity 98%, MS (m/e) 506 (MH+).

Procedure for the preparation of trans-4-(3-(alkylamino)-8-((4-methylpiperazin-1-yl)methyl)-6-oxopyrimido[4,5-c]isoquinolin-5(6H)-yl)cyclohexane-1-carboxylic acids and trans-4-(3-(alkylamino)-8-((4-methylpiperazin-1-yl)methyl)-6-oxopyrimido[4,5-c]isoquinolin-5(6H)-yl)cyclohexane-1-carboxamides was added LiOH:H$_2$O (65 mg, 2.7 mmol). Upon stirring at room temperature overnight, reaction solution was concentrated under reduced pressure and neutralized with 1N aq. HCl (pH 6). The resulting solid was filtered and dried to provide crude trans-4-(3-(butylamino)-8-chloro-6-oxopyrimido[4,5-c]isoquinolin-5(6H)-yl)cyclohexane-1-carboxylic acid (300 mg) [LCMS: Purity 96%, MS (m/e) 443]. A stirring mixture of trans-4-(3-(butylamino)-8-chloro-6-oxopyrimido[4,5-c]isoquinolin-5(6H)-yl)cyclohexane-1-carboxylic acid (300 mg, 0.7 mmol), HOBt (142 mg, 1.0 mmol), EDCl.HCl (202 mg, 1.0 mmol) and dry THF (7 mL) under nitrogen was treated with i-Pr$_2$NEt (0.35 mL, 260 mg, 2.1 mL). After 1 h, 28% ammonia solution (2.5 mL) was added to the stirring reaction mixture and concentrated after

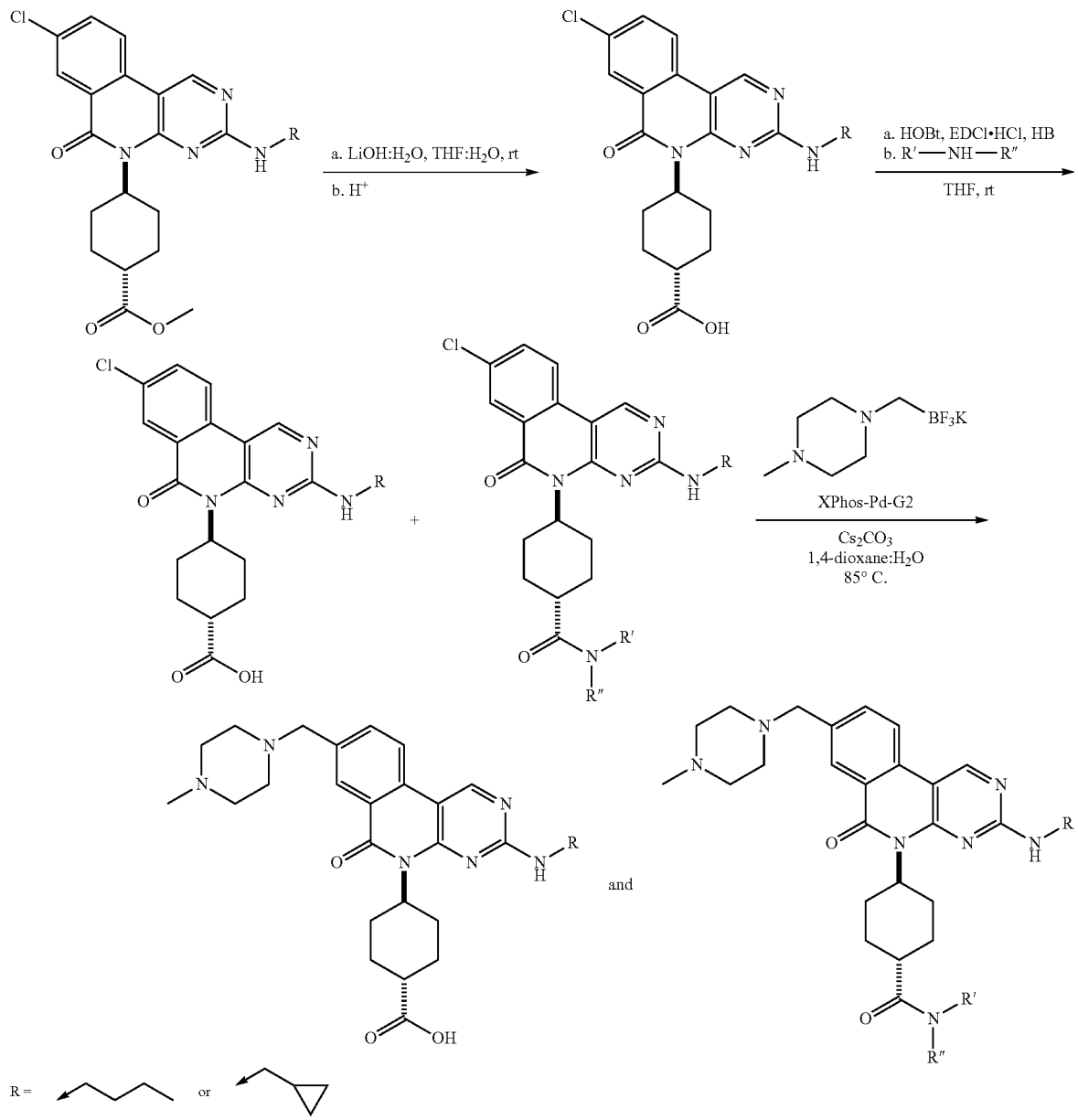

trans-methyl 4-(3-(butylamino)-8-chloro-6-oxopyrimido[4,5-c]isoquinolin-5(6H)-yl)cyclohexane-1-carboxylate (600 mg, 1.35 mmol) dissolved in THF (10 mL):H$_2$O (5 mL) 16 h. Upon diluting the concentrate with water, the resulting white solid (200 mg), a 1:1 mixture of acid and amide, was filtered, suction dried and used in the next step of Suzuki reaction with no further purification. Thus, 1:1 mixture of acid:amide (200 mg, 0.47 mmol), potassium 1-methyl-4-trifluoroboratomethyl piperazine (150 mg, 0.75 mmol), Cs$_2$CO$_3$ (350 mg, 1.1 mmol), XPhos-Pd-G2 (30 mg, 0.04 mmol), 1,4-dioxane (3 mL) and water were added successively to a Teflon screw cap vial containing a stir bar. Following three degassing cycles of vacuum and argon purge, reaction mixture was stirred at 85° C. for 17 h. Subsequently, reaction mixture was diluted with THF (7 mL) and filtered through Celite®. Upon concentration of the filtrate, the crude residue was purified (preparative reverse phase HPLC using acetonitrile:water containing TFA modifier) to obtain acid and amide separately either as tris trifluoroacetic acid salt or solvates.

trans-4-(3-(Butylamino)-8-((4-methylpiperazin-1-yl)methyl)-6-oxopyrimido[4,5-c]isoquinolin-5(6H)-yl)cyclohexane-1-carboxylic acid tris trifluoroacetic acid salt or solvate (132)

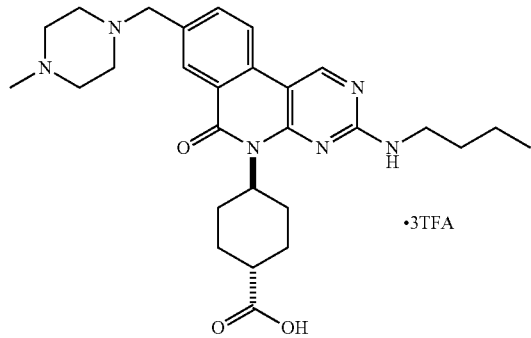

LCMS: Purity 98%, MS (m/e) 507 (MH$^+$-3TFA).

trans-4-(3-(Butylamino)-8-((4-methylpiperazin-1-yl)methyl)-6-oxopyrimido[4,5-c]isoquinolin-5(6H)-yl)cyclohexane-1-carboxamide tris trifluoroacetic acid salt or solvate (131)

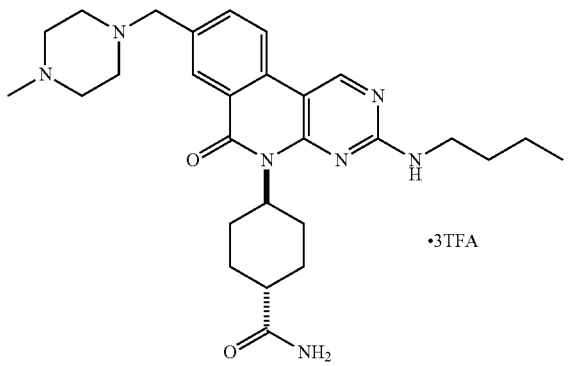

$^1$H NMR (400 MHz, Methanol-d$_4$) δ 9.13 (s, 1H), 8.31 (s, 1H), 8.21 (d, J=8.3 Hz, 1H), 7.81 (dd, J=8.3, 1.9 Hz, 1H), 5.54 (s, 1H), 3.86 (s, 2H), 3.47-3.37 (m, 4H), 3.38-3.33 (m, 4H), 2.90 (s, 3H), 2.87-2.76 (br s, 4H), 2.39 (app t, J=12.3 Hz, 1H), 2.06 (d, J=12.7 Hz, 2H), 1.85-1.62 (m, 4H), 1.27-1.16 (m, 1H), 0.65-0.55 (m, 2H), 0.37 (q, J=5.1 Hz, 2H). LCMS: Purity 99%, MS (m/e) 504 (MH$^+$-3TFA).

The following amides were prepared in the similar manner to the preparation of trans-4-(3-(butylamino)-8-((4-methylpiperazin-1-yl)methyl)-6-oxopyrimido[4,5-c]isoquinolin-5(6H)-yl)cyclohexane-1-carboxamide and purified by either reverse phase HPLC using acetonitrile:water containing TFA/formic acid as modifier or flash silica gel column chromatography [Combiflash with RediSep® silica gel column 12 g and eluted with 0-5% 7N NH$_3$ MeOH:CH$_2$Cl$_2$ solvent gradient).

trans-4-(3-((Cyclopropylmethyl)amino)-8-((4-methylpiperazin-1-yl)methyl)-6-oxopyrimido[4,5-c]isoquinolin-5(6H)-yl)cyclohexane-1-carboxamide (tris trifluoroacetic acid salt or solvate (134)

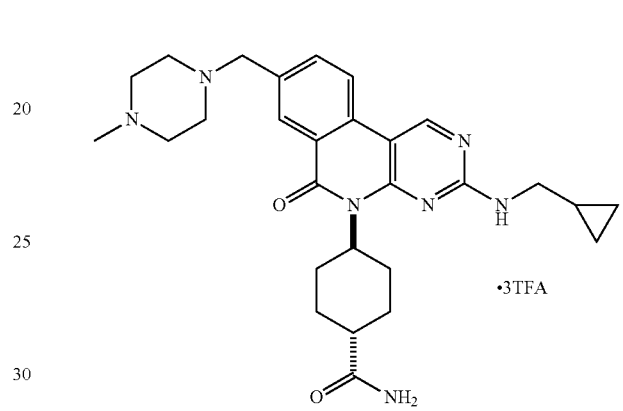

$^1$H NMR (400 MHz, Methanol-d$_4$) δ 9.13 (s, 1H), 8.31 (s, 1H), 8.21 (d, J=8.3 Hz, 1H), 7.81 (dd, J=8.3, 1.9 Hz, 1H), 5.54 (s, 1H), 3.86 (s, 2H), 3.47-3.37 (m, 4H), 3.38-3.33 (m, 4H), 2.90 (s, 3H), 2.87-2.76 (br s, 4H), 2.39 (app t, J=12.3 Hz, 1H), 2.06 (d, J=12.7 Hz, 2H), 1.85-1.62 (m, 4H), 1.27-1.16 (m, 1H), 0.65-0.55 (m, 2H), 0.37 (q, J=5.1 Hz, 2H). LCMS: Purity 99%, MS (m/e) 504 (MH$^+$-3TFA).

trans-4-(3-((Cyclopropylmethyl)amino)-8-((4-methylpiperazin-1-yl)methyl)-6-oxopyrimido[4,5-c]isoquinolin-5(6H)-yl)cyclohexane-1-carboxylic acid tris trifluoroacetic acid salt or solvate (135)

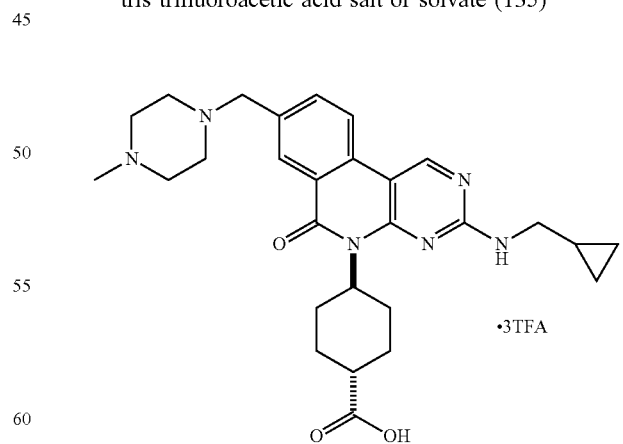

$^1$H NMR (400 MHz, Methanol-d$_4$) δ 9.12 (s, 1H), 8.29 (d, J=1.7 Hz, 1H), 8.21 (d, J=8.3 Hz, 1H), 7.78 (dd, J=8.4, 1.8 Hz, 1H), 5.56 (s, 1H), 3.80 (s, 2H), 3.39 (s, 4H), 3.98-2.62 (app m, 11H), 2.46-2.39 (m, 1H), 2.19 (app d, J=13.0 Hz, 2H), 1.79 (d, J=12.2 Hz, 2H), 1.71-1.55 (m, 2H), 1.26-1.19

(m, 1H), 0.63-0.53 (m, 2H), 0.35 (t, J=4.9 Hz, 2H). LCMS: Purity 99%, MS (m/e) 505 (MH+-3TFA).

trans-4-(3-(Butylamino)-8-((4-methylpiperazin-1-yl)methyl)-6-oxopyrimido[4,5-c]isoquinolin-5(6H)-yl)-N-methylcyclohexane-1-carboxamide (138)

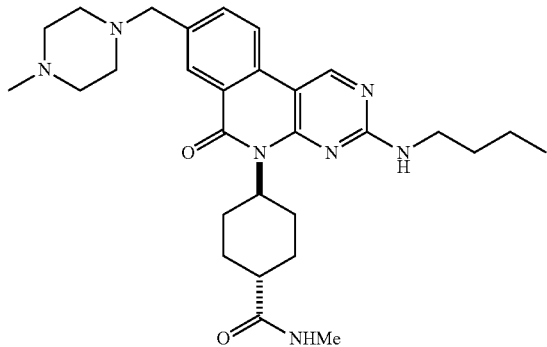

¹H NMR (400 MHz, DMSO-d₆) δ 9.20 (s, 1H), 8.24 (d, J=8.3 Hz, 1H), 8.08 (s, 1H), 7.73 (app q, J=5.5, 5.0 Hz, 2H), 7.64 (dd, J=8.3, 1.8 Hz, 1H), 5.46 (s, 1H), 3.53 (s, 2H), 3.35 (q, J=6.7 Hz, 2H), 2.56 (d, J=4.5 Hz, 3H), 2.42-2.22 (br m, 9H), 2.13 (s, 3H), 1.85 (d, J=12.6 Hz, 2H), 1.68-1.44 (m, 7H), 1.42-1.31 (m, 2H), 0.91 (t, J=7.3 Hz, 3H). LCMS: Purity 99%, MS (m/e) 520 (MH+).

trans-4-(3-(Butylamino)-8-((4-methylpiperazin-1-yl)methyl)-6-oxopyrimido[4,5-c]isoquinolin-5(6H)-yl)-N-(2,2,2-trifluoroethyl)cyclohexane-1-carboxamide (139)

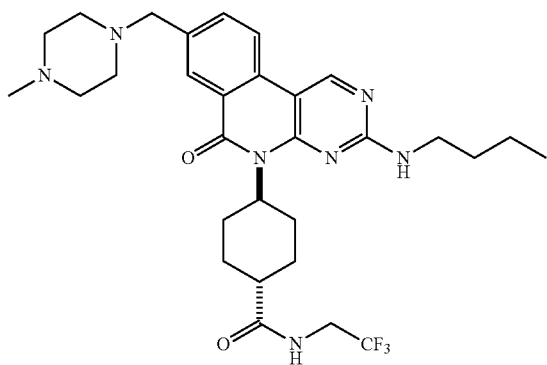

¹H NMR (400 MHz, Methanol-d₄) δ 9.10 (s, 1H), 8.23 (d, J=1.6 Hz, 1H), 8.17 (d, J=8.4 Hz, 1H), 7.73 (dd, J=8.3, 1.9 Hz, 1H), 5.65 (br s, 1H), 3.91 (q, J=9.4 Hz, 2H), 3.65 (s, 2H), 3.57-3.38 (m, 2H), 2.98-2.35 (m, 10H), 2.29 (s, 3H), 2.02 (d, J=12.9 Hz, 2H), 1.88-1.58 (m, 7H), 1.48 (dt, J=14.9, 7.4 Hz, 2H), 0.99 (t, J=7.3 Hz, 3H). LCMS: Purity 97%, MS (m/e) 586 (MH+).

trans-4-(3-(Butylamino)-8-((4-methylpiperazin-1-yl)methyl)-6-oxopyrimido[4,5-c]isoquinolin-5(6H)-yl)-N-(oxetan-3-yl)cyclohexane-1-carboxamide (140)

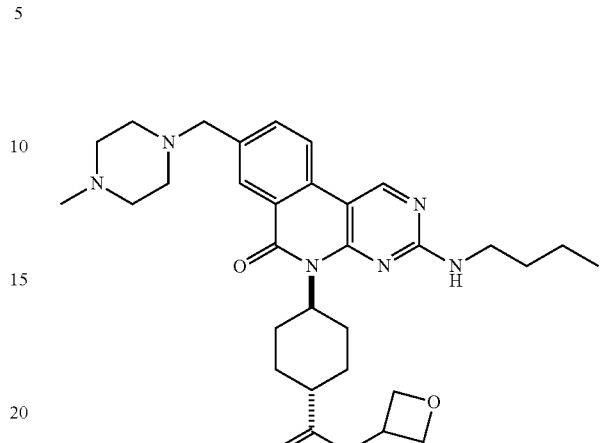

¹H NMR (400 MHz, DMSO-d₆) δ 9.20 (s, 1H), 8.55 (d, J=6.7 Hz, 1H), 8.24 (d, J=8.2 Hz, 1H), 8.08 (d, J=1.7 Hz, 1H), 7.72 (s, 1H), 7.64 (dd, J=8.3, 1.8 Hz, 1H), 5.46 (s, 1H), 4.78 (dq, J=13.1, 6.5 Hz, 1H), 4.69 (dd, J=7.5, 6.0 Hz, 2H), 4.40 (t, J=6.2 Hz, 2H), 3.54 (s, 2H), 3.35 (q, J=6.7 Hz, 2H), 2.67 (br s, 1H), 2.43-2.18 (m, 9H), 2.13 (s, 3H), 1.96-1.80 (m, 2H), 1.75-1.27 (m, 9H), 0.90 (t, J=7.3 Hz, 3H). LCMS: Purity 97%, MS (m/e) 562 (MH+).

trans-4-(3-(Butylamino)-8-((4-methylpiperazin-1-yl)methyl)-6-oxopyrimido[4,5-c]isoquinolin-5(6H)-yl)-N-(cyclopropylmethyl)cyclohexane-1-carboxamide tris formic acid salt or solvate (141)

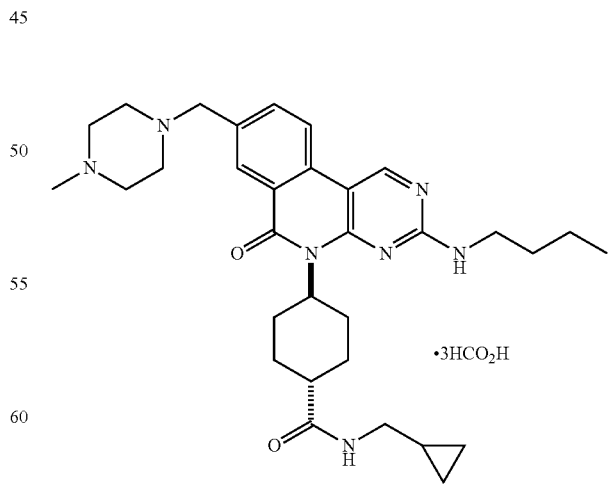

LCMS: Purity 99%, MS (m/e) 560 (MH+-3HCO₂H).

331 trans-4-(3-(Butylamino)-8-((4-methylpiperazin-1-yl)methyl)-6-oxopyrimido[4,5-c]isoquinolin-5(6H)-yl)-N,N-dimethylcyclohexane-1-carboxamide tris trifluoroacetic acid salt or solvate (142)

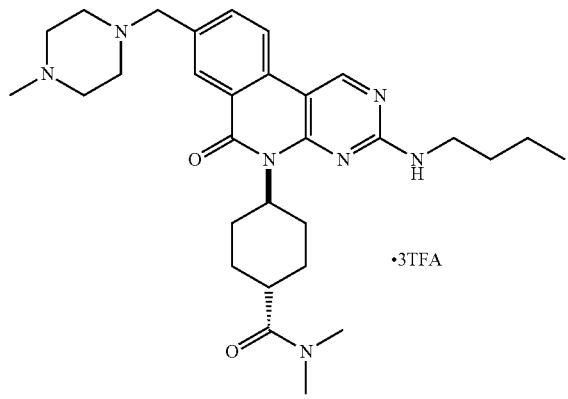

LCMS: Purity 99%, MS (m/e) 534 (MH$^+$-3TFA).

trans-3-(Butylamino)-5-(4-hydroxycyclohexyl)-8-methylpyrimido[5,4-f][1,7]naphthyridin-6(5H)-one tris trifluoroacetic acid salt or solvate (8a)

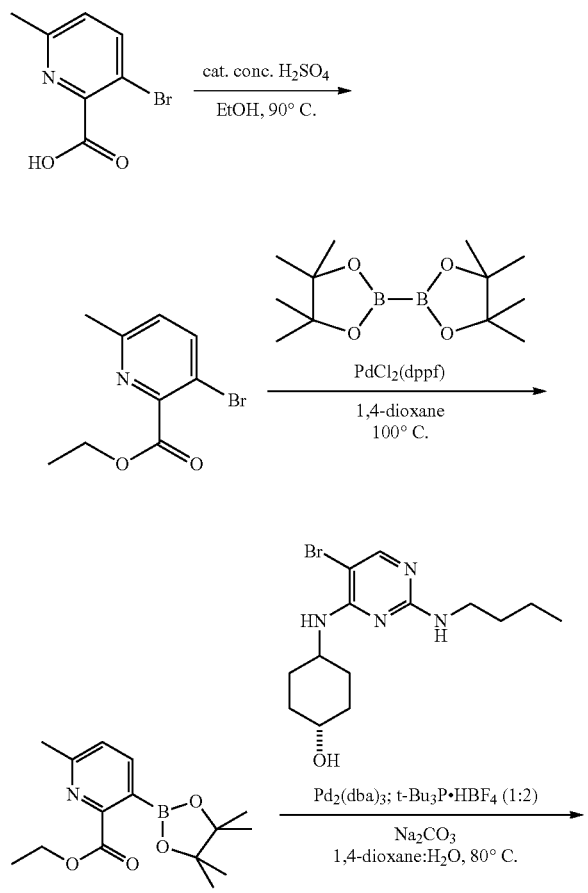

332

-continued

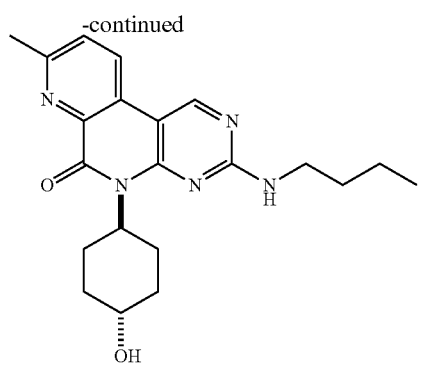

A solution of 6-bromo-6-methylpicolinic acid (2 g), EtOH (40 mL) and conc. H$_2$SO$_4$ was heated to reflux for three days under nitrogen, cooled to room temperature and concentrated. Crude residue was neutralized with aq. NaHCO$_3$ in an ice-bath and extracted into EtOAc (3×80 mL). Combined organic layers were stirred over anhydrous MgSO$_4$, filtered, concentrated, dried under high vacuum, purified by silica gel column chromatography with 50% EtOAc/hexanes as an eluent and obtained 1.5 g of ethyl 3-bromo-6-methylpicolinate as viscous liquid. LCMS: Purity 98%, MS (m/e) 245 (MH$^+$). A stirring mixture of 3-bromo-6-methylpicolinate (1.5 g, 6.14 mmol), bis(pinacolato)diboron (2.0 g, 7.99 mmol), KOAc (1.8 g, 18.4 mmol) and 1,4-dioxane (30 mL) was degassed under high vacuum, back filled with argon successively in three degassing cycles over a period of 10 min. PdCl$_2$(dppf) (0.5 g, 0.61 mmol) was added to degassed reaction mixture, repeated degassing cycles and heated at 100° C. After 17 h, dark reaction mixture was cooled to room temperature, diluted with EtOAc (50 mL) and filtered through Celite®. The crude ethyl 6-methyl-3-(4,4,5,5-tetramethyl-1,3,2-dioxaborolan-2-yl)picolinate (LC/MS: Purity 72%) obtained after concentration of the filtrate to dryness was used in the next step with no further purification. Similar to the general reaction conditions described for the preparation of trans-3-(butylamino)-8-chloro-5-(4-hydroxycyclohexyl)pyrimido[4,5-c]isoquinolin-6(5H)-one, ethyl 6-methyl-3-(4,4,5,5-tetramethyl-1,3,2-dioxaborolan-2-yl)picolinate (400 mg) was reacted with trans-4-((5-bromo-2-(butylamino)pyrimidin-4-yl)amino)cyclohexan-1-ol (200 mg, 0.58 mmol) and Na$_2$CO$_3$ (216 mg, 2.0 mmol) in 1,4-dioxane:H$_2$O (2.5 mL:0.5 mL) in the presence of Pd$_2$(dba)$_3$:t-BuP$_3$·HBF$_4$ (1:2) (22 mg, 0.014 mmol) [instead of previously described PdCl$_2$(dppf)] as a catalyst at 80° C. under argon after degassing cycles. After overnight heating, reaction mixture was diluted with THF (8 mL), filtered through Celite®. Upon concentration of the filtrate, the crude residue was purified on preparative reverse phase HPLC using acetonitrile:water containing TFA modifier and obtained trans-3-(butylamino)-5-(4-hydroxycyclohexyl)-8-methylpyrimido[5,4-f][1,7]naphthyridin-6(5H)-one tris trifluoroacetic acid salt or solvate. $^1$H NMR (400 MHz, Methanol-d$_4$) δ 9.15 (s, 1H), 8.82 (d, J=8.5 Hz, 1H), 7.84 (d, J=8.5 Hz, 1H), 5.53 (d, J=37.1 Hz, 1H), 3.71 (td, J=10.9, 10.2, 5.0 Hz, 1H), 3.64-3.42 (m, 2H), 3.13-2.83 (m, 2H), 2.78 (s, 3H), 2.12 (d, J=12.1 Hz, 2H), 1.92-1.60 (m, 4H), 1.60-1.33 (m, 4H), 1.00 (t, J=7.4 Hz, 3H). LCMS: Purity 97%, MS (m/e) 382 (MH$^+$-3TFA).

333 trans-3-(Butylamino)-5-(4-hydroxycyclohexyl)-8-(4-methylpiperazin-1-yl)pyrimido[5,4-f][1,7]naphthyridin-6(5H)-one (9a)

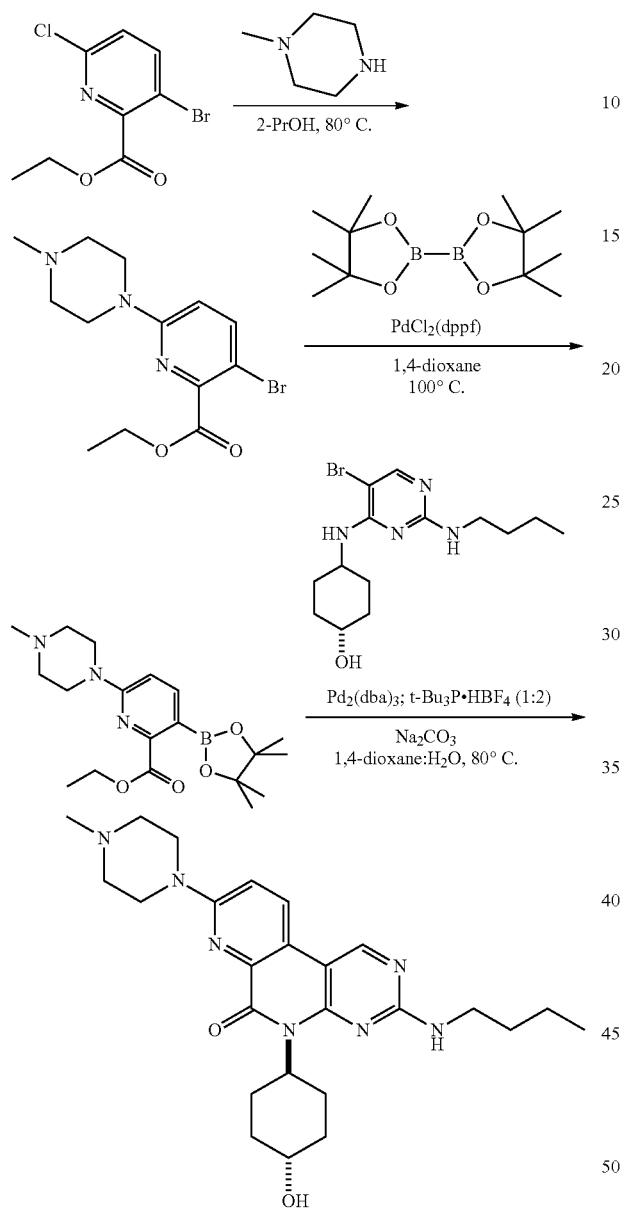

A solution of ethyl 3-bromo-6-chloropicolinate (900 mg, 3.4 mmol), 1-methylpiperazine (600 mg, 6 mmol) and 2-propanol (10 mL) was stirred at 80° C. in a sealed tube. After 48 h, reaction solution was cooled to room temperature and concentrated under reduced pressure. The crude orange viscous liquid was purified by silica gel column chromatography by eluting with 5-8% 7N NH$_3$ MeOH/EtOAc and obtained 400 mg of ethyl 3-bromo-6-(4-methylpiperazin-1-yl)picolinate (LCMS: Purity 90%). A stirring mixture of 3-bromo-6-(4-methylpiperazin-1-yl)picolinate (400 mg, 1.2 mmol), bis(pinacolato)diboron (418 mg, 1.6 mmol), KOAc (360 mg, 3.6 mmol) and 1,4-dioxane (10 mL) was degassed under high vacuum, back filled with argon successively in three degassing cycles over a period of 10 min. PdCl$_2$(dppf)

334

(100 mg, 0.12 mmol) was added to degassed reaction mixture, degassed and heated at 95° C. under argon. After overnight, dark reaction mixture was cooled to room temperature, diluted with EtOAc (50 mL) and filtered through Celite®. The resulting dark filtrated was concentrated, diluted with water (15 mL) and extracted into EtOAc (2×75 mL). Upon stirring and filtration of the combined organic layers over anhydrous MgSO$_4$, filtrate was concentrated to dryness and obtained ethyl 6-(4-methylpiperazin-1-yl)-3-(4,4,5,5-tetramethyl-1,3,2-dioxaborolan-2-yl)picolinate (280 mg, LCMS: Purity 77%) Thus obtained crude ethyl 6-(4-methylpiperazin-1-yl)-3-(4,4,5,5-tetramethyl-1,3,2-dioxaborolan-2-yl)picolinate (150 mg) was reacted with trans-4-((5-bromo-2-(butylamino)pyrimidin-4-yl)amino)cyclohexan-1-ol (83 mg, 0.24 mmol), Pd$_2$(dba)$_3$:t-BuP$_3$.HBF$_4$ (1:2) (13 mg, 0.008 mmol) and Na$_2$CO$_3$ (90 mg, 0.84 mmol) in 1,4-dioxane:H$_2$O (2.5 mL:0.5 mL) at 85° C. under argon after degassing cycles. After overnight heating, reaction mixture was diluted with THF (8 mL) and filtered through Celite®. Upon concentration of the filtrate, the crude residue was dissolved in 7% 7N NH$_3$ MeOH/CH$_2$Cl$_2$, adsorbed on silica gel, dried and purified by flash silica gel column chromatography [Combiflash with RediSep® silica gel column 12 g (pre-conditioned with CH$_2$Cl$_2$) and eluted with 0-10% 7N NH$_3$ MeOH:CH$_2$Cl$_2$ solvent gradient) and obtained trans-3-(butylamino)-5-(4-hydroxycyclohexyl)-8-(4-methylpiperazin-1-yl)pyrimido[5,4-f][1,7]naphthyridin-6(5H)-one (23 mg). $^1$H NMR (400 MHz, DMSO-d$_6$) δ 9.07 (s, 1H), 8.46 (d, J=9.1 Hz, 1H), 7.52 (s, 1H), 7.32 (d, J=9.1 Hz, 1H), 5.42 (br s, 1H), 4.63 (d, J=4.2 Hz, 1H), 3.73-3.57 (m, 5H), 3.50 (s, 1H), 3.41-3.19 (m, 1H), 2.98-2.62 (br s, 2H), 2.39 (t, J=5.1 Hz, 4H), 2.21 (s, 3H), 1.94 (app d, J=12.1 Hz, 2H), 1.55 (app p, J=7.4 Hz, 4H), 1.47-1.19 (m, 4H), 0.91 (t, J=7.3 Hz, 3H). LCMS: Purity 97%, MS (m/e) 466 (MH$^+$).

Synthesis of 3-(butylamino)-5-((1S,4S)-4-hydroxycycloheptyl)-8-((4-methylpiperazin-1-yl)methyl)pyrimido[4,5-c]isoquinolin-6(5H)-one (229)

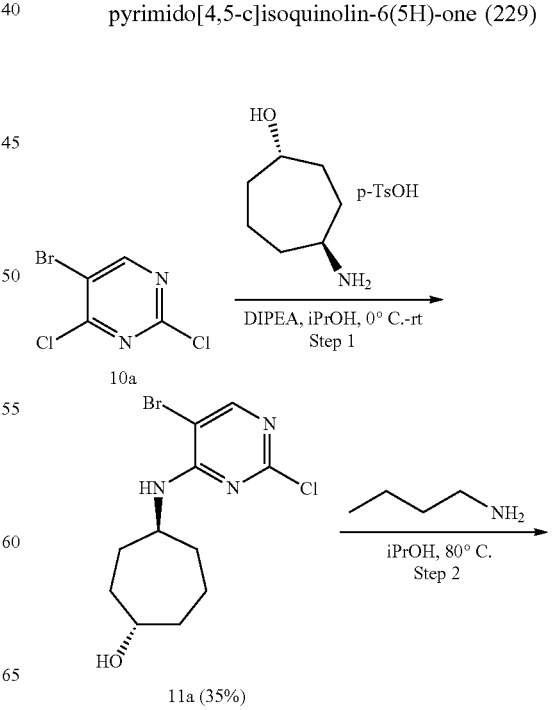

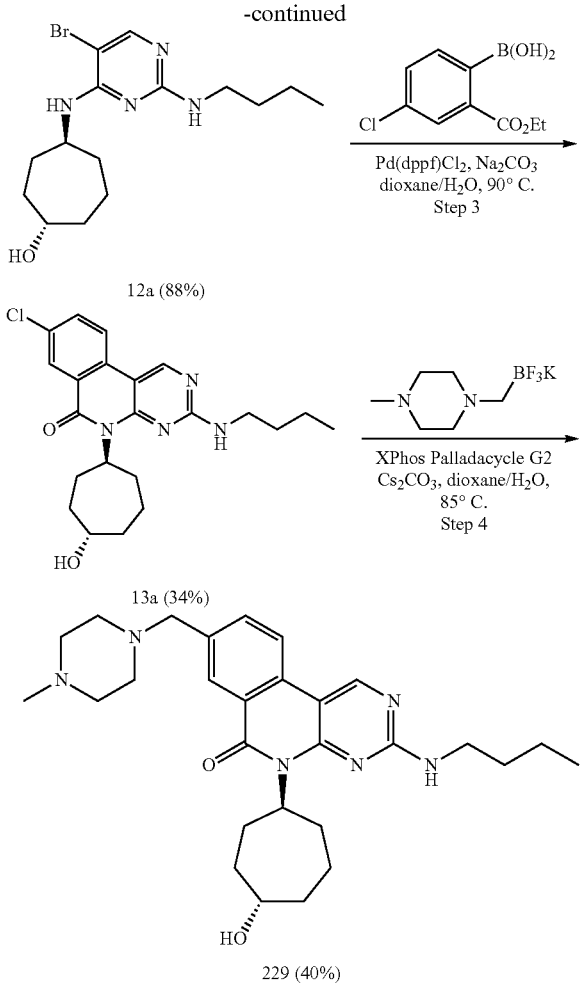

Step 1.

To a solution of 2,4-dichloro-5-bromopyrimidine (0.46 g, 2.00 mmol) and N,N-diisopropylethylamine (0.44 ml, 2.59 mmol) in anhydrous isopropyl alcohol (1 mL) was slowly added (1S,4S)-4-aminocycloheptan-1-ol p-TsOH (1:1) (0.61 g, 2.03 mmol) in anhydrous isopropyl alcohol (1 mL) at 0° C. The resulting reaction mixture was stirred at 0° C. for 4 h, then stirred at room temperature overnight. The reaction mixture was concentrated under reduced pressure to give a residue, which was purified by chromatography eluting with ethyl acetate/hexanes (3/7) to provide (1S,4S)-4-((5-bromo-2-chloropyrimidin-4-yl)amino)cycloheptan-1-ol (0.22 g, 35%). $^1$H NMR (CDCl$_3$, 400 MHz) 8.10 (s, 1H), 5.39 (m, 1H), 4.24 (m, 1H), 3.91 (m, 1H), 2.09 (m, 5H), 1.74 (m, 6H) ppm; MS m/e: 321.9 (M+H)$^+$.

Step 2.

A mixture of (1S,4S)-4-((5-bromo-2-chloropyrimidin-4-yl)amino)cycloheptan-1-ol (0.30 g, 0.94 mmol), n-butylamine (0.46 mL, 4.70 mmol) and DIEA (0.25 mL, 1.41 mmol) in anhydrous isopropyl alcohol (1 mL) was stirred at 80° C. overnight. The reaction mixture was then concentrated under reduced pressure to give a residue, which was purified by chromatography eluting with ethyl acetate/hexanes (8/2) to (1S,4S)-4-((5-bromo-2-(butylamino)pyrimidin-4-yl)amino)cycloheptan-1-ol (0.29 g, 88%). MS m/e: 357.1 (M+H)$^+$.

Step 3.

A mixture of (1S,4S)-4-((5-bromo-2-(butylamino)pyrimidin-4-yl)amino)cycloheptan-1-ol (0.29 g, 0.81 mmol), (4-chloro-2-(ethoxycarbonyl)phenyl)boronic acid (0.22 g, 0.97 mmol), [1,1'-bis(diphenylphosphino)ferrocene]dichloropalladium(II) (0.03 g, 0.04 mmol), and Na$_2$CO$_3$ (0.14 g, 1.62 mmol) in dioxane (3.2 mL) and water (0.4 mL) was stirred at 90° C. for 18 h. The mixture was then concentrated under reduced pressure to give a residue, which was purified by chromatography eluting with ethyl acetate/hexanes (7/3) to provide 3-(butylamino)-8-chloro-5-((1S,4S)-4-hydroxycycloheptyl)pyrimido[4,5-c]isoquinolin-6(5H)-one (0.11 g, 34%). $^1$H NMR (CDCl$_3$, 400 MHz) 8.96 (s, 1H), 8.34 (s, 1H), 7.94 (m, 1H), 7.62 (m, 1H), 5.77 (bs, 1H), 5.38 (bs, 1H), 3.95 (m, 1H), 3.51 (m, 2H), 2.64 (m, 1H), 2.39 (m, 1H), 2.19 (m, 1H), 2.04 (m, 1H), 1.74 (m, 8H), 1.47 (m, 3H), 0.99 (m, 3H) ppm; MS m/e: 415.1 (M+H)$^+$.

Step 4.

A mixture of 3-(butylamino)-8-chloro-5-((1S,4S)-4-hydroxycycloheptyl)pyrimido[4,5-c]isoquinolin-6(5H)-one (0.04 g, 0.09 mmol), potassium 1-methyl-4-trifluoroboratomethylpiperazine (0.03 g, 0.14 mmol), XPhos-Pd-G2 (0.01 g, 0.01 mmol), and Cs$_2$CO$_3$ (0.58 g, 0.18 mmol) in dioxane (1 mL) and water (0.2 mL) was stirred at 85° C. for 18 h. The mixture was then concentrated under reduced pressure to give a residue, which was purified by reversed phase HPLC to provide 229 3-(butylamino)-5-((1S,4S)-4-hydroxycycloheptyl)-8-((4-methylpiperazin-1-yl)methyl)pyrimido[4,5-c]isoquinolin-6(5H)-one (0.02 g, 40%).

229 3-(butylamino)-5-((1S,4S)-4-hydroxycycloheptyl)-8-((4-methylpiperazin-1-yl)methyl)pyrimido[4,5-c]isoquinolin-6(5H)-one $^1$H NMR (CD$_3$OD, 400 MHz) 9.10 (s, 1H), 8.22 (bs, 1H), 8.17 (m, 1H), 7.73 (m, 1H), 3.85 (m, 1H), 3.65 (s, 2H), 3.48 (m, 2H), 2.53 (m, 9H), 2.29 (s, 3H), 2.17 (m, 1H), 2.02 (m, 2H), 1.75 (m, 7H), 1.55 (m, 4H), 0.99 (m, 3H) ppm; MS m/e: 493.4 (M+H)$^+$.

230 3-((cyclopropylmethyl)amino)-5-((1S,4S)-4-hydroxycycloheptyl)-8-((4-methylpiperazin-1-yl)methyl)pyrimido[4,5-c]isoquinolin-6(5H)-one $^1$H NMR (DMSO-d$_6$, 400 MHz) 9.21 (s, 1H), 8.24 (m, 1H), 8.38 (m, 1H), 8.07 (m, 1H), 7.79 (m, 1H), 7.63 (m, 1H), 5.74 (m, 1H), 5.42 (bs, 1H), 4.49 (m, 1H), 3.68 (m, 1H), 3.54 (s, 2H), 3.25 (m, 2H), 2.33 (m, 8H), 2.13 (s, 3H), 1.66 (m, 10H), 1.11 (m, 1H), 0.44 (m, 2H), 0.25 (m, 2H) ppm; MS m/e: 491.5 (M+H)$^+$.

231 tert-butyl ((1S,3S)-3-(3-(butylamino)-8-((4-methylpiperazin-1-yl)methyl)-6-oxopyrimido[4,5-c]isoquinolin-5(6H)-yl)cyclopentyl)carbamate MS m/e: 564.3 (M+H)$^+$.

232 5-((1S,3S)-3-aminocyclopentyl)-3-(butylamino)-8-((4-methylpiperazin-1-yl)methyl)pyrimido[4,5-c]isoquinolin-6(5H)-one $^1$H NMR (CD$_3$OD, 400 MHz) 9.02 (s, 1H), 8.28 (s, 1H), 7.97 (m, 1H), 7.70 (m, 1H), 6.32 (m, 1H), 5.31 (bs, 1H), 4.00 (m, 1H), 3.61 (s, 2H), 3.51 (m, 2H), 2.52 (m, 10H), 2.29 (s, 3H), 2.08 (m, 2H), 1.69 (m, 4H), 1.49 (m, 4H), 0.99 (m, 3H) ppm; MS m/e: 464.3 (M+H)$^+$.

233 N-((1S,3S)-3-(3-(butylamino)-8-((4-methylpiperazin-1-yl)methyl)-6-oxopyrimido[4,5-c]isoquinolin-5(6H)-yl)cyclopentyl)acetamide MS m/e: 506.3 (M+H)+.

234 3-(butylamino)-8-chloro-5-((1R,3R)-3-hydroxycyclopentyl)pyrimido[4,5-c]isoquinolin-6(5H)-one $^1$H NMR (CD$_3$OD, 400 MHz) 9.25 (m, 1H), 8.35 (m, 1H), 8.12 (m, 1H), 7.77 (m, 1H), 7.66 (bs, 1H), 6.24 (m, 1H), 4.57 (bs, 1H), 4.37 (bs, 1H), 3.34 (m, 2H), 2.21 (m, 2H), 1.96 (m, 2H), 1.64 (m, 4H), 1.35 (m, 2H), 0.90 (m, 3H) ppm; MS m/e: 387.2 (M+H)+.

235 3-(butylamino)-5-((1R,3R)-3-hydroxycyclopentyl)-8-((4-methylpiperazin-1-yl)methyl)pyrimido[4,5-c]isoquinolin-6(5H)-one $^1$H NMR (CD$_3$OD, 400 MHz) 9.11 (s, 1H), 8.23 (bs, 1H), 8.18 (m, 1H), 7.74 (m, 1H), 6.44 (m, 1H), 4.64 (m, 1H), 3.65 (s, 2H), 3.47 (m, 2H), 2.53 (m, 10H), 2.29 (s, 3H), 2.14 (m, 2H), 1.88 (m, 1H), 1.77 (m, 1H), 1.67 (m, 2H), 1.45 (m, 2h), 0.99 (m, 3H) ppm; MS m/e: 465.3 (M+H)+.

236 3-(butylamino)-5-((1S,3S)-3-(dimethylamino)cyclopentyl)-8-((4-methylpiperazin-1-yl)methyl)pyrimido[4,5-c]isoquinolin-6(5H)-one MS m/e: 492.3 (M+H)+.

237 2-(((1S,3S)-3-(3-(butylamino)-8-((4-methylpiperazin-1-yl)methyl)-6-oxopyrimido[4,5-c]isoquinolin-5(6H)-yl)cyclopentyl)amino)acetamide MS m/e: 521.3 (M+H)

238 3-(butylamino)-5-((1S,3S)-3-((2-hydroxyethyl)amino)cyclopentyl)-8-((4-methylpiperazin-1-yl)methyl)pyrimido[4,5-c]isoquinolin-6(5H)-one MS m/e: 508.2 (M+H)+.

239 1-((1S,3S)-3-(3-(butylamino)-8-((4-methylpiperazin-1-yl)methyl)-6-oxopyrimido[4,5-c]isoquinolin-5(6H)-yl)cyclopentyl)guanidine MS m/e: 506.3 (M+H)+.

Example 4: PAKT HTRF-HUVEC Assay

Materials

Dimethyl Sulfoxide (DMSO) (Sigma-Aldrich, D2650)
Corning™ Costar™ 96-Well White Clear-Bottom Plates (Fisher Scientific, 07-200-587)
ProxiPlate-384 Plus, White 384-shallow well Microplate (Perkin Elmer, 6008280)
Phospho Akt (Ser473) Assay kit-10,000 tests (Cisbio US, 64AKSPEH)
HUVEC cells (Lonza, CC-2519)
EGM-2 BulletKit (Lonza, CC-3162)
EBM-2 Basal Medium (Lonza, CC-3156)
Biotin-SP-conjugated Anti-mouse IgG (Jackson Immunoresearch Labs, 115-065-003)
Anti-human MerTK antibody (Clone 125518) (R&D Systems, MAB8912)

Equipment

SpectraMax Paradigm Multi-Mode Microplate Reader (Molecular Devices)

Method

Seed HUVECs (10K cells/well) in EBM-2 complete media (EBM-2 basal medium plus EGM-2 BulletKit supplements) overnight at 37° C., 5% CO$_2$ in Costar 96-well white clear-bottom plates. Remove culture media and starve cells for 3-4 hours in 50 µL/well EBM-2 basal medium. Perform serial dilution of compounds in DMSO from 2.5 mM in 4-fold dilutions, and then dilute 1:125 in EBM-2 basal media. Mix 50 µL/well 2× compounds with 50 µL/well HUVECs in duplicate in Costar 96-well white clear-bottom plates. Incubate plates for 1 hour at 37° C., 5% CO$_2$. Cross-link anti-human MerTK antibody to Biotin-SP-conjugated anti-mouse IgG antibody (1:1) to give final concentrations of 5 ug/mL of anti-human MerTK-XL. Stimulate HUVECs with 25 µL/well 5× anti-human MerTK-XL to give final concentrations of 1 ug/mL for 10 minutes at 37° C., 5% CO$_2$. Completely remove media and lyse HUVECs with 40 uL/WELL per well of Cisbio HTRF 1× lysis buffer. Performed pAkt(Ser473) HTRF assay in ProxiPlate-384 Plus, white 384-shallow well microplate according to the vendor protocol and read plates with a SpectralMax Paradigm plate reader. Enter the HTRF values into Athena (Rigel) for curve fitting, EC$_{50}$ calculation, and database storage.

Representative results for inhibition of MerTK (µM)) is shown in Table 1:

| No. | MerTK |
|---|---|
| 1 | 0.2471 |
| 2 | 0.0442 |
| 3 | 0.0288 |
| 4 | 0.1743 |
| 5 | 0.098 |
| 6 | 2.043 |
| 7 | N/A |
| 8 | N/A |
| 9 | 0.1165 |
| 10 | 0.1456 |
| 11 | N/A |
| 12 | 0.1165 |
| 13 | 0.1442 |
| 14 | 0.0564 |
| 15 | 0.0059 |
| 16 | 0.0639 |
| 17 | 0.068 |
| 18 | 0.2773 |
| 19 | 0.6972 |
| 20 | 0.0182 |
| 21 | 0.0307 |
| 22 | 0.5893 |
| 23 | 1.177 |
| 24 | 0.2208 |
| 25 | 1.679 |
| 26 | 0.0167 |
| 27 | 0.0459 |
| 28 | 0.0366 |
| 29 | 0.0062 |
| 30 | 0.0183 |
| 31 | 0.0125 |
| 32 | 0.0065 |
| 33 | 0.0046 |
| 34 | 0.0074 |
| 35 | 0.0467 |
| 36 | 0.0168 |
| 37 | 0.0538 |
| 38 | 0.0333 |
| 39 | 0.0646 |

| No. | MerTK |
|---|---|
| 40 | 0.0507 |
| 41 | 0.1263 |
| 42 | 0.0459 |
| 43 | 0.0513 |
| 44 | 0.066 |
| 45 | 0.1495 |
| 46 | 0.1165 |
| 47 | 0.0497 |
| 48 | 0.0487 |
| 49 | 0.2207 |
| 50 | 0.0259 |
| 51 | 11.9 |
| 52 | 0.4007 |
| 53 | 0.0363 |
| 54 | 0.309 |
| 55 | 0.0364 |
| 56 | 0.0512 |
| 57 | 0.072 |
| 58 | 0.1146 |
| 59 | 0.2924 |
| 60 | 0.0042 |
| 61 | 0.0231 |
| 62 | 0.0952 |
| 63 | 0.1385 |
| 64 | N/A |
| 65 | 0.0783 |
| 66 | 0.2978 |
| 67 | 8.03 |
| 68 | 0.0784 |
| 69 | 0.0204 |
| 70 | 0.184 |
| 71 | 0.0334 |
| 72 | 0.2201 |
| 73 | 0.021 |
| 74 | 0.2181 |
| 75 | 1.076 |
| 76 | 0.0115 |
| 77 | 0.0219 |
| 78 | 0.009 |
| 79 | 0.1556 |
| 80 | 0.0345 |
| 81 | 0.0139 |
| 82 | 0.2163 |
| 83 | 0.0318 |
| 84 | 0.2881 |
| 85 | 0.2211 |
| 86 | 0.0199 |
| 87 | 0.1148 |
| 88 | 0.051 |
| 89 | 0.152 |
| 90 | 0.0131 |
| 91 | 3.911 |
| 92 | 0.0388 |
| 93 | 0.3581 |
| 94 | 1.104 |
| 95 | 3.924 |
| 96 | 0.0414 |
| 97 | 0.0691 |
| 98 | 0.0357 |
| 99 | 0.0948 |
| 100 | 0.1126 |
| 101 | 0.2957 |
| 102 | 0.1232 |
| 103 | 0.129 |
| 104 | 0.2893 |
| 105 | 0.3538 |
| 106 | 0.0704 |
| 107 | 0.0582 |
| 108 | 0.17 |
| 109 | 0.0975 |
| 110 | 0.4829 |
| 111 | 0.3795 |
| 112 | 0.4717 |
| 113 | 0.0449 |
| 114 | 0.7434 |
| 115 | 0.5543 |
| 116 | 4.619 |
| 117 | 0.3257 |
| 118 | N/A |
| 119 | 15.75 |
| 120 | 0.3523 |
| 121 | 0.6202 |
| 122 | 0.1651 |
| 123 | 0.0765 |
| 124 | 0.0362 |
| 125 | 9999 |
| 126 | 9999 |
| 127 | 0.0891 |
| 128 | 0.1263 |
| 129 | 0.0459 |
| 130 | 0.0512 |
| 131 | 0.0546 |
| 132 | 1.555 |
| 133 | 1.672 |
| 134 | 0.3471 |
| 135 | 4.04 |
| 136 | 0.3197 |
| 137 | 0.0196 |
| 138 | 0.0688 |
| 139 | 0.1343 |
| 140 | 0.1474 |
| 141 | 0.1873 |
| 142 | 0.1146 |
| 143 | 13.47 |
| 144 | 0.0573 |
| 145 | 0.0257 |
| 146 | 0.0074 |
| 147 | 0.0467 |
| 148 | 0.0168 |
| 149 | 0.0538 |
| 150 | 0.0333 |
| 151 | 0.0646 |
| 152 | 0.0507 |
| 153 | 0.0513 |
| 154 | 0.066 |
| 155 | 0.1495 |
| 156 | 0.1165 |
| 157 | 0.0497 |
| 158 | 0.0948 |
| 159 | 0.0487 |
| 160 | 0.2207 |
| 161 | 0.0259 |
| 162 | 11.9 |
| 163 | 0.1126 |
| 164 | 0.2957 |
| 165 | 0.4007 |
| 166 | 0.1232 |
| 167 | 0.129 |
| 168 | 0.2893 |
| 169 | 0.3538 |
| 170 | 0.0363 |
| 171 | 0.309 |
| 172 | 0.0704 |
| 173 | 0.0582 |
| 174 | 0.17 |
| 175 | 0.0364 |
| 176 | 0.0975 |
| 177 | 0.4829 |
| 178 | 0.3795 |
| 179 | 0.1146 |
| 180 | 9999 |
| 181 | 0.2924 |
| 182 | 0.0076 |
| 183 | 13.77 |
| 184 | 5.138 |
| 185 | 0.0287 |
| 186 | 0.0454 |
| 187 | 9999 |
| 188 | 11.32 |
| 189 | 0.0764 |
| 190 | 0.073 |
| 191 | 0.8752 |
| 192 | 4.04 |
| 193 | 0.9572 |

-continued

| No. | MerTK |
|---|---|
| 194 | 0.0336 |
| 195 | 0.0721 |
| 196 | 0.2396 |
| 197 | 0.0977 |
| 198 | 0.0132 |
| 199 | 0.0108 |
| 200 | 11.26 |
| 201 | 0.0725 |
| 202 | 0.0473 |
| 203 | 0.1667 |
| 204 | 0.0577 |
| 205 | 0.2926 |
| 206 | 1.279 |
| 207 | 0.5374 |
| 208 | 0.4153 |
| 209 | 0.0139 |
| 210 | 0.0856 |
| 211 | 9999 |
| 212 | 0.0636 |
| 213 | 0.0304 |
| 214 | 0.0105 |
| 215 | 0.0037 |
| 216 | 0.0225 |
| 217 | 0.0041 |
| 218 | 0.0242 |
| 219 | 0.0183 |
| 220 | 0.0112 |
| 221 | 0.0861 |
| 222 | 0.0145 |
| 223 | 0.0143 |
| 224 | 0.0283 |
| 225 | 0.021 |
| 226 | 0.0109 |
| 227 | 0.0024 |
| 228 | 0.0266 |
| 229 | 0.072 |
| 230 | 0.1397 |
| 231 | 1.907 |
| 232 | 0.043 |
| 233 | 0.5118 |
| 234 | 9999 |
| 235 | 0.2642 |
| 236 | 0.1301 |
| 237 | 0.2203 |
| 238 | 0.16 |
| 239 | 0.9468 |

What is claimed:
1. A compound having the structure formula (I):

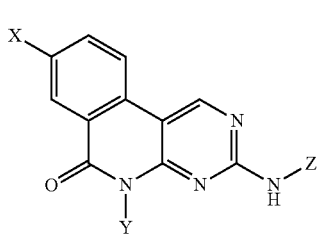

(I)

or a pharmaceutically acceptable salt, or N-oxide thereof, or a solvate or hydrate thereof,
wherein
X is hydrogen, Cak($C_0$-$C_6$alkyl), Hca($C_0$-$C_6$alkyl), Ar($C_0$-$C_6$alkyl), Het($C_0$-$C_6$alkyl), halogen or Hca($C_1$-$C_6$alkyl)-O—, wherein Ar, Het, Cak, Hca and the alkyl group is optionally substituted by one to four —$R^{X1}$ groups, wherein
each —$R^{X1}$ is independently halogen, cyano, $C_1$-$C_6$alkyl, $C_1$-$C_6$haloalkyl, —$C_1$-$C_6$alkoxy, oxo, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, OP(O)(OR)$_2$, —CH$_2$—OP(O)(OR), Ar($C_0$-$C_6$alkyl), Het($C_0$-$C_6$alkyl), Cak($C_0$-$C_6$alkyl) or Hca($C_0$-$C_6$alkyl),
or two —$R^{X1}$ groups taken together, when attached to adjacent atoms, form a Cak, Hca or Het, wherein the Cak Hca and the Het comprise a 3-8 membered ring optionally substituted with one or two —$R^{X2}$ groups,
or two —$R^{X1}$ groups taken together, when attached to the same carbon atom, form a Hca, wherein the Hca comprises a 3-8 membered ring optionally substituted with one or two —$R^{X2}$ groups,
or two —$R^{X1}$ groups taken together, when attached to non-adjacent atoms, and combined with X, form a bridged Hca optionally substituted with one or two —$R^{X2}$ groups,
wherein each —$R^{X2}$ is independently halogen, cyano, nitro, oxo, —OR, —SR, —NR$_2$, —C(O)OR, —C(O)NR$_2$, —C(O)R, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, —N(R)S(O)$_2$R, $C_1$-$C_6$alkyl, or $C_1$-$C_6$haloalkyl;
Y is Cak($C_0$-$C_8$alkyl) or Hca($C_0$-$C_6$alkyl), each optionally substituted by one or two —$R^{Y1}$ groups;
wherein each —$R^{Y1}$ is independently halogen, cyano, $C_1$-$C_6$alkyl, $C_1$-$C_6$haloalkyl, —$C_1$-$C_6$alkoxy, oxo, —OR, —SR, —NR$_2$, N(R)C(NR$_2$)NR$_2$, —C(O)R, —C(O)OR, C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR);
Z is $C_1$-$C_6$alkyl or Cak($C_0$-$C_6$alkyl), each optionally substituted by one to three —$R^{X1}$ groups;
wherein each —$R^{Z1}$ is independently halogen, cyano, $C_1$-$C_6$alkyl, $C_1$-$C_6$haloalkyl, —$C_1$-$C_6$alkoxy, oxo, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR); and
each R is independently hydrogen, $C_1$-$C_6$alkyl, $C_1$-$C_6$haloalkyl, Hca($C_0$-$C_6$alkyl), Cak($C_0$-$C_8$alkyl), $C_1$-$C_6$alkyl-CN, —CH$_2$C(O)NH$_2$, $C_1$-$C_6$alkyl-OH, wherein
Hca is a 3-15 membered ring or ring system comprising at least one ring, 1-4 O, S, or N atoms, provided no O or S is adjacent to another O or S;
Het is a 5-15 membered aromatic ring or ring system comprising at least one ring and 1-4 O, S, or N atoms, provided no O or S is adjacent to another O or S;
Cak is a 3-8 membered non-aromatic carbocyclic ring or ring system, which may be saturated or partially unsaturated; and
Ar is a 6-16 membered aromatic ring or ring system having at least one carbocyclic aromatic ring optionally fused one or more aromatic or non-aromatic rings;

provided that the compound is not
3-(butylamino)-8-chloro-5-(4-hydroxycyclohexyl)pyrimido[4,5-c]isoquinolin-6(5H)-one;
3-(butylamino)-5-(4-hydroxycyclohexyl)-8-(morpholinomethyl)pyrimido[4,5-c]isoquinolin-6(5H)-one;
3-(butylamino)-8-(2,6-difluorophenyl)-5-(4-hydroxycyclohexyl)pyrimido[4,5-c]isoquinolin-6(5H)-one; or
3-(butylamino)-5-(4-hydroxycyclohexyl)-8-(1-methyl-1H-pyrazol-4-yl)pyrimido[4,5-c]isoquinolin-6(5H)-one.

2. The compound of claim 1, wherein
X is hydrogen, Cak($C_0$-$C_6$alkyl), Hca($C_0$-$C_6$alkyl), Ar($C_0$-$C_6$alkyl) or Het($C_0$-$C_6$alkyl), wherein Ar, Het, Cak, Hca and the alkyl group is optionally substituted by one to four —$R^{X1}$ groups, wherein
each —$R^{X1}$ is independently halogen, cyano, $C_1$-$C_6$alkyl, $C_1$-$C_6$haloalkyl, —$C_1$-$C_6$alkoxy, oxo, —OR, —SR, —$NR_2$, —C(O)R, —C(O)OR, —C(O)$NR_2$, —S(O)$_2$$NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$, —$CH_2$—OP(O)(OR), Ar($C_0$-$C_6$alkyl), Het ($C_0$-$C_6$alkyl), Cak($C_0$-$C_6$alkyl) or Hca($C_0$-$C_6$alkyl),
or two —$R^{X1}$ groups taken together, when attached to adjacent atoms, form a Cak, Hca or Het, wherein the Cak Hca and the Het comprise a 3-8 membered ring optionally substituted with one or two —$R^{X2}$ groups,
or two —$R^{X1}$ groups taken together, when attached to the same carbon atom, form a Hca, wherein the Hca comprises a 3-8 membered ring optionally substituted with one or two —$R^{X2}$ groups,
or two —$R^{X1}$ groups taken together, when attached to non-adjacent atoms, and combined with X, form a bridged Hca optionally substituted with one or two —$R^{X2}$ groups,
wherein each —$R^{X2}$ is independently halogen, cyano, nitro, oxo, —OR, —SR, —$NR_2$, —C(O)OR, —C(O)$NR_2$, —C(O)R, —S(O)R, —S(O)$_2$R, —S(O)OR, —S(O)$_2$OR, —S(O)$NR_2$, —S(O)$_2$$NR_2$, —OC(O)R, —OC(O)OR, —OC(O)$NR_2$, —N(R)C(O)R, —N(R)C(O)OR, —N(R)C(O)$NR_2$, —N(R)S(O)R, —N(R)S(O)$_2$R, $C_1$-$C_6$alkyl, or $C_1$-$C_6$haloalkyl;
Y is Cak($C_0$-$C_6$alkyl) optionally substituted by one or two —$R^{Y1}$ groups;
wherein each —$R^{Y1}$ is independently halogen, cyano, $C_1$-$C_6$haloalkyl, —$C_1$-$C_6$alkoxy, oxo, —OR, —SR, —$NR_2$, —C(O)R, —C(O)OR, C(O)$NR_2$, —S(O)$_2$$NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$ or —$CH_2$—OP(O)(OR);
Z is $C_1$-$C_6$alkyl or Cak($C_0$-$C_6$alkyl), each optionally substituted by one to three —$R^{Z1}$ groups;
wherein each —$R^{Z1}$ is independently halogen, cyano, $C_1$-$C_6$haloalkyl, —$C_1$-$C_6$alkoxy, oxo, —OR, —SR, —$NR_2$, —C(O)R, —C(O)OR, —C(O)$NR_2$, —S(O)$_2$$NR_2$, —S(O)$_2$R, —OC(O)R, —N(R)C(O)R, —OC(O)OR, —OC(O)$NR_2$, —N(R)C(O)OR, —N(R)C(O)$NR_2$, —N(R)S(O)$_2$R, —OP(O)(OR)$_2$ or —$CH_2$—OP(O)(OR); and
each R is independently hydrogen or $C_1$-$C_6$alkyl, wherein
Hca is a 3-15 membered ring or ring system comprising at least one ring, 1-4 O, S, or N atoms, provided no O or S is adjacent to another O or S;
Het is a 5-15 membered aromatic ring or ring system comprising at least one ring and 1-4 O, S, or N atoms, provided no O or S is adjacent to another O or S;
Cak is a 3-8 membered non-aromatic carbocyclic ring or ring system, which may be saturated or partially unsaturated; and
Ar is a 6-16 membered aromatic ring or ring system having at least one carbocyclic aromatic ring optionally fused one or more aromatic or non-aromatic rings.

3. The compound of claim 2, having the structure of formula (Ie):

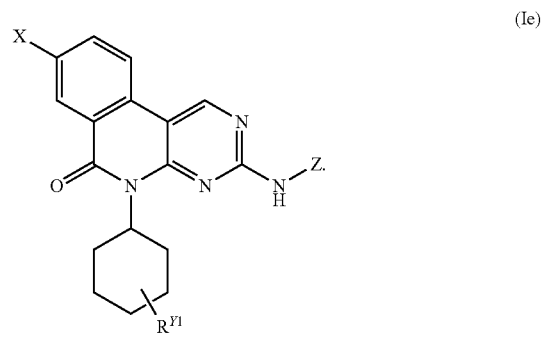

4. The compound of claim 3, wherein m is 1 and $R^{Y1}$ is —OH.

5. The compound of claim 1, wherein X is hydrogen, Cak($C_0$-$C_6$alkyl) or Hca($C_0$-$C_6$alkyl), wherein each Cak, Hca and alkyl group is optionally substituted by one to three —$R^{X1}$ groups.

6. The compound of any of claim 1, wherein X is hydrogen or Hca($C_0$-$C_6$alkyl), wherein each Hca and alkyl group is optionally substituted by one to three —$R^{X1}$ groups.

7. The compound of claim 2, having the structure of formula (If):

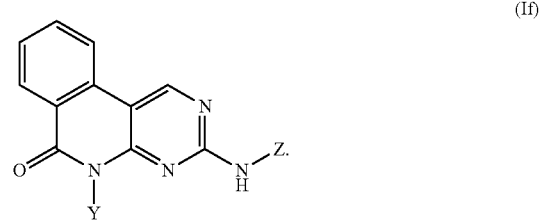

8. The compound of claim 2, having the structure of formula (II):

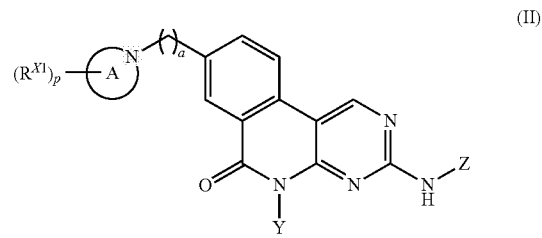

or a pharmaceutically acceptable salt, or N-oxide thereof, or a solvate or hydrate thereof, wherein
ring A is Hca;
a is 0 or 1; and
p is 1, 2, 3 or 4; and
each —$R^{X1}$ is independently halogen, cyano, $C_1$-$C_6$alkyl, $C_1$-$C_6$haloalkyl, —$C_1$-$C_6$alkoxy, oxo, —OR, —SR, —$NR_2$, —C(O)R, —C(O)OR, —C(O)$NR_2$, —$S(O)_2NR_2$, —$S(O)_2R$, —OC(O)R, —N(R)C(O)R, —OC(O)OR, —OC(O)$NR_2$, —N(R)C(O)OR, —N(R)C(O)$NR_2$, —N(R)$S(O)_2R$, —OP(O)(OR)$_2$, —$CH_2$—OP(O)(OR), Ar($C_0$-$C_6$alkyl), Het ($C_0$-$C_6$alkyl), Cak($C_0$-$C_6$alkyl) or Hca($C_0$-$C_6$alkyl).

9. The compound of claim 8, wherein
(a) ring A is

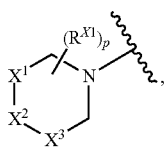

wherein
p is 0, 1, 2, 3 or 4;
$X^1$ is —O—, —S—, —S(O)—, —$S(O)_2$—, —$CR^2$—, —C(R)($R^{X1}$)—, —C($R^{X1}$)$_2$—, —N(R)— or —N($R^{X1}$)—;
$X^2$ is —O—, —S—, —S(O)—, —$S(O)_2$—, —$CR^2$—, —C(R)($R^{X1}$)—, —C($R^{X1}$)$_2$—, —N(R)— or —N($R^{X1}$)—; and
$X^3$ is —O—, —S—, —S(O)—, —$S(O)_2$—, —$CR^2$—, —C(R)($R^{X1}$)—, —C($R^{X1}$)$_2$—, —N(R)— or —N($R^{X1}$)—;
(b) ring A is

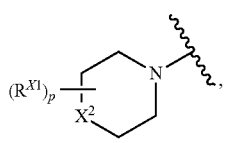

wherein
p is 0, 1, 2, 3 or 4;
$X^2$ is —O—, —S—, —S(O)—, —$S(O)_2$—, —$CR^2$—, —C(R)($R^{X1}$)—, —C($R^{X1}$)$_2$—, —N(R)— or —N($R^{X1}$)—;
(c) ring A is

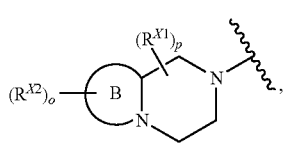

wherein
p is 0, 1 or 2;
o is 0, 1 or 2; and
ring B is Hca or Het, each comprising a 3-8 membered ring optionally substituted with one or two —$R^{X2}$ groups;

(d) ring A is

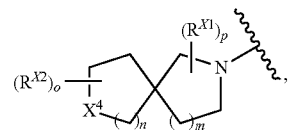

wherein
p is 0, 1 or 2;
o is 0, 1 or 2;
n is 0, 1 or 2;
m is 0, 1 or 2; and
$X^4$ is —O—, —S—, —$S(O)_2$—, —$CR^2$—, —C(R)($R^{X1}$)—, —C($R^{X1}$)$_2$—, —N(R)— or —N($R^{X1}$)—;
(e) ring A is

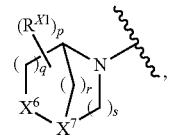

wherein
$X^6$ is —O—, —S—, —S(O)—, —$S(O)_2$—, —$CR^2$—, —C(R)($R^{X1}$)—, —C($R^{X1}$)$_2$—, —N(R)— or —N($R^{X1}$)—; and
$X^7$ is —CR—, —C($R^{X1}$)— or —N—;
p is 0, 1 or 2;
q is 0, 1 or 2;
r is 0, 1 or 2; and
s is 0, 1 or 2.

10. The compound of claim 8, wherein
(a) ring A is

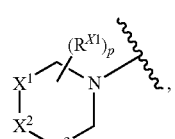

wherein
p is 0, 1, 2, 3 or 4;
$X^1$ is —O—, —S—, —S(O)—, —$S(O)_2$—, —$CR^2$—, —C(R)($R^{X1}$)—, —C($R^{X1}$)$_2$—, —N(R)— or —N($R^{X1}$)—;
$X^2$ is —S—, —S(O)—, —$S(O)_2$—, —$CR^2$—, —C(R)($R^{X1}$)—, —C($R^{X1}$)$_2$—, —N(R)— or —N($R^{X1}$)—; and
$X^3$ is —O—, —S—, —S(O)—, —$S(O)_2$—, —$CR^2$—, —C(R)($R^{X1}$)—, —C($R^{X1}$)$_2$—, —N(R)— or —N($R^{X1}$)—;
(b) ring A is

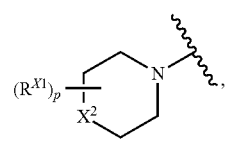

wherein
p is 0, 1, 2, 3 or 4;
$X^2$ is —S—, —S(O)—, —S(O)$_2$—, —CR$^2$—, —C(R)(R$^{X1}$)—, —C(R$^{X1}$)$_2$—, —N(R)— or —N(R$^{X1}$)—;
(c) ring A is

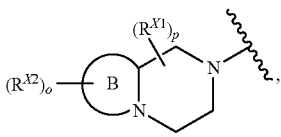

wherein
p is 0, 1 or 2;
o is 0, 1 or 2; and
ring B is Hca or Het, each comprising a 3-8 membered ring optionally substituted with one or two —R$^{X2}$ groups;
(d) ring A is

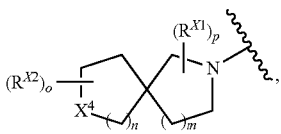

wherein
p is 0, 1 or 2;
o is 0, 1 or 2;
n is 0, 1 or 2;
m is 0, 1 or 2; and
$X^4$ is —O—, —S—, —S(O)$_2$—, —CR$^2$—, —C(R)(R$^{X1}$)—, —C(R$^{X1}$)$_2$—, —N(R)— or —N(R$^{X1}$)—;
(e) ring A is

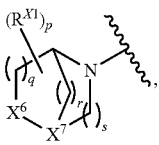

wherein
$X^6$ is —O—, —S—, —S(O)—, —S(O)$_2$—, —CR$^2$—, —C(R)(R$^{X1}$)—, —C(R$^{X1}$)$_2$—, —N(R)— or —N(R$^{X1}$)—; and
$X^7$ is —CR—, —C(R$^{X1}$)— or —N—;
p is 0, 1 or 2;
q is 0, 1 or 2;
r is 0, 1 or 2; and
s is 0, 1 or 2.

11. The compound of claim 8, wherein a is 0.
12. The compound of claim 8, wherein a is 1.
13. The compound of claim 1, wherein
Z is $C_1$-$C_6$alkyl optionally substituted by one to three —R$^{Z1}$ groups;
wherein each —R$^{Z1}$ is independently halogen, $C_1$-$C_6$alkyl or $C_1$-$C_6$haloalkyl;
or Z is $C_1$-$C_6$alkyl optionally substituted by one to three —R$^{Z1}$ groups;
wherein each —R$^{Z1}$ is independently halogen, cyano, $C_1$-$C_6$alkyl, $C_1$-$C_6$haloalkyl, —$C_1$-$C_6$alkoxy, oxo, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR);
or Z is $C_1$-$C_6$alkyl optionally substituted by one to three —R$^{Z1}$ groups;
wherein each —R$^{Z1}$ is independently halogen, $C_1$-$C_6$alkyl or $C_1$-$C_6$haloalkyl.

14. The compound of claim 1, wherein
Z is Cak($C_0$-$C_6$alkyl) optionally substituted by one to three —R$^{Z1}$ groups;
wherein each —R$^{Z1}$ is independently halogen, cyano, $C_1$-$C_6$alkyl, $C_1$-$C_6$haloalkyl, —$C_1$-$C_6$alkoxy, oxo, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR)
or Z is Cak($C_0$-$C_6$alkyl) optionally substituted by one to three —R$^{Z1}$ groups;
wherein each —R$^{Z1}$ is independently halogen, $C_1$-$C_6$alkyl or $C_1$-$C_6$haloalkyl.

15. The compound of claim 1, wherein
Z is Cak optionally substituted by one to three —R$^{Z1}$ groups;
wherein each —R$^{Z1}$ is independently halogen, cyano, $C_1$-$C_6$alkyl, $C_1$-$C_6$haloalkyl, —$C_1$-$C_6$alkoxy, oxo, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR);
or Z is Cak optionally substituted by one to three —R$^{Z1}$ groups;
wherein each —R$^{Z1}$ is independently halogen, $C_1$-$C_6$alkyl or $C_1$-$C_6$haloalkyl.

16. The compound of claim 1, wherein
Z is Cak($C_1$alkyl) optionally substituted by one to three —R$^{Z1}$ groups;
wherein each —R$^{Z1}$ is independently halogen, cyano, $C_1$-$C_6$alkyl, $C_1$-$C_6$haloalkyl, —$C_1$-$C_6$alkoxy, oxo, —OR, —SR, —NR$_2$, —C(O)R, —C(O)OR, —C(O)NR$_2$, —S(O)$_2$NR$_2$, —S(O)$_2$R, —OC(O)R, —N(R)C(O)R, —OC(O)OR, —OC(O)NR$_2$, —N(R)C(O)OR, —N(R)C(O)NR$_2$, —N(R)S(O)$_2$R, —OP(O)(OR)$_2$ or —CH$_2$—OP(O)(OR);
or Z is Cak($C_1$alkyl) optionally substituted by one to three —R$^{Z1}$ groups;
wherein each —R$^{Z1}$ is independently halogen, $C_1$-$C_6$alkyl or $C_1$-$C_6$haloalkyl.

17. The compound of claim 2, having the structure of formula (III):

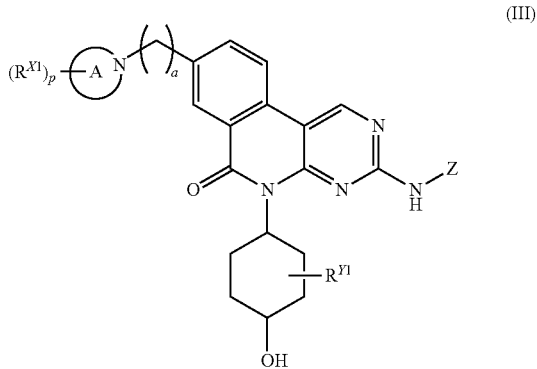

or a pharmaceutically acceptable salt or N-oxide thereof, or solvate or hydrate thereof, wherein a is 0 or 1;

ring A is (a)
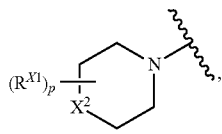

wherein p is 0, 1, 2 or 3;

$X^2$ is —O—, —S—, —CR$_2$—, —C(R)(R$^{X1}$)—, —C(R$^{X1}$)$_2$—, —N(R)— or —N(R$^{X1}$)—;

(b)
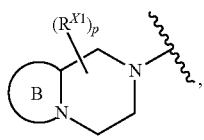

wherein p is 0, 1 or 2;

ring B is 5-membered Hca or Het; or (c)
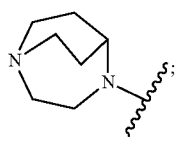

each —R$^{X1}$ is independently hydrogen, C$_1$-C$_6$alkyl, —C(O)OR, Cak(C$_0$-C$_6$alkyl) or Hca(C$_0$-C$_6$alkyl);

R$^{Y1}$ is hydrogen or C$_1$-C$_6$alkyl;

Z is C$_1$-C$_6$alkyl or Cak(C$_1$-C$_6$alkyl); and each R is independently hydrogen or C$_1$-C$_6$alkyl.

18. The compound of claim 17, wherein a is 0.

19. The compound of claim 17, wherein a is 1.

20. The compound of claim 17, wherein ring A is

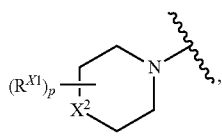

wherein p is 0, 1, 2 or 3; and $X^2$ is —O—, —S—, —CR$_2$—, —C(R)(R$^{X1}$)—, —C(R$^{X1}$)$_2$—, —N(R)— or —N(R$^{X1}$)—.

21. The compound of claim 17, wherein ring A is

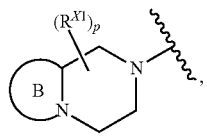

wherein p is 0, 1 or 2; and ring B is 5-membered Hca or Het.

22. The compound of claim 17, wherein ring A is

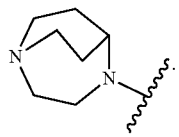 [SMILES: *N1CCN2CCC1CC2]

23. The compound of claim 2, having the structure of formula (IV):

(IV)
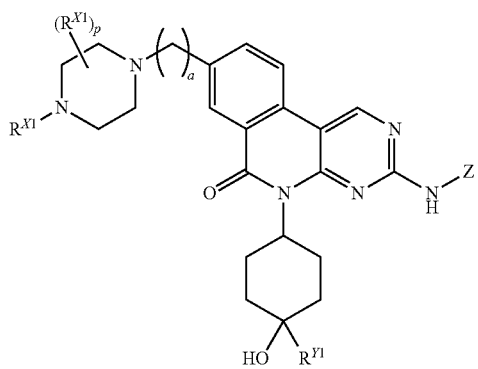

or a pharmaceutically acceptable salt, prodrug or N-oxide thereof, or solvate or hydrate thereof, wherein a is 0 or 1;

each —R$^{X1}$ is independently hydrogen or C$_1$-C$_6$alkyl;

—R$^{Y1}$ is hydrogen or C$_1$-C$_6$alkyl; and

Z is C$_1$-C$_6$alkyl or Cak(C$_1$-C$_6$alkyl).

24. The compound of claim 22, wherein a is 0.

25. The compound of claim 22, wherein a is 1.

26. The compound of claim 22, wherein Z is C$_1$-C$_6$alkyl.

27. The compound of claim 22, wherein Z is Cak(C$_1$-C$_6$alkyl).

28. The compound of claim 1, wherein X is hydrogen, Cak(C$_0$-C$_6$alkyl), Hca(C$_0$-C$_6$alkyl) or Het(C$_0$-C$_6$alkyl, wherein Ar, Het, Cak, Hca and the alkyl group is optionally substituted by one to four —R$^{X1}$ groups, provided that when X is morpholinyl(C$_1$alkyl), Z is C$_1$-C$_6$alkyl substituted by one to three —R$^{Z1}$ groups, or Cak(C$_0$-C$_6$alkyl) optionally substituted by one to three —R$^{Z1}$ groups.

29. A compound that is:

trans-3-((2,2-Difluorobutyl)amino)-5-(4-hydroxycyclohexyl)-8-(morpholinomethyl)pyrimido[4,5-c]isoquinolin-6(5H)-one trans-3-(Butylamino)-5-(4-hydroxycyclohexyl)-8-(morpholinomethyl)pyrimido[4,5-c]isoquinolin-6(5H)-one trans-3-(Butylamino)-5-(4-hydroxycyclohexyl)-8-((4-methylpiperazin-1-yl)methyl)pyrimido[4,5-c]isoquinolin-6(5H)-one
cis-3-(Butylamino)-5-(4-hydroxycyclohexyl)-8-(morpholinomethyl)pyrimido[4,5-c]isoquinolin-6(5H)-one
cis-3-(Butylamino)-5-(4-hydroxycyclohexyl)-8-((4-methylpiperazin-1-yl)methyl)pyrimido[4,5-c]isoquinolin-6(5H)-one
3-(Butylamino)-5-(4-hydroxycyclohexyl)methyl)-8-((4-methylpiperazin-1-yl)methyl)pyrimido[4,5-c]isoquinolin-6(5H)-one
tert-Butyl (4-((3-(butylamino)-8-(morpholinomethyl)-6-oxopyrimido[4,5-c]isoquinolin-5(6H)-yl)methyl)cyclohexyl)carbamate
tert-Butyl (4-((3-(butylamino)-8-(4-methylpiperazin-1-yl)methyl)-6-oxopyrimido[4,5-c]isoquinolin-5(6H)-yl)methyl)cyclohexyl)carbamate
5-((4-Aminocyclohexyl)methyl)-3-(butylamino)-8-(morpholinomethyl)pyrimido[4,5-c]isoquinolin-6(5H)-one
5-((4-Aminocyclohexyl)methyl)-3-(butylamino)-8-((4-methylpiperazin-1-yl)methyl)pyrimido[4,5-c]isoquinolin-6(5H)-one
trans-3-Amino-5-(4-hydroxycyclohexyl)-8-((4-methylpiperazin-1-yl)methyl)pyrimido[4,5-c]isoquinolin-6(5H)-one
trans-3-((3,3-Difluorocyclobutyl)amino)-5-(4-hydroxycyclohexyl)-8-((4-methylpiperazin-1-yl)methyl)pyrimido[4,5-c]isoquinolin-6(5H)-one
trans-3-((3-Fluorocyclobutyl)amino)-5-(4-hydroxycyclohexyl)-8-(4-methylpiperazin-1-yl)methyl)pyrimido[4,5-c]isoquinolin-6(5H)-one
3-(Butylamino)-5-(6-hydroxyspiro[3.3]heptan-2-yl)-8-((4-methylpiperazin-1-yl)methyl)pyrimido[4,5-c]isoquinolin-6(5H)-one
trans-3-(Butylamino)-5-(4-hydroxy-4-methylcyclohexyl)-8-((4-methylpiperazin-1-yl)methyl)pyrimido[4,5-c]isoquinolin-6(5H)-one
trans-3-((Cyclopropylmethyl)amino)-5-(4-hydroxycyclohexyl)-8-((4-methylpiperazin-1-yl)methyl)pyrimido[4,5-c]isoquinolin-6(5H)-one
cis-3-(Butylamino)-5-(4-hydroxy-4-methylcyclohexyl)-8-((4-methylpiperazin-1-yl)methyl)pyrimido[4,5-c]isoquinolin-6(5H)-one
trans-3-(((1-Ethylcyclobutyl)methyl)amino)-5-(4-hydroxycyclohexyl)-8-((4-methylpiperazin-1-yl)methyl)pyrimido[4,5-c]isoquinolin-6(5H)-one
trans-3-(((1-Ethylcyclobutyl)methyl)amino)-5-(4-hydroxycyclohexyl)-8-(morpholinomethyl)pyrimido[4,5-c]isoquinolin-6(5H)-one
trans-3-((1-Ethylcyclobutyl)methyl)amino)-5-(4-hydroxycyclohexyl)-8-(morpholinomethyl)pyrimido[4,5-c]isoquinolin-6(5H)-one
trans-3-((Cyclobutylmethyl)amino)-5-(4-hydroxycyclohexyl)-8-(morpholinomethyl)pyrimido[4,5-c]isoquinolin-6(5H)-one
trans-3-(((1-Ethylcyclopropyl)methyl)amino)-5-(4-hydroxycyclohexyl)-8-((4-methylpiperazin-1-yl)methyl)pyrimido[4,5-c]isoquinolin-6(5H)-one
trans-3-(((1-Ethylcyclopropyl)methyl)amino)-5-((4-hydroxycyclohexyl)-8-(morpholinomethyl)pyrimido[4,5-c]isoquinolin-6(5H)-one
trans-3-((2,2-Difluorobutyl)amino)-5-(4-hydroxycyclohexyl)-8-((4-methylpiperazin-1-yl)methyl)pyrimido[4,5-c]isoquinolin-6(5H)-one
trans-5-(4-hydroxycyclohexyl)-8-((4-methylpiperazin-1-yl)methyl)-3-((4,4,4-trifluorobutyl)amino)pyrimido[4,5-c]isoquinolin-6(5H)-one trans-3-((2-Cyclopropylethyl)amino)-5-(4-hydroxycyclohexyl)-8-((4-methylpiperazin-1-yl)methyl)pyrimido[4,5-c]isoquinolin-6(5H)-one
trans-3-((2-Cyclopropylethyl)amino)-5-(4-hydroxycyclohexyl)-8-(morpholinomethyl)pyrimido[4,5-c]isoquinolin-6(5H)-one
trans-3-((Cyclopropylmethyl)amino)-5-(4-hydroxy-4-methylcyclohexyl)-8-((4-methylpiperazin-1-yl)methyl)pyrimido[4,5-c]isoquinolin-6(5H)-one
trans-3-((2-Cyclopropylethyl)amino)-5-(4-hydroxy-4-methylcyclohexyl)-8-((4-methylpiperazin-1-yl)methyl)pyrimido[4,5-c]isoquinolin-6(5H)-one
trans-3-((Cyclopropylmethyl)amino)-5-(4-hydroxycyclohexyl)-8-((4-isopropylpiperazin-1-yl)methyl)pyrimido[4,5-c]isoquinolin-6(5H)-one
trans-3-((Cyclopropylmethyl)amino)-5-(4-hydroxy-4-methylcyclohexyl)-8-((4-isopropylpiperazin-1-yl)methyl)pyrimido[4,5-c]isoquinolin-6(5H)-one
trans-3-((2-Cyclopropylethyl)amino)-5-(4-hydroxy-4-methylcyclohexyl)-8-((4-isopropylpiperazin-1-yl)methyl)pyrimido[4,5-c]isoquinolin-6(5H)-one
trans-3-((Cyclobutylmethyl)amino)-5-(4-hydroxycyclohexyl)-8-((4-isopropylpiperazin-1-yl)methyl)pyrimido[4,5-c]isoquinolin-6(5H)-one
trans-3-((Cyclobutylmethyl)amino)-5-(4-hydroxy-4-methylcyclohexyl)-8-((4-methylpiperazin-1-yl)methyl)pyrimido[4,5-c]isoquinolin-6(5H)-one
trans-3-((Cyclopropylmethyl)amino)-5-(4-hydroxycyclohexyl)-8-((4-(oxetan-3-yl)piperazin-1-yl)methyl)pyrimido[4,5-c]isoquinolin-6(5H)-one
trans-3-((Cyclopropylmethyl)amino)-5-(4-hydroxy-4-methylcyclohexyl)-8-((4-(oxetan-3-yl)piperazin-1-yl)methyl)pyrimido[4,5-c]isoquinolin-6(5H)-one
trans-3-((Cyclopropylmethyl)amino)-5-(4-hydroxycyclohexyl)-8-((4-(pyrrolidin-1-yl)piperidin-1-yl)methyl)pyrimido[4,5-c]isoquinolin-6(5H)-one
trans-3-((Cyclopropylmethyl)amino)-5-(4-hydroxy-4-methylcyclohexyl)-8-((4-(pyrrolidin-1-yl)piperidin-1-yl)methyl)pyrimido[4,5-c]isoquinolin-6(5H)-one
trans-3-((Cyclopropylmethyl)amino)-8-((5,6-dihydro-[1,2,4]triazolo[1,5-a]pyrazin-7(8H)-yl)methyl)-5-(4-hydroxycyclohexyl)pyrimido[4,5-c]isoquinolin-6(5H)-one
trans-3-((Cyclopropylmethyl)amino)-5-(4-hydroxycyclohexyl)-8-((4-(2,2,2-trifluoroethyl)piperazin-1-yl)methyl)pyrimido[4,5-c]isoquinolin-6(5H)-one
trans-(3-(butylamino)-8-((4-methylpiperazin-1-yl)methyl)-6-oxopyrimido[4,5-c]isoquinolin-5(6H)-yl)cyclohexane-1-carbonitrile
trans-5-(4-hydroxycyclohexyl)-3-(isopentylamino)-8-((4-methylpiperazin-1-yl)methyl)pyrimido[4,5-c]isoquinolin-6(5H)-one
trans-3-((Cyclopropylmethyl)amino)-8-((4-(2,2-difluoroethyl)piperazin-1-yl)methyl)-5-(4-hydroxycyclohexyl)pyrimido[4,5-c]isoquinolin-6(5H)-one
trans-3-(Butylamino)-5-(4-hydroxycyclohexyl)-8-(piperazin-1-ylmethyl)pyrimido[4,5-c]isoquinolin-6(5H)-one
trans-3-((Cyclopropylmethyl)amino)-5-(4-hydroxycyclohexyl)-8-(morpholinomethyl)pyrimido[4,5-c]isoquinolin-6(5H)-one
trans-3-((Cyclopropylmethyl)amino)-5-(4-hydroxy-4-methylcyclohexyl)-8-(morpholinomethyl)pyrimido[4,5-c]isoquinolin-6(5H)-one
trans-3-((Cyclopropylmethyl)amino)-8-(((S)-hexahydropyrrolo[1,2-a]pyrazin-2(1H)-yl)methyl)-5-(4-hydroxycyclohexyl)pyrimido[4,5-c]isoquinolin-6(5H)-one trans-3-((Cyclopropylmethyl)amino)-8-(((R)-hexahydropyrrolo[1,2-a]pyrazin-2(1H)-yl)methyl)-5-(4-hydroxycyclohexyl)pyrimido[4,5-c]isoquinolin-6(5H)-one trans-3-((Cyclopropylmethyl)amino)-8-((1,1-dioxidothiomorpholino)methyl)-5-(4-hydroxycyclohexyl)pyrimido[4,5-c]isoquinolin-6(5H)-one trans-Ethyl 1-((3-((Cyclopropylmethyl)amino)-5-(4-hydroxycyclohexyl)-6-oxo-5,6-dihydropyrimido[4,5-c]isoquinolin-8-yl)methyl)piperidine-4-carboxylate trans-4-((3-((Cyclopropylmethyl)amino)-5-(4-hydroxycyclohexyl)-6-oxo-5,6-dihydropyrimido[4,5-c]isoquinolin-8-yl)methyl)-1,4-diazabicyclo[3.2.2]nonane 1-oxide trans-3-((cyclopropylmethyl)amino)-5-(4-hydroxycyclohexyl)-8-((1-oxidothiomorpholino)methyl)pyrimido[4,5-c]isoquinolin-6(5H)-one trans-3-((Cyclopropylmethyl)amino)-5-(4-hydroxycyclohexyl)-8-(thiomorpholinomethyl)pyrimido[4,5-c]isoquinolin-6(5H)-one trans-3-((Cyclopropylmethyl)amino)-5-(4-hydroxycyclohexyl)-8-(piperazin-1-ylmethyl)pyrimido[4,5-c]isoquinolin-6(5H)-one trans-3-((Cyclopropylmethyl)amino)-8-(((R)-3,4-dimethylpiperazin-1-yl)methyl)-5-(4-hydroxycyclohexyl)pyrimido[4,5-c]isoquinolin-6(5H)-one trans-5-(4-Hydroxycyclohexyl)-3-(isobutylamino)-8-((4-methylpiperazin-1-yl)methyl)pyrimido[4,5-c]isoquinolin-6(5H)-one 3-(Butylamino)-5-((1S,4S)-4-hydroxycycloheptyl)-8-((4-methylpiperazin-1-yl)methyl)pyrimido[4,5-c]isoquinolin-6(5H)-one trans-8-((1,4-Diazabicyclo[3.2.2]nonan-4-yl)methyl)-3-((cyclopropylmethyl)amino)-5-(4-hydroxycyclohexyl)pyrimido[4,5-c]isoquinolin-6(5H)-one trans-4-(3-((Cyclopropylmethyl)amino)-8-((4-methylpiperazin-1-yl)methyl)-6-oxopyrimido[4,5-c]isoquinolin-5(6H)-yl)cyclohexyl carbamate trans-8-((4-(tert-butyl)piperazin-1-yl)methyl)-3-((cyclopropylmethyl)amino)-5-(4-hydroxycyclohexyl)pyrimido[4,5-c]isoquinolin-6(5H)-one trans-3-(Butylamino)-5-(4-hydroxycyclohexyl)-8-(4-methylpiperazin-1-yl)pyrimido[4,5-c]isoquinolin-6(5H)-one trans-3-(Butylamino)-5-(4-hydroxycyclohexyl)-8-morpholinopyrimido[4,5-c]isoquinolin-6(5H)-one cis-3-(Butylamino)-5-(4-hydroxycyclohexyl)-8-(4-methylpiperazin-1-yl)pyrimido[4,5-c]isoquinolin-6(5H)-one tert-Butyl (4-((3-(Butylamino)-8-(4-methylpiperazin-1-yl)-6-oxopyrimido[4,5-c]isoquinolin-5(6H)-yl)methyl)cyclohexyl)carbamate 5-((4-Aminocyclohexyl)methyl)-3-(butylamino)-8-(4-methylpiperazin-1-yl)pyrimido[4,5-c]isoquinolin-6(5H)-one trans-3-((3,3-Difluorocyclobutyl)amino)-5-(4-hydroxycyclohexyl)-8-(6-methyl-2,6-diazaspiro[3.3]heptan-2-yl)pyrimido[4,5-c]isoquinolin-6(5H)-one trans-3-((3,3-difluorocyclobutyl)amino)-5-(4-hydroxycyclohexyl)-8-(2-oxa-6-azaspiro[3.3]heptan-6-yl)pyrimido[4,5-c]isoquinolin-6(5H)-one trans-3-(Butylamino)-5-(4-hydroxycyclohexyl)-8-(2-oxa-6-azaspiro[3.3]heptan-6-yl)pyrimido[4,5-c]isoquinolin-6(5H)-one trans-3-(Butylamino)-5-(4-hydroxycyclohexyl)-8-(4-isopropylpiperazin-1-yl)pyrimido[4,5-c]isoquinolin-6(5H)-one 3-(Butylamino)-8-(4-isopropylpiperazin-1-yl)-5-(4-oxocyclohexyl)pyrimido[4,5-c]isoquinolin-6(5H)-one trans-3-(Butylamino)-5-(4-hydroxycyclohexyl)-8-(4-(pyrrolidin-1-yl)piperidin-1-yl)pyrimido[4,5-c]isoquinolin-6(5H)-one 3-(Butylamino)-5-(4-oxocyclohexyl)-8-(4-(pyrrolidin-1-yl)piperidin-1-yl)pyrimido[4,5-c]isoquinolin-6(5H)-one trans-3-(Butylamino)-8-((S)-hexahydropyrrolo[1,2-a]pyrazin-2(1H)-yl)-5-((1r,4S)-4-hydroxycyclohexyl)pyrimido[4,5-c]isoquinolin-6(5H)-one trans-3-((3-Fluorocyclobutyl)amino)-5-(4-hydroxycyclohexyl)-8-(6-methyl-2,6-diazaspiro[3.3]heptan-2-yl)pyrimido[4,5-c]isoquinolin-6(5H)-one trans-3-((3-Fluorocyclobutyl)amino)-5-(4-hydroxycyclohexyl)-8-(2-oxa-6-azaspiro[3.3]heptan-6-yl)pyrimido[4,5-c]isoquinolin-6(5H)-one trans-3-(Butylamino)-8-((R)-hexahydropyrrolo[1,2-a]pyrazin-2(1H)-yl)-5-(4-hydroxycyclohexyl)pyrimido[4,5-c]isoquinolin-6(5H)-one trans-3-(Butylamino)-5-(4-hydroxycyclohexyl)-8-(4-(oxetan-3-yl)piperazin-1-yl)pyrimido[4,5-c]isoquinolin-6(5H)-one trans-3-(Butylamino)-5-(4-hydroxycyclohexyl)-8-((2 S,5R)-2,4,5-trimethylpiperazin-1-yl)pyrimido[4,5-c]isoquinolin-6(5H)-one 3-(Butylamino)-5-(4-oxocyclohexyl)-8-((2 S, 5R)-2,4,5-trimethylpiperazin-1-yl)pyrimido[4,5-c]isoquinolin-6(5H)-one trans-3-(Butylamino)-8-(5,6-dihydro-[1,2,4]triazolo[1,5-a]pyrazin-7(8H)-yl)-5-(4-hydroxycyclohexyl)pyrimido[4,5-c]isoquinolin-6(5H)-one trans-8-(1,4-Diazabicyclo[3.2.2]nonan-4-yl)-3-(butylamino)-5-(4-hydroxycyclohexyl)pyrimido[4,5-c]isoquinolin-6(5H)-one 8-(1,4-Diazabicyclo[3.2.2]nonan-4-yl)-3-(butylamino)-5-(4-oxocyclohexyl)pyrimido[4,5-c]isoquinolin-6(5H)-one trans-3-(Butylamino)-5-(4-hydroxycyclohexyl)-8-(piperazin-1-yl)pyrimido[4,5-c]isoquinolin-6(5H)-one 3-(Butylamino)-5-(4-oxocyclohexyl)-8-(piperazin-1-yl)pyrimido[4,5-c]isoquinolin-6(5H)-one trans-3-((3,3-Difluorocyclobutyl)amino)-5-(4-hydroxycyclohexyl)-8-(4-methylpiperazin-1-yl)pyrimido[4,5-c]isoquinolin-6(5H)-one trans-3-(Butylamino)-5-(4-hydroxy-4-methylcyclohexyl)-8-(4-methylpiperazin-1-yl)pyrimido[4,5-c]isoquinolin-6(5H)-one trans-3-((Cyclopropylmethyl)amino)-5-(4-hydroxycyclohexyl)-8-(4-methylpiperazin-1-yl)pyrimido[4,5-c]isoquinolin-6(5H)-one 3-(Butylamino)-5-(6-hydroxyspiro[3.3]heptan-2-yl)-8-(4-methylpiperazin-1-yl)pyrimido[4,5-c]isoquinolin-6(5H)-one cis-3-(Butylamino)-5-(4-hydroxy-4-methylcyclohexyl)-8-(4-methylpiperazin-1-yl)pyrimido[4,5-c]isoquinolin-6(5H)-one trans-3-(Butylamino)-8-((R)-3,4-dimethylpiperazin-1-yl)-5-(4-hydroxycyclohexyl)pyrimido[4,5-c]isoquinolin-6(5H)-one trans-3-(((1-Ethylcyclobutyl)methyl)amino)-5-(4-hydroxycyclohexyl)-8-(4-methylpiperazin-1-yl)pyrimido[4,5-c]isoquinolin-6(5H)-one trans-3-((Cyclobutylmethyl)amino)-5-(4-hydroxycyclohexyl)-8-(4-methylpiperazin-1-yl)pyrimido[4,5-c]isoquinolin-6(5H)-one trans-3-((2,2-Difluorobutyl)amino)-5-(4-hydroxycyclohexyl)-8-(4-methylpiperazin-1-yl)pyrimido[4,5-c]isoquinolin-6(5H)-one trans-3-(((1-Ethylcyclopropyl)methyl)amino)-5-(4-hydroxycyclohexyl)-8-(4-methylpiperazin-1-yl)pyrimido[4,5-c]isoquinolin-6(5H)-one
trans-5-(4-Hydroxycyclohexyl)-8-(4-methylpiperazin-1-yl)-3-((4,4,4-trifluorobutyl)amino)pyrimido[4,5-c]isoquinolin-6(5H)-one
trans-3-((2-Cyclopropylethyl)amino)-5-(4-hydroxycyclohexyl)-8-(4-methylpiperazin-1-yl)pyrimido[4,5-c]isoquinolin-6(5H)-one
trans-3-((Cyclopropylmethyl)amino)-5-(4-hydroxy-4-methylcyclohexyl)-8-(4-methylpiperazin-1-yl)pyrimido[4,5-c]isoquinolin-6(5H)-one
trans-3-((2-Cyclopropylethyl)amino)-5-(4-hydroxy-4-methylcyclohexyl)-8-(4-methylpiperazin-1-yl)pyrimido[4,5-c]isoquinolin-6(5H)-one
trans-3-((Cyclopropylmethyl)amino)-5-(4-hydroxycyclohexyl)-8-(4-(pyrrolidin-1-yl)piperidin-1-yl)pyrimido[4,5-c]isoquinolin-6(5H)-one
trans-8-(1,4-diazabicyclo[3.2.2]nonan-4-yl)-3-((cyclopropylmethyl)amino)-5-(4-hydroxycyclohexyl)pyrimido[4,5-c]isoquinolin-6(5H)-one
trans-3-((Cyclopropylmethyl)amino)-8-(5,6-dihydro-[1,2,4]triazolo[1,5-a]pyrazin-7(8H)-yl)-5-(4-hydroxycyclohexyl)pyrimido[4,5-c]isoquinolin-6(5H)-one
trans-3-((Cyclopropylmethyl)amino)-8-((S)-hexahydropyrrolo[1,2-a]pyrazin-2(1H)-yl)-5-(4-hydroxycyclohexyl)pyrimido[4,5-c]isoquinolin-6(5H)-one
trans-3-((Cyclopropylmethyl)amino)-8-((R)-hexahydropyrrolo[1,2-a]pyrazin-2(1H)-yl)-5-(4-hydroxycyclohexyl)pyrimido[4,5-c]isoquinolin-6(5H)-one
trans-3-((Cyclopropylmethyl)amino)-5-(4-hydroxycyclohexyl)-8-(4-(2,2,2-trifluoroethyl)piperazin-1-yl)pyrimido[4,5-c]isoquinolin-6(5H)-one
trans-3-((Cyclopropylmethyl)amino)-8-(4-(2,2-difluoroethyl)piperazin-1-yl)-5-(4-hydroxycyclohexyl)pyrimido[4,5-c]isoquinolin-6(5H)-one
trans-3-((Cyclopropylmethyl)amino)-8-((R)-3,4-dimethylpiperazin-1-yl)-5-(4-hydroxycyclohexyl)pyrimido[4,5-c]isoquinolin-6(5H)-one
trans-3-((Cyclopropylmethyl)amino)-5-(4-hydroxycyclohexyl)-8-((2S,5R)-2,4,5-trimethylpiperazin-1-yl)pyrimido[4,5-c]isoquinolin-6(5H)-one
trans-3-((Cyclopropylmethyl)amino)-5-(4-hydroxycyclohexyl)-8-(piperazin-1-yl)pyrimido[4,5-c]isoquinolin-6(5H)-one
trans-3-((Cyclopropylmethyl)amino)-5-(4-hydroxycyclohexyl)-8-(4-isopropylpiperazin-1-yl)pyrimido[4,5-c]isoquinolin-6(5H)-one
trans-3-((Cyclopropylmethyl)amino)-8-(4-cyclopropylpiperazin-1-yl)-5-(4-hydroxycyclohexyl)pyrimido[4,5-c]isoquinolin-6(5H)-one
trans-3-((Cyclopropylmethyl)amino)-5-(4-hydroxycyclohexyl)-8-(4-(oxetan-3-yl)piperazin-1-yl)pyrimido[4,5-c]isoquinolin-6(5H)-one
3-(Butylamino)-5-(6-hydroxyspiro[3.3]heptan-2-yl)pyrimido[4,5-c]isoquinolin-6(5H)-one
trans-3-(Butylamino)-5-(4-hydroxy-4-methylcyclohexyl)pyrimido[4,5-c]isoquinolin-6(5H)-one
trans-3-((Cyclopropylmethyl)amino)-5-(4-hydroxycyclohexyl)pyrimido[4,5-c]isoquinolin-6(5H)-one
cis-3-(Butylamino)-5-(4-hydroxy-4-methylcyclohexyl)pyrimido[4,5-c]isoquinolin-6(5H)-one
trans-3-(((1-Ethylcyclobutyl)methyl)amino)-5-(4-hydroxycyclohexyl)pyrimido[4,5-c]isoquinolin-6(5H)-one
trans-3-((Cyclobutylmethyl)amino)-5-(4-hydroxycyclohexyl)pyrimido[4,5-c]isoquinolin-6(5H)-one 3-(((1-Ethylcyclopropyl)methyl)amino)-5-(4-hydroxycyclohexyl)pyrimido[4,5-c]isoquinolin-6(5H)-one
trans-3-((2,2-difluorobutyl)amino)-5-(4-hydroxycyclohexyl)pyrimido[4,5-c]isoquinolin-6(5H)-one
trans-3-((2-Cyclopropylethyl)amino)-5-(4-hydroxycyclohexyl)pyrimido[4,5-c]isoquinolin-6(5H)-one
trans-3-((Cyclopropylmethyl)amino)-5-(4-hydroxy-4-methylcyclohexyl)pyrimido[4,5-c]isoquinolin-6(5H)-one
trans-3-((2-Cyclopropylethyl)amino)-5-(4-hydroxy-4-methylcyclohexyl)pyrimido[4,5-c]isoquinolin-6(5H)-one
trans-3-((Cyclobutylmethyl)amino)-5-(4-hydroxy-4-methylcyclohexyl)pyrimido[4,5-c]isoquinolin-6(5H)-one
trans-3-((Cyclopropylmethyl)amino)-5-(4-hydroxycyclohexyl)-8-((4-(pyridin-4-yl)piperazin-1-yl)methyl)pyrimido[4,5-c]isoquinolin-6(5H)-one
3-(Butylamino)-5-((1r,5r)-5-((tert-butyldimethylsilyl)oxy)cyclooctyl)-8-chloropyrimido[4,5-c]isoquinolin-6(5H)-one
3-(Butylamino)-5-((1r,5r)-5-((tert-butyldimethylsilyl)oxy)cyclooctyl)-8-((4-methylpiperazin-1-yl)methyl)pyrimido[4,5-c]isoquinolin-6(5H)-one
3-(Butylamino)-5-((1r,5r)-5-hydroxycyclooctyl)-8-((4-methylpiperazin-1-yl)methyl)pyrimido[4,5-c]isoquinolin-6(5H)-one

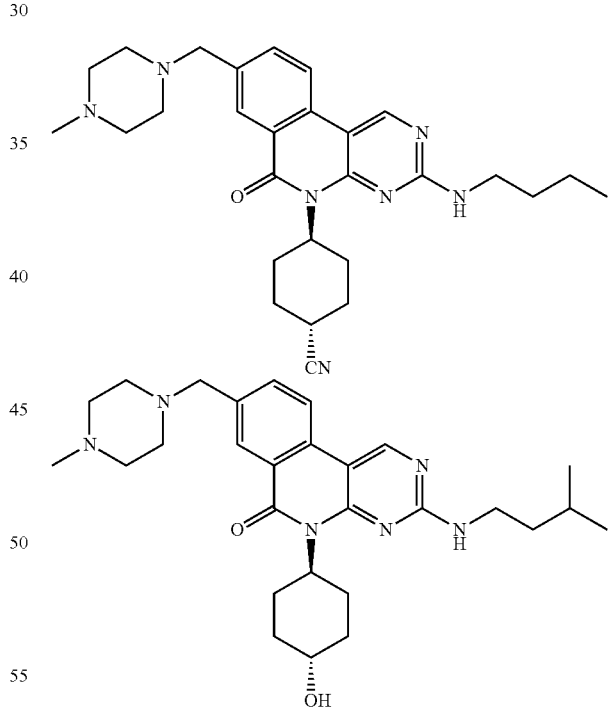

trans-5-(4-hydroxycyclohexyl)-3-(isobutylamino)-8-((4-methylpiperazin-1-yl)methyl)pyrimido[4,5-c]isoquinolin-6(5H)-one
trans-4-(3-(Butylamino)-8-((4-methylpiperazin-1-yl)methyl)-6-oxopyrimido[4,5-c]isoquinolin-5 (6H)-yl)cyclohexane-1-carboxamide
trans-4-(3-(Butylamino)-8-((4-methylpiperazin-1-yl)methyl)-6-oxopyrimido[4,5-c]isoquinolin-5(6H)-yl)cyclohexane-1-carboxylic acid

357

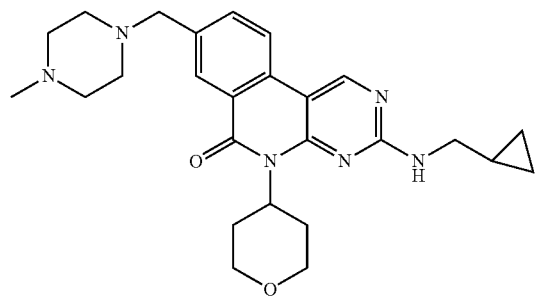 [SMILES: CN1CCN(Cc2ccc3c(c2)c(=O)n(C2CCOCC2)c2nc(NCC4CC4)ncc32)CC1]

trans-4-(3-((Cyclopropylmethyl)amino)-8-((4-methylpiperazin-1-yl)methyl)-6-oxopyrimido[4,5-c]isoquinolin-5(6H)-yl)cyclohexane-1-carboxamide trans-4-(3-((Cyclopropylmethyl)amino)-8-((4-methylpiperazin-1-yl)methyl)-6-oxopyrimido[4,5-c]isoquinolin-5(6H)-yl)cyclohexane-1-carboxylic acid

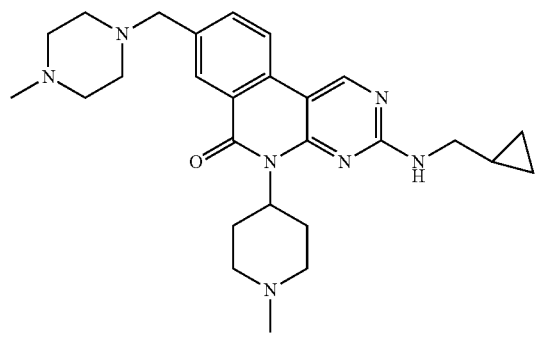 [SMILES: CN1CCC(n2c(=O)c3cc(CN4CCN(C)CC4)ccc3c3cnc(NCC4CC4)nc32)CC1]

trans-3-(cyclobutylamino)-5-(4-hydroxycyclohexyl)-8-((4-methylpiperazin-1-yl)methyl)pyrimido[4,5-c]isoquinolin-6(5H)-one trans-4-(3-(Butylamino)-8-((4-methylpiperazin-1-yl)methyl)-6-oxopyrimido[4,5-c]isoquinolin-5 (6H)-yl)-N-methylcyclohexane-1-carboxamide trans-4-(3-(Butylamino)-8-((4-methylpiperazin-1-yl)methyl)-6-oxopyrimido[4,5-c]isoquinolin-5 (6H)-yl)-N-(2,2,2-trifluoroethyl)cyclohexane-1-carboxamide trans-4-(3-(Butylamino)-8-((4-methylpiperazin-1-yl)methyl)-6-oxopyrimido[4,5-c]isoquinolin-5(6H)-yl)-N-(oxetan-3-yl)cyclohexane-1-carboxamide trans-4-(3-(Butylamino)-8-((4-methylpiperazin-1-yl)methyl)-6-oxopyrimido[4,5-c]isoquinolin-5 (6H)-yl)-N-(cyclopropylmethyl)cyclohexane-1-carboxamide trans-4-(3-(Butylamino)-8-((4-methylpiperazin-1-yl)methyl)-6-oxopyrimido[4,5-c]isoquinolin-5(6H)-yl)-N,N-dimethylcyclohexane-1-carboxamide 8-((4-(1H-tetrazol-5-yl)piperidin-1-yl)methyl)-3-((cyclopropylmethyl)amino)-5-((1s,4s)-4-hydroxycyclohexyl)pyrimido[4,5-c]isoquinolin-6(5H)-one 3-((cyclopropylmethyl)amino)-8-((4-ethoxypiperidin-1-yl)methyl)-5-((1s,4s)-4-hydroxycyclohexyl)pyrimido[4,5-c]isoquinolin-6(5H)-one 3-((cyclopropylmethyl)amino)-8-((4-hydroxy-4-methylpiperidin-1-yl)methyl)-5-((1s,4s)-4-hydroxycyclohexyl)pyrimido[4,5-c]isoquinolin-6(5H)-one

358

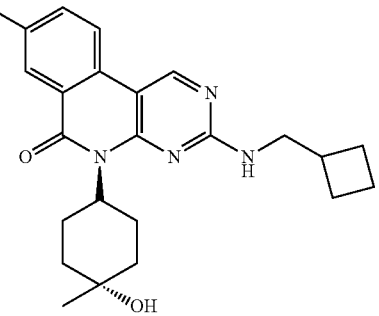

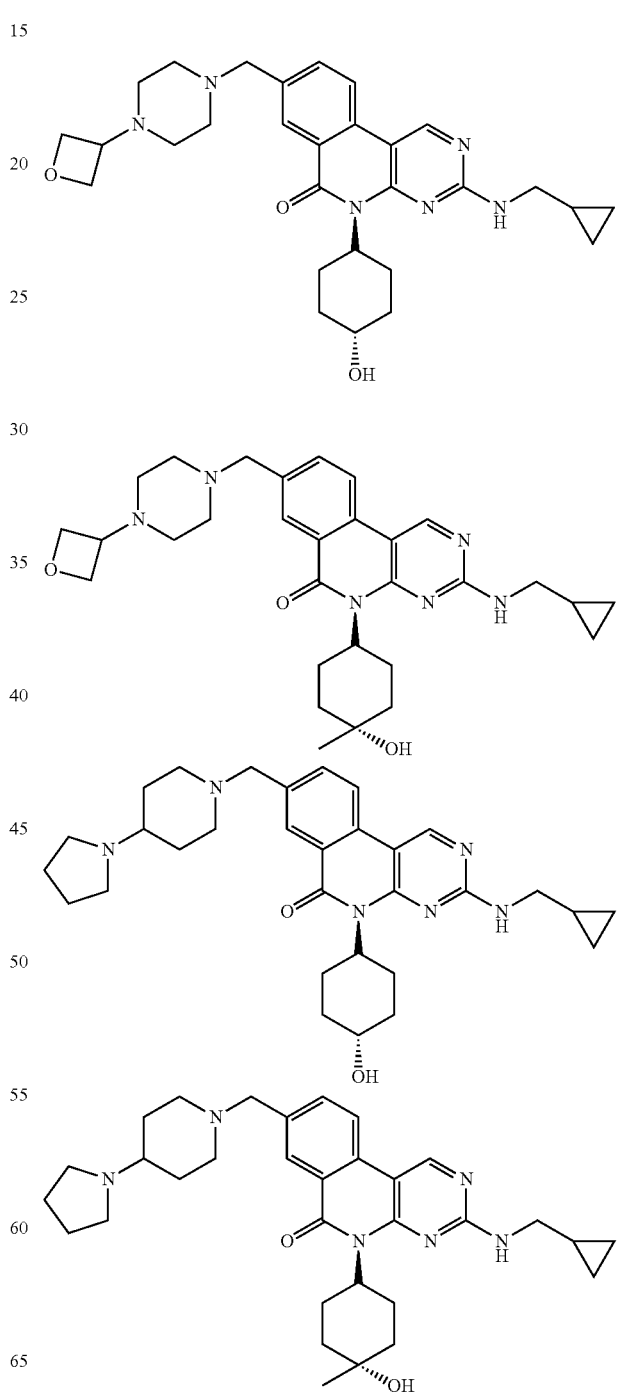

359
-continued
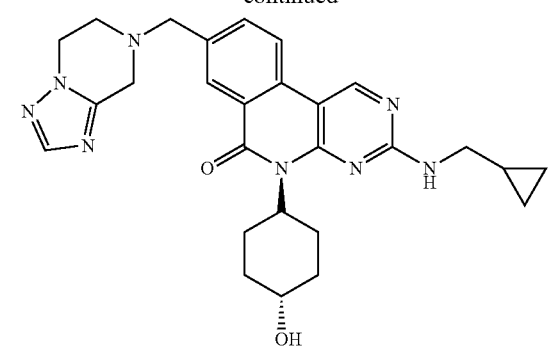
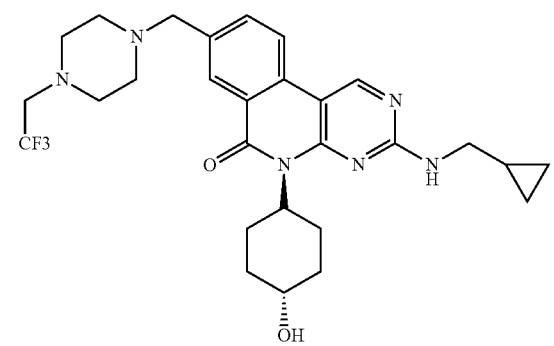
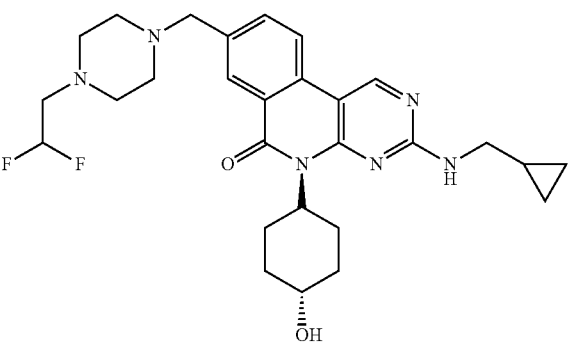
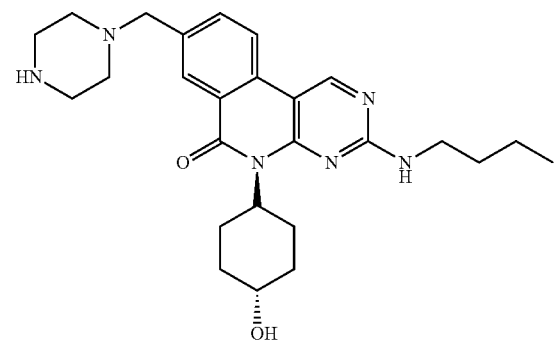
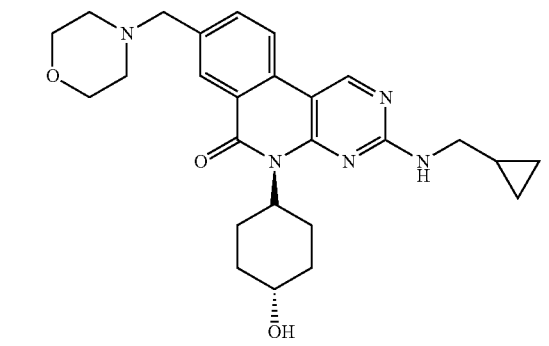
360
-continued
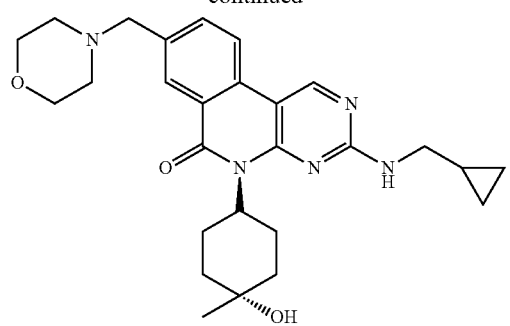
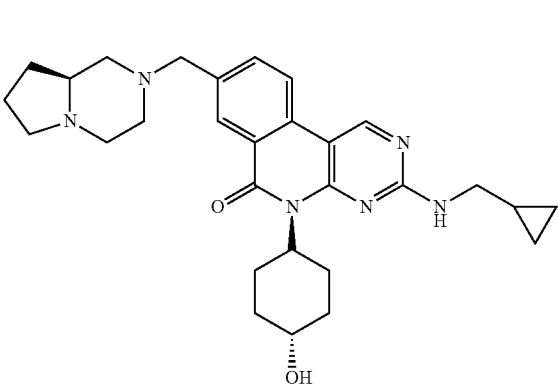
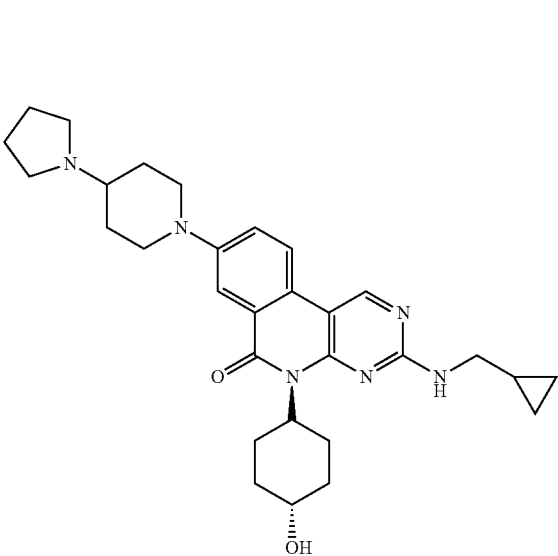
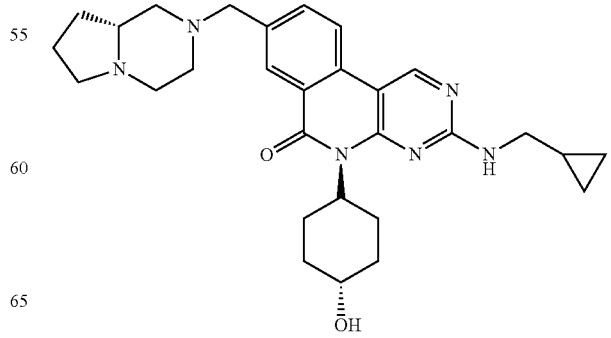

US 10,130,623 B2

361
-continued

362
-continued

363
-continued
364
-continued
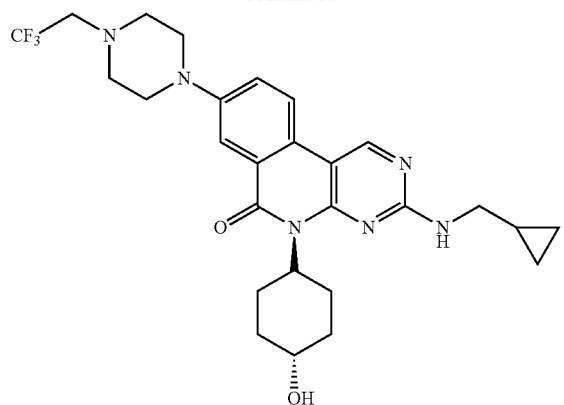
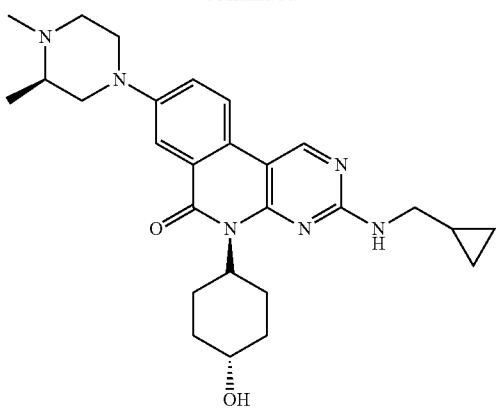
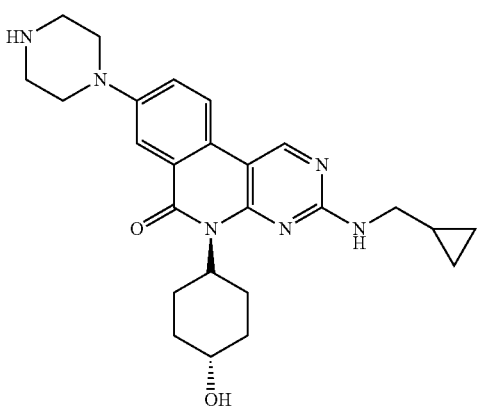

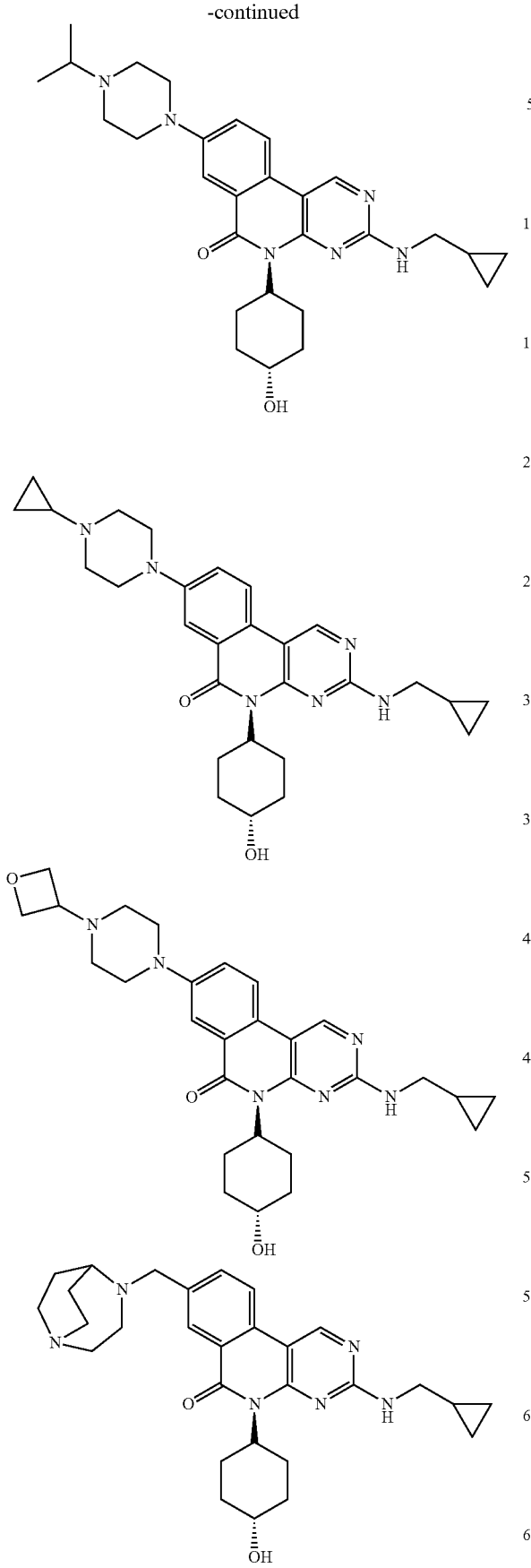
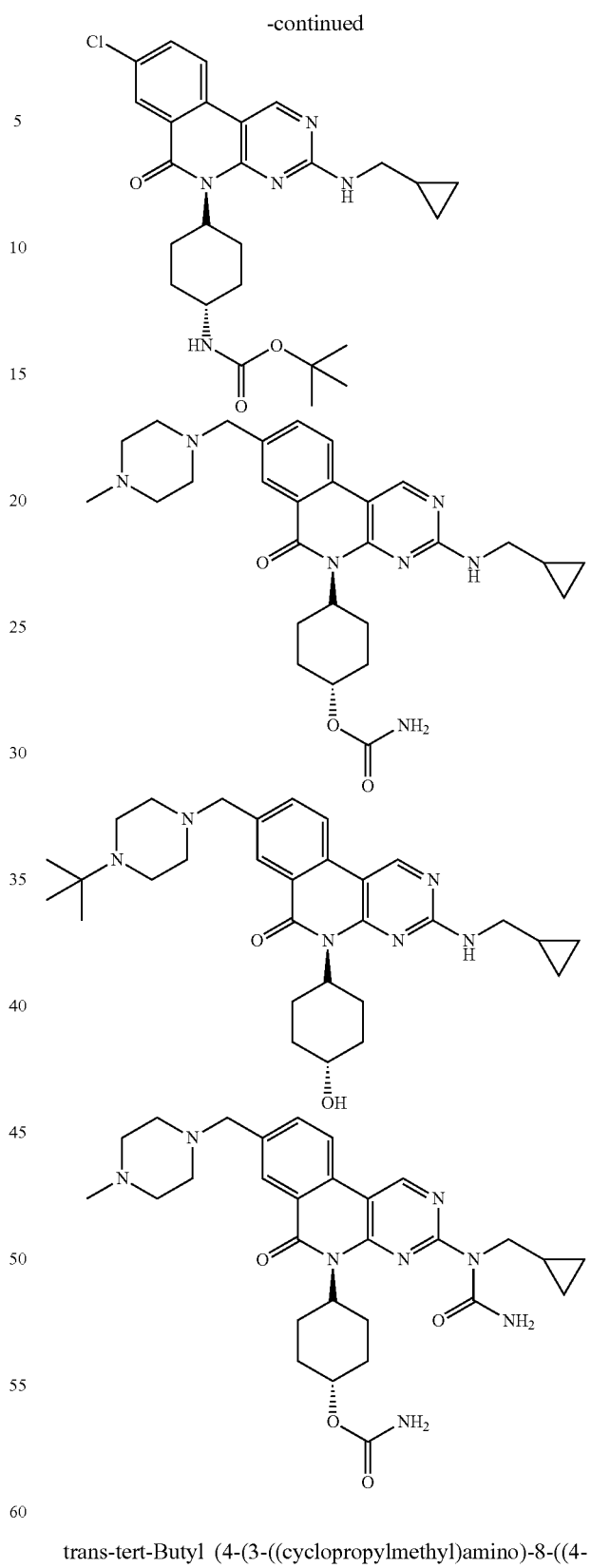
trans-tert-Butyl (4-(3-((cyclopropylmethyl)amino)-8-((4-methylpiperazin-1-yl)methyl)-6-oxopyrimido[4,5-c]isoquinolin-5(6H)-yl)cyclohexyl)carbamate
trans-5-(4-aminocyclohexyl)-3-((cyclopropylmethyl)amino)-8-((4-methylpiperazin-1-yl)methyl)pyrimido[4,5-c]isoquinolin-6(5H)-one

367 trans-8-((2-Oxa-7-azaspiro[3.5]nonan-7-yl)methyl)-3-((cyclopropylmethyl)amino)-5-(4-hydroxycyclohexyl)pyrimido[4,5-c]isoquinolin-6(5H)-one

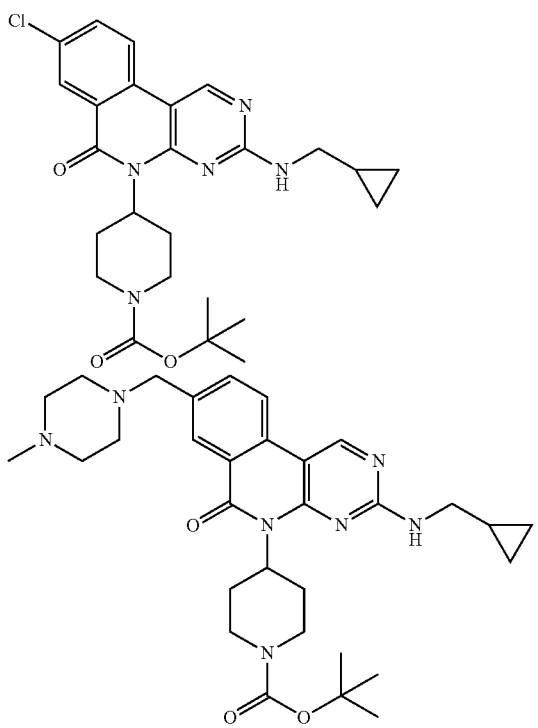

trans-3-((cyclopropylmethyl)amino)-5-(4-hydroxycyclohexyl)-8-((1-methylpiperidin-4-yl)amino)pyrimido[4,5-c]isoquinolin-6(5H)-one trans-2-Cyano-N-(4-(3-((cyclopropylmethyl)amino)-8-((4-methylpiperazin-1-yl)methyl)-6-oxopyrimido[4,5-c]isoquinolin-5(6H)-yl)cyclohexyl)acetamide

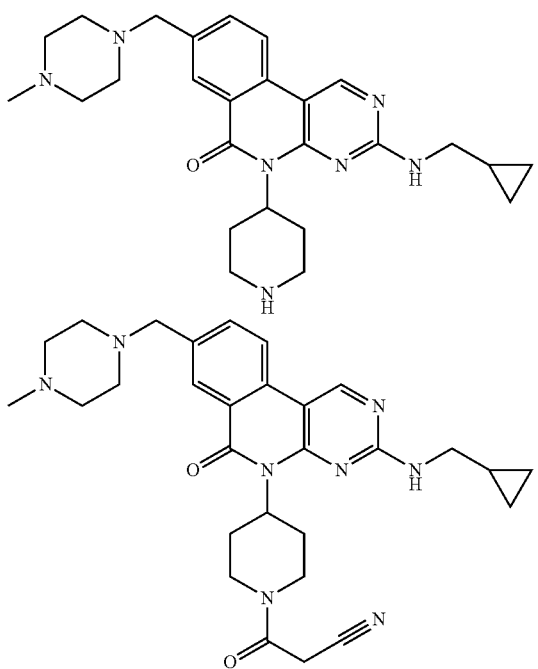

368

-continued

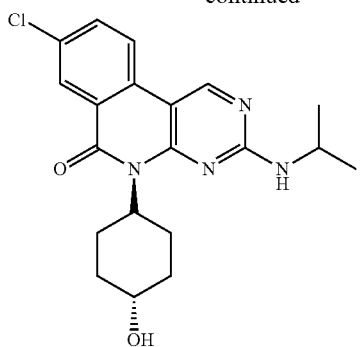

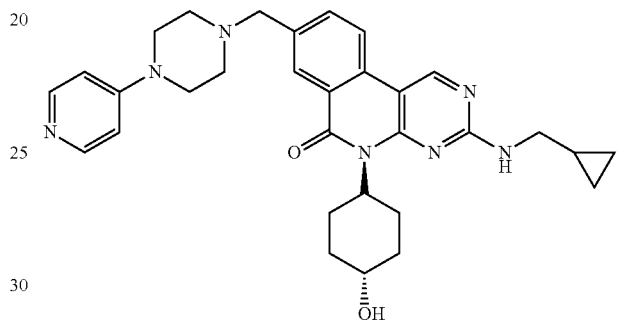

trans-5-(4-Hydroxycyclohexyl)-3-(isopropylamino)-8-((4-methylpiperazin-1-yl)methyl)pyrimido[4,5-c]isoquinolin-6(5H)-one trans-3-(Cyclopropylamino)-5-(4-hydroxycyclohexyl)-8-((4-methylpiperazin-1-yl)methyl)pyrimido[4,5-c]isoquinolin-6(5H)-one trans-8-((2-Oxa-7-azaspiro[3.5]nonan-7-yl)methyl)-3-((2,2-difluorobutyl)amino)-5-(4-hydroxycyclohexyl)pyrimido[4,5-c]isoquinolin-6(5H)-one trans-8-((4-(tert-Butyl)piperazin-1-yl)methyl)-3-((2,2-difluorobutyl)amino)-5-(4-hydroxycyclohexyl)pyrimido[4,5-c]isoquinolin-6(5H)-one trans-8-((4-(tert-Butyl)piperazin-1-yl)methyl)-3-((3,3-difluorocyclobutyl)amino)-5-(4-hydroxycyclohexyl)pyrimido[4,5-c]isoquinolin-6(5H)-one trans-1-((3-((Cyclopropylmethyl)amino)-5-(4-hydroxycyclohexyl)-6-oxo-5,6-dihydropyrimido[4,5-c]isoquinolin-8-yl)methyl)piperidine-4-carboxylic acid trans-tert-Butyl 1-((3-((cyclopropylmethyl)amino)-5-(4-hydroxycyclohexyl)-6-oxo-5,6-dihydropyrimido[4,5-c]isoquinolin-8-yl)methyl)piperidine-4-carboxylate trans-3-((Cyclopropylmethyl)amino)-5-(4-hydroxycyclohexyl)-8-(piperidin-1-ylmethyl)pyrimido[4,5-c]isoquinolin-6(5H)-one trans-1-((3-((Cyclopropylmethyl)amino)-5-(4-hydroxycyclohexyl)-6-oxo-5,6-dihydropyrimido[4,5-c]isoquinolin-8-yl)methyl)piperidine-4-carboxamide trans-1-((3-((Cyclopropylmethyl)amino)-5-(4-hydroxycyclohexyl)-6-oxo-5,6-dihydropyrimido[4,5-c]isoquinolin-8-yl)methyl)piperidine-4-carbonitrile

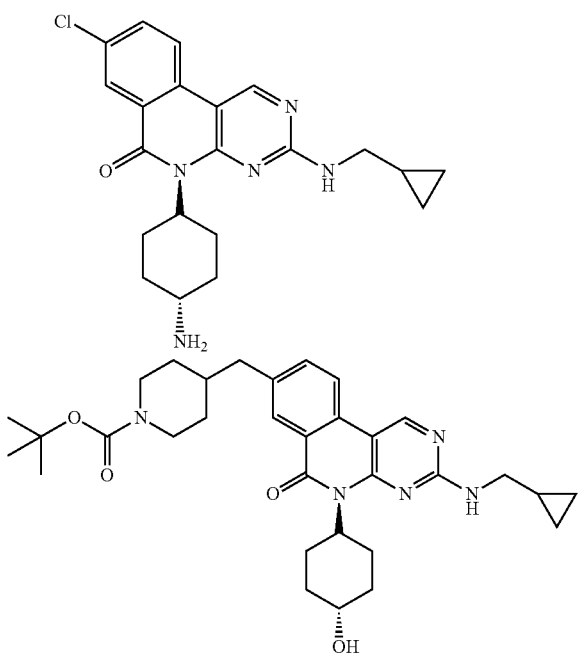

trans-3-((Cyclopropylmethyl)amino)-5-(4-hydroxycyclohexyl)-8-(piperidin-4-ylmethyl)pyrimido[4,5-c]isoquinolin-6(5H)-one
trans-3-((Cyclopropylmethyl)amino)-5-(4-hydroxycyclohexyl)-8-(3-morpholinopropoxy)pyrimido[4,5-c]isoquinolin-6(5H)-one
trans-8-((2-Oxa-7-azaspiro[3.5]nonan-7-yl)methyl)-3-(cyclobutylamino)-5-(4-hydroxycyclohexyl)pyrimido[4,5-c]isoquinolin-6(5H)-one
trans-8-((2-Oxa-7-azaspiro[3.5]nonan-7-yl)methyl)-3-((3,3-difluorocyclobutyl)amino)-5-(4-hydroxycyclohexyl)pyrimido[4,5-c]isoquinolin-6(5H)-one

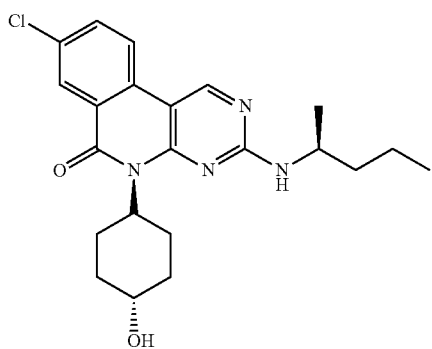

trans-3-((3,3-Difluorocyclobutyl)amino)-5-(4-hydroxycyclohexyl)-8-((4-(pyridin-4-yl)piperazin-1-yl)methyl)pyrimido[4,5-c]isoquinolin-6(5H)-one
trans-5-(4-hydroxycyclohexyl)-8-((4-methylpiperazin-1-yl)methyl)-3-(((S)-pentan-2-yl)amino)pyrimido[4,5-c]isoquinolin-6(5H)-one
trans-8-((2-oxa-7-azaspiro[3.5]nonan-7-yl)methyl)-5-(4-hydroxycyclohexyl)-3-(((S)-pentan-2-yl)amino)pyrimido[4,5-c]isoquinolin-6(5H)-one
trans-8-((4-(tert-Butyl)piperazin-1-yl)methyl)-5-(4-hydroxycyclohexyl)-3-(((S)-pentan-2-yl)amino)pyrimido[4,5-c]isoquinolin-6(5H)-one
trans-3-((Cyclopropylmethyl)amino)-5-(4-hydroxycyclohexyl)-8-((4-(pyrimidin-4-yl)piperazin-1-yl)methyl)pyrimido[4,5-c]isoquinolin-6(5H)-one
trans-3-((Cyclopropylmethyl)amino)-5-(4-hydroxycyclohexyl)-8-((4-(pyridin-4-yl)piperidin-1-yl)methyl)pyrimido[4,5-c]isoquinolin-6(5H)-one
trans-3-((Cyclopropylmethyl)amino)-5-(4-hydroxycyclohexyl)-8-((1-(pyridin-4-yl)piperidin-4-yl)methyl)pyrimido[4,5-c]isoquinolin-6(5H)-one
trans-5-(4-Hydroxycyclohexyl)-3-(((S)-pentan-2-yl)amino)-8-((4-(pyridin-4-yl)piperazin-1-yl)methyl)pyrimido[4,5-c]isoquinolin-6(5H)-one
trans-3-((Cyclobutylmethyl)amino)-5-(4-hydroxycyclohexyl)-8-((4-(pyridin-4-yl)piperazin-1-yl)methyl)pyrimido[4,5-c]isoquinolin-6(5H)-one
trans-3-((2,2-Difluorobutyl)amino)-5-(4-hydroxycyclohexyl)-8-((4-(pyridin-4-yl)piperazin-1-yl)methyl)pyrimido[4,5-c]isoquinolin-6(5H)-one
trans-3-((2-Cyclopropylethyl)amino)-5-(4-hydroxycyclohexyl)-8-((4-(pyridin-4-yl)piperazin-1-yl)methyl)pyrimido[4,5-c]isoquinolin-6(5H)-one
trans-5-(4-Hydroxycyclohexyl)-3-(isopentylamino)-8-((4-(pyridin-4-yl)piperazin-1-yl)methyl)pyrimido[4,5-c]isoquinolin-6(5H)-one
trans-3-((Cyclopropylmethyl)amino)-5-(4-hydroxy-4-methylcyclohexyl)-8-((4-(pyridin-4-yl)piperazin-1-yl)methyl)pyrimido[4,5-c]isoquinolin-6(5H)-one
trans-3-(Cyclobutylamino)-5-(4-hydroxycyclohexyl)-8-((4-(pyridin-4-yl)piperazin-1-yl)methyl)pyrimido[4,5-c]isoquinolin-6(5H)-one
trans-3-(Cyclobutylamino)-5-(4-hydroxycyclohexyl)-8-((4-(pyrimidin-4-yl)piperazin-1-yl)methyl)pyrimido[4,5-c]isoquinolin-6(5H)-one
trans-3-(Cyclobutylamino)-5-(4-hydroxycyclohexyl)-8-((4-(pyridin-4-yl)piperidin-1-yl)methyl)pyrimido[4,5-c]isoquinolin-6(5H)-one
trans-3-((Cyclopropylmethyl)amino)-8-((4-hydroxy-4-(pyridin-4-yl)piperidin-1-yl)methyl)-5-(4-hydroxycyclohexyl)pyrimido[4,5-c]isoquinolin-6(5H)-one
3-(butylamino)-5-((1S,4S)-4-hydroxycycloheptyl)-8-((4-methylpiperazin-1-yl)methyl)pyrimido[4,5-c]isoquinolin-6(5H)-one
3-((cyclopropylmethyl)amino)-5-((1S,4S)-4-hydroxycycloheptyl)-8-((4-methylpiperazin-1-yl)methyl)pyrimido[4,5-c]isoquinolin-6(5H)-one
tert-butyl ((1S,3S)-3-(3-(butylamino)-8-((4-methylpiperazin-1-yl)methyl)-6-oxopyrimido[4,5-c]isoquinolin-5(6H)-yl)cyclopentyl)carbamate
5-((1S,3S)-3-aminocyclopentyl)-3-(butylamino)-8-((4-methylpiperazin-1-yl)methyl)pyrimido[4,5-c]isoquinolin-6(5H)-one
N-((1S,3S)-3-(3-(butylamino)-8-((4-methylpiperazin-1-yl)methyl)-6-oxopyrimido[4,5-c]isoquinolin-5(6H)-yl)cyclopentyl)acetamide
3-(butylamino)-8-chloro-5-((1R,3R)-3-hydroxycyclopentyl)pyrimido[4,5-c]isoquinolin-6(5H)-one
3-(butylamino)-5-((1R,3R)-3-hydroxycyclopentyl)-8-((4-methylpiperazin-1-yl)methyl)pyrimido[4,5-c]isoquinolin-6(5H)-one
3-(butylamino)-5-((1S,3S)-3-(dimethylamino)cyclopentyl)-8-((4-methylpiperazin-1-yl)methyl)pyrimido[4,5-c]isoquinolin-6(5H)-one
2-(((1S,3S)-3-(3-(butylamino)-8-((4-methylpiperazin-1-yl)methyl)-6-oxopyrimido[4,5-c]isoquinolin-5(6H)-yl)cyclopentyl)amino)acetamide 3-(butylamino)-5-((1S,3S)-3-((2-hydroxyethyl)amino)cyclopentyl)-8-((4-methylpiperazin-1-yl)methyl)pyrimido[4,5-c]isoquinolin-6(5H)-one 1-((1S,3S)-3-(3-(butylamino)-8-((4-methylpiperazin-1-yl)methyl)-6-oxopyrimido[4,5-c]isoquinolin-5(6H)-yl)cyclopentyl)guanidine or a pharmaceutically acceptable salt or N-oxide thereof, or solvate or hydrate thereof.

30. A pharmaceutical composition comprising a pharmaceutically acceptable diluent, carrier, or excipient and a compound according to claim 1.

31. A method of inhibiting a cellular TAM receptor, the method comprising contacting a cell comprising a TAM receptor with a compound according to claim 1.

32. The method of claim 30, wherein the TAM receptor is a Tyro receptor, an Axl receptor, or a Mer receptor.

33. A method for treating a disease or condition mediated by or involving the TAM receptor family in a subject in need thereof, the method comprising administering to the subject an effective TAM receptor inhibiting amount of a compound of any of claims 1-28, or a composition of claim 29, wherein the disease or condition is cancer, an autoimmune disease or condition, or an inflammatory disease or condition.

34. The method of claim 32, wherein the TAM receptor is a Tyro receptor, an Axl receptor, or a Mer receptor.

35. The method of claim 33, wherein the disease or condition is a hematological neoplasms.

36. The method of claim 34, wherein the hematological neoplasms is acute myeloid leukemia AML.

37. A method for treating a disease or condition mediated by or involving the TAM receptor family in a subject in need thereof, comprising administering an effective TAM receptor inhibiting amount of a compound of any of claims 1-28, or a composition of claim 29, in combination with the administration of a therapeutically effective amount of one or more chemotherapeutic agents, wherein the disease or condition is cancer, an autoimmune disease or condition, or an inflammatory disease or condition.

38. The method of claim 31, wherein the cell is in a human.

39. The method of claim 32, wherein the cell is in a human.

* * * * *